(12) United States Patent
Laali

(10) Patent No.: US 11,117,907 B2
(45) Date of Patent: *Sep. 14, 2021

(54) CURCUMINOID-INSPIRED SYNTHETIC COMPOUNDS AS ANTI-TUMOR AGENTS

(71) Applicant: Kenneth K. Laali, Jacksonville, FL (US)

(72) Inventor: Kenneth K. Laali, Jacksonville, FL (US)

(73) Assignee: University of North Florida Board of Trustees, Jacksonville, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/112,328

(22) Filed: Dec. 4, 2020

(65) Prior Publication Data

US 2021/0087208 A1 Mar. 25, 2021

Related U.S. Application Data

(63) Continuation-in-part of application No. 16/010,822, filed on Jun. 18, 2018, now Pat. No. 10,934,241.

(Continued)

(51) Int. Cl.
*C07F 5/02* (2006.01)
*A61P 35/00* (2006.01)
(Continued)

(52) U.S. Cl.
CPC .............. *C07F 5/025* (2013.01); *A61P 35/00* (2018.01); *C07C 49/235* (2013.01);
(Continued)

(58) Field of Classification Search
CPC ..... C07C 49/255; C07C 49/235; C07C 69/21; C07C 323/22; C07F 5/022; C07F 5/025;
(Continued)

(56) References Cited

U.S. PATENT DOCUMENTS

| 7,355,081 B2 | 4/2008 | Lee et al. |
| 9,375,408 B2 | 6/2016 | Singh |
| 10,092,550 B2 | 10/2018 | Zaid et al. |

OTHER PUBLICATIONS

Gupta, Subash C. et al. Multitargeting by curcumin as revealed by molecular interaction studies. Nat Prod Rep. Nov. 2011; 28(12): 1937-1955.

(Continued)

*Primary Examiner* — Savitha M Rao
*Assistant Examiner* — Andrew P Lee
(74) *Attorney, Agent, or Firm* — Michele L. Lawson; Smith & Hopen, P.A.

(57) ABSTRACT

Novel CUR— and CUR—BF$_2$ compounds as well as novel bis and mono-NSAID/CUR—BF$_2$ and NSAID/CUR hybrids exhibiting anti-tumor properties are presented. CUR compounds bearing fluorinated moieties with selective fluorine introduction into the α-carbonyl moiety as well as CUR—BF$_2$ adducts and CURs with diverse substitution patterns in the phenyl rings including fluorinated substituents (SCF$_3$, OCF$_3$, and F) and/or bulky activating groups (OMe, OAc, and OBz) are presented. Fluorinated arylpyrazoles and isoxazoles as well as novel CUR and CUR—BF$_2$ compounds with monocyclic aromatic and bicyclicheteroaromatic lateral rings, bearing fluorine(s), OCF$_3$, CF$_3$, and SCF$_3$ groups, and their alpha-carbonyl-fluorinated analogs, as well as their pyrazole and isoxazole derivatives are presented. The CUR-pyrazoles embody analogs that are fluorinated at the phenyl-pyrazole moiety. The hybrids, compounds, and their derivatives exhibited exceptional cytotoxic and anti-proliferative activity against several cancer cell-lines. The hybrid NSAID/CUR compounds also exhibited exceptional anti-inflammatory activity over NSAID or curcumin alone.

12 Claims, 261 Drawing Sheets

Related U.S. Application Data

(60) Provisional application No. 62/520,788, filed on Jun. 16, 2017.

(51) Int. Cl.

| | | |
|---|---|---|
| *C07C 49/255* | (2006.01) | |
| *C07C 49/235* | (2006.01) | |
| *C07C 69/21* | (2006.01) | |
| *C07C 323/22* | (2006.01) | |
| *C07D 403/06* | (2006.01) | |
| *C07D 261/08* | (2006.01) | |
| *C07D 409/06* | (2006.01) | |
| *C07D 407/06* | (2006.01) | |
| *C07D 405/14* | (2006.01) | |
| *C07D 409/14* | (2006.01) | |
| *C07D 231/12* | (2006.01) | |

(52) U.S. Cl.
CPC ............ *C07C 49/255* (2013.01); *C07C 69/21* (2013.01); *C07C 323/22* (2013.01); *C07D 231/12* (2013.01); *C07D 261/08* (2013.01); *C07D 403/06* (2013.01); *C07D 405/14* (2013.01); *C07D 407/06* (2013.01); *C07D 409/06* (2013.01); *C07D 409/14* (2013.01)

(58) Field of Classification Search
CPC .. C07D 409/06; C07D 261/08; C07D 231/12; C07D 407/06; C07D 403/06; C07D 405/14; C07D 409/14; A61P 35/00
See application file for complete search history.

(56) References Cited

OTHER PUBLICATIONS

Minassi, Alberto et al. Dissecting the Pharmacophore of Curcumin. Which Structural Element Is Critical for Which Action? J. Nat. Prod., Feb. 20, 2013, 76: 1105-1112.

Bairwa, Khemraj et al. Recent developments in chemistry and biology of curcumin analogues. RSC Adv., 2014, 4: 13946-13978.

Vyas, Alok et al. Perspectives on New Synthetic Curcumin Analogs and their Potential Anticancer Properties. Curr Pharm Des. 2013; 19(11): 2047-2069.

Pillai, G. Radhakrishna et al. Induction of apoptosis in human lung cancer cells by curcumin. Cancer Letters 208(2004): 163-170.

Lopresti, Adrian L. et al. Multiple antidepressant potential modes of action of curcumin: a review of its anti-inflammatory, monoaminergic, antioxidant, immune-modulating and neuroprotective effects. Journal of Psychopharmacology, 2012, 26(12): 1512-1524.

Perrone, Donatella et al. Biological and therapeutic activities, and anticancer properties of curcumin (Review). Experimental and Therapeutic Medicine, 2015, 10: 1615-1623.

Tan, Kheng-Lin et al. Curcumin Analogues with Potent and Selective Anti-proliferative Activity on Acute Promyelocytic Leukemia: Involvement of Accumulated Misfolded Nuclear Receptor Co-repressor (N-CoR) Protein as a Basis for Selective Activity. ChemMedChem 2012, 7: 1567-1579.

Cheng, Ce et al. Improved bioavailability of curcumin in liposomes prepared using a pH-driven, organic solvent-free, easily scalable process. RSC Adv., 2017, 7: 25978-25986.

Zhang, Lili et al. Curcumin-cyclodextrin complexes enhanced the anti-cancer effects of curcumin. Environmental Toxicology and Pharmacology 48 (2016) 31-38.

Yallapu, Murali Mohan et al. Beta-Cyclodextrin-curcumin self-assembly enhances curcumin delivery in prostate cancer cells. Colloids and Surfaces B: Biointerfaces 79 (2010) 113-125.

Liu, Jieying et al. Recent Progress in Studying Curcumin and its Nano-preparations for Cancer Therapy. Current Pharmaceutical Design, 2013, 19, 1974-1993.

Simoni, Daniele et al. Antitumor effects of curcumin and structurally Beta-diketone modified analogs on multidrug resistant cancer cells. Bioorganic & Medicinal Chemistry Letters 18 (2008) 845-849.

Nieto, Carla I. et al. Fluorination Effects on NOS Inhibitory Activity of Pyrazoles Related to Curcumin. Molecules 2015, 20, 15643-15665.

Amolins, Michael W. et al. Synthesis and evaluation of electron-rich curcumin analogues. Bioorg Med Chem. Jan. 1, 2009; 17(1): 360-367.

Labbozzetta, Manuela et al. Lack of nucleophilic addition in the isoxazole and pyrazole diketone modified analogs of curcumin; implications for their antitumor and chemosensitizing activities. Chemico-Biological Interactions 181 (2009) 29-36.

Narlawar, Rajeshwar et al. Curcumin-Derived Pyrazoles and Isoxazoles: Swiss Army Knives or Blunt Tools for Alzheimer's Disease? ChemMedChem 2008, 3, 165-172.

Wan, Sheng Biao et al. Evaluation of curcumin acetates and amino acid conjugates as proteasome inhibitors. International Journal of Molecular Medicine, 2010; 26: 447-455.

Feng, Ling et al. Synthesis and Biological Evaluation of Curcuminoid Derivatives. Chem. Pharm. Bull., 2015; 63(11): 873-881.

Wichitnithad, Wisut et al. Synthesis, Characterization and Biological Evaluation of Succinate Prodrugs of Curcuminoids for Colon Cancer Treatment. Molecules 2011, 16, 1888-1900.

Cheikh-Ali, Zakaria et al. "Squalenoylcurcumin" Nanoassemblies as Water-Disperable Drug Candidates with Antileishmanial Activity. ChemMedChem 2015, 10, 411-418.

Sribalan, Rajendran et al. Synthesis and biological evaluation of new symmetric curcumin derivatives. Bioorganic & Medicinal Chemistry Letters 25 (2015) 4282-4286.

Wada, Koji et al. Novel curcumin analogs to overcome EGFR-TKI lung adenocarcinoma drug resistance and reduce EGFR-TKI-induced GI adverse effects. Bioorganice & Medicinal Chemistry 23 (2015) 1507-1514.

Lin, Li et al. Antitumor agents 247. New 4-ethoxycarboylethyl curcumin analogs as potential antiandrogenic agents. Bioorganic & Medicinal Chemistry 14 (2006) 2527-2534.

Lin, Li et al. Antitumor Agents. 250. Design and Synthesis of New Curcumin Analogues as Potential Anti-Prostate Cancer Agents. J. Med. Chem. 2006, 49, 3963-3792.

Martinez-Cifuentes, Maximiliano et al. Heterocyclic Curcumin Derivatives of Pharmacological Interest: Recent Progress. Current Topics in Medicinal Chemistry, 2015, 15, 1663-1672.

Wang, Jiang et al. Fluorine in Pharmaceutical Industry: Fluorine-Containing Drugs Introduced to the Market in the Last Decade (2001-2011). Chem. Rev., 2014, 114, 2432-2506.

Rao, E. Venkata and P. Sudheer. Revisiting Curcumin Chemistry Part I: a New Strategy for the Synthesis of Curcuminoids. Indian J Pharm Sci. May-Jun. 2011; 73(3): 262-270.

Megna, Bryant W. et al. The aryl hydrocarbon receptor as an antitumor target of synthetic curcuminoids in colorectal cancer. Journal of Surgical Research, Jun. 2017 (213) 16-24.

Elavarasan, S. et al. An Efficient Green Procedure for Synthesis of Some Fluorinated Curcumin Analogues Catalyzed by Calcium Oxide under Microwave Irradiation and Its Antibacterial Evaluation. Journal of Chemistry, vol. 2013, Article ID 640936; 1-8.

Padhye, Subhash et al. Fluorocurcumins as Cyclooxygenase-2 Inhibitor: Molecular Docking, Pharmacokinetics and Tissue Distribution in Mice. Pharmaceutical Research, vol. 26, No. 11, Nov. 2009:2438-2445.

Mimeault, Murielle and Surinder K. Batra. Potential applications of curcumin and its novel synthetic analogs and nanotechnology-based formulations in cancer prevention and therapy. Mimeault and Batra Chinese Medicine 2011, 6:31.

Kamada, Kenji et al. Boron Difluoride Curcuminoid Fluorophores with Enhanced Two-Photon Excited Fluorescence Emission and Versatile Living-Cell Imaging Properties. Chem. Eur. J. 2016, 22, 5219-5232.

Bai, Guifeng et al. Syntheses and photophysical properties of BF2 complexes of curcumin analogues. Org. Biomol. Chem., 2014, 12, 1618-1626.

(56) References Cited

OTHER PUBLICATIONS

Aertgeerts, Kathleen et al. Structural Analysis of the Mechanism of Inhibition and Allosteric Activation of the Kinase Domain of HER2 Protein. The Journal of Biological Chemistry, May 27, 2011; vol. 286, No. 21: 18756-18765.

Laali, Kenneth K. et al. Fluoro-curcuminoids and curcuminoid-BF2 adducts: Synthesis, X-ray structures, bioassay, and computational/docking study. Journal of Fluorine Chemistry 191 (2016) 29-41.

Laali, Kenneth K. et al. Novel fluorinated curcuminoids and their pyrazole and isoxazole derivatives: Synthesis, structural studies, Computational/Docking and in-vitro bioassay. Journal of Fluorine Chemistry 206 (2018) 82-98.

Padhye, Subhash et al. New Difluoro Knoevenagel Condensates of Curcumin, Their Schiff Bases and Copper Complexes as Proteasome Inhibitors and Apoptosis Inducers in Cancer Cells. Pharmaceutical Research, vol. 26, No. 8, Aug. 2009, 1874-1880.

Restriction Requirement issued by the the United States Patent and Trademark Office dated Feb. 27, 2019 for corresponding U.S. Appl. No. 16/010,822, filed Jun. 18, 2018.

Non-Final Office Action issued by the the United States Patent and Trademark Office dated Sep. 30, 2019 for corresponding U.S. Appl. No. 16/010,822, filed Jun. 18, 2018.

Non-Final Office Action issued by the the United States Patent and Trademark Office dated Jun. 23, 2020 for corresponding U.S. Appl. No. 16/010,822, filed Jun. 18, 2018.

Non-Final Office Action issued by the the United States Patent and Trademark Office dated May 7, 2019 for corresponding U.S. Appl. No. 16/010,822, filed Jun. 18, 2018.

Final Office Action issued by the the United States Patent and Trademark Office dated Dec. 30, 2019 for corresponding U.S. Appl. No. 16/010,822, filed Jun. 18, 2018.

Binding energies for Curcuminoids

| Curcuminoids | AutoDock Vina (kcal/mol) | | | | |
|---|---|---|---|---|---|
| | HER2 | Proteasome | VEGFR2 | BRAF | BCL-2 |
| Known inhibitor | −11.4 (SYR) | −7.8 (Bortezomib)<br>−7.8 (Ixazomib)<br>−8.5 (Carfilzomib) | −9.2 (Axitinib)<br>−10.0 (Sorafenib)<br>−8.9 (Lenvatinib) | −9.3 (Vemurafenib)<br>−12.9 (Dabrafenib) | −8.3 (Navitoclax)<br>−8.2 (Venetoclax) |
| (7) | −7.9 | −7.2 | −7.4 | −8.0 | −7.0 |
| (6) | −8.4 | −8.3 | −8.2 | −9.1 | −8.7 |
| (11) | −7.4 | −8.5 | −8.4 | −7.8 | −6.8 |
| (10) | −8.0 | −7.9 | −8.3 | −8.5 | −8.7 |
| (9) | −7.5 | −7.3 | −7.2 | −7.6 | −6.3 |
| (8) | −7.8 | −8.0 | −7.8 | −8.3 | −5.6 |
| (3) | −9.6 | −9.9 | −10.1 | −10.7 | −9.9 |
| (2) | −10.8 | −10.3 | −11.7 | −11.2 | −8.3 |
| (5) | −10.4 | −9.6 | −10.4 | −10.0 | −9.8 |
| (4) | −10.9 | −9.4 | −11.1 | −10.7 | −7.9 |
| (17) | −9.5 | −8.2 | −10.7 | −8.8 | −6.6 |
| (16) | −10.5 | −8.9 | −11.8 | −9.8 | −7.2 |
| (15) | −10.6 | −9.0 | −10.9 | −10.2 | −9.2 |
| (14) | −10.7 | −9.3 | −12.1 | −10.6 | −10.0 |
| (19) | −9.0 | −7.6 | −10.5 | −8.7 | −7.6 |
| (18) | −10.4 | −8.5 | −11.5 | −9.8 | −7.8 |

FIG. 36

| Compounds | AutoDock Vina (kcal/mol)[a] | | | | |
|---|---|---|---|---|---|
| | HER2 | Proteasome | VEGFR2 | BRAF | BCL-2 |
| 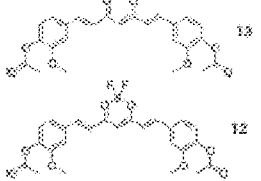 13 | −8.4 | −8.7 | −9.4 | −8.7 | −6.2 |
| 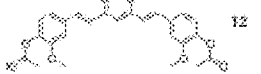 12 | −10.1 | −8.7 | −10.2 | −8.9 | −7.1 |
[a] Most stable binding mode (more favorable values in bold).
FIG. 36 Cont.

|          | Control | WM      | MM       | ALL   |
|----------|---------|---------|----------|-------|
| Compound | PBMC    | BCWM.1  | RPMI 8226 | RS4;11 |
| 7        | 7812    | 3884    | 6584     | 7171  |
| 6        | 516.5   | 473.9   | 500.4    | 506.7 |
| 9        | 17647   | 15289   | 26.33    | 1.018 |
| 8        | 21701   | 8765    | 14914    | 11126 |
| 11       | 240.8   | 269.5   | 235.6    | 305.8 |
| 10       | 615.3   | 1541    | 1419     | 1888  |
| 15       | 6159    | 6985    | 12114    | 9911  |
| 14       | 1267    | 2242    | 1923     | 954.5 |
| 17       | 15315   | 9902    | 9867     | 15113 |
| 16       | 669.3   | 1422    | 1344     | 934.6 |
| 13       | 587.6   | 2225    | 2508     | 2408  |
| 12       | 54.97   | 371.3   | 550.6    | 450.9 |
| 5        | 30000   | 56644   | 27.69    | 30000 |
| 4        | 14444   | 15784   | 14930    | 12034 |
| 3        | 18943   | 7475    | 8898     | 8117  |
| 2        | 4058    | 6533    | 14332    | 7751  |

FIG. 37

A
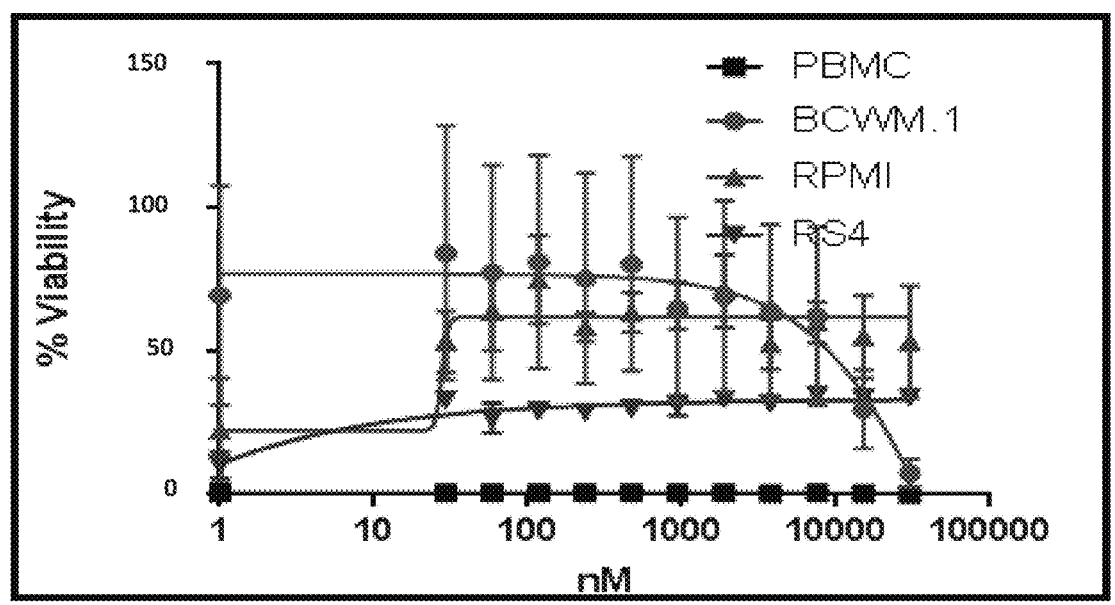
B
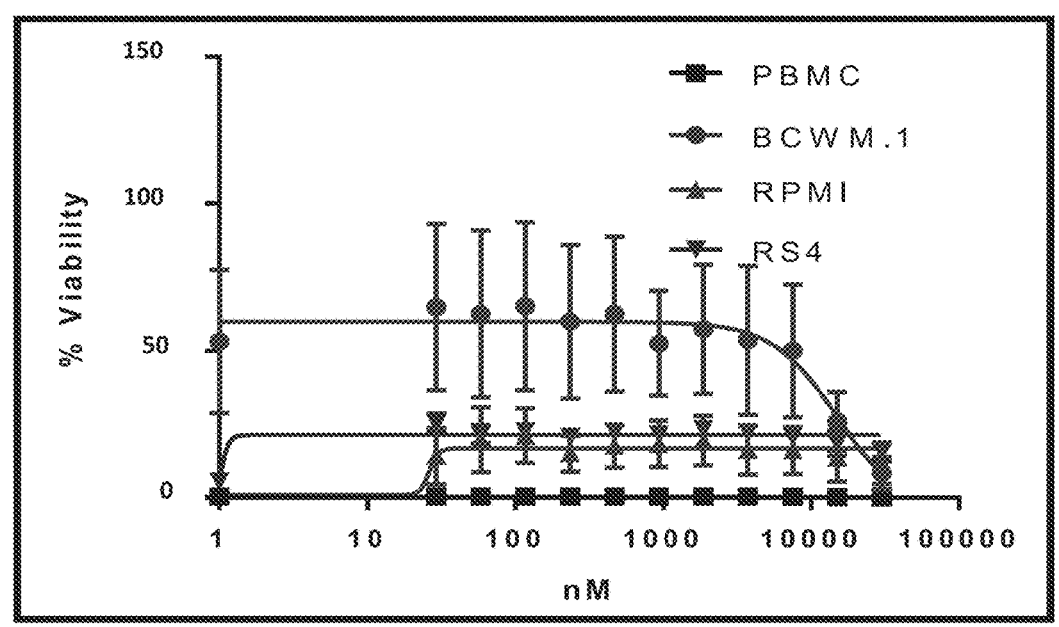
FIG. 38A-B

Synthesis of S-methylated curcuminoid dications salts
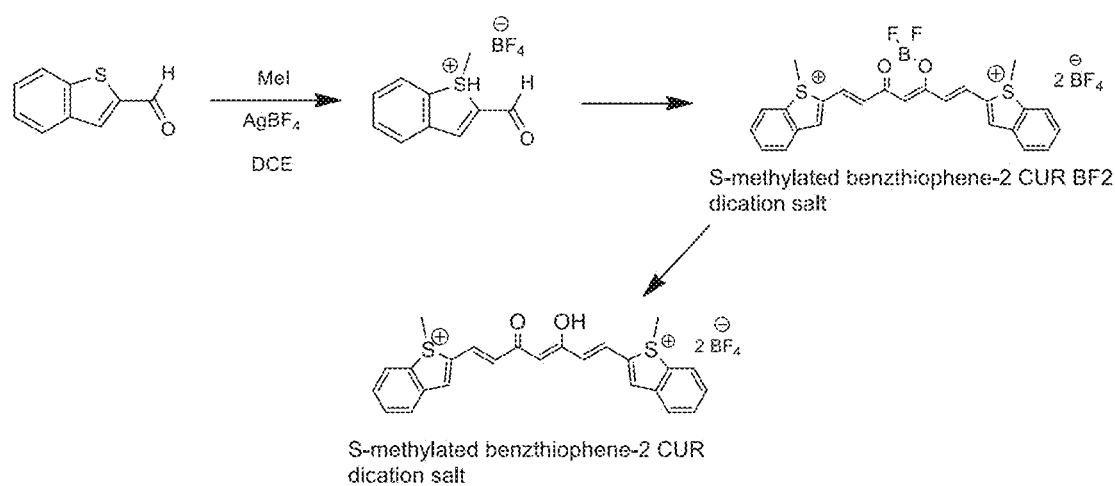
S-methylated benzthiophene-2 CUR BF2 dication salt
S-methylated benzthiophene-2 CUR dication salt
A similar strategy is used for the preparation of isomeric 3-CUR dication salts
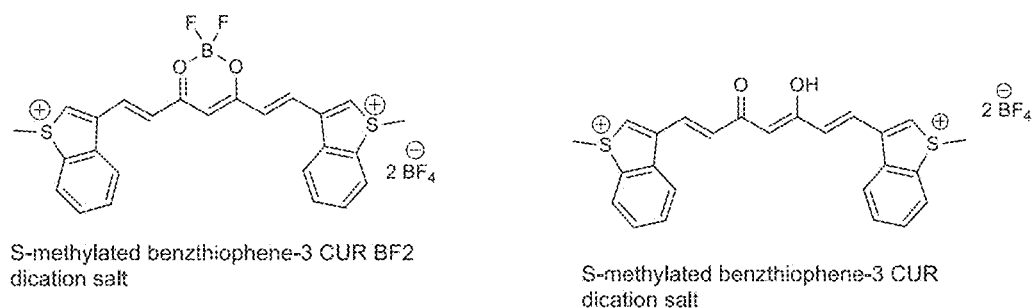
S-methylated benzthiophene-3 CUR BF2 dication salt
S-methylated benzthiophene-3 CUR dication salt
FIG. 47

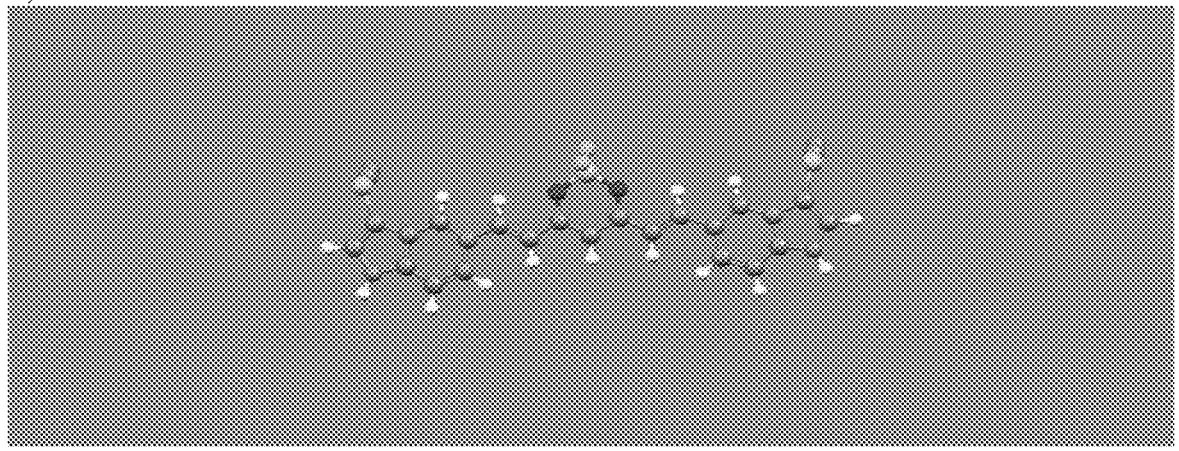
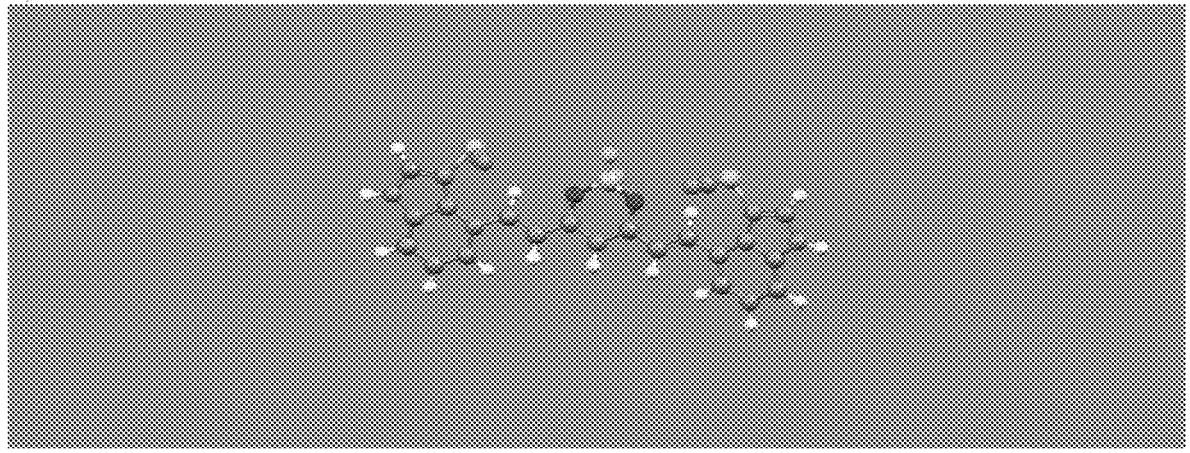
FIG. 52A-B

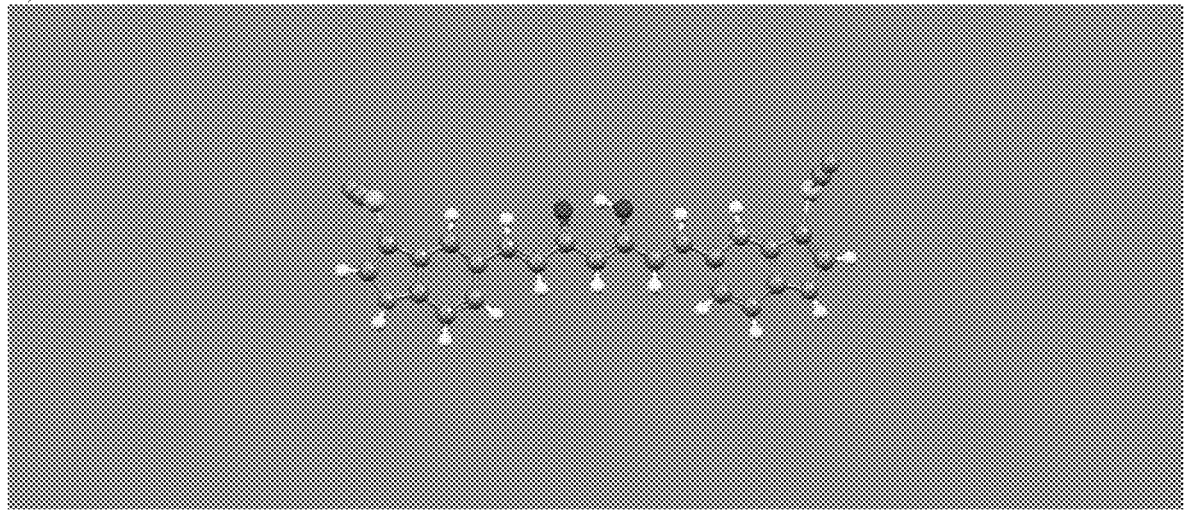
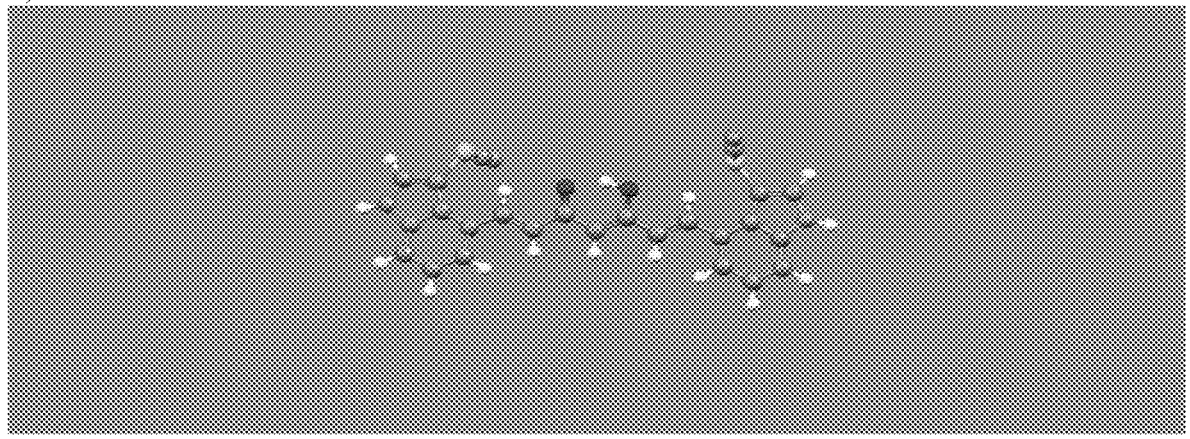
FIG. 53A-B

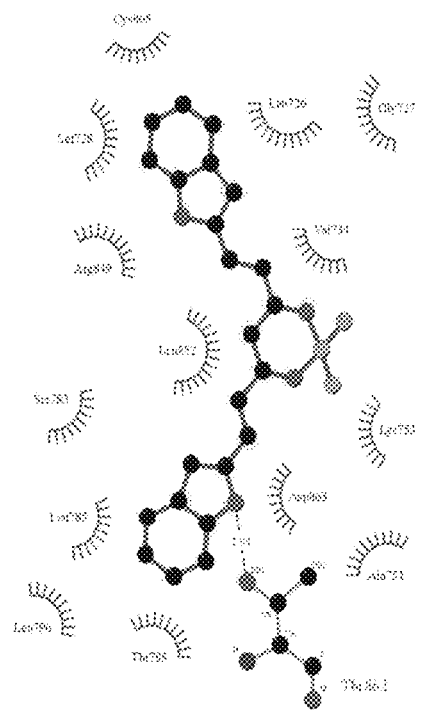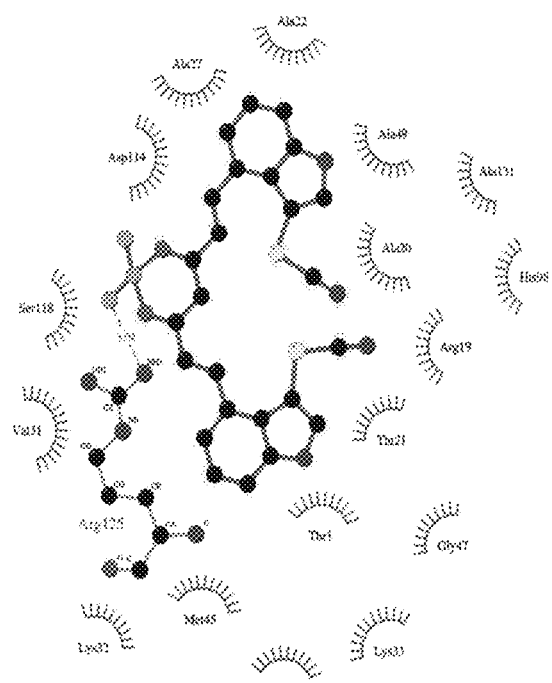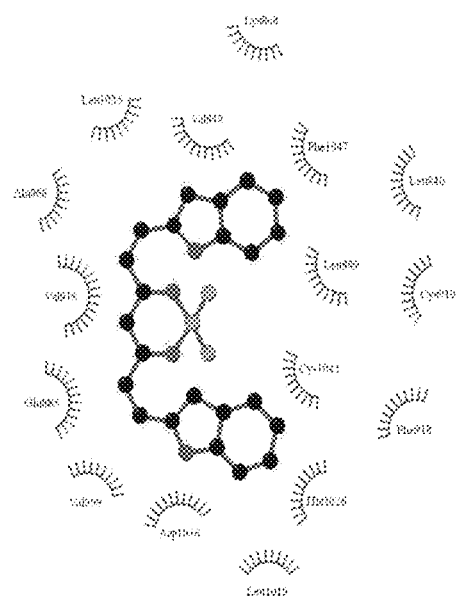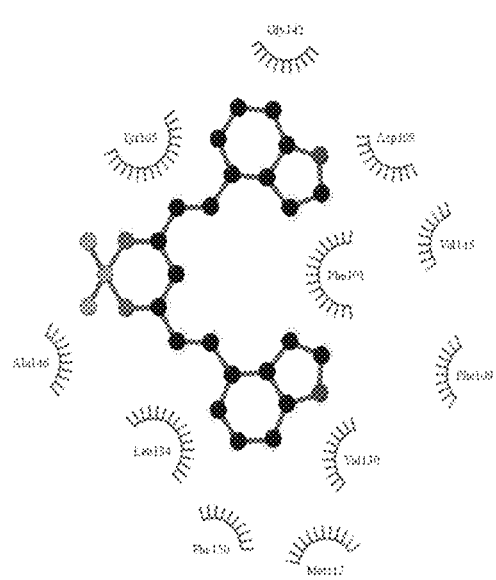
FIG. 58A-D

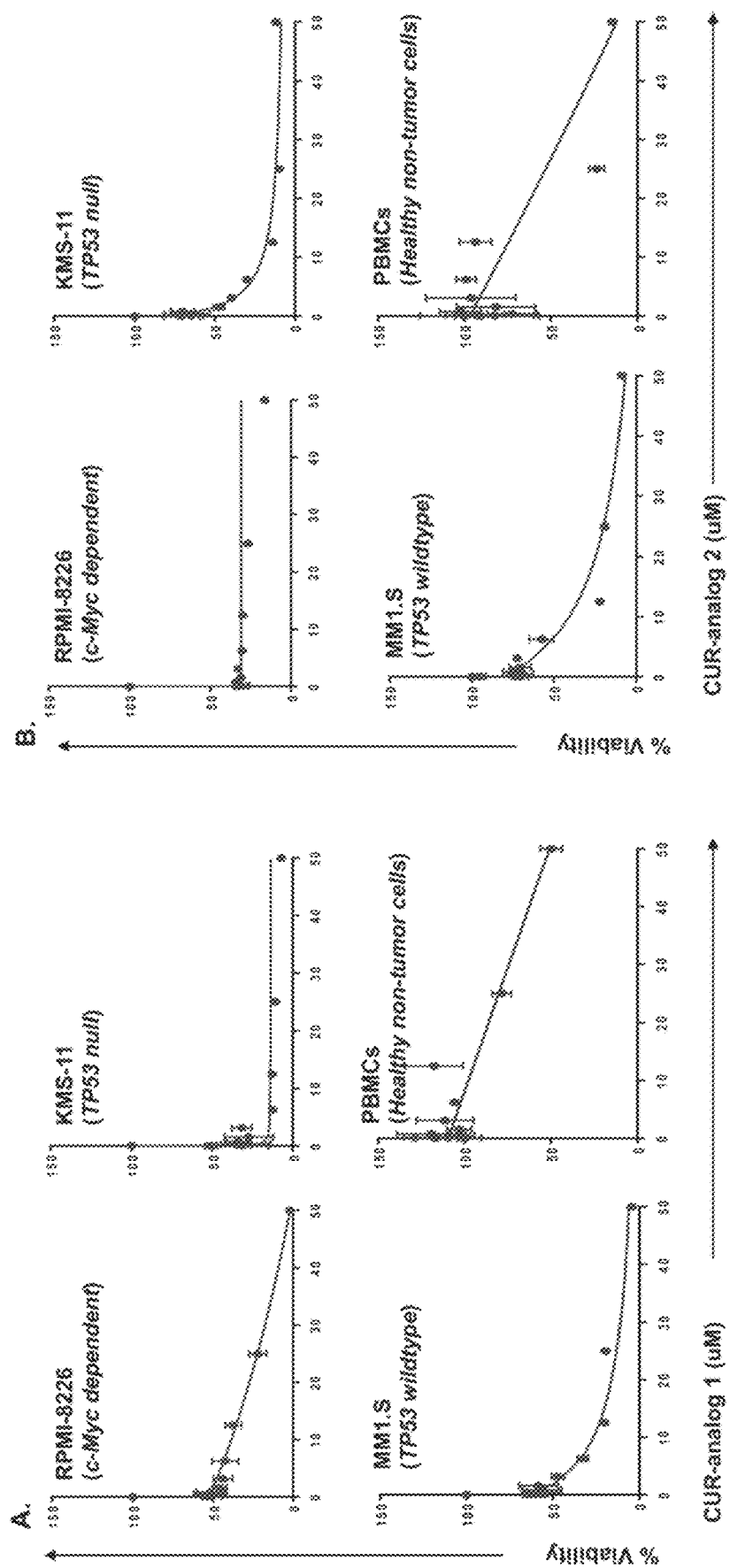
FIG. 61A-B

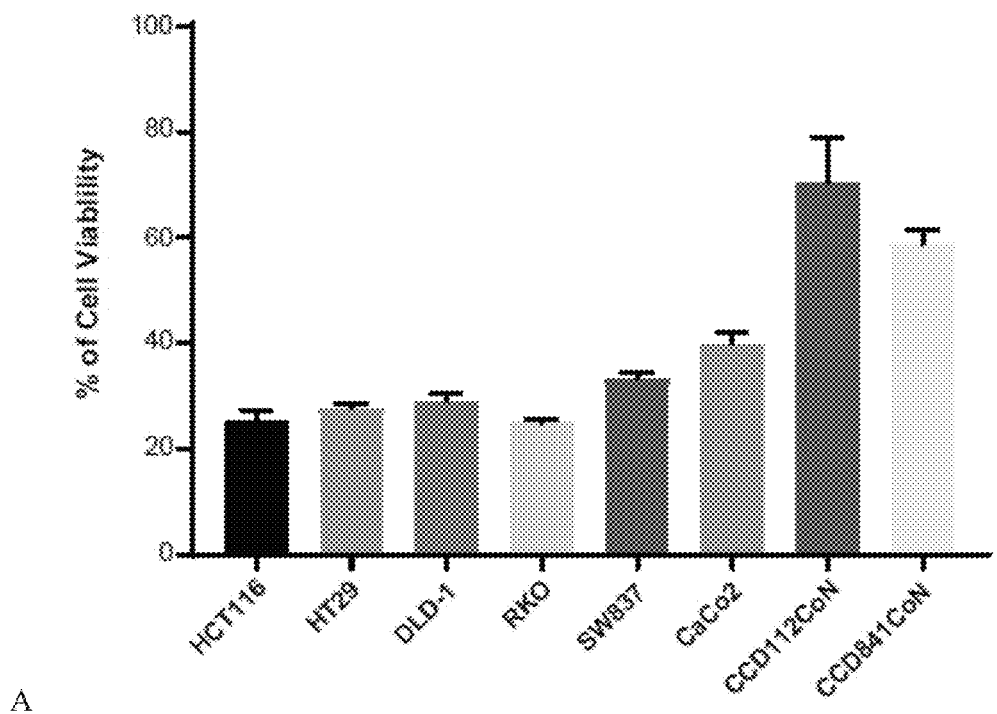
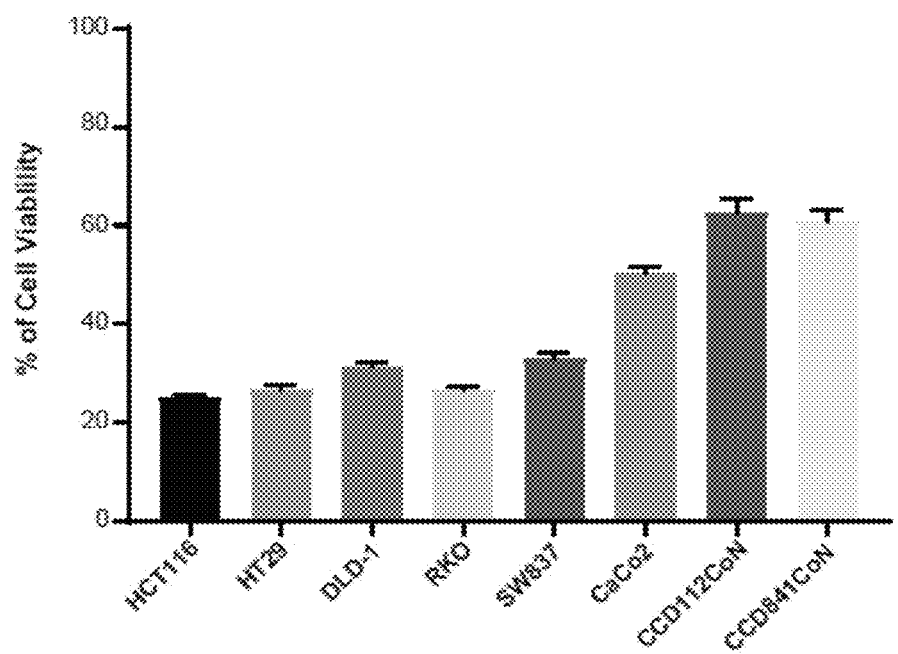
FIG. 62A-B

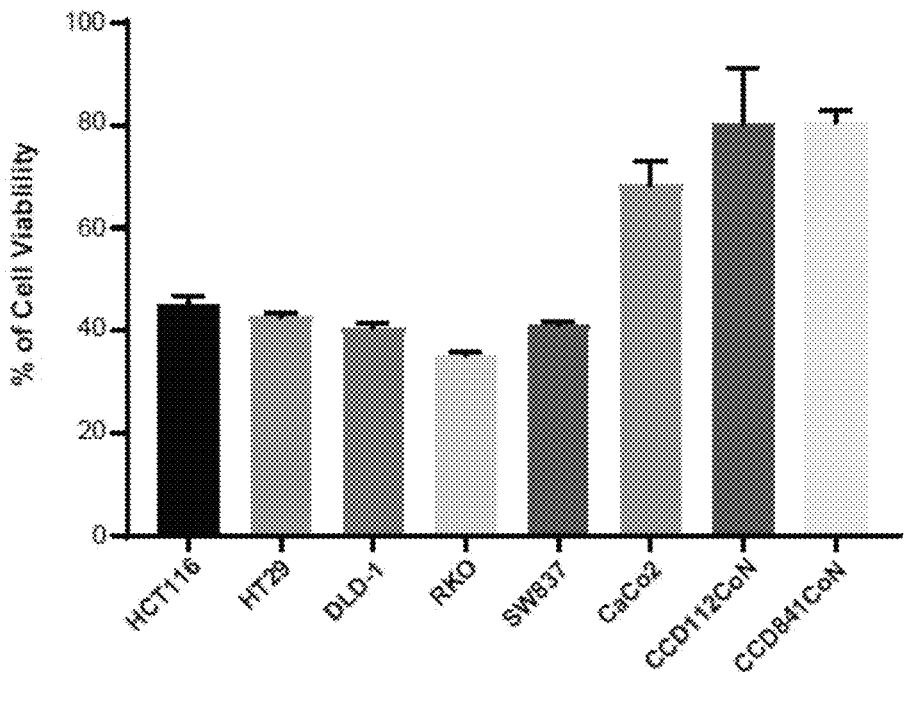
C
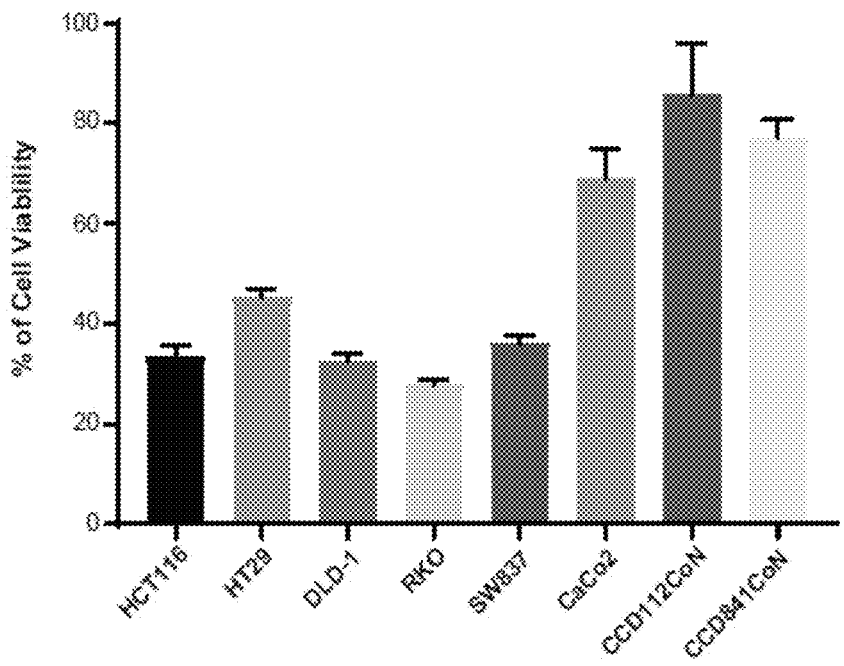
D
FIG. 62C-D

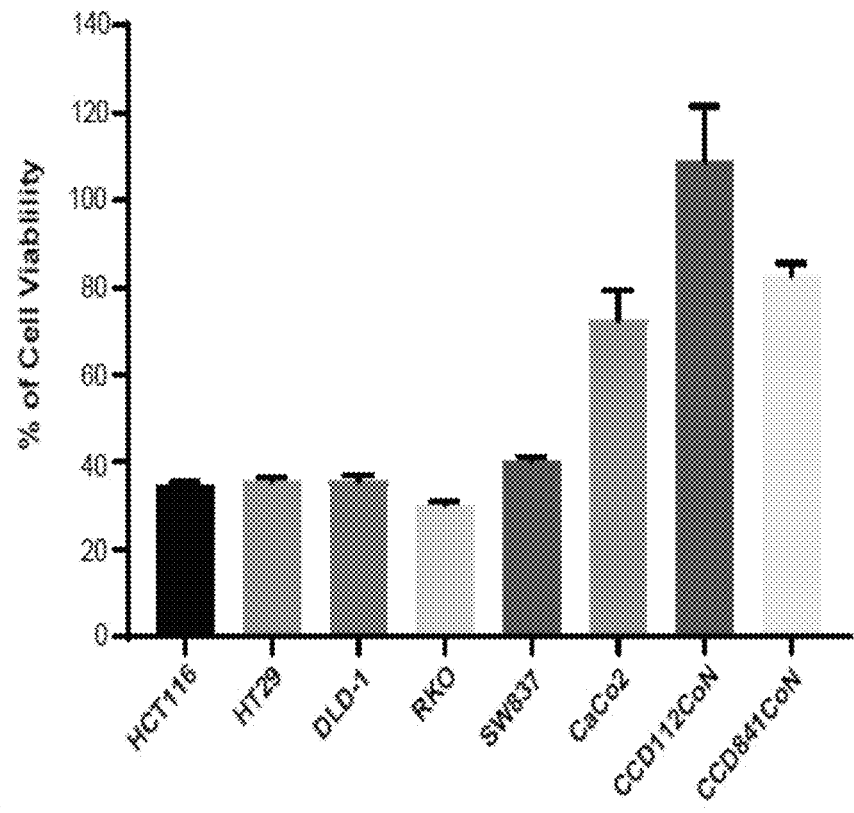
E
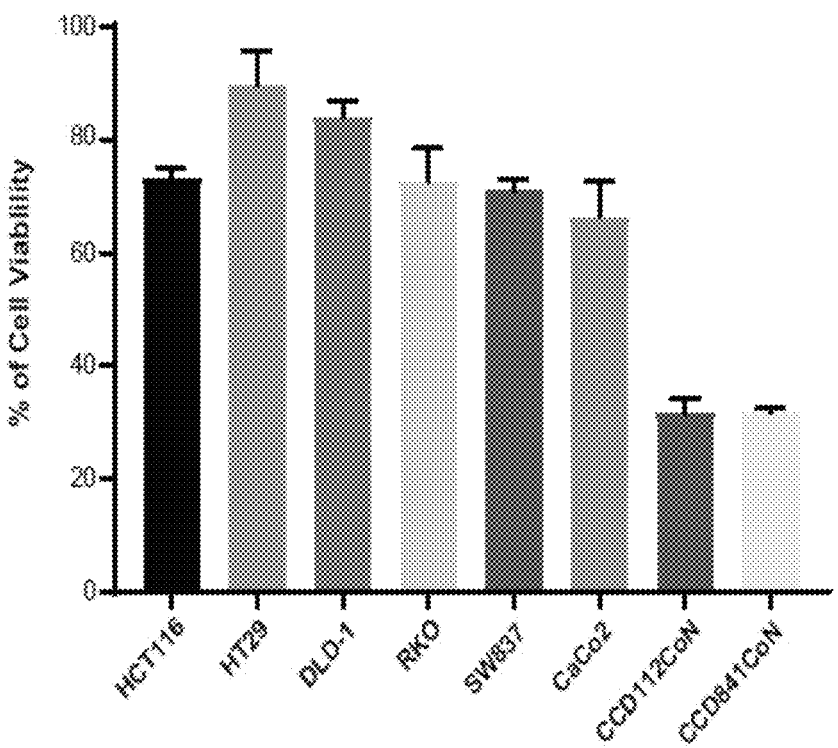
F
FIG. 62E-F

| | Organism | Tissue | Morphology | Disease | ATCC-Cat. |
|---|---|---|---|---|---|
| HCT116 | human | colon | epithelial | Colorectal carcinoma | CCL-247 |
| HT29 | human | colon | epithelial | Colorectal adenocarcinoma | HTB-38 |
| DLD-1 | human | colon | epithelial | Dukes' type C, colorectal adenocarcinoma | CCL-221 |
| RKO | human | colon | epithelial | Carcinoma | CRL-2577 |
| SW837 | human | rectum | epithelial | Grade IV, adenocarcinoma | CCL-235 |
| Caco2 | human | colon | epithelial-like | Colorectal adenocarcinoma | HTB-37 |
| CCD112CoN | human | colon | fibroblast | Normal | CRL-1541 |
| CCD841CoN | human | colon | epithelial | Normal | CRL-1790 |

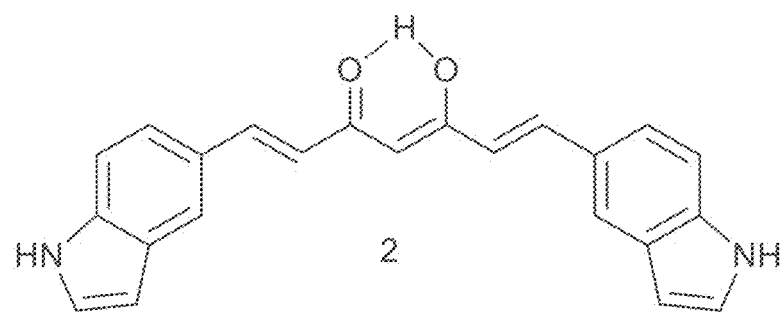
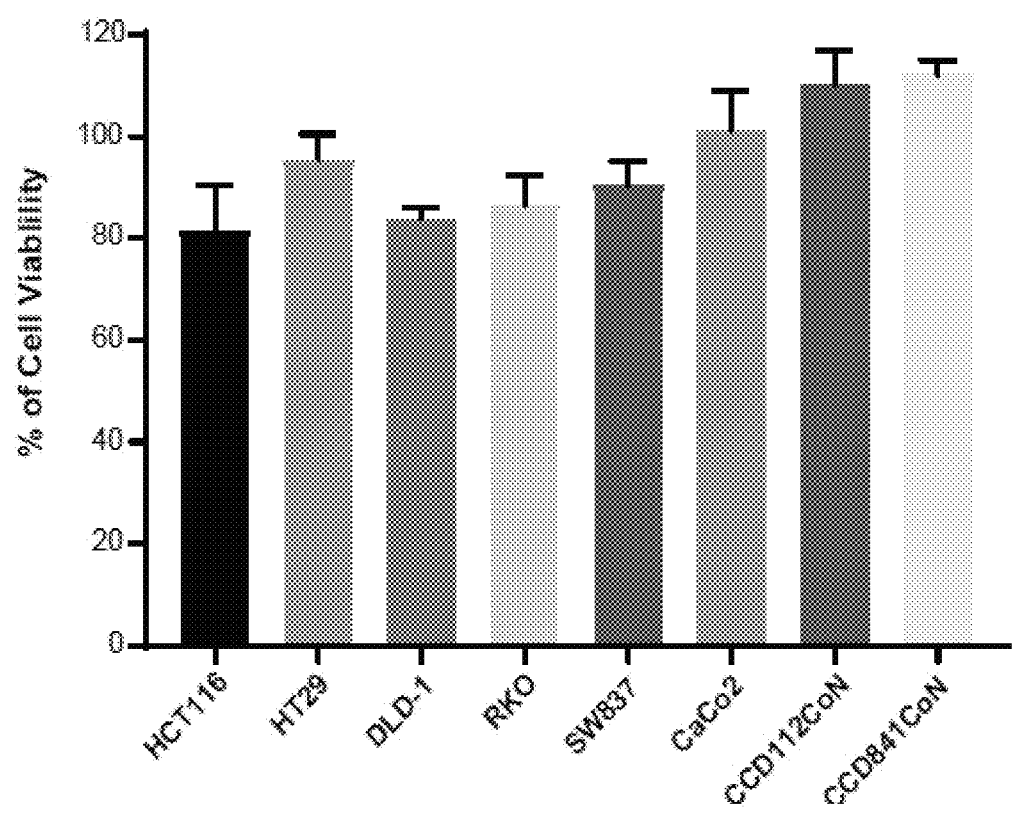
FIG. 74C

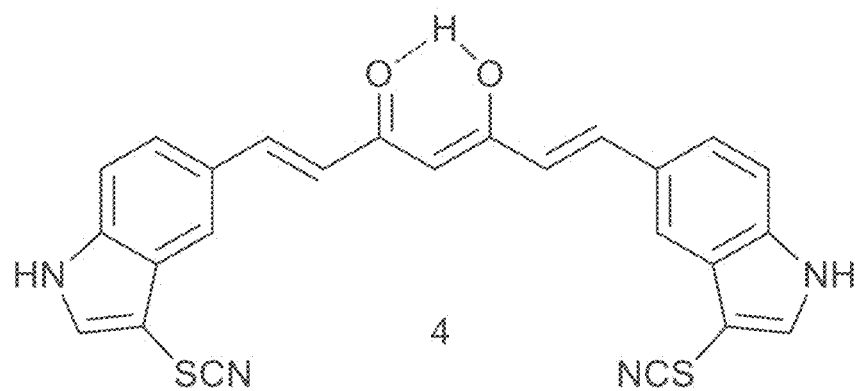
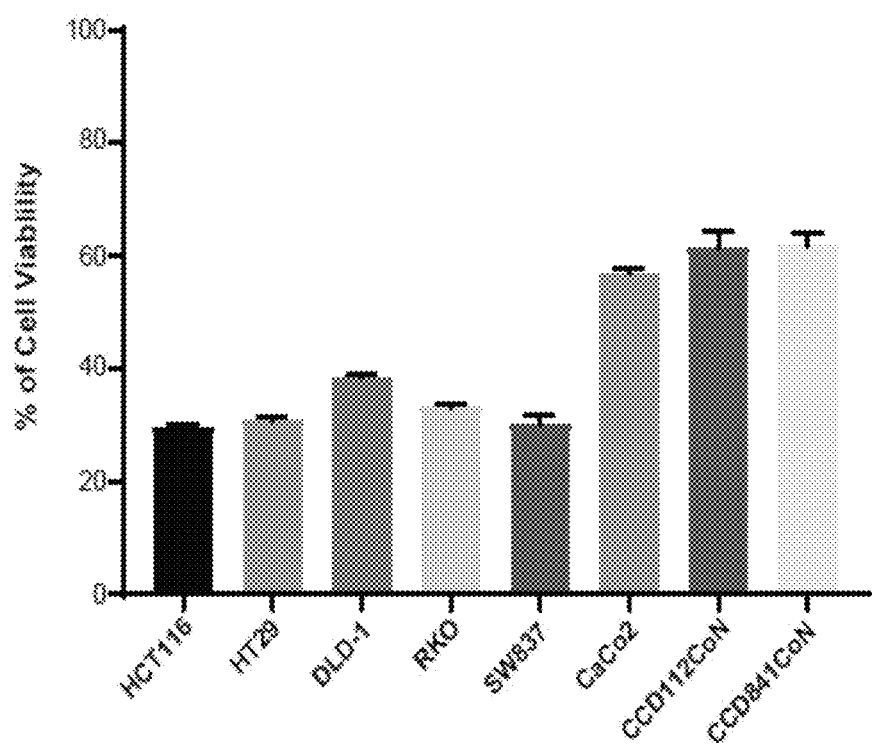
D
FIG. 74D

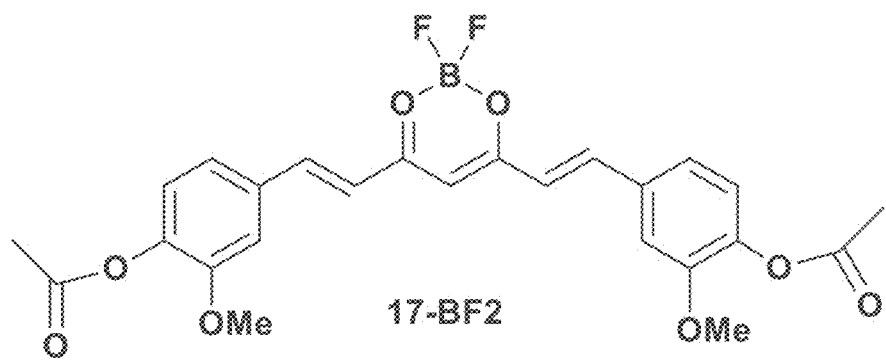
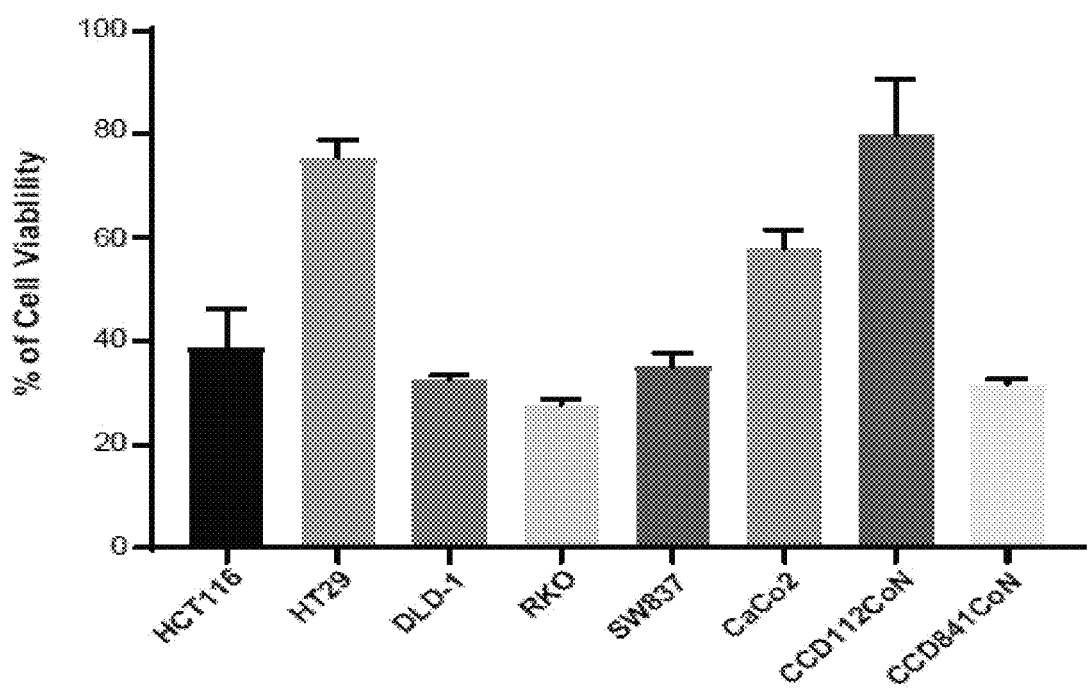
E
FIG. 74E

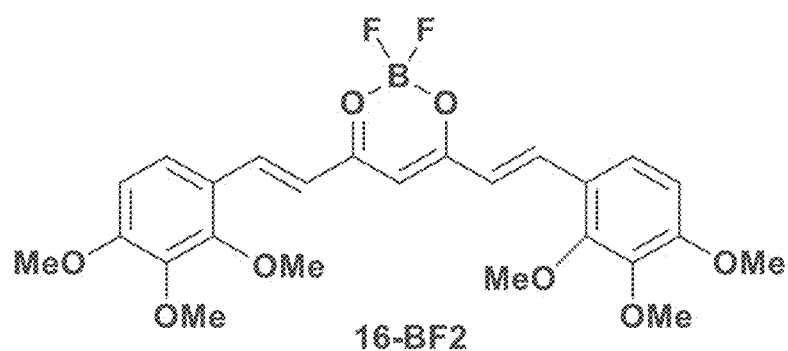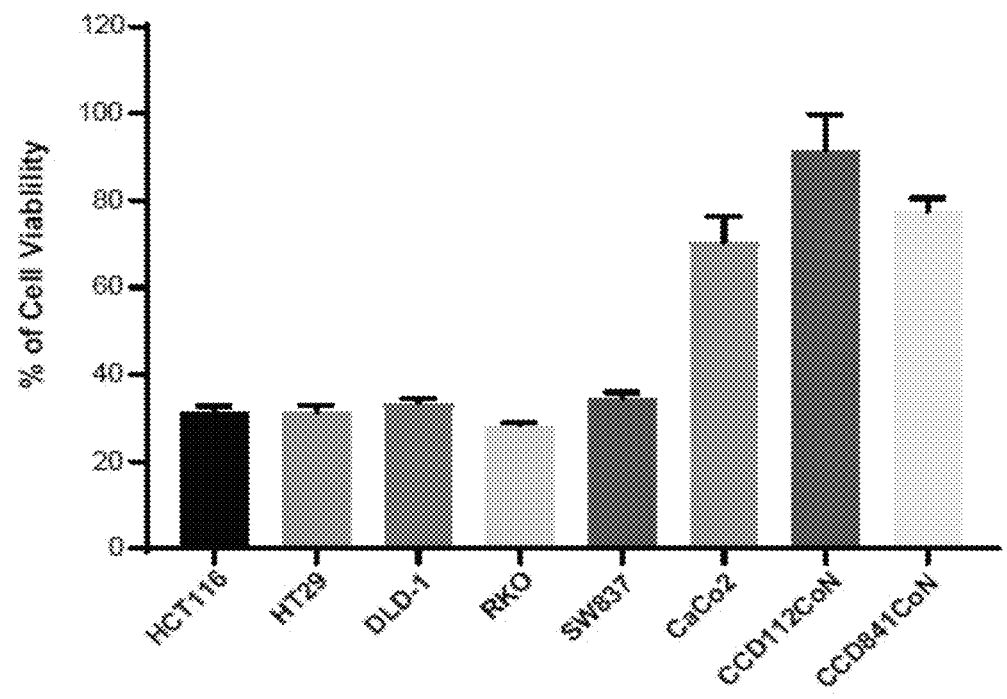
FIG. 74F

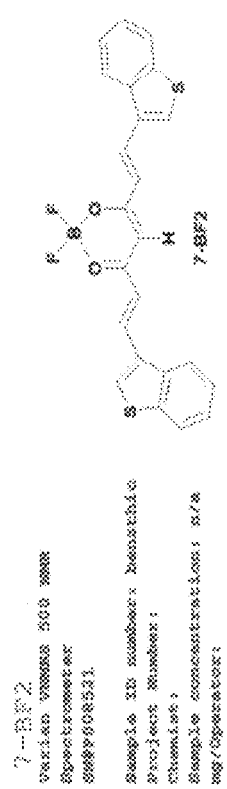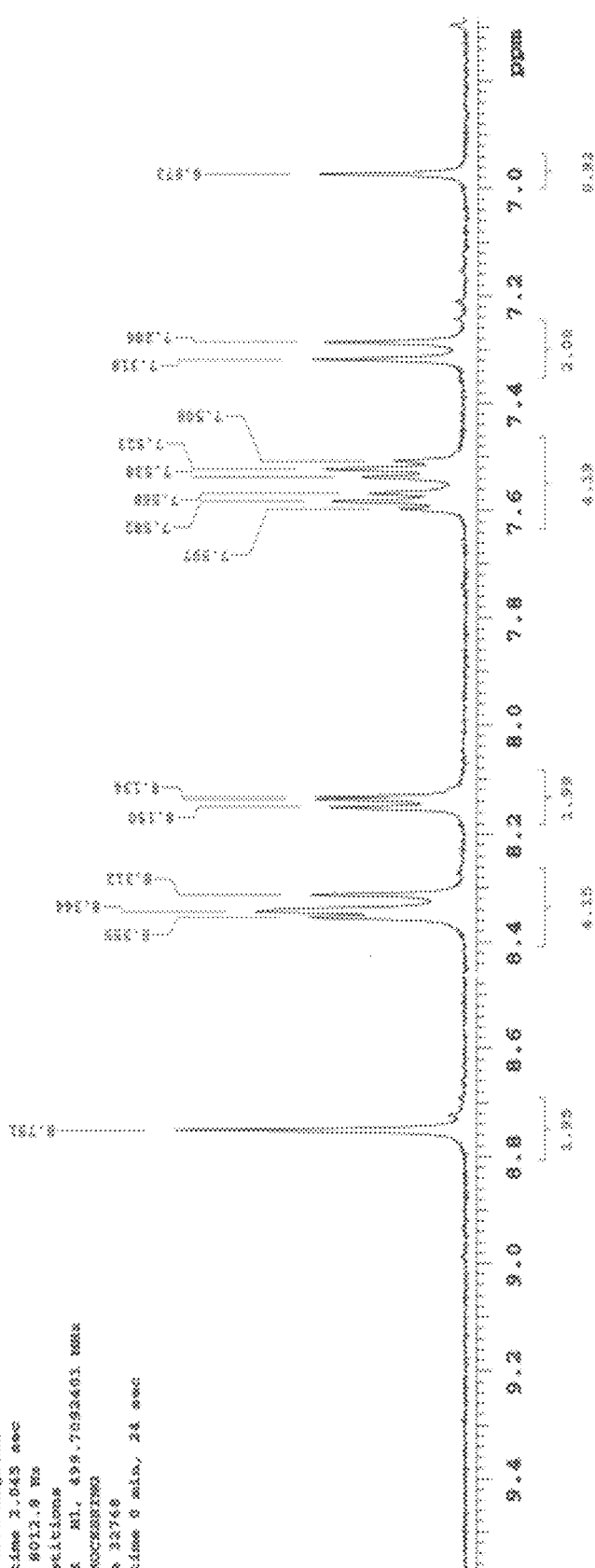
FIG. 75E

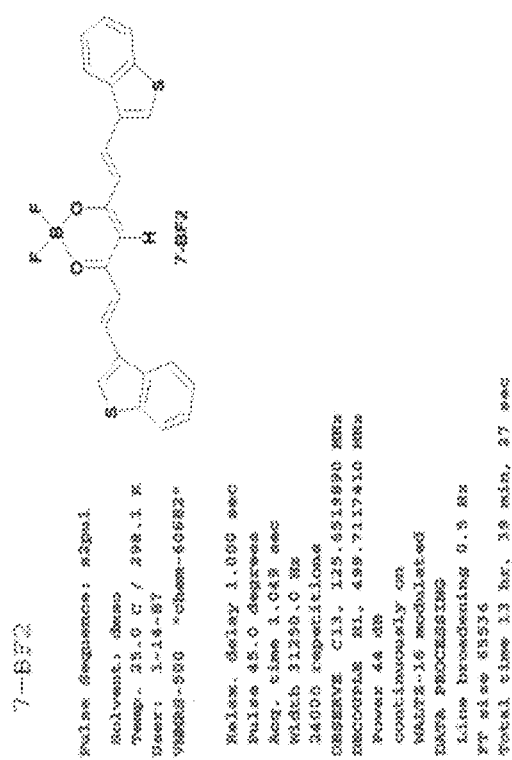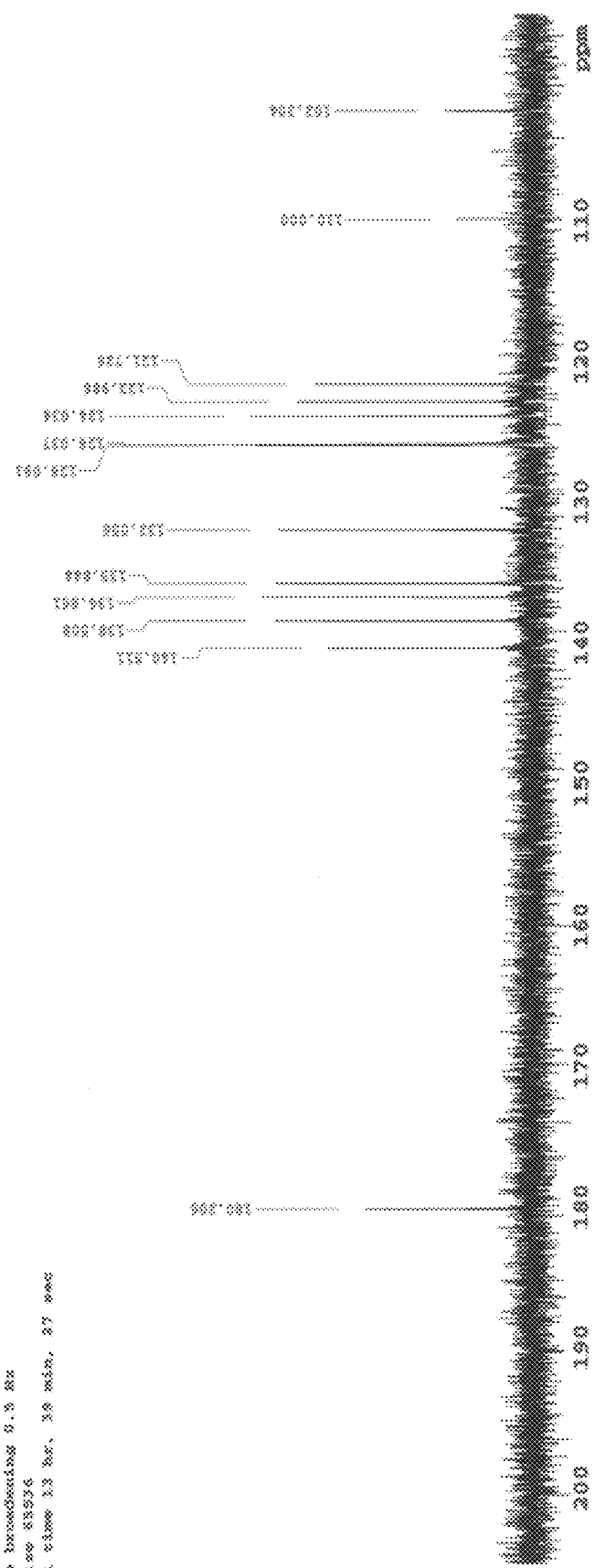
FIG. 75F

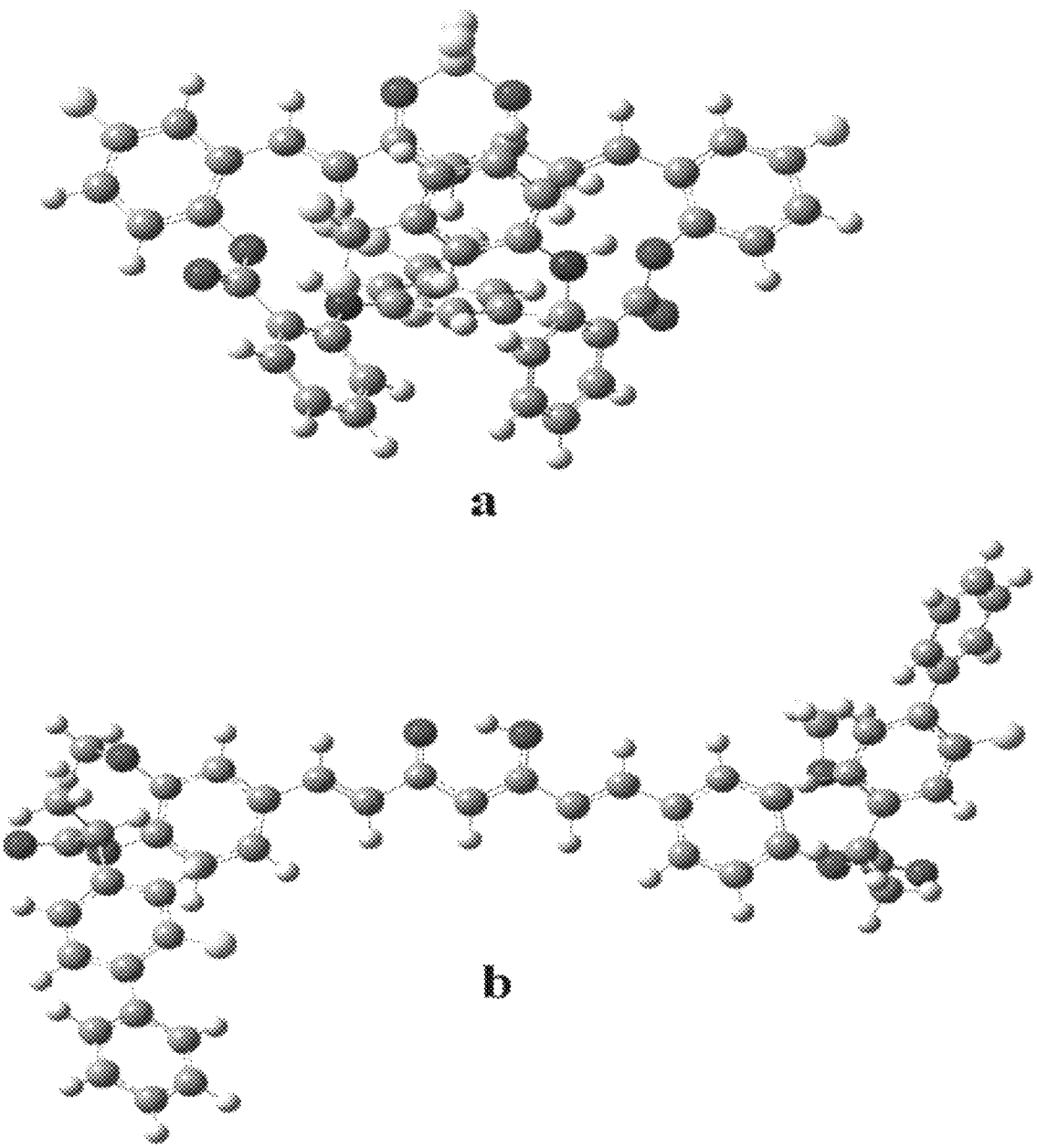
FIG. 84A-B

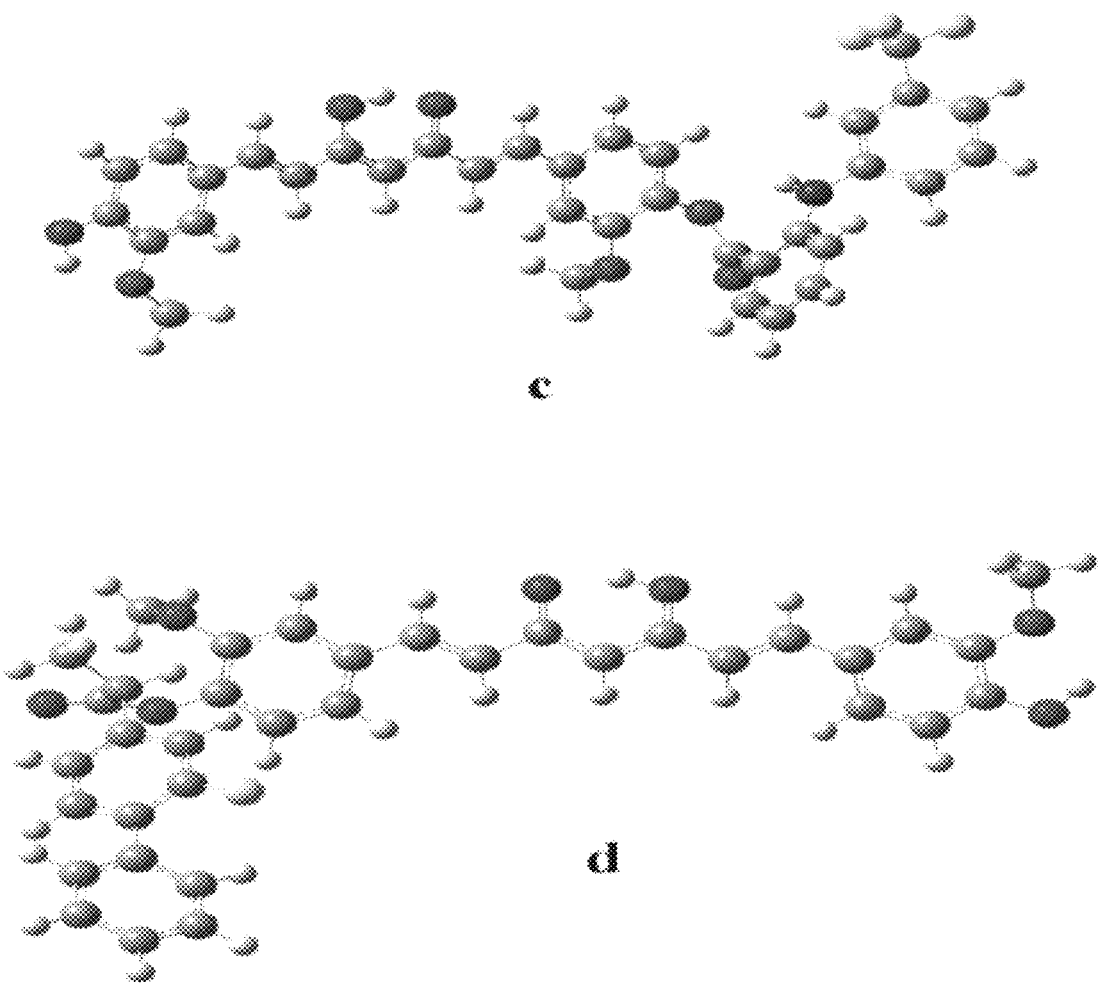
FIG. 84C-D

A HT29
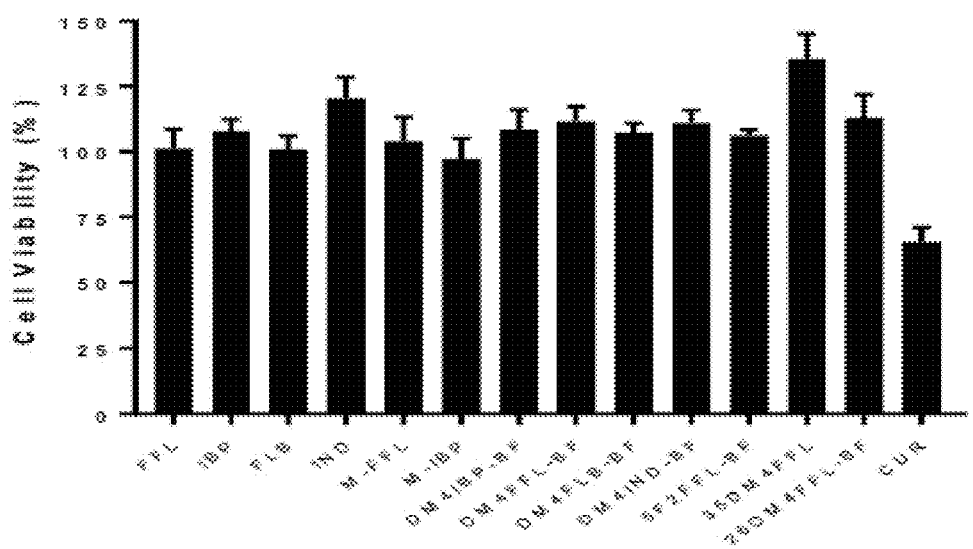
B DLD-1
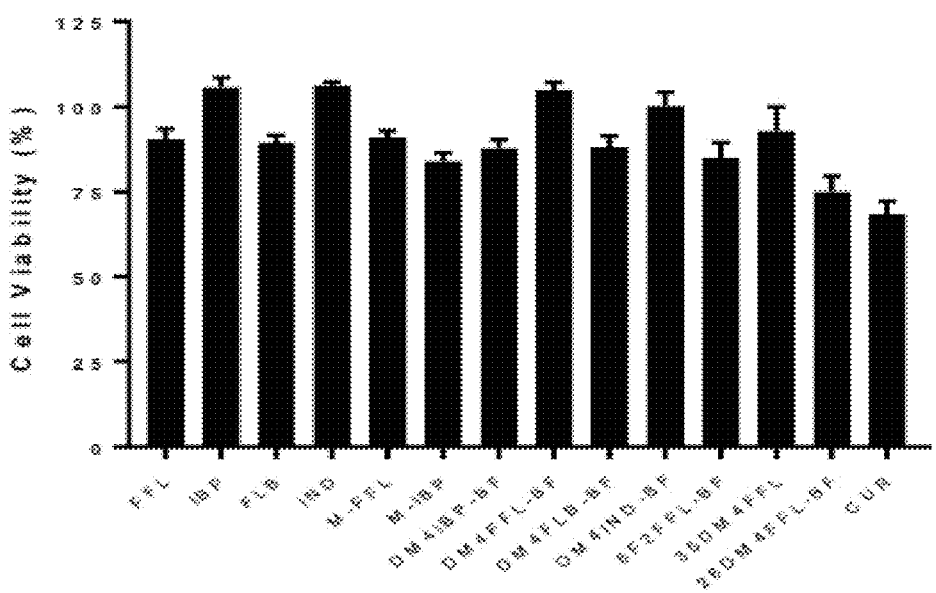
FIG. 85A-B

C  RKO
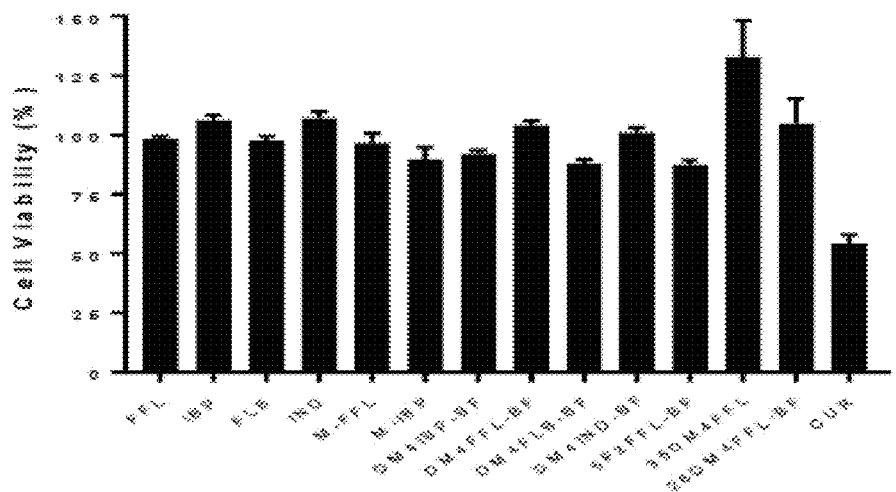
D  SW837
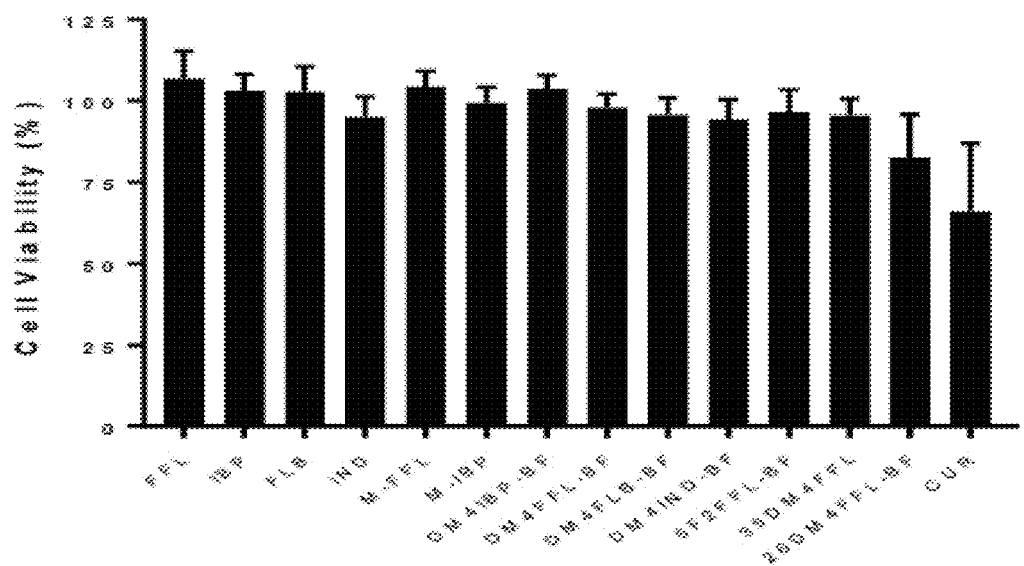
FIG. 85C-D

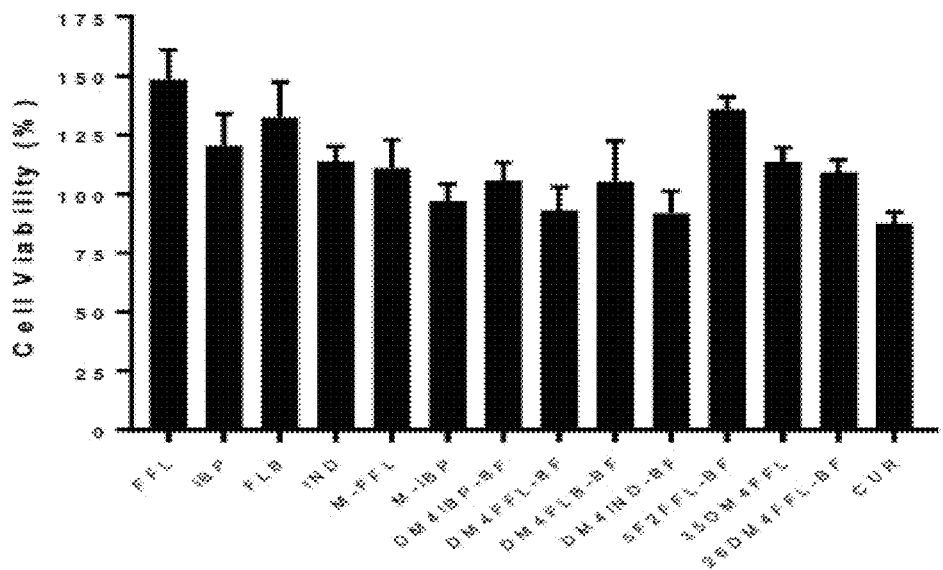
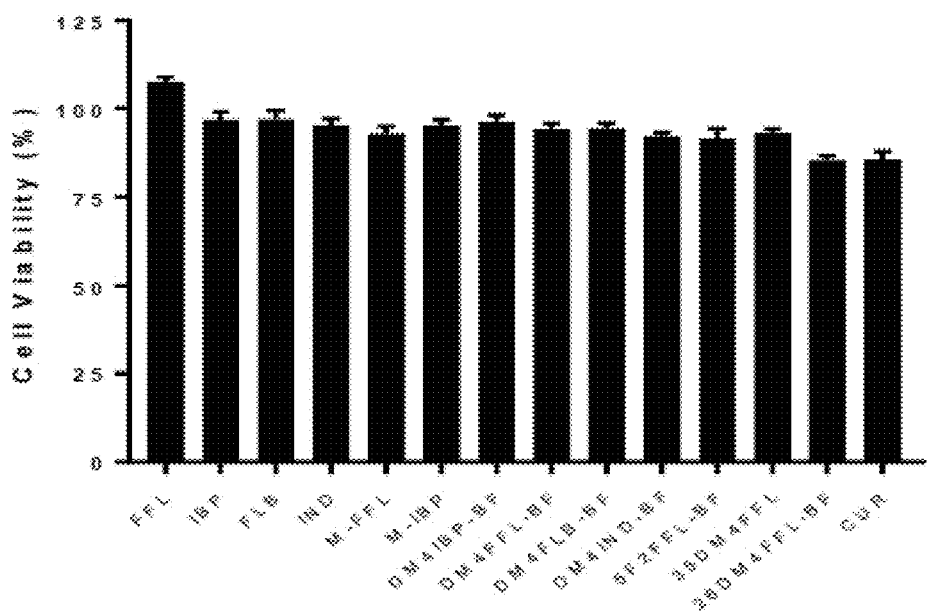
FIG. 85E-F

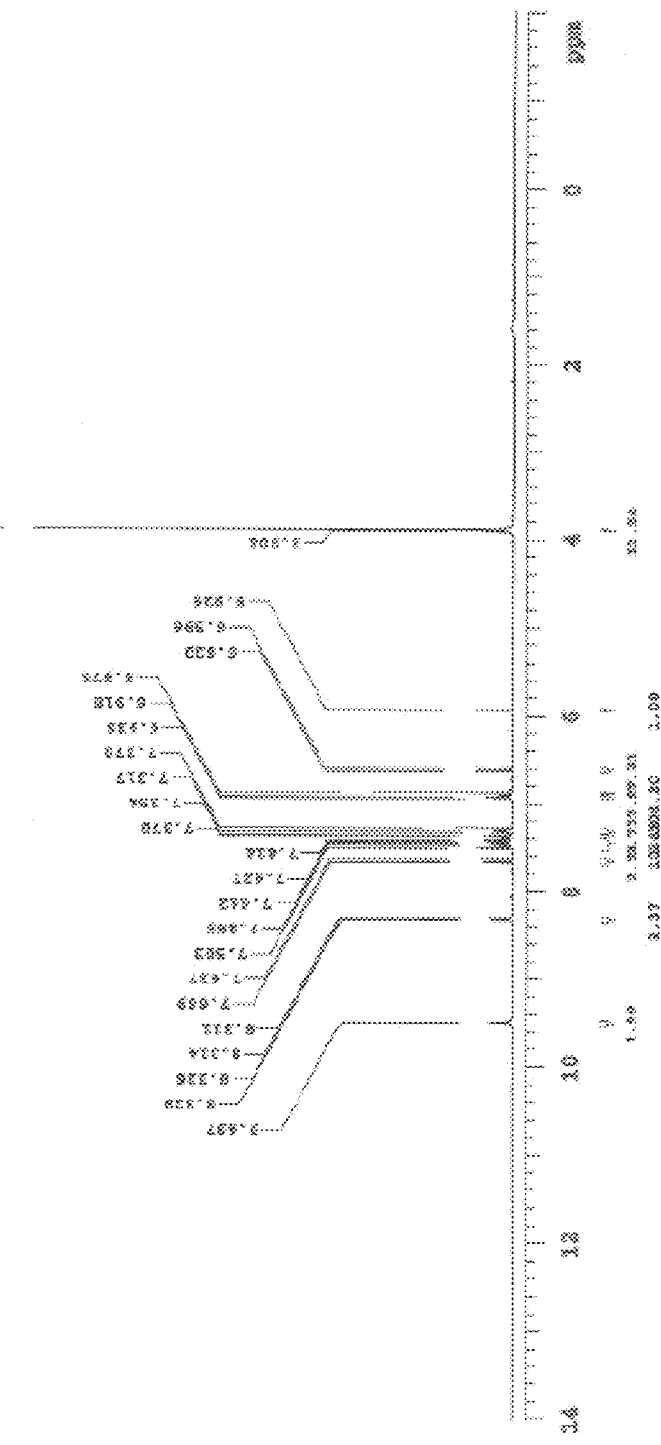
FIG. 111

FIG. 113

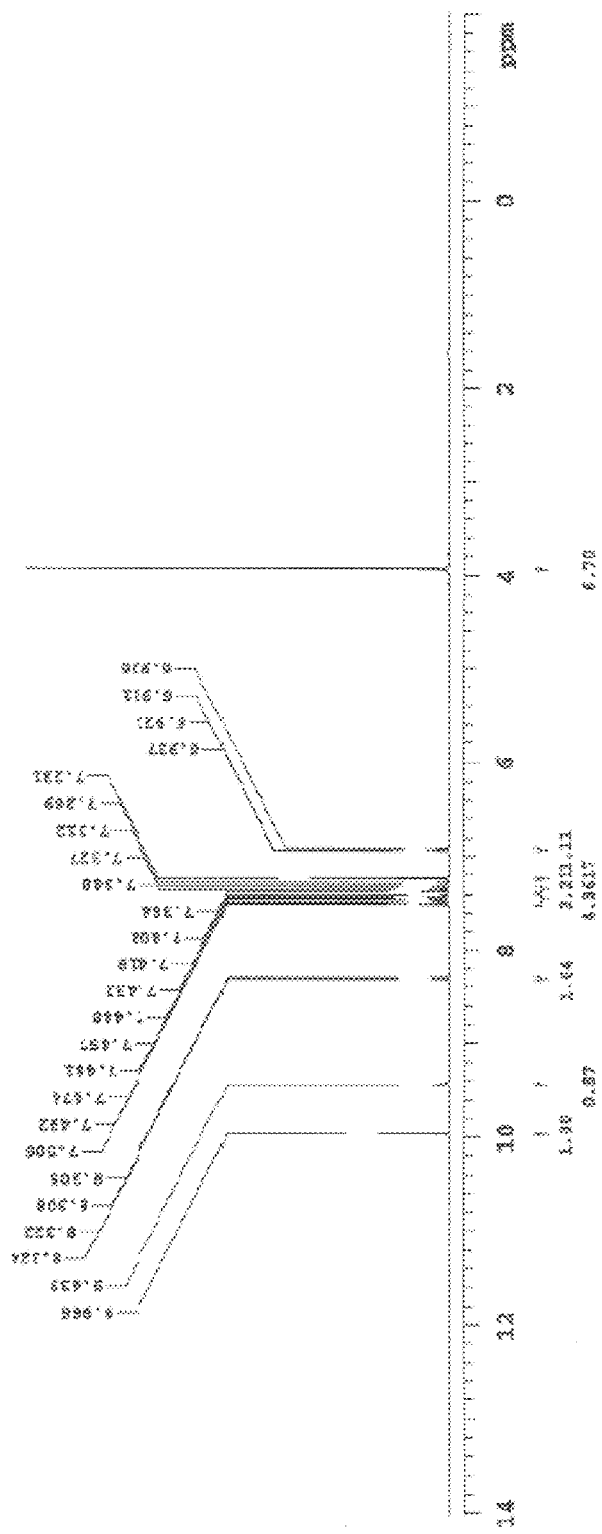
FIG. 207

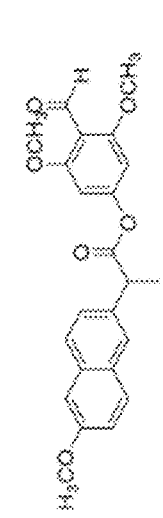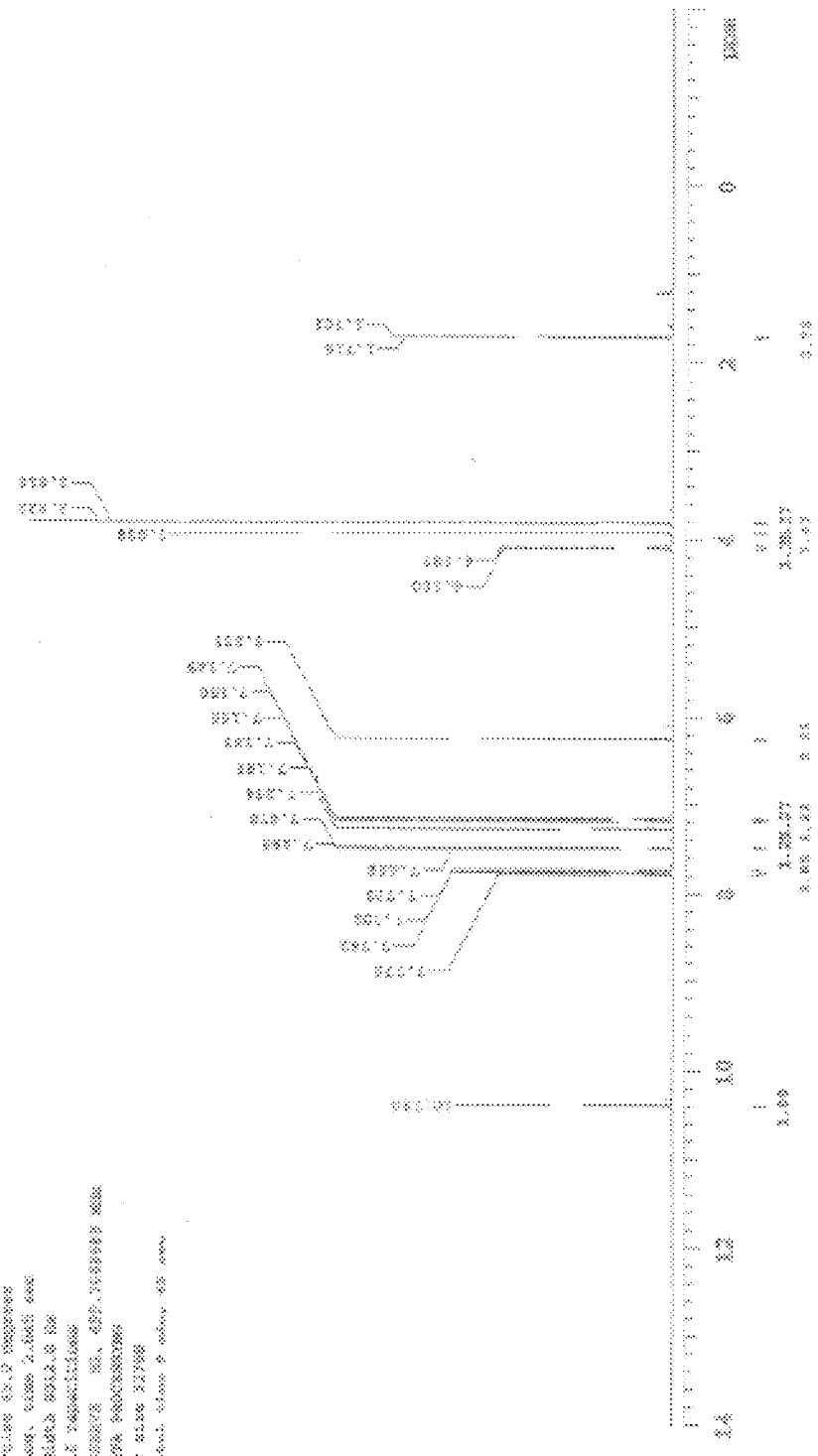
FIG. 228

CURCUMINOID-INSPIRED SYNTHETIC COMPOUNDS AS ANTI-TUMOR AGENTS

CROSS REFERENCE TO RELATED APPLICATIONS

This application is a continuation in part of and claims priority to currently pending U.S. application Ser. No. 16/010,822, entitled "Novel Curcuminoid-Inspired Synthetic Compounds as Anti-Tumor Agents", filed Jun. 18, 2018, which is a nonprovisional of and claims priority to U.S. Provisional Application No. 62/520,788 entitled "Novel Curcuminoid-Inspired Synthetic Compounds (with Potent Cytotoxicity and Anti-Proliferative Properties) as Anti-Tumor Agents", filed Jun. 16, 2017, the contents of each of which are hereby incorporated by reference into this disclosure.

FIELD OF THE INVENTION

The invention relates to antitumor agents. More specifically, the invention relates to a series of new CUR— and CUR—BF2 compounds with monocyclic aromatic and bicyclic-heteroaromatic lateral rings, bearing diverse substituents including fluorine(s), OCF3, CF3, and SCF3 groups (to increase polarity and lipophilicity), and their alpha-carbonyl-fluorinated analogs, as well as their pyrazole and isoxazole derivatives. The invention also relates to heterocyclic CUR—$BF_2$ adducts and CUR compounds based on indole, benzothiophene, and benzofuran along with their aryl-pyrazoles.

BACKGROUND OF THE INVENTION

Parent compound curcumin 1 (FIG. 1) is a non-toxic phenolic natural product. The central core of 1 is a conjugated β-keto-enolic moiety that can participate in hydrogen bonding, act as Michael acceptor, and coordinate to metal ions, while its hydrophobic phenyl domains are potential sites for π-π interactions with the aromatic side chains in amino acids, and the phenolic OH groups are capable of H-bonding interactions. (S. C. Gupta, et al., *Nat. Prod. Rep.* 2011, 28, 1937-1955).

Combination of these structural features, and its ability to influence multiple signaling molecules made it very challenging to unravel the biological profile of CUR and to identify its pharmacophore, despite extensive studies aimed at improving its pharmacokinetic profile and potency. (A. Minassi, et al., *J. Nat. Prod.* 2013, 76, 1105-1112; K. Bairwa, et al., *RSC. Adv.* 2014, 4, 13946-13978; A. Vyas, et al., *Curr. Pharm. Des.* 2013, 19, 2047-2069).

Whereas potential health benefits of 1 and its anti-cancer, anti-inflammatory, antioxidant and anti-mutagenic effects are extensively studied and documented, unfavorable biophysicochemical features namely poor solubility, low absorption, low bioavailability, and rapid metabolism have so far prevented the development of a CUR-based anticancer drug. (G. R. Pillail, et al., *Cancer Letters* 2004, 208, 163-170; A. L. Loprestil, et al., *J. Psychopharmacology* 2012, 26, 1512-1524; D. Perrone, et al., *Experimental and Therapeutic Medicine* 2015, 10, 1615-1623; K.-L. Tan, et al., *ChemMedChem* 2012 7, 1567-1579).

To address these shortcomings, extensive research has focused on synthesis of structurally modified CURs. These included changes in the aryl substitution patterns, synthesis of unsymmetrical CUR compounds by introducing two different aryl groups, introduction of diverse substituents at the central methylene carbon, as well as more drastic structural modifications such as converting the 1,3-diketone moiety to prazoles and isoxazoles, or complete deconstruction to monocarbonyl derivatives in order to prepare CUR mimics. These highly diverse structural modifications and their biological activity outcomes were summarized in a 2014 review. (K. Bairwa, et al., *RSC. Adv.* 2014, 4, 13946-13978). Considering drug delivery aspects, encapsulation into water-soluble hosts, conjugation with nanoparticles, polymeric micelles, or liposomes have been explored as possible methods to deliver curcumin to cancer cells. (M. Mimeault, et al., *Chin. Med.* 2011, 6, 31; C. Cheng, et al., *RSC Adv.* 2017, 7, 25978-25986; L. Zhang, et al., *Environ. Tox. Pharm.* 2016, 48, 31-38; M. M. Yallapu, et al., *Colloids and Surfaces B: Biointerfaces* 2010, 79, 113-125; J. Liu, et al., *Curr. Pharm. Des.* 2013, 19, 1974-1993).

Structural modifications have included introduction of enaminone, oxime, and dienone, and replacement of the central moiety with pyrazole and isoxazole rings. (D. Simoni, et al., *Biorg. Med. Chem. Lett.*, 2008, 18, 845-849; K.-L. Tan, et al., *ChemMedChem*, 2012, 7, 1567-1579; C. L. Nieto, et al., *Molecules*, 2015, 20, 15643-15665; M. W. Amolins, et al., *Bioorg. Med. Chem.*, 2009, 17, 360-367; M. Labbozzetta, et al., *Chem. Biol. Interact.*, 2009, 181, 29-36; R. Narlawar, et al., *ChemMedChem*, 2008, 3, 165-172). It is noteworthy that many of these synthetic modifications represent significant departure from CUR's original skeleton. Other studies have reported improved bioactivity by transforming the phenolic OH in CUR to acetates and amino acid conjugates, cinnamic and succinyl esters, other types of esters, and acetamides. (S. B. Wan, et al., *Int. J. Mol. Med.*, 2010, 26, 447-455; L. Feng, et al., *Chem. Pharm. Bull.*, 2015, 63, 873-881; W. Wichitnithd, et al., *Molecules*, 2011, 16, 1888-1900; Z. Cheikh-Ali, et al., *ChemMedChem*, 2015, 10, 411-418; R. Sribalan, et al., *Bioorg. Med. Chem. Lett.*, 2015, 25, 4282-4286). Introduction of ester or α,β-unsaturated ester linkers into the active methylene region has been used to prepare curcuminoid libraries as potential antitumor agents for lung and prostate cancer. (K. Wada, et al., *Bioorg. Med. Chem.*, 2015, 23, 1507-1514; L. Lin, et al., *Bioorg. Med. Chem.*, 2006, 14, 2527-2534; L. Lin, et al., *J. Med. Chem.*, 2006, 49, 3964-3972).

Studies of heterocyclic curcuminoids have so far mainly focused on systems in which the diketo-linker was replaced with piperid-4-one, tetrahydrothiopyran-4-one, or terahydropyran-4-one moieties. There are also limited examples in which phenyl rings were replaced with thiophene, pyrrole, or pyridine, while maintaining the 1,3-keto-enolic structural motif. Synthetic progress along with the pharmacological properties of these compounds have been reviewed. (M. Martinez-Cifuentes, et al., *Curr. Topic. Med. Chem.* 2015, 15, 1663-1672).

Selective fluorine introduction into pharmaceuticals is a powerful strategy for improving metabolic stability and physiochemical properties, but this approach has remained greatly under-utilized with respect to curcuminoids. (J. Wang, et al., *Chem. Rev.,* 2014, 114, 2432-2506; H.-J. Bohm, et al., *ChemBioChem,* 2004, 5, 637-643).

Since the standard approach for the assembly of symmetrical CUR analogs is via a "double aldol" condensation of aldehydes with acetylacetone, ring fluorinated derivatives can be synthesized via this route, however very few examples have been reported, and with limited NMR data. (E. V. Rao, et al., *Indian. J. Pharm. Sci.,* 2011, 73, 262-270; B. W. Megna, et al., *J. Surg. Res.,* 2017, 213, 16-24; S. Elavarasan, et al., *Journal of Chemistry,* 2013, 1-8; (a) S.

Padhye, et al., *Pharm. Res.,* 2009, 26, 1874-1880; (b) S. Padhye, et al., *Pharm. Res.,* 2009, 26, 2438-2445).

Examples of curcuminoids bearing a single fluorine at the active methylene position (along with an ester linker or a methyl group) have been very rare. (L. Lin, et al., *Bioorg. Med. Chem.,* 2006, 14, 2527-2534; L. Lin, et al., *J. Med. Chem.,* 2006, 49, 3964-3972). The reported methods required additional steps, namely deprotonation (NaH/DMF) followed by fluorination, as well as additional steps for protection and deprotection of the phenolic OH in the case of parent CUR.

Considering the importance of the 1,3-diketo moiety in the CUR skeleton for interaction with target proteins, development of methods for direct fluorine introduction into the active methylene position is highly desirable, but no such methods have been reported.

It is also noteworthy that despite extensive bioassay studies on curcuminoids, the potential of CUR—$BF_2$ complexes as anti-proliferation agents has remained largely unexplored. (S. C. Gupta, et al., *Nat. Prod. Rep.* 2011, 28, 1937-1955; A. Vyas, et al., *Curr. Pharm. Des.* 2013, 19, 2047-2069; M. Mimeault, et al., *Chin. Med.* 2011, 6, 1-19). Review of the published literature shows that these compounds are usually treated as "intermediates" en-route to curcuminoids, and only few examples exist in which they have been characterized, albeit with limited NMR data, except in two independent recent studies, where a series of CUR—$BF_2$ complexes bearing various donor end-groups were synthesized and their photophysical properties were explored. ((E. V. Rao, et al., *Indian. J. Pharm. Sci.,* 2011, 73, 262-270; K. Kamada, K., et al., *Chem. Eur. J.,* 2016, 22, 5219-5232; G. Bai, et al., *Org. Biomol. Chem.,* 2014, 12, 1618-1626; K. Aertgeerts, et al., *J. Biol. Chem.,* 2011, 286, 18756-18765).

In order to address the shortcomings of the previous work, the inventors have used selective fluorine introduction as a strategy to increase metabolic stability and polarity, producing a library of "CUR-inspired" compounds bearing fluorinated moieties which employ practical methods for selective fluorine introduction into the α-carbonyl moiety, as described in Laali 2016, herein incorporated in its entirety into this application. (K. K. Laali, et al., *J. Fluorine. Chem.,* 2016, 191, 29-41).

The inventors have also synthesized a library of CUR—$BF_2$ adducts and CURs with diverse substitution patterns in the phenyl rings. To that end, fluorinated substituents ($SCF_3$, $OCF_3$, and F) were introduced in an effort to improve lipophilicity and metabolic stability, whereas bulky activating groups (OMe, OAc, and OBz) were introduced as a way to tune steric/electronic effects. To gauge the potential role of the enolic moiety in interaction with proteins, a library of fluorinated aryl-pyrazoles and isoxazoles were also synthesized and characterized, as described in Laali, 2018, herein incorporated in its entirety into this application. (K. K. Laali, et al., *J. Fluorine. Chem.* 2018, 206, 82-98).

The inventors have also synthesized novel heterocyclic CURs and CUR—$BF_2$ adducts based on indole, benzothiophene and benzofuran as well as their aryl-pyrazoles. The inventors have shown that the novel compounds presented favorable binding affinities, in some cases more favorable than currently known inhibitors, for various cancers including multiple myeloma and colorectal cancer. The novel compounds exhibited high anti-proliferative and apoptotic activity against cancer cells while exhibiting significantly lower cytotoxicity in normal cells.

SUMMARY OF INVENTION

In an embodiment, the invention discloses the synthesis, isolation, and characterization (including by X-ray analysis) of a series of new CUR— and CUR—$BF_2$ compounds with monocyclic aromatic and bicyclic-heteroaromatic lateral rings, bearing diverse substituents including fluorine(s), $OCF_3$, $CF_3$, and $SCF_3$ groups (to increase polarity and lipophilicity), and their alpha-carbonyl-fluorinated analogs, as well as their pyrazole and isoxazole derivatives. The CUR-pyrazoles synthesized embody analogs that are fluorinated at the phenyl-pyrazole moiety.

Inspired by the earlier fluorination study of carbonyl compound, the inventors report here the synthesis of novel curcuminoids that are mono- and difluorinated at the methylene position by direct one-pot fluorination with Selectfluor (F-TEDA-$BF_4$) without using a base or additive (see FIG. 2). In addition to parent CUR (1) and its symmetrical O-dimethylated analog (DMC; 6), symmetrical curcuminoids bearing fluorines (11 and 14) and trifluoromethyl groups (20) in the phenyl rings were also synthesized, and subsequently mono- and difluorinated at the active methylene position, seen in FIG. 2. The corresponding curcuminoid-$BF_2$ adducts which serve as synthetic intermediates en-route to these curcuminoids were isolated and characterized. The X-ray crystal structures were obtained for CUR—$BF_2$ adducts 5, 10, and 14, and for the F—CUR 8. The cell growth inhibitory and apoptosis inducing effects of these compounds were examined by in-vitro assays against leukemia (MOLT-4), prostate cancer (PC3 and LNCap), as well as lung (A549) and breast cancer (MDA231) cell lines. A selected group of compounds were screened by the NCI 60 cell panel. Computational docking studies were also performed on CUR—$BF_2$ adducts and fluorinated curcuminoids to compare their binding energies in HER2 protein relative to a well-known ligand (SYR), versus trends from bioactivity data for breast cancer ($IC_{50}$ MDA231), and in proteasome in comparison with bioassay data in leukemia ($IC_{50}$ MOLT-4).

Further, the inventors have synthesized a library of heterocyclic CUR—$BF_2$ and CUR compounds based on indole, benzothiophene, and benzofuran, including several examples of their aryl-pyrazole derivatives. Computational/docking studies were performed on 20 heterocyclic CUR—$BF_2$ and CUR compounds to compare binding efficiency to target proteins involved in specific cancers, namely HER2, proteasome, VEGFR, BRAF, and BCL-2 versus known inhibitor drugs. The majority presented very favorable binding affinities that were comparable and, in some cases, more favorable than the known-inhibitors. The indole-based CUR—$BF_2$ and CUR compounds and their bis-thiocyanato derivatives exhibited high anti-proliferative and apoptotic activity by in-vitro bioassay against a panel of 60 cancer cell lines, and more specifically against multiple myeloma (MM) cell lines (KMS11, MM1.S, and RPMI-8226) with significantly lower IC50s versus healthy PBMC cells. The indole-based CUR—$BF_2$ adducts and their bis-thiocyanato derivatives exhibited significantly higher anti-proliferative activity in human colorectal cancer cells (HCT116, HT29, DLD-1, RKO, SW837, and Caco2) compared to parent curcumin, while showing significantly lower cytotoxicity in normal cells (CCD112CoN and CCD841CoN).

In one aspect of the invention, a composition is presented which may be used in the treatment or prophylaxis of cancer which included identifying a cancerous tumor or growth in the patient and administering a therapeutically effective amount of a composition comprising formula (I) or (II):

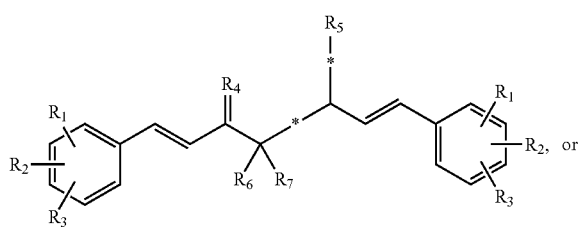
(I)

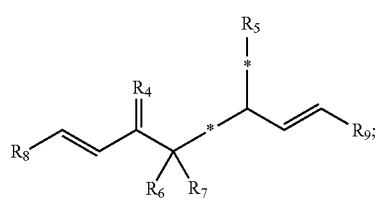
(II)

where * is a double bond or a single bond;
wherein * is a double bond when at least one of $R_6$ and $R_7$ is unsubstituted or a single bond when $R_6$ is fluorine or hydrogen and $R_7$ is fluorine;
where * is a double bond or a single bond;
wherein * is a double bond when * is a single bond;
where $R_1$ is o-OCH$_3$, m-OCH$_3$, o-F, H;
where $R_2$ is o-OCH$_3$, m-OCH$_3$, H, m-OCF$_3$,

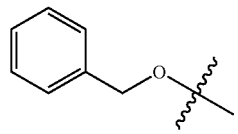 [SMILES: *OCc1ccccc1]

at a meta position,

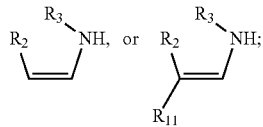

where $R_3$ is p-F, p-OCH$_3$, m-CF$_3$, p-CF$_3$, p-SCF$_3$, p-OH,

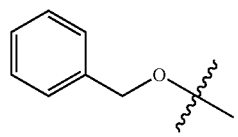

at a para position,

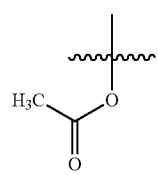

at a para position,
where $R_4$ is O, a pyrazole formed with $R_5$, O associated with a difluoroboron adduct,

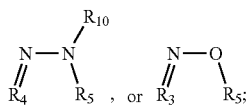

where $R_5$ is OH, O associated with a difluoroboron adduct,

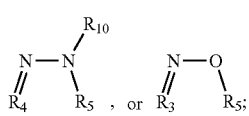

where $R_6$ is H, F, or unsubstituted forming a double bond at *;
where $R_7$ is H, or F;
where $R_8$ is

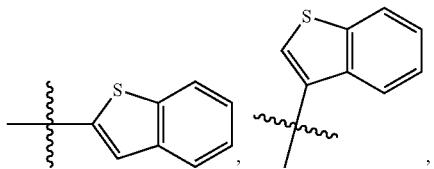

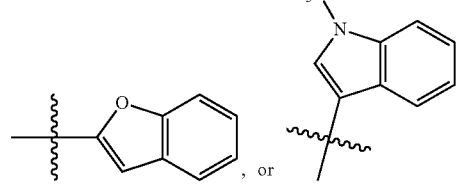

where $R_9$ is

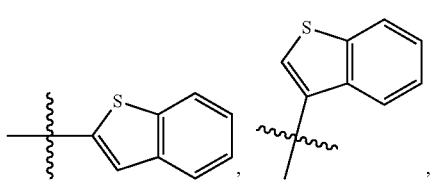

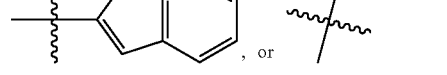

where $R_{10}$ is H, phenyl, 4-benzonitrile,

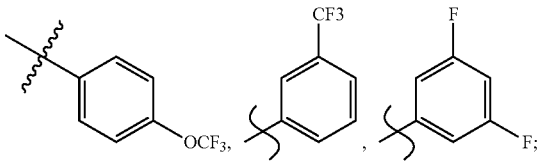

and where $R_{11}$ is SCN.

In some embodiments, there may be at least one deuterated substituent on the aryl which may be a deuterated methoxy such as R—O—CD$_3$.

In some embodiments, there may be at least one deuterated substitution on the aryl with the at least one substitution being a plurality of deuterated substitutions which may be at the meta positions.

In another aspect of the invention, a composition is presented which may be used in the treatment or prophylaxis of cancer which included identifying a cancerous tumor or growth in the patient and administering a therapeutically effective amount of a composition comprising formula (I):

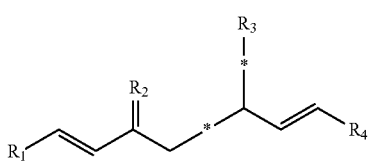

where * is a double bond or a single bond;
  wherein * is a single bond when * is a double bond;
where * is a double bond or a single bond;
  wherein * is a double bond when * is a single bond;
where $R_1$ is

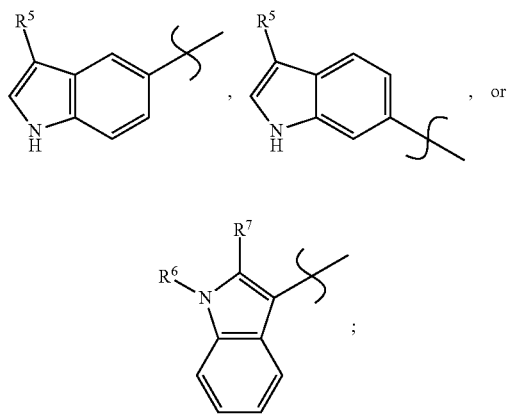

where $R_2$ is O, a pyrazole formed with $R_3$, or O associated with a difluoroboron adduct;
where $R_3$ is OH or O associated with a difluoroboron adduct;

where $R_4$ is

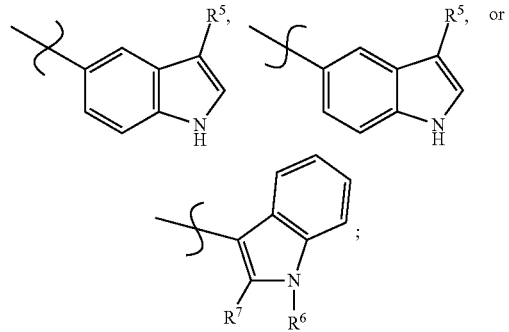

where $R_5$ is H or SCN;
where $R_6$ is H or CH3; and
where $R_7$ is H or CH3

In an effort to combine the anti-proliferative effect of CUR—BF$_2$ and CUR compounds with anti-inflammatory benefits of nonsteroidal anti-inflammatory drugs (NSAIDs), a library of the bis and mono-NSAID/CUR—BF$_2$ and NSAID/CUR conjugates were synthesized by coupling flufenamic acid, flurbiprofen, naproxen, indomethacin, and ibuprofen to diversely substituted hydroxybenzaldehydes via an ester linkage, and by subsequent reaction with acetylacetone-BF$_2$ to form the bis- and the mono-NSAID/CUR—BF2 adducts. Since conversion to NSAID/CUR by the previously developed decomplexation protocol showed limited success, a set of NSAID/CUR conjugates were independently prepared by directly coupling the NSAIDs with parent curcumin.

The bis-NSAID/CUR—BF$_2$ and bis-NSAID-CUR hybrids exhibited low cytotoxicity in NCI-60 assay, and in independent cell viability assay on colorectal cancer (CRC) cells (HCT116, HT29, DLD-1, RKO, SW837, CaCo2) and in normal CR cells (CCD841CoN). By contrast, the mono-naproxin and monoflurbiprofen CUR—BF2 adducts exhibited remarkable anti-proliferative and apoptotic activity in NCI-60 assay most notably against HCT-116 (colon), OVCAR-3 (ovarian), and ACHN (renal) cells. Computational molecular docking calculations showed favorable binding energies to HER2, VEGFR2, BRAF, and Bcl-2 as well as to COX-1 and COX-2, which in several cases exceeded known inhibitors. The main interactions between the ligands and the proteins were hydrophobic, although several hydrogen bonds were also observed. A sub-set of six compounds that had exhibited little or no cytotoxicity were tested for their anti-inflammatory response with THP-1 human macrophages in comparison to parent NSAIDs or parent curcumin.

In an embodiment, a composition is presented comprising Formula (I):

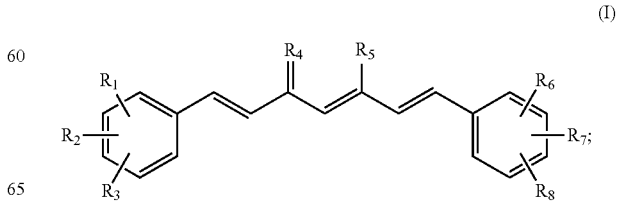

where R₁ is o-OCH₃, m-OCH₃, or H;
where R₂ is o-OCH₃, m-OCH₃, H, or m-F;
where R₃ is
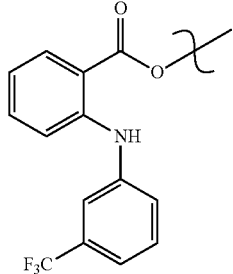 [SMILES: CCOC(=O)c1ccccc1Nc1cccc(C(F)(F)F)c1]
at a para position,
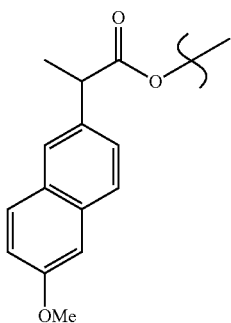
at a para position,
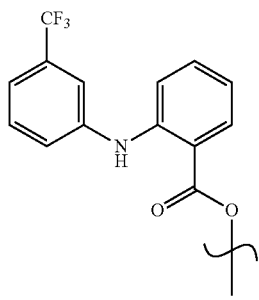 [SMILES: CCOC(=O)c1ccccc1Nc1cccc(C(F)(F)F)c1]
at an ortho position,
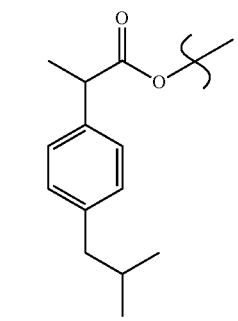
at a para position,
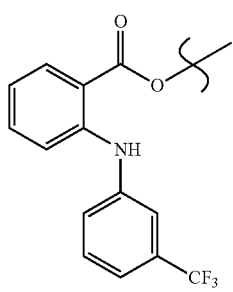 [SMILES: CCOC(=O)c1ccccc1Nc1cccc(C(F)(F)F)c1]
at a para position,
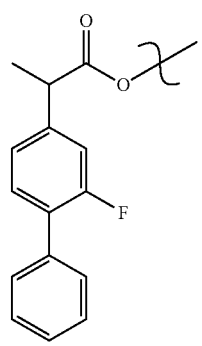 [SMILES: CCOC(=O)C(C)c1ccc(-c2ccccc2)c(F)c1]
at a para position, or
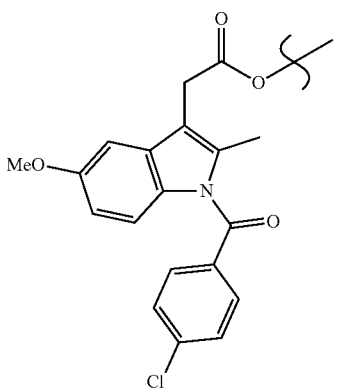 [SMILES: CCOC(=O)Cc1c(C)n(C(=O)c2ccc(Cl)cc2)c2ccc(OC)cc12]
in a para position;
where R₄ is O or O associated with a difluoroboron adduct;
where R₅ is OH or O associated with a difluoroboron adduct;

where R₆ is o-OCH₃, m-OCH₃, or H;
where R₇ is o-OCH₃, m-OCH₃, H, or m-F; and
where R₈ is p-OH,

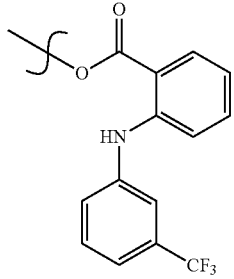 [SMILES: CCOC(=O)c1ccccc1Nc1cccc(C(F)(F)F)c1]

in a para position,

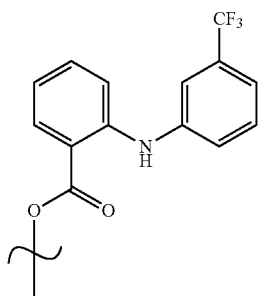 [SMILES: CCOC(=O)c1ccccc1Nc1cccc(C(F)(F)F)c1]

in an ortho position,

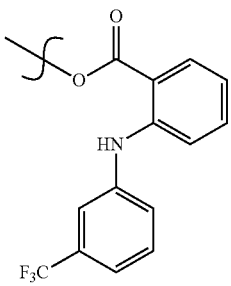 [SMILES: CCOC(=O)c1ccccc1Nc1cccc(C(F)(F)F)c1]

in a para position,

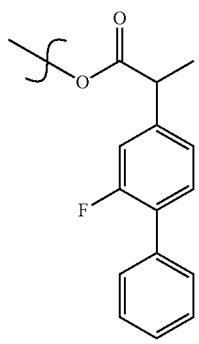 [SMILES: CCOC(=O)C(C)c1ccc(-c2ccccc2)c(F)c1]

in a para position,

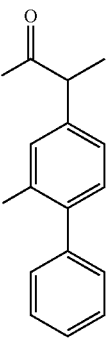

in a para position,

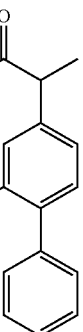

in a para position, or

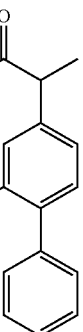

in a para position.

A therapeutically effective amount of the composition may be used in treating cancer. Specifically, the composition may be used to inhibit proliferation and/or induce apoptosis in at least one cancer cell or at least one type of cancer cell. In some embodiments, the cancer cells may be colorectal cancer cells. Other non-limiting examples of potential cancers that may be treated using the composition include leukemia, non-small cell lung cancer, CNS cancer, melanoma, ovarian cancer, renal cancer, prostate cancer and breast cancer. The composition also exhibits a synergistic anti-inflammatory effect that is greater than that shown with NSAID alone or curcumin alone.

BRIEF DESCRIPTION OF THE DRAWINGS

For a fuller understanding of the invention, reference should be made to the following detailed description, taken in connection with the accompanying drawings, in which:

FIG. 36. is a table listing binding affinities for CURs of FIG. 35.

FIG. 37 is a table of tumor-cell specific cytotoxicity by cell viability assay to determine EC50 (concentration at which 50% of the cells remain viable). These assays indicated that curcuminoids 9 and 5 of FIG. 35 were highly effective against RPMI-8226 (multiple myeloma cell line) while exhibiting significantly less cytotoxicity in peripheral blood mononuclear cells (PBMCs) from healthy donors (non-tumor control cells).

Structure of 9:

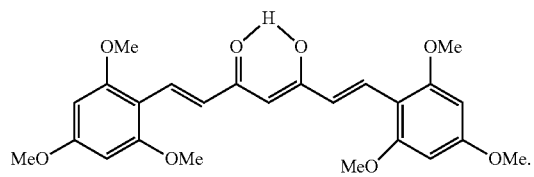

Structure of 5:

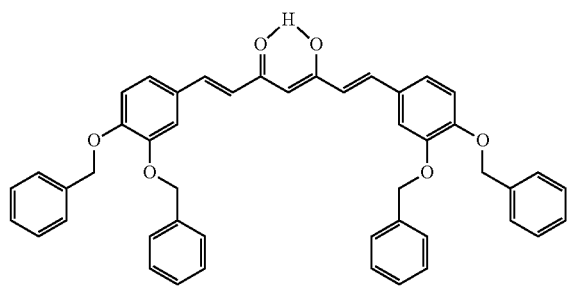

Figure 35:
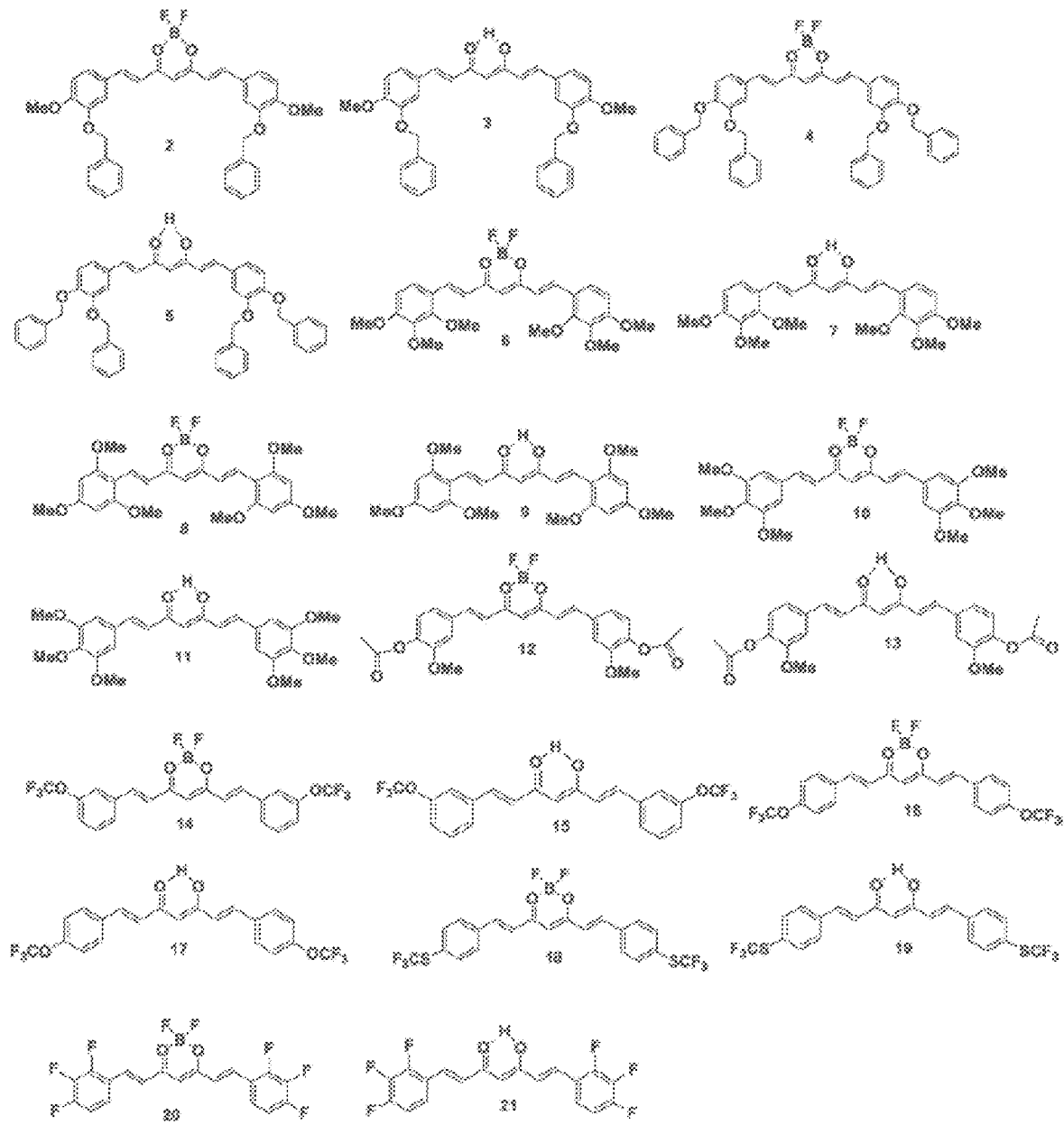
FIG. 35 is a consolidated list of CUR and CUR—$BF_2$ compounds of FIGS. 32-34.

FIG. 38A-B is a series of graphs depicting EC50 curve plots for compounds 5 (A) and 9 (B) of FIG. 35 respectively. PBMCs (non-cancer cells, controls); BCWM (BCWM.1 WM cell line); RPMI (RPMI-8266, MM cell line); RS4 (RS4; 11, ALL cell line).

Figure 39:
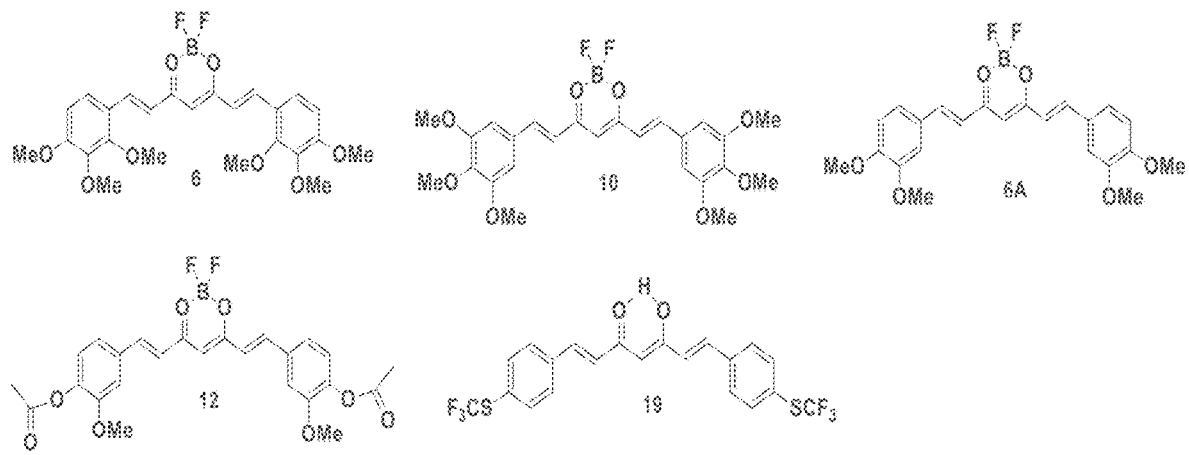

FIG. 39 is a list of CURs from FIG. 35 with anti-tumor activity based on NCI-60 immunoassay.

Figure 40:
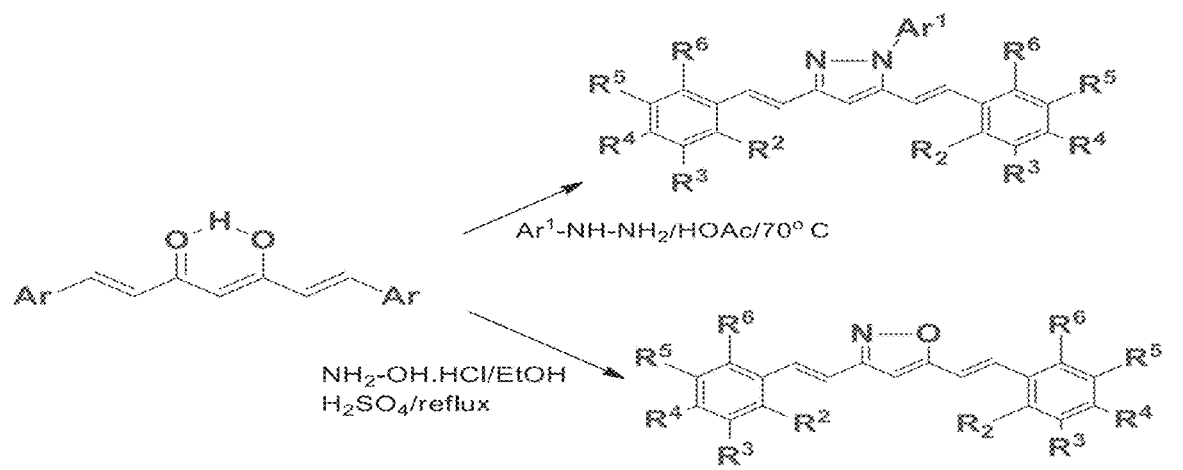

FIG. 40 is a scheme depicting the synthesis of CUR-pyrazoles and CUR-isoxazoles.

Figure 41:
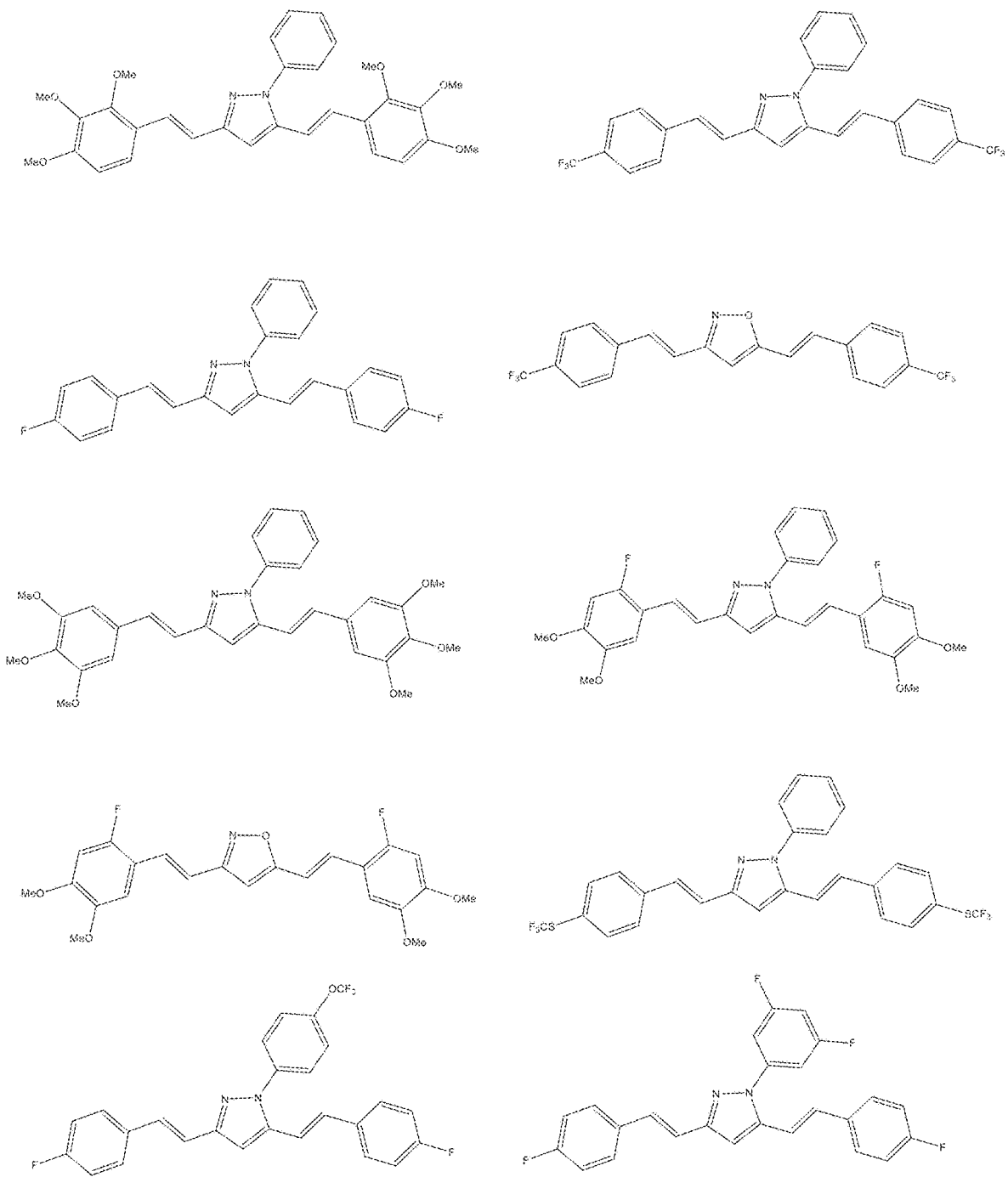

FIG. 41 is a list of pyrazole curcuminoid compounds, 1,2-oxazole curcuminoid compounds.

Figure 42:

FIG. 42. List of pyrazole curcuminoid compounds, 1,2-oxazole curcuminoid compounds, and difluoroboron-curcuminoid adducts.

Figure 43:
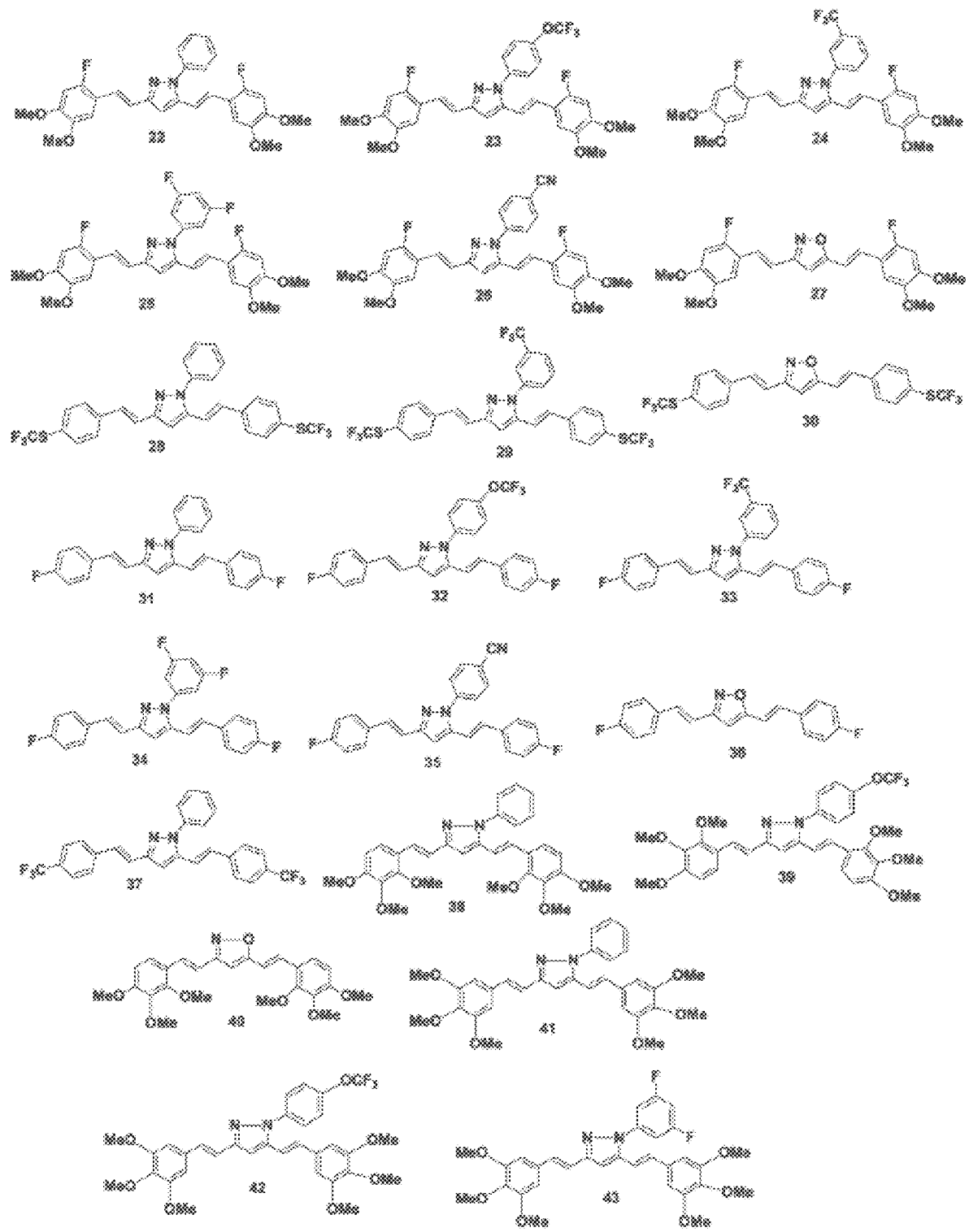

FIG. 43 is a list of CUR-pyrazoles and CUR-isoxazoles.

Figure 44:
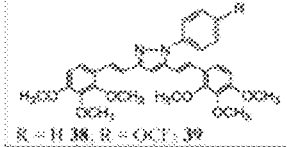

FIG. 44 is a table listing binding affinities for CUR-pyrazoles and CUR-isoxazoles of FIG. 43.

Figure 45:
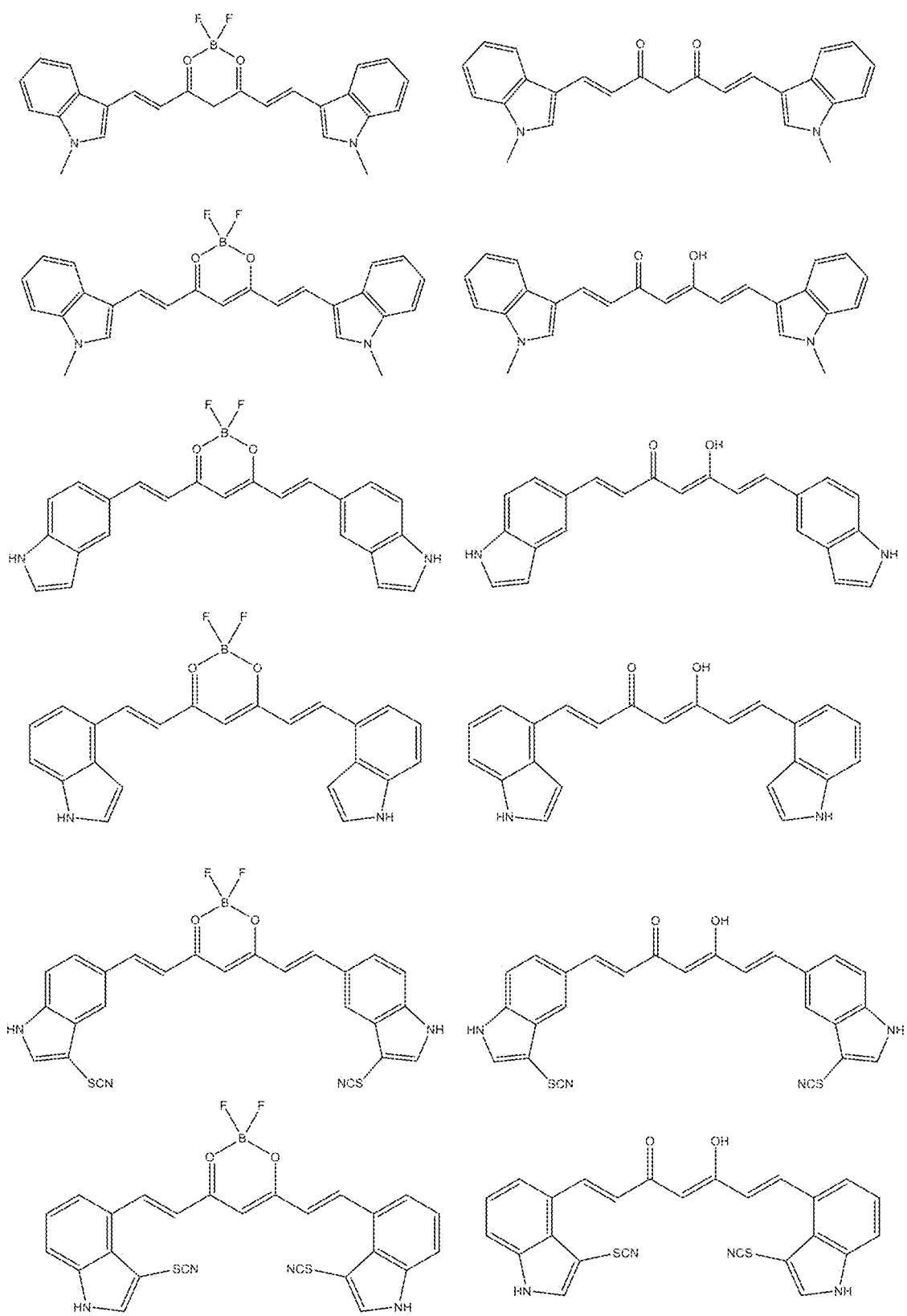

FIG. 45 is a list of indole-based curcuminoid compounds, thiocyano-curcuminoid compounds and difluoroboron-curcuminoid adducts.

Figure 46:
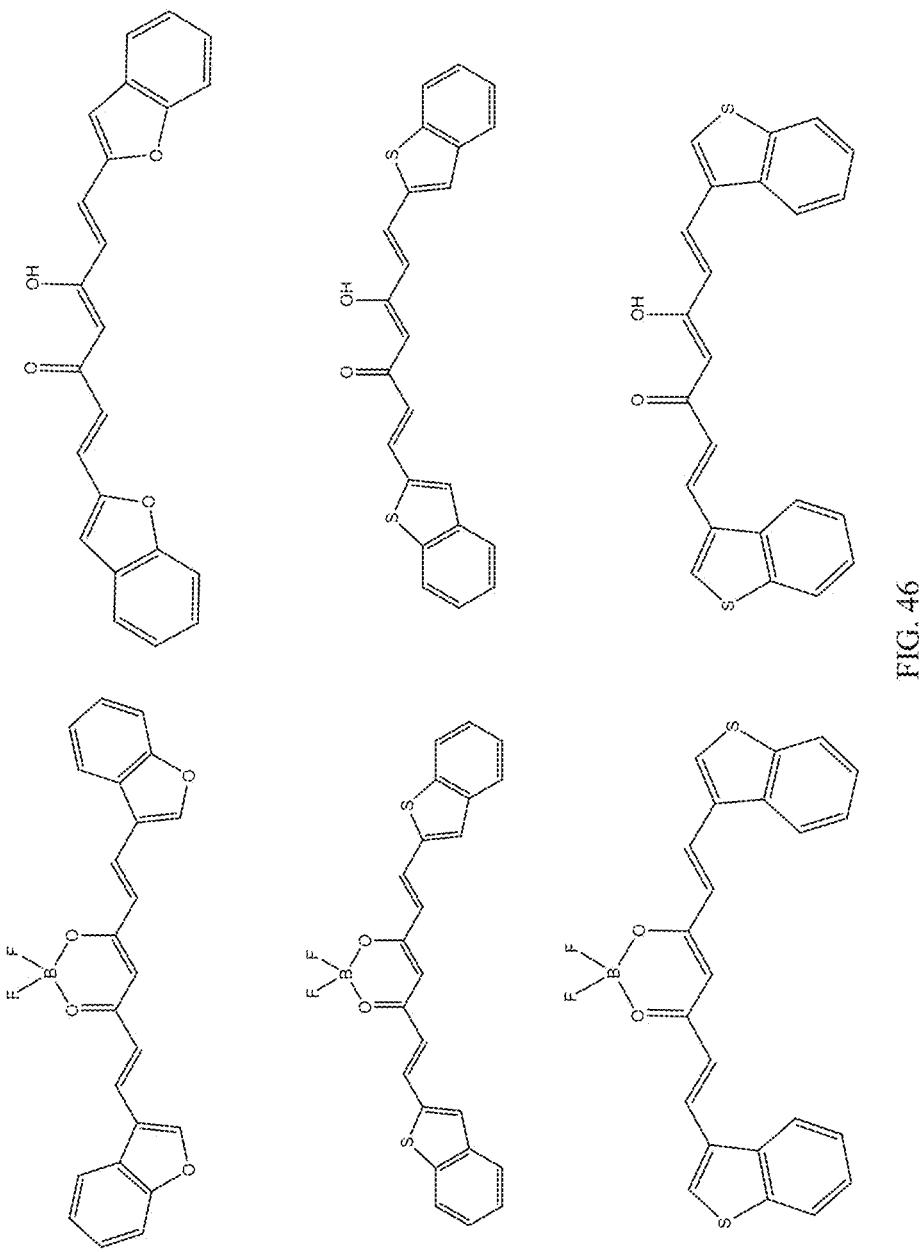

FIG. 46 is a list of benzothiophene-curcuminoid compounds, benzofuran-curcuminoid compounds, and difluoroboron-curcuminoid adducts.

FIG. 47. Reaction schemes to produce curcuminoid-based and curcuminoid-boron difluoride adduct di-cation salts.

Figure 48:
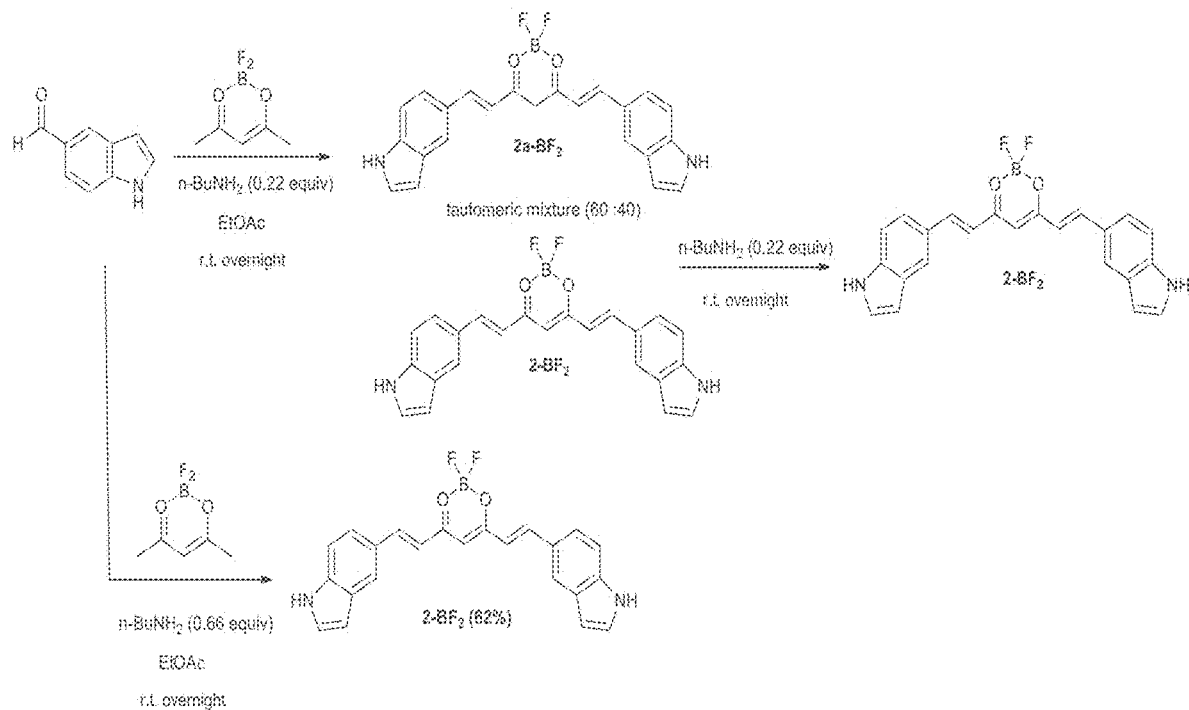

FIG. 48 is a schematic for the formation of CUR—BF$_2$ from indole-5-aldehyde.

Figure 49:
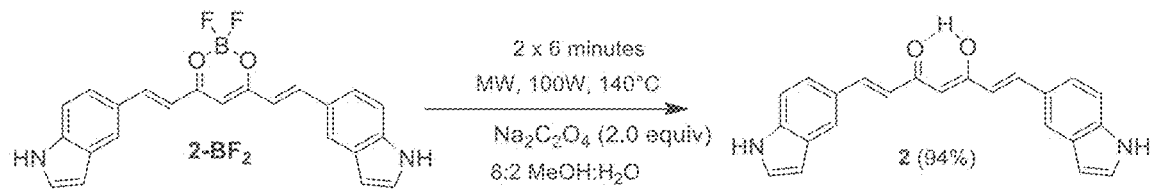

FIG. 49 is a schematic of MW-assisted synthesis of curcuminoid 2.

Figure 50:
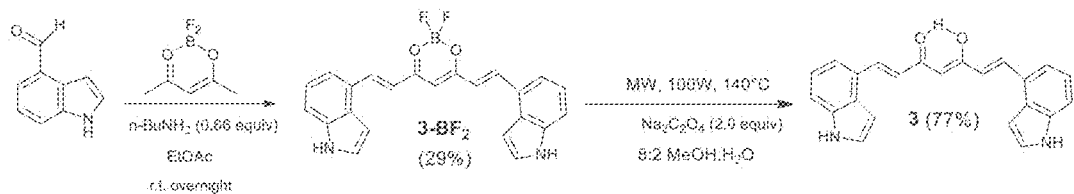

FIG. 50 is a schematic of 3-BF$_2$ and 3 from indole-4-aldehyde.

Figure 51:
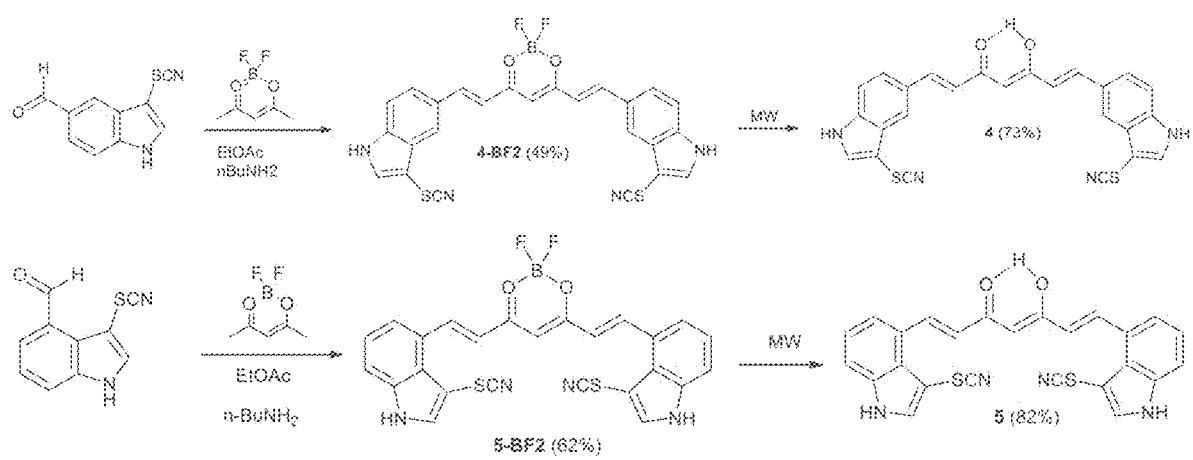

FIG. 51 is a schematic of the synthesis of bis-thiocyanato CUR—BF$_2$ and CUR compounds.

FIG. 52A-B are optimized structures of 4-BF$_2$ and 5-BF$_2$ by B3LYP/6-311+G(d,p).

FIG. 53A-B are optimized structures of compounds 4 and 5 by B3LYP/6-311+G(d,p).

Figure 54:
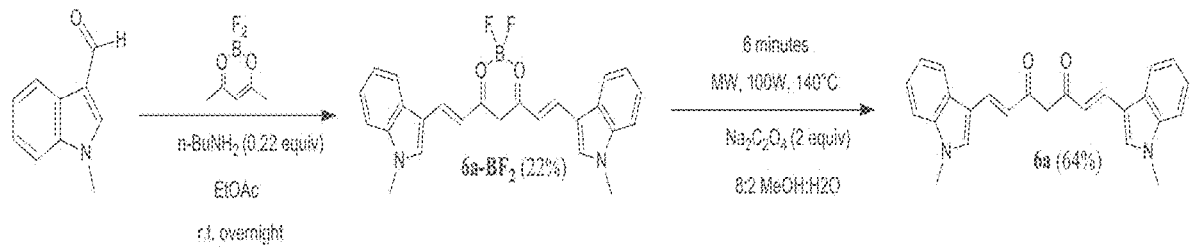

FIG. 54 is a schematic depicting isolation of 6a-BF$_2$ and its decomplexation to 6a.

Figure 55:
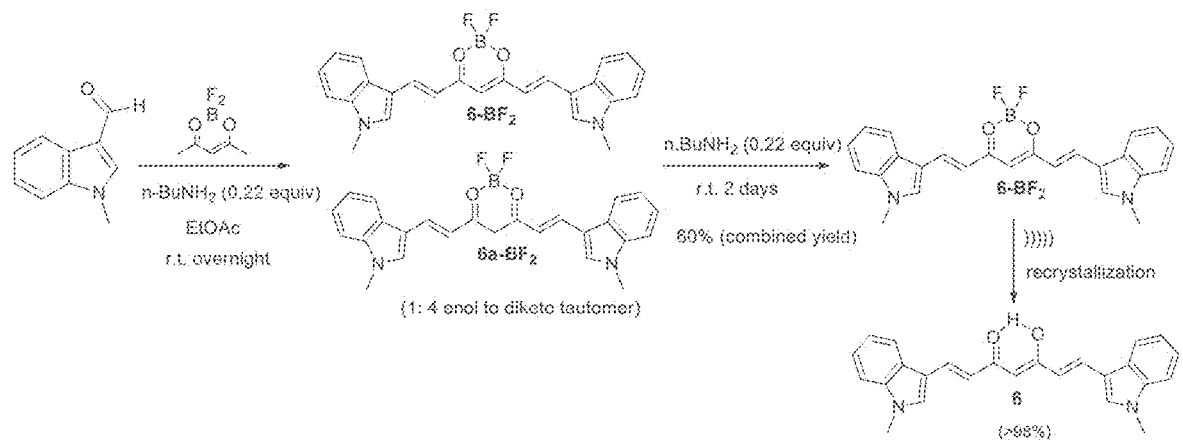

FIG. 55 is a schematic of the synthesis of 6-BF$_2$/6a-BF$_2$ and decomplexation to 6.

Figure 56:
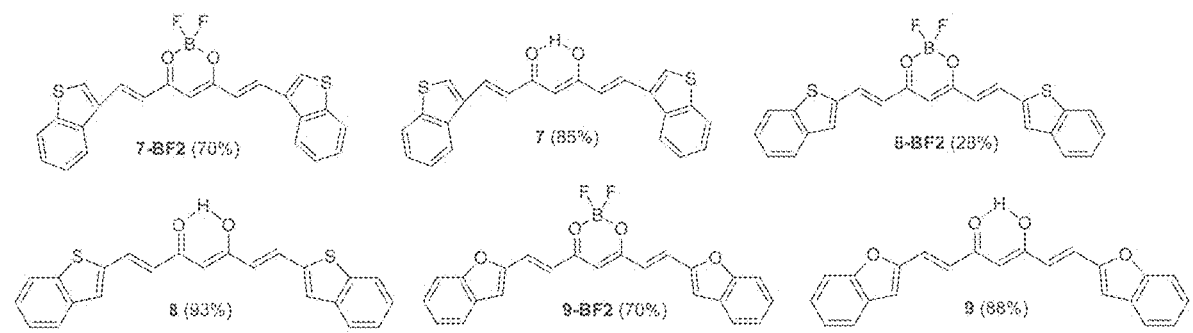

FIG. 56 is a schematic of heterocyclic CUR—BF$_2$ and CUR based on benzothiophene and benzofuran.

Figure 57:
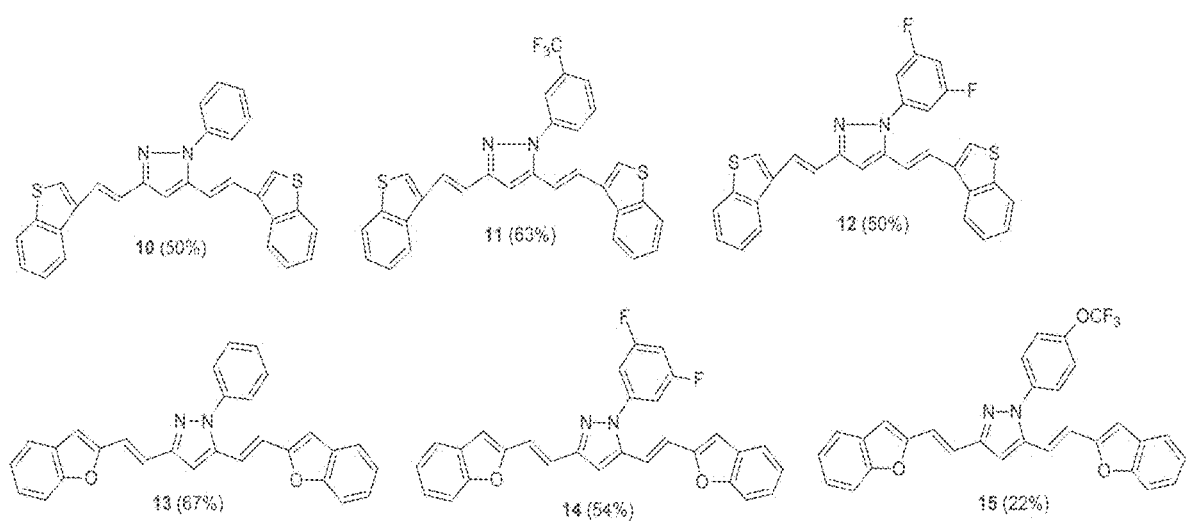

FIG. 57 is a schematic of heterocyclic CUR-acylpyrazoles based on benzothiophene and benzofuran.

FIG. 58A-D are a series of images depicting the most favorable binding interactions in the active sites of the studied enzymes. (a) 9-BF$_2$ in HER2; (b) 5-BF$_2$ in proteasome; (c) 9-BF$_2$ in VEGFR2; (d) 3-BF$_2$ in BCL-2.

Figure 59:
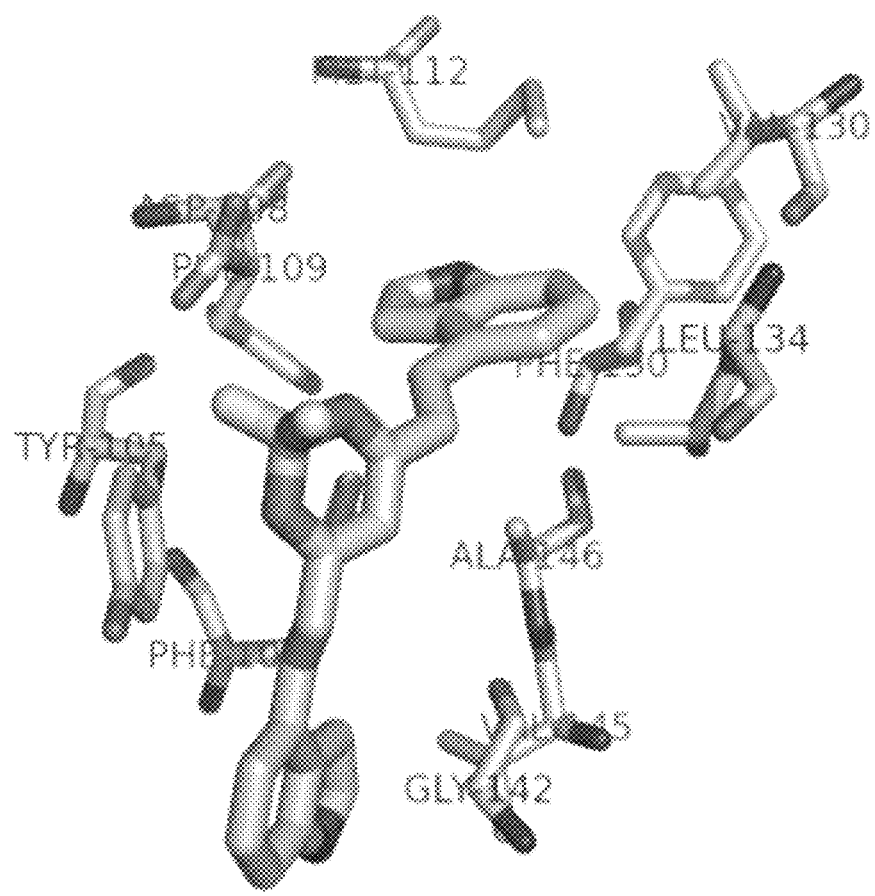

FIG. 59 is a 3D Representation of 3-BF$_2$ in BCl-2.

Figure 60:
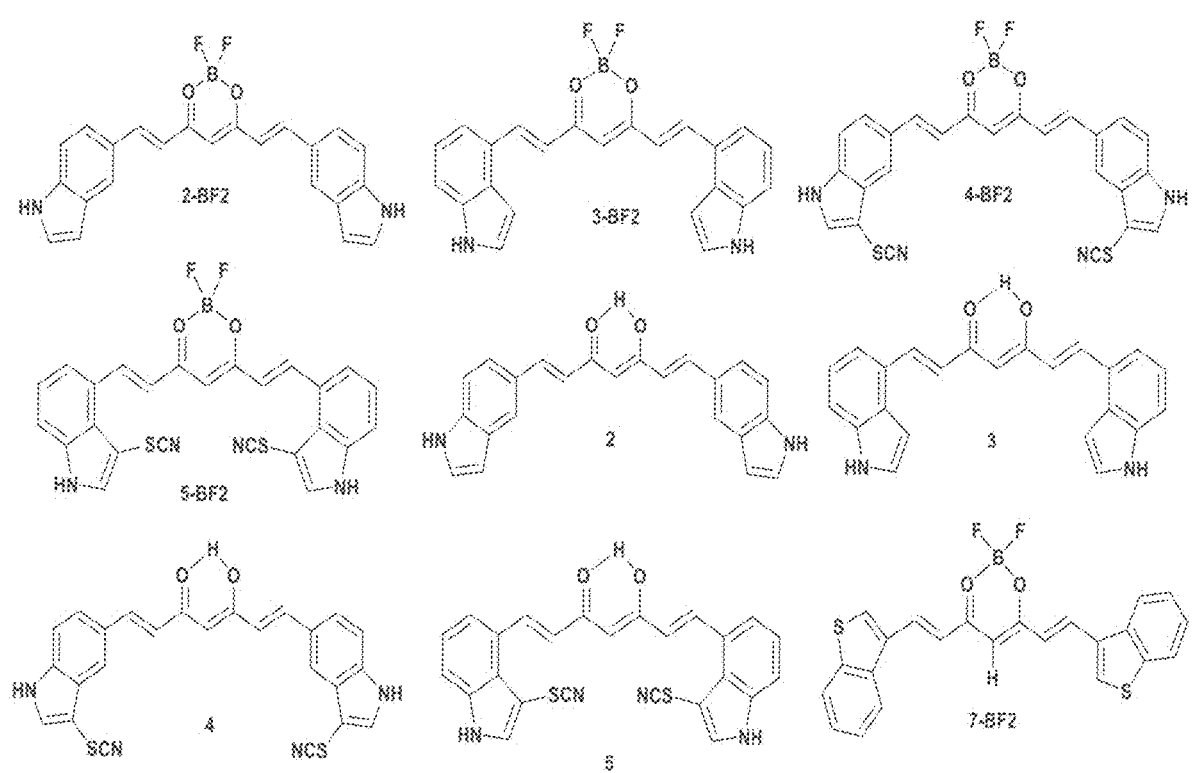

FIG. 60 is an image depicting compounds with high anti-proliferative and apoptotic activity based on NCI-60 assay.

FIG. 61A-B is a series of images depicting indole-based CUR analogs are significantly more toxic to tumor cells than to healthy cells. Cell proliferation and viability were determined in multiple myeloma (MM) cancer cell lines (RPMI-8226, KMS-11, MM1.S) as well as in peripheral blood mononuclear cells (PBMCs) from healthy donors that were exposed to various concentrations of (A) CUR-analog 1 (3-BF$_2$) and (B) CUR-analog 2 (CUR 2) for 72 hours using the CellTiter Glo 2.0 assay. The inhibitory concentration of CUR-analog 1 and 2 at which 50% of MM cell lines and PBMCs remained viable after 72 hours (IC$_{50}$) was determined and is presented in Table A. Calculated fold changes in IC$_{50}$ between MM cell lines relative to healthy PBMCs are presented in Table B.

FIG. 62A-F are a series of graphs depicting cell-viability assay for 5-BF$_2$(A), 4-BF$_2$ (B), 3-BF$_2$ (C), 7-BF$_2$(D), 2-BF$_2$ (E), curcumin (F).

FIG. 63 is a table depicting the cell lines employed in the study of FIG. 62.

Figure 64:
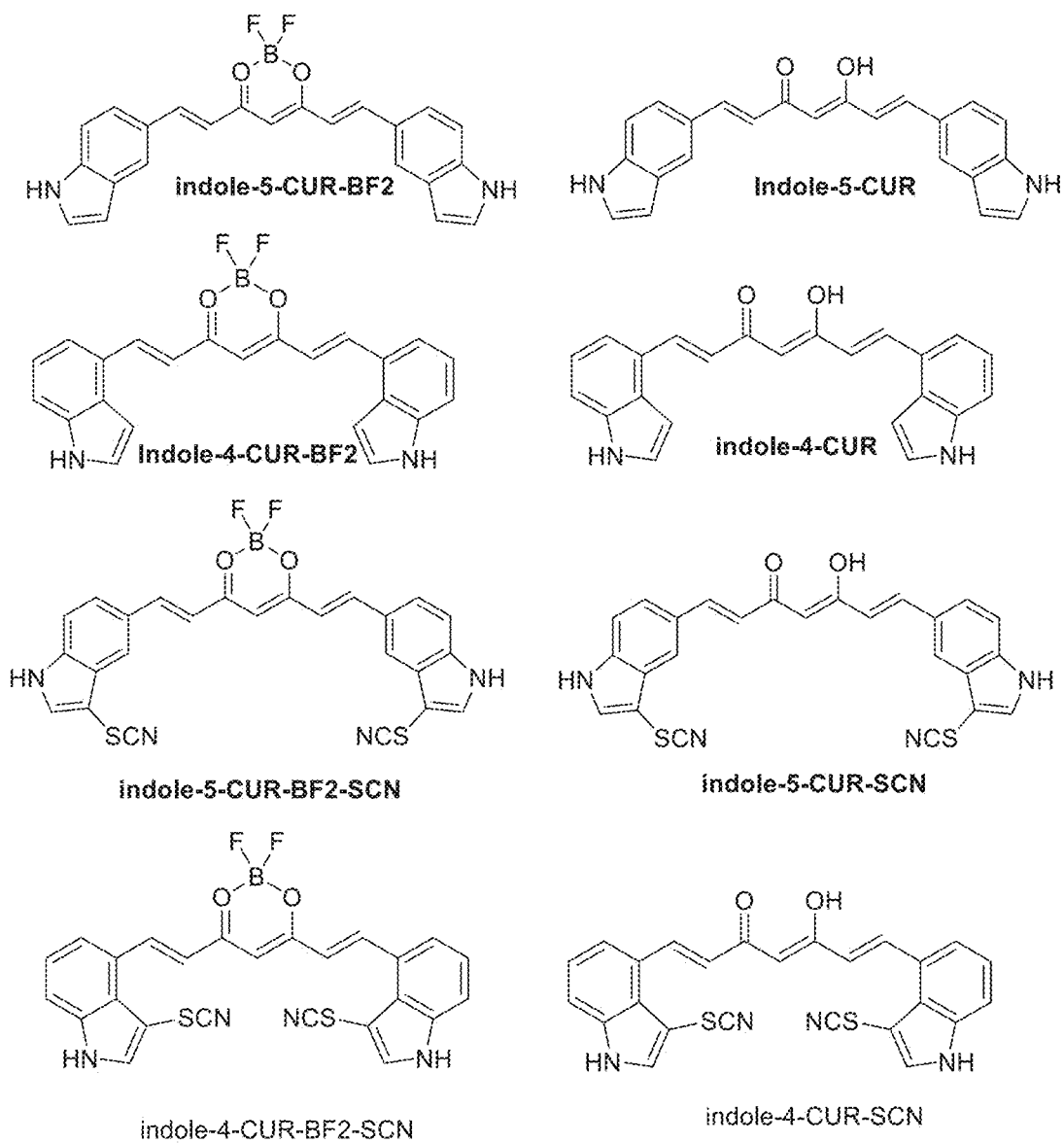

FIG. 64 is a list of indole-based CUR—BF2 and CUR compounds

Figure 65:
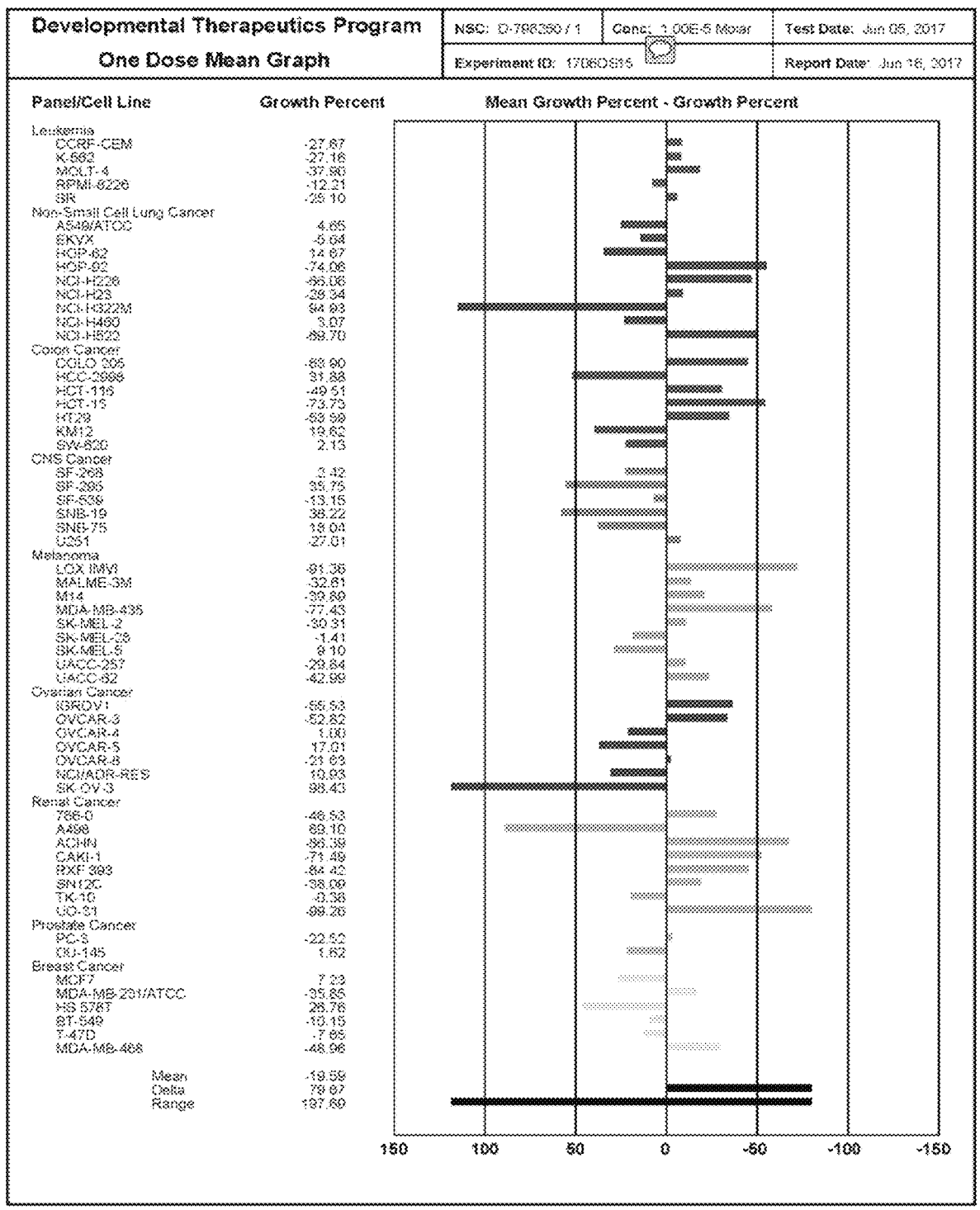

FIG. 65 is a dose mean graph of indole-5-CUR—BF2-SCN for various cancer cell lines at 1×10$^{-5}$ M.

Figure 66:
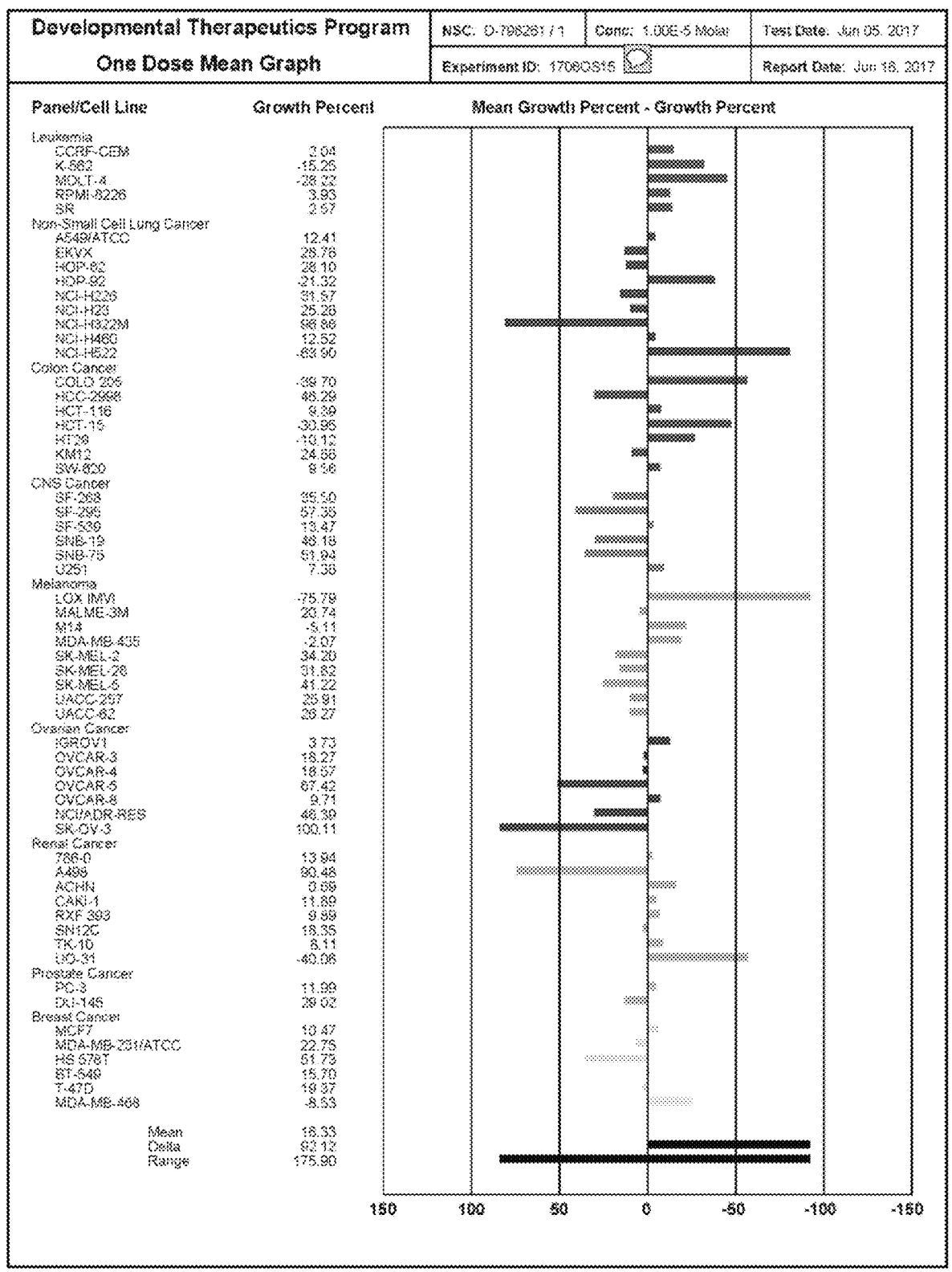

FIG. 66 is a dose mean graph of indole-5-CUR—SCN for various cancer cell lines at 1×10$^{-5}$ M.

Figure 67:
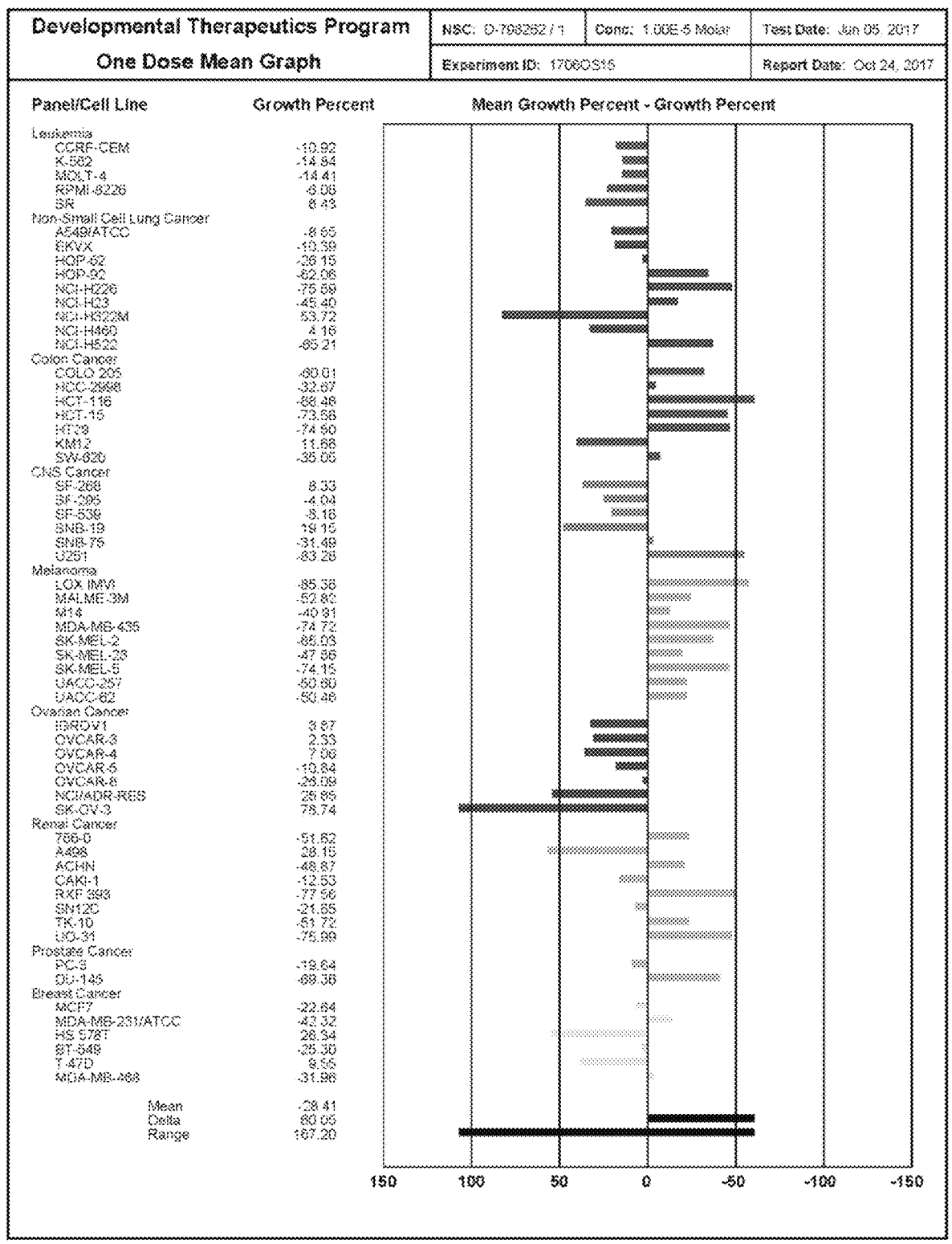

FIG. 67 is a dose mean graph of indole-4-CUR—BF2-SCN for various cancer cell lines at 1×10$^{-5}$ M.

Figure 68:
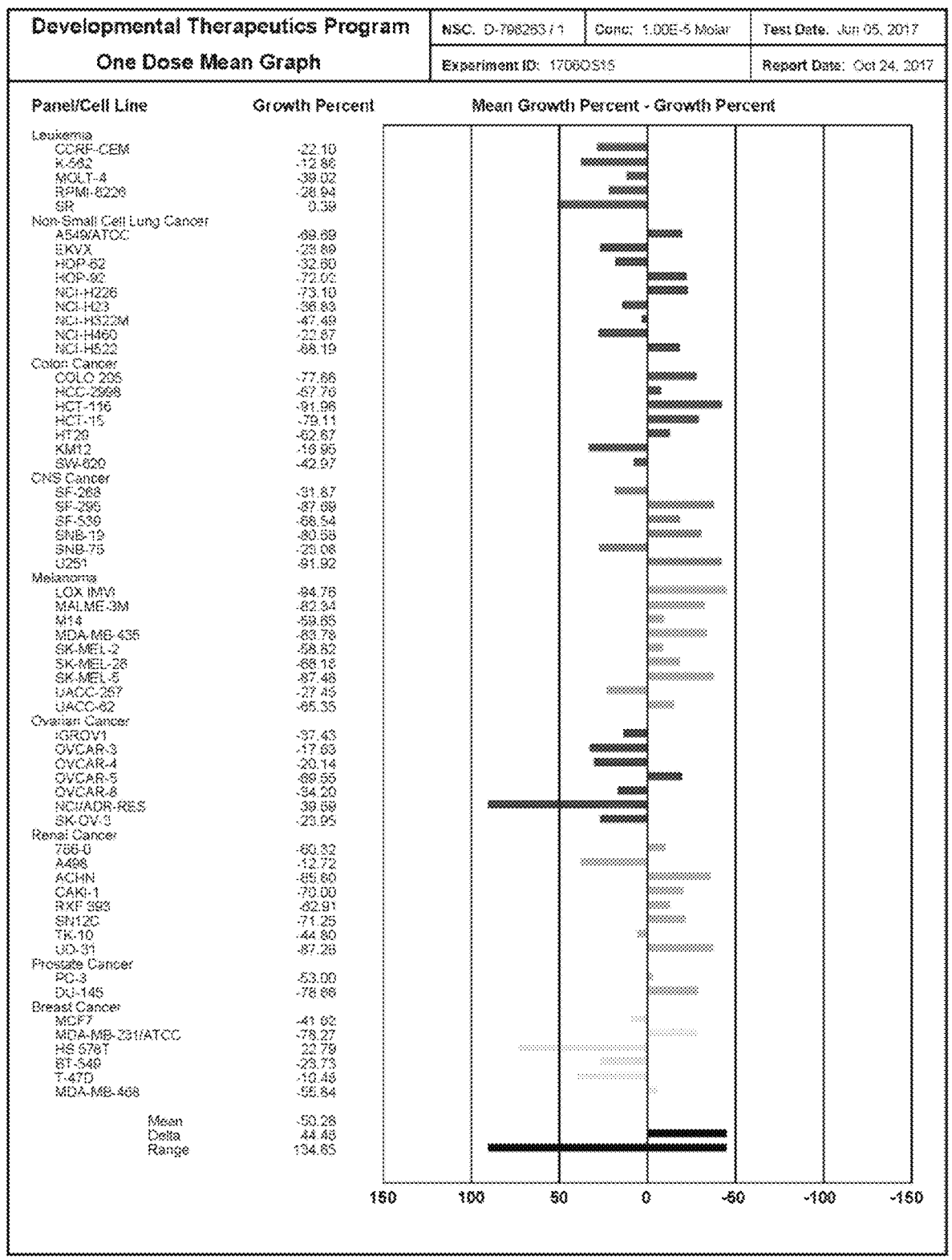

FIG. 68 is a dose mean graph of indole-4-CUR-SCN for various cancer cell lines at 1×10$^{-5}$ M.

Figure 69:
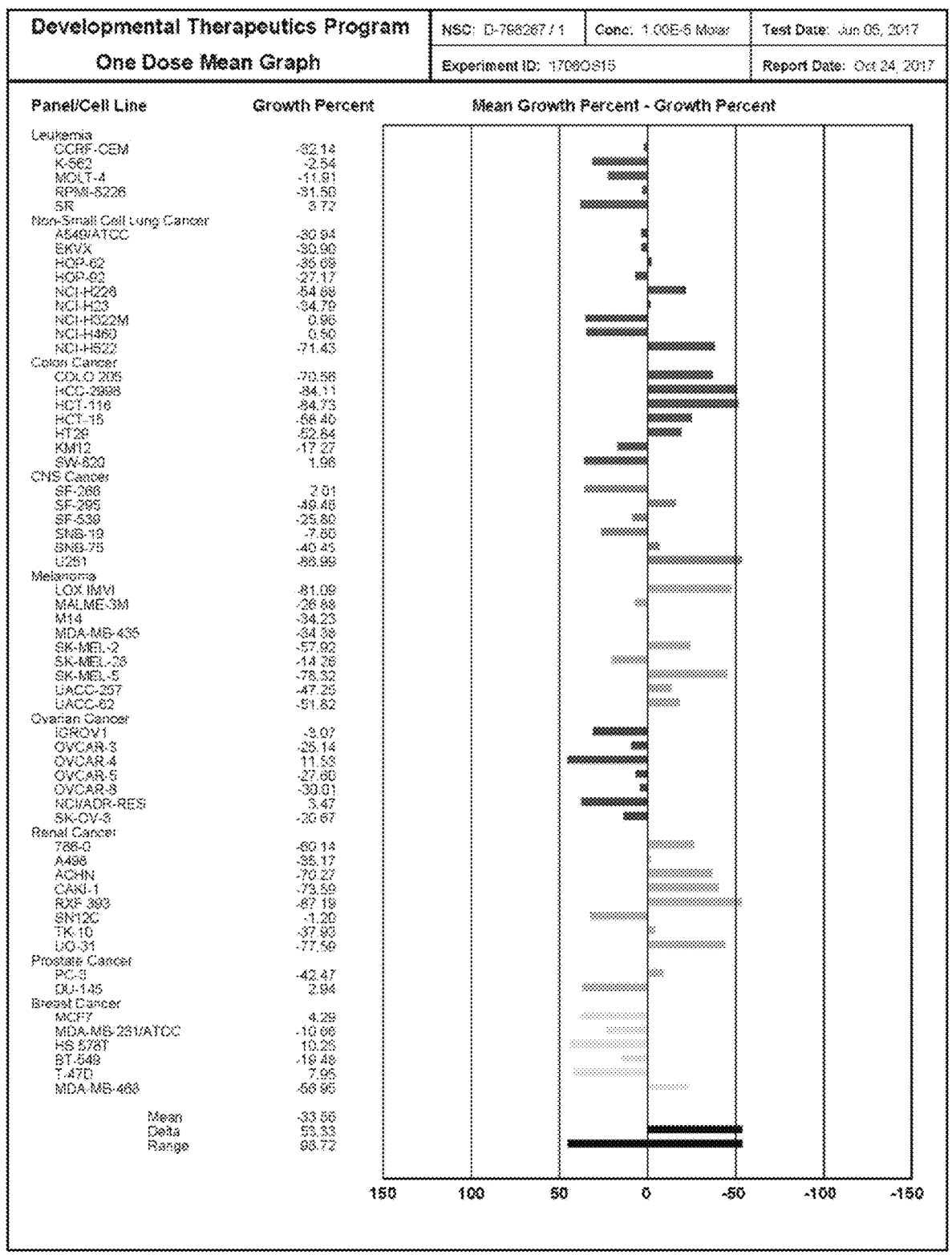

FIG. 69 is a dose mean graph of indole-4-CUR—BF2 for various cancer cell lines at 1×10$^{-5}$ M.

Figure 70:
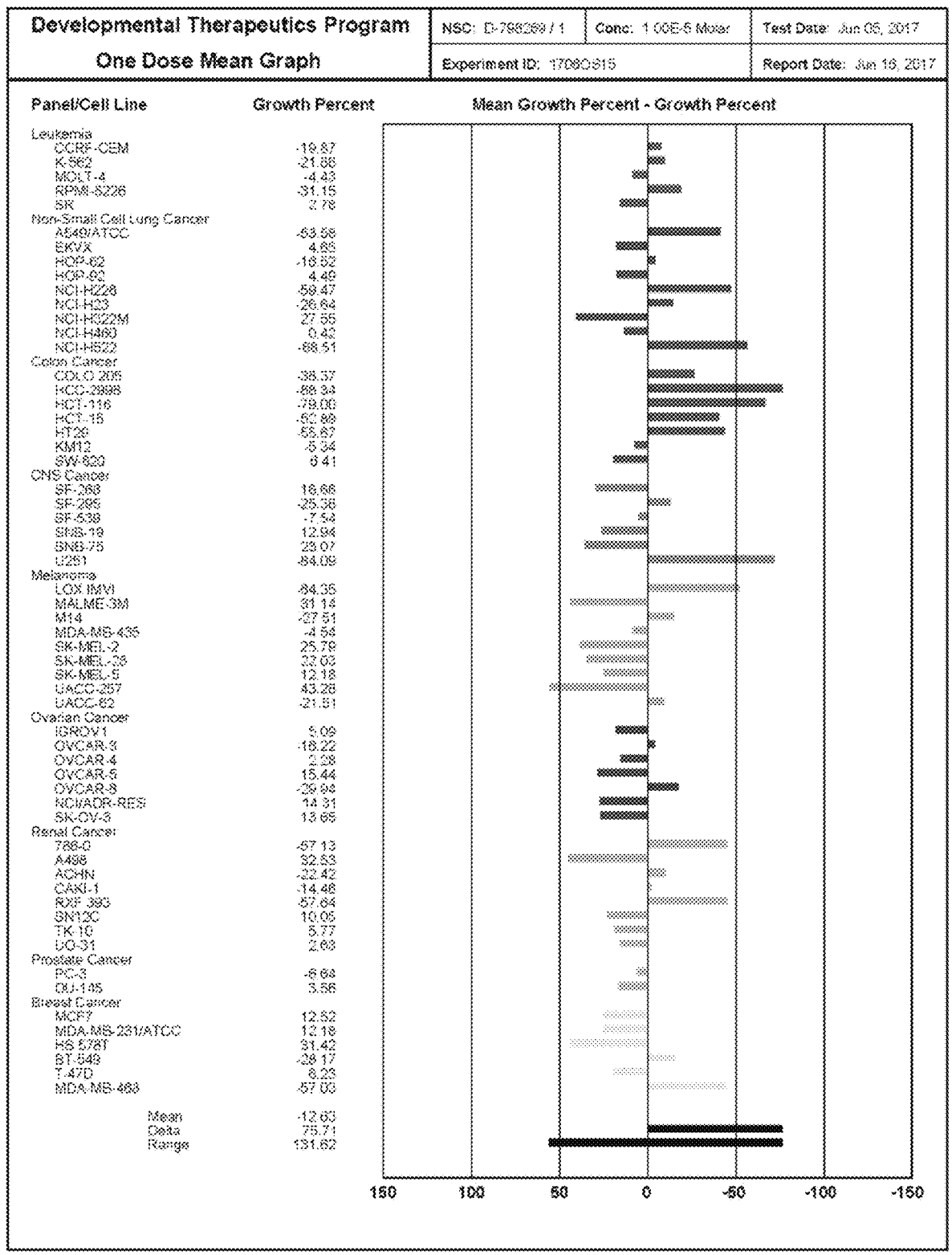

FIG. 70 is a dose mean graph of indole-5-CUR—BF2 for various cancer cell lines at 1×10$^{-5}$ M.

Figure 71:
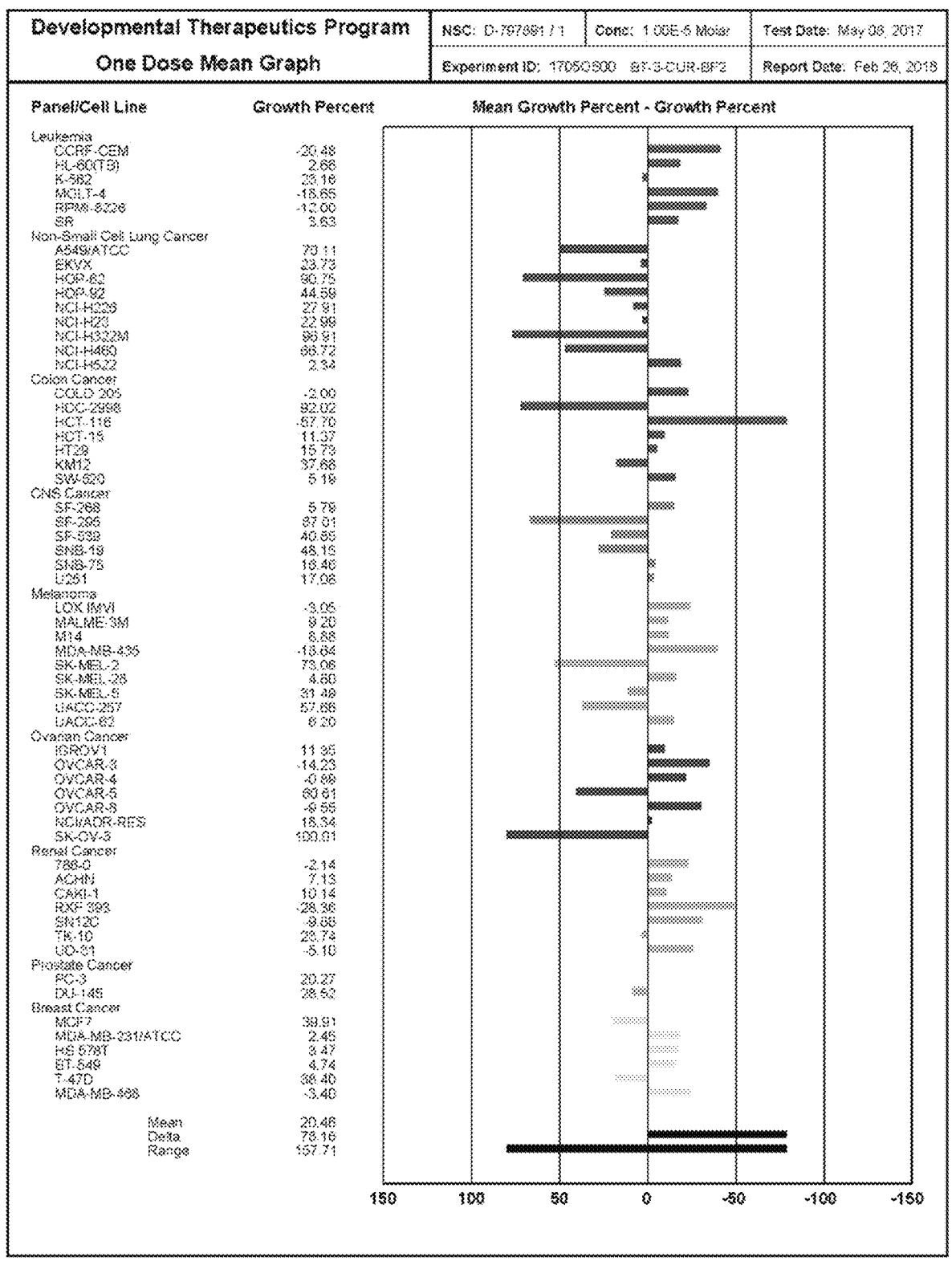

FIG. 71 is a dose mean graph of

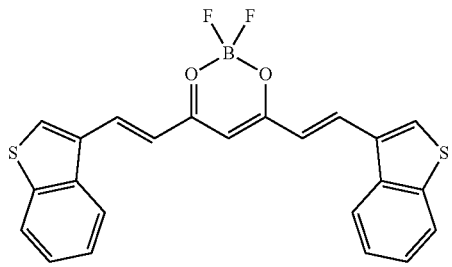

for various cancer cell lines at 1×10$^{-5}$ M.

FIG. 72A-C is a series of images depicting CUR-analogs induce apoptosis in multiple myeloma tumor cells but are significantly less toxic to healthy cells. Apoptotic cell death in multiple myeloma (MM) cancer cell lines (RPMI-8226, KMS-11, MM1.S) as well as peripheral blood mononuclear cells (PBMCs) from healthy donors that were exposed to various concentrations of (A) CUR-analog 1 (Indole-4 CUR—$BF_2$) and (B) CUR-analog 2 (Indole-5 CUR) or (C) the FDA-approved Bcl-2 inhibitor (venetoclax, used for comparison) was assessed. Bar graphs show % of apoptotic cells (annexin-V+PI positive cells) normalized to basal apoptosis observed in control (DMSO-treated) cells. Below each bar graph are representative scatterplots showing % of apoptotic cells exposed to DMSO (control) or CUR-analogs/venetoclax. *$p<0.05$, shows concentrations where a statistically significant difference was noted compared to DMSO-treated cells.

Figure 73:
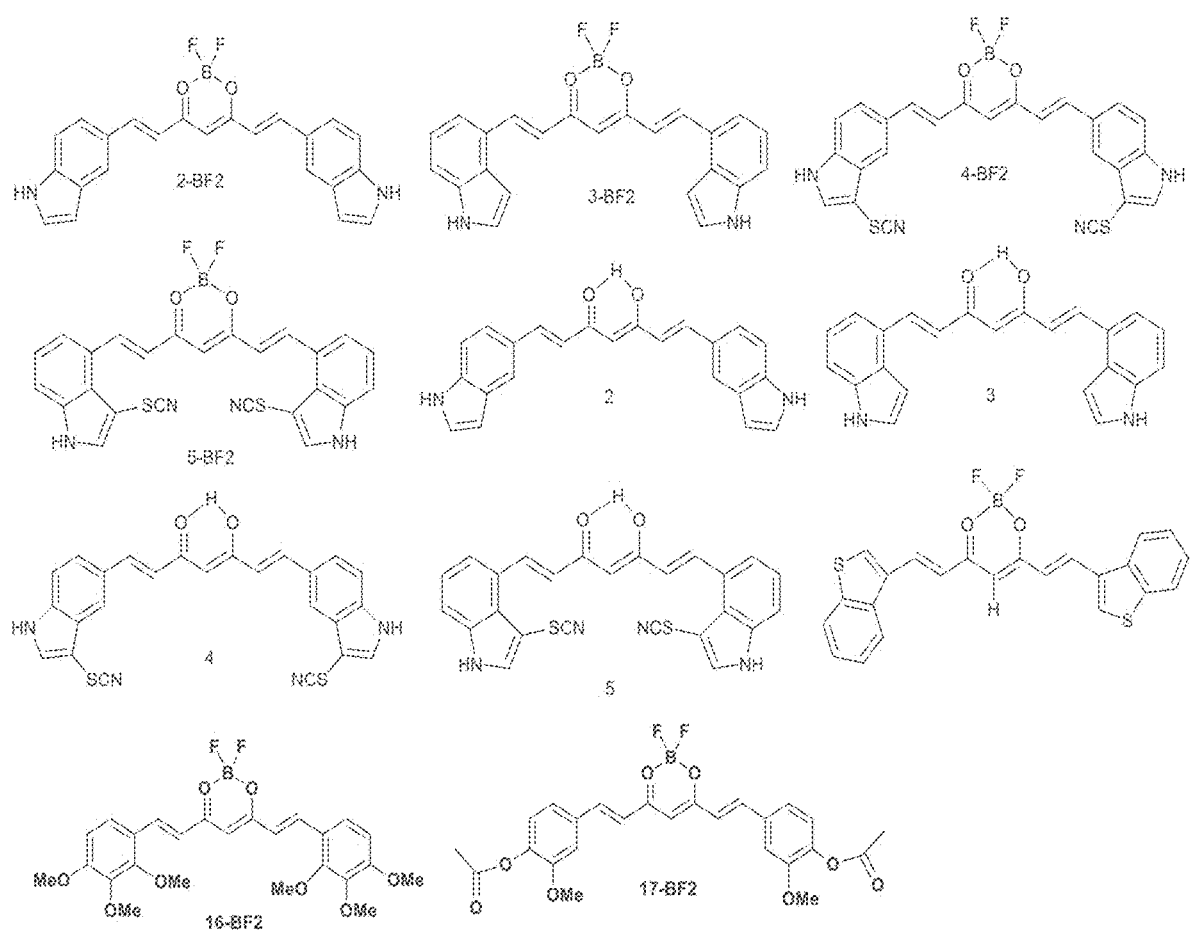

FIG. 73 is a list of compounds tested against CRC cells.

Figure 74A:
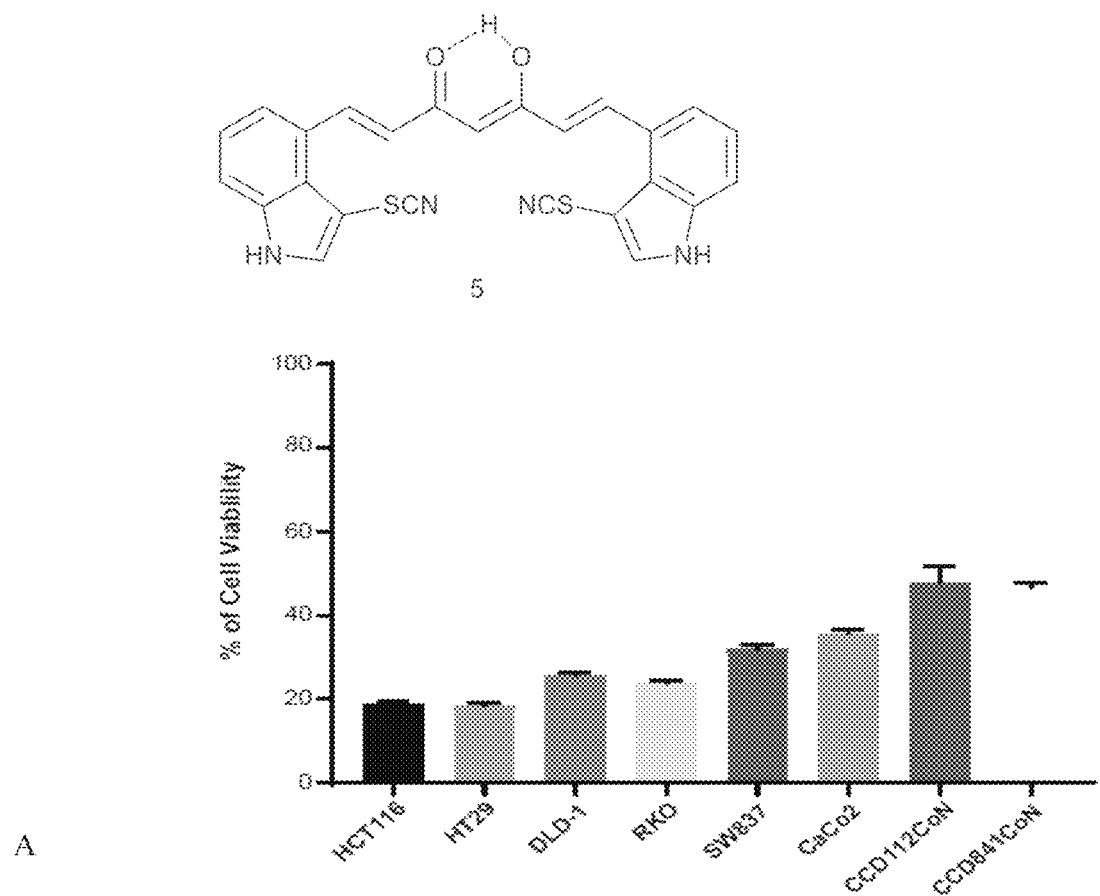

FIG. 74A is a graph depicting comparative CRC viability assay for the associated compound.

Figure 74B:
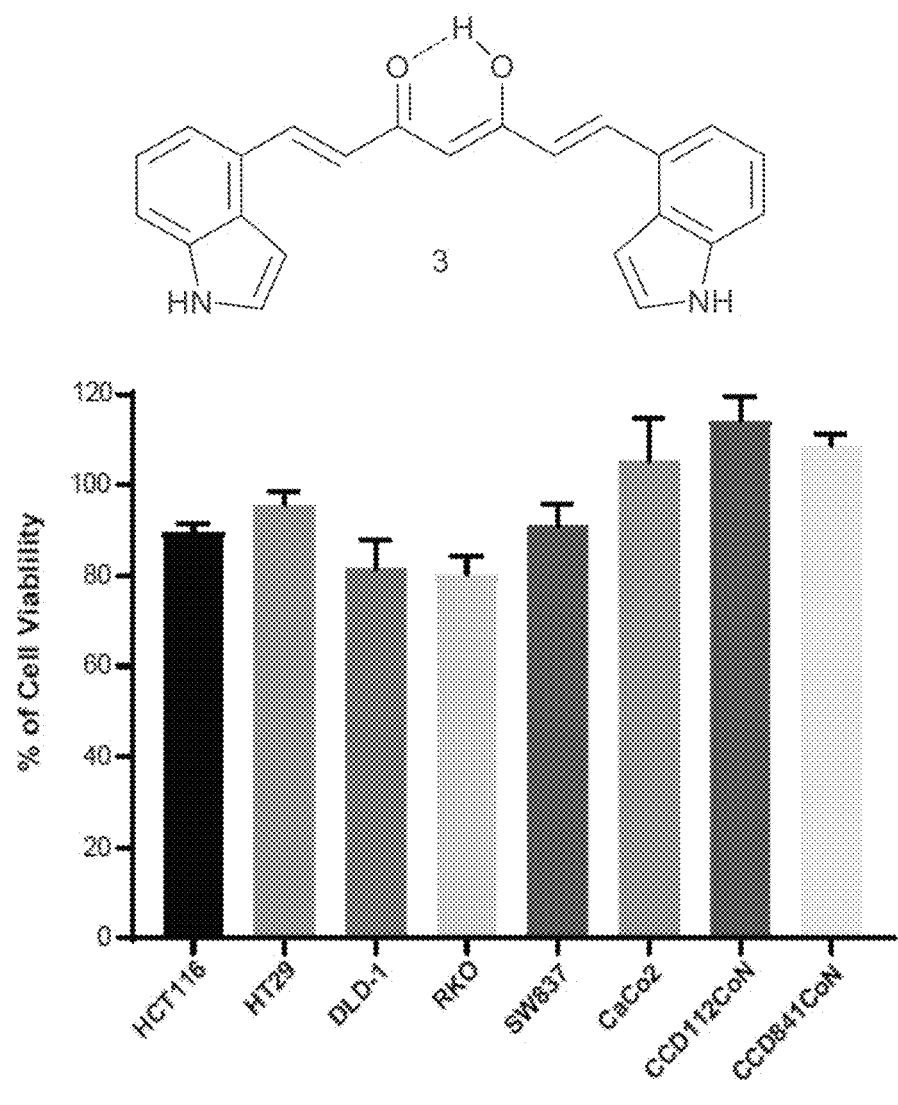

FIG. 74B is a graph depicting comparative CRC viability assay for the associated compound.

FIG. 74C is a graph depicting comparative CRC viability assay for the associated compound.

FIG. 74D is a graph depicting comparative CRC viability assay for the associated compound.

FIG. 74E is a graph depicting comparative CRC viability assay for the associated compound.

FIG. 74F is a graph depicting comparative CRC viability assay for the associated compound.

Figure 75A:
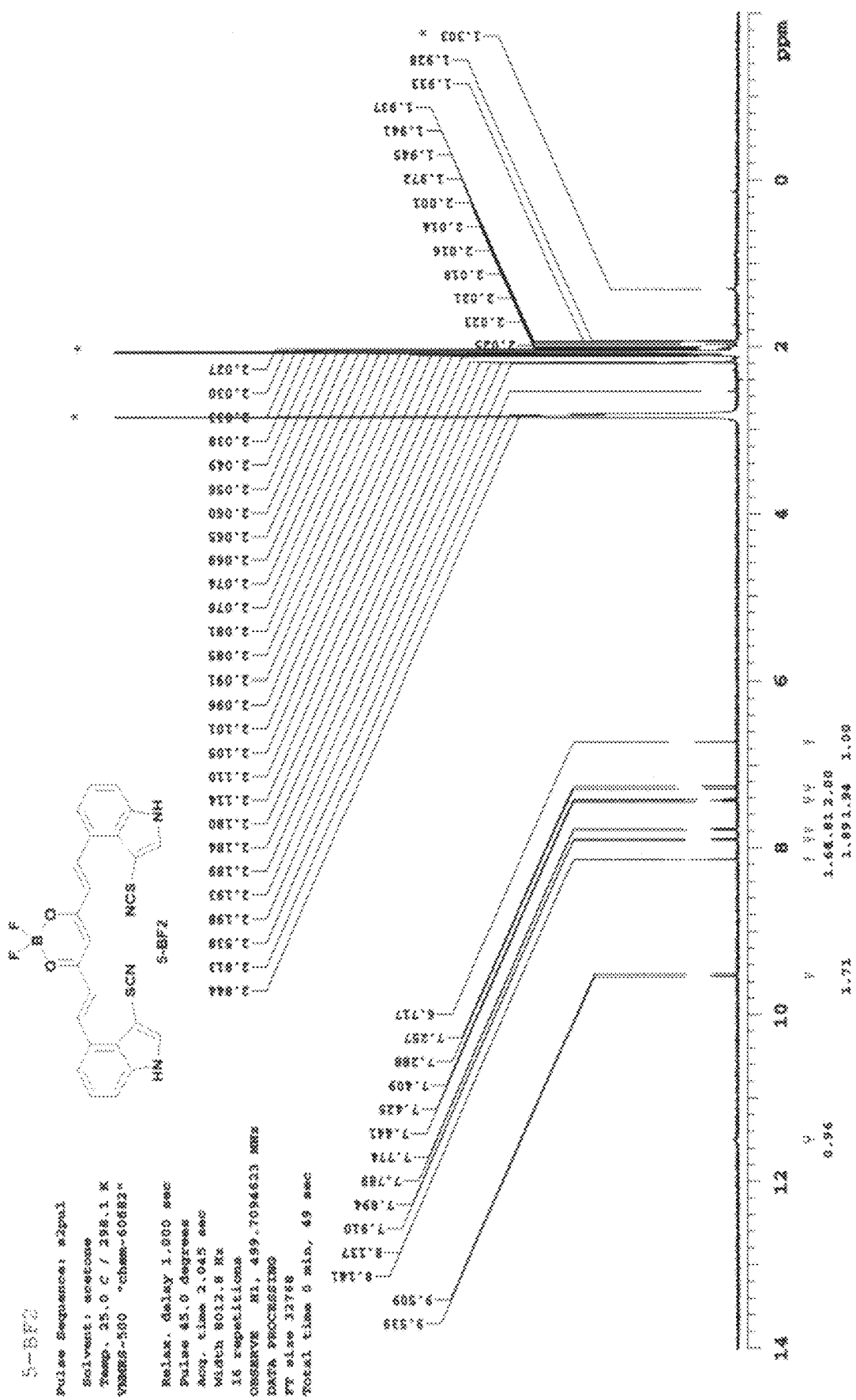

FIG. 75A is representative NMR spectrum for the bioactive compound 5-$BF_2$.

Figure 75B:
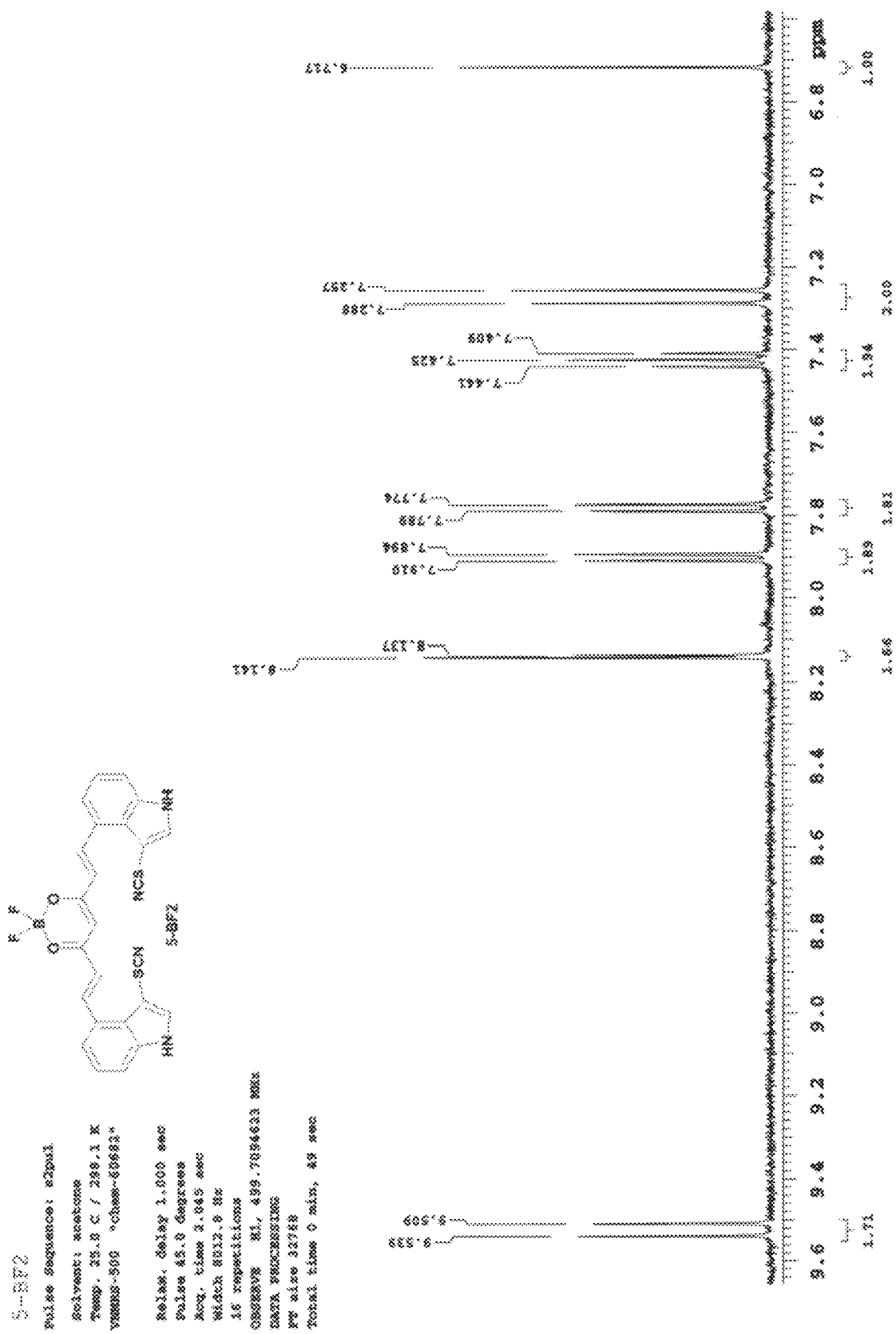

FIG. 75B is representative NMR spectrum for the bioactive compound 5-$BF_2$.

Figure 75C:
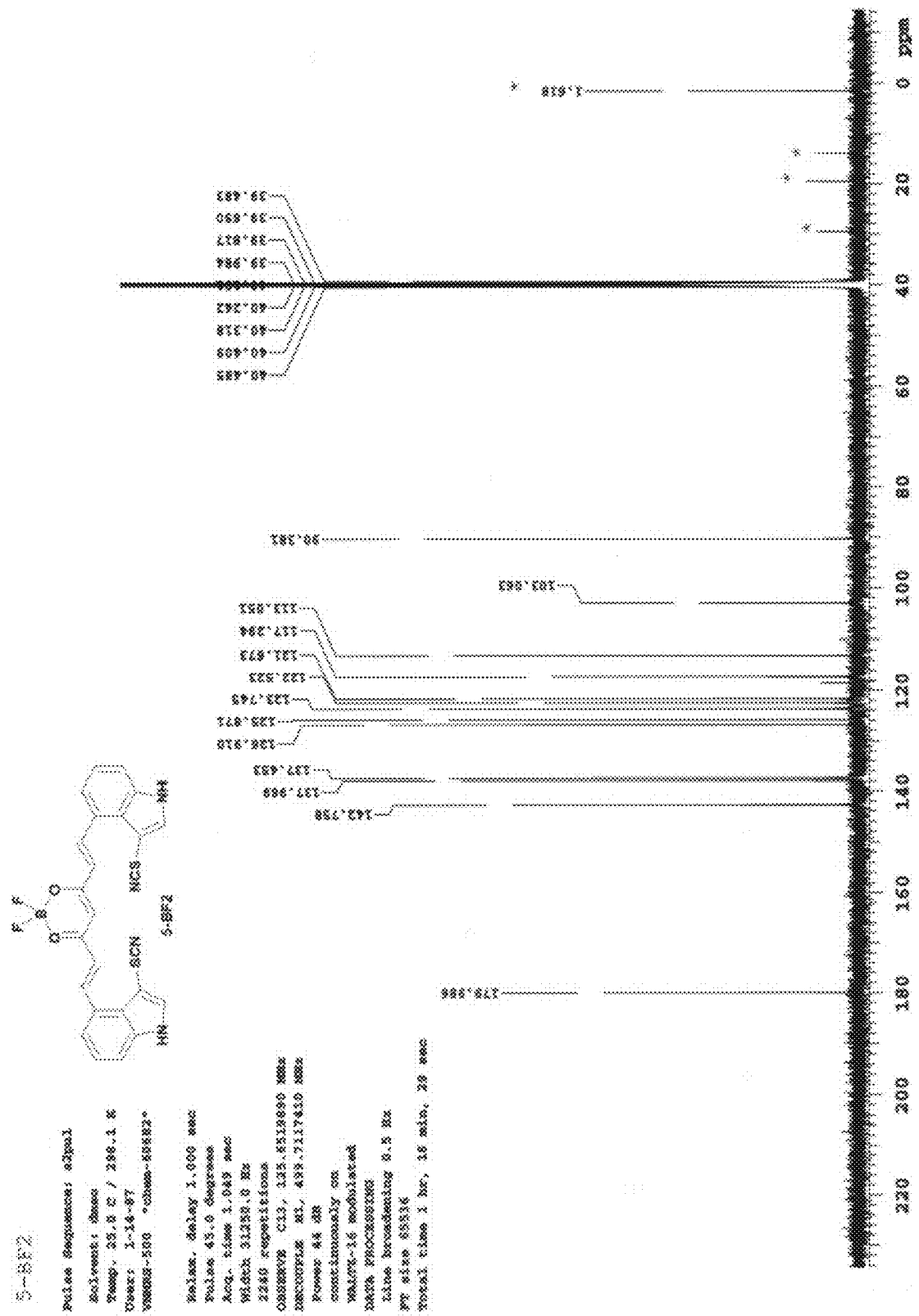

FIG. 75C is representative NMR spectrum for the bioactive compound 5-$BF_2$.

Figure 75D:
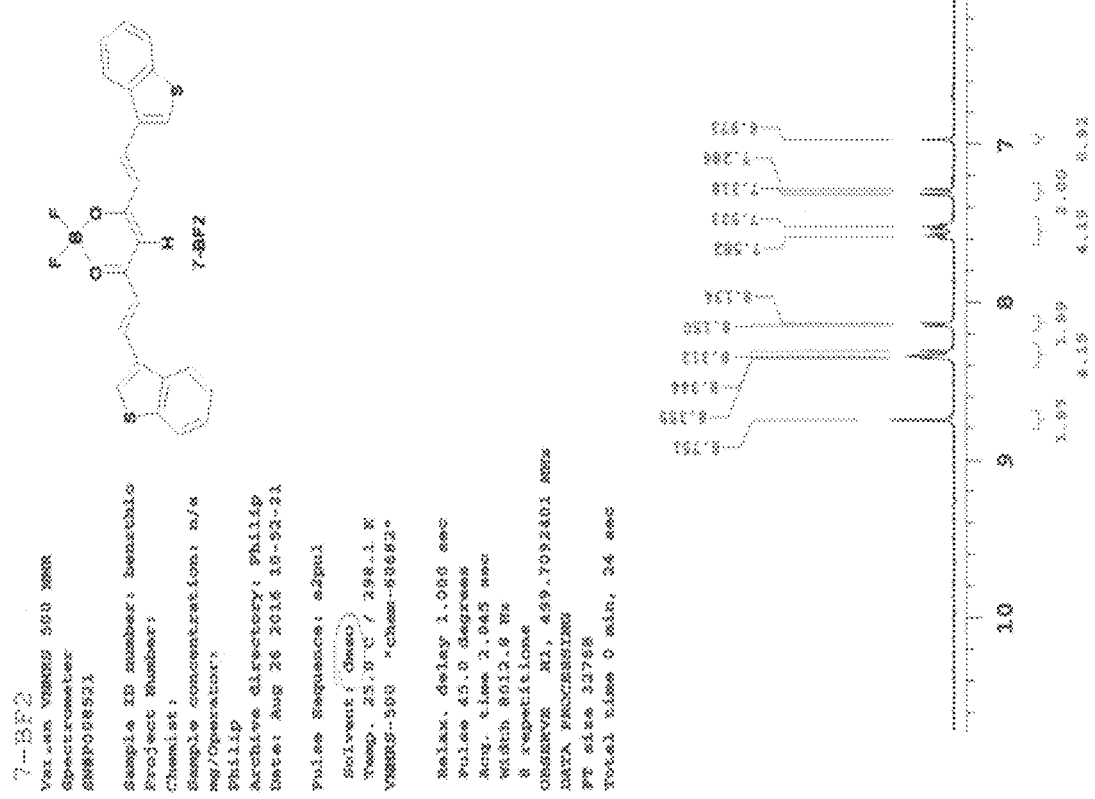

FIG. 75D is representative NMR spectrum for the bioactive compound 7-$BF_2$.

FIG. 75E is representative NMR spectrum for the bioactive compound 7-$BF_2$.

FIG. 75F is representative NMR spectrum for the bioactive compound 7-$BF_2$.

Figure 75G:
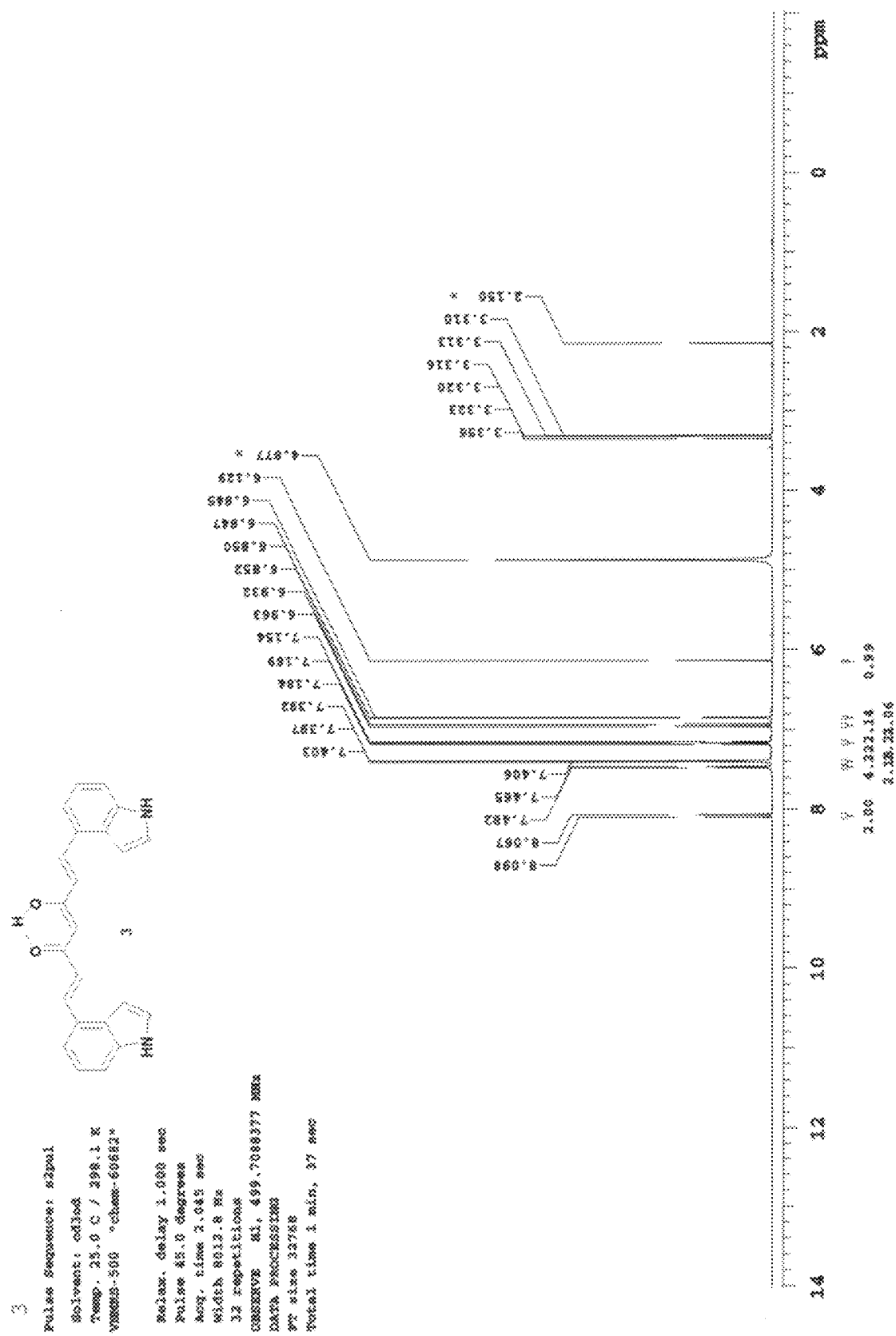

FIG. 75G is representative NMR spectrum for the bioactive compound 3.

Figure 75H:
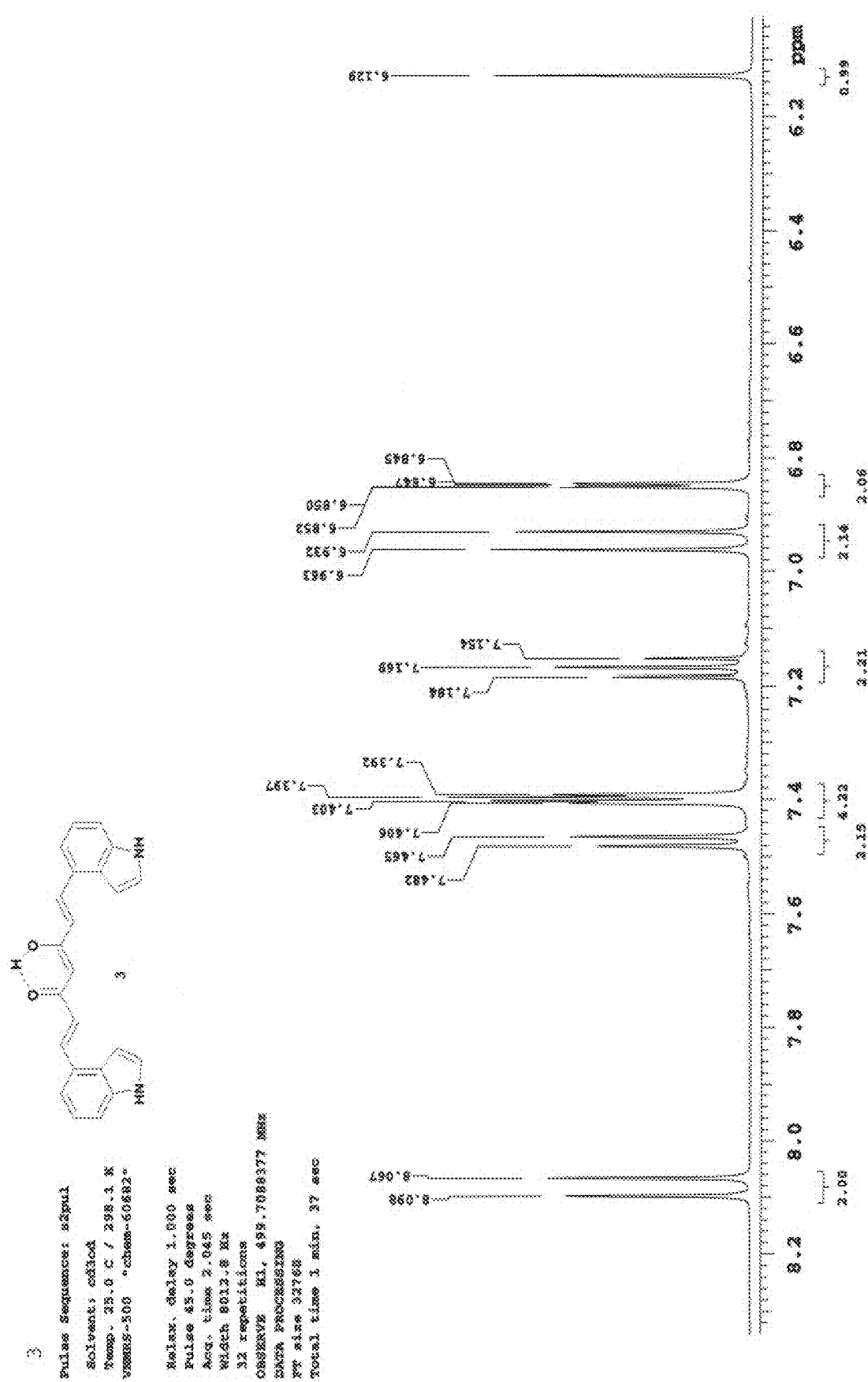

FIG. 75H is representative NMR spectrum for the bioactive compound 3.

Figure 75I:
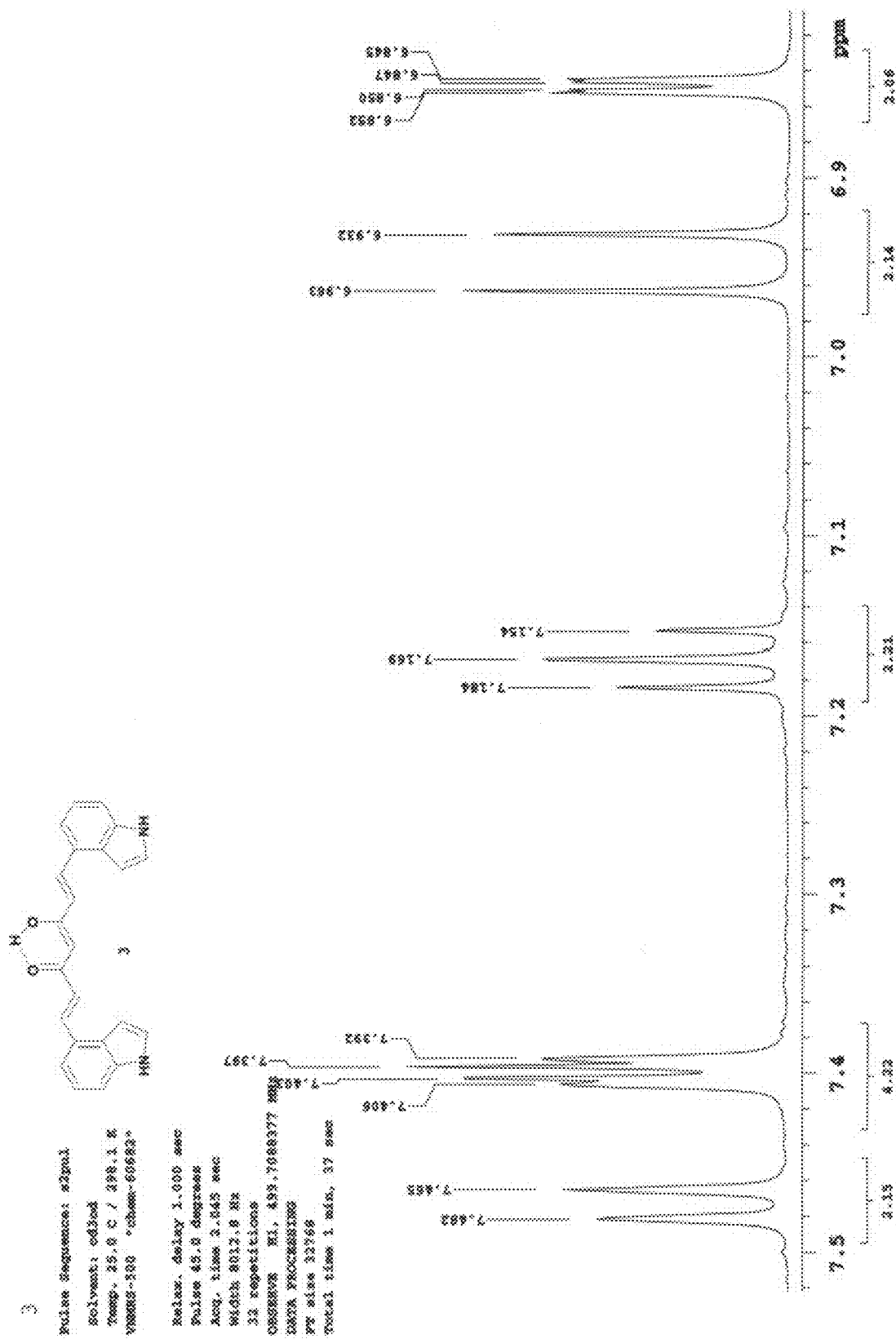

FIG. 75I is representative NMR spectrum for the bioactive compound 3.

Figure 75J:
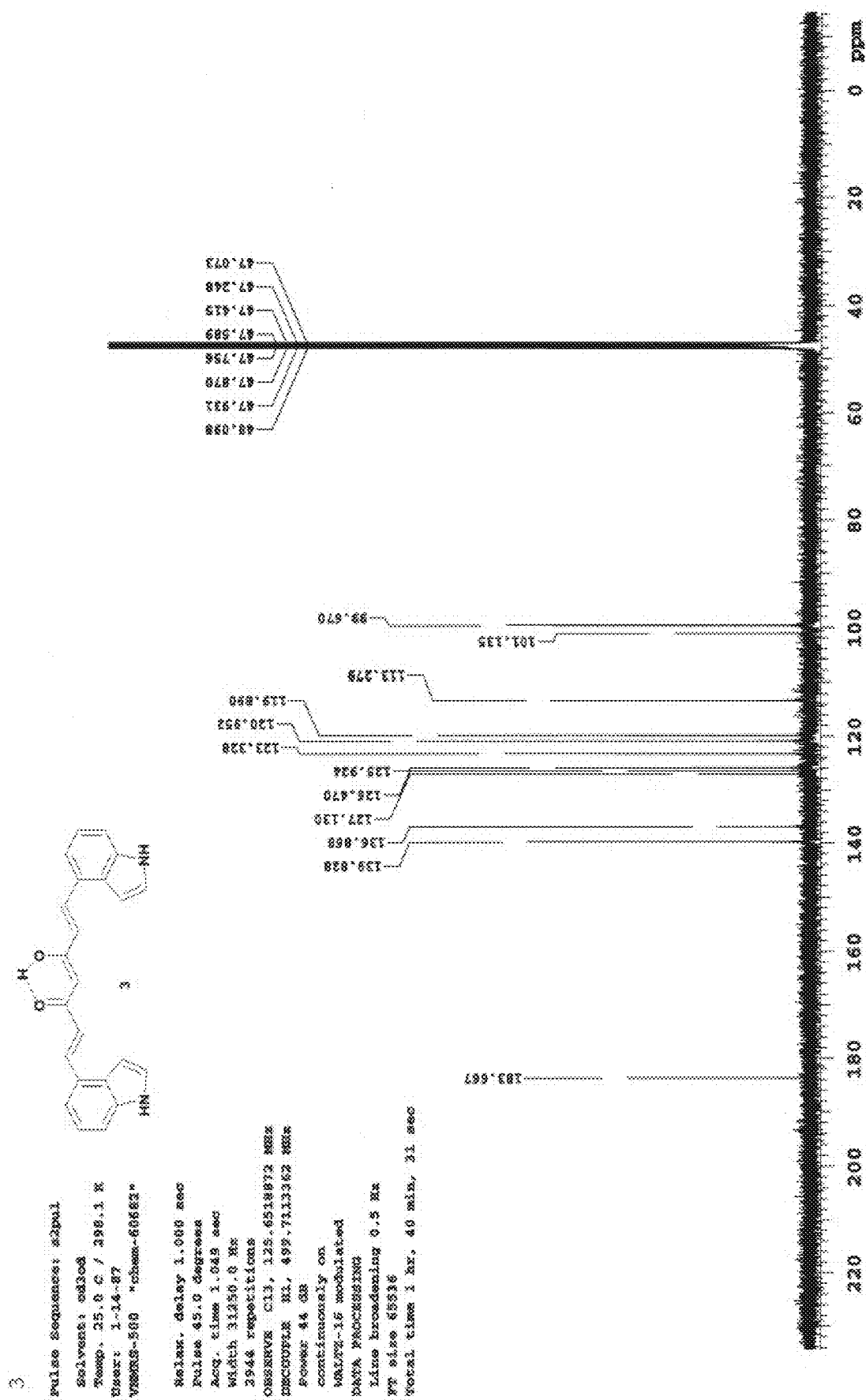

FIG. 75J is representative NMR spectrum for the bioactive compound 3.

Figure 75K:
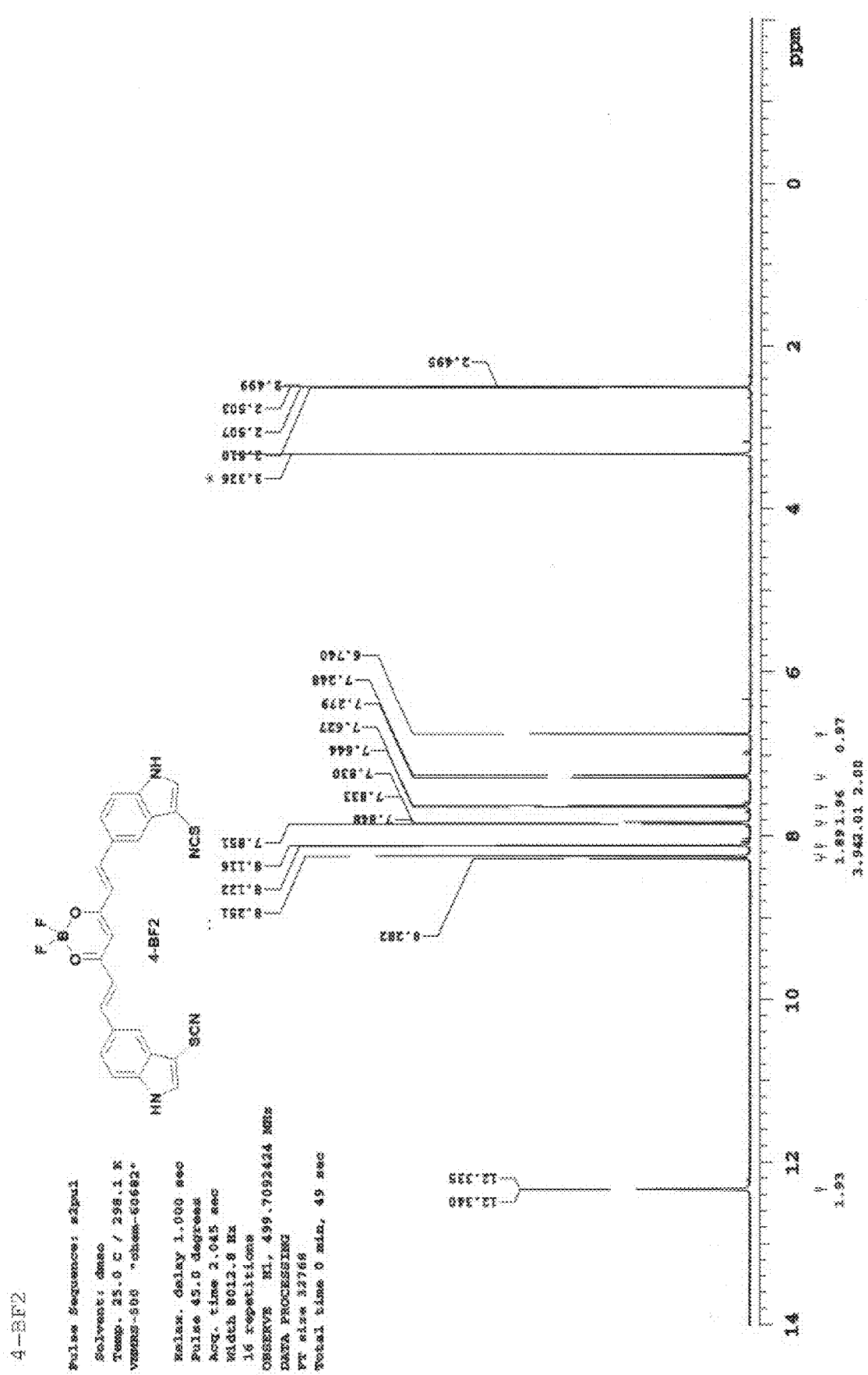

FIG. 75K is representative NMR spectrum for the bioactive compound 4-$BF_2$.

Figure 75L:
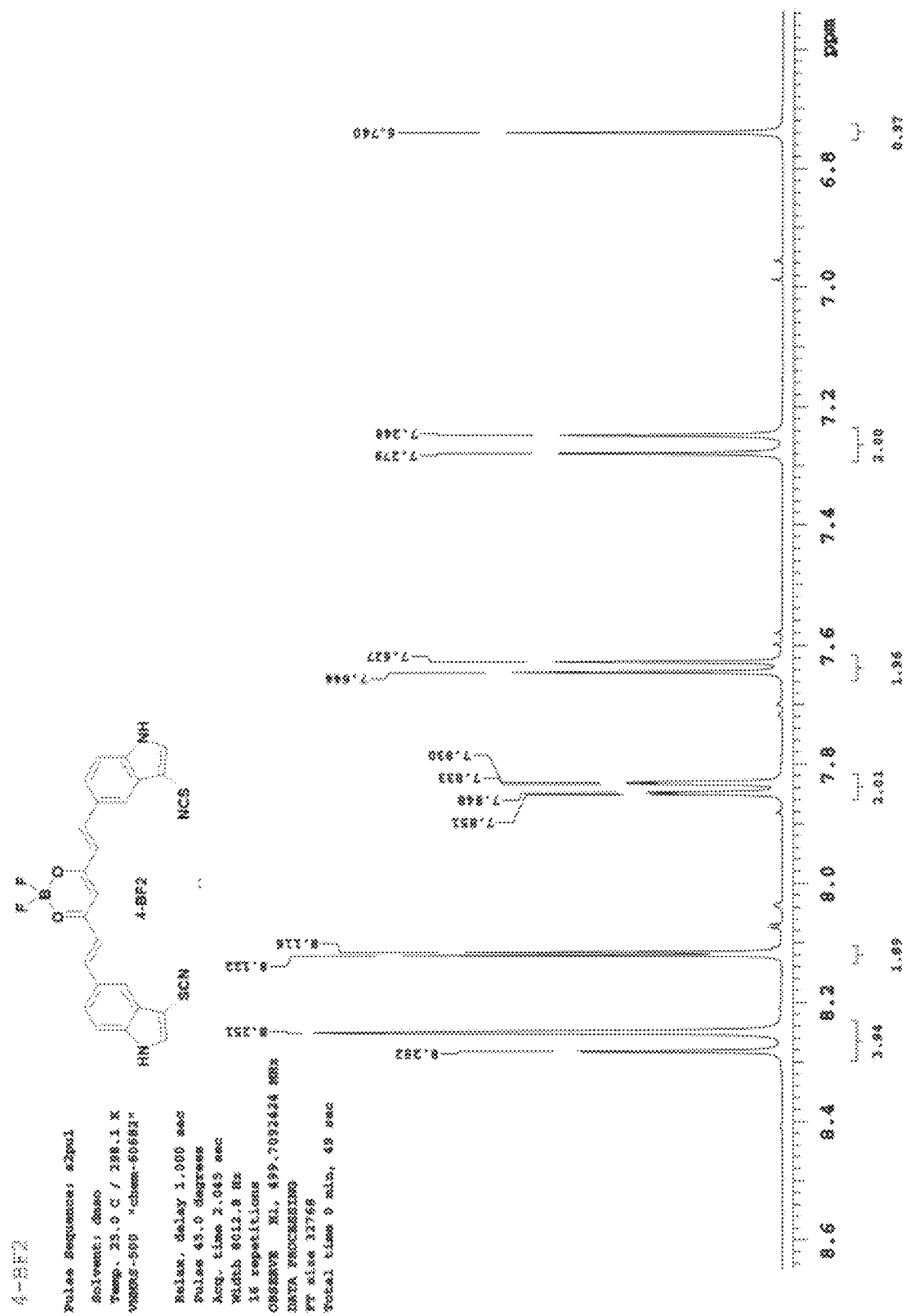

FIG. 75L is representative NMR spectrum for the bioactive compound 4-$BF_2$.

Figure 75M:
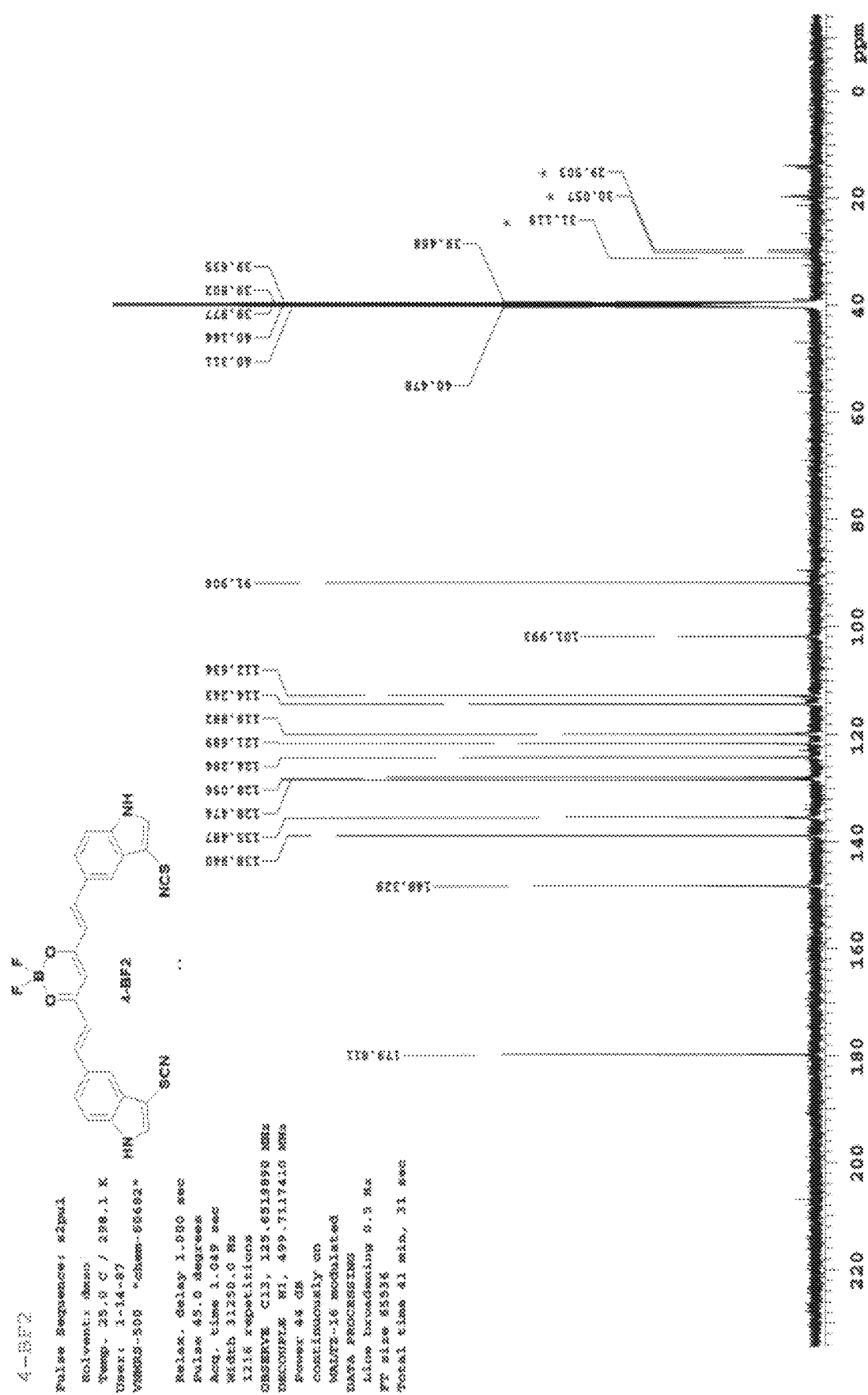

FIG. 75M is representative NMR spectrum for the bioactive compound 4-$BF_2$.

Figure 75N:
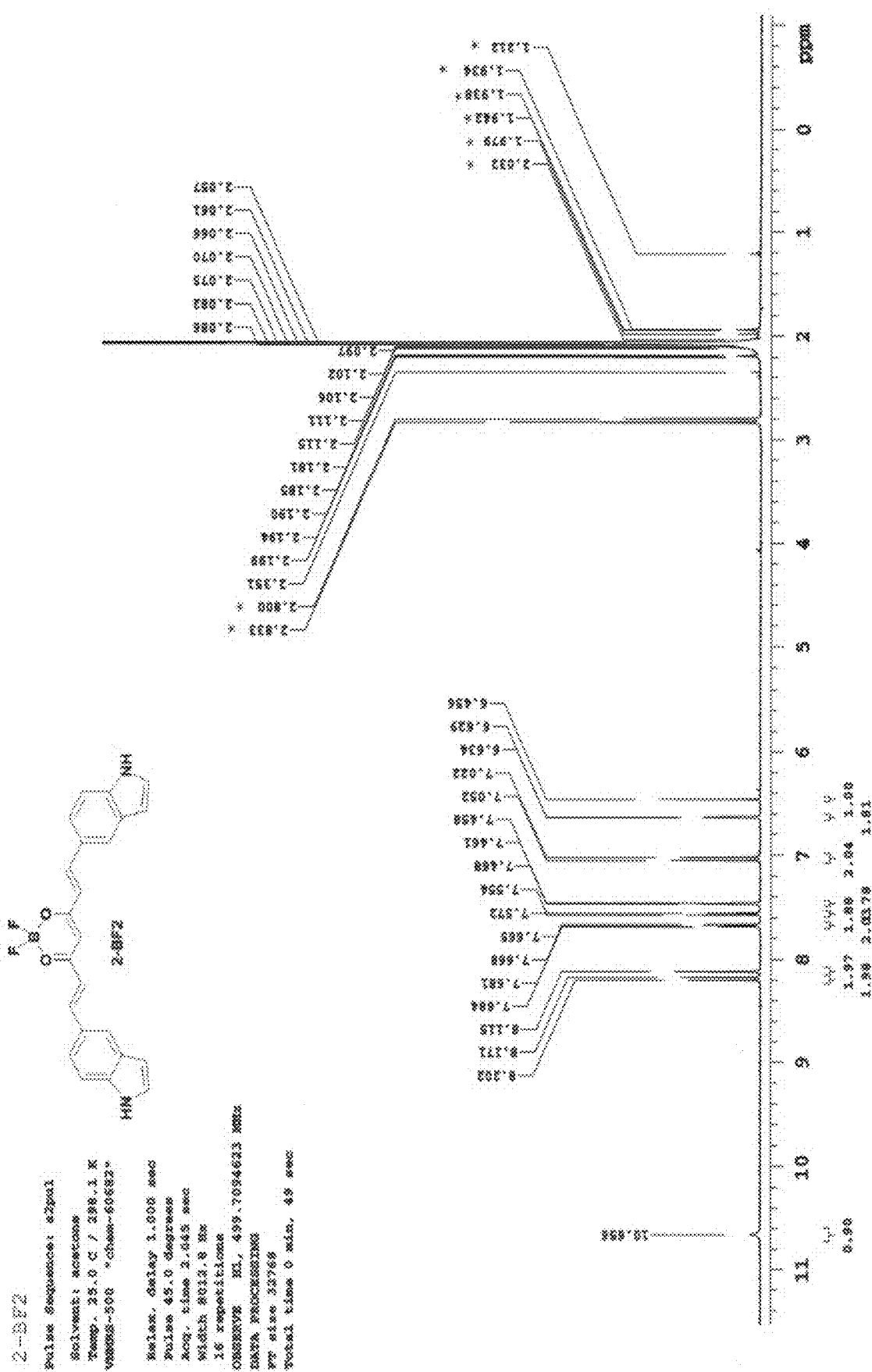

FIG. 75N is representative NMR spectrum for the bioactive compound 2-$BF_2$.

Figure 75O:
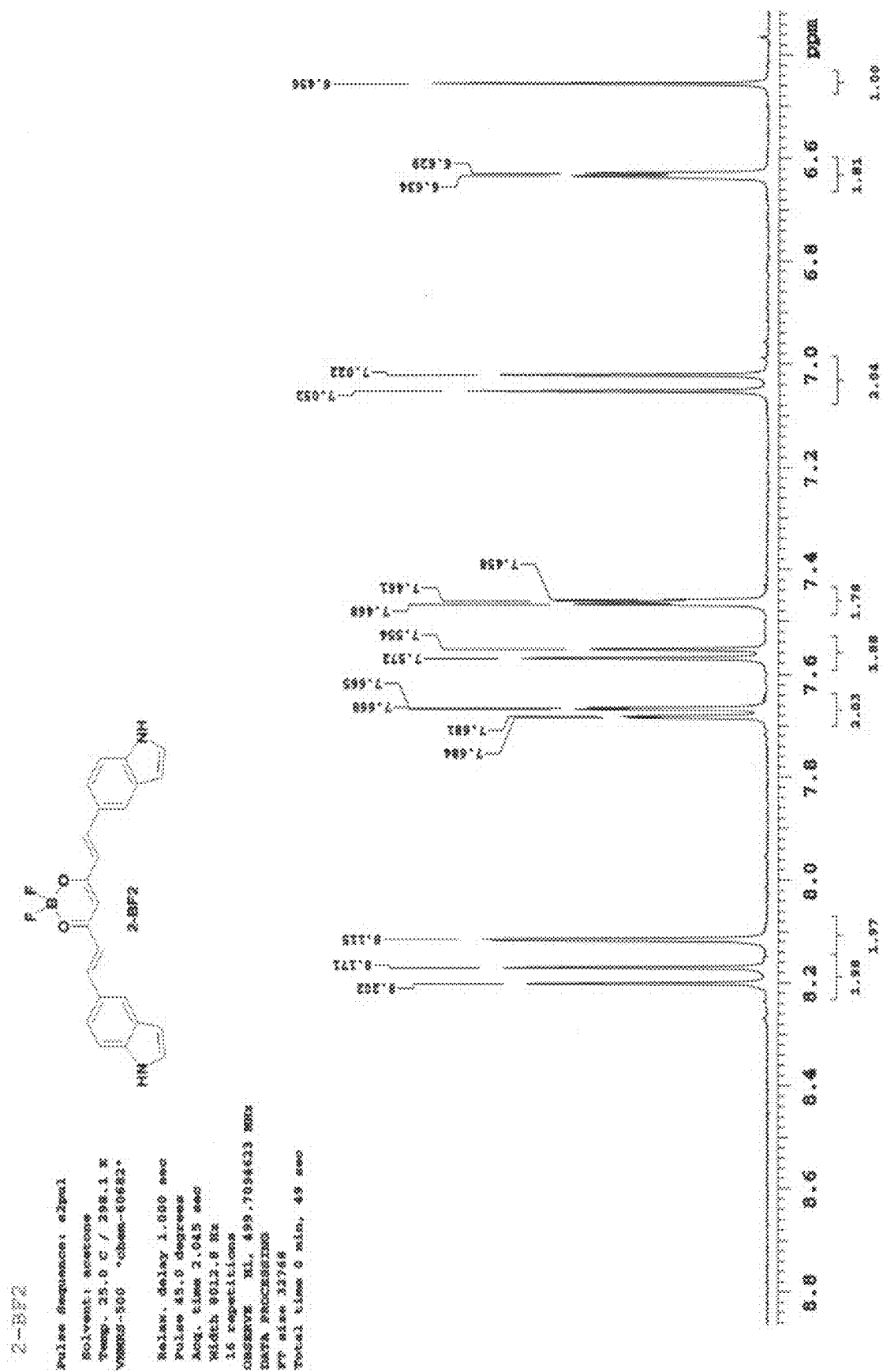

FIG. 75O is representative NMR spectrum for the bioactive compound 2-$BF_2$.

Figure 75P:
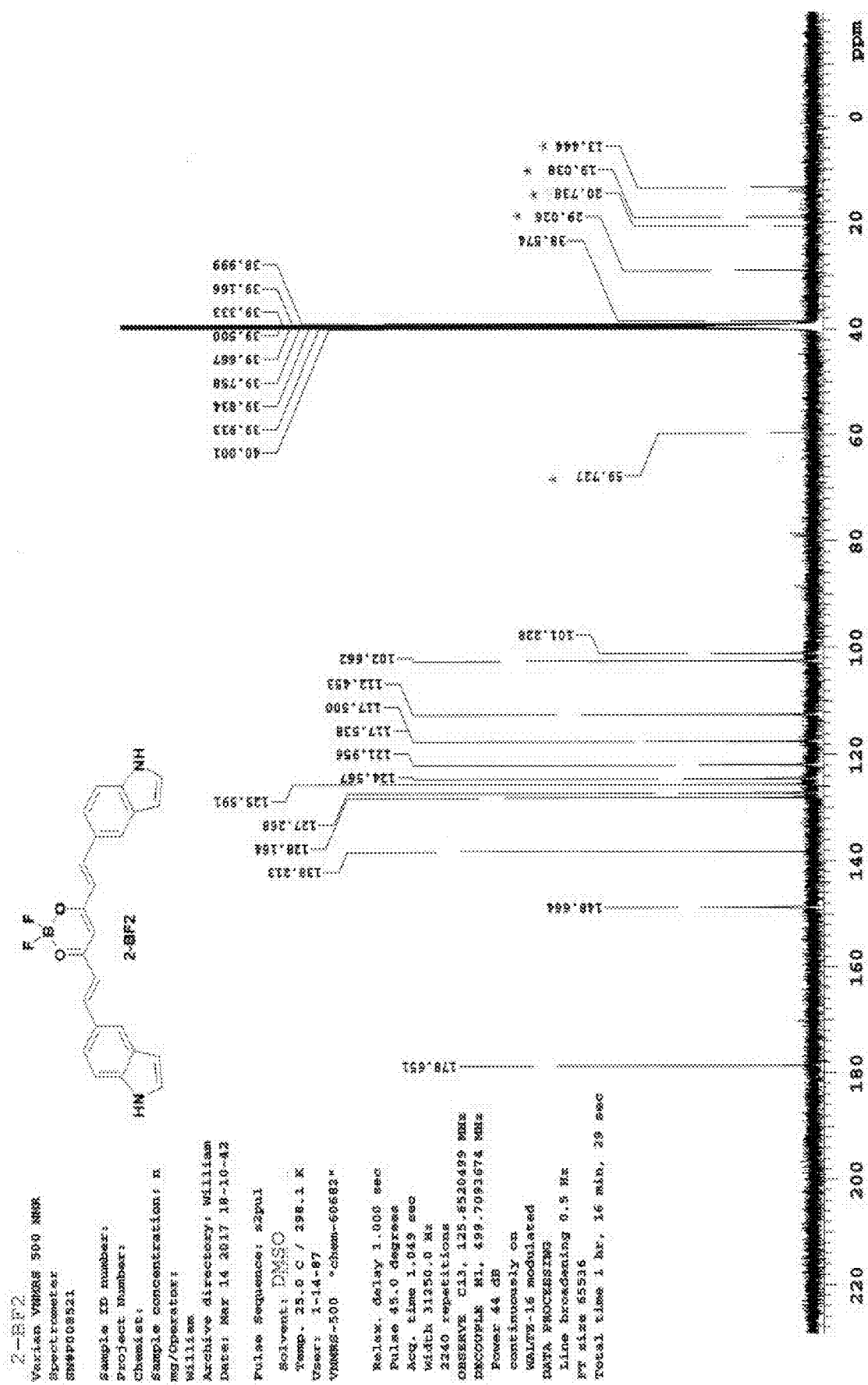

FIG. 75P is representative NMR spectrum for the bioactive compound 2-$BF_2$.

Figure 75Q:
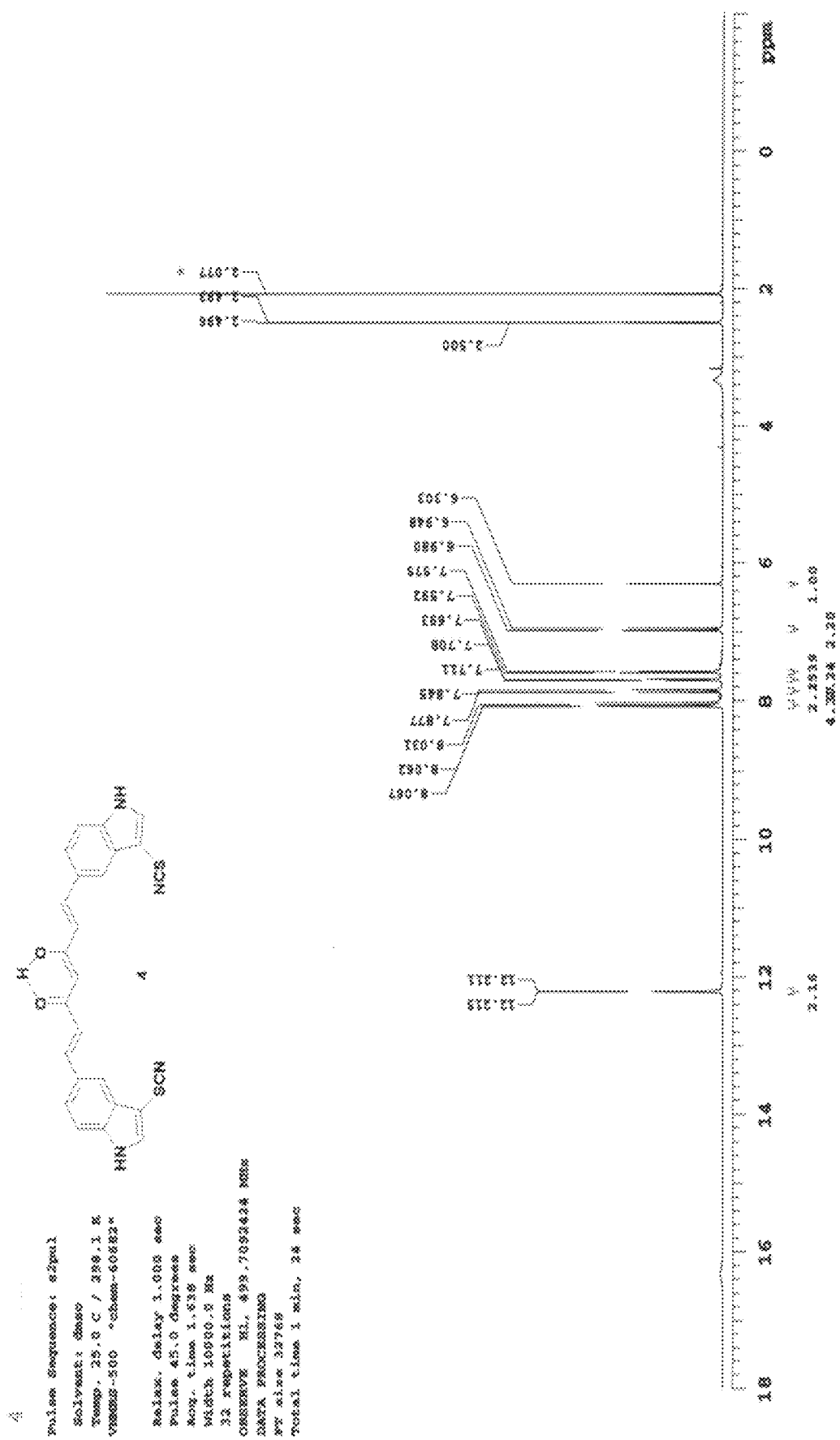

FIG. 75Q is representative NMR spectrum for the bioactive compound 4.

Figure 75R:
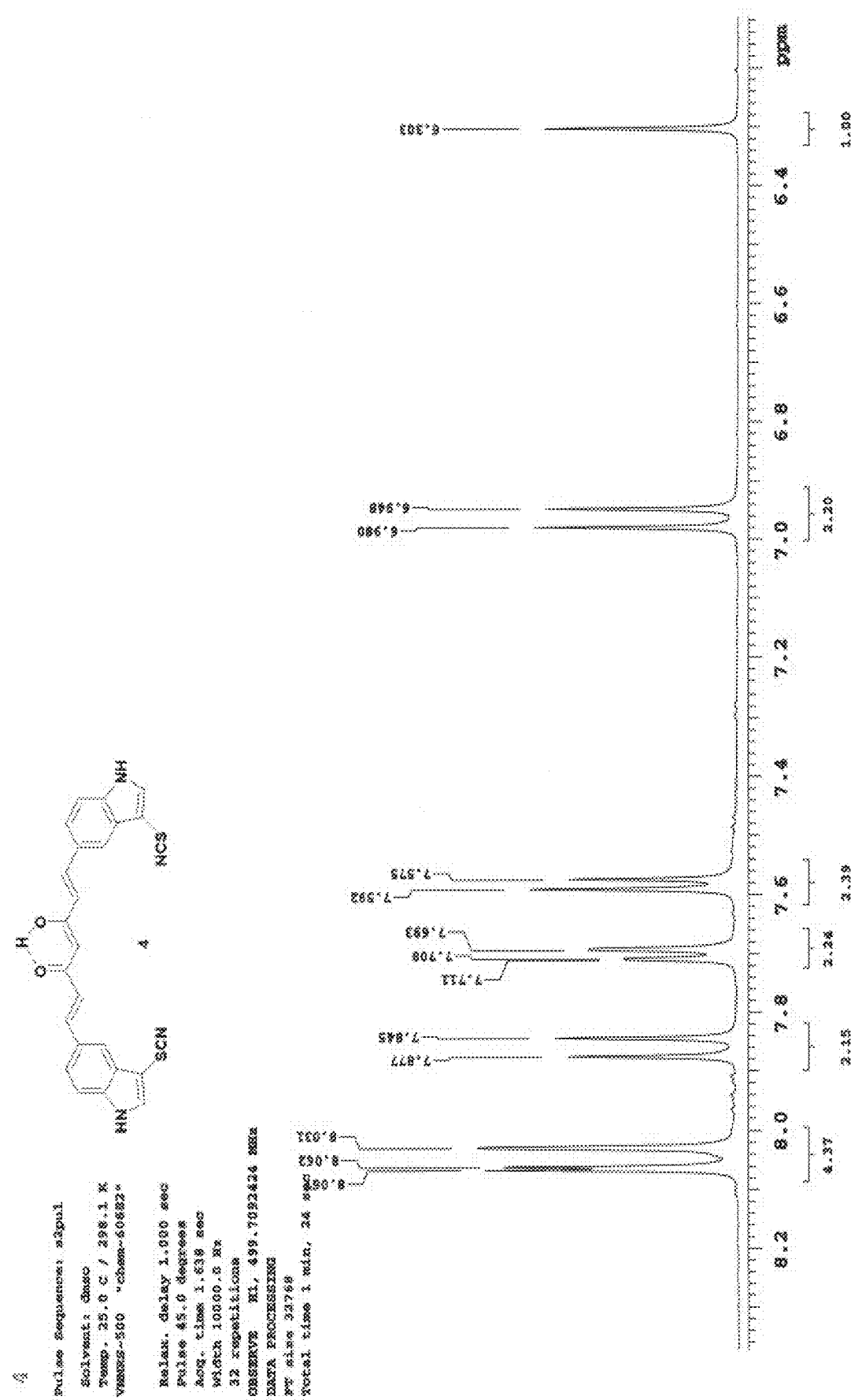

FIG. 75R is representative NMR spectrum for the bioactive compound 4.

Figure 75S:
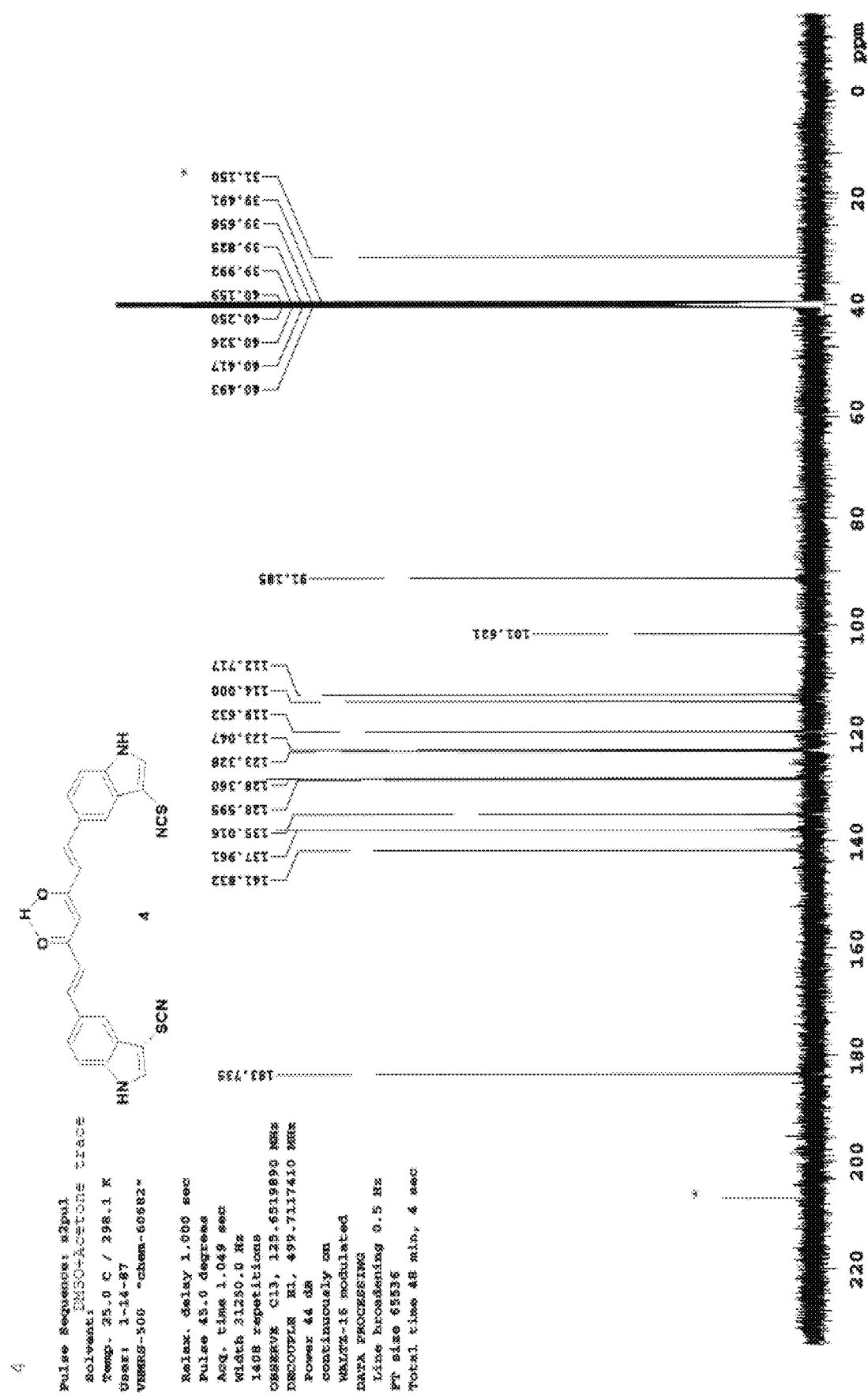

FIG. 75S is representative NMR spectrum for the bioactive compound 4.

Figure 75T:
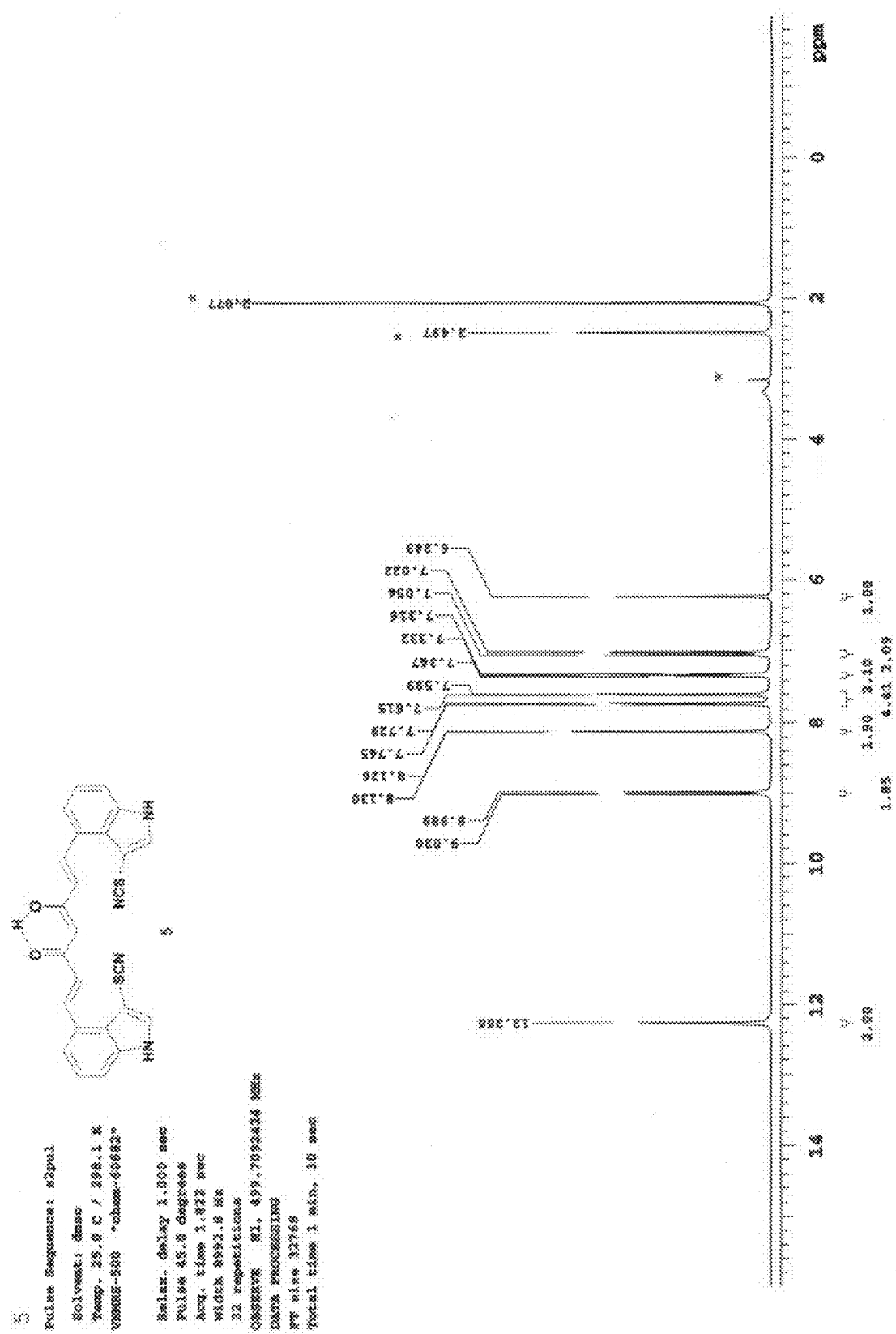

FIG. 75T is representative NMR spectrum for the bioactive compound 5.

Figure 75U:
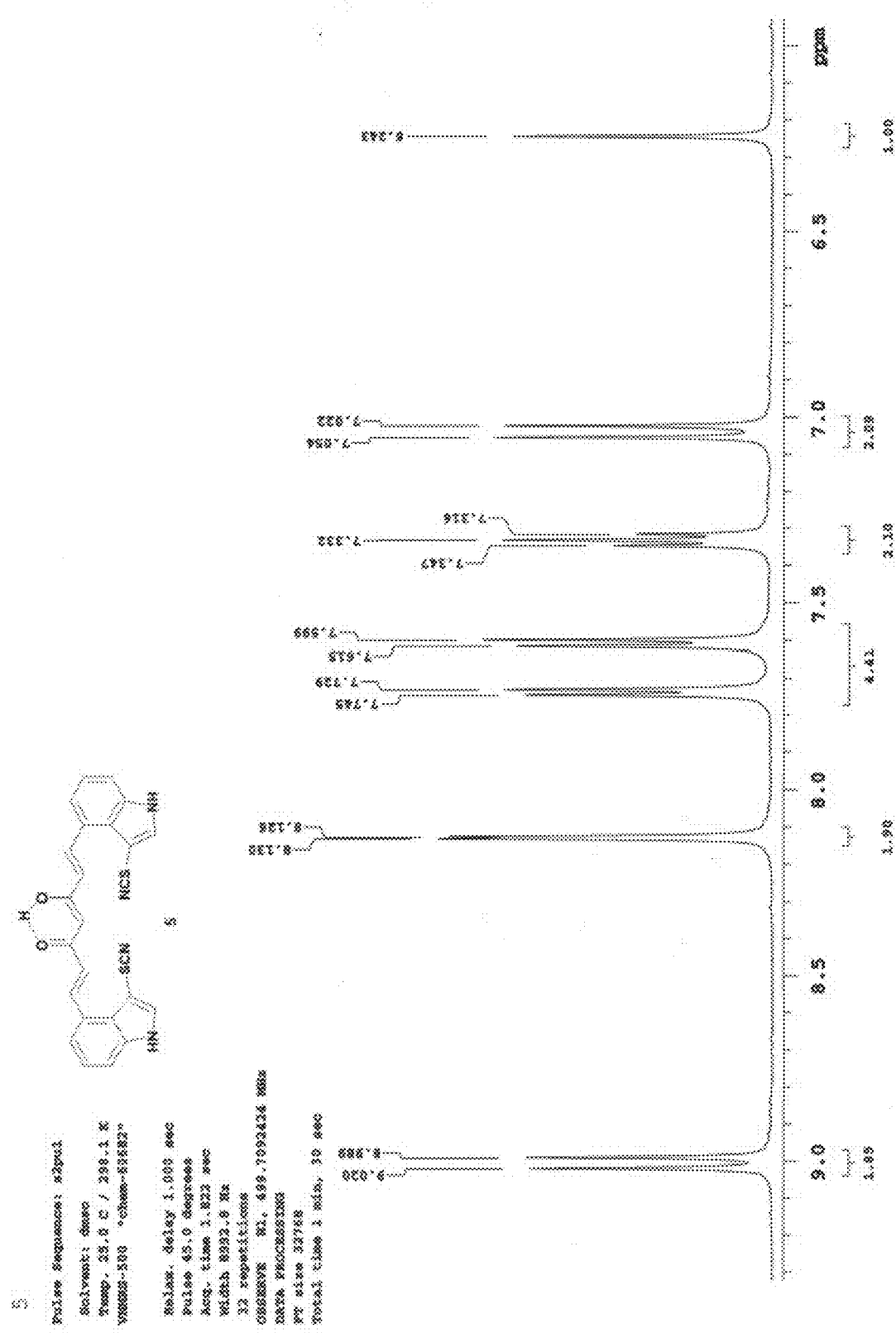

FIG. 75U is representative NMR spectrum for the bioactive compound 5.

Figure 75V:
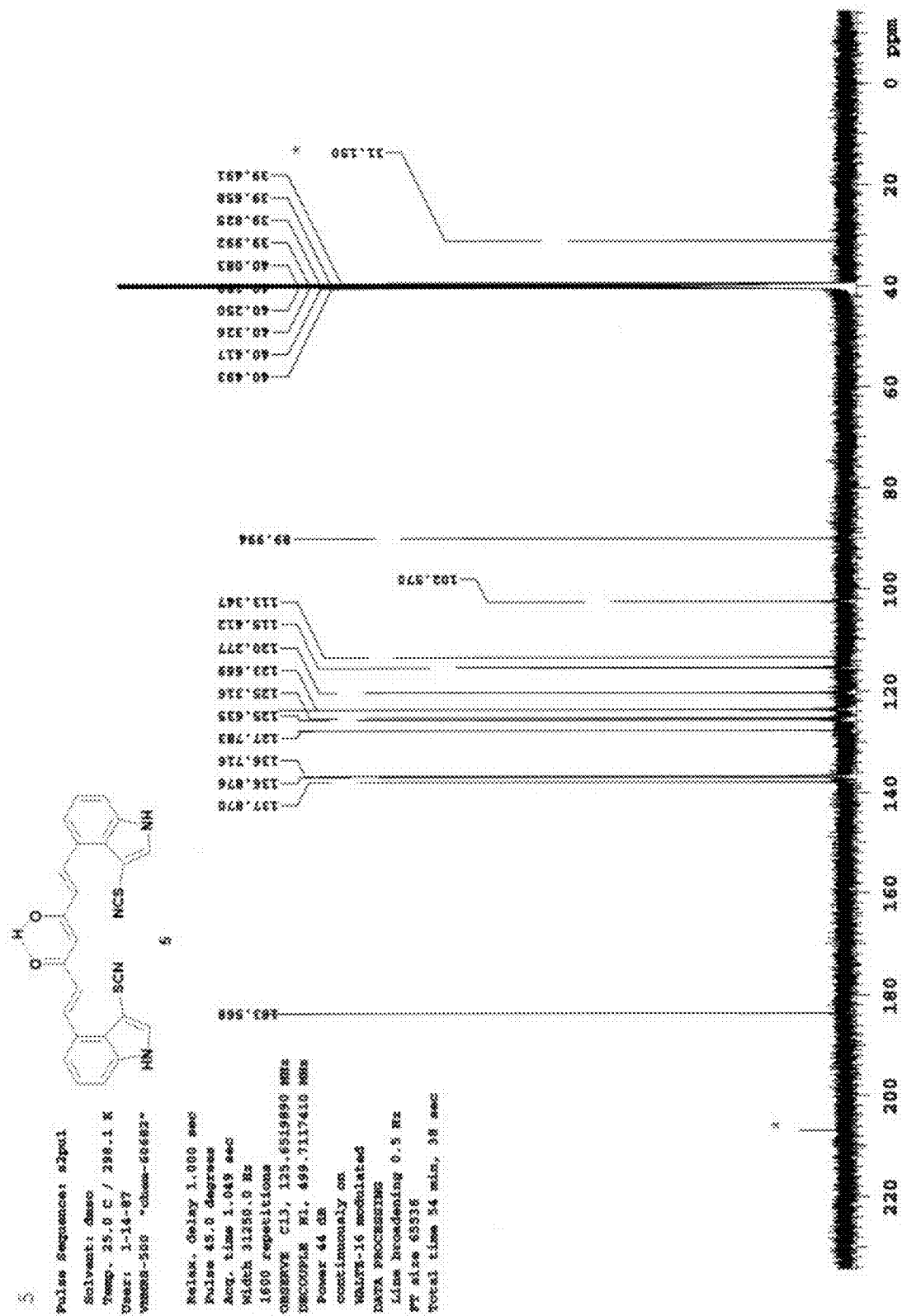

FIG. 75V is representative NMR spectrum for the bioactive compound 5.

Figure 75W:
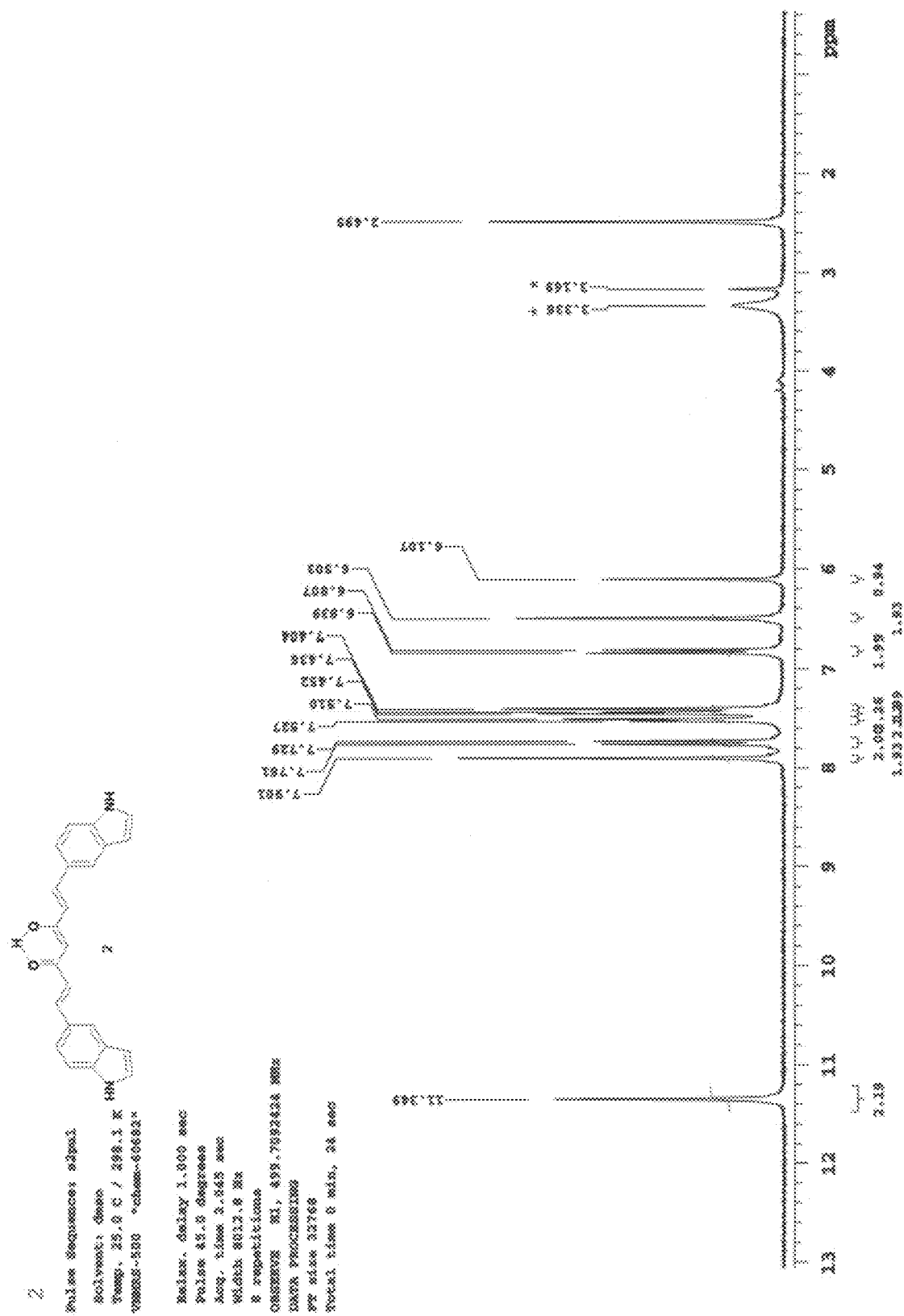

FIG. 75W is representative NMR spectrum for the bioactive compound 2.

Figure 75X:
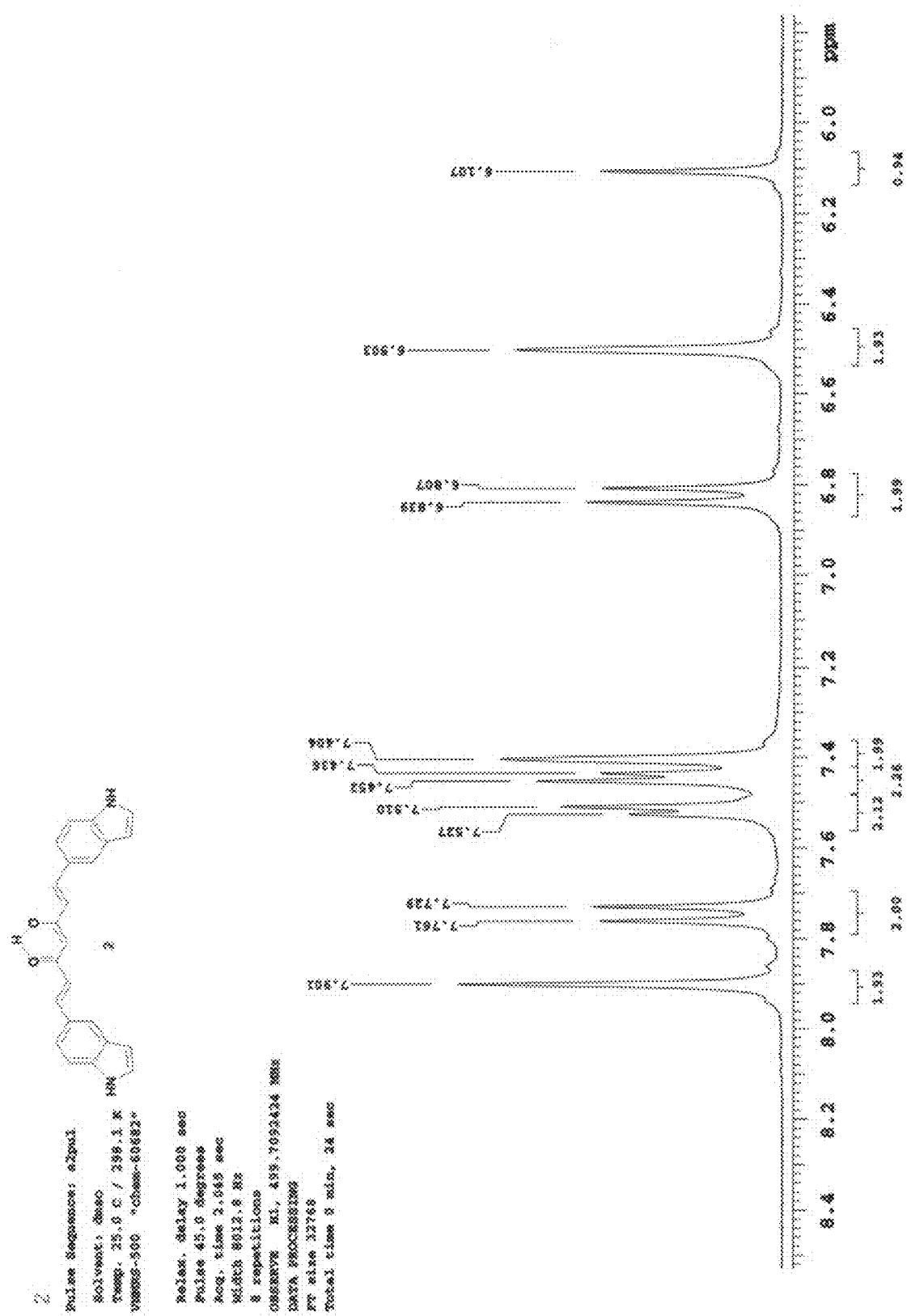

FIG. 75X is representative NMR spectrum for the bioactive compound 2.

Figure 75Y:
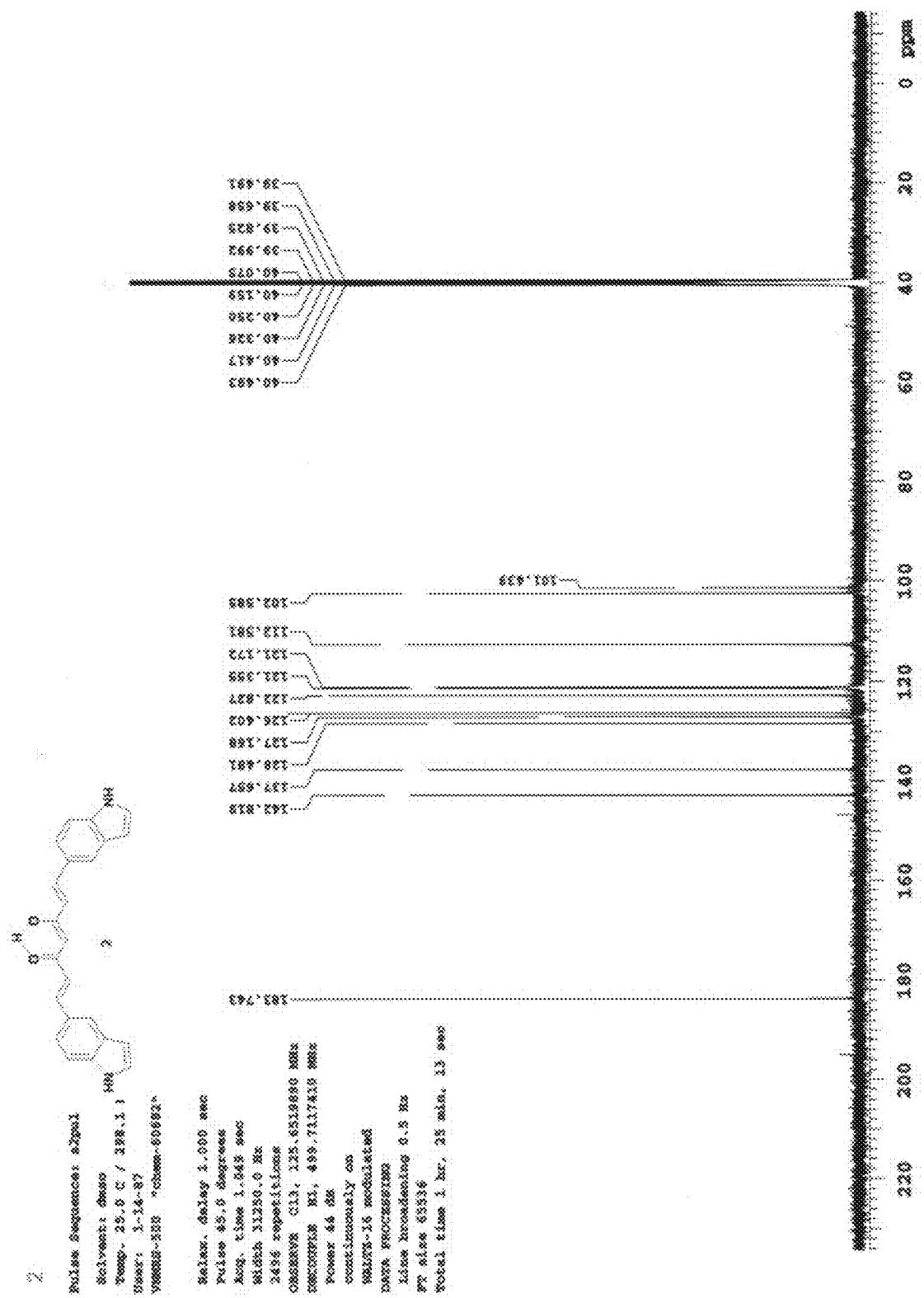

FIG. 75Y is representative NMR spectrum for the bioactive compound 2.

Figure 75Z:
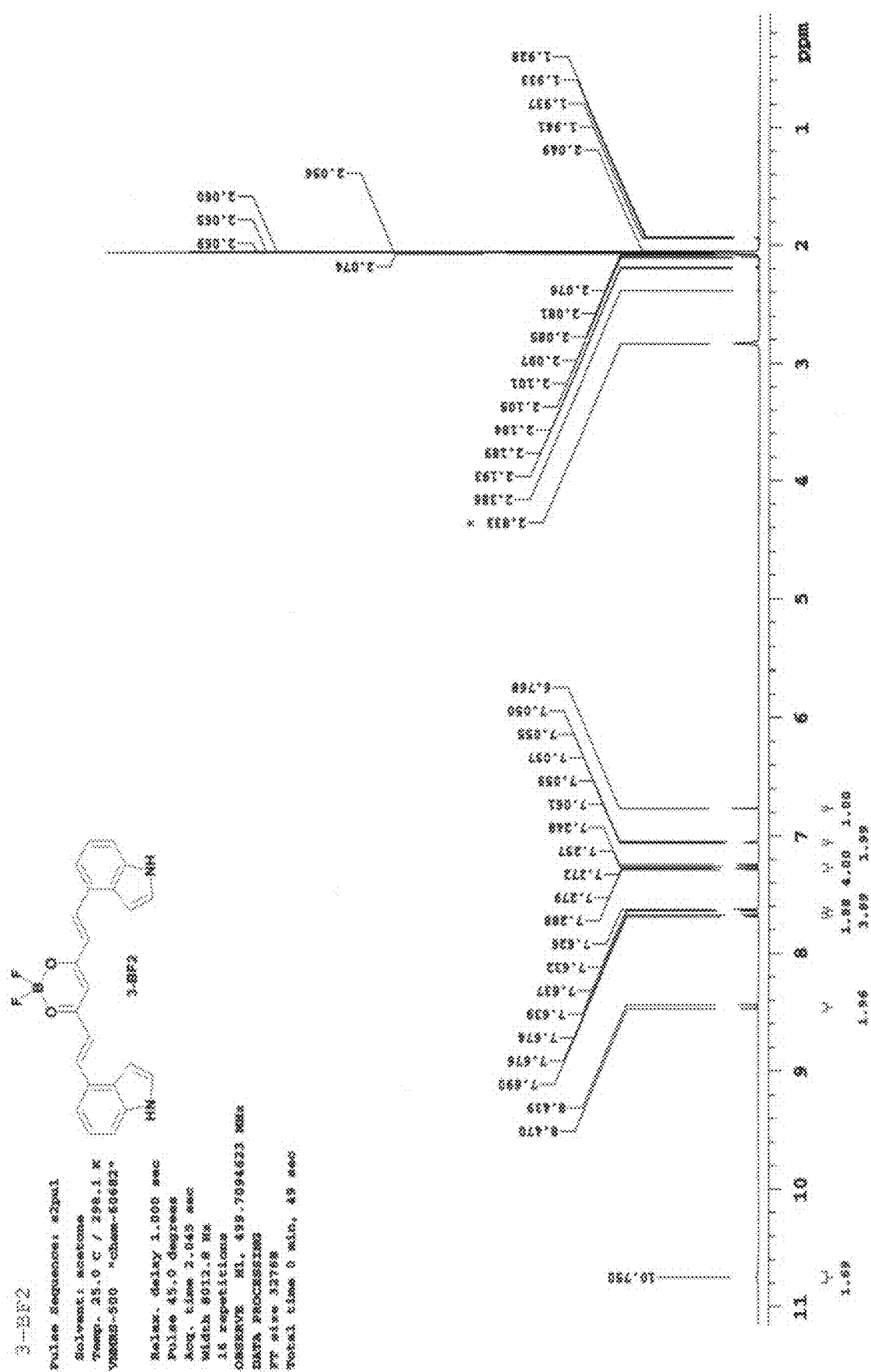
Figure 75A:
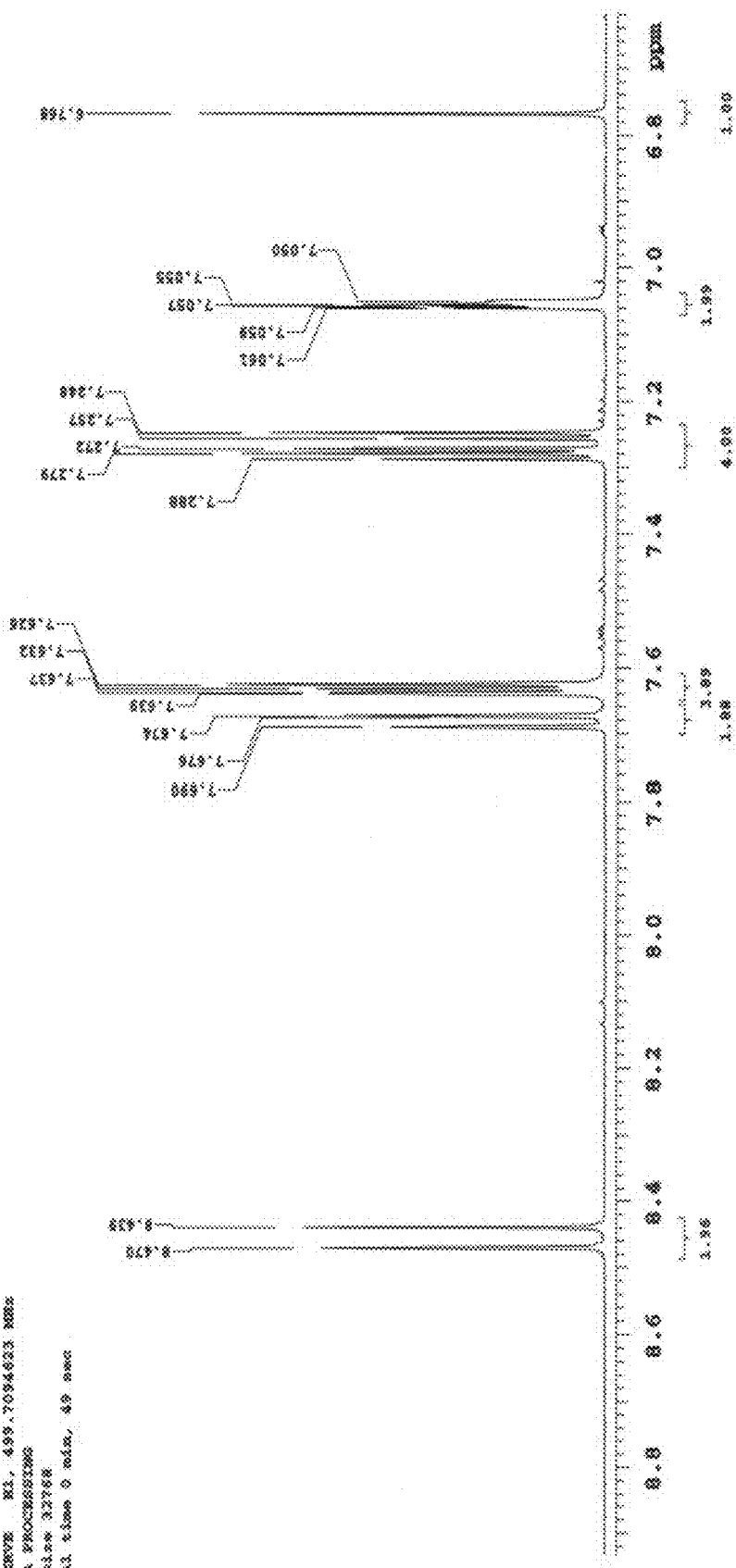
Figure 75B:
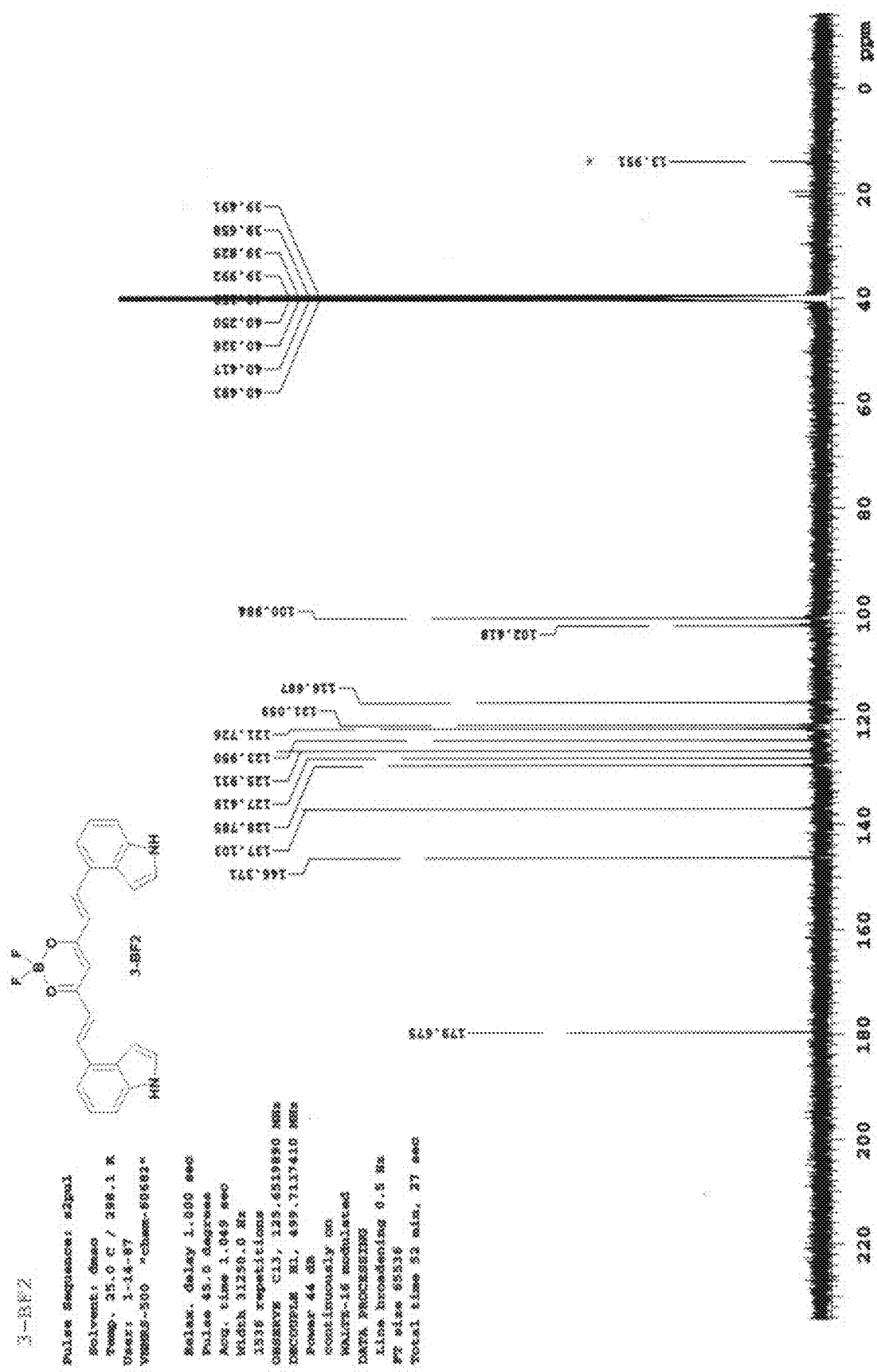

FIG. 75Z is representative NMR spectrum for the bioactive compound 3-BF2.

FIG. 75AA is representative NMR spectrum for the bioactive compound 3-BF2.

FIG. 75BB is representative NMR spectrum for the bioactive compound 3-BF2.

Figure 76:
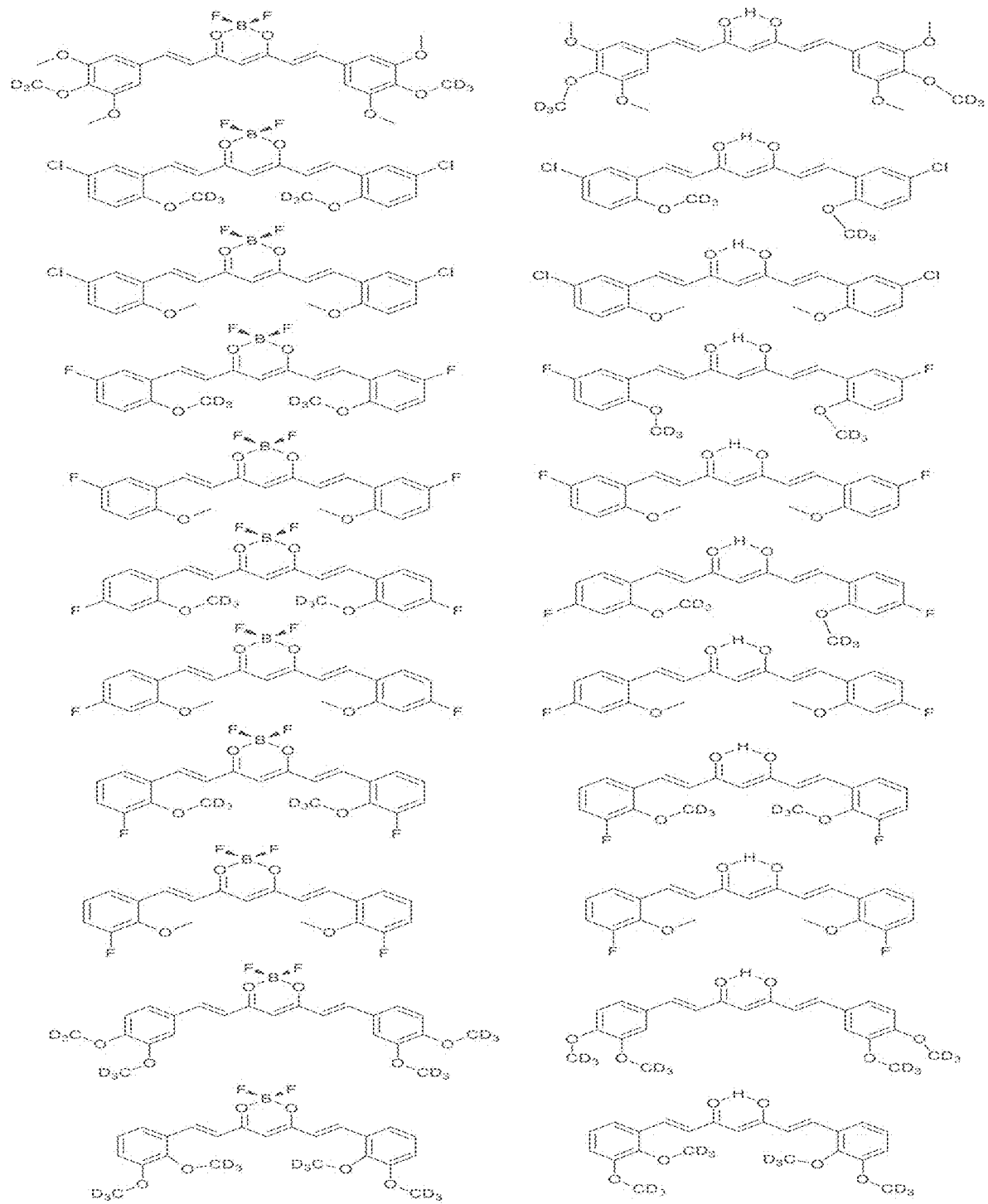

FIG. 76 is an image depicting deuterated versus non-deuterated CUR—$BF_2$ and CUR compounds synthesized for comparative bioactivity study.

Figure 77:
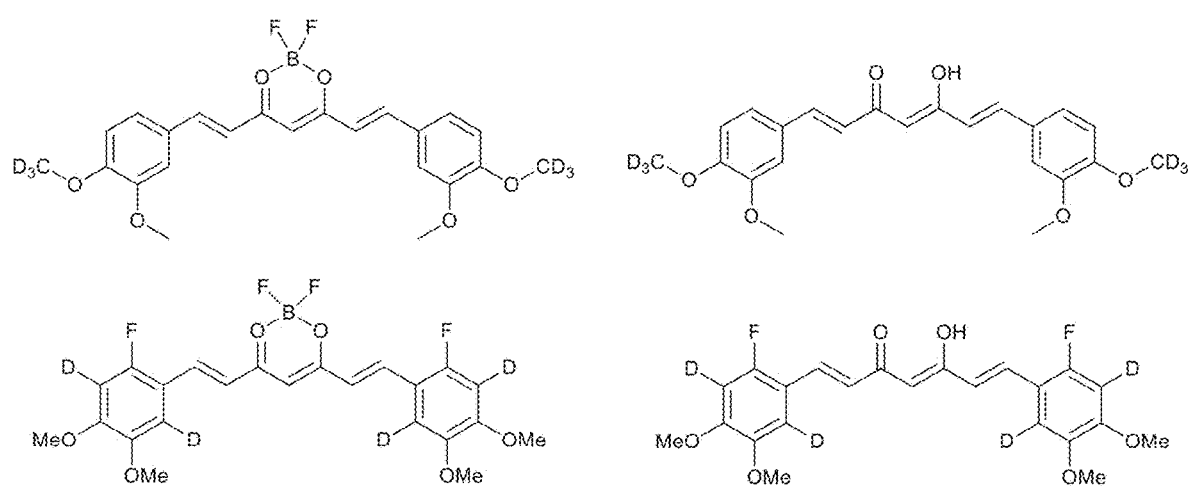

FIG. 77. List of deuterated curcuminoid compounds, and difluoroboron-curcuminoid adducts.

Figure 78:
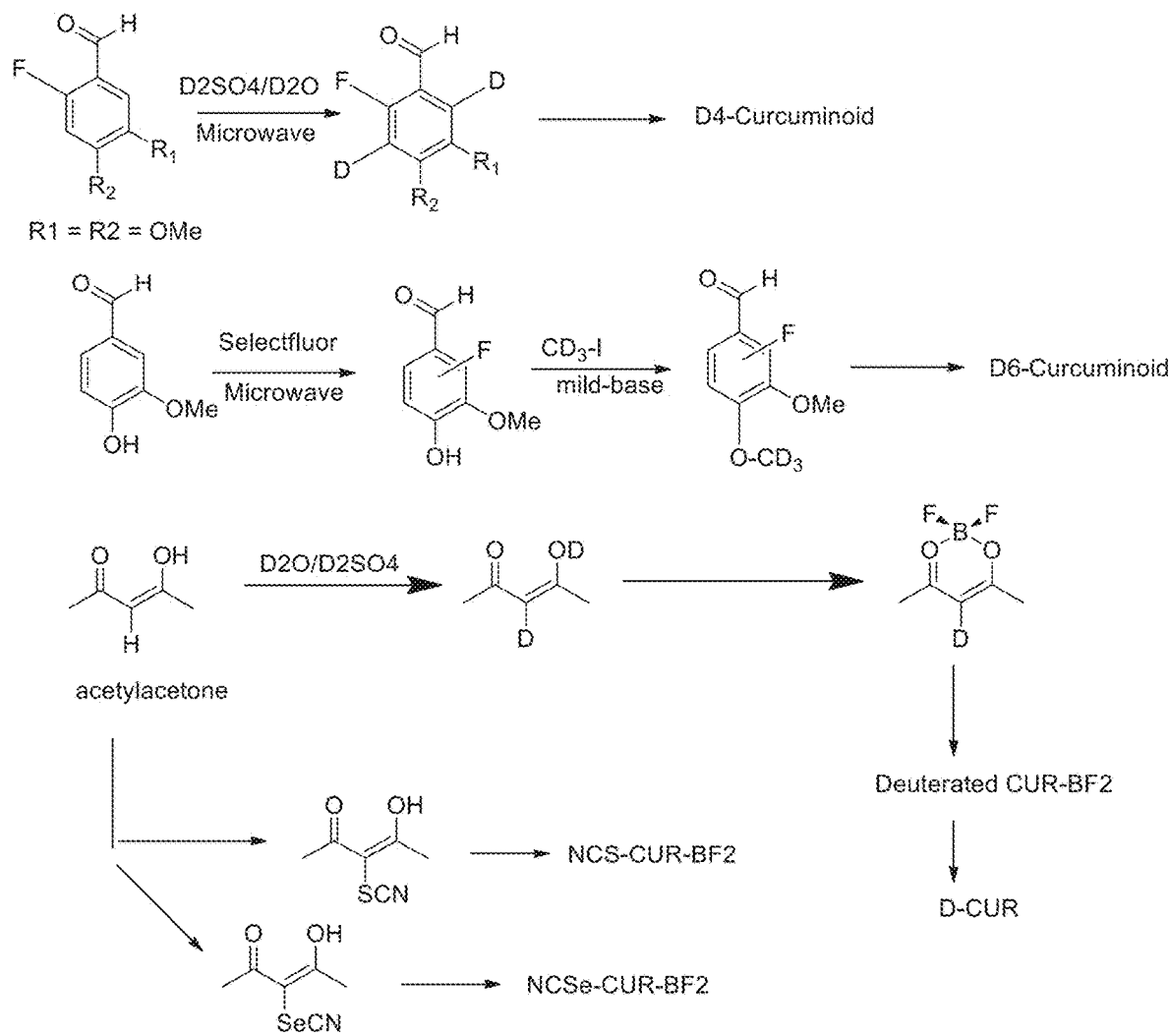

FIG. 78. Reaction scheme to produce deuterated CUR—$BF_2$ compounds and deuterated curcuminoids, and strategies to introduce SCN and SeCN groups into the alpha carbonyl position.

Figure 79:
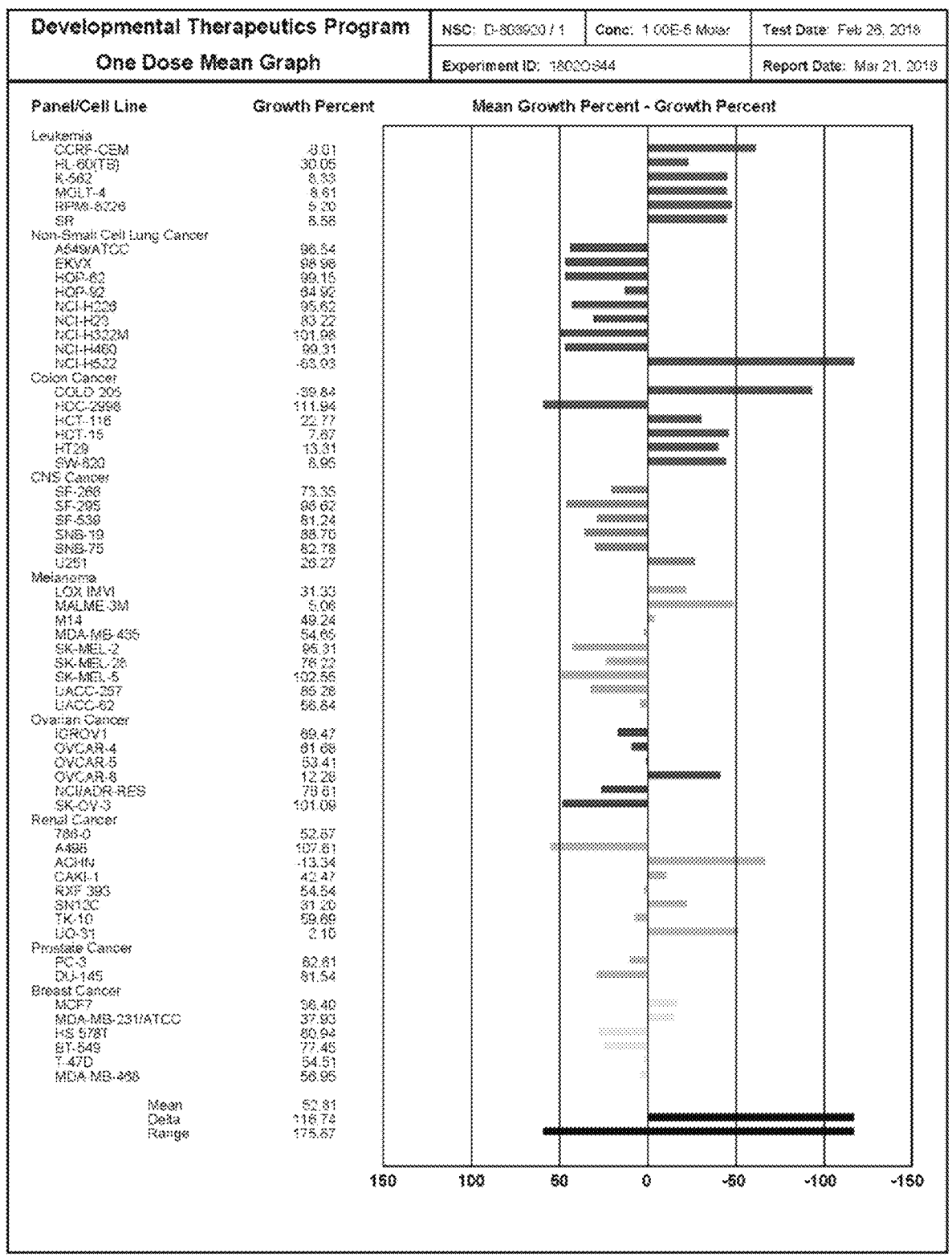

FIG. 79 is a dose mean graph of

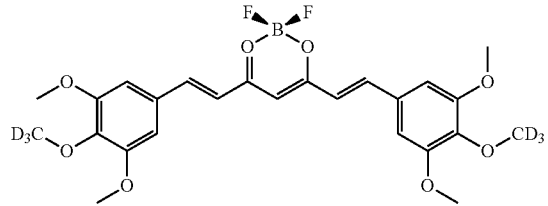

for various cancer cell lines at $1\times10^{-5}$ M.

Figure 80:
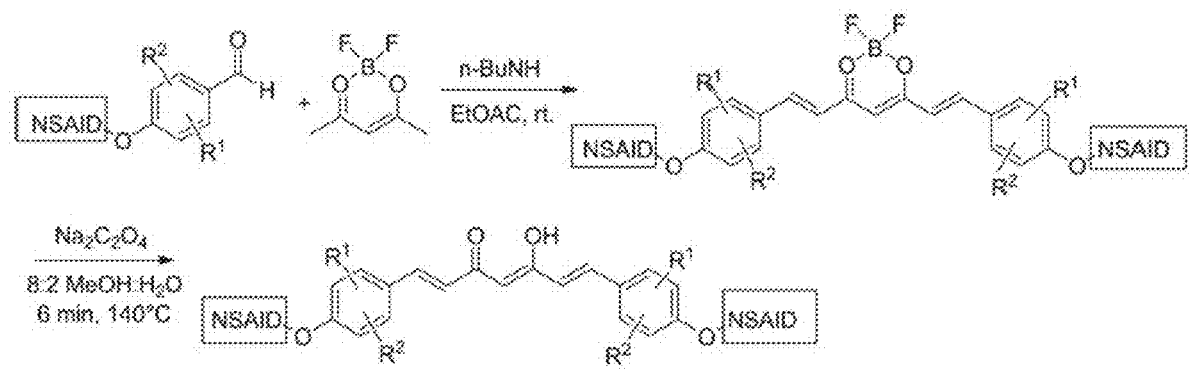

FIG. 80 is an image of Scheme 1 depicting the general procedures for the synthesis of symmetrical bis-NSAID/CUR—$BF_2$->NSAID/CUR. $R^1/R^2$=3,5-dimethoxy and 2,6-dimethoxy; NSAID=flufenamic acid; flurbiprofen; indomethacin; ibuprofen; $R^1$=5–F/$R^2$=H. $R^1/R^2$=3,5 dimethoxy and 2,6-dimethoxy; NSAID—flufenamic acid; flurbiprofen; indomethacin; ibuprofen; $R^1$=5–F/$R^2$=H; NSAID—flufenamic acid.

Figure 81:
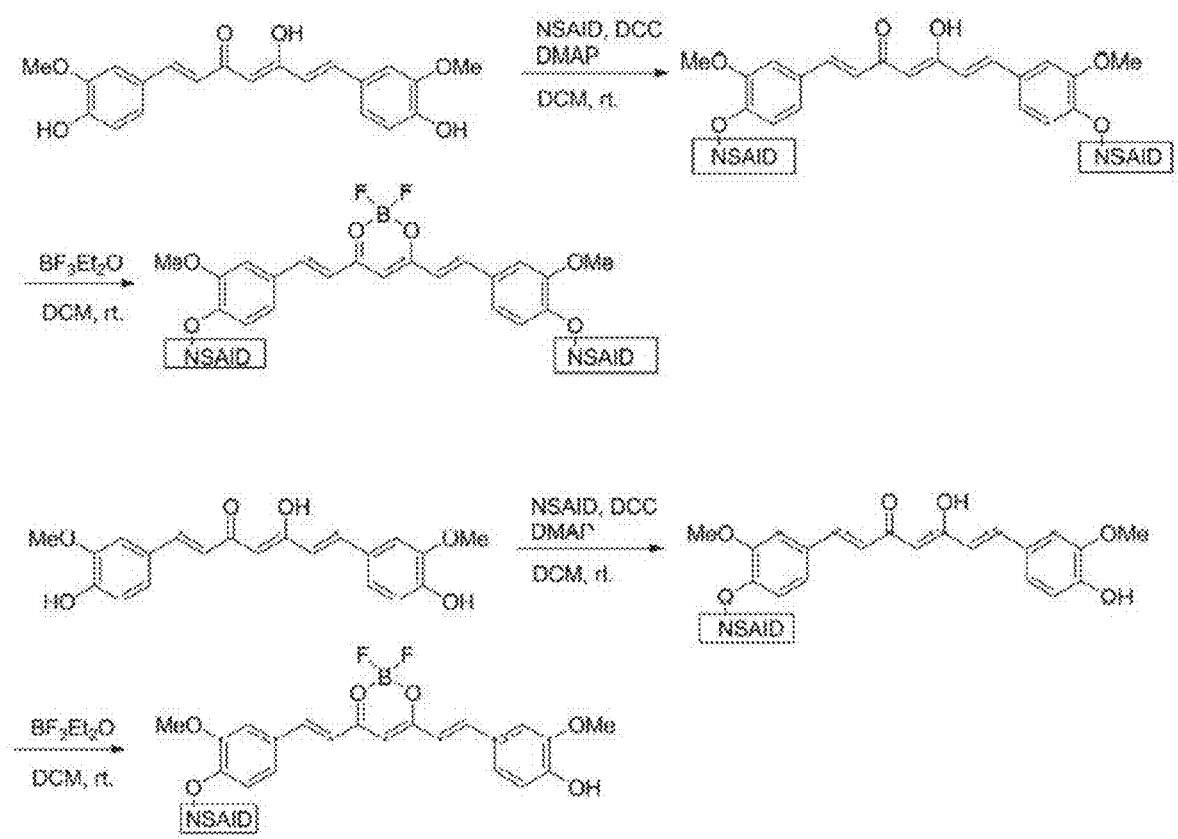

FIG. 81 is an image depicting Scheme 2 synthesis of symmetrical bis-NSAID/CUR->bis-NSAID/CUR—$BF_2$ and mono-NSAID/CUR->mono-NSAID/CUR—$BF_2$. NSAID=flufenamic acid; naproxen, flurbiprofen; ibuprofen.

Figure 82:
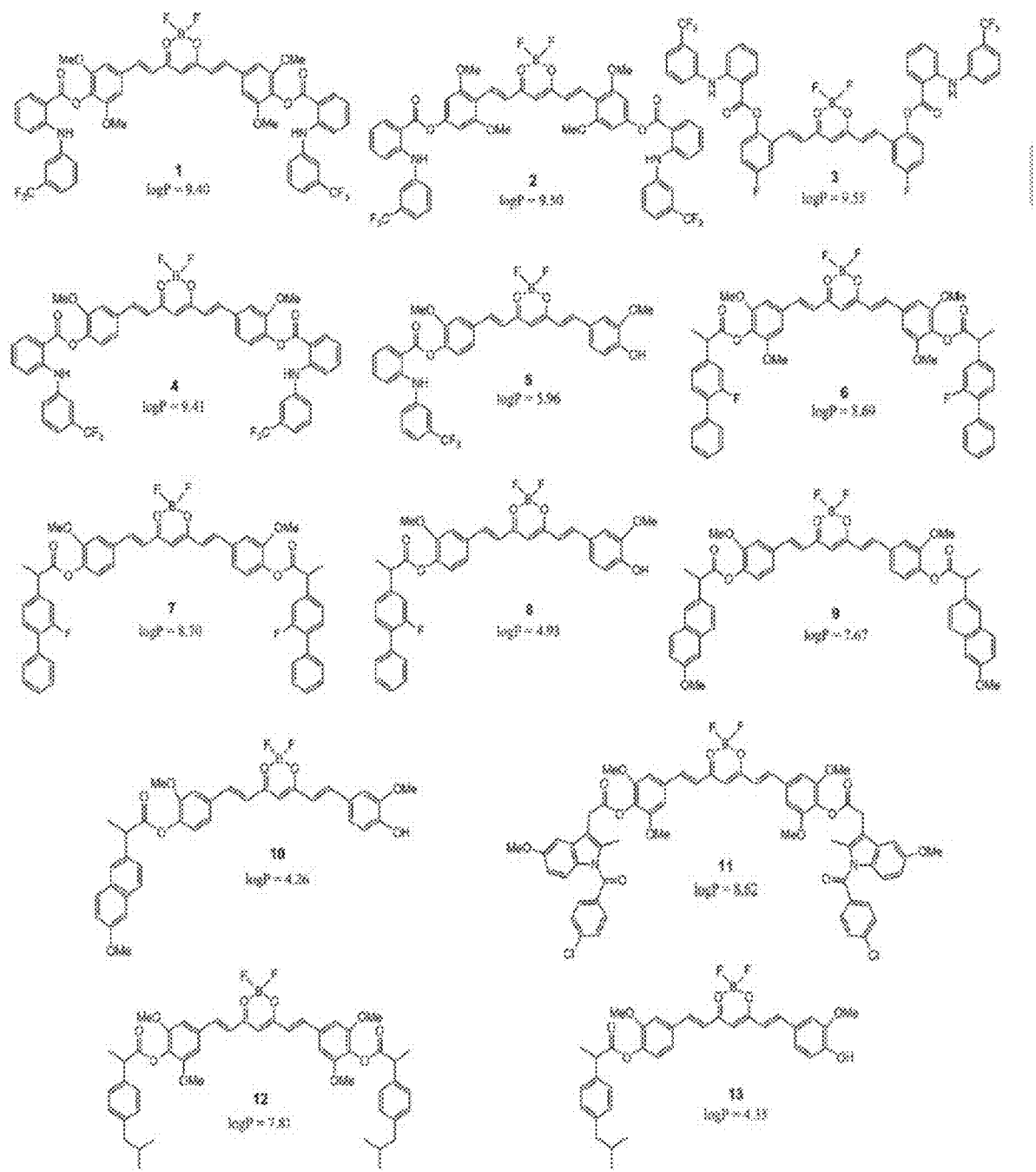

FIG. 82 is a series of images depicting compounds in the NSAID/CUR—$BF_2$ library with calculated log P values (octanol/water partition coefficient).

Figure 83:
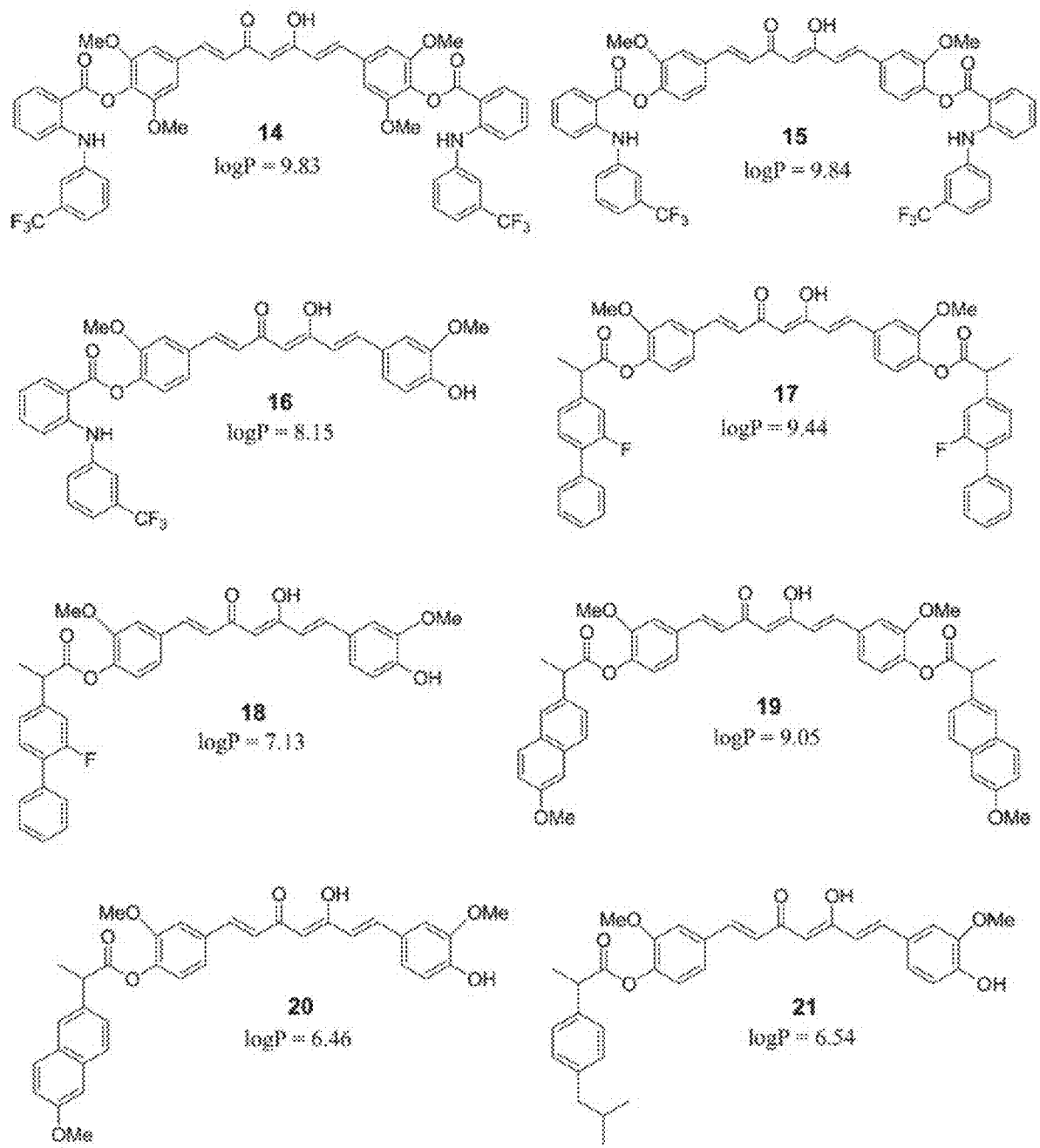

FIG. 83 is a series of images depicting compounds in the NSAID/CUR library with calculated log P values (octanol/water partition coefficient).

FIG. 84A-D are a series of images depicting representative analogs of CUR-NSAID compounds FIG. 85A-F is a series of graphs depicting independent cell viability assay on colorectal cancer (CRC) cells (A) HT29; (B) DLD-1; (C) RKO; (D) SW837; (E) CaCo2; and normal CR cells (F) CCD841CoN. Abbreviations:

FFL=flufenamic acid; IBP=ibuprofen; FL=flubiprofen; IND=indomethacin; M-FFL=compound 16; M-IBP=compound 21; DM4IBP-BF=compound 12; DM4FFL-BF=compound 1; DM4FLB-BF=compound 6; BM4IND-BF=compound 11; 5F2FFL-BF=compound 3; 35DM4FFL=compound 14; 26DM4FFL-BF=compound 2.

Figure 86:
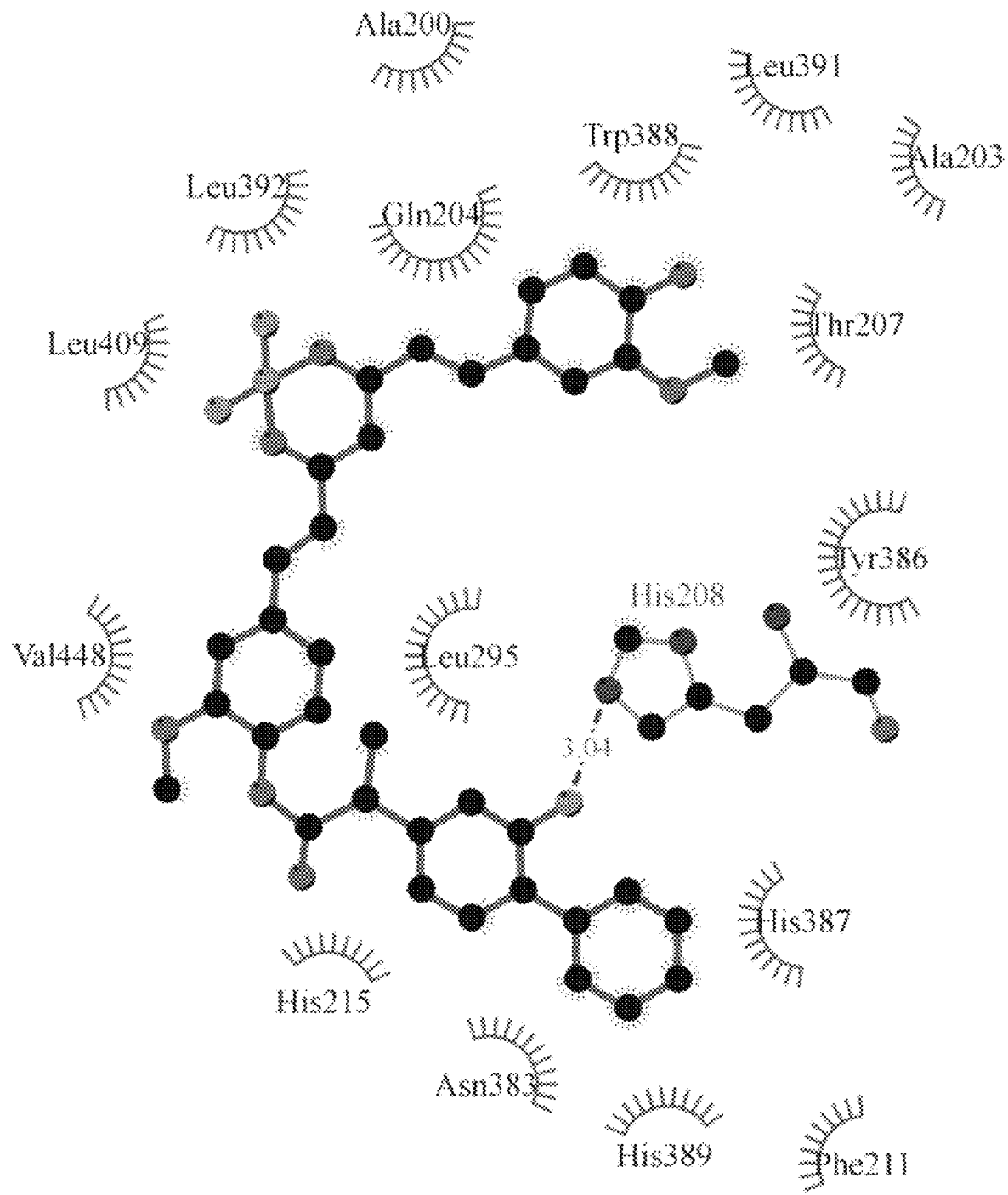

FIG. 86 is an image of a 2D representation of the most favorable binding pose of the mono-NSAID-CUR 8 in the active site of COX-2. The hydrophobic interactions between the ligand atoms and the protein residues are illustrated as red radial lines and the hydrogen bonds as green dotted lines.

Figure 87:
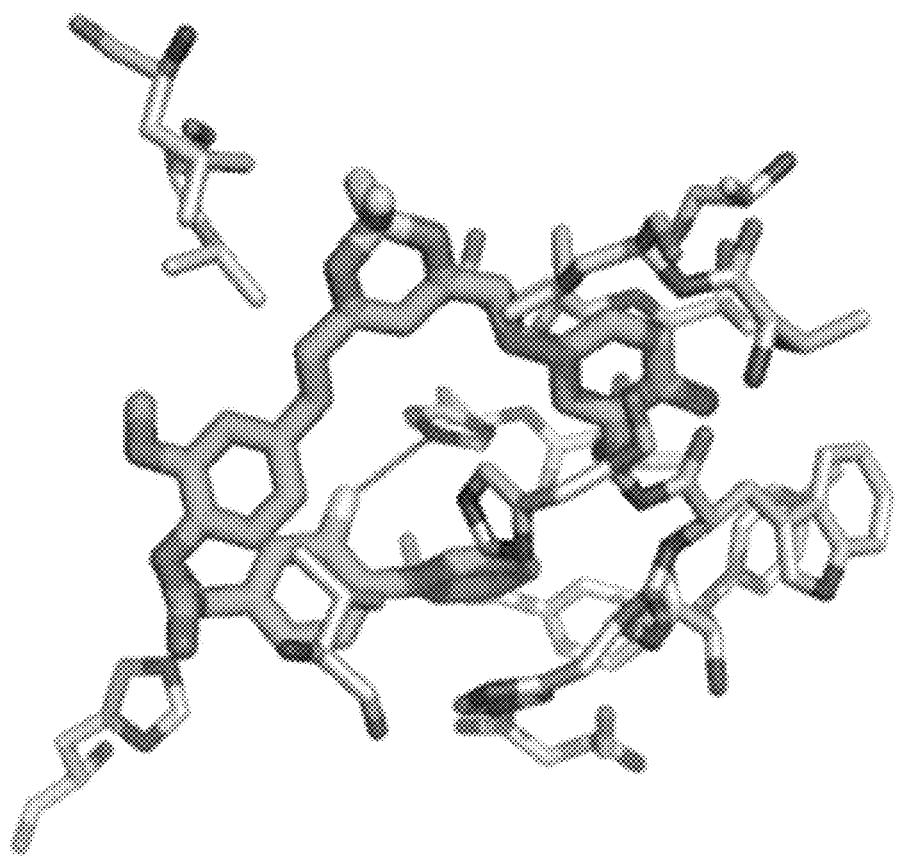

FIG. 87 is a 3D representation of the most favorable binding mode of compound 8 in the active site of COX-2. Hydrogen-bond interactions are depicted as green lines.

Figure 88:
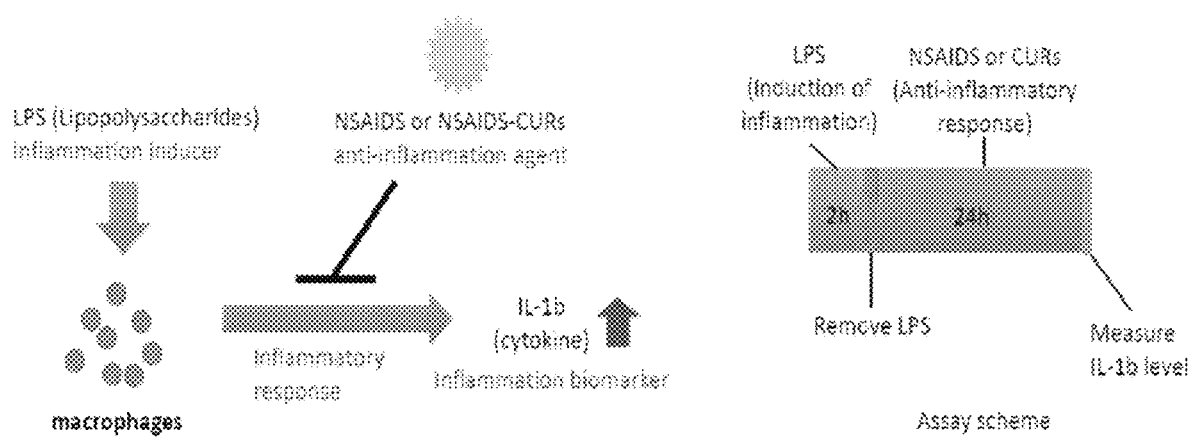

FIG. 88 is a schematic depicting the inflammatory response assay scheme.

Figure 89:
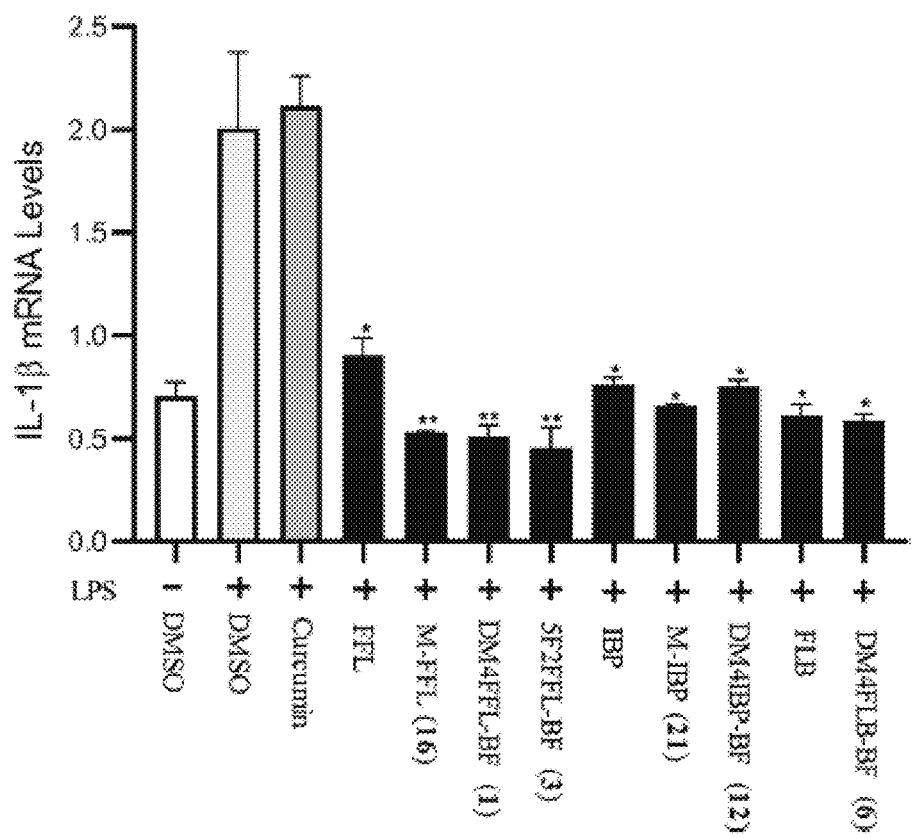

FIG. 89 is a table depicting an inflammation assay. THP-1 cells were treated with LPS (100 ng/ml) for two hours. After the induction of inflammatory response by LPS treatment, cells were treated with DMSO or CUR compounds (10 µM) for 24 hours. The IL-1β expression levels were normalized using the β-actin gene expression. Error bars represent SEM. Each groups contained more than two samples. * significantly different relative to LPS-treated controls ($p<0.05$), ** significantly different relative to LPS/flufenamic acid-treated samples. Abbreviations: FFL: flufenamic acid; IBP: ibuprofen; FLB: flurbiprofen; M-FFL: compound 16; M-IBP: compound 21; DM4IBP-BF: compound 12; DM4FFL-BF: compound 1; DM4FLB-BF: compound 6; 5F2FFL-BF: compound 3.

Figure 90:
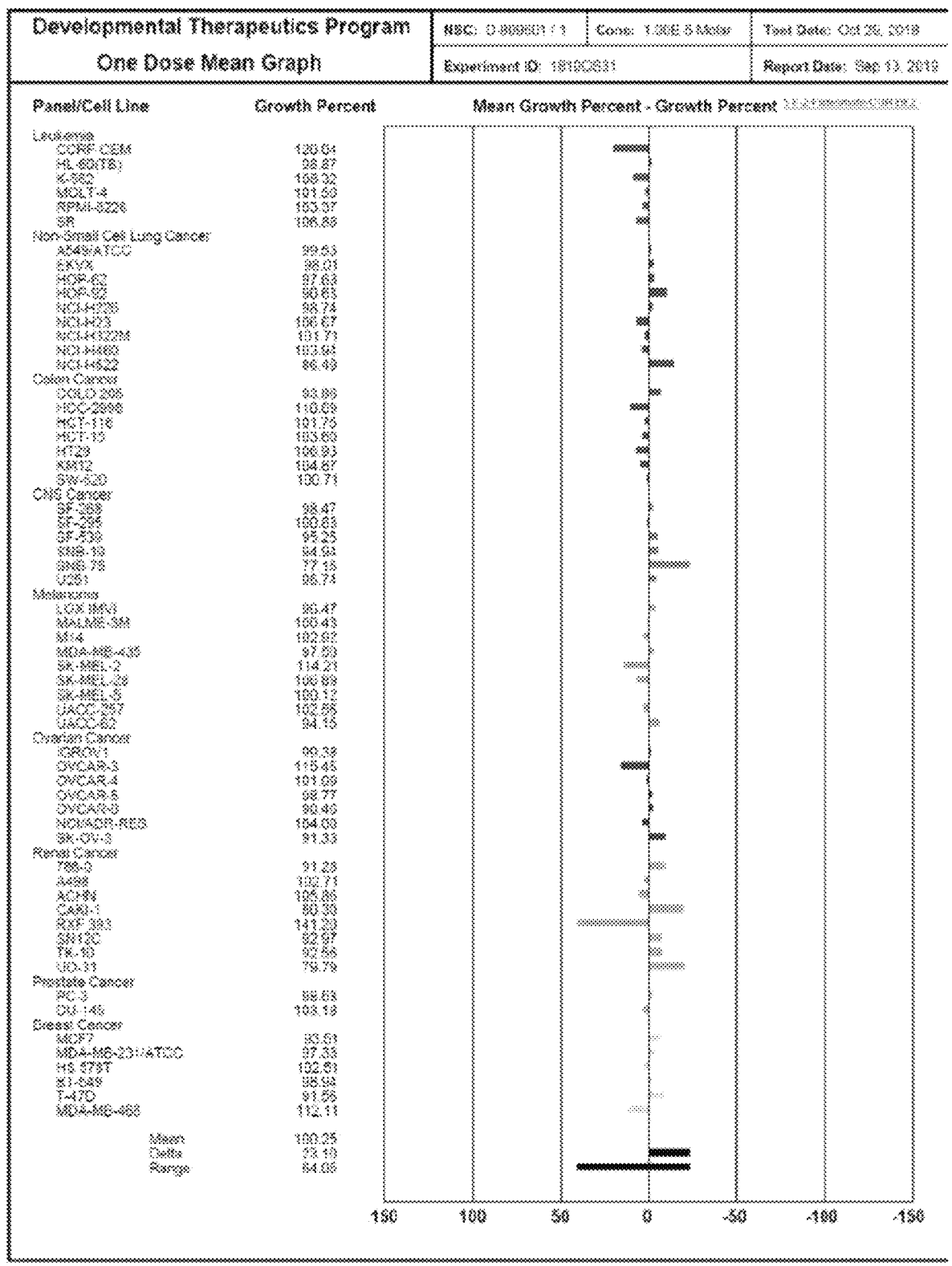

FIG. 90 is a dose mean graph depicting NCI-60 data for compound 3 of Example 7.

Figure 91:
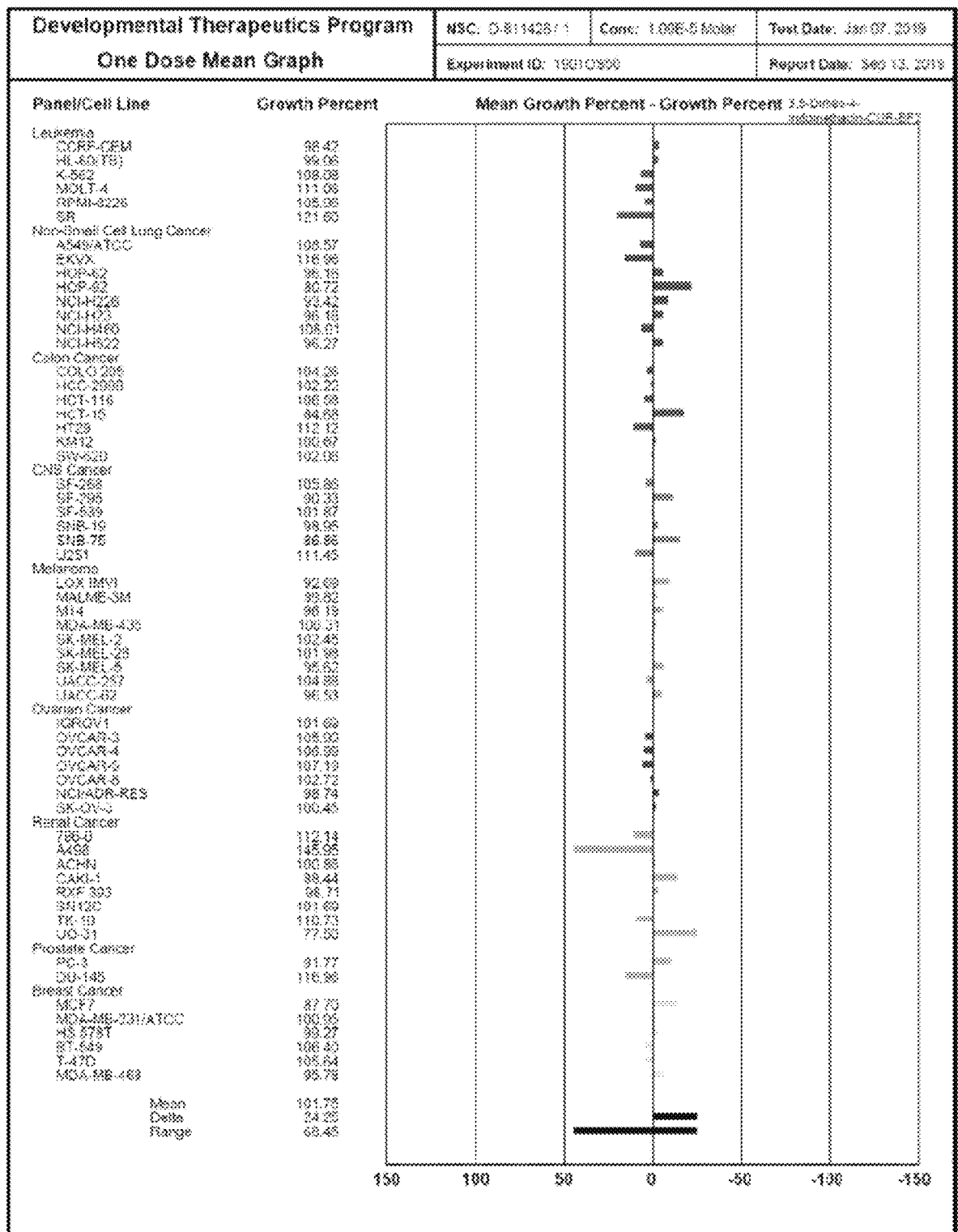

FIG. 91 is a dose mean graph depicting NCI-60 data for compound 11 of Example 7.

Figure 92:
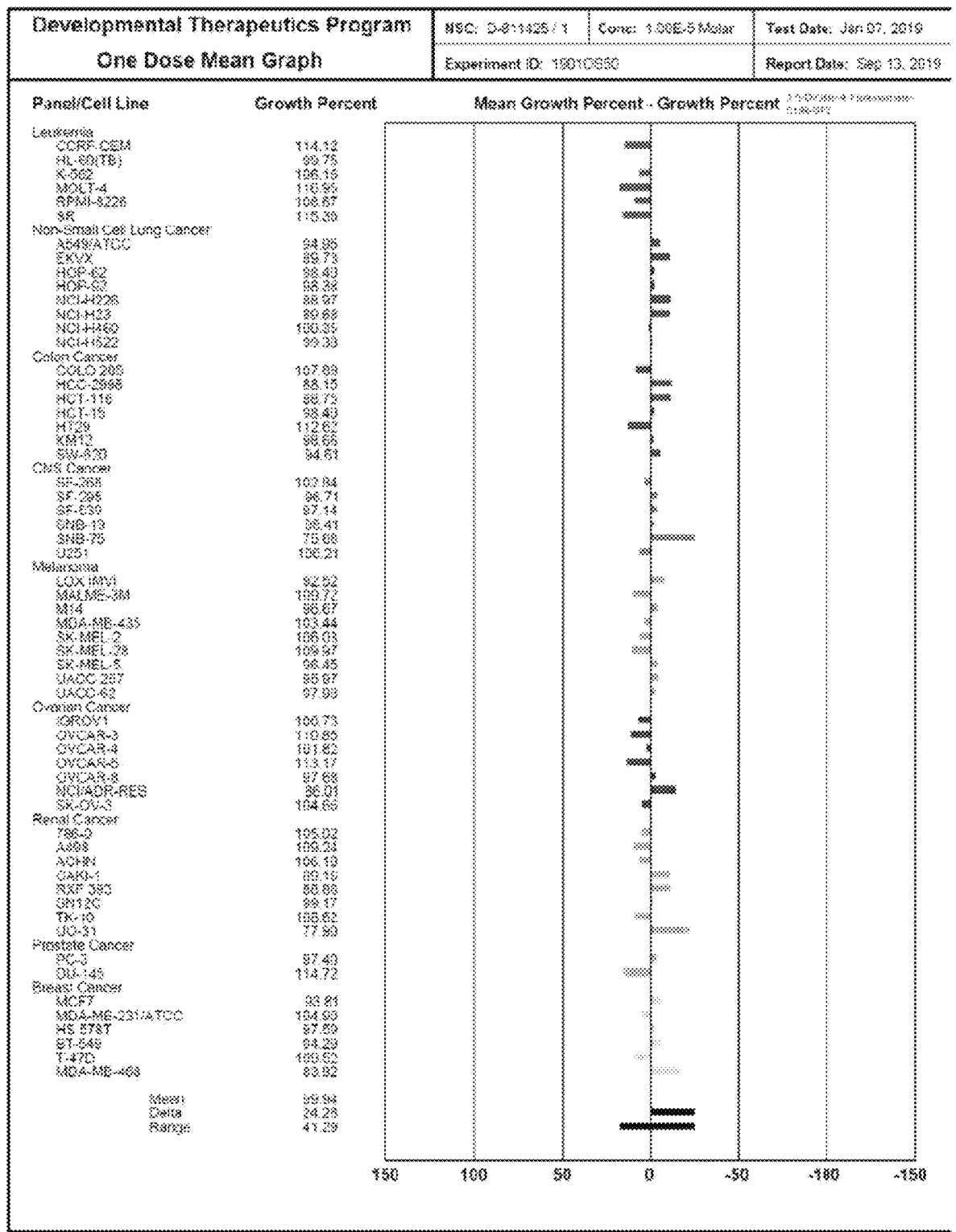

FIG. 92 is a dose mean graph depicting NCI-60 data for compound 1 of Example 7.

Figure 93:
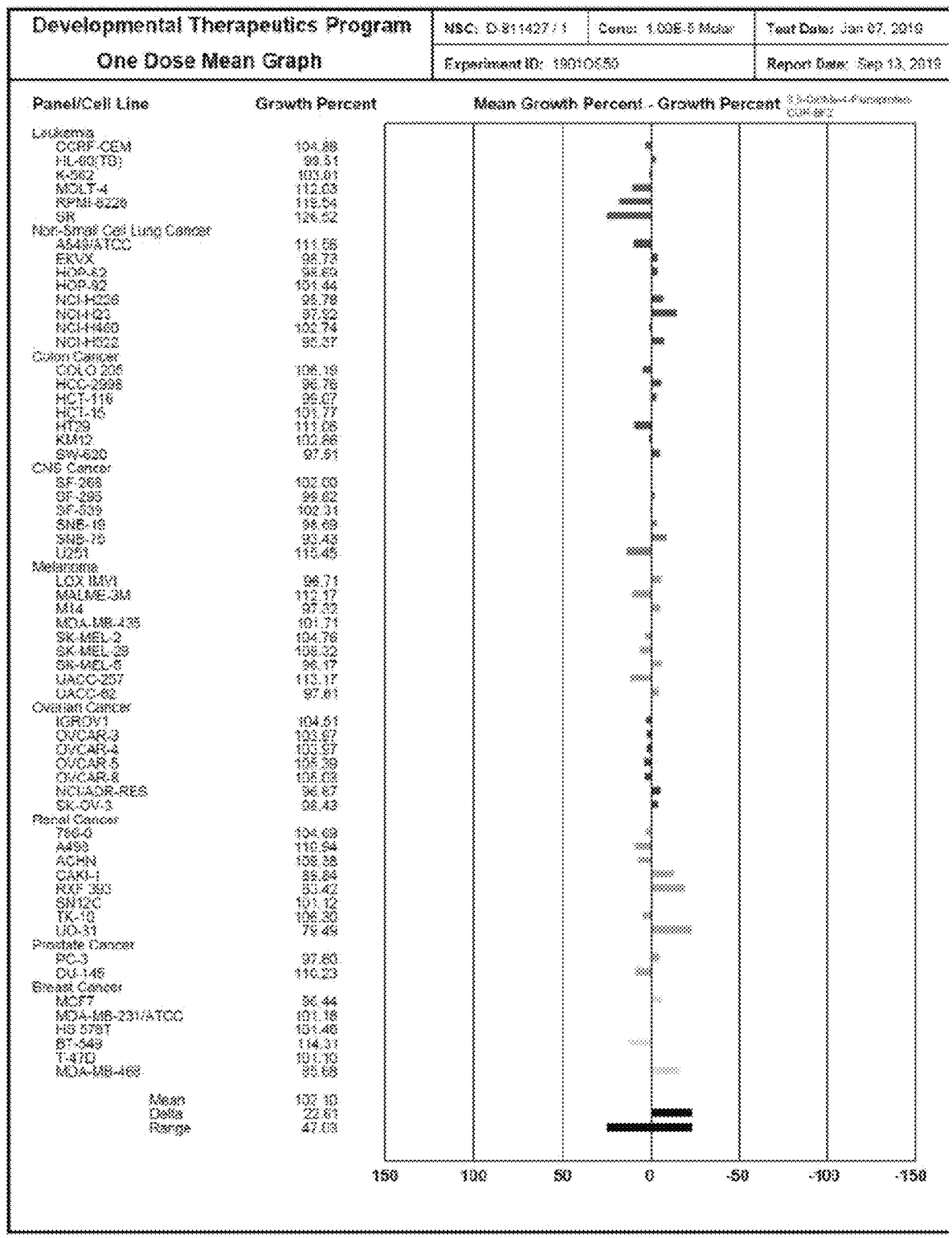

FIG. 93 is a dose mean graph depicting NCI-60 data for compound 6 of Example 7.

Figure 94:
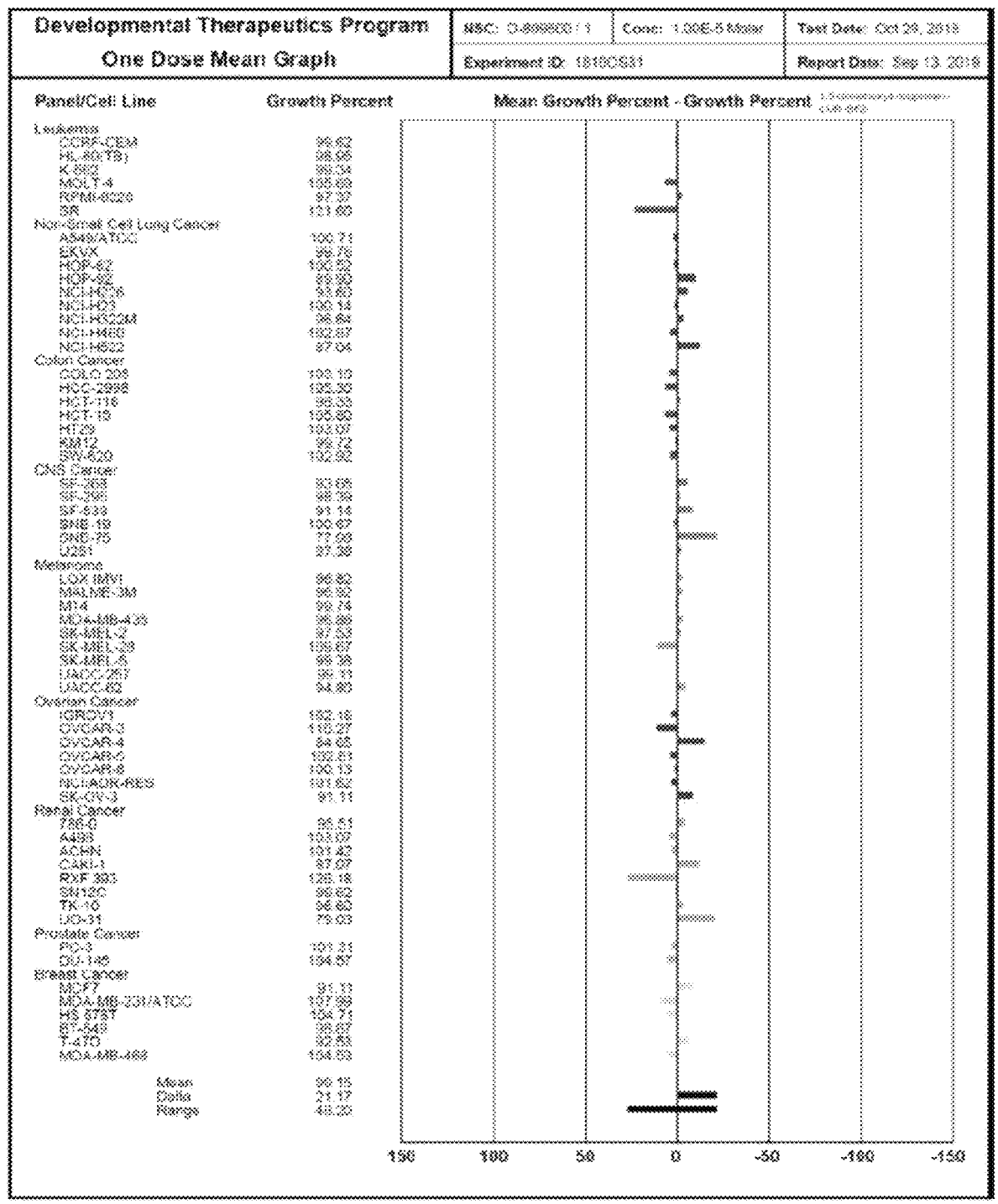

FIG. 94 is a dose mean graph depicting NCI-60 data for compound 12 of Example 7.

Figure 95:
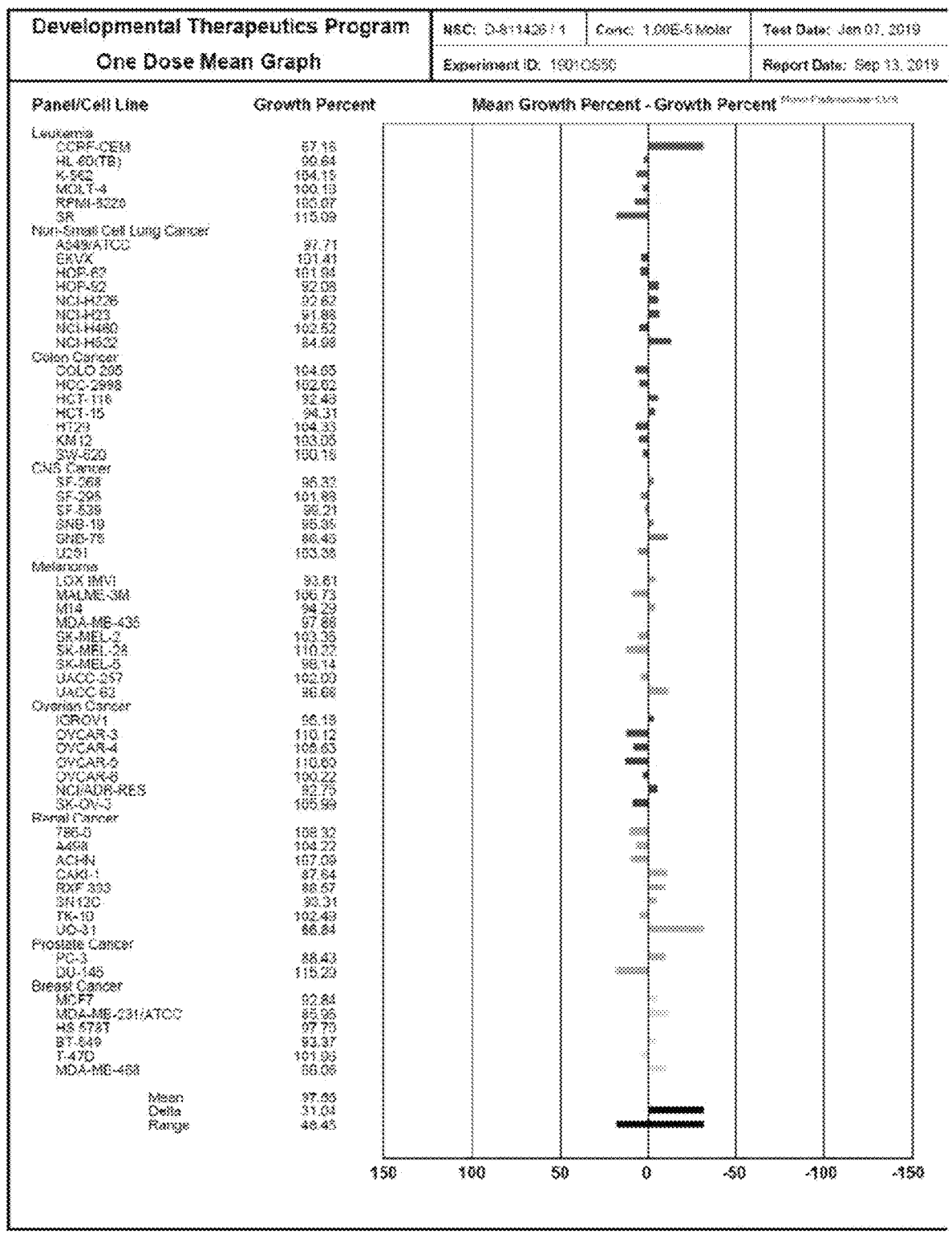

FIG. 95 is a dose mean graph depicting NCI-60 data for compound 16 of Example 7.

Figure 96:
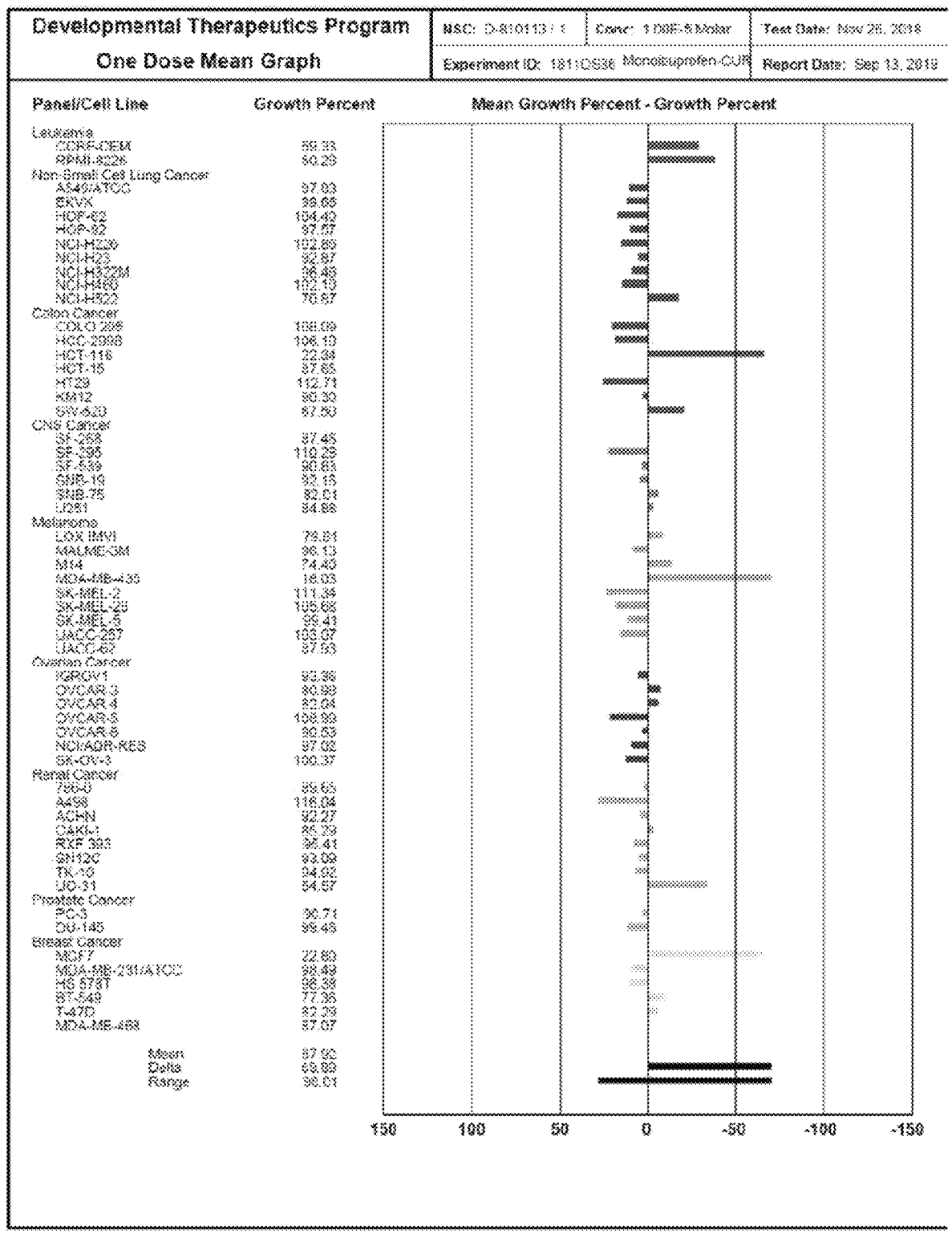

FIG. 96 is a dose mean graph depicting NCI-60 data for compound 21 of Example 7.

Figure 97:
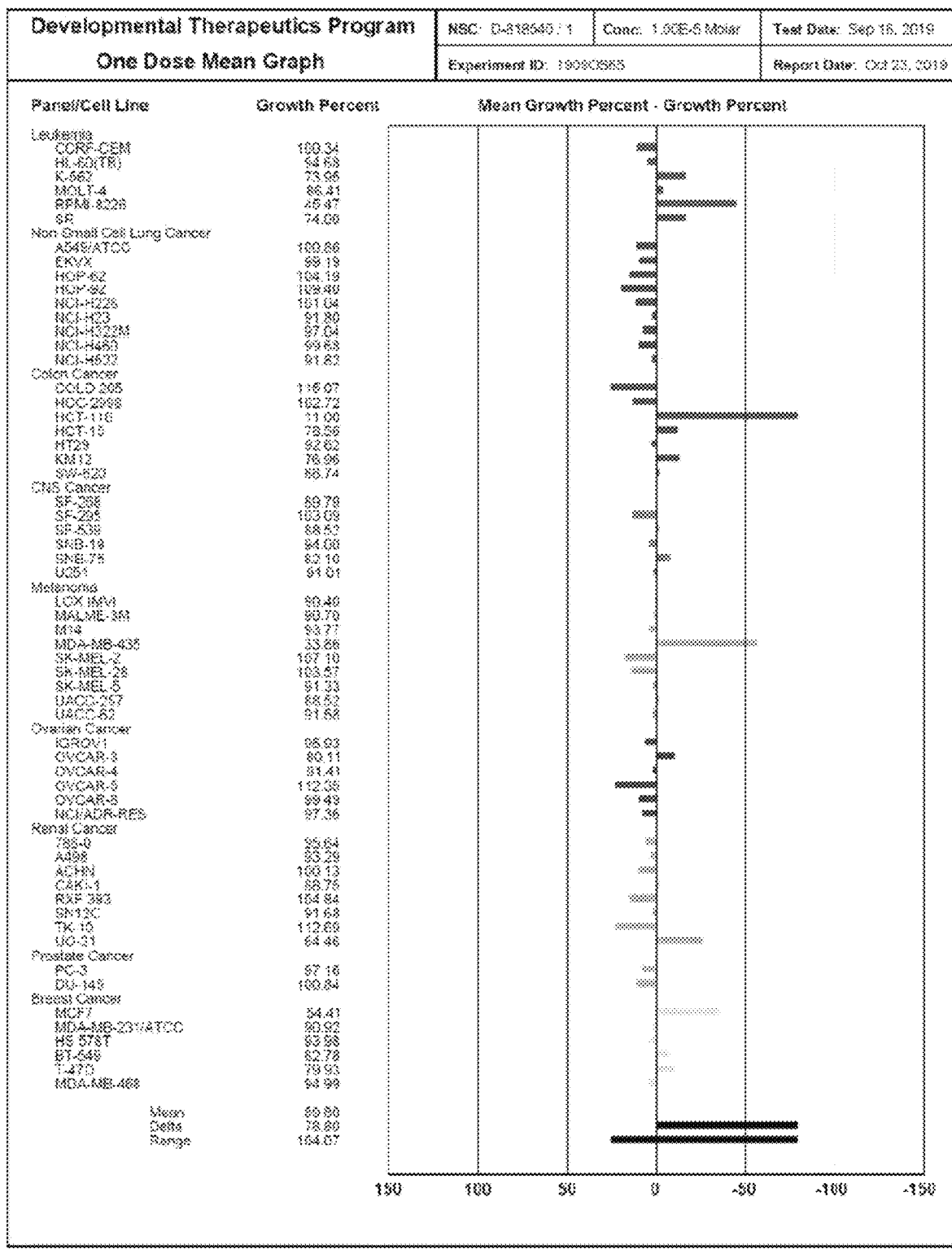

FIG. 97 is a dose mean graph depicting NCI-60 data for compound 20 of Example 7.

Figure 98:
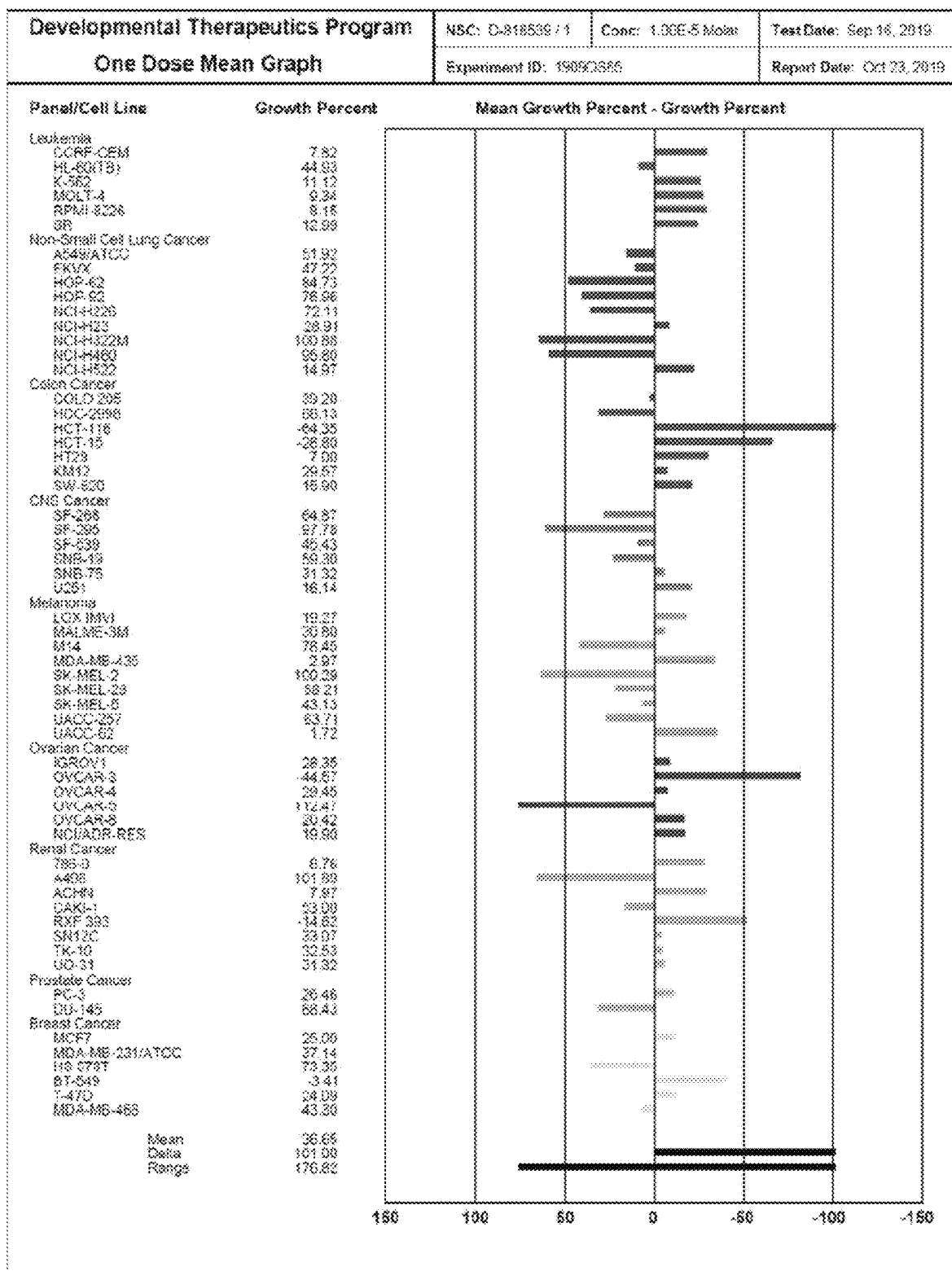

FIG. 98 is a dose mean graph depicting NCI-60 data for compound 10 (one dose assay) of Example 7.

Figure 99:
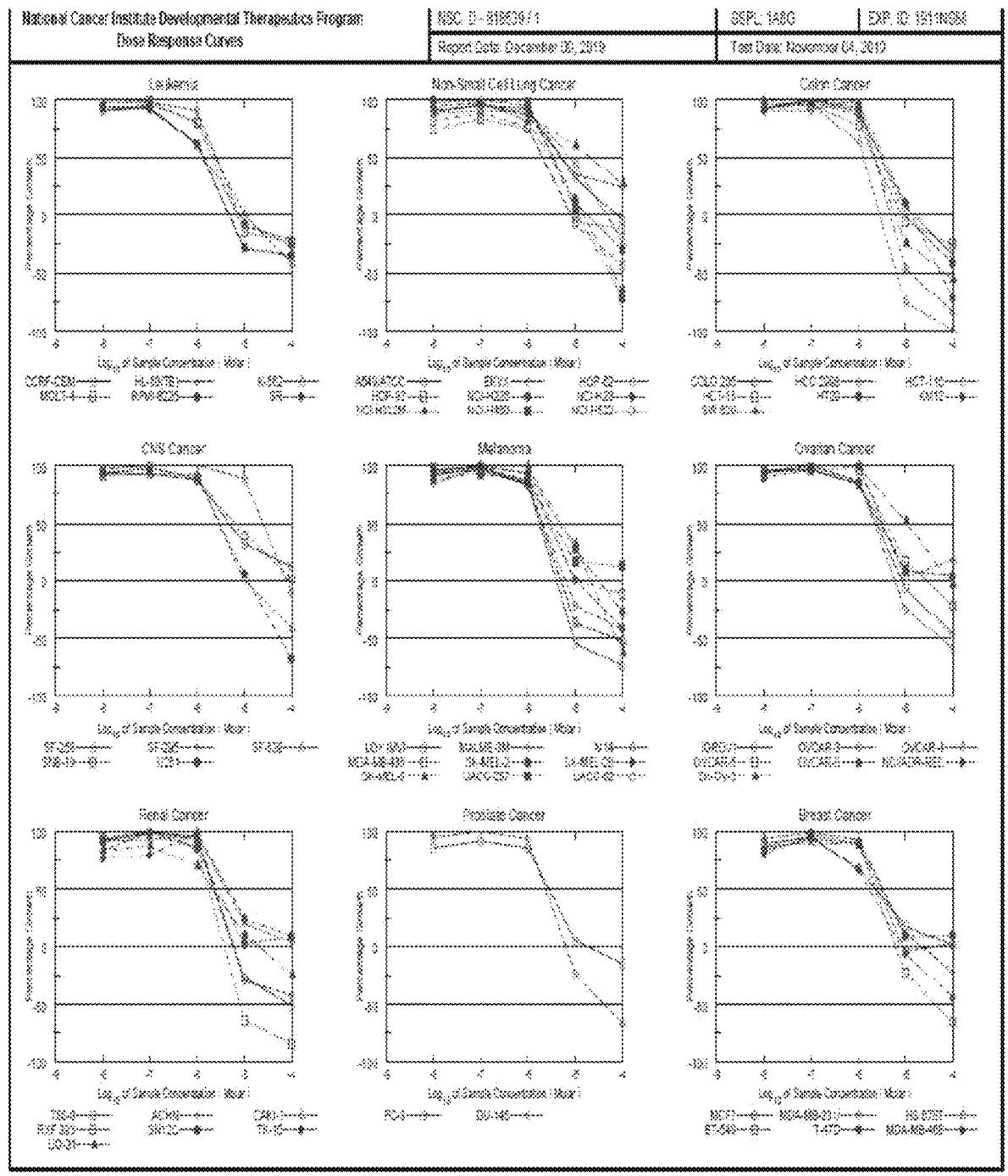

FIG. 99 is a series of graphs depicting NCI-60 data for compound 10 (five-dose assay) of Example 7.

Figure 100:
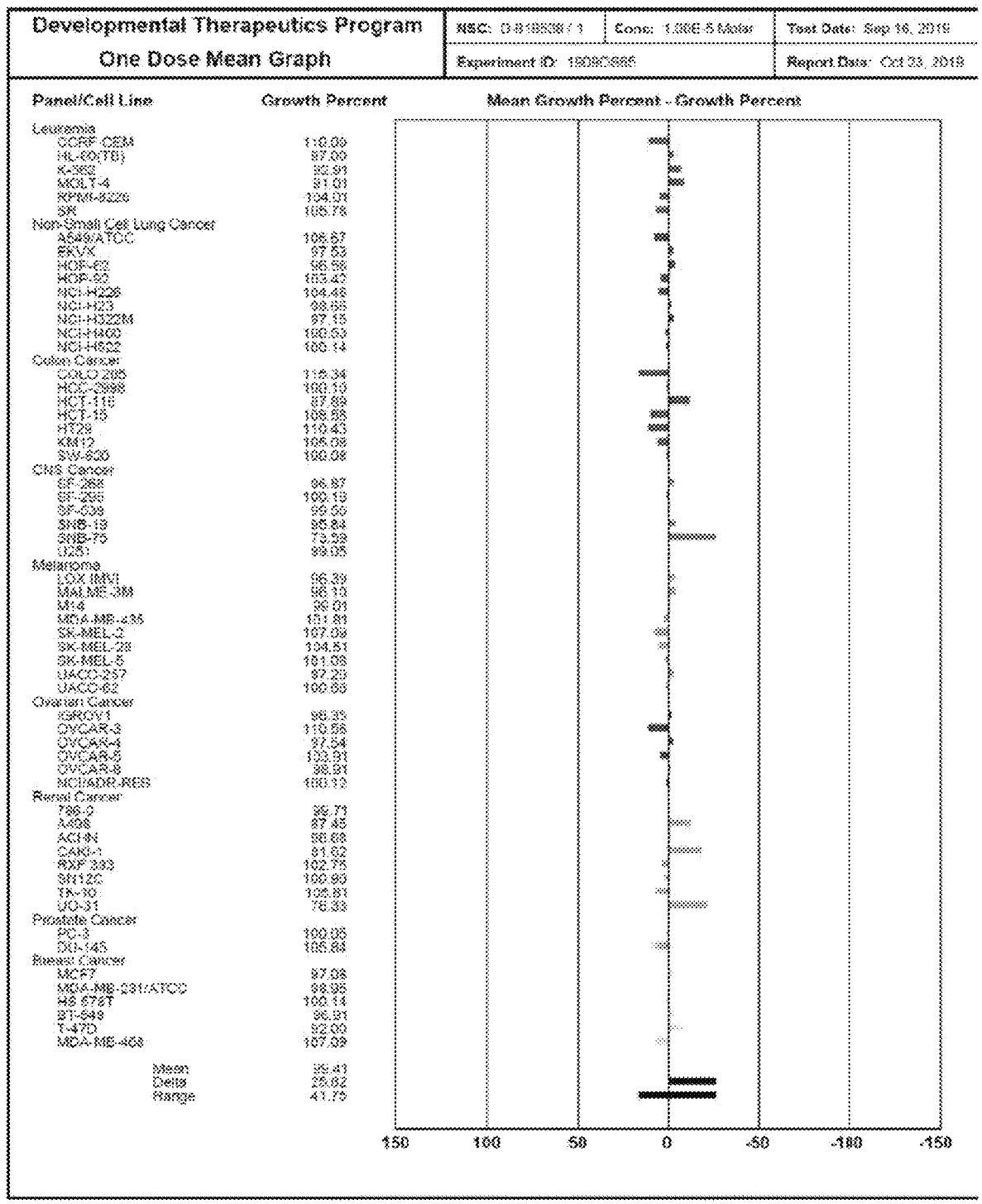

FIG. 100 is a dose mean graph depicting NCI-60 data for compound 19 of Example 7.

Figure 101:
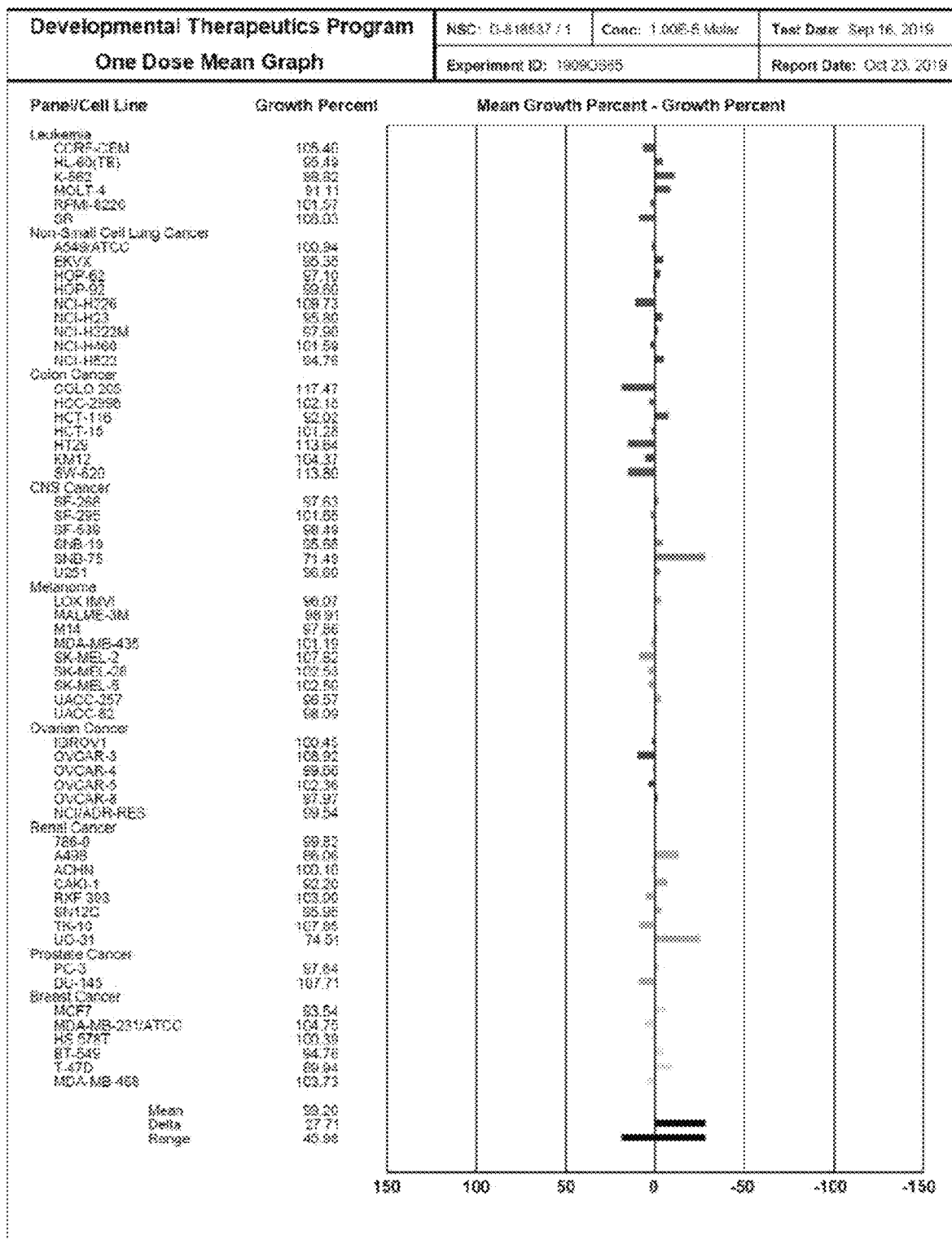

FIG. 101 is a dose mean graph depicting NCI-60 data for compound 9 of Example 7.

Figure 102:
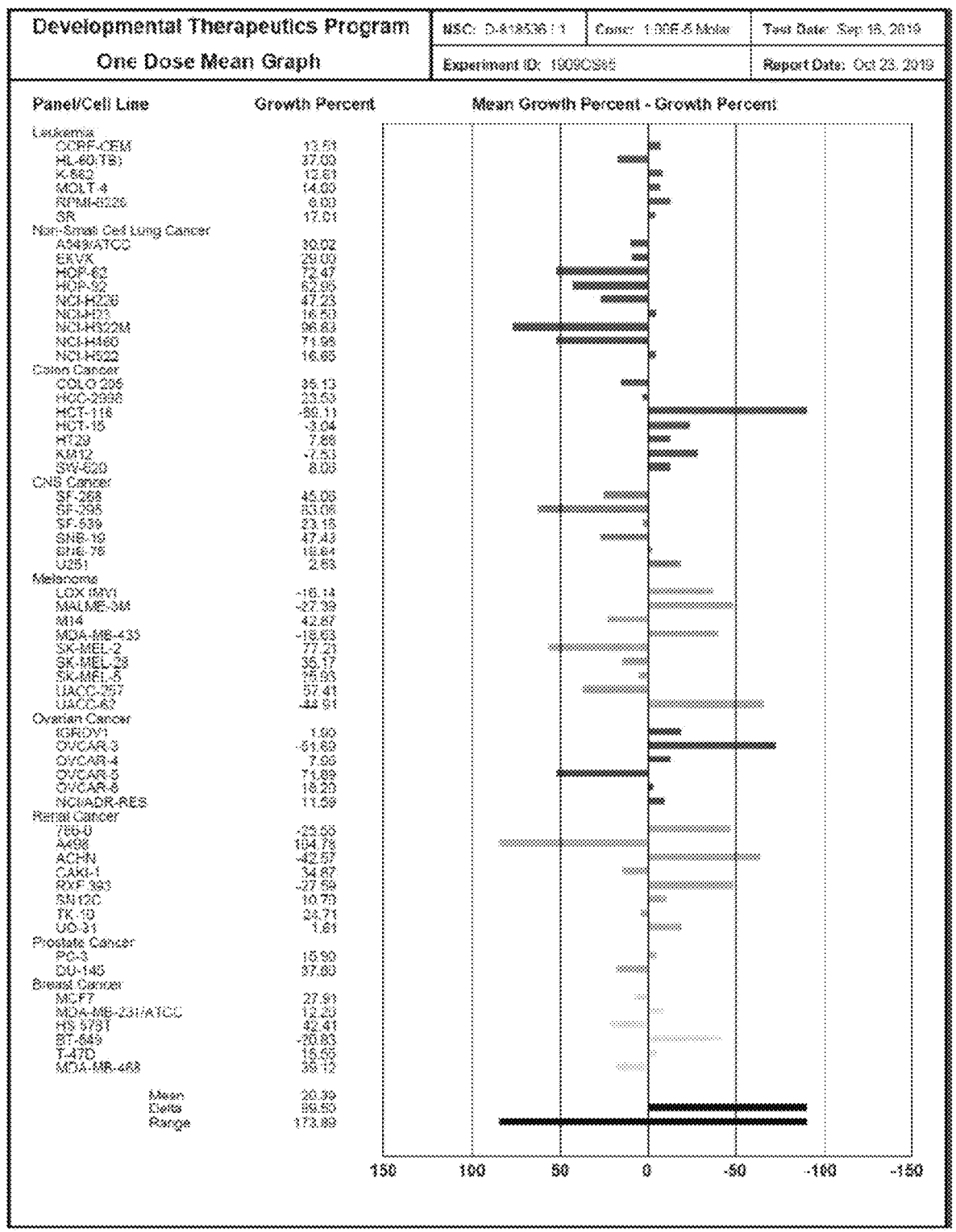

FIG. 102 is a dose mean graph depicting NCI-60 data for compound 8 (one dose assay) of Example 7.

Figure 103:
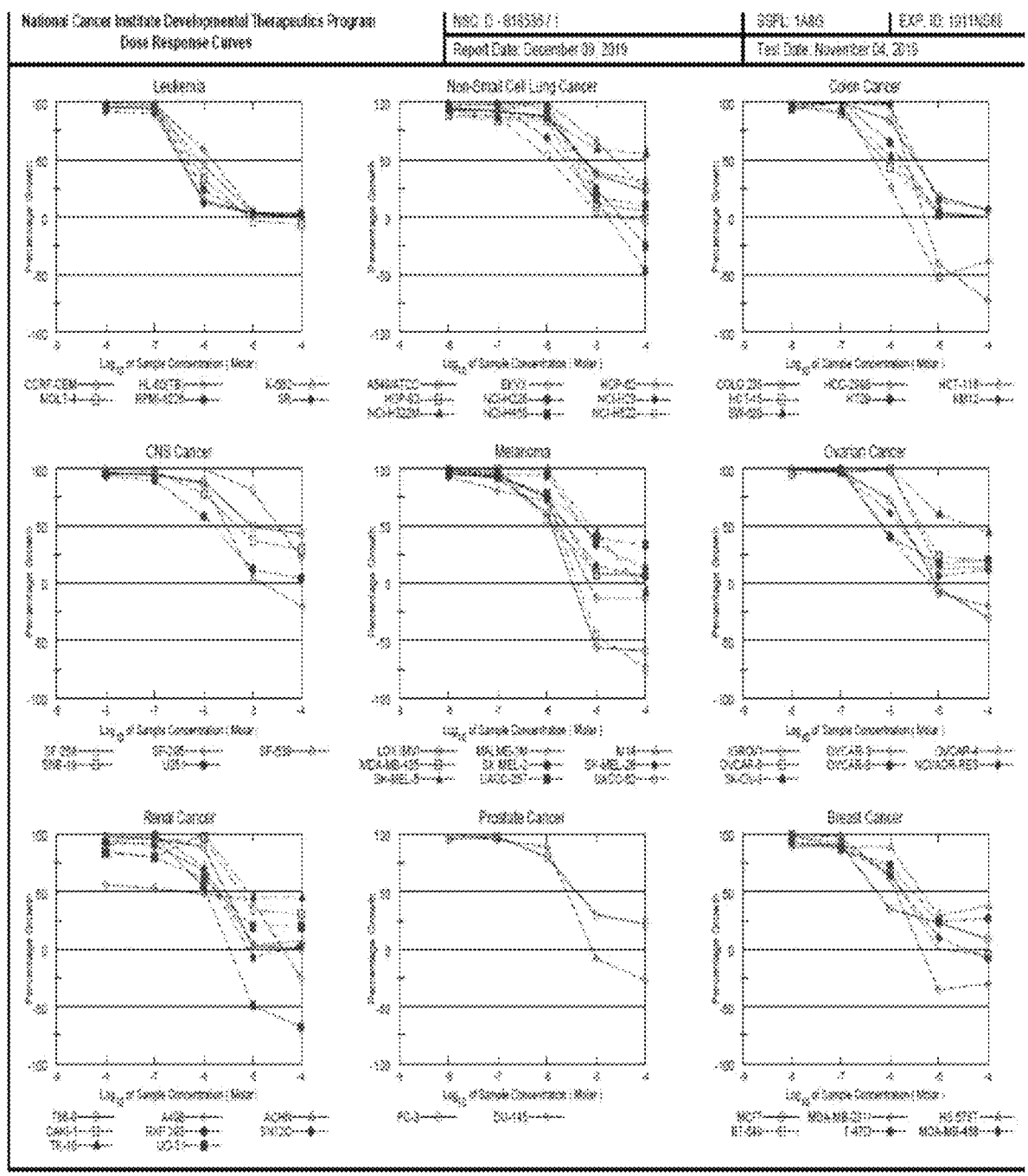

FIG. 103 is a series of graphs depicting NCI-60 data for compound 8 (five dose screening assay) of Example 7.

Figure 104:
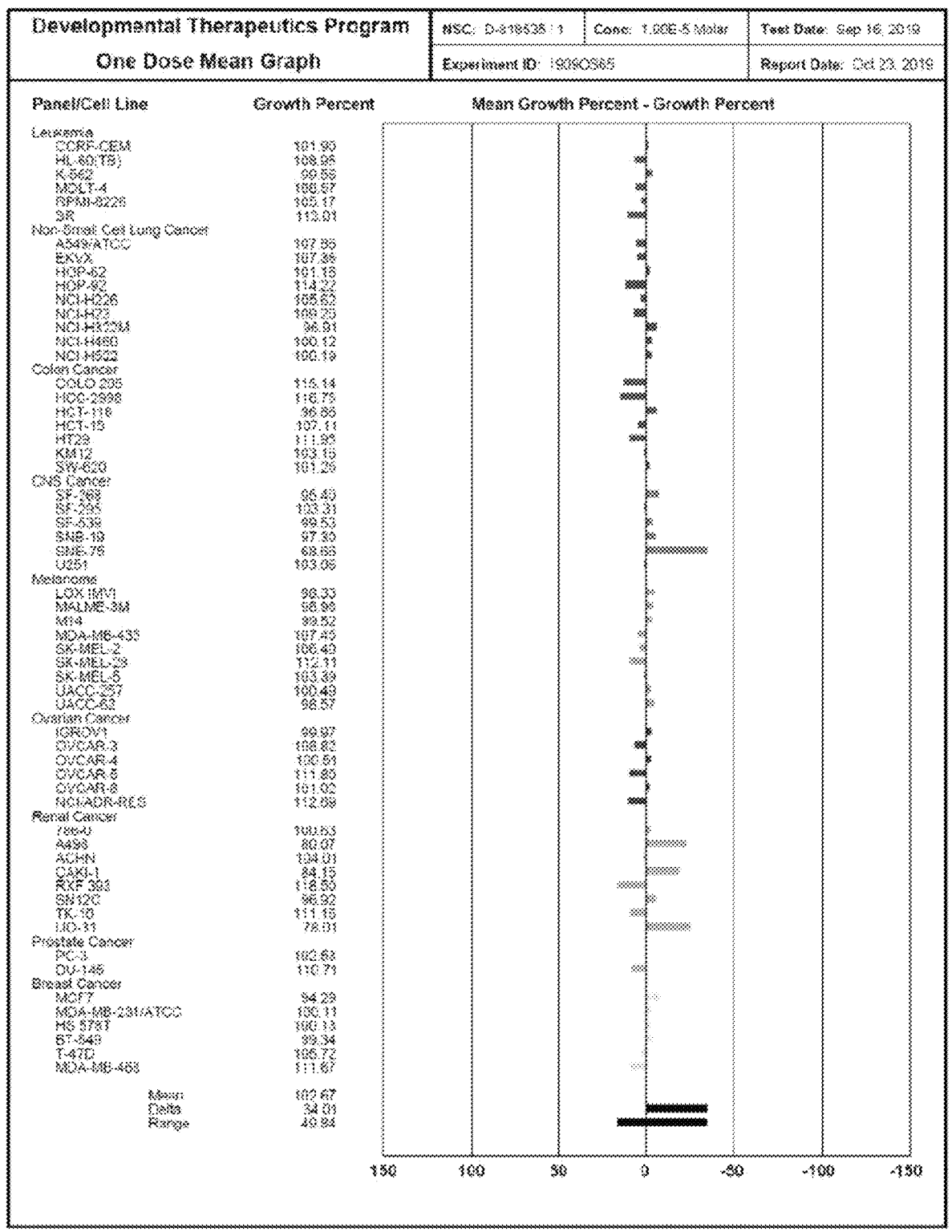

FIG. 104 is a dose mean graph depicting NCI-60 data for compound 7 of Example 7.

Figure 105:
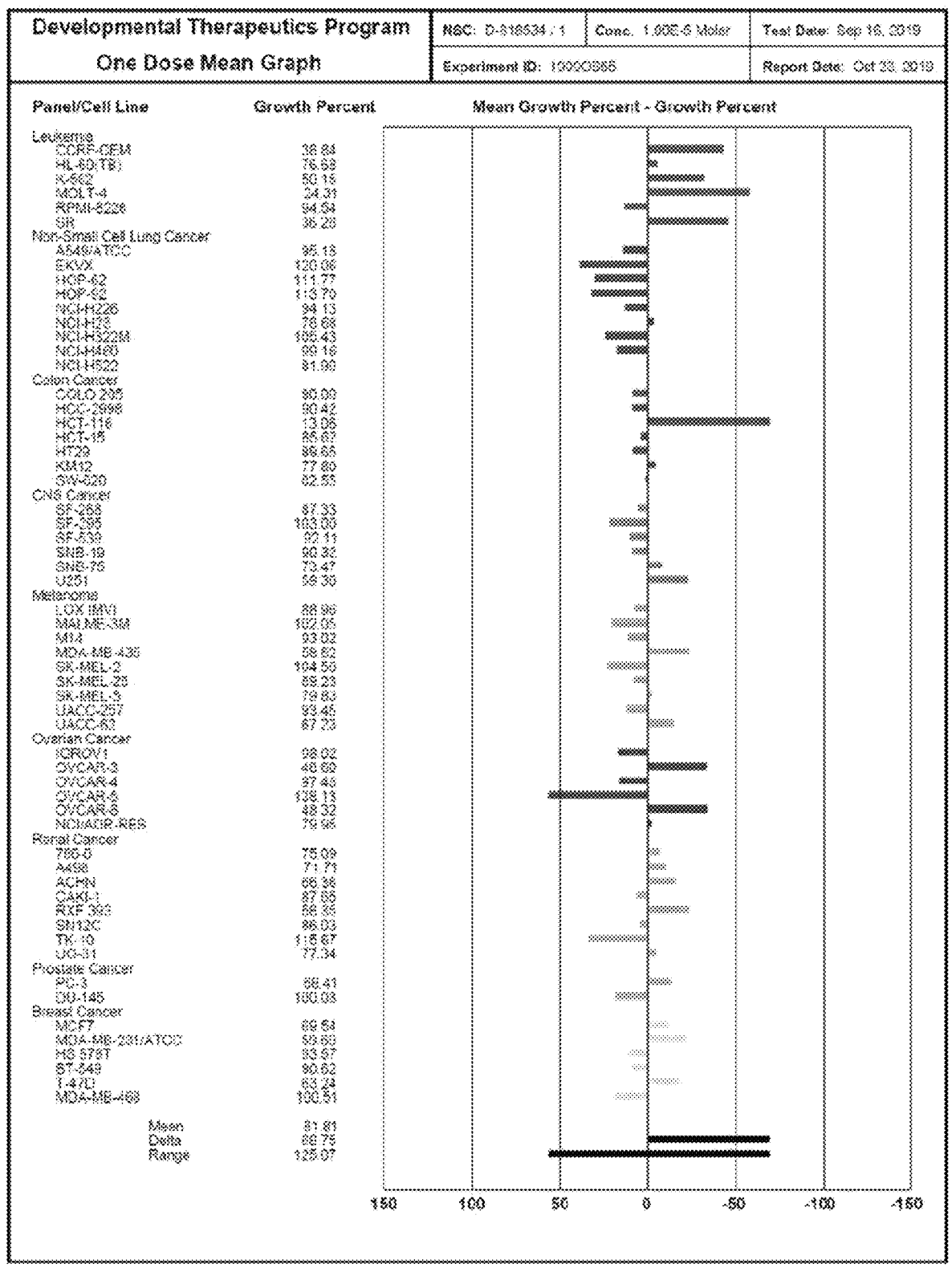

FIG. 105 is a dose mean graph depicting NCI-60 data for compound 5 of Example 7.

Figure 106:
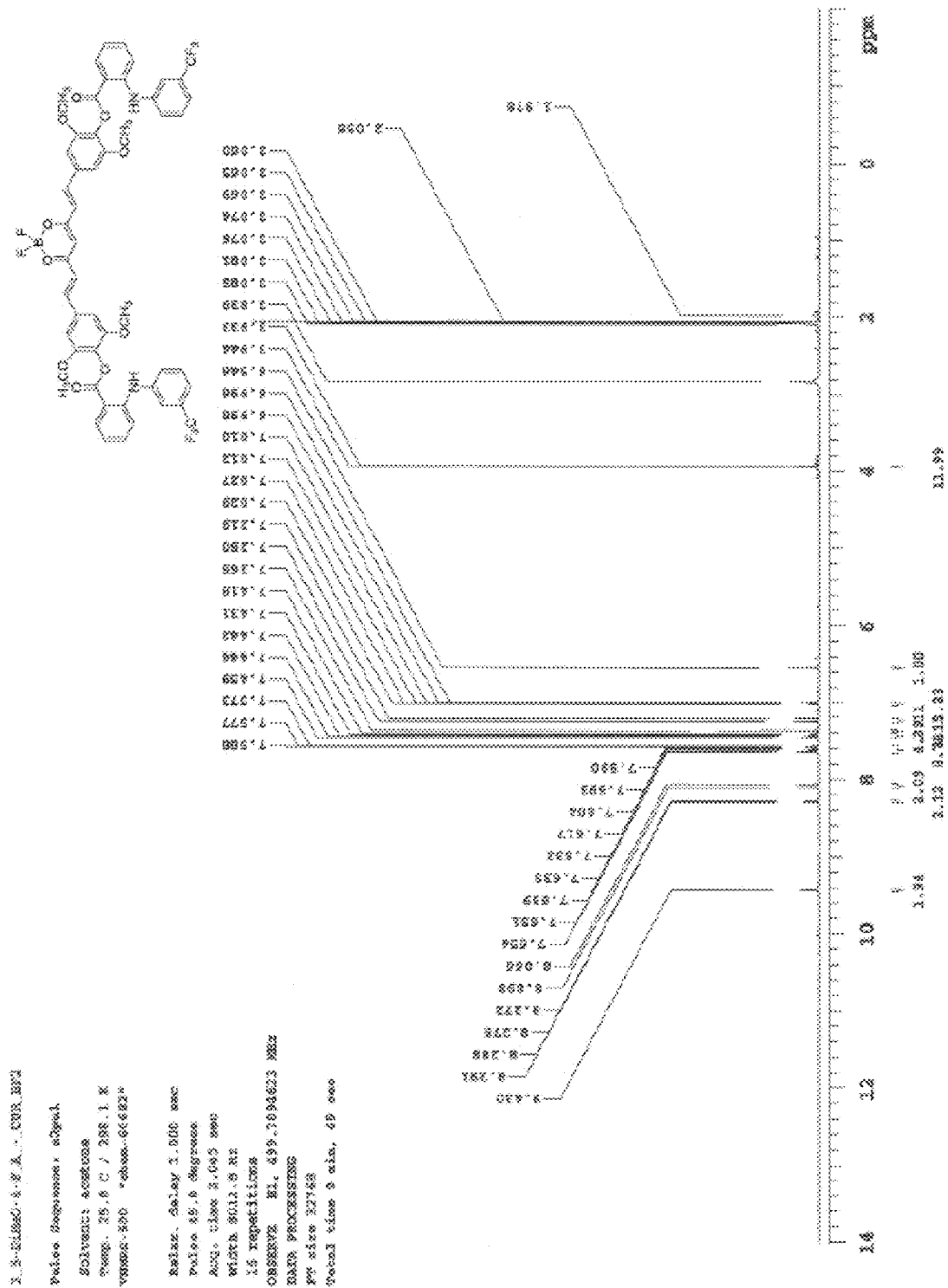

FIG. 106 is a representative NMR spectrum for compound 1 of Example 7.

Figure 107:
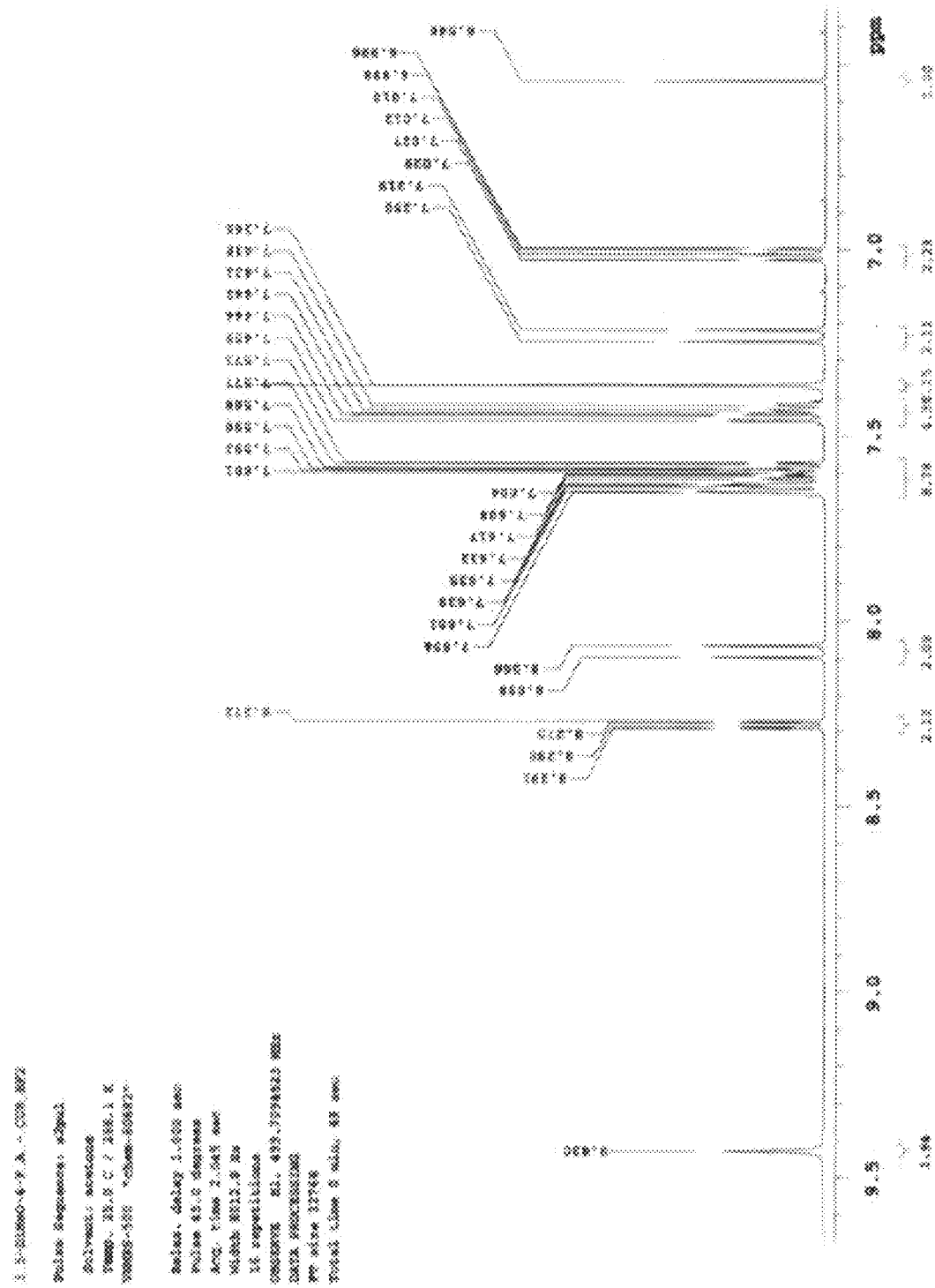

FIG. 107 is a representative NMR spectrum for compound 1 of Example 7.

Figure 108:
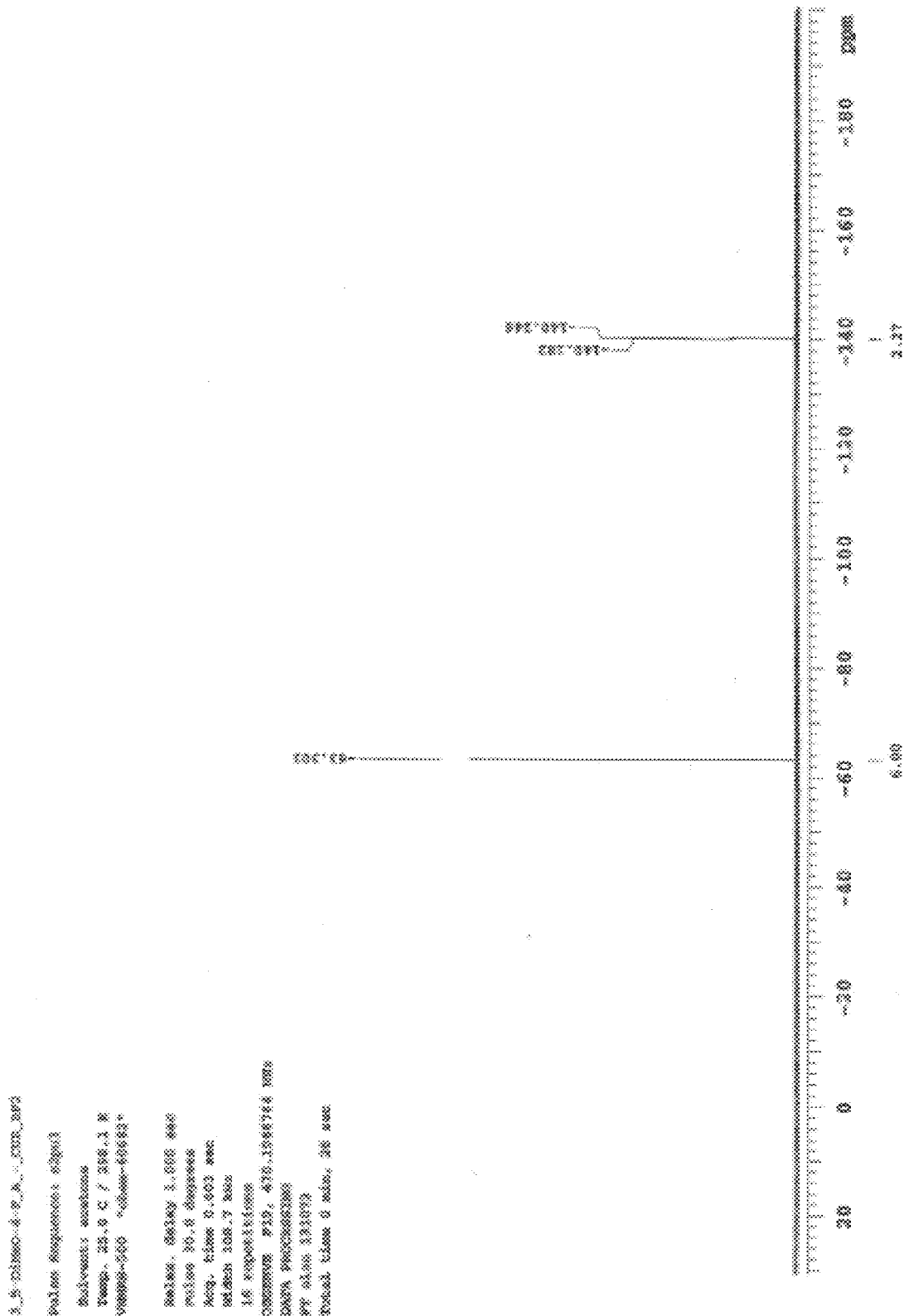

FIG. 108 is a representative NMR spectrum for compound 1 of Example 7.

Figure 109:
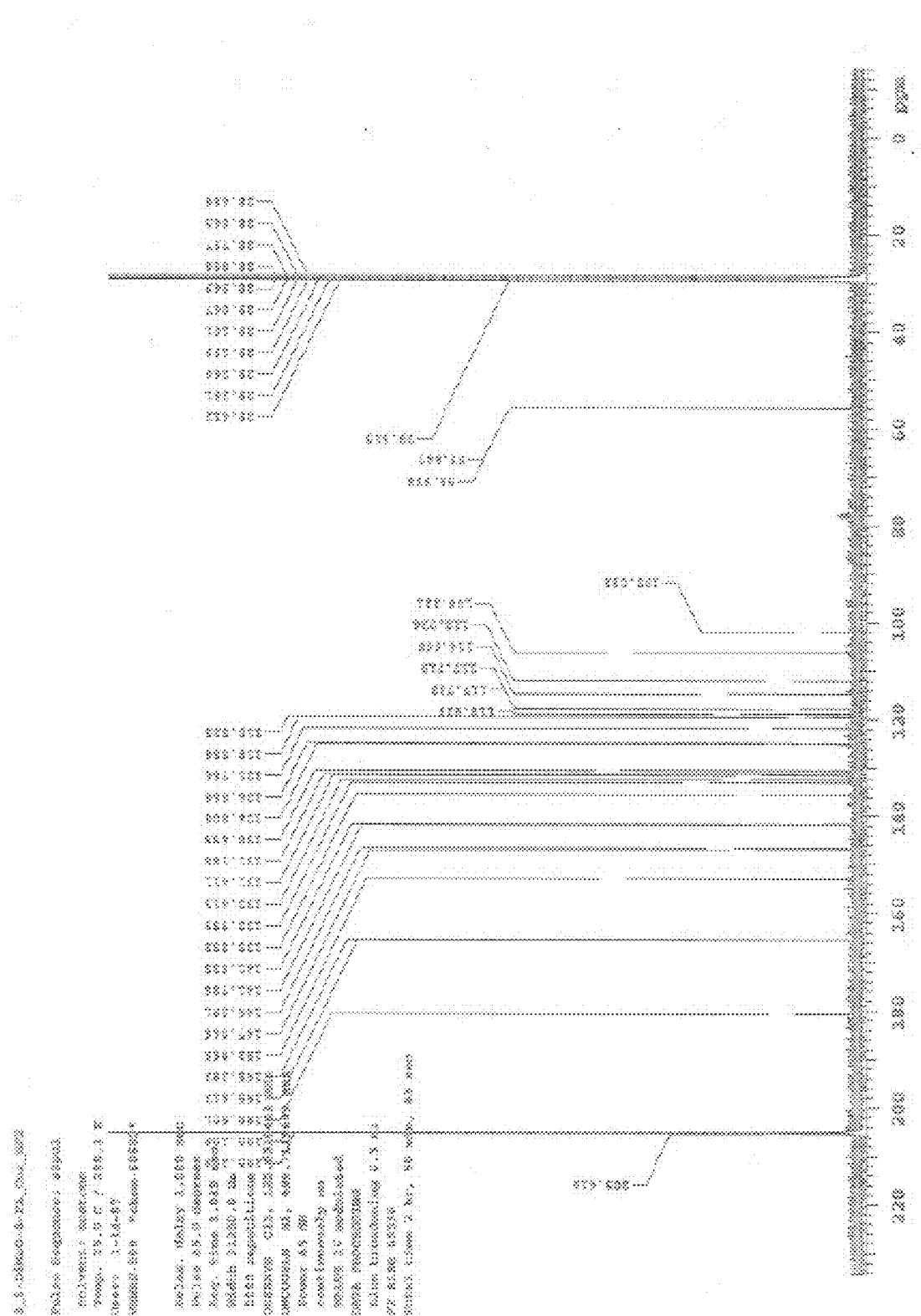

FIG. 109 is a representative NMR spectrum for compound 1 of Example 7.

Figure 110:
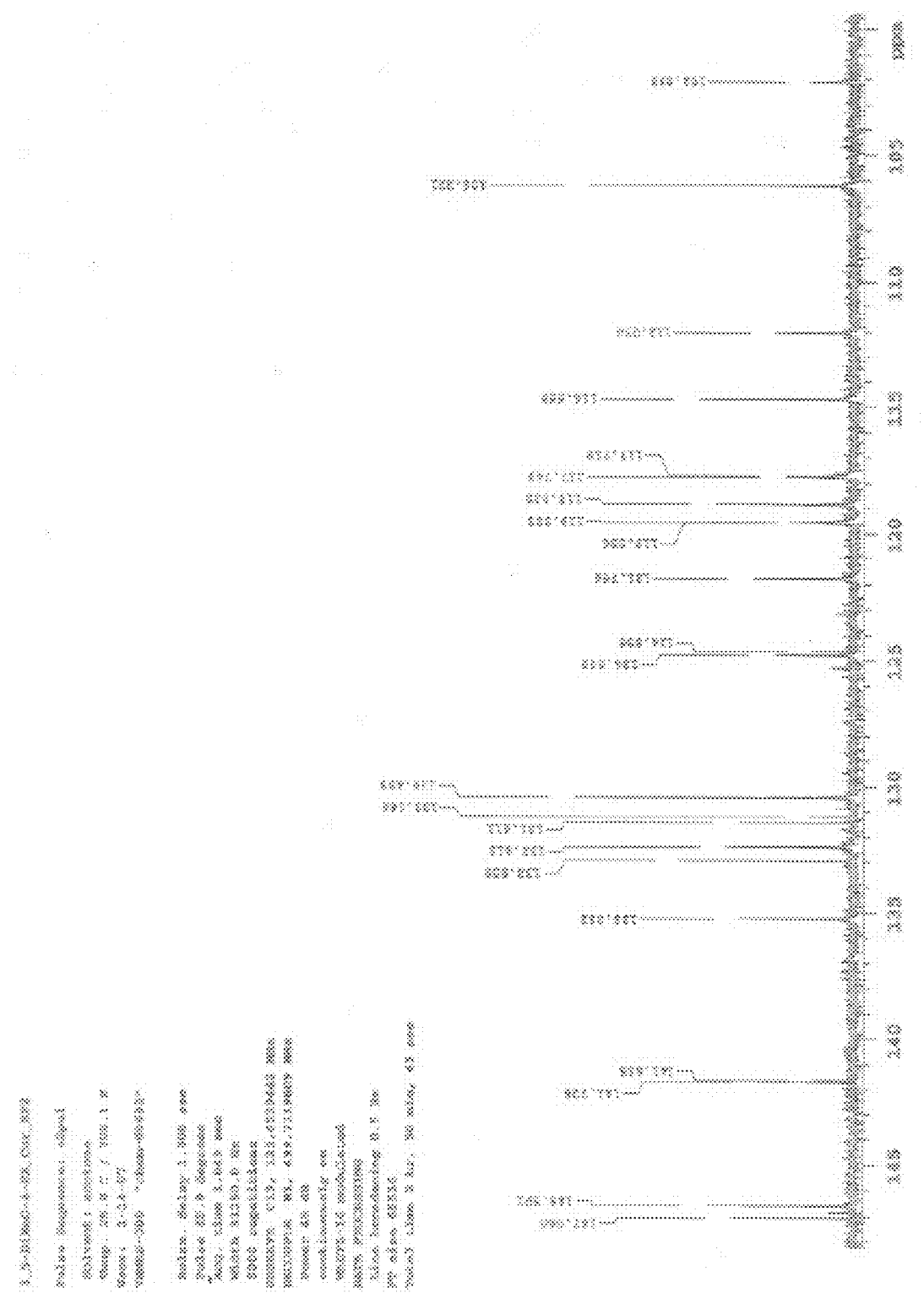

FIG. 110 is a representative NMR spectrum for compound 1 of Example 7.

FIG. 111 is a representative NMR spectrum for compound 14 of Example 7.

Figure 112:
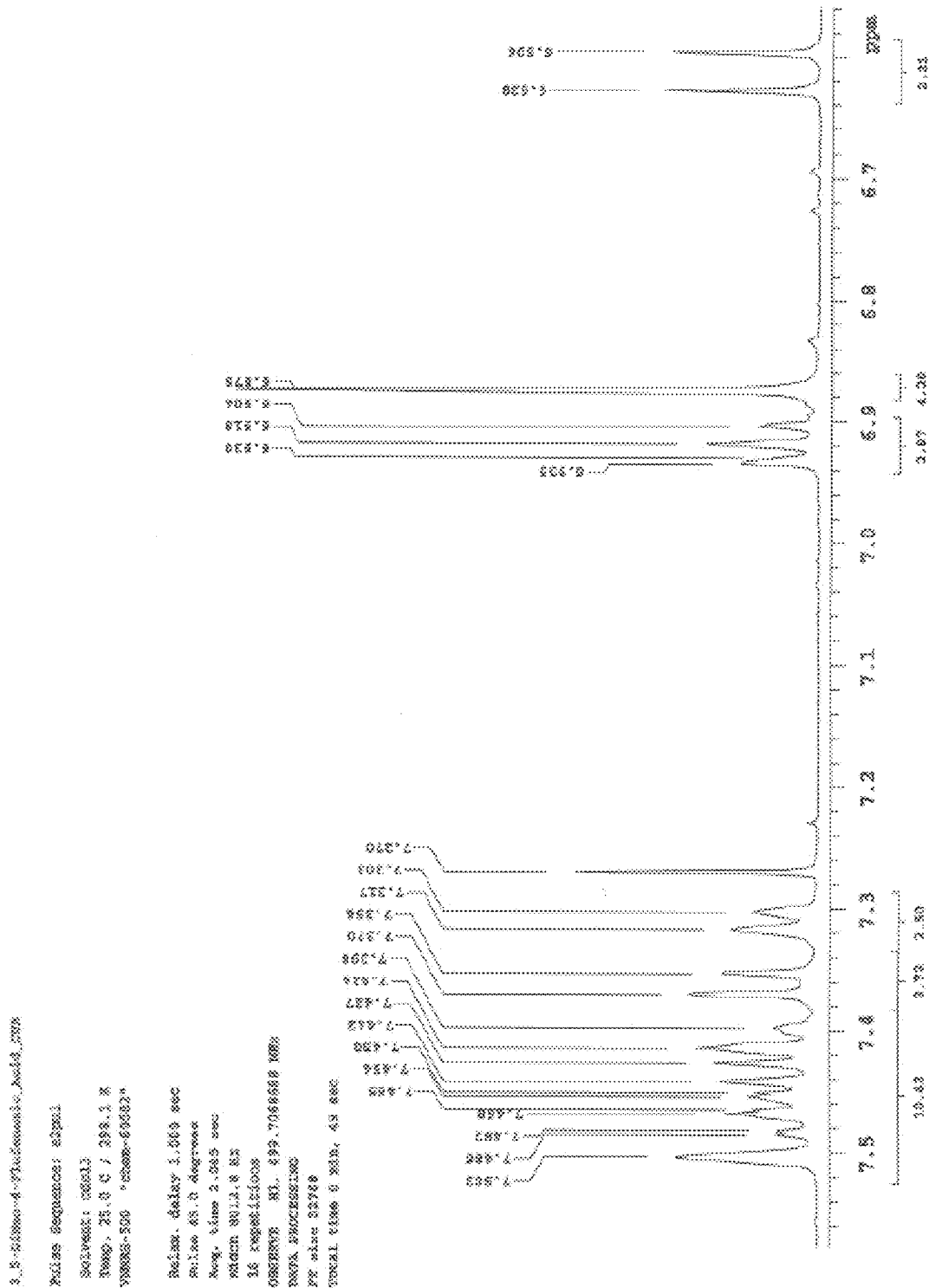

FIG. 112 is a representative NMR spectrum for compound 14 of Example 7.

Figure 113:
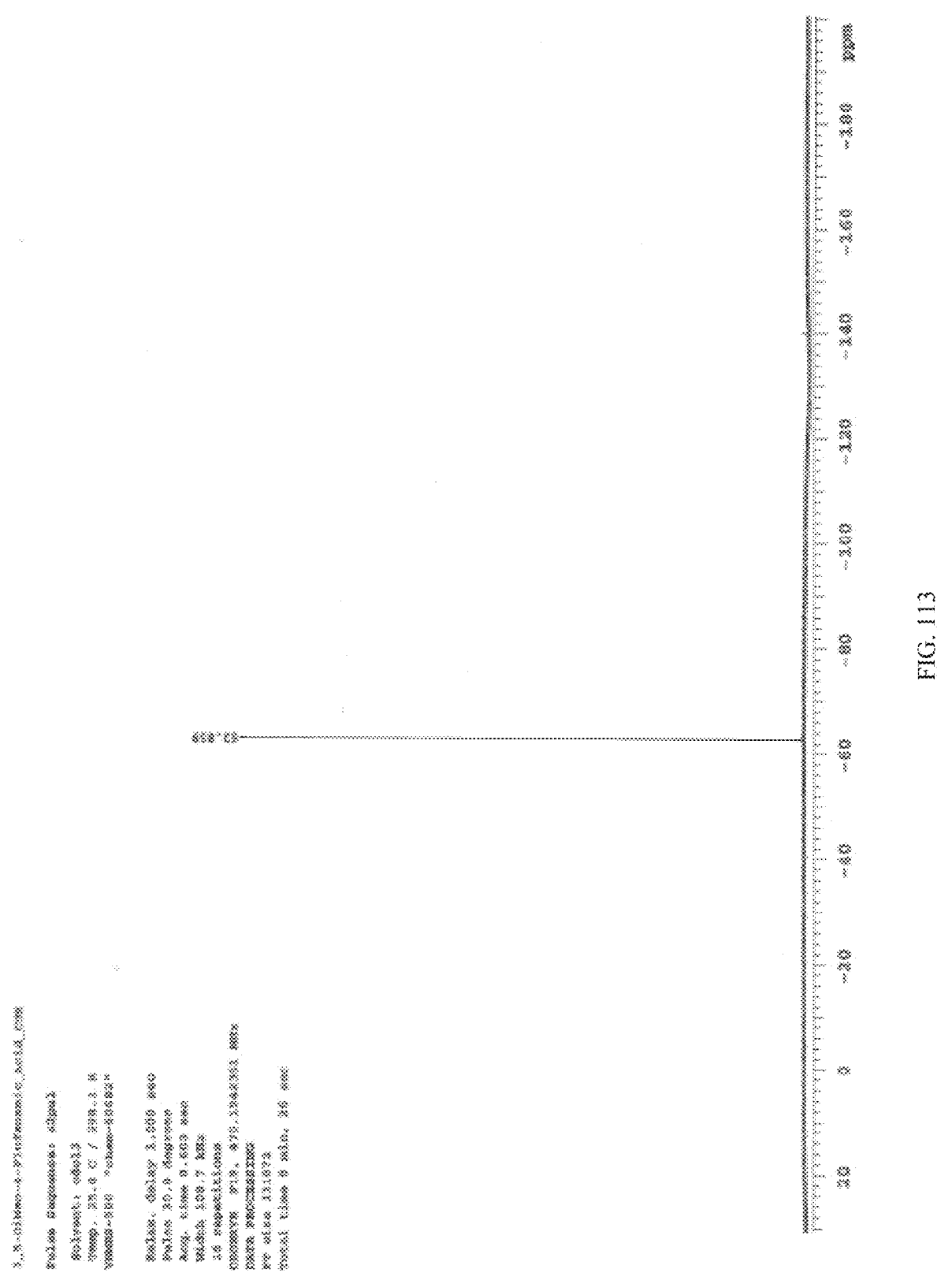

FIG. 113 is a representative NMR spectrum for compound 14 of Example 7.

Figure 114:
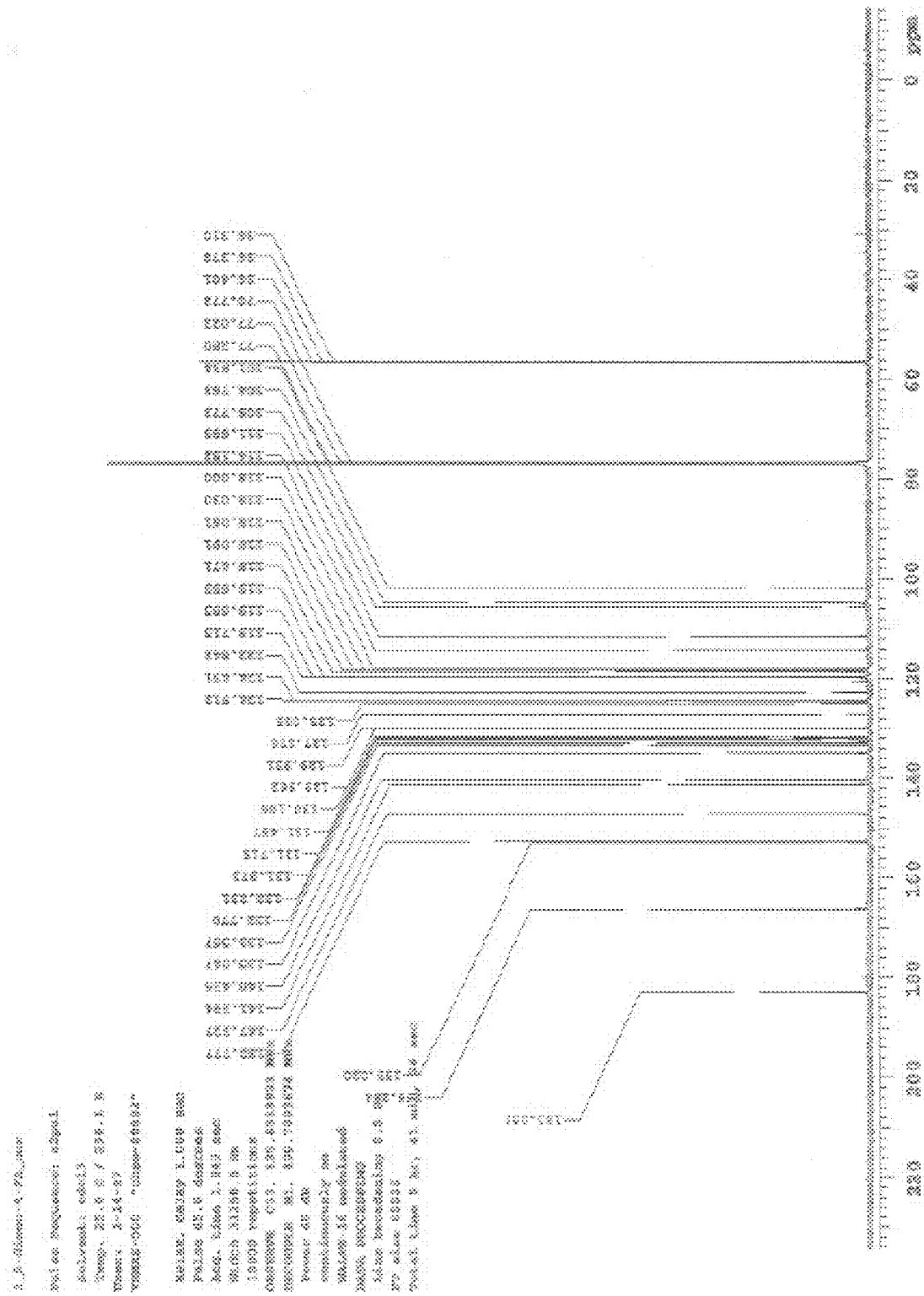

FIG. 114 is a representative NMR spectrum for compound 14 of Example 7.

Figure 115:
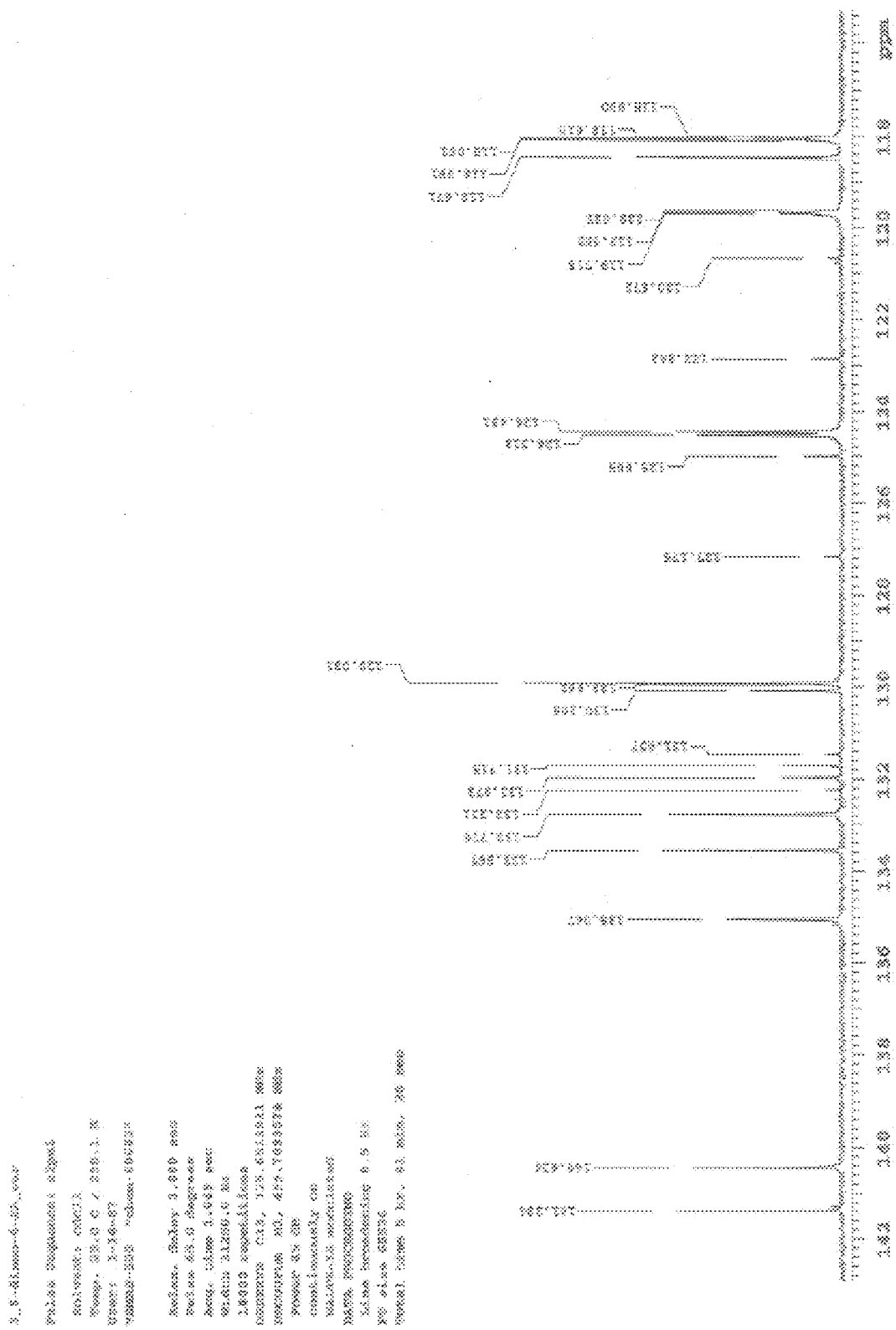

FIG. 115 is a representative NMR spectrum for compound 14 of Example 7.

Figure 116:
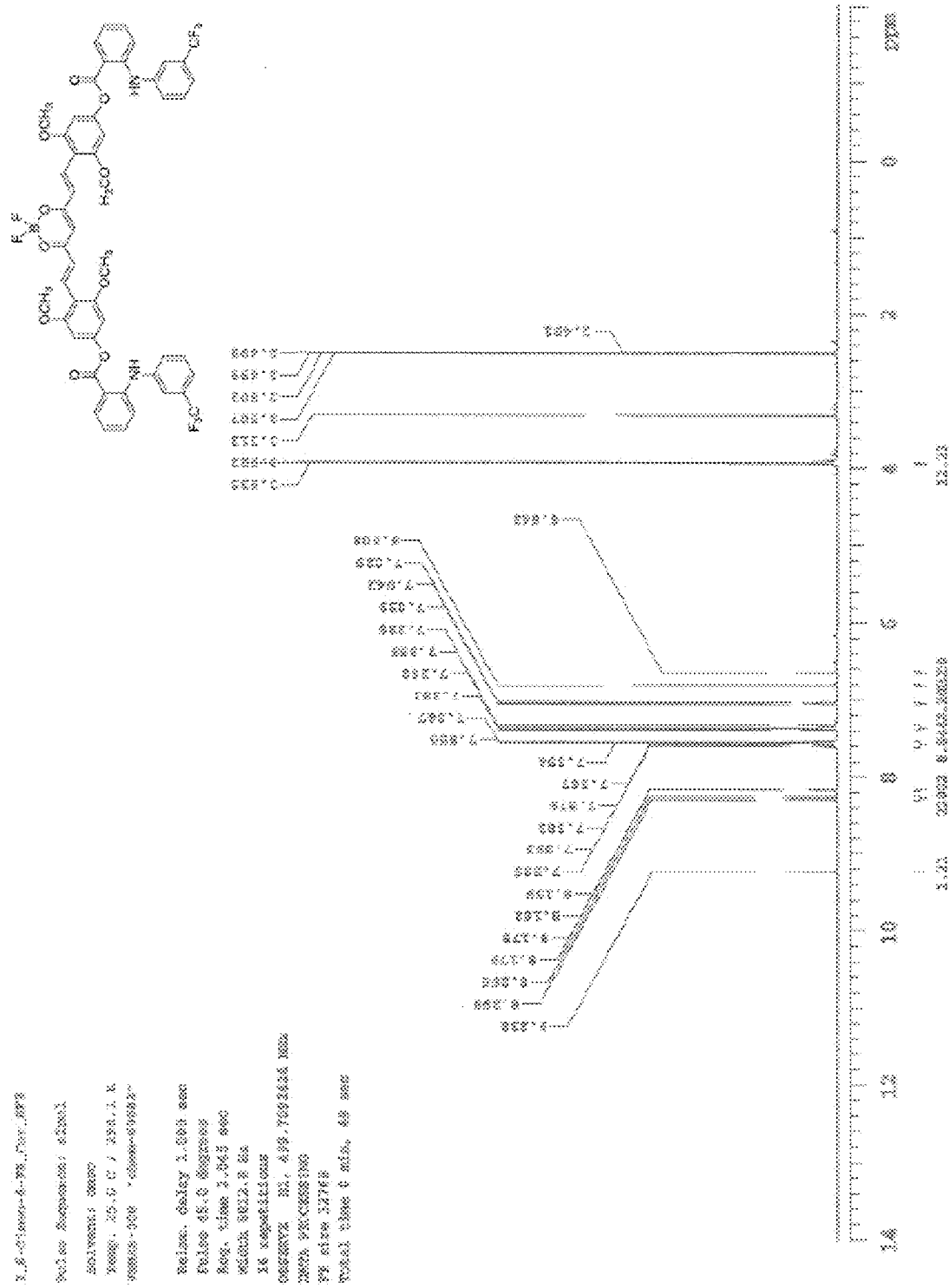

FIG. 116 is a representative NMR spectrum for compound 2 of Example 7.

Figure 117:
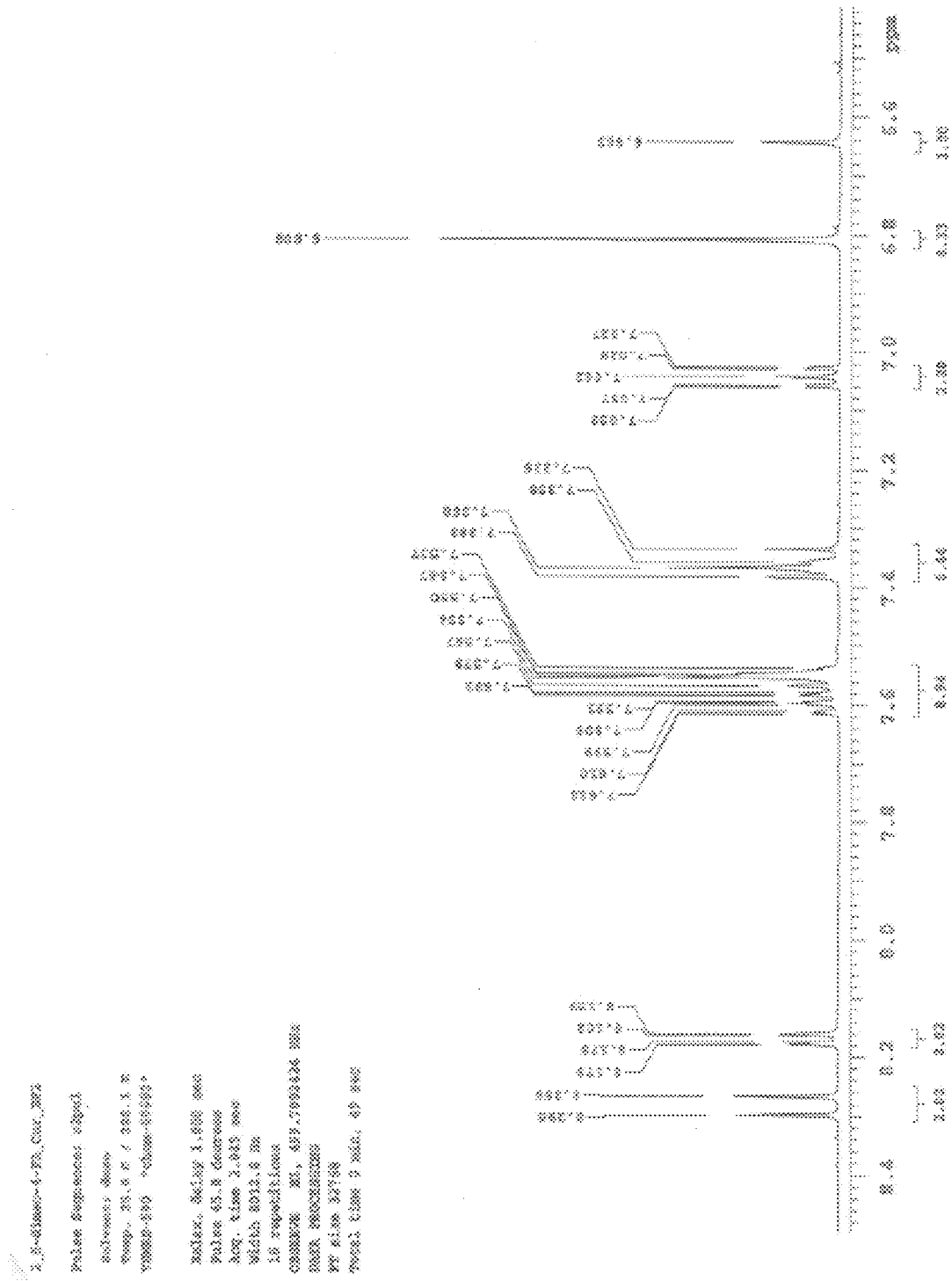

FIG. 117 is a representative NMR spectrum for compound 2 of Example 7.

Figure 118:
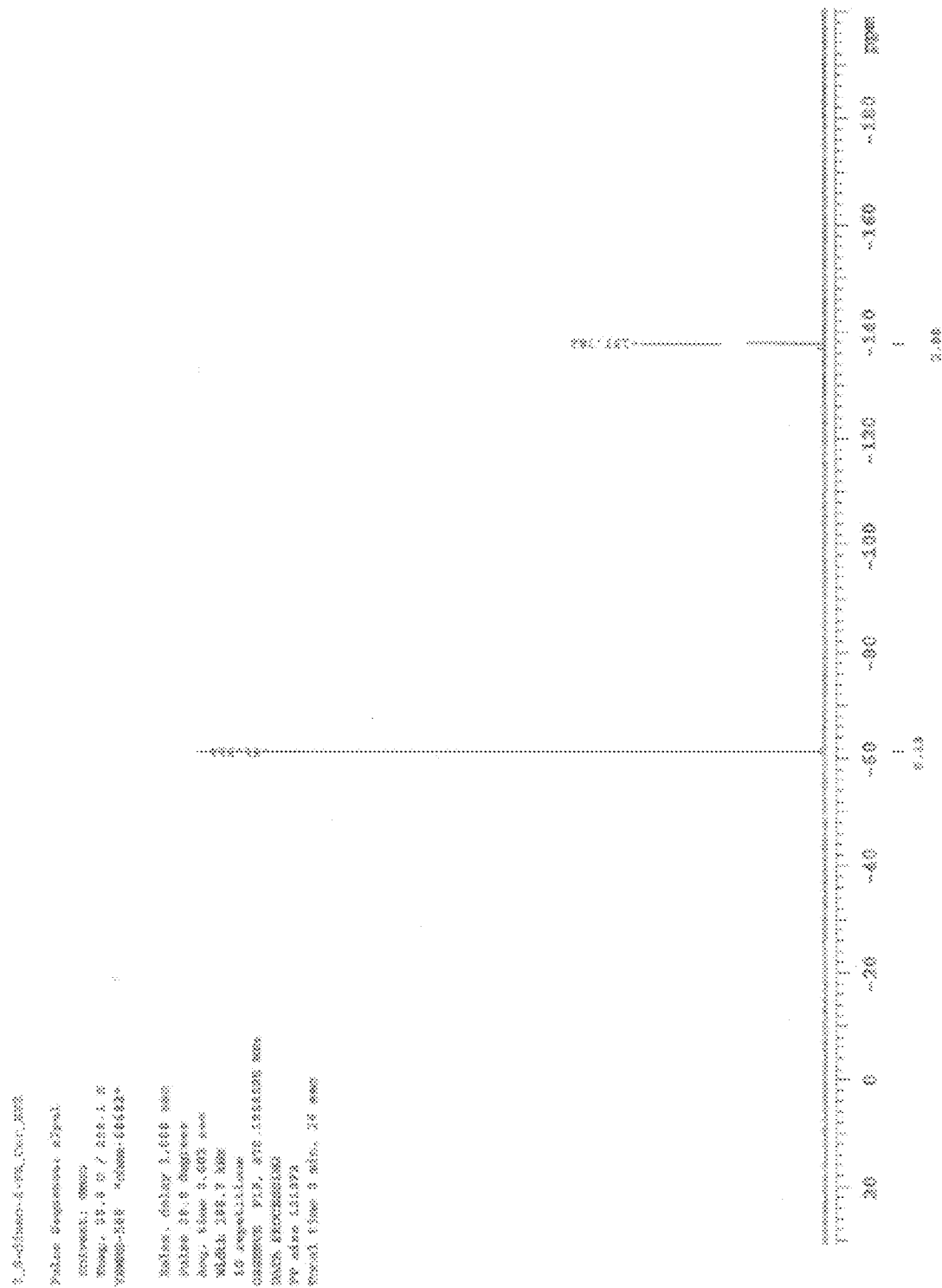

FIG. 118 is a representative NMR spectrum for compound 2 of Example 7.

Figure 119:
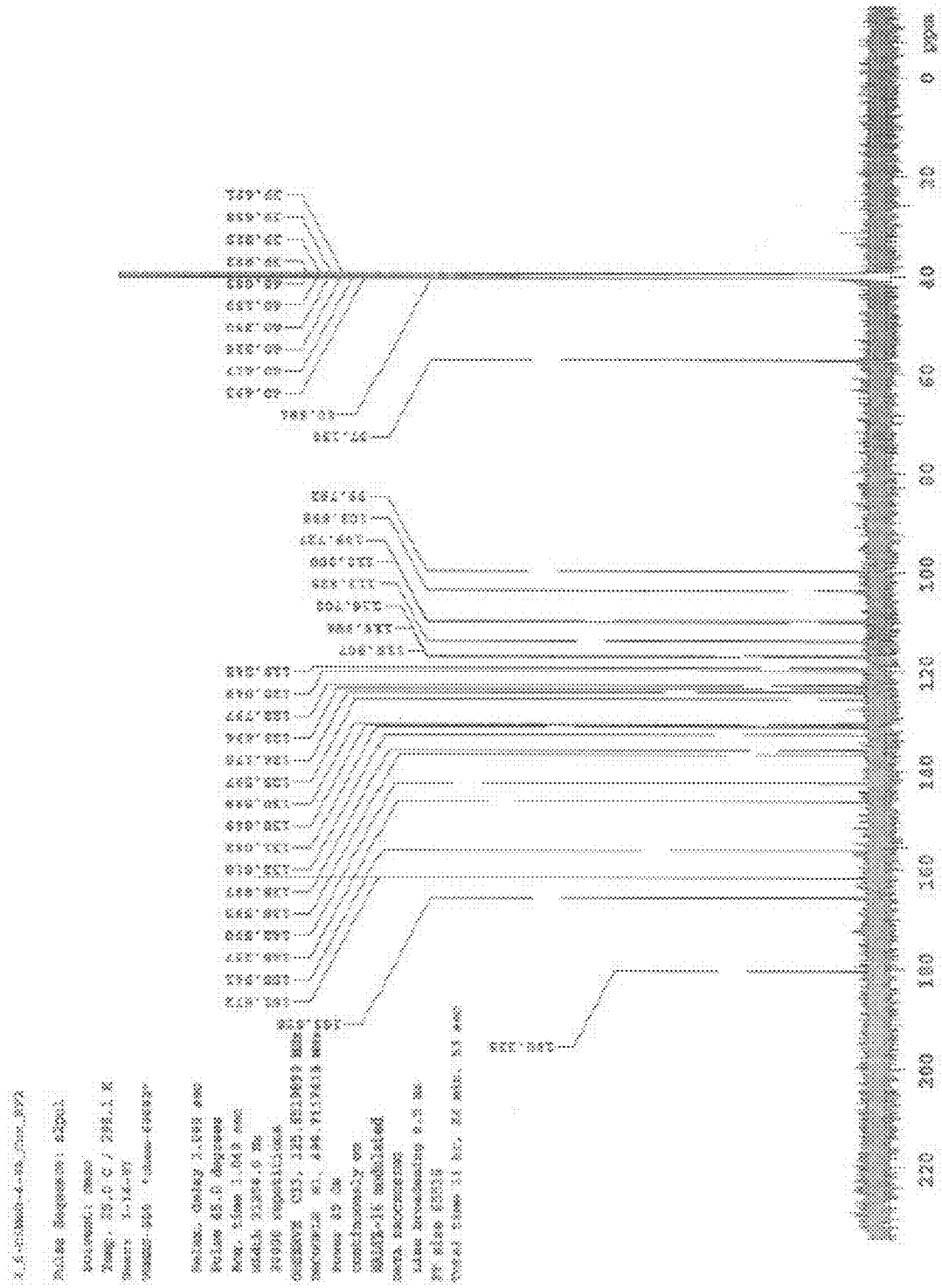

FIG. 119 is a representative NMR spectrum for compound 2 of Example 7.

Figure 120:
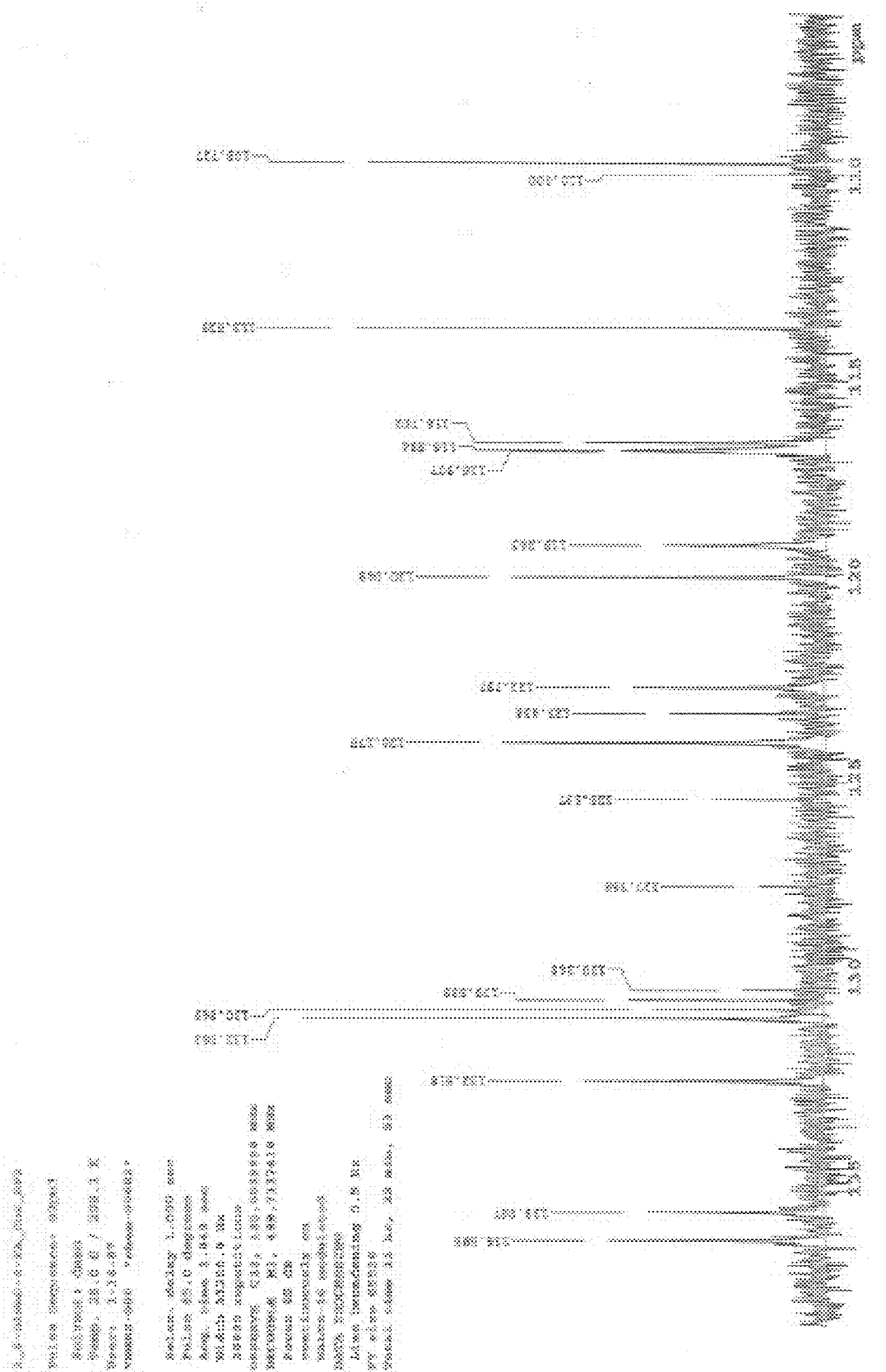

FIG. 120 is a representative NMR spectrum for compound 2 of Example 7.

Figure 121:
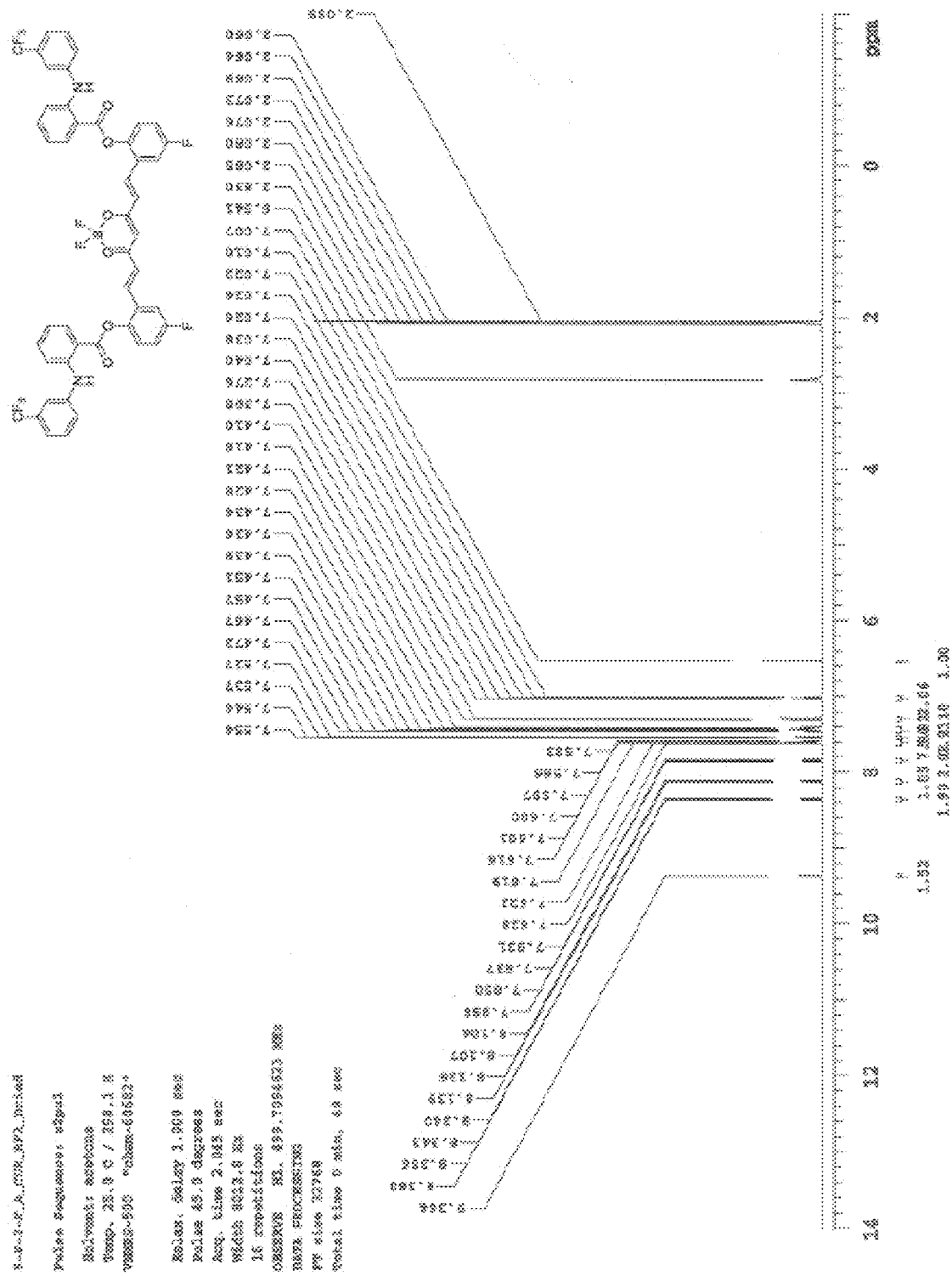

FIG. 121 is a representative NMR spectrum for compound 3 of Example 7.

Figure 122:
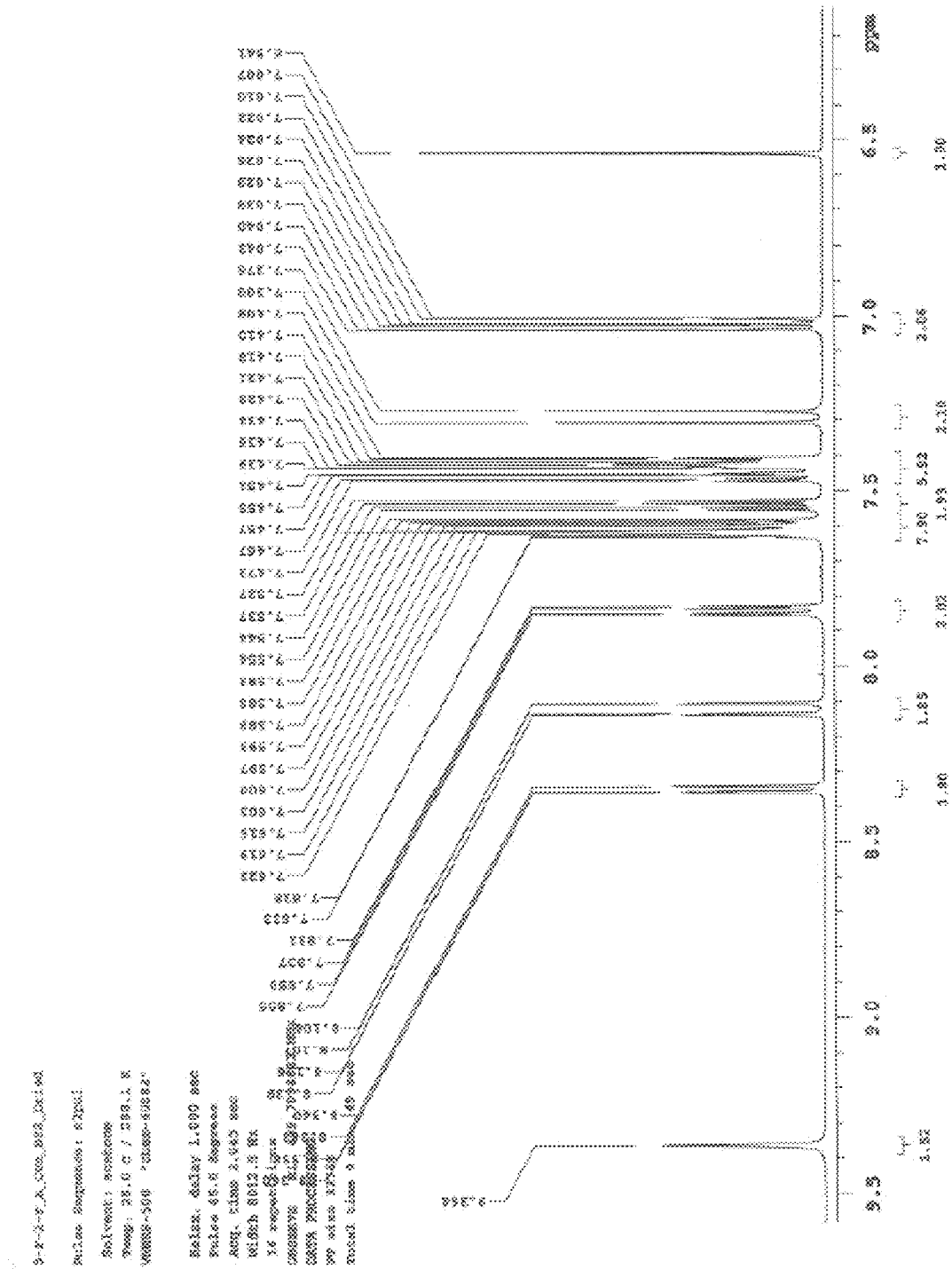

FIG. 122 is a representative NMR spectrum for compound 3 of Example 7.

Figure 123:
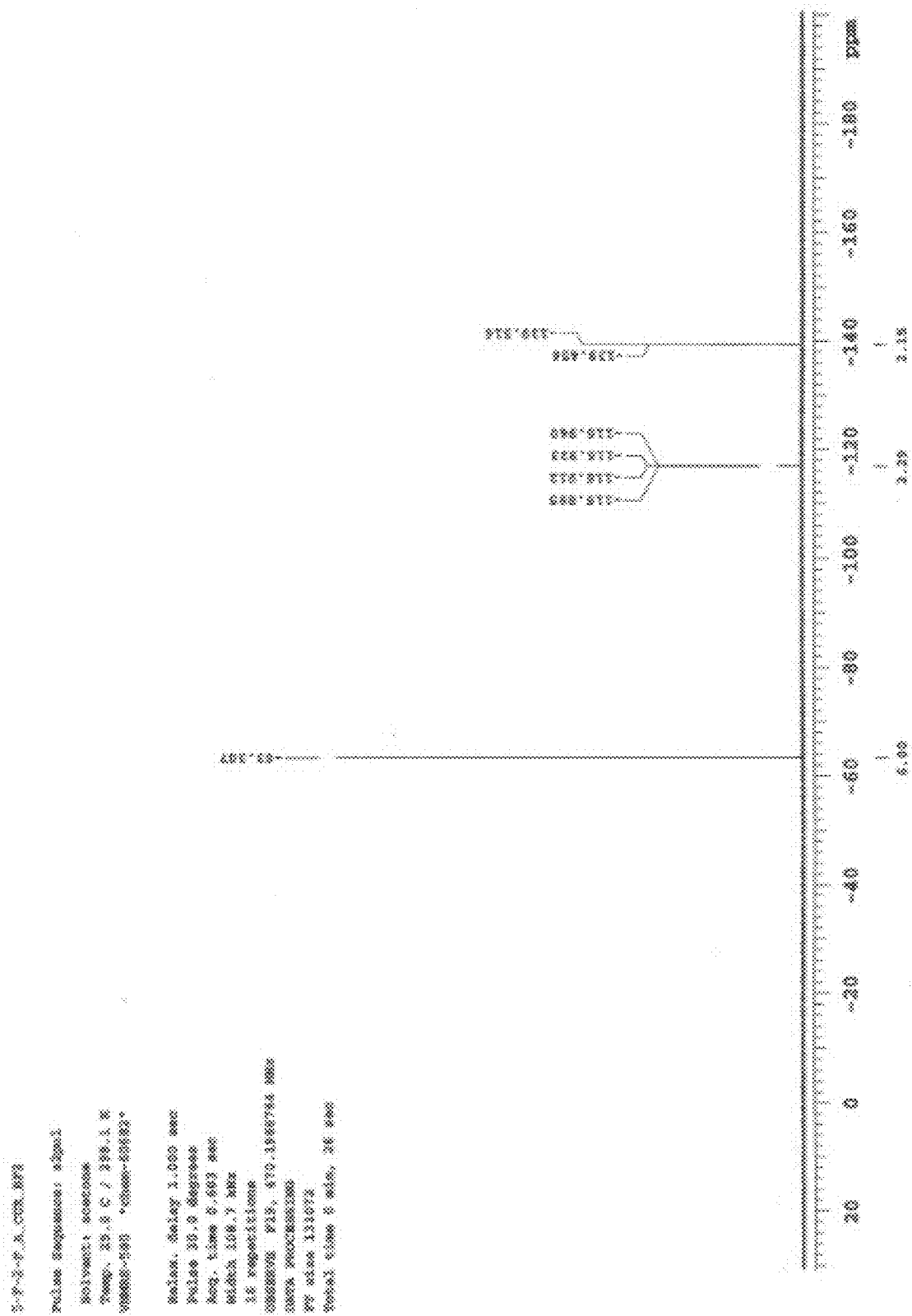

FIG. 123 is a representative NMR spectrum for compound 3 of Example 7.

Figure 124:
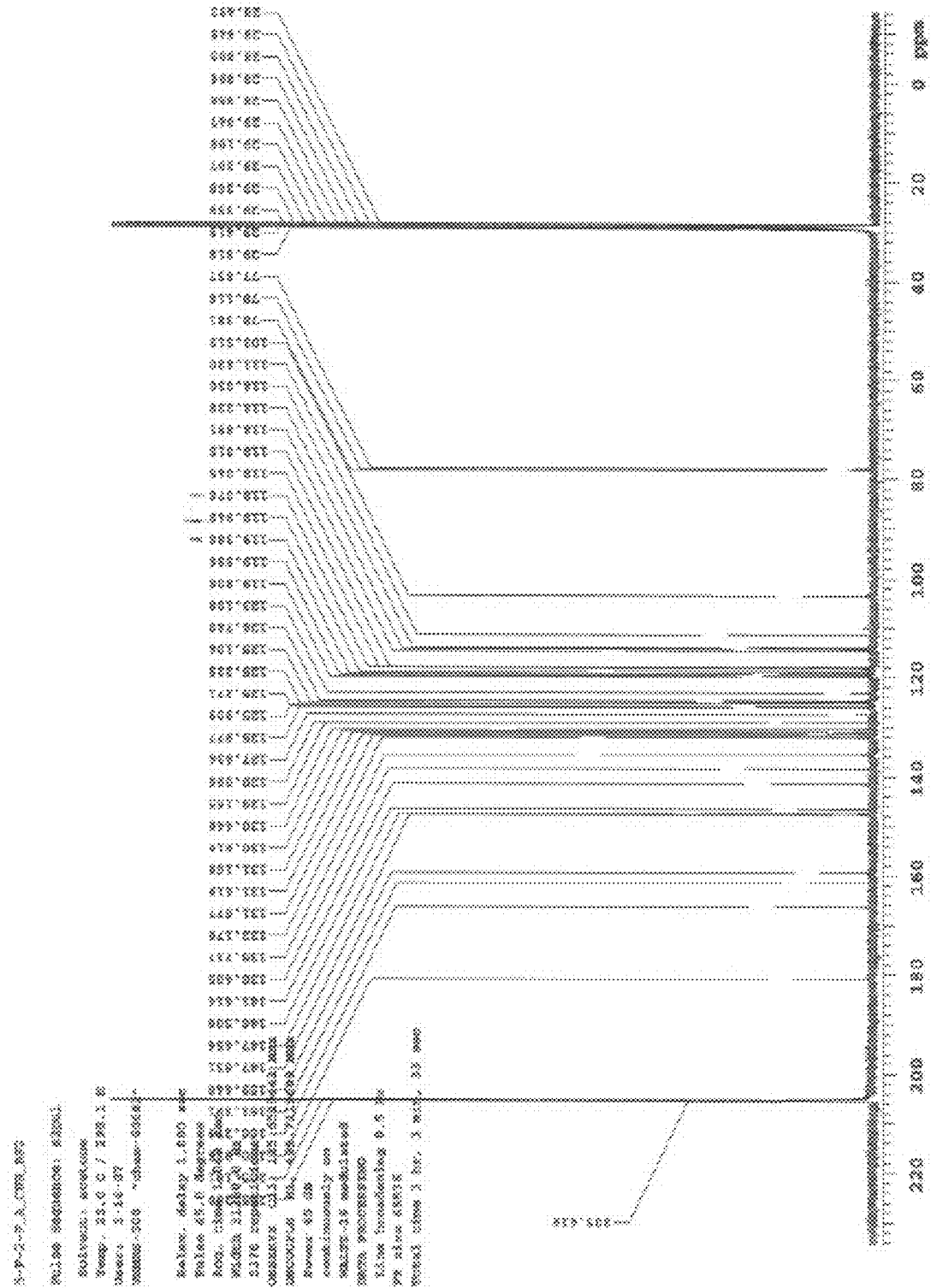

FIG. 124 is a representative NMR spectrum for compound 3 of Example 7.

Figure 125:
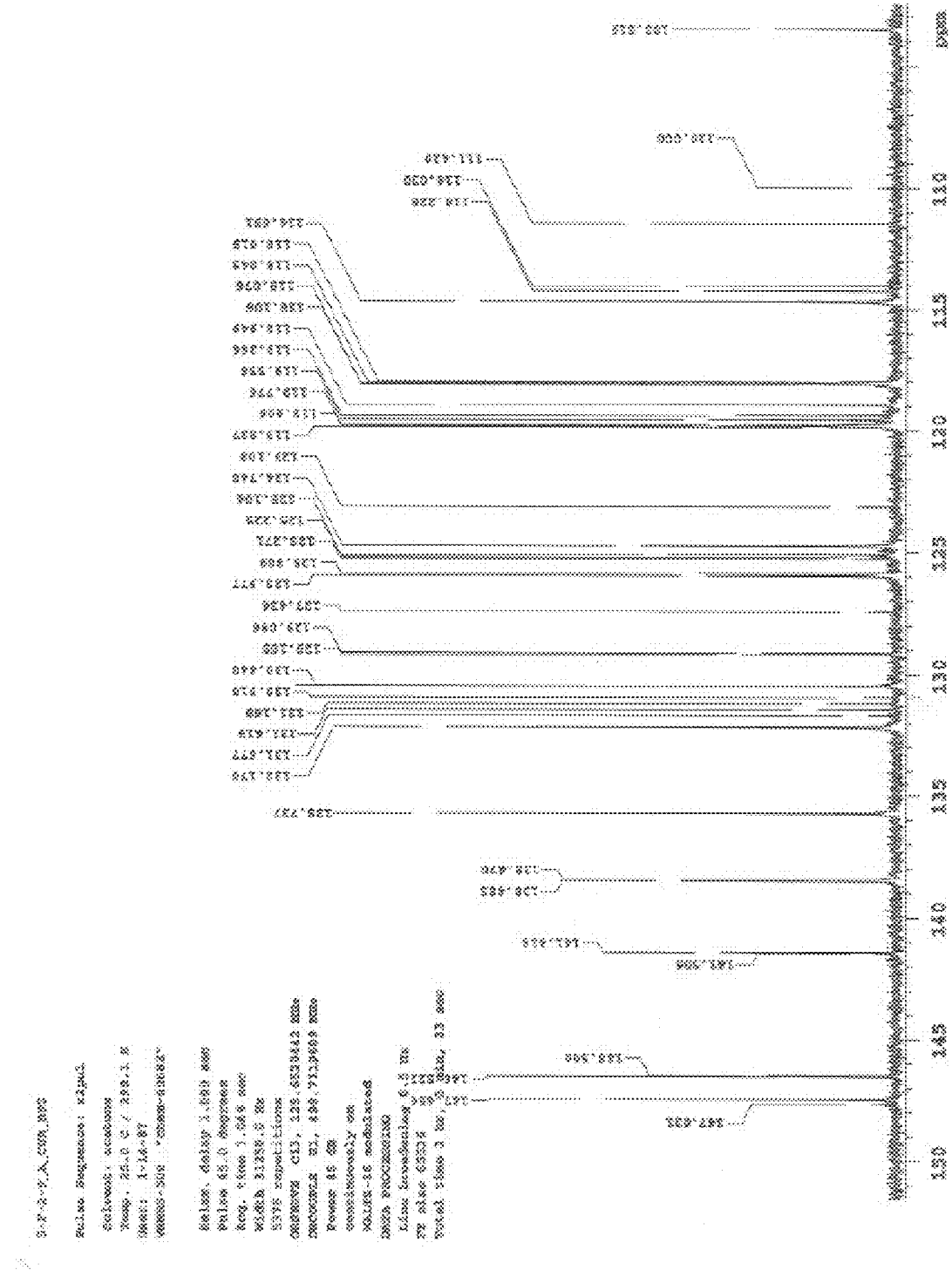

FIG. 125 is a representative NMR spectrum for compound 3 of Example 7.

Figure 126:
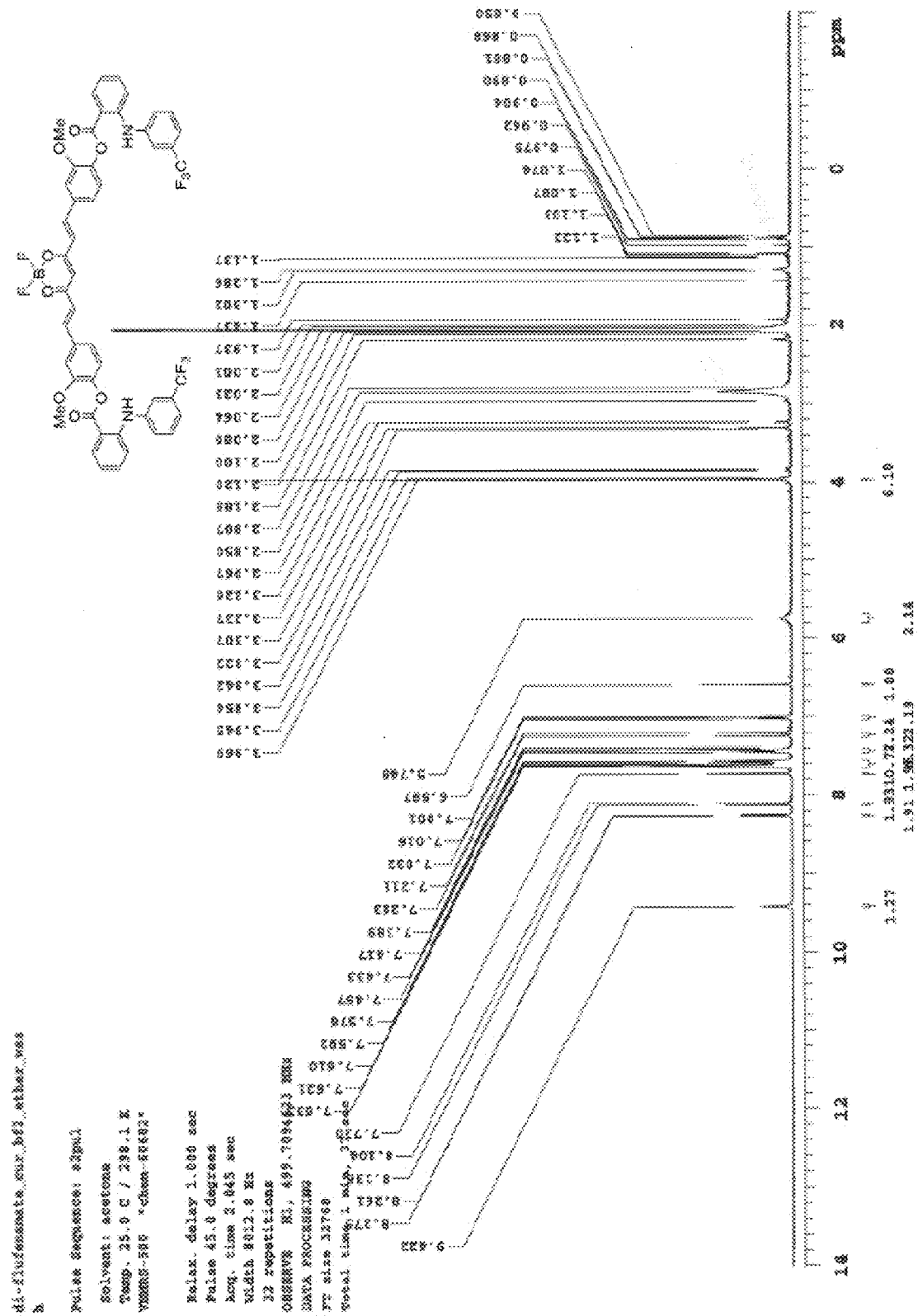

FIG. 126 is a representative NMR spectrum for compound 4 of Example 7.

Figure 127:
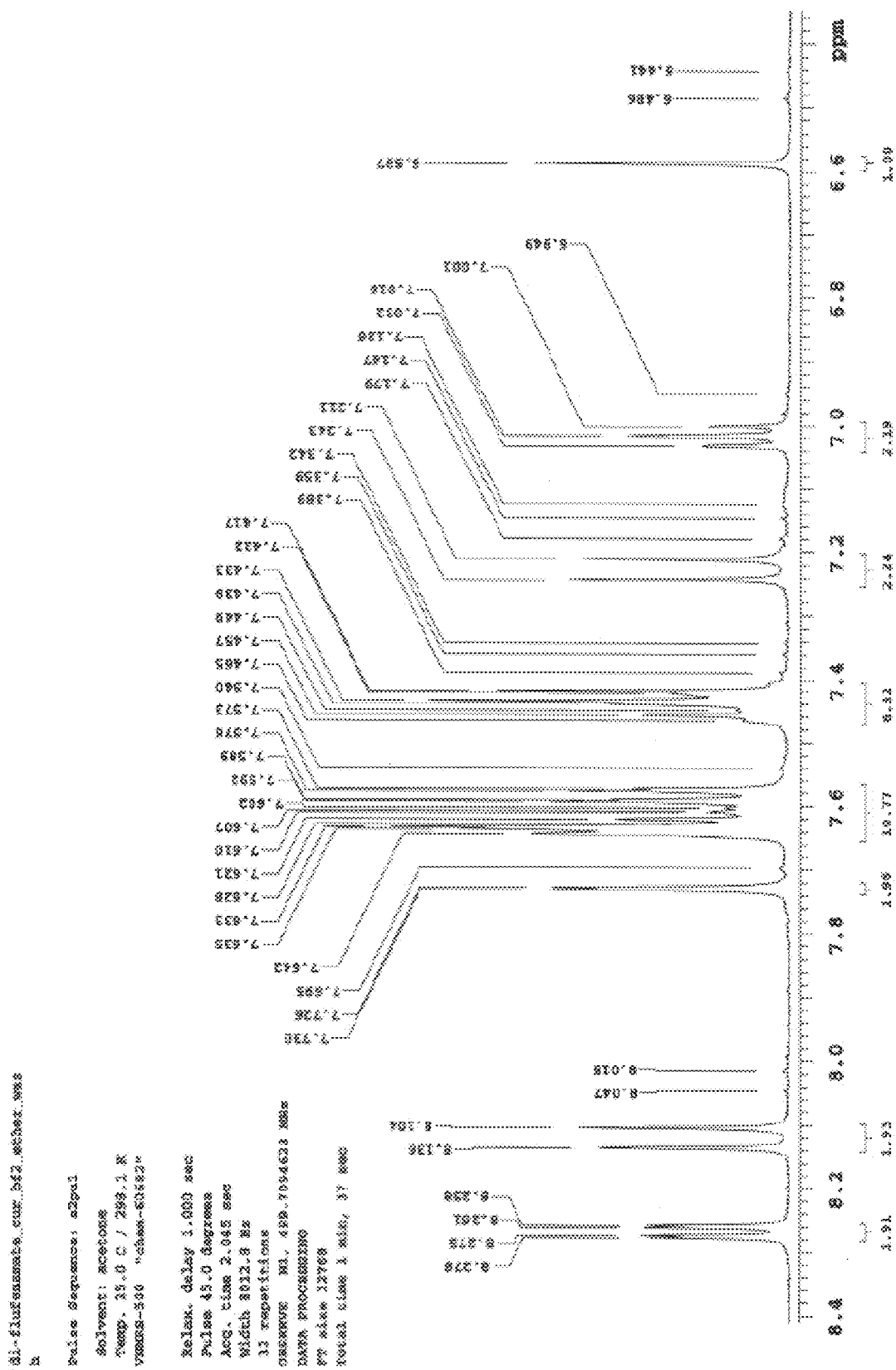

FIG. 127 is a representative NMR spectrum for compound 4 of Example 7.

Figure 128:
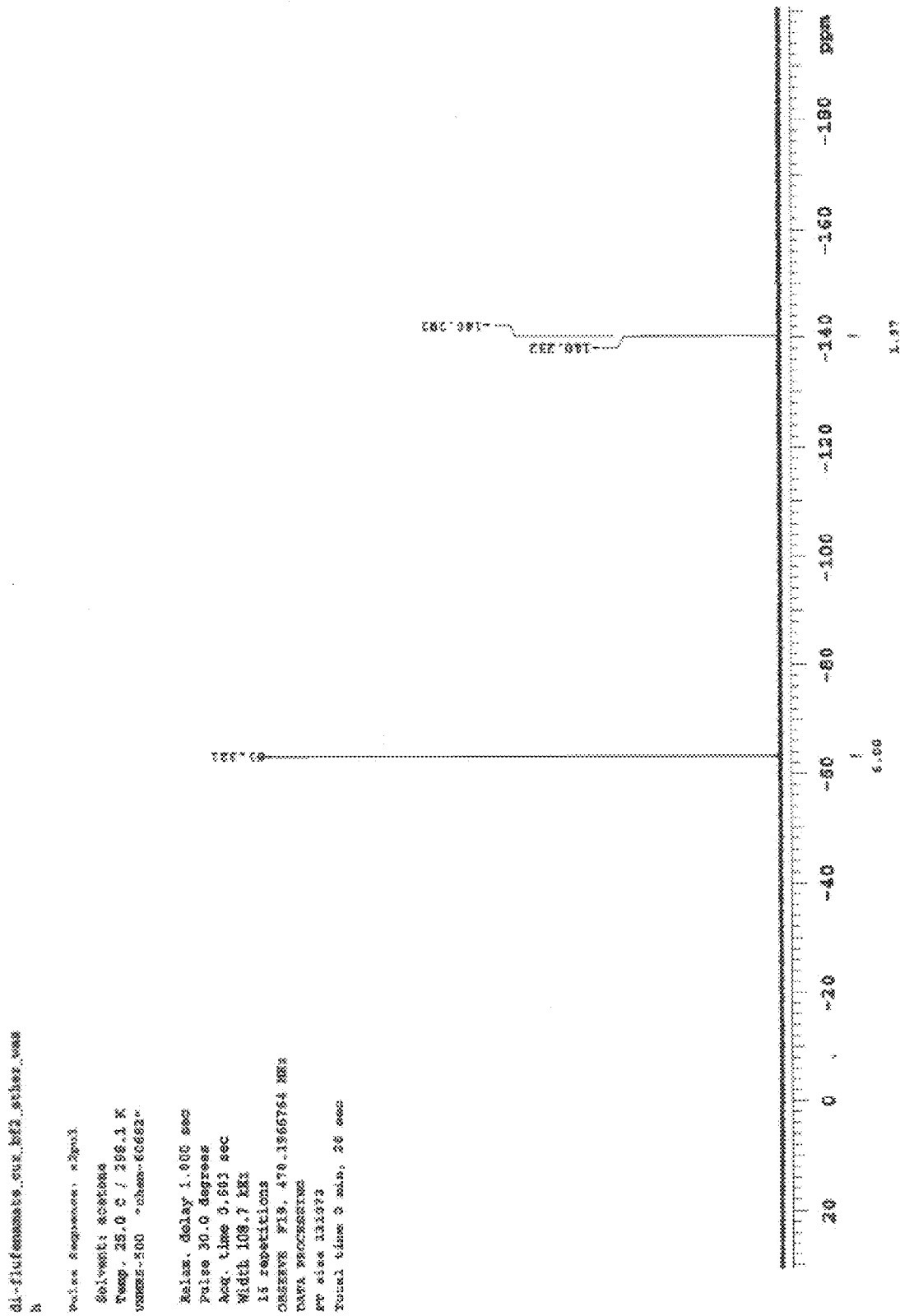

FIG. 128 is a representative NMR spectrum for compound 4 of Example 7.

Figure 129:
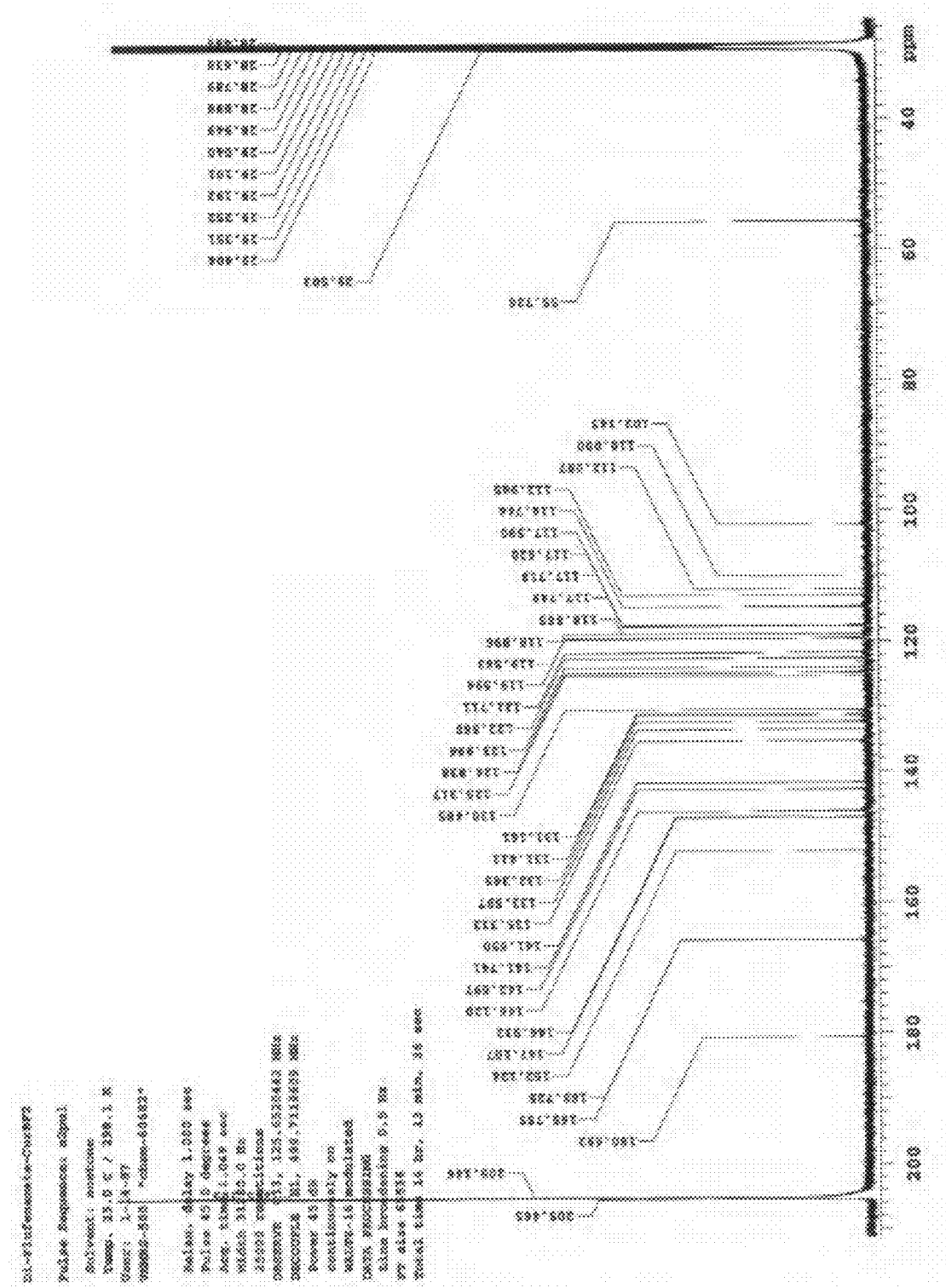

FIG. 129 is a representative NMR spectrum for compound 4 of Example 7.

Figure 130:
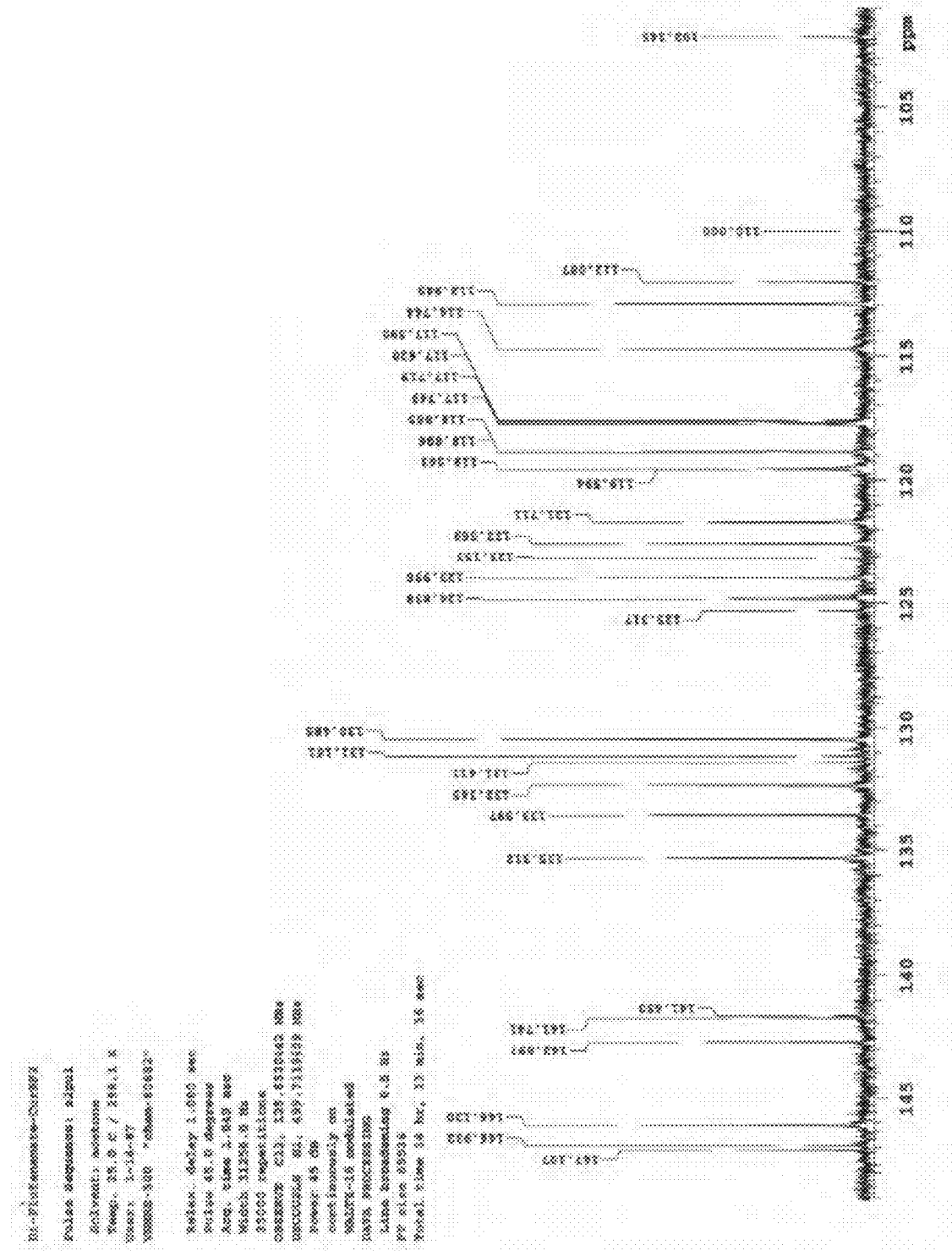

FIG. 130 is a representative NMR spectrum for compound 4 of Example 7.

Figure 131:
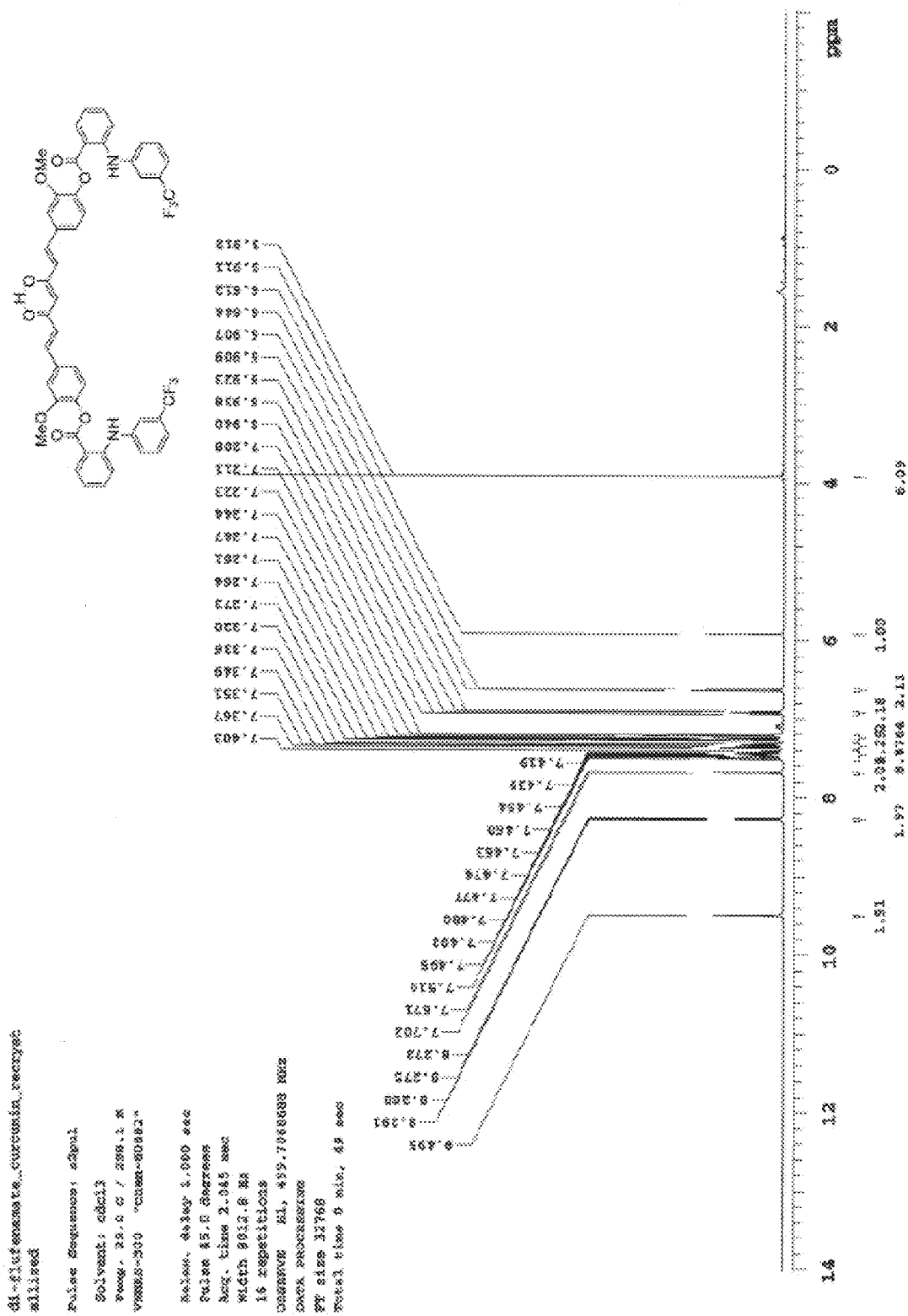

FIG. 131 is a representative NMR spectrum for compound 15 of Example 7.

Figure 132:
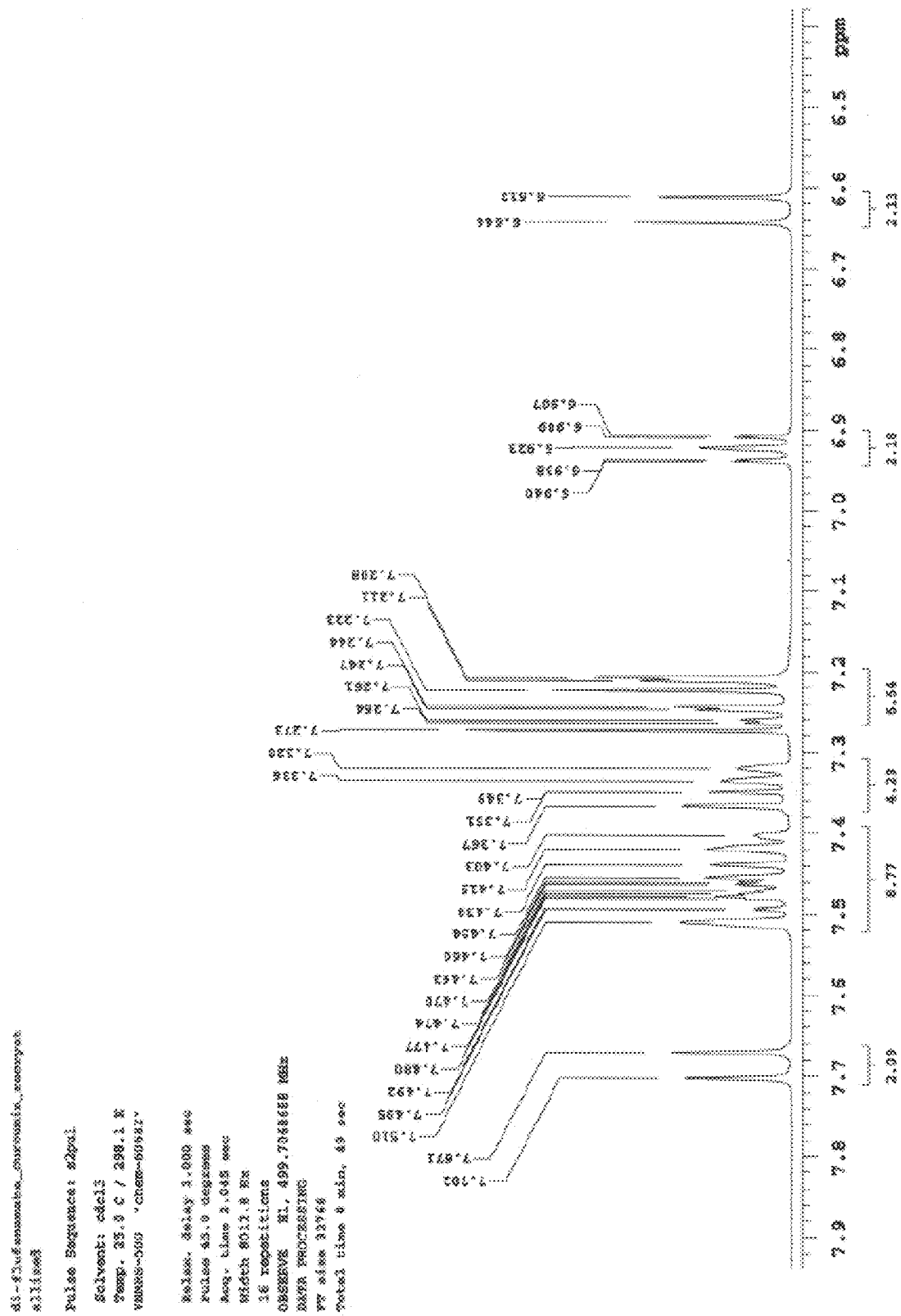

FIG. 132 is a representative NMR spectrum for compound 15 of Example 7.

Figure 133:
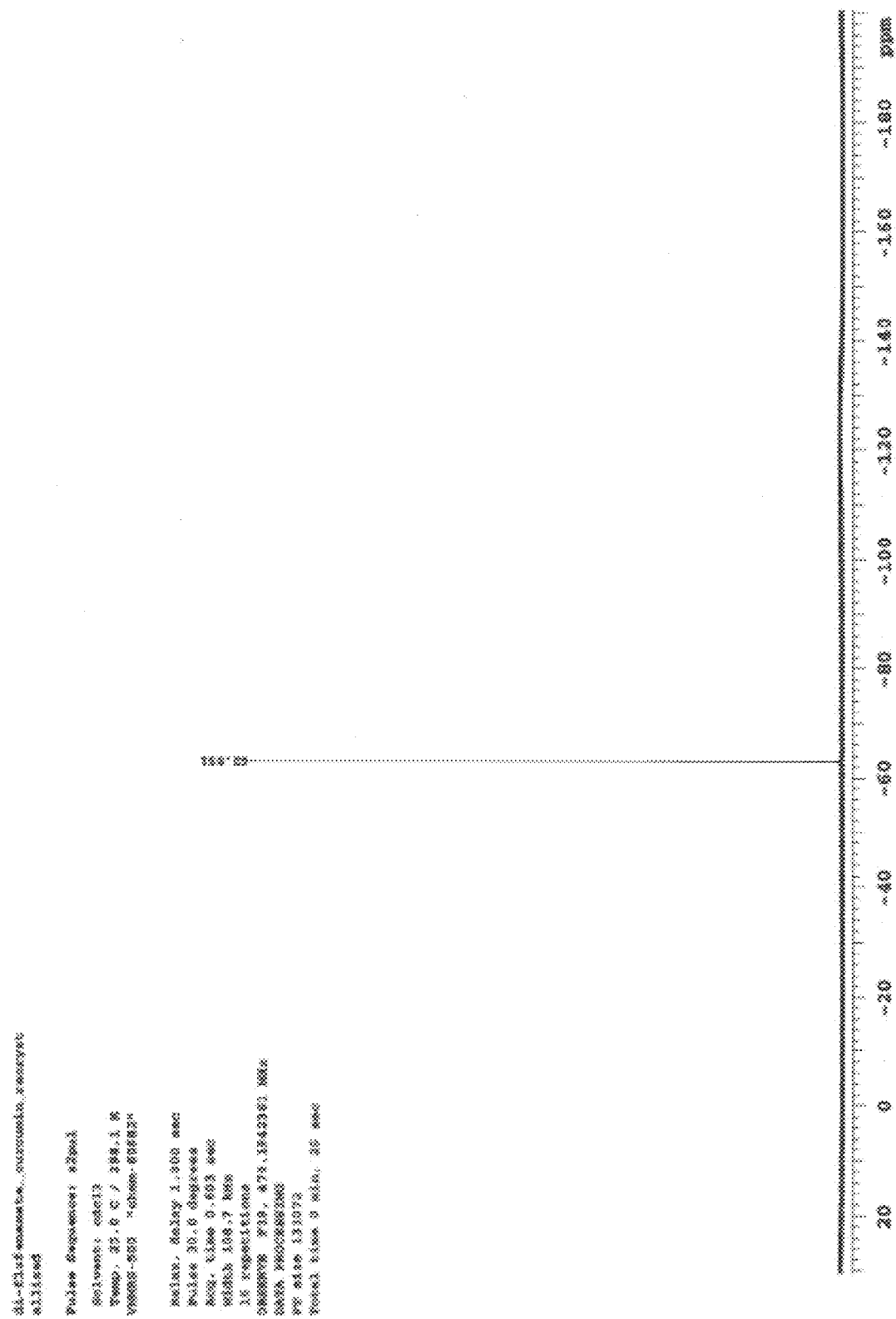

FIG. 133 is a representative NMR spectrum for compound 15 of Example 7.

Figure 134:
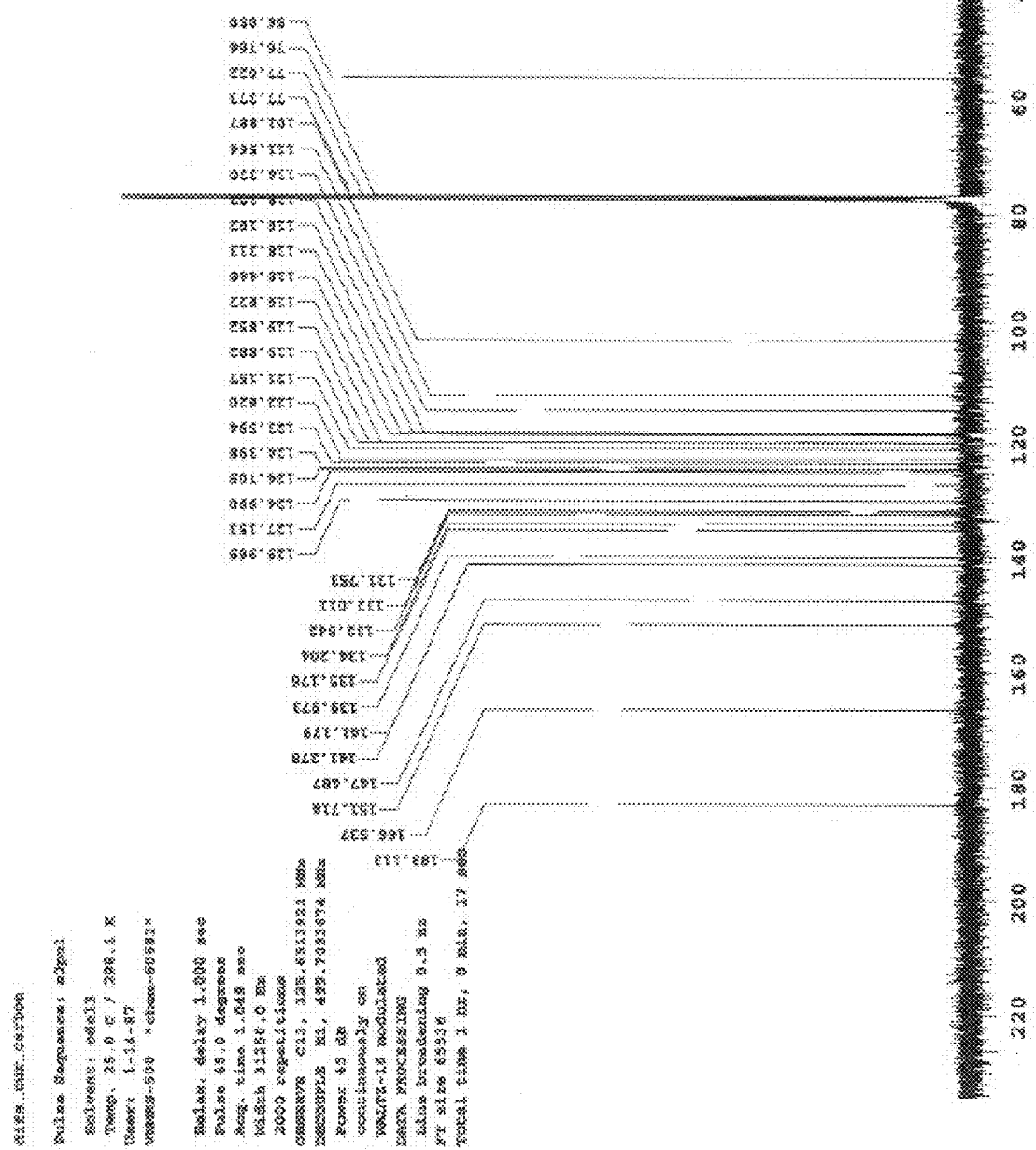

FIG. 134 is a representative NMR spectrum for compound 15 of Example 7.

Figure 135:
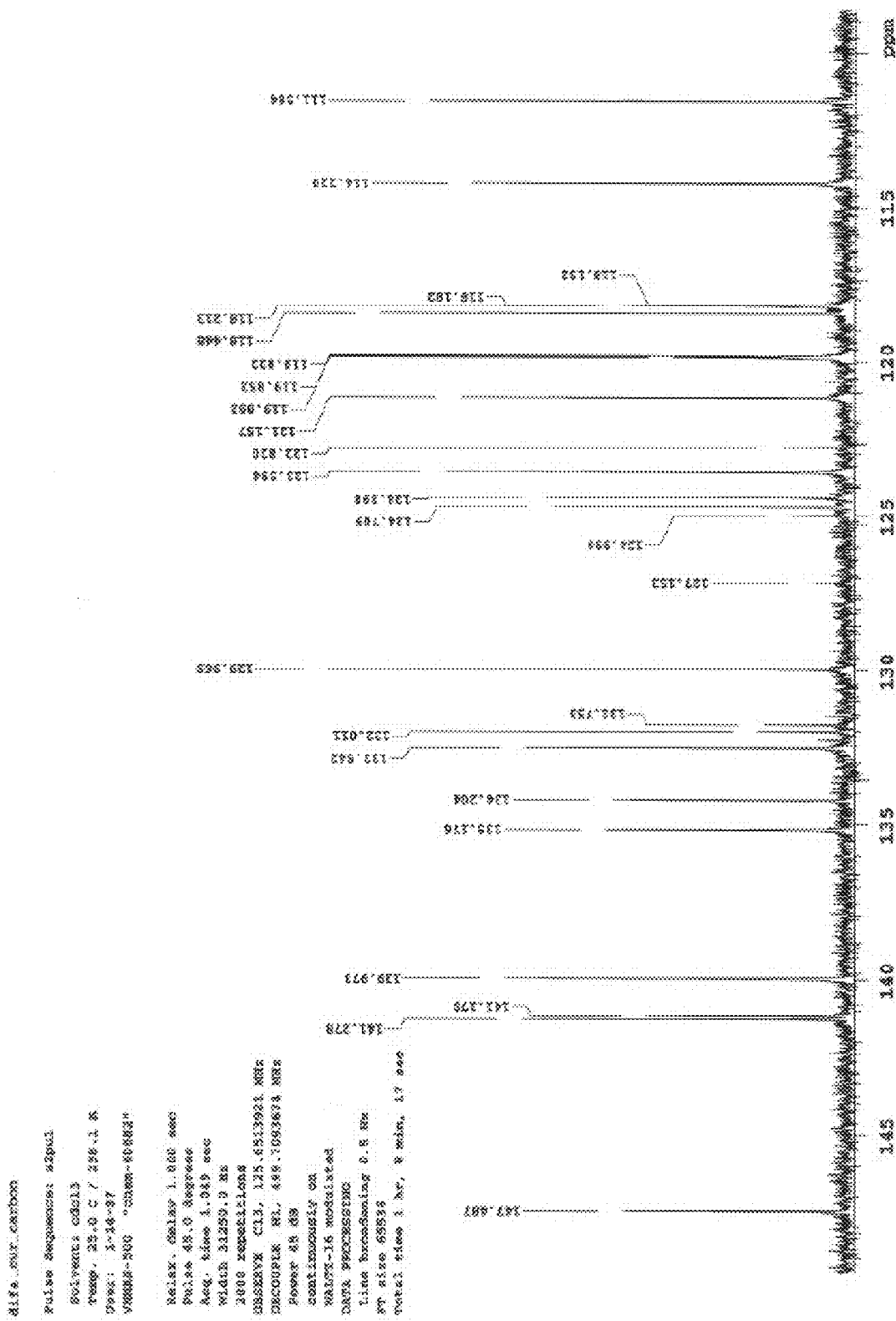

FIG. 135 is a representative NMR spectrum for compound 15 of Example 7.

Figure 136:
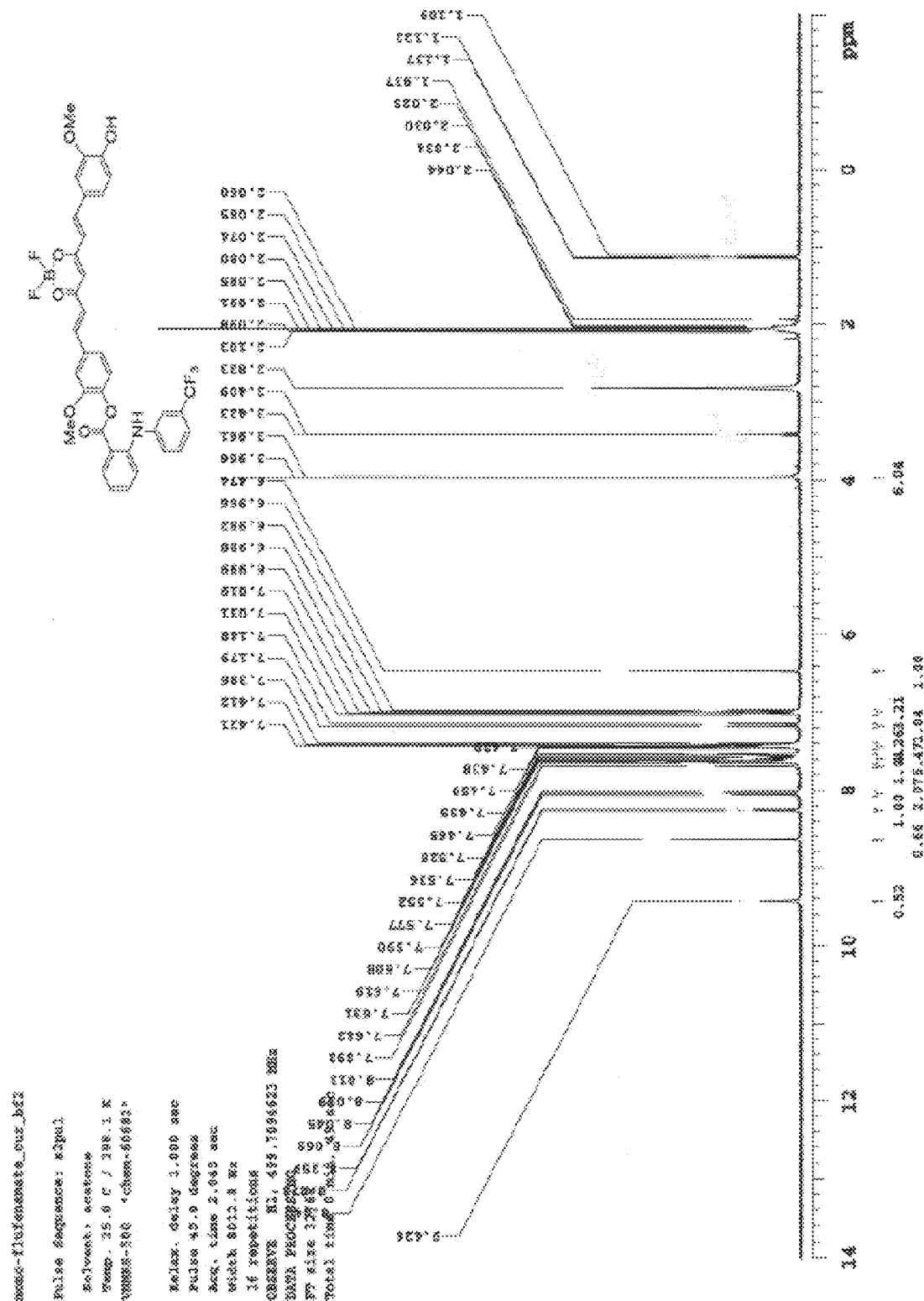

FIG. 136 is a representative NMR spectrum for compound 5 of Example 7.

Figure 137:
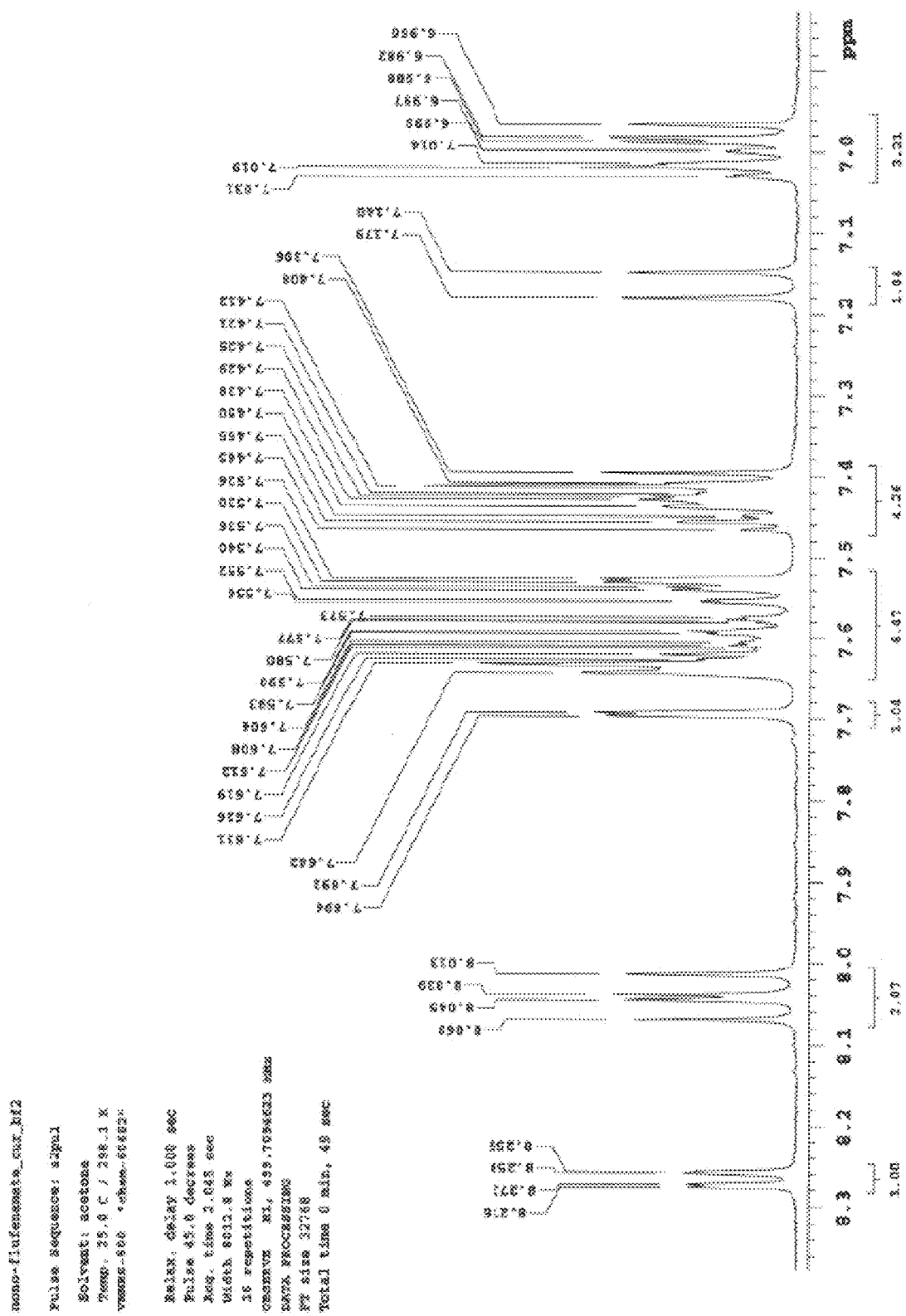

FIG. 137 is a representative NMR spectrum for compound 5 of Example 7.

Figure 138:
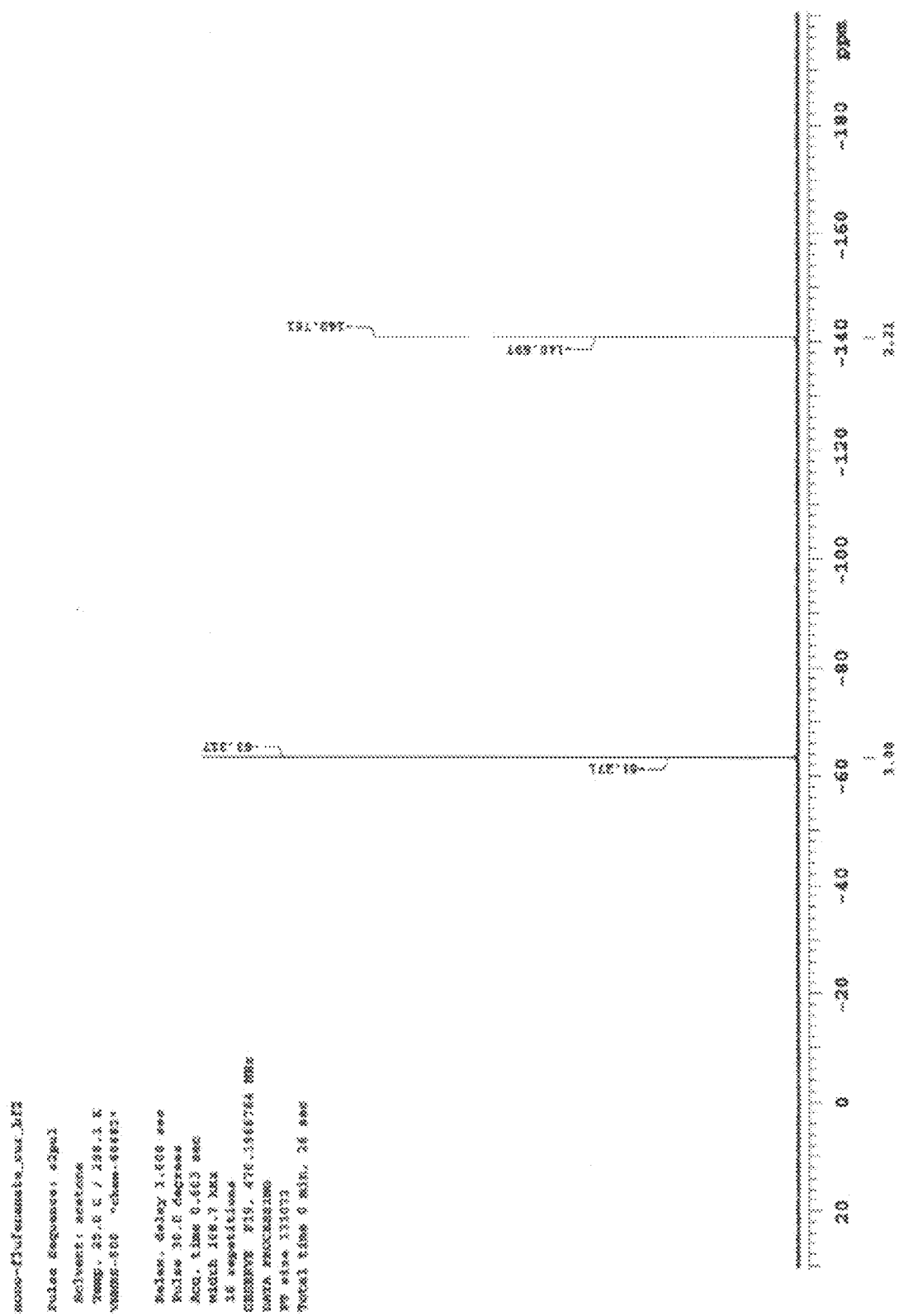

FIG. 138 is a representative NMR spectrum for compound 5 of Example 7.

Figure 139:
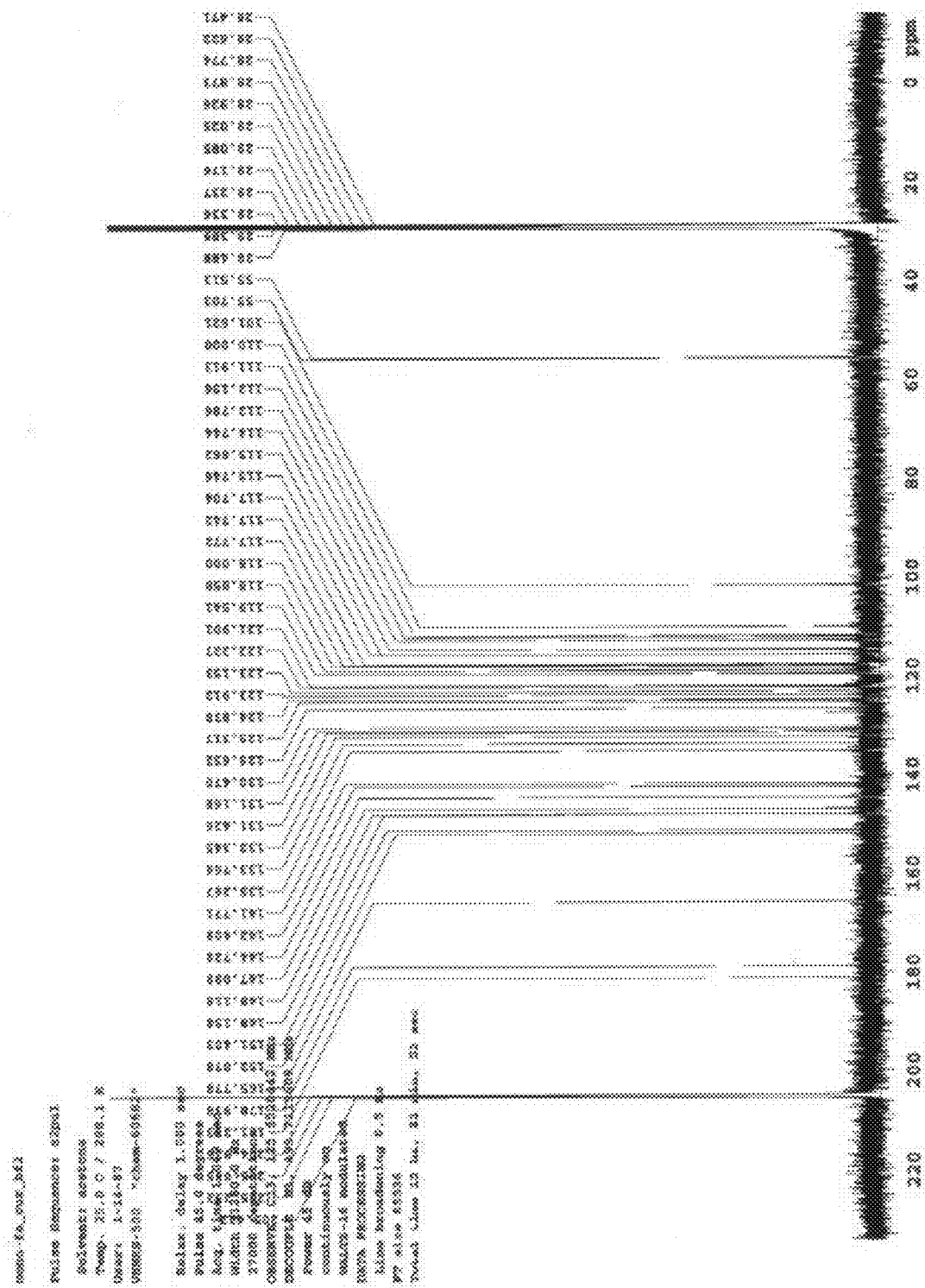

FIG. 139 is a representative NMR spectrum for compound 5 of Example 7.

Figure 140:
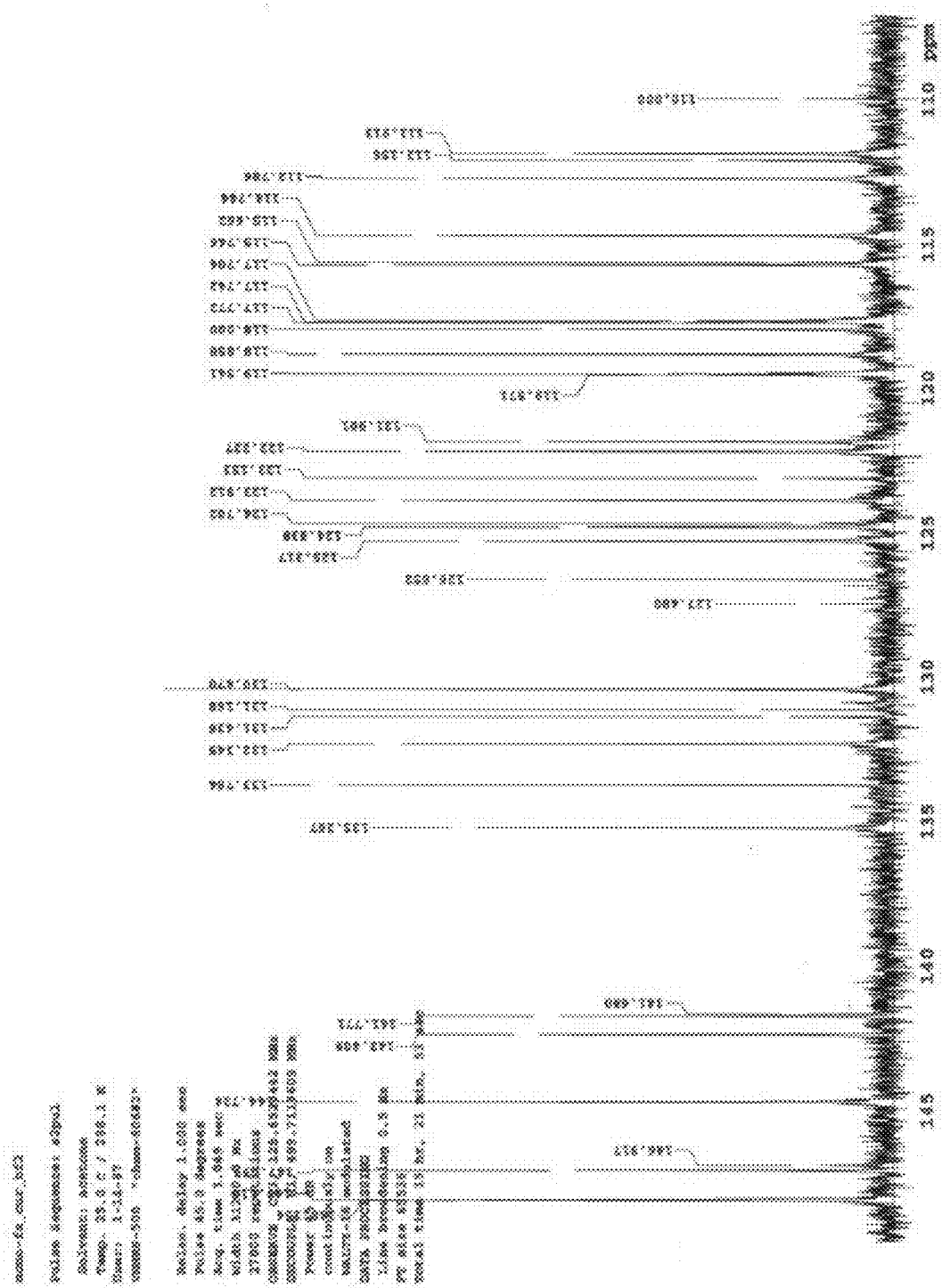

FIG. 140 is a representative NMR spectrum for compound 5 of Example 7.

Figure 141:
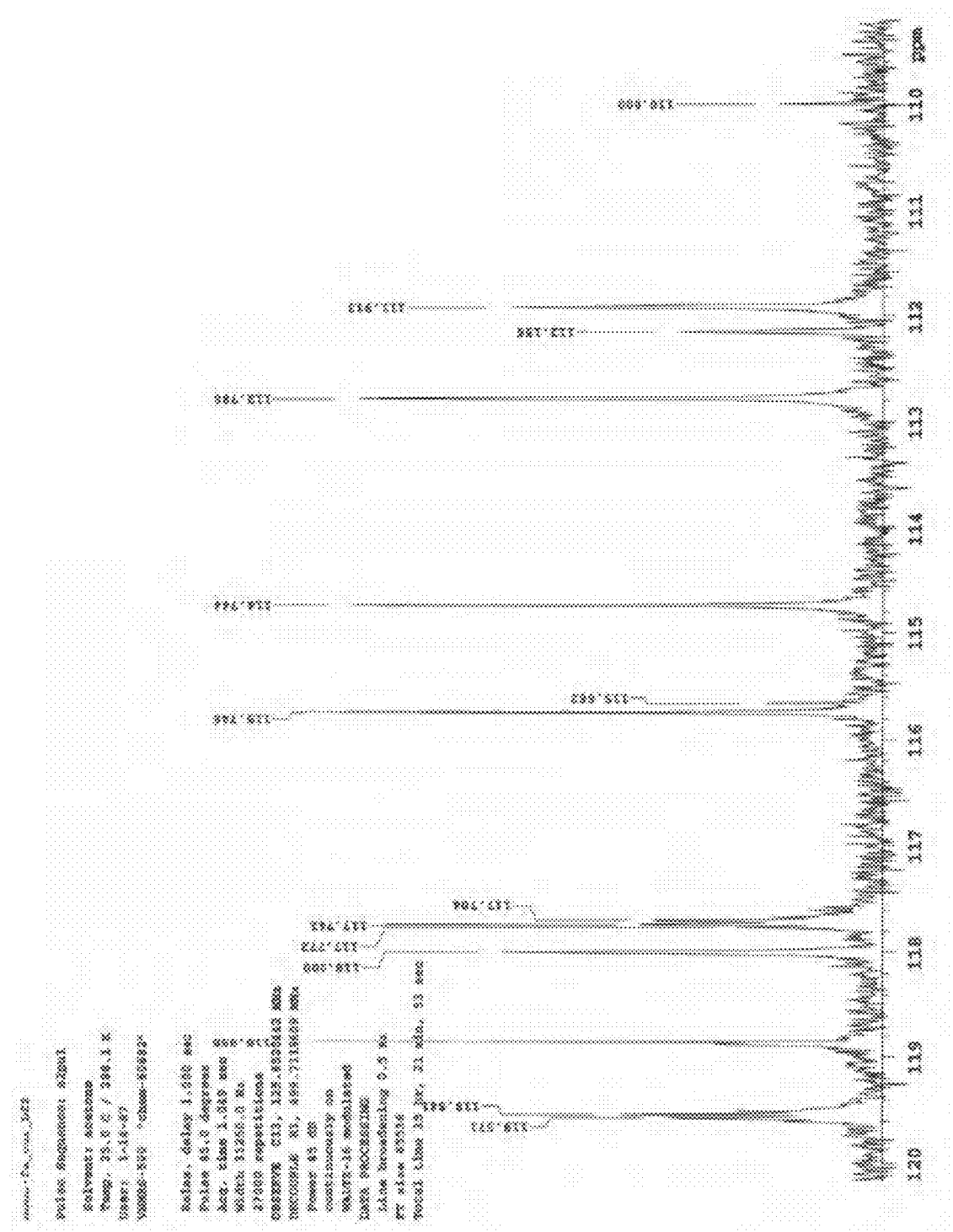

FIG. 141 is a representative NMR spectrum for compound 5 of Example 7.

Figure 142:
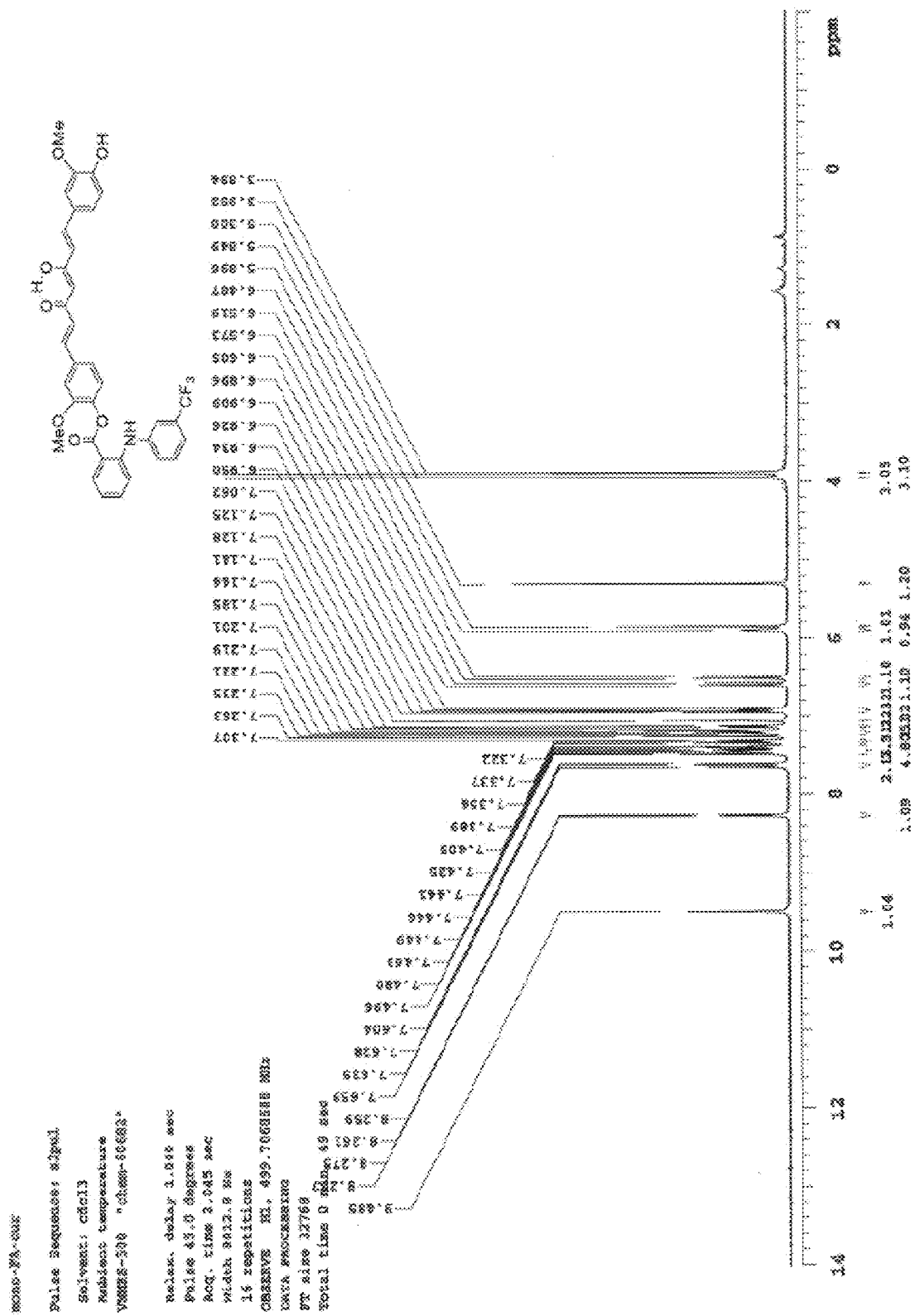

FIG. 142 is a representative NMR spectrum for compound 16 of Example 7.

Figure 143:
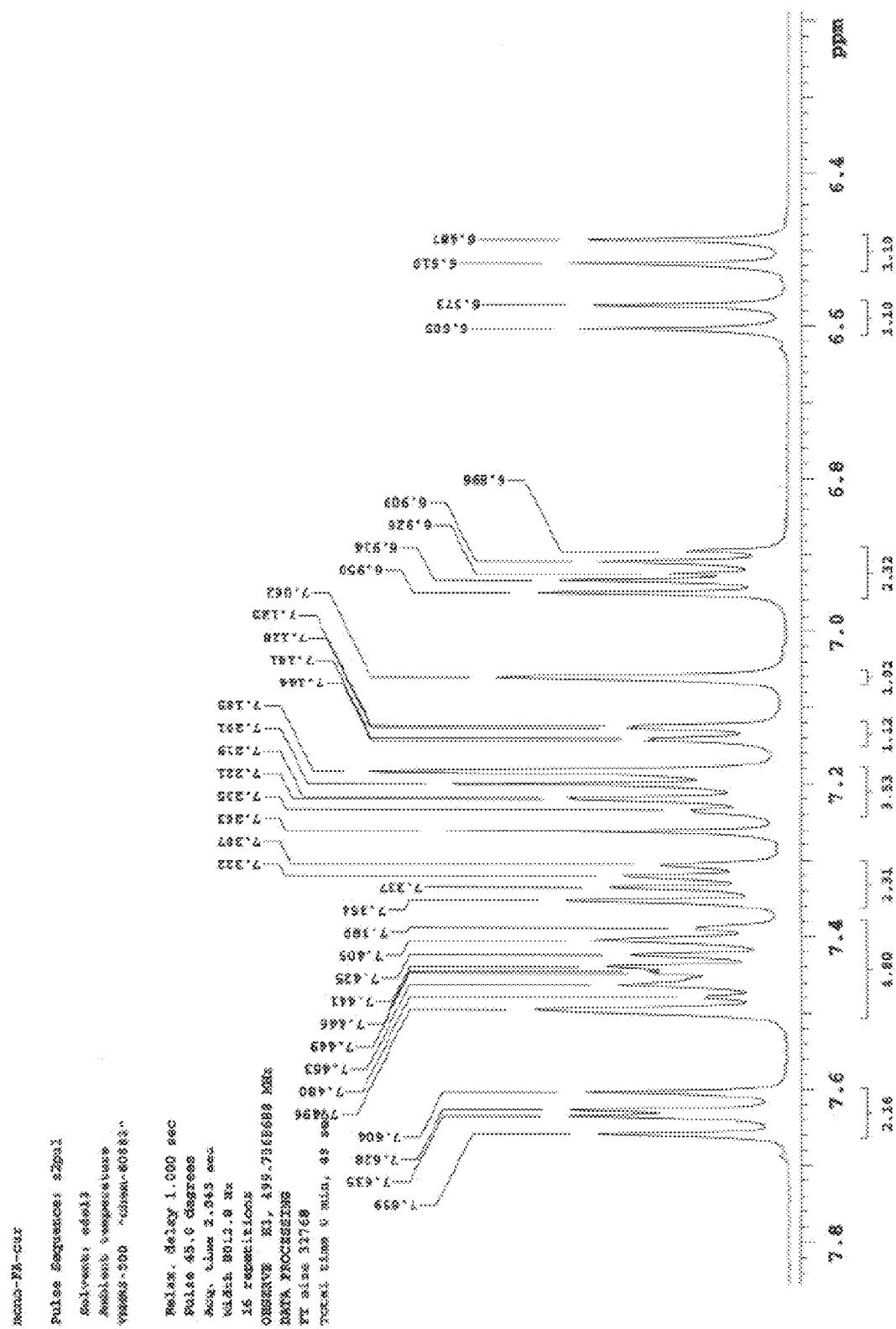

FIG. 143 is a representative NMR spectrum for compound 16 of Example 7.

Figure 144:
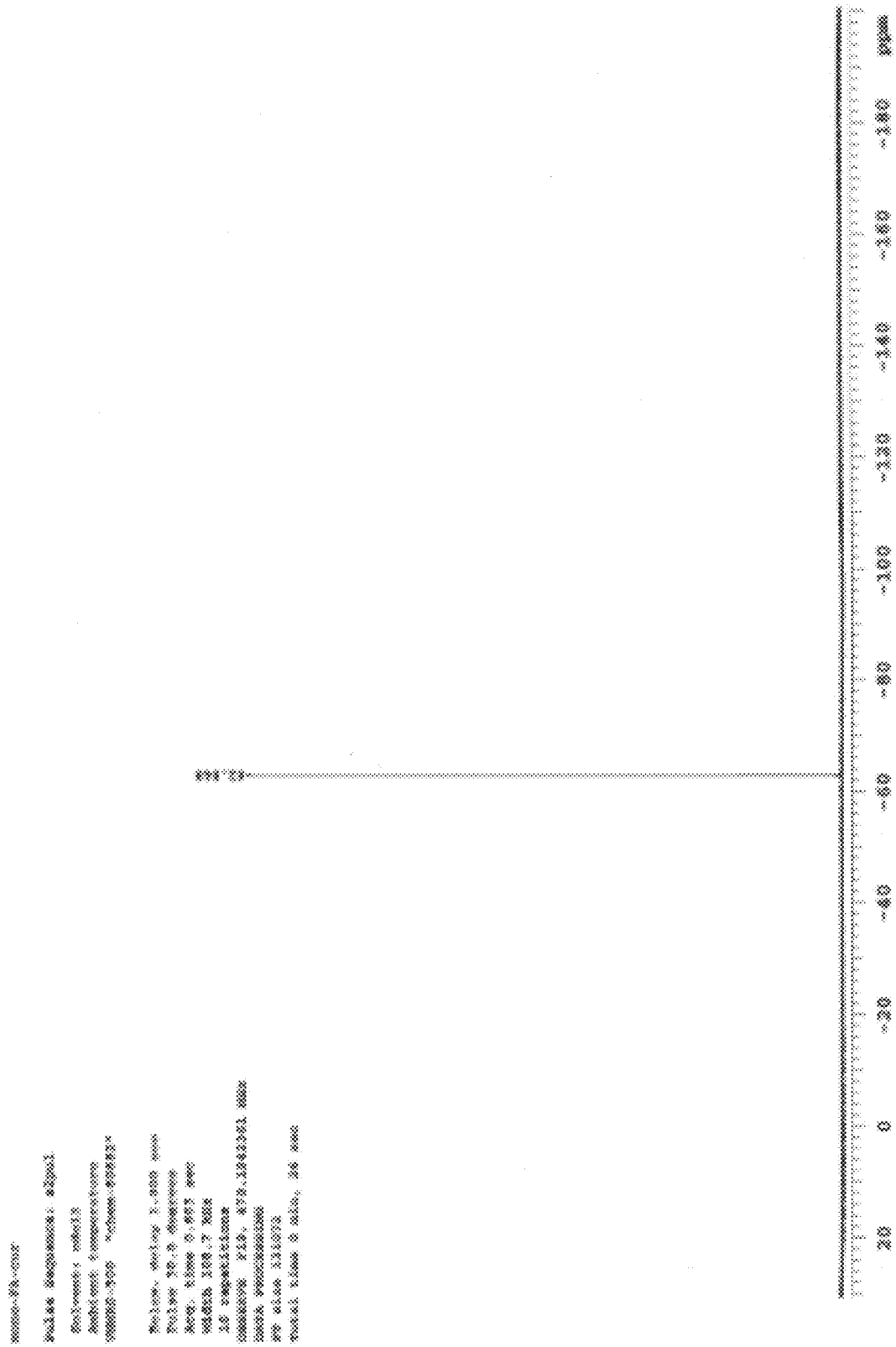

FIG. 144 is a representative NMR spectrum for compound 16 of Example 7.

Figure 145:
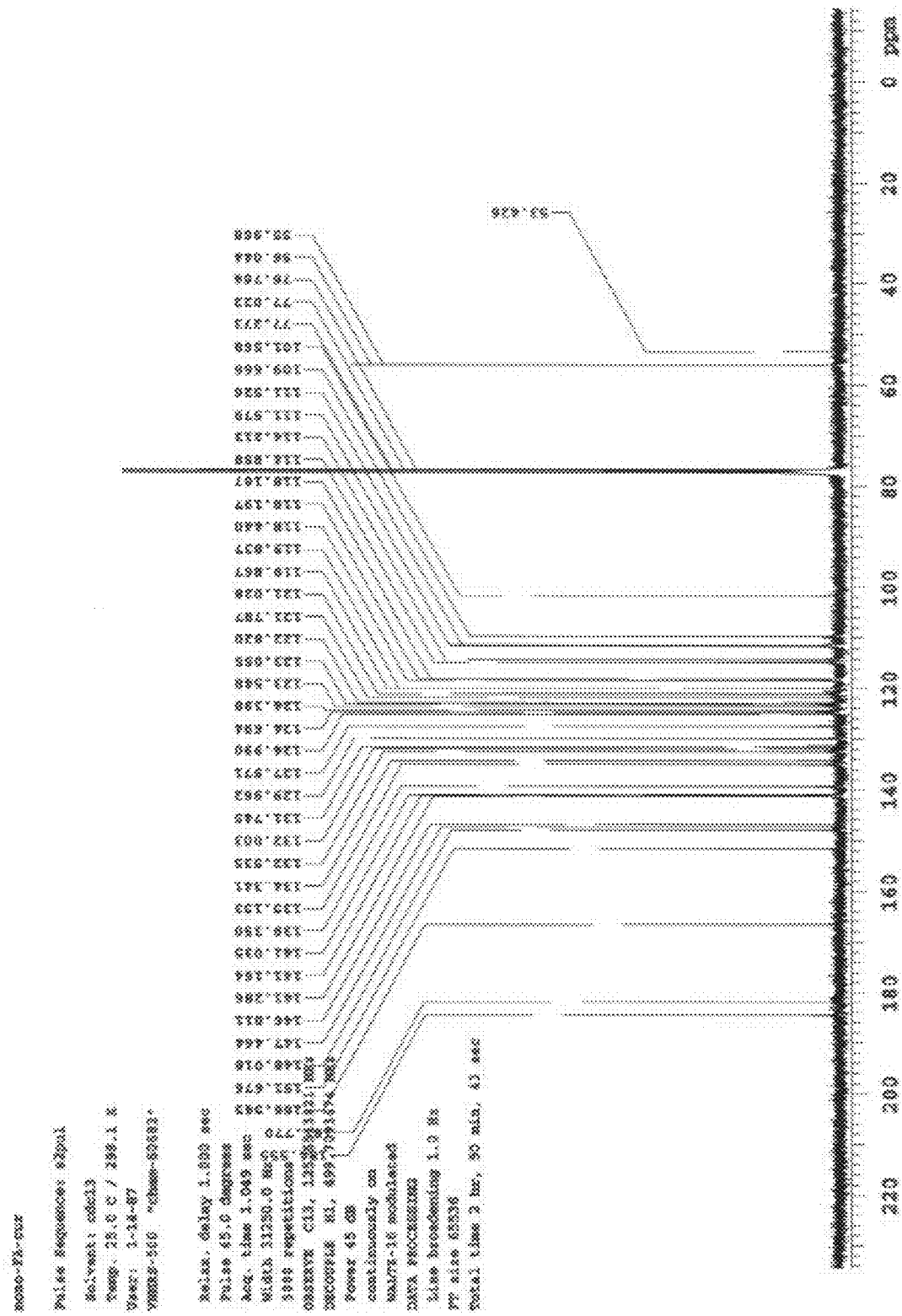

FIG. 145 is a representative NMR spectrum for compound 16 of Example 7.

Figure 146:
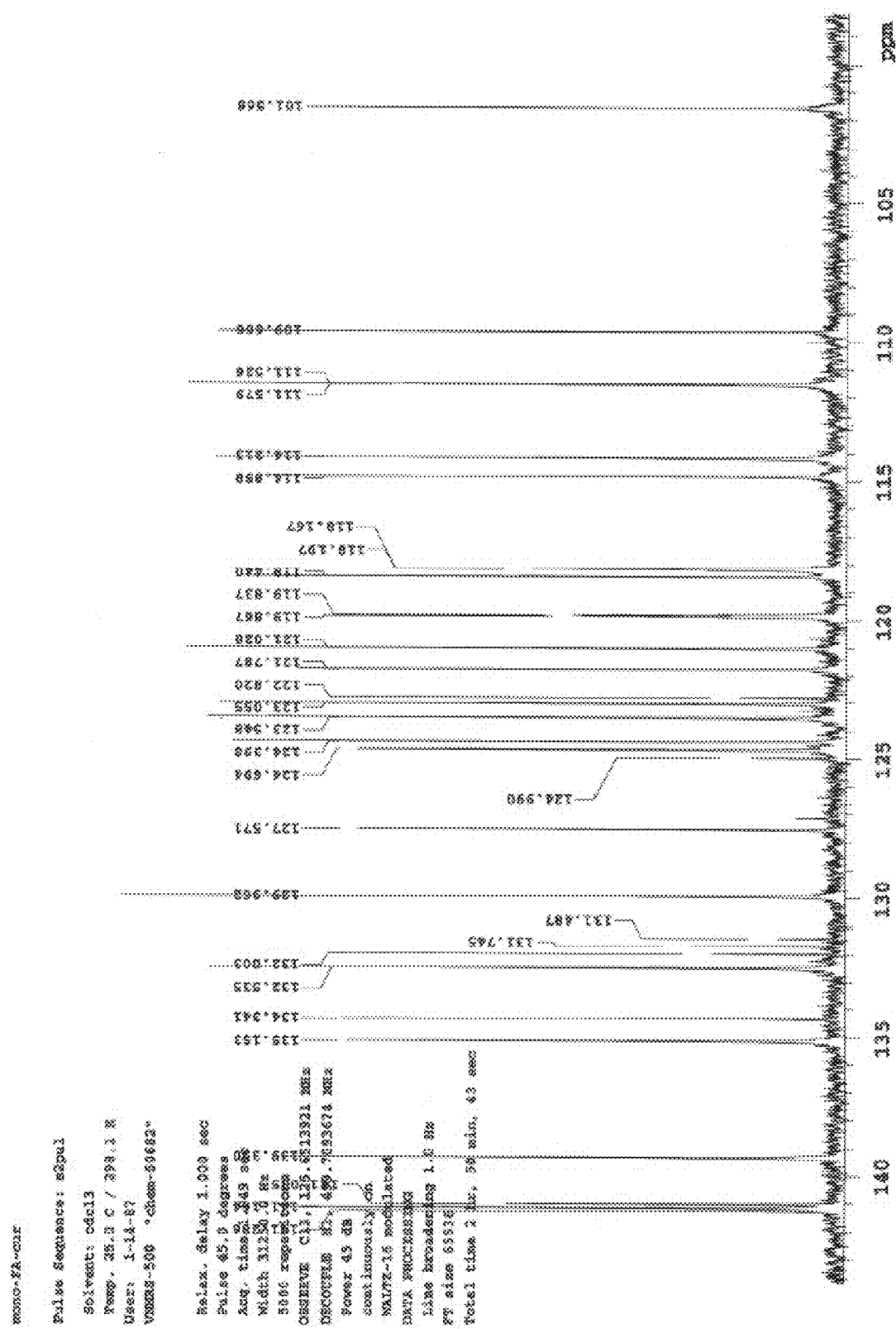

FIG. 146 is a representative NMR spectrum for compound 16 of Example 7.

Figure 147:
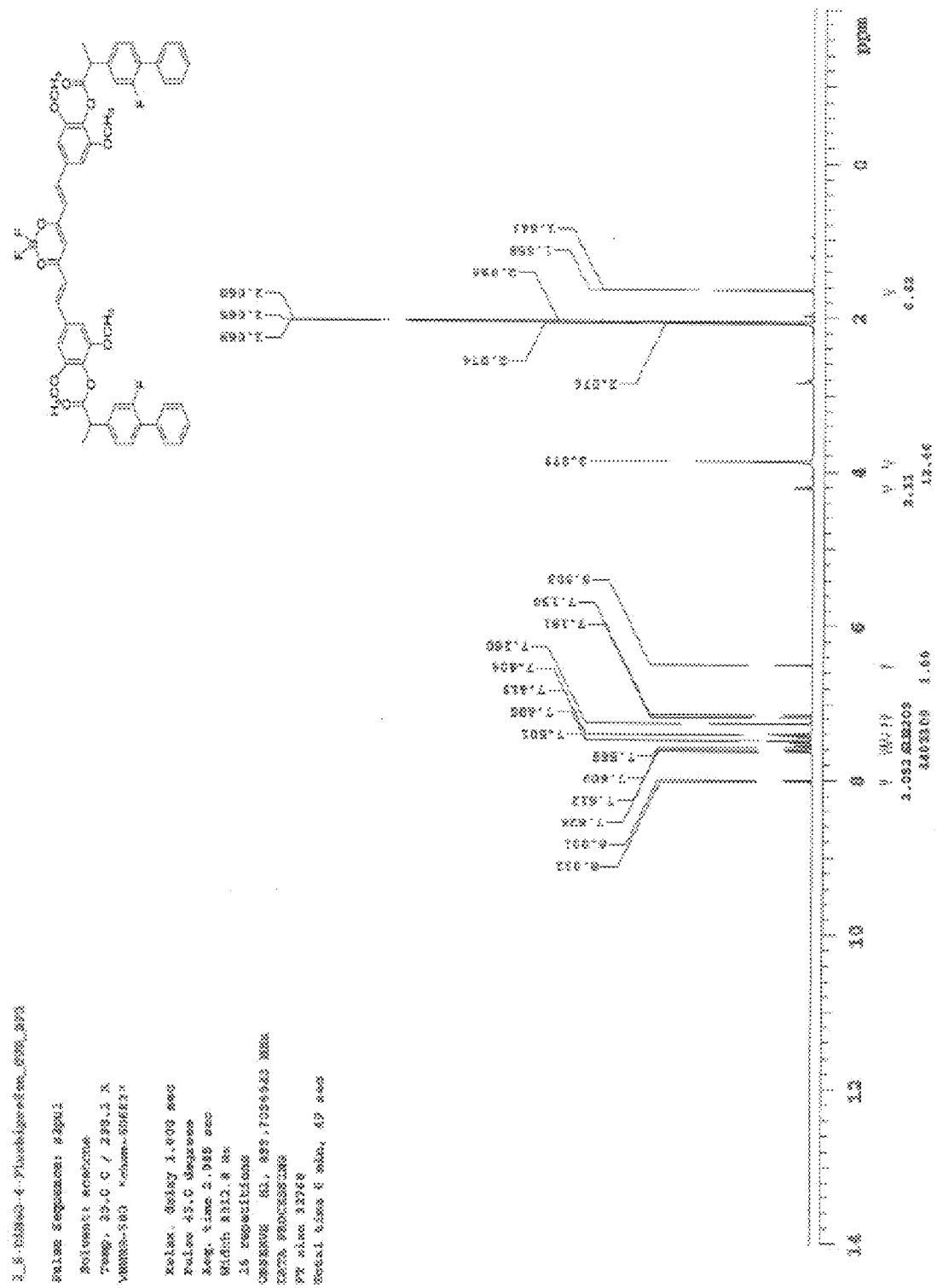

FIG. 147 is a representative NMR spectrum for compound 6 of Example 7.

Figure 148:
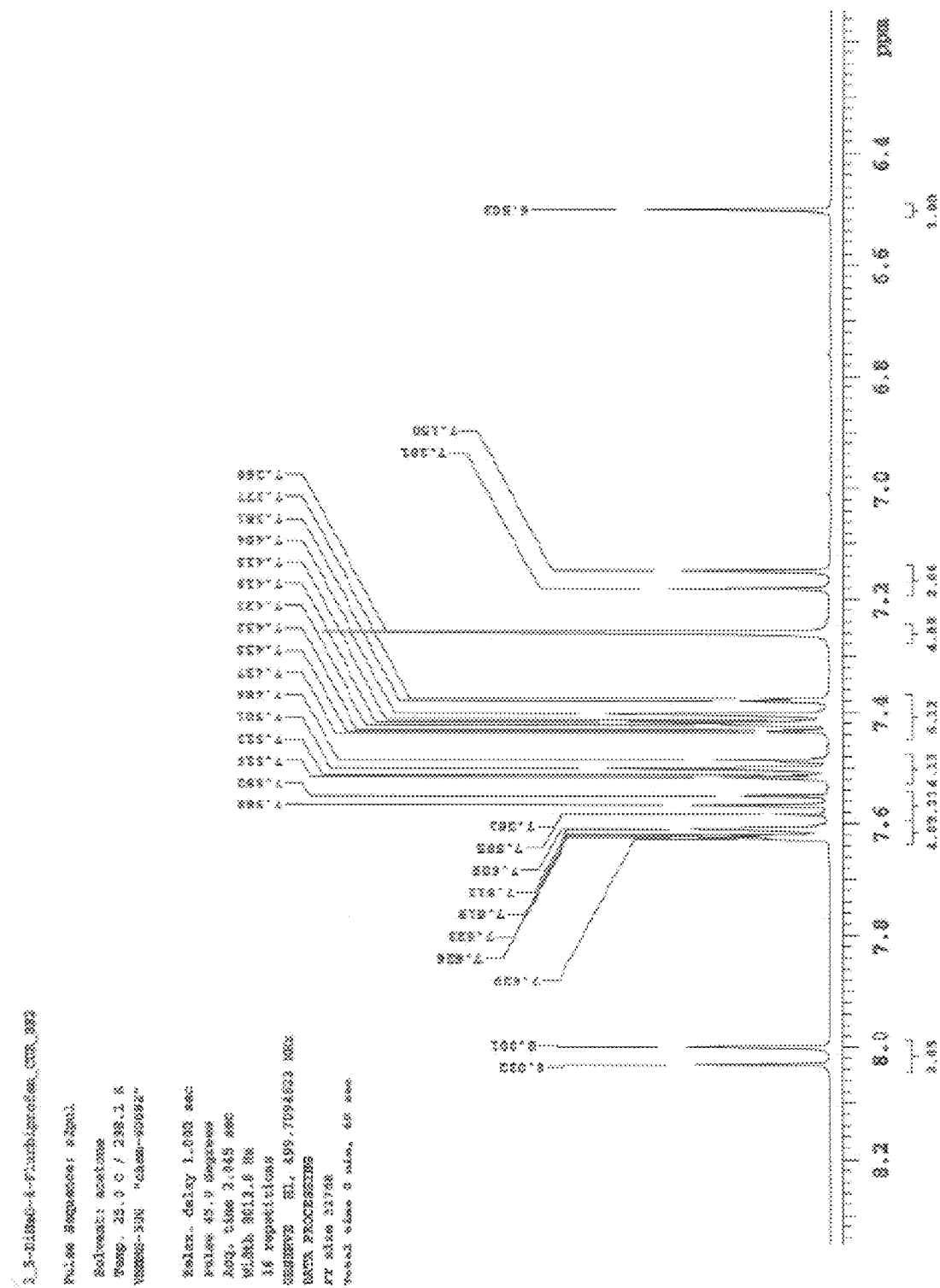

FIG. 148 is a representative NMR spectrum for compound 6 of Example 7.

Figure 149:
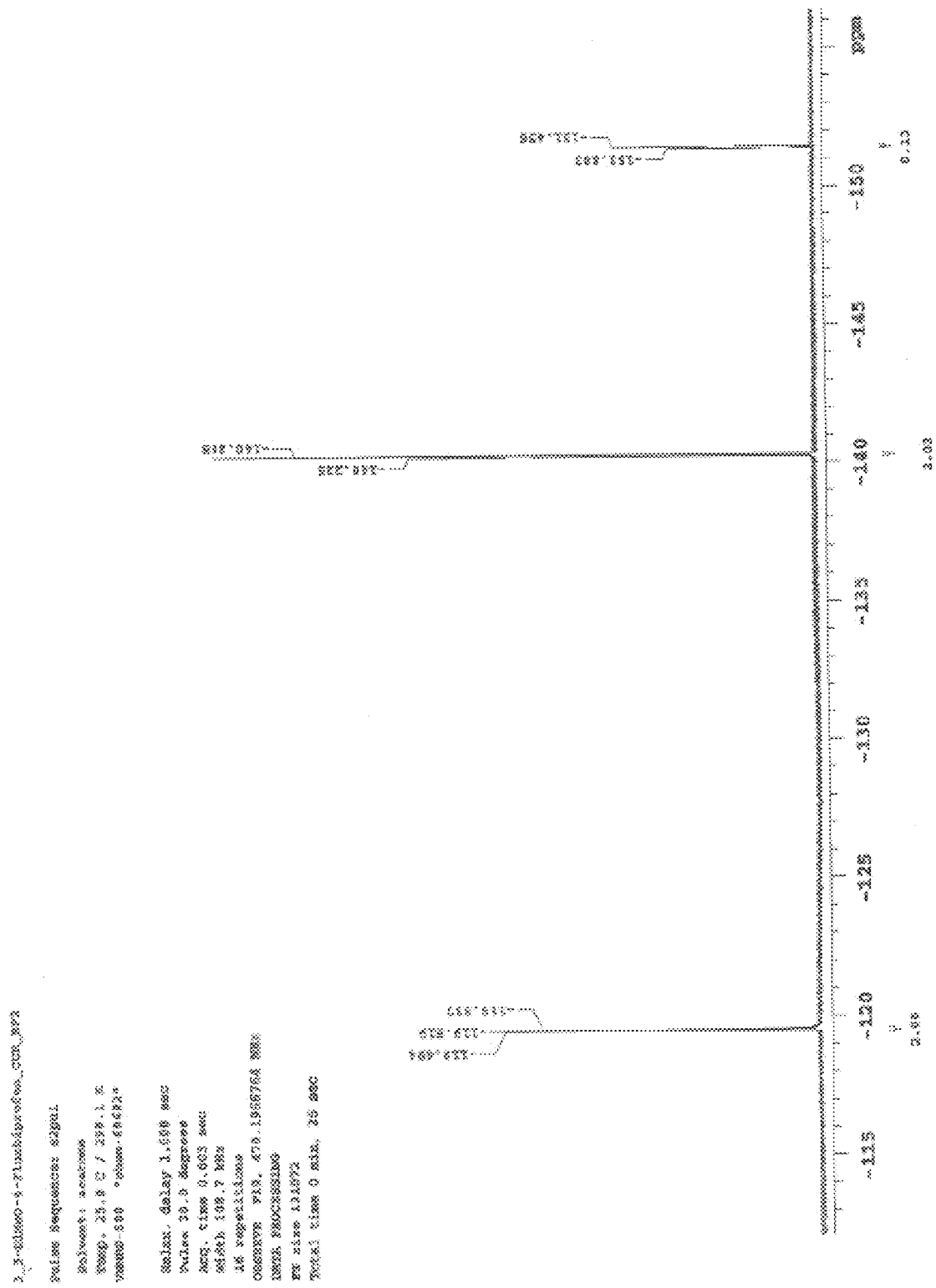

FIG. 149 is a representative NMR spectrum for compound 6 of Example 7.

Figure 150:
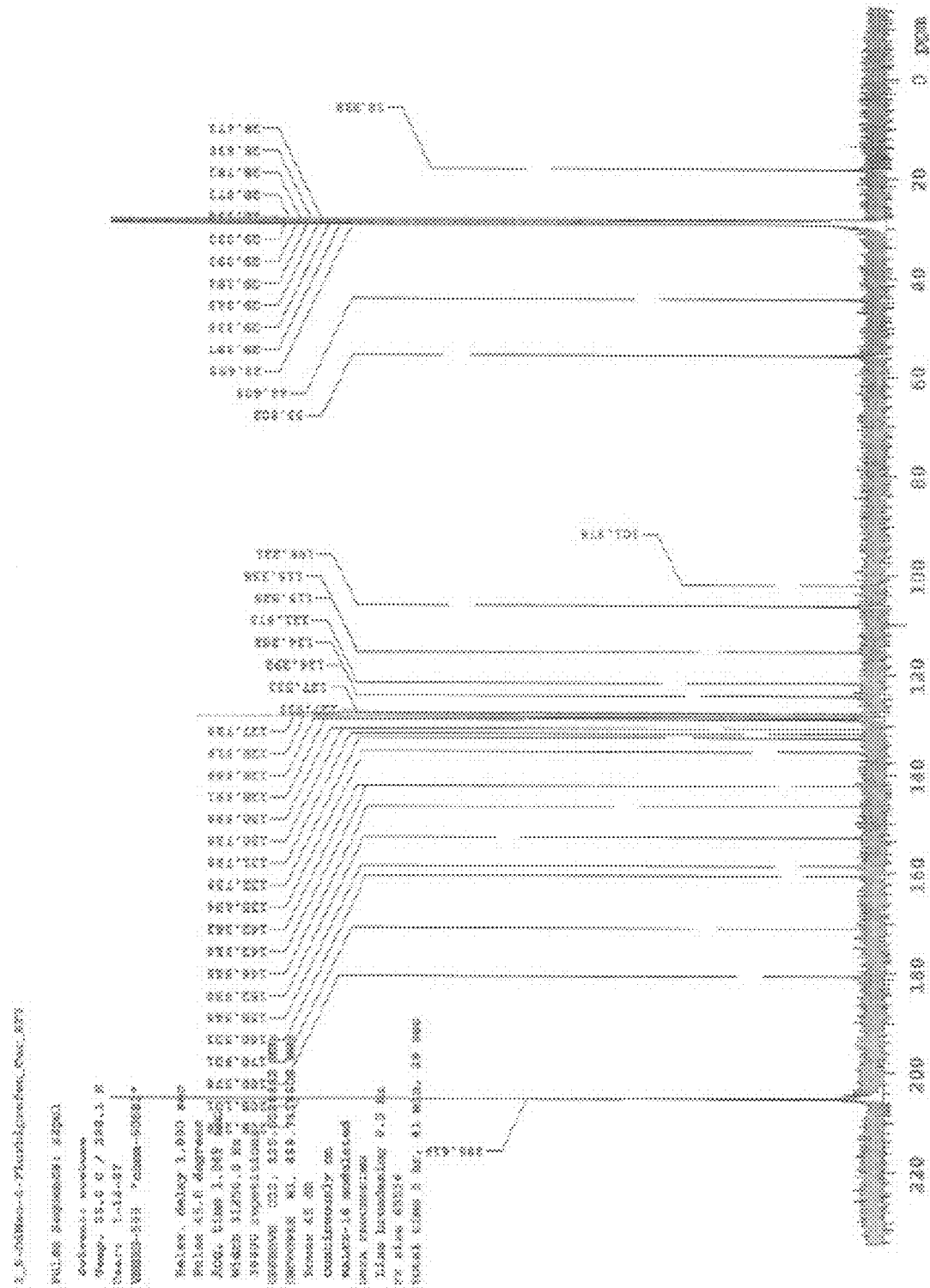

FIG. 150 is a representative NMR spectrum for compound 6 of Example 7.

Figure 151:
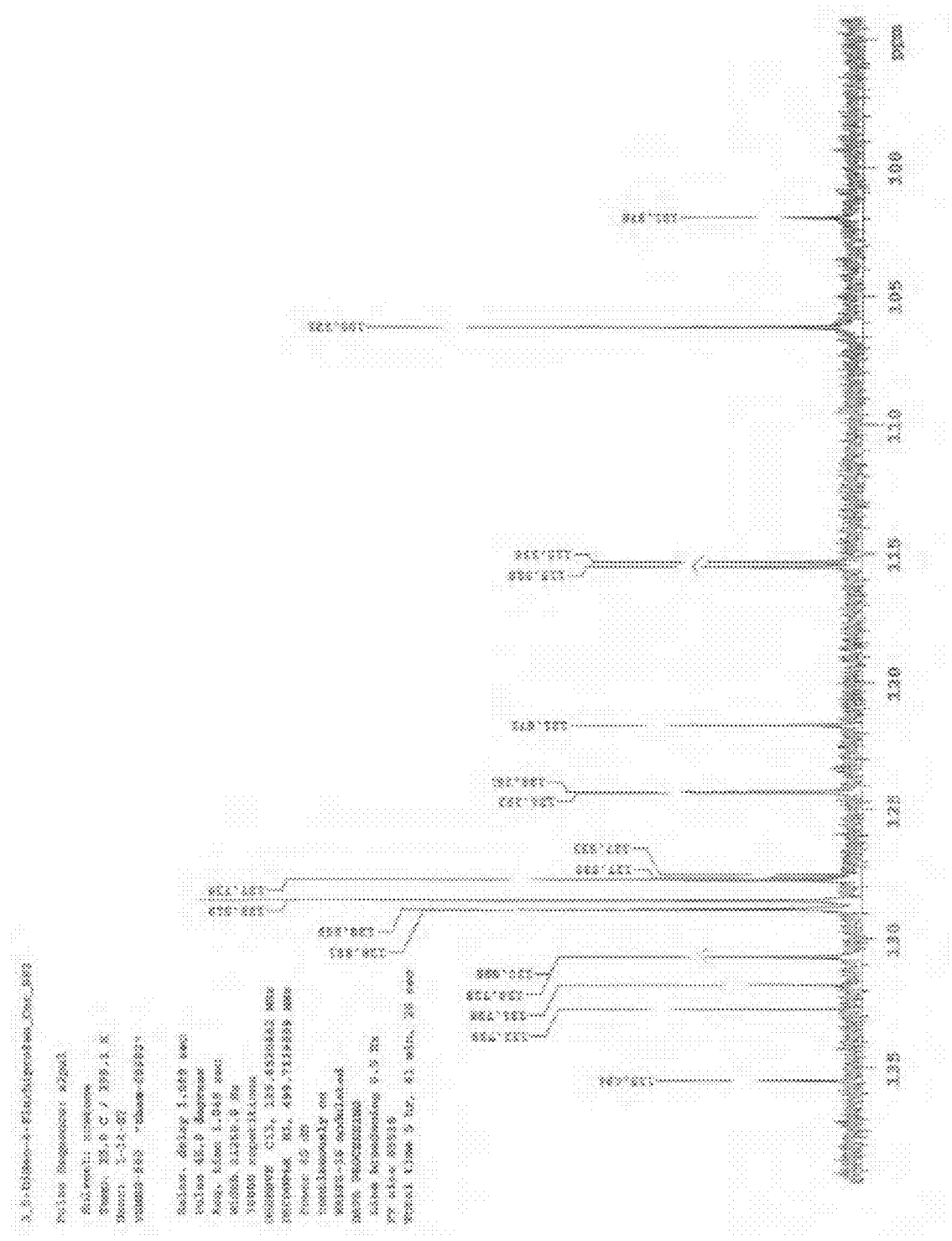

FIG. 151 is a representative NMR spectrum for compound 6 of Example 7.

Figure 152:
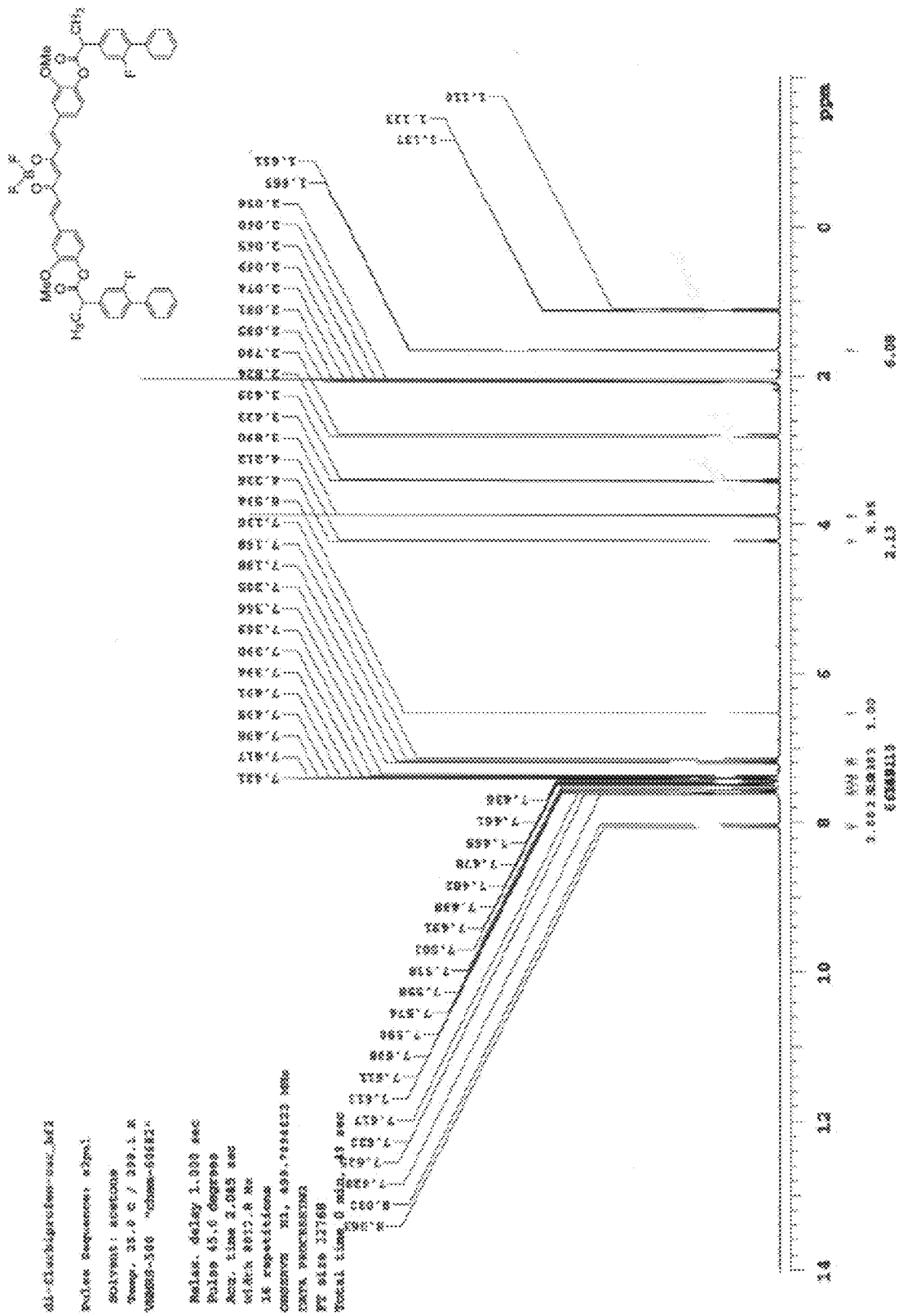

FIG. 152 is a representative NMR spectrum for compound 7 of Example 7.

Figure 153:
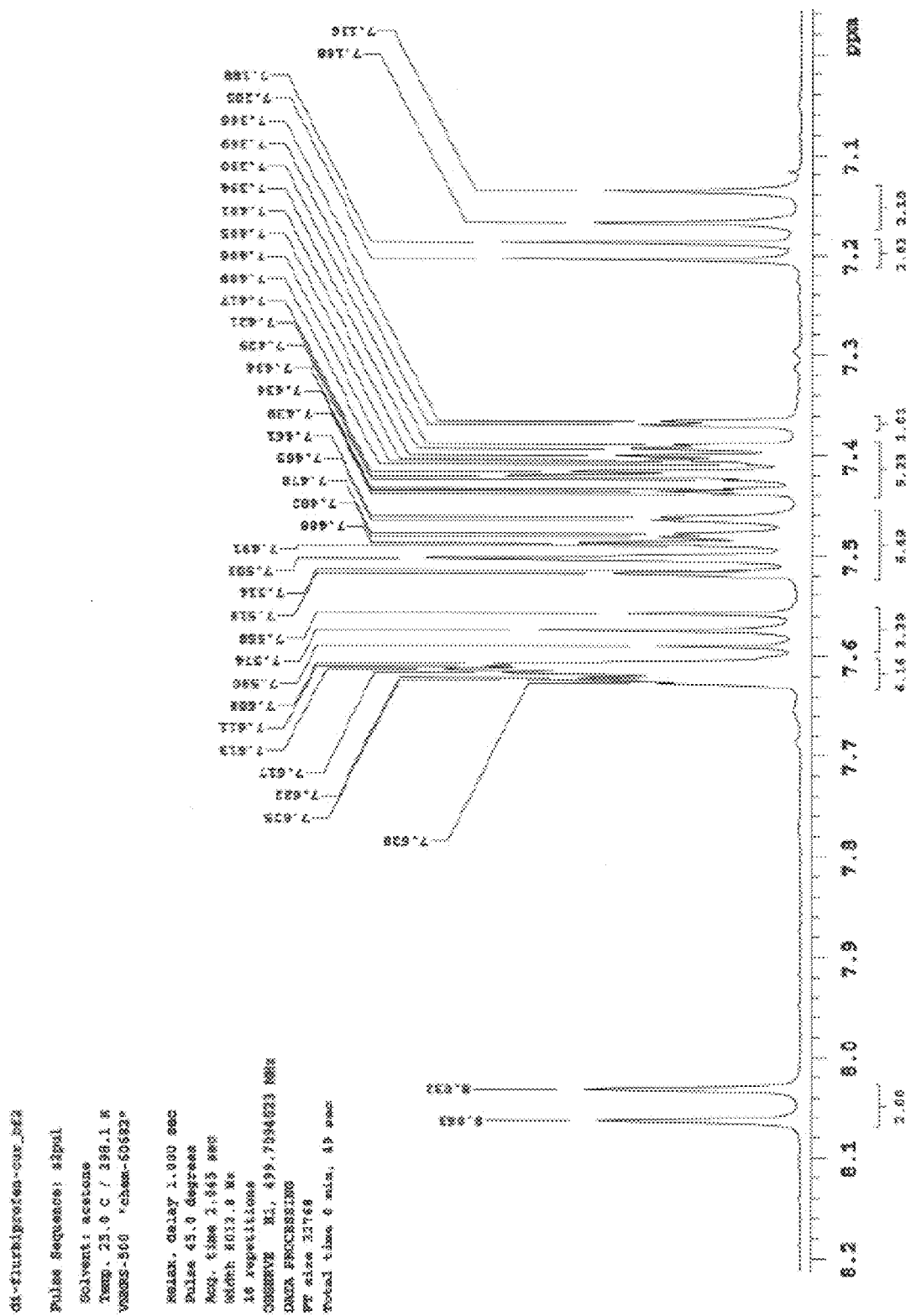

FIG. 153 is a representative NMR spectrum for compound 7 of Example 7.

Figure 154:
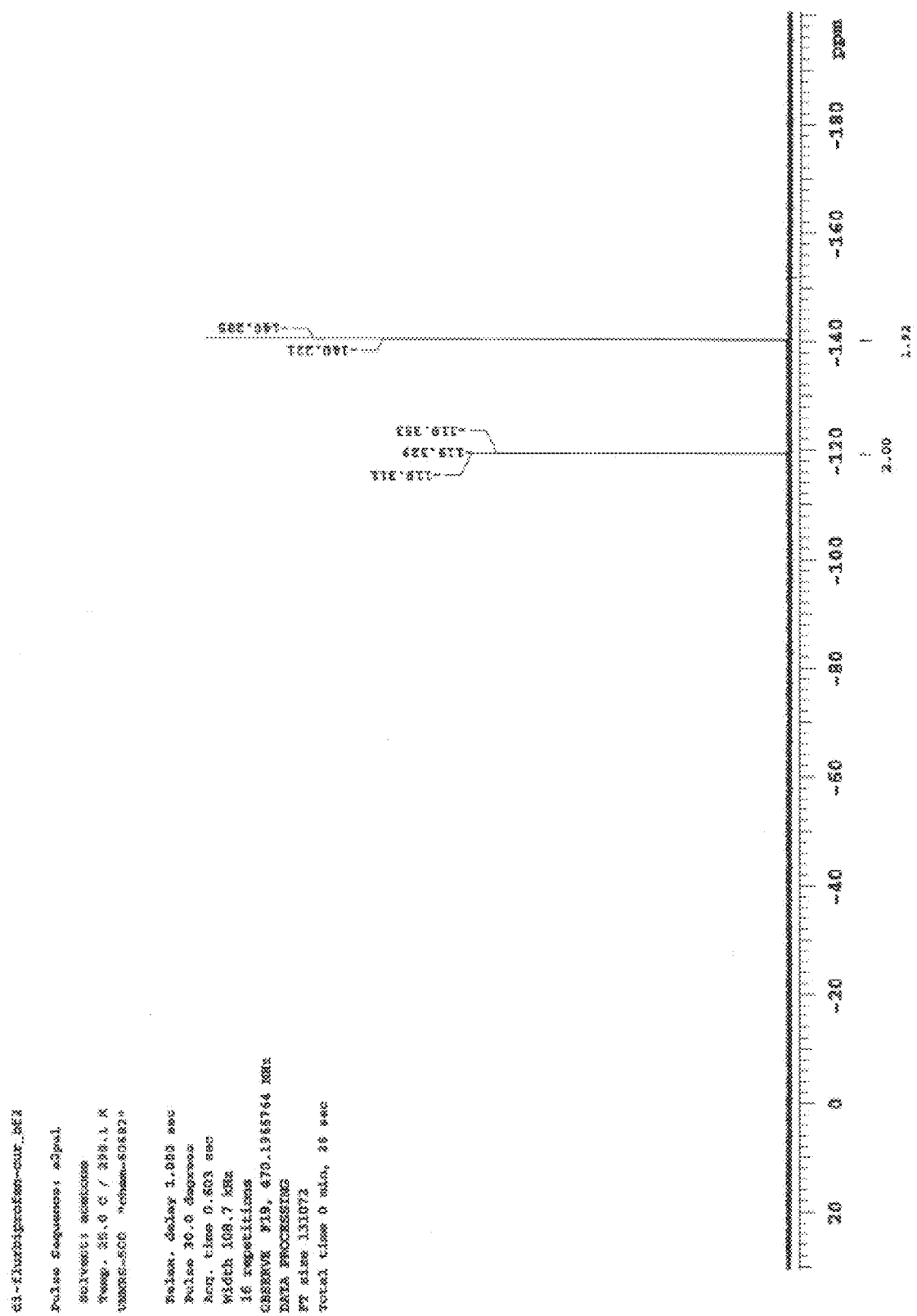

FIG. 154 is a representative NMR spectrum for compound 7 of Example 7.

Figure 155:
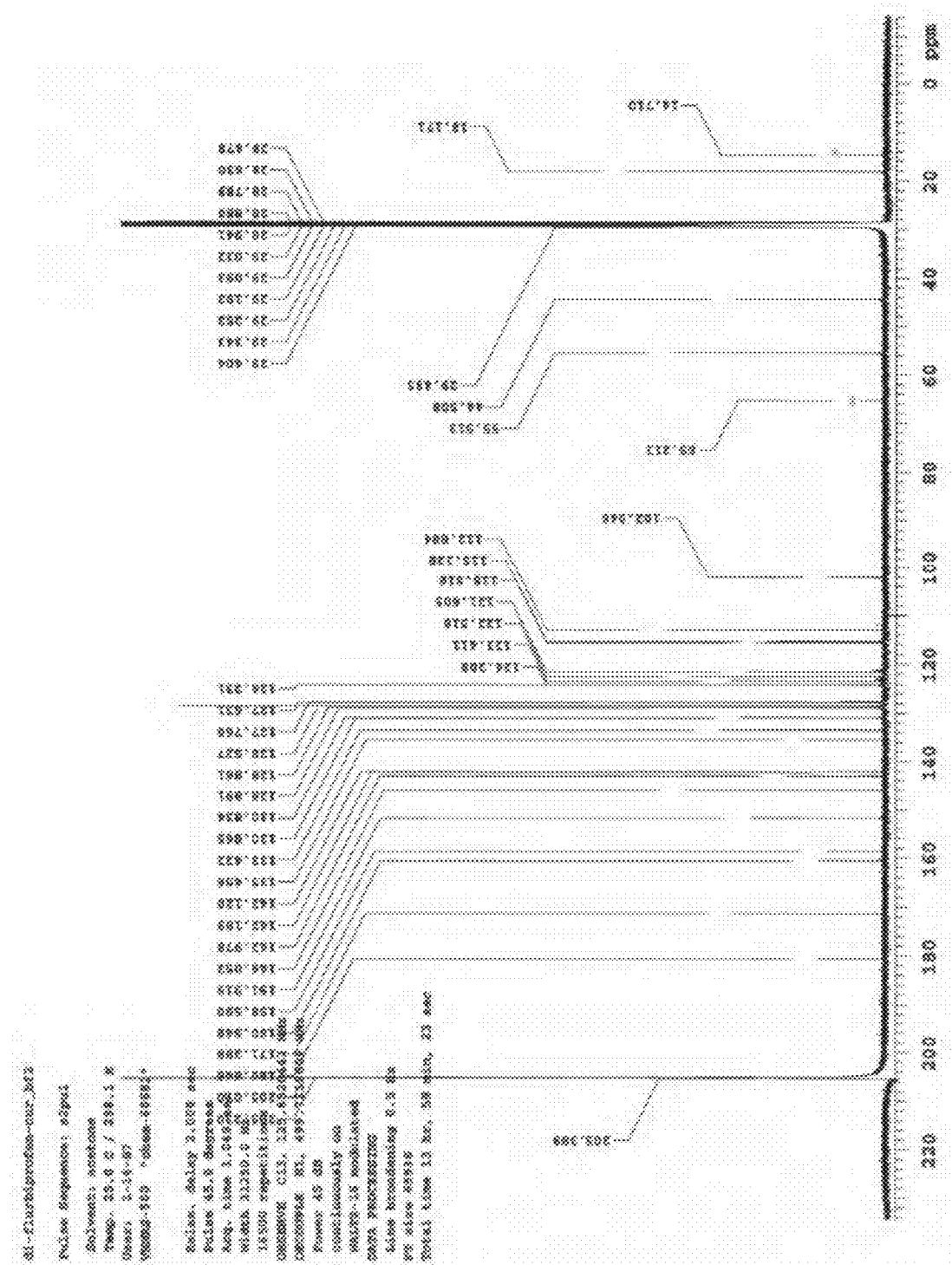

FIG. 155 is a representative NMR spectrum for compound 7 of Example 7.

Figure 156:
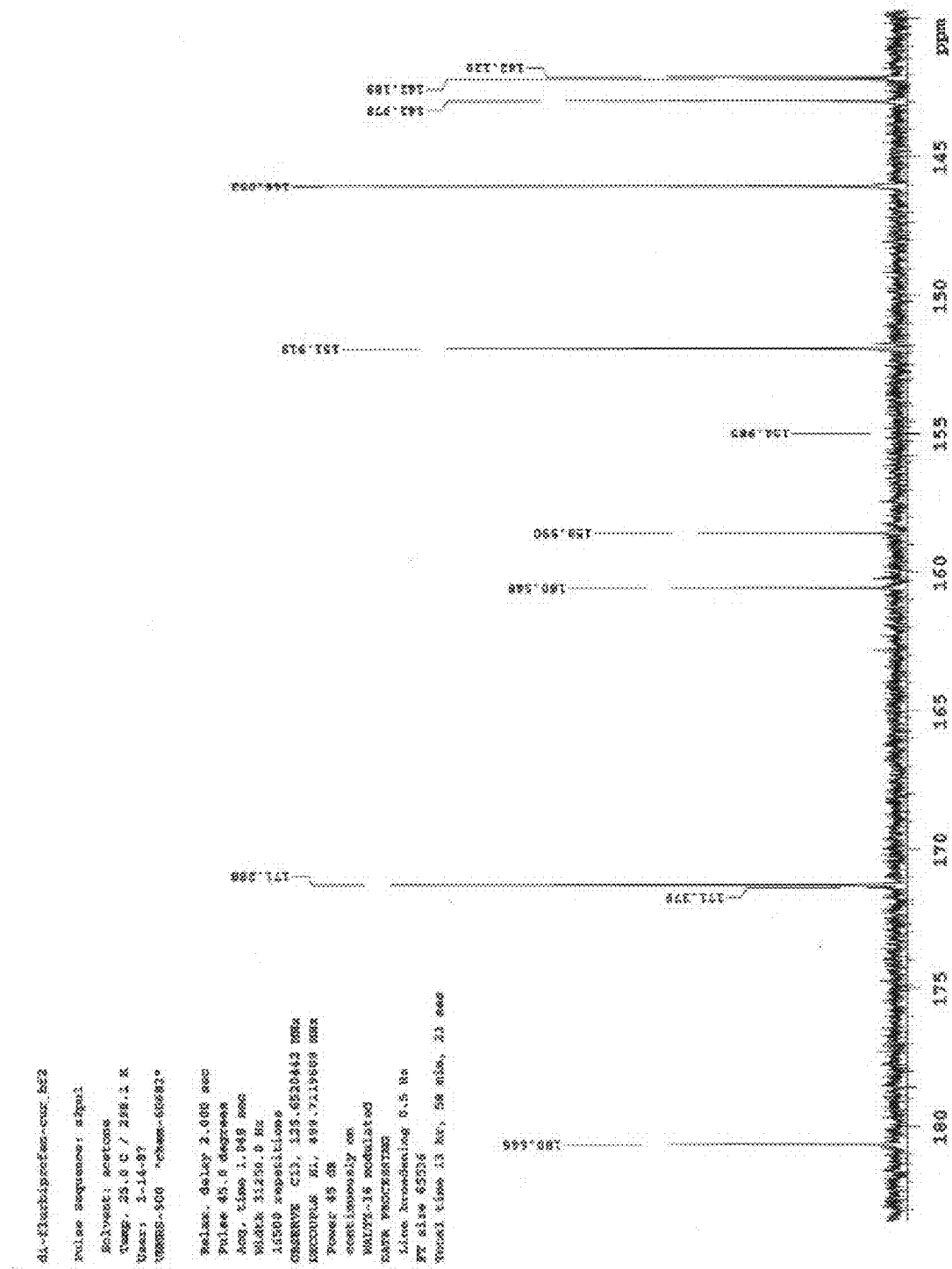

FIG. 156 is a representative NMR spectrum for compound 7 of Example 7.

Figure 157:
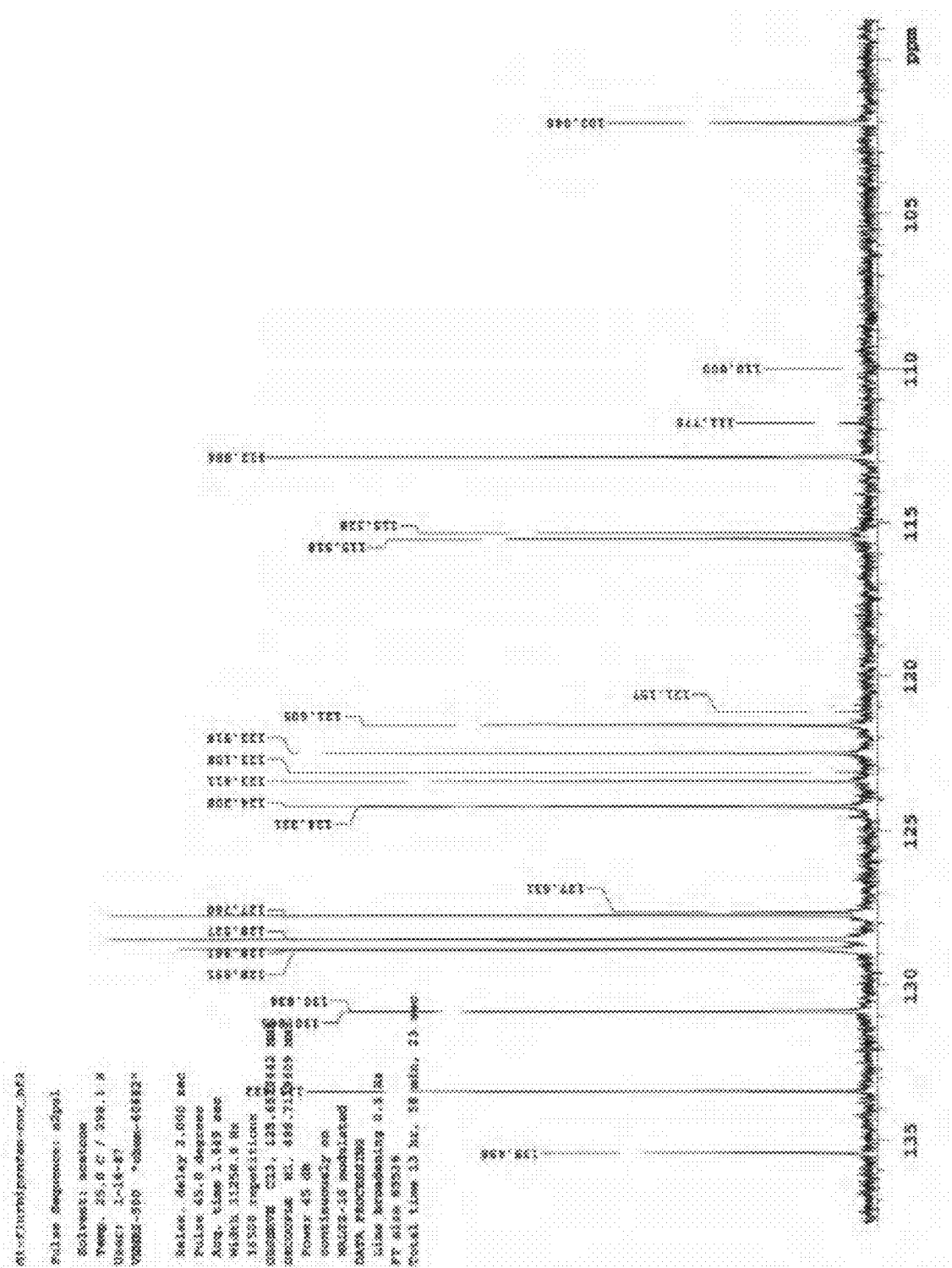

FIG. 157 is a representative NMR spectrum for compound 7 of Example 7.

Figure 158:
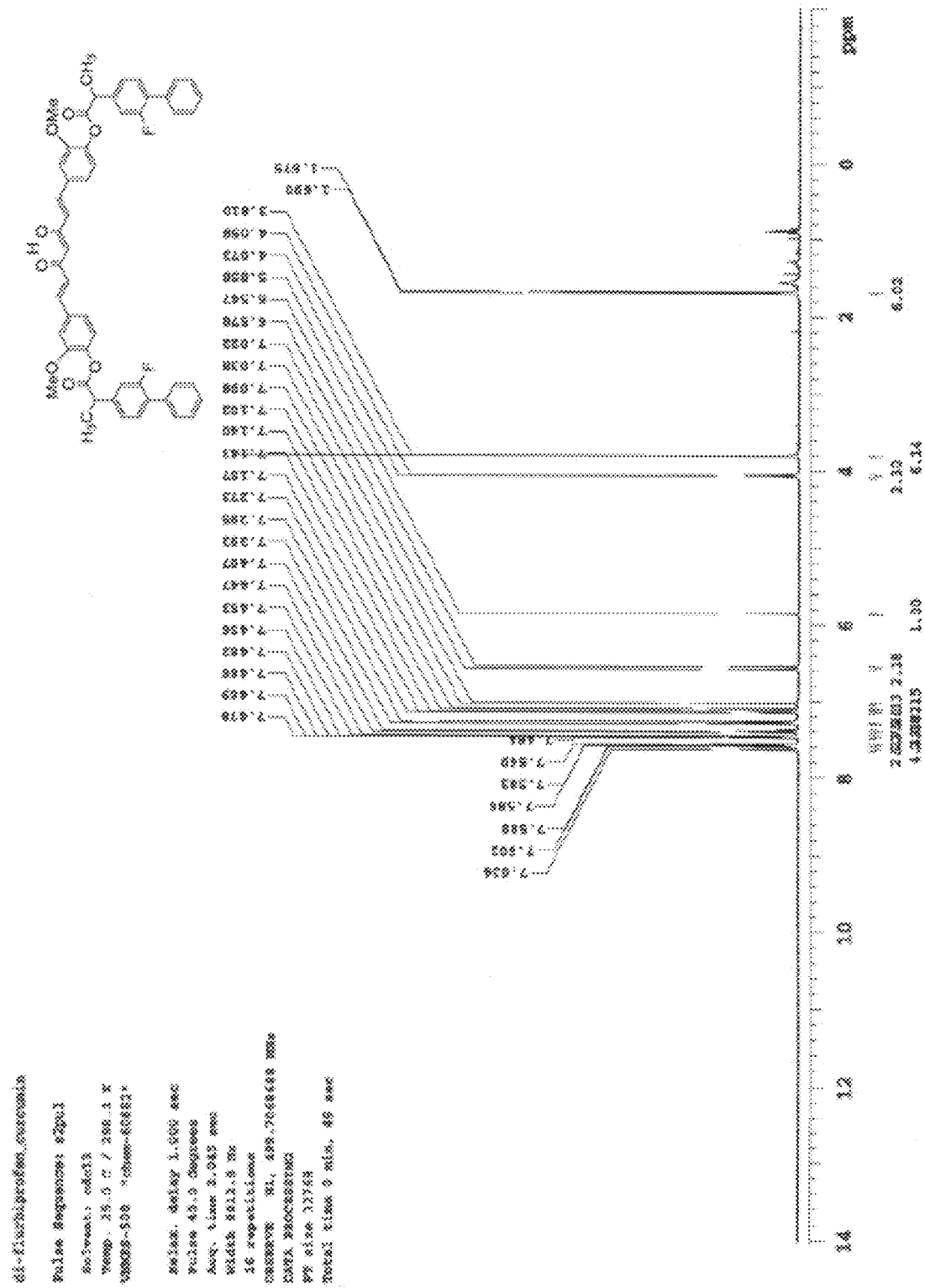

FIG. 158 is a representative NMR spectrum for compound 17 of Example 7.

Figure 159:
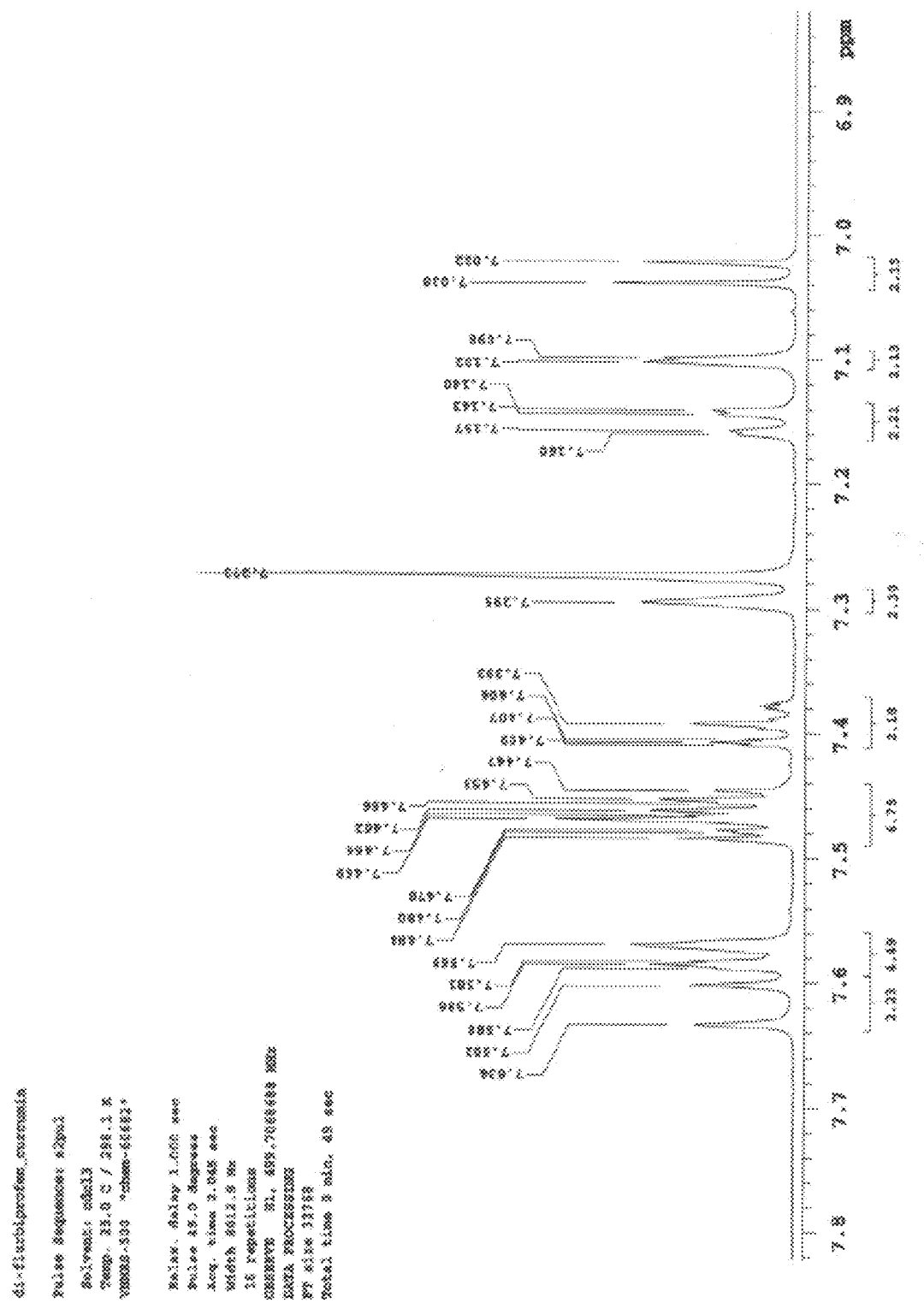

FIG. 159 is a representative NMR spectrum for compound 17 of Example 7.

Figure 160:
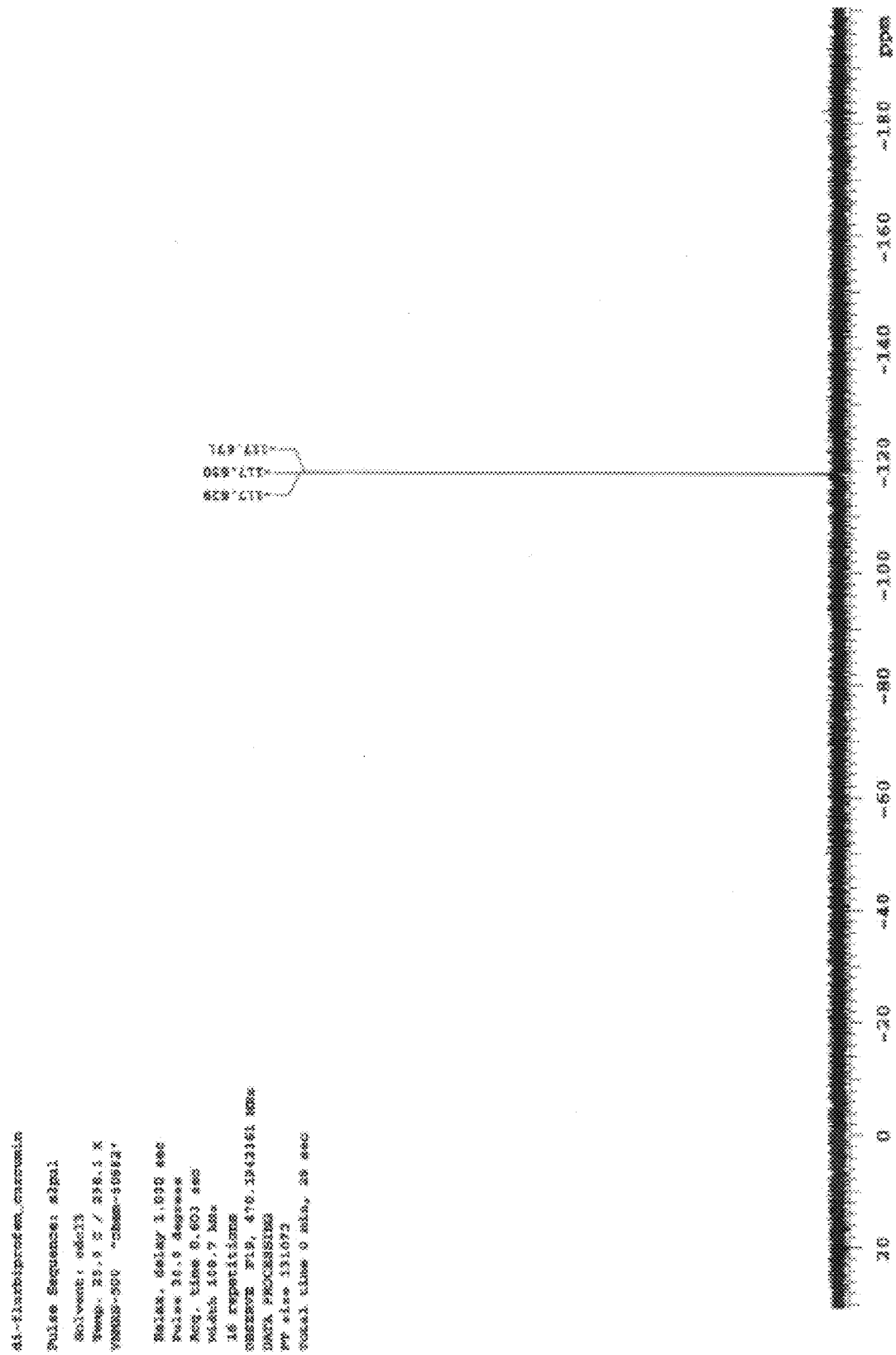

FIG. 160 is a representative NMR spectrum for compound 17 of Example 7.

Figure 161:
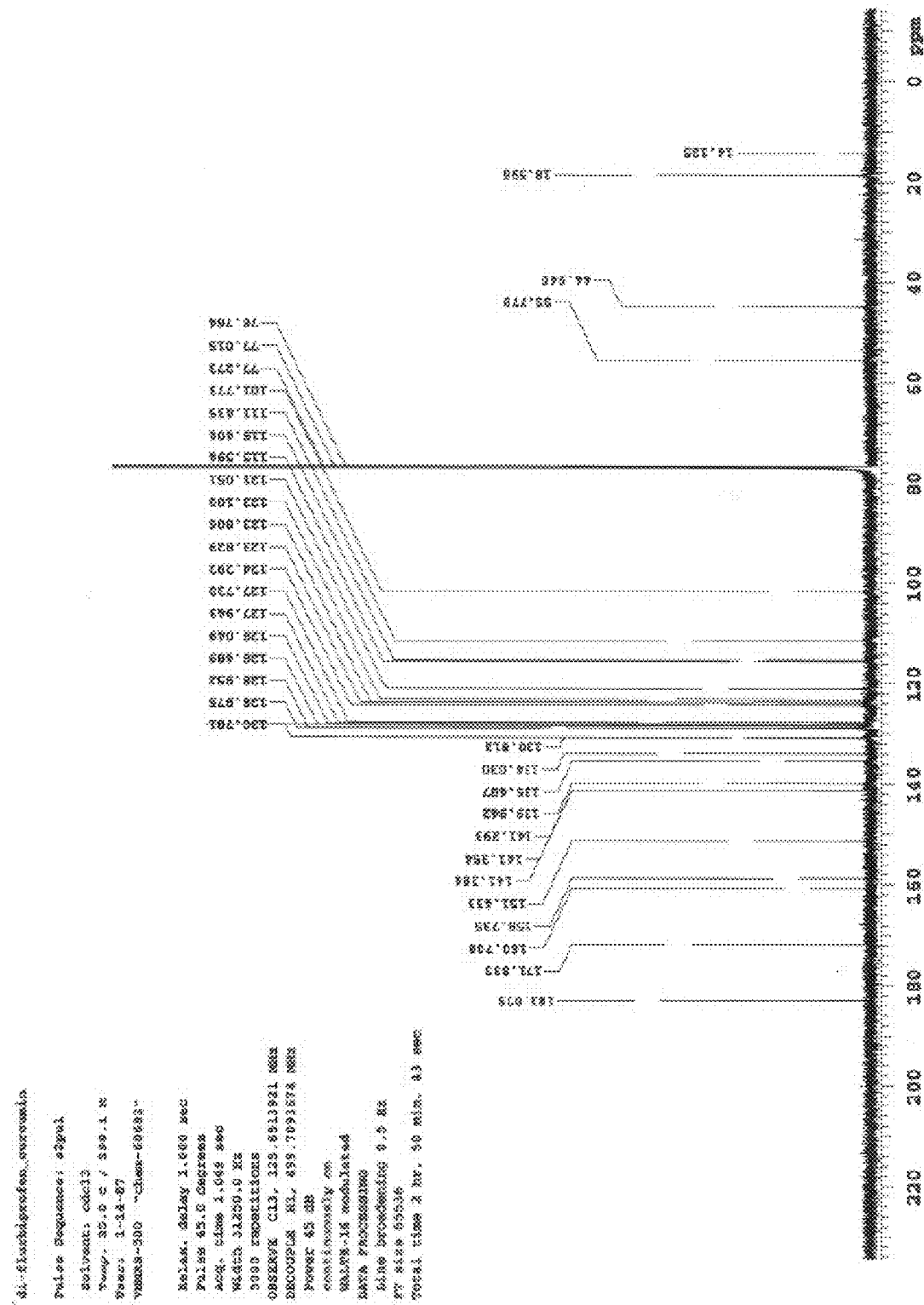

FIG. 161 is a representative NMR spectrum for compound 17 of Example 7.

Figure 162:
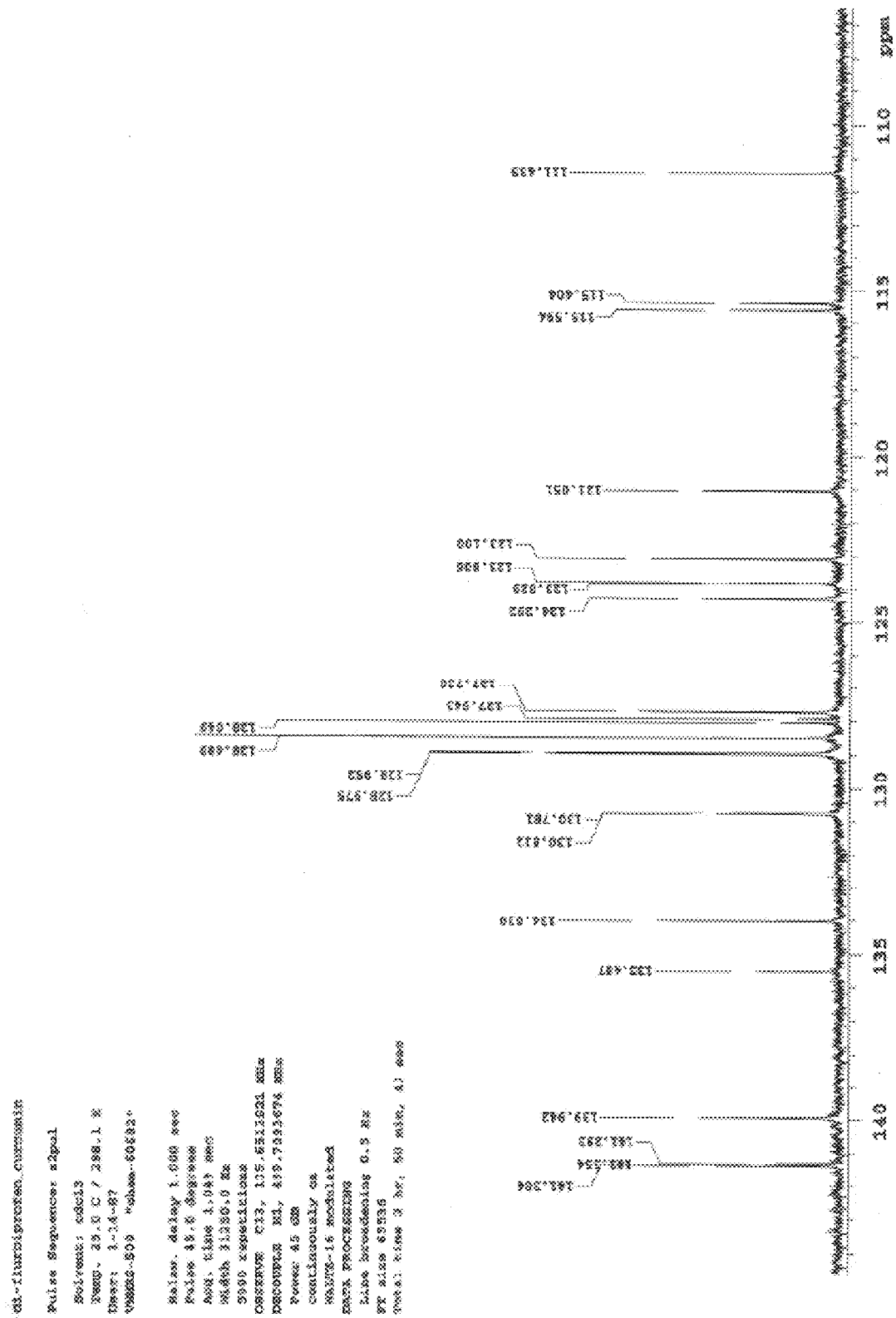

FIG. 162 is a representative NMR spectrum for compound 17 of Example 7.

Figure 163:
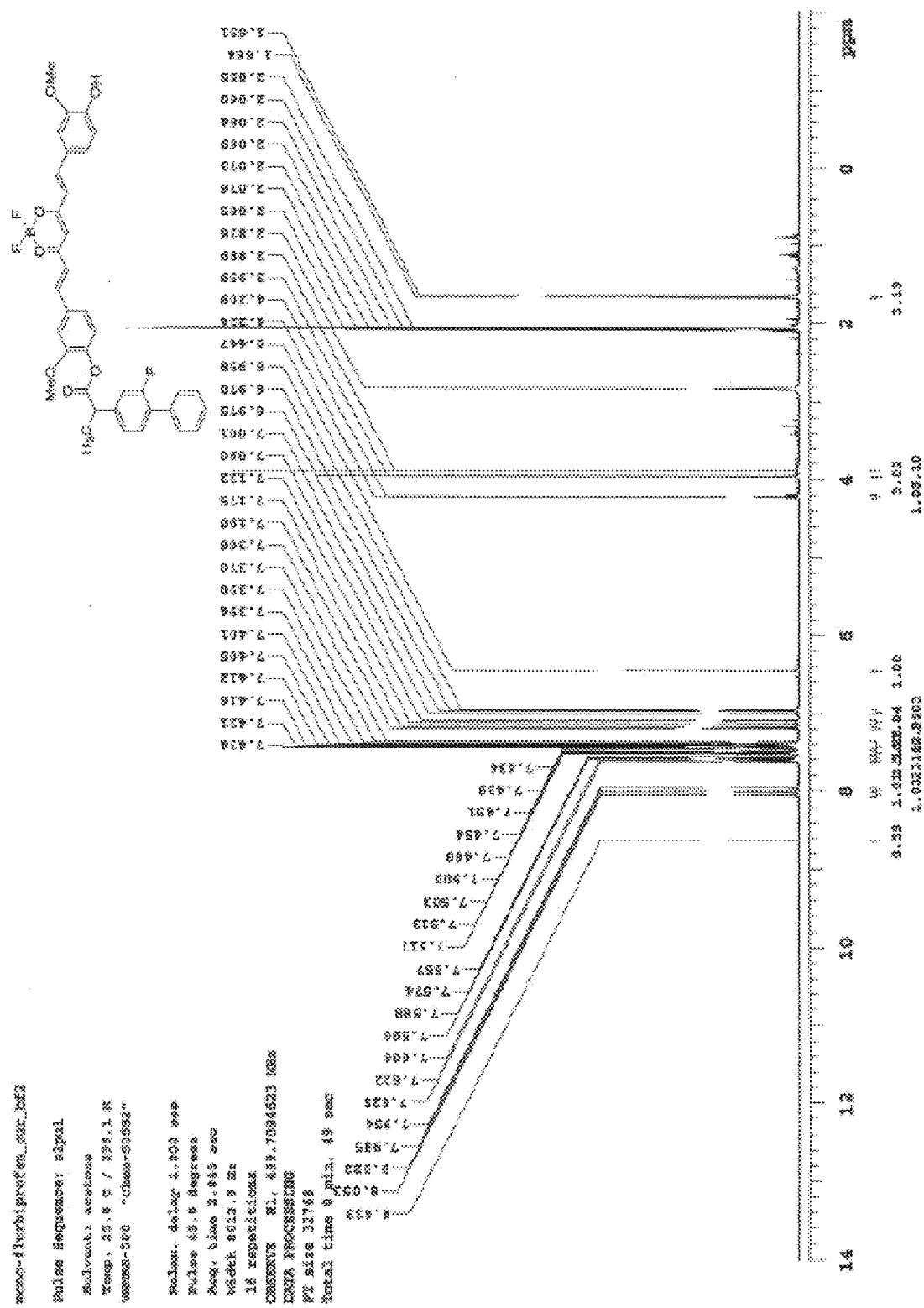

FIG. 163 is a representative NMR spectrum for compound 8 of Example 7.

Figure 164:
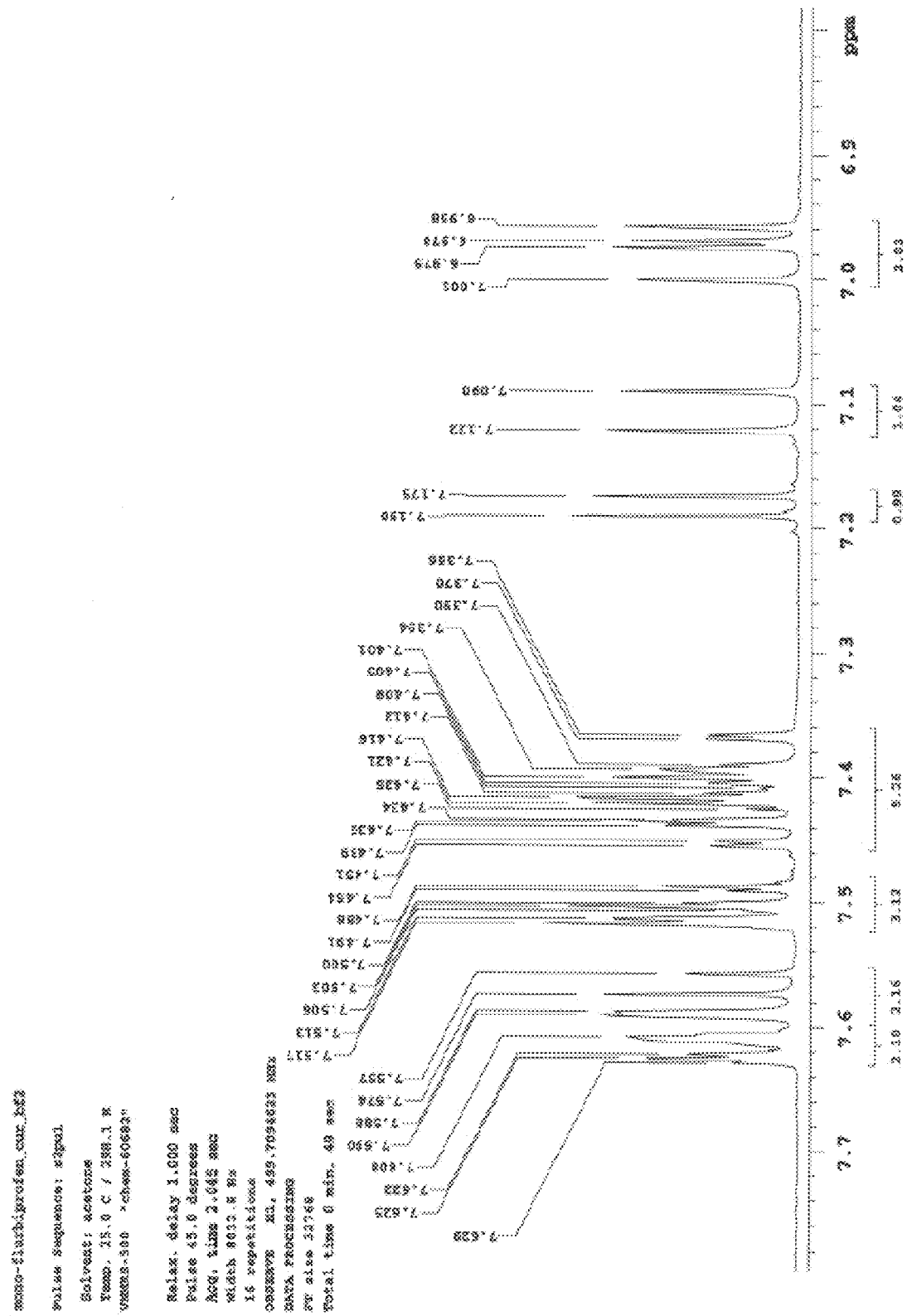

FIG. 164 is a representative NMR spectrum for compound 8 of Example 7.

Figure 165:
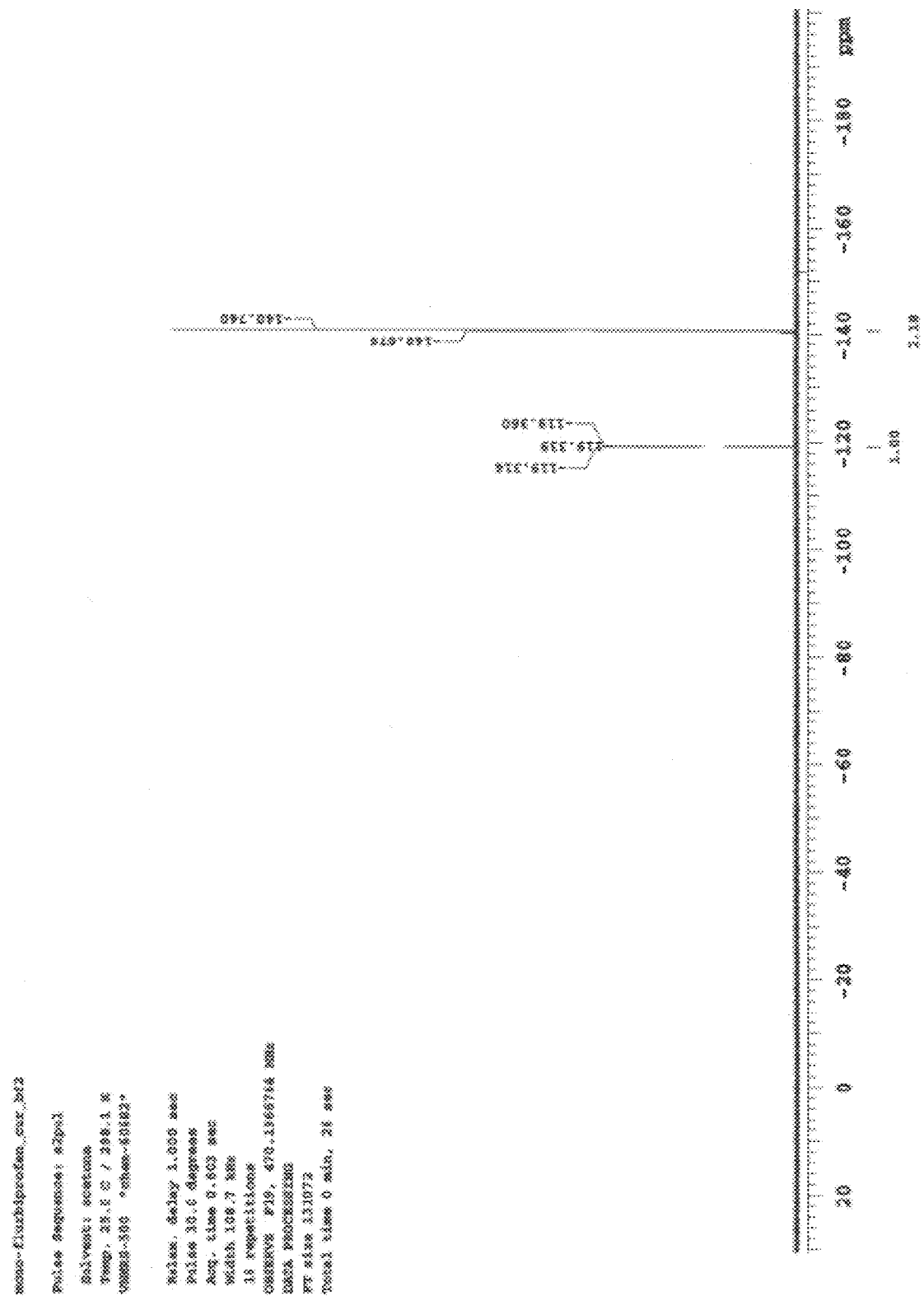

FIG. 165 is a representative NMR spectrum for compound 8 of Example 7.

Figure 166:
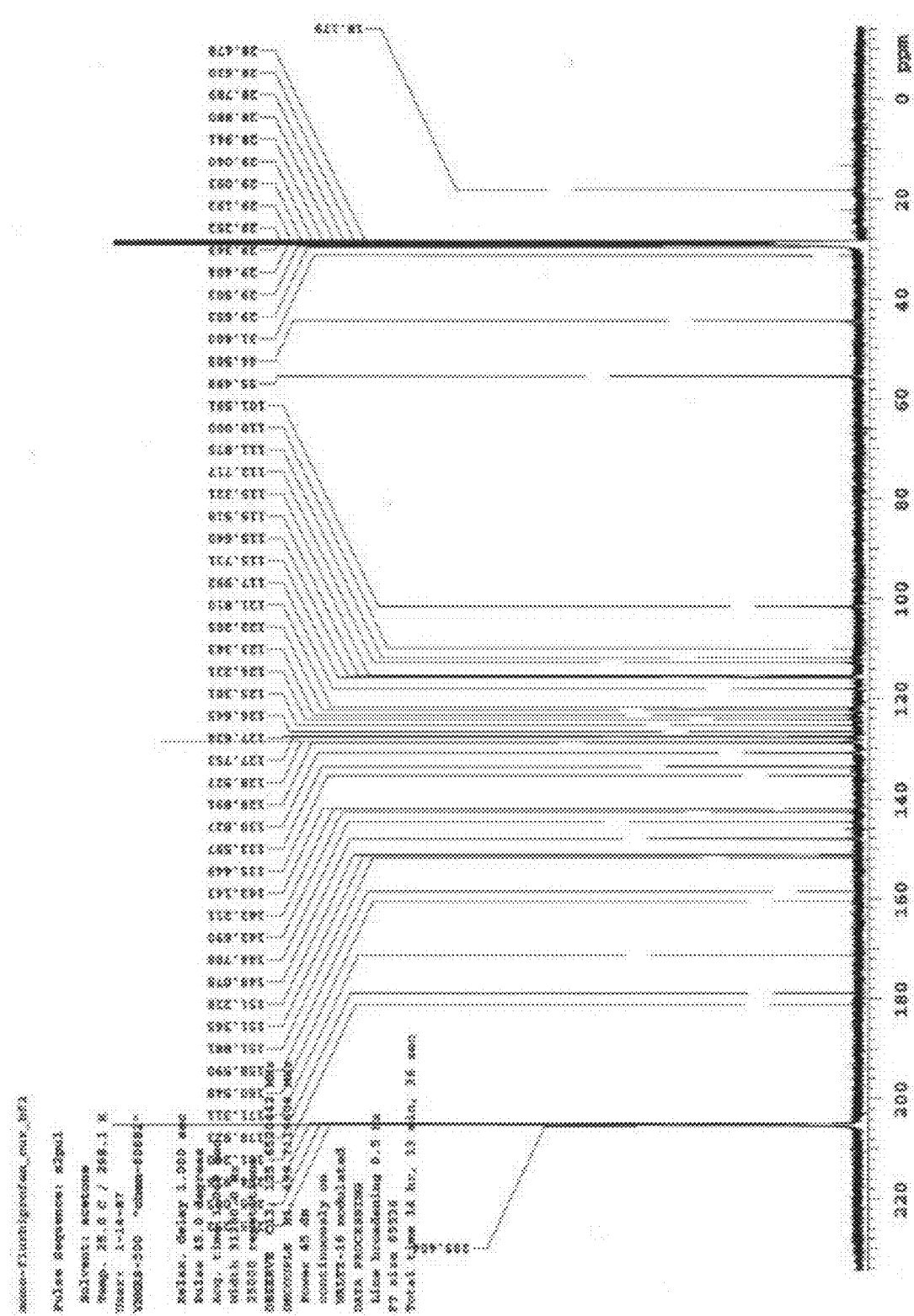

FIG. 166 is a representative NMR spectrum for compound 8 of Example 7.

Figure 167:
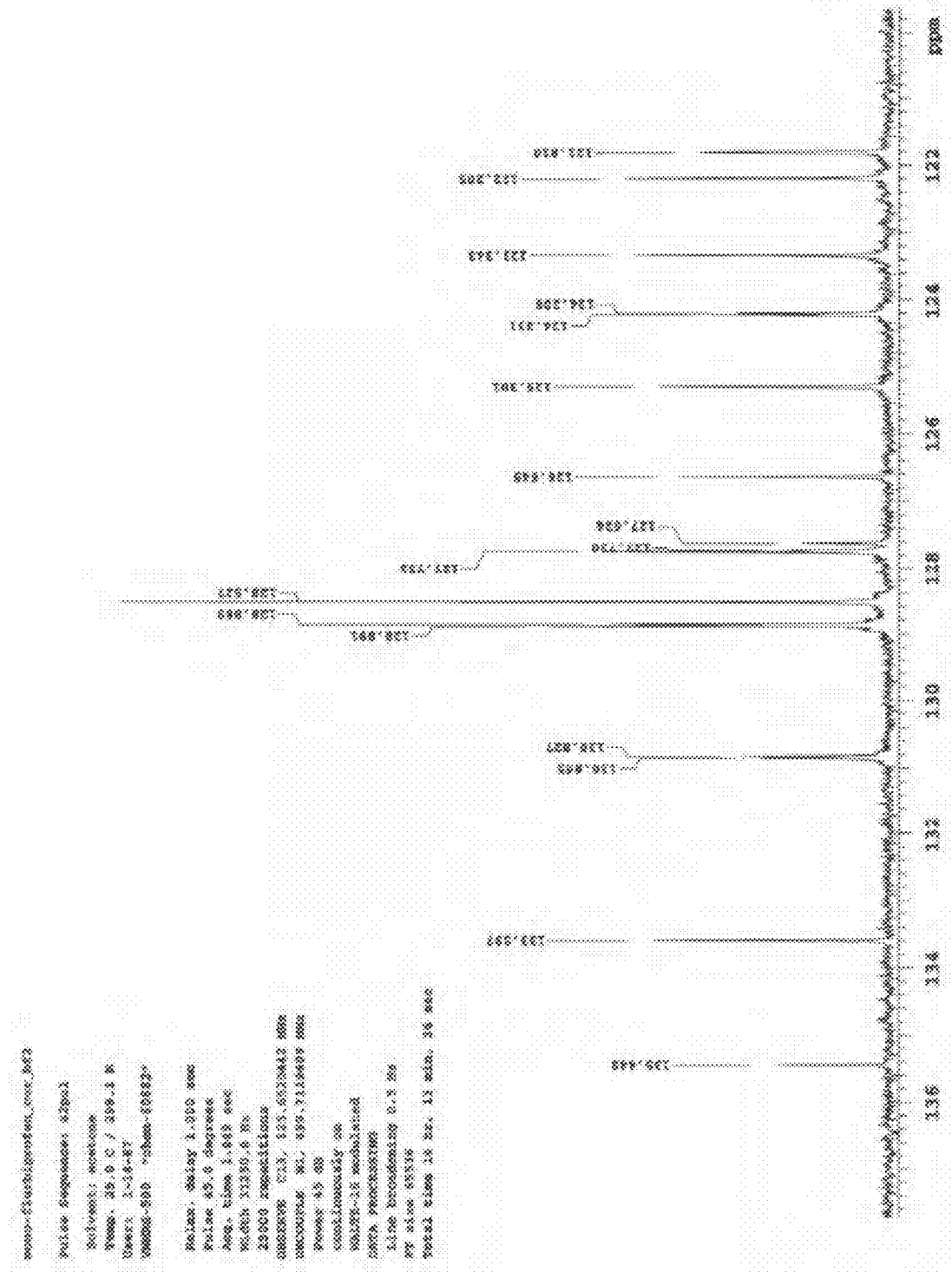

FIG. 167 is a representative NMR spectrum for compound 8 of Example 7.

Figure 168:
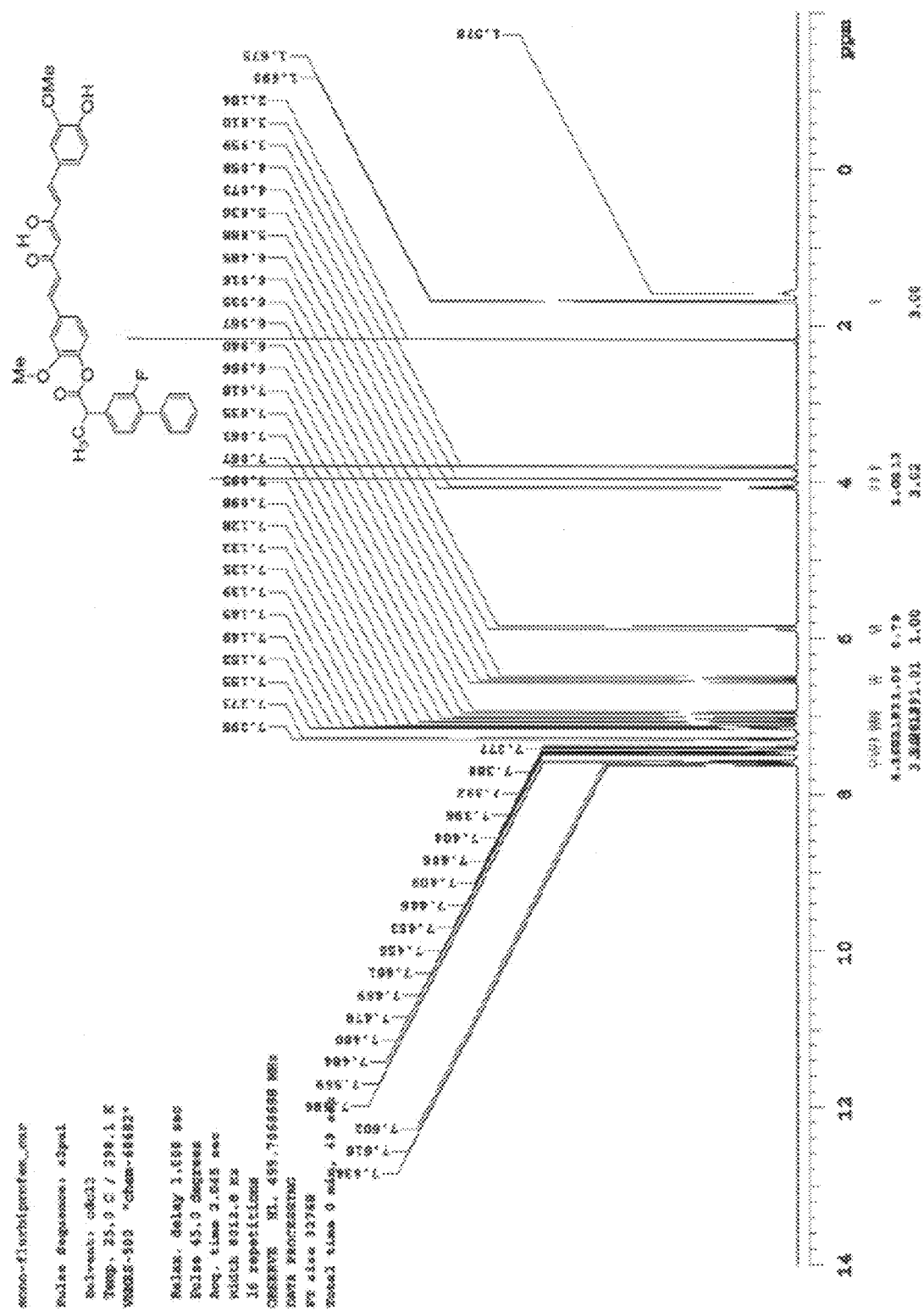

FIG. 168 is a representative NMR spectrum for compound 18 of Example 7.

Figure 169:
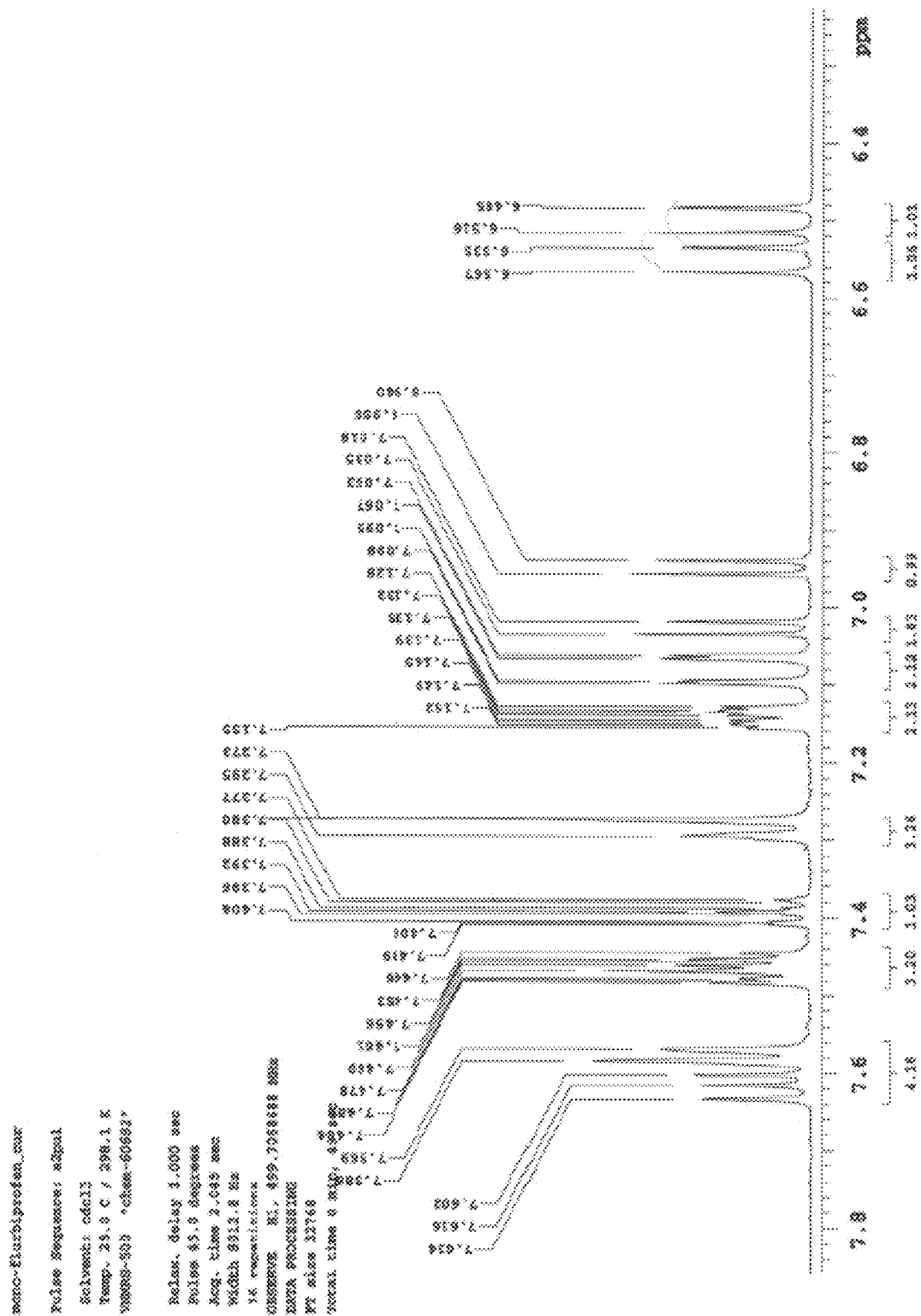

FIG. 169 is a representative NMR spectrum for compound 18 of Example 7.

Figure 170:
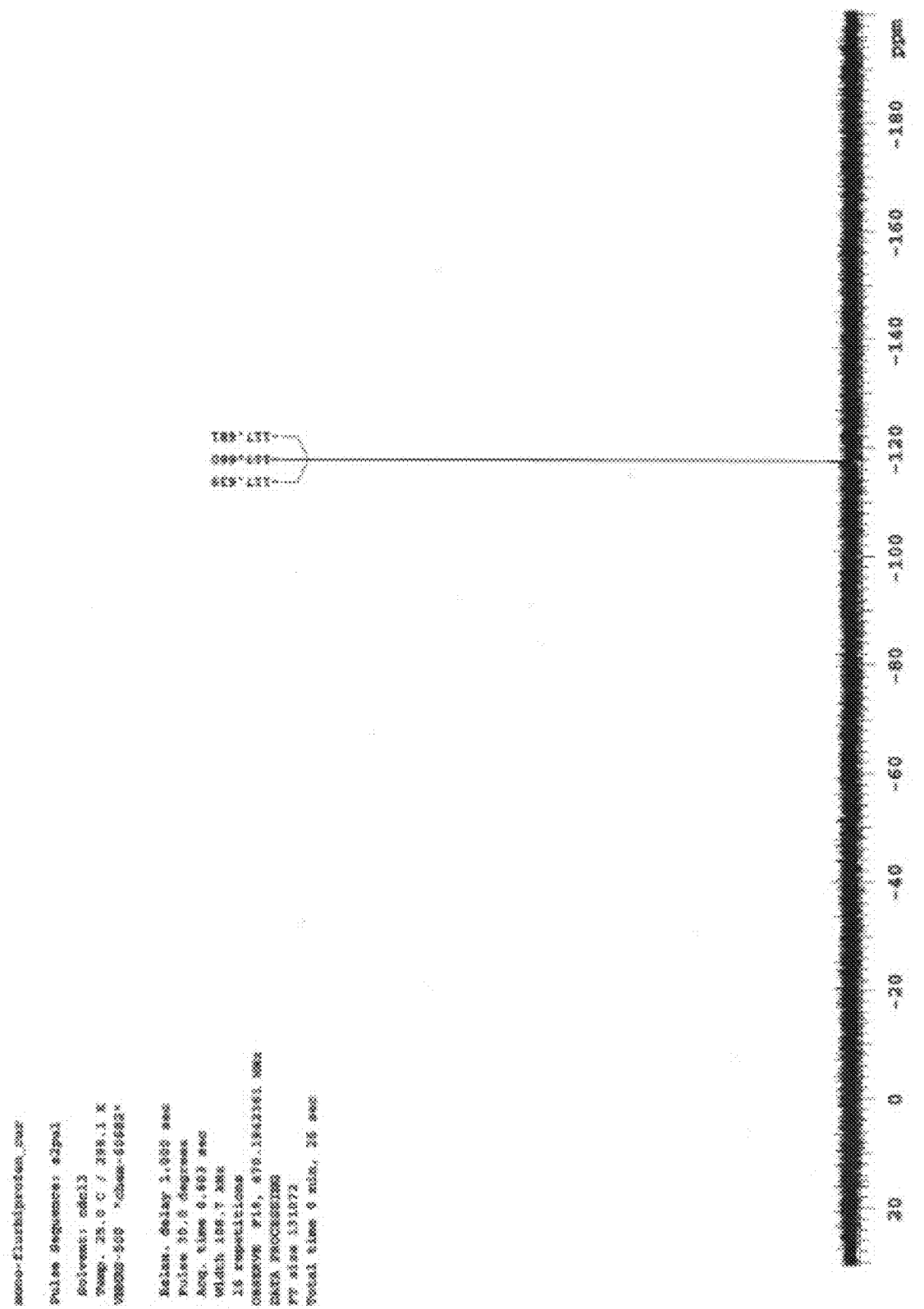

FIG. 170 is a representative NMR spectrum for compound 18 of Example 7.

Figure 171:
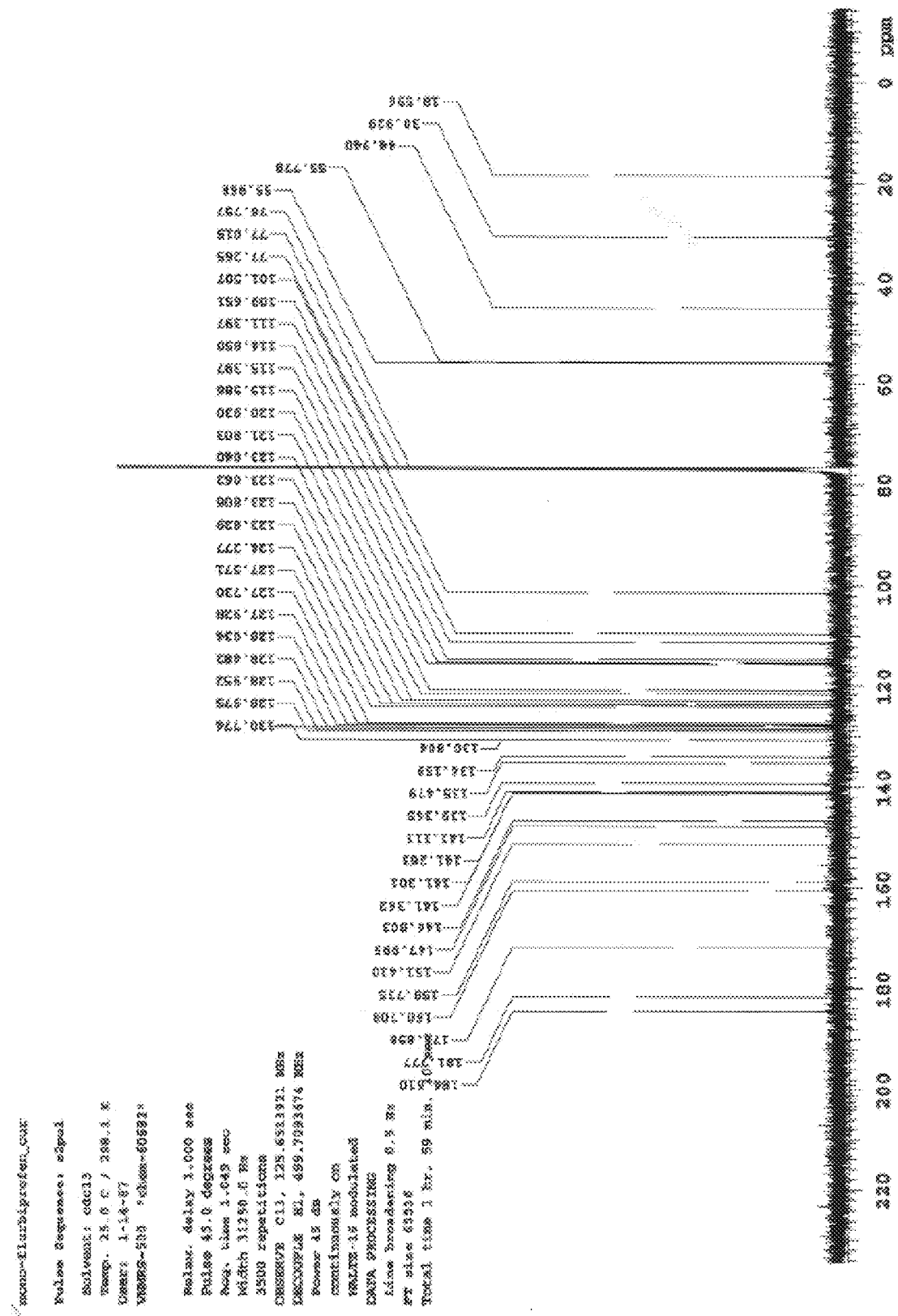

FIG. 171 is a representative NMR spectrum for compound 18 of Example 7.

Figure 172:
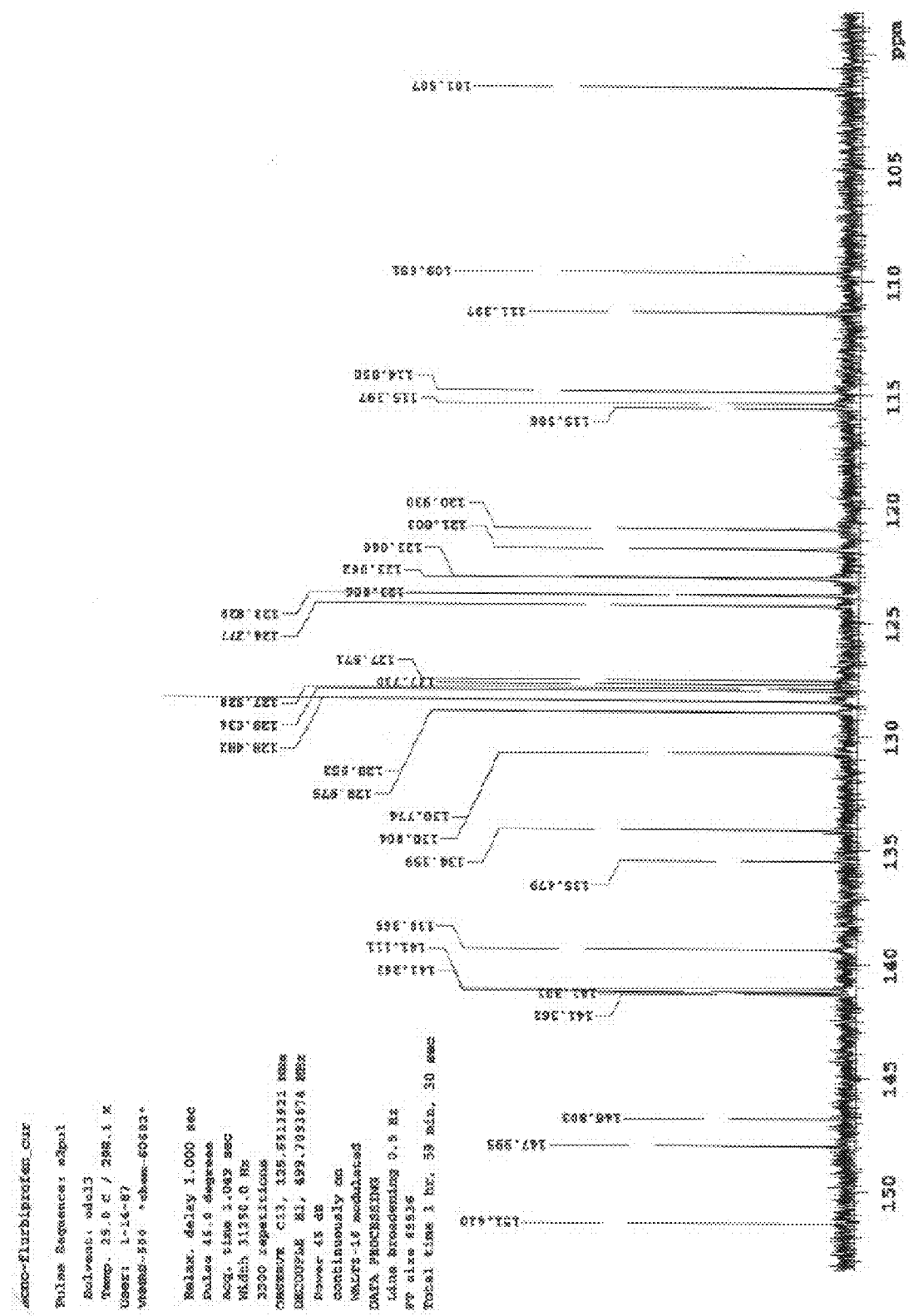

FIG. 172 is a representative NMR spectrum for compound 18 of Example 7.

Figure 173:
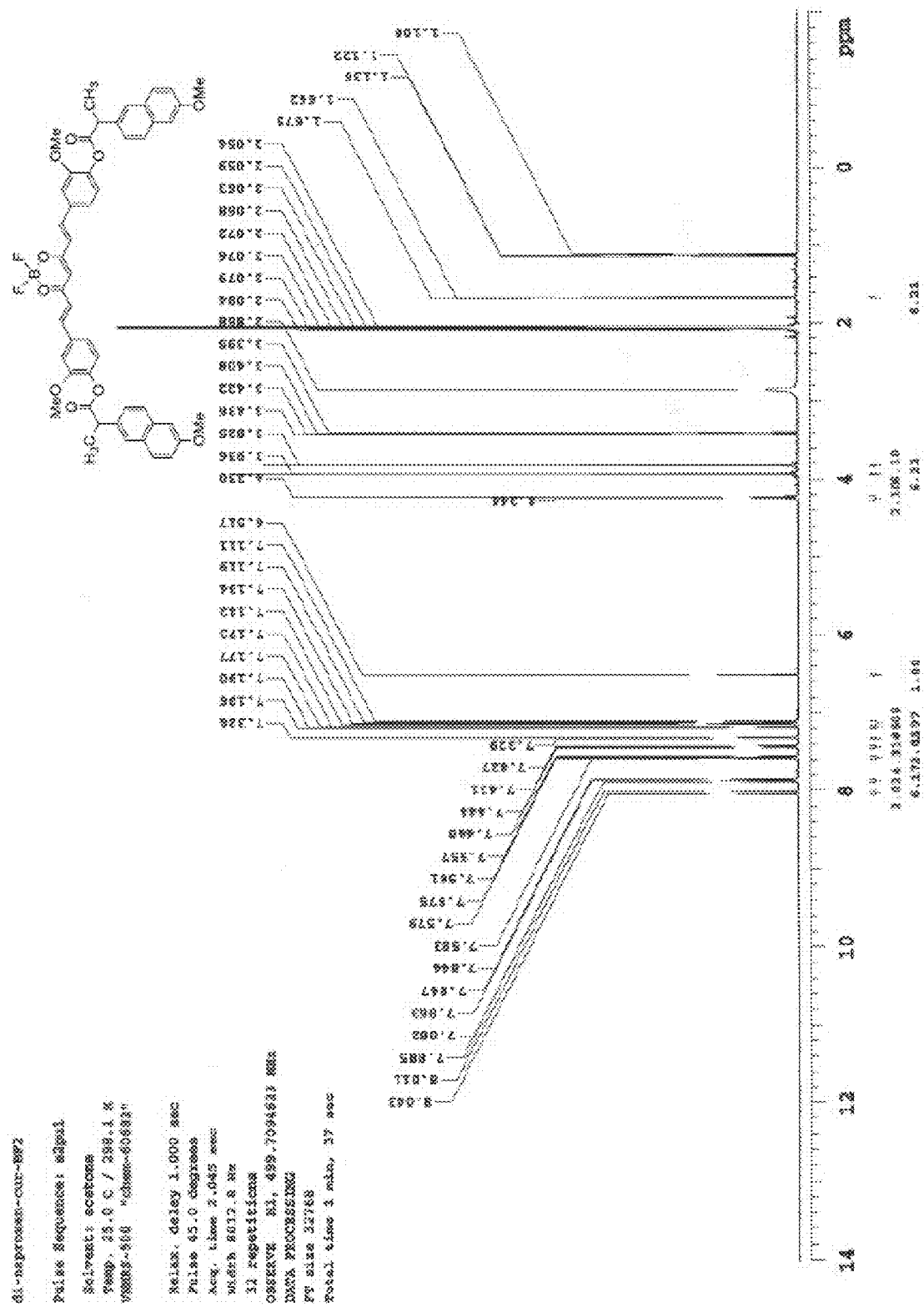

FIG. 173 is a representative NMR spectrum for compound 9 of Example 7.

Figure 174:
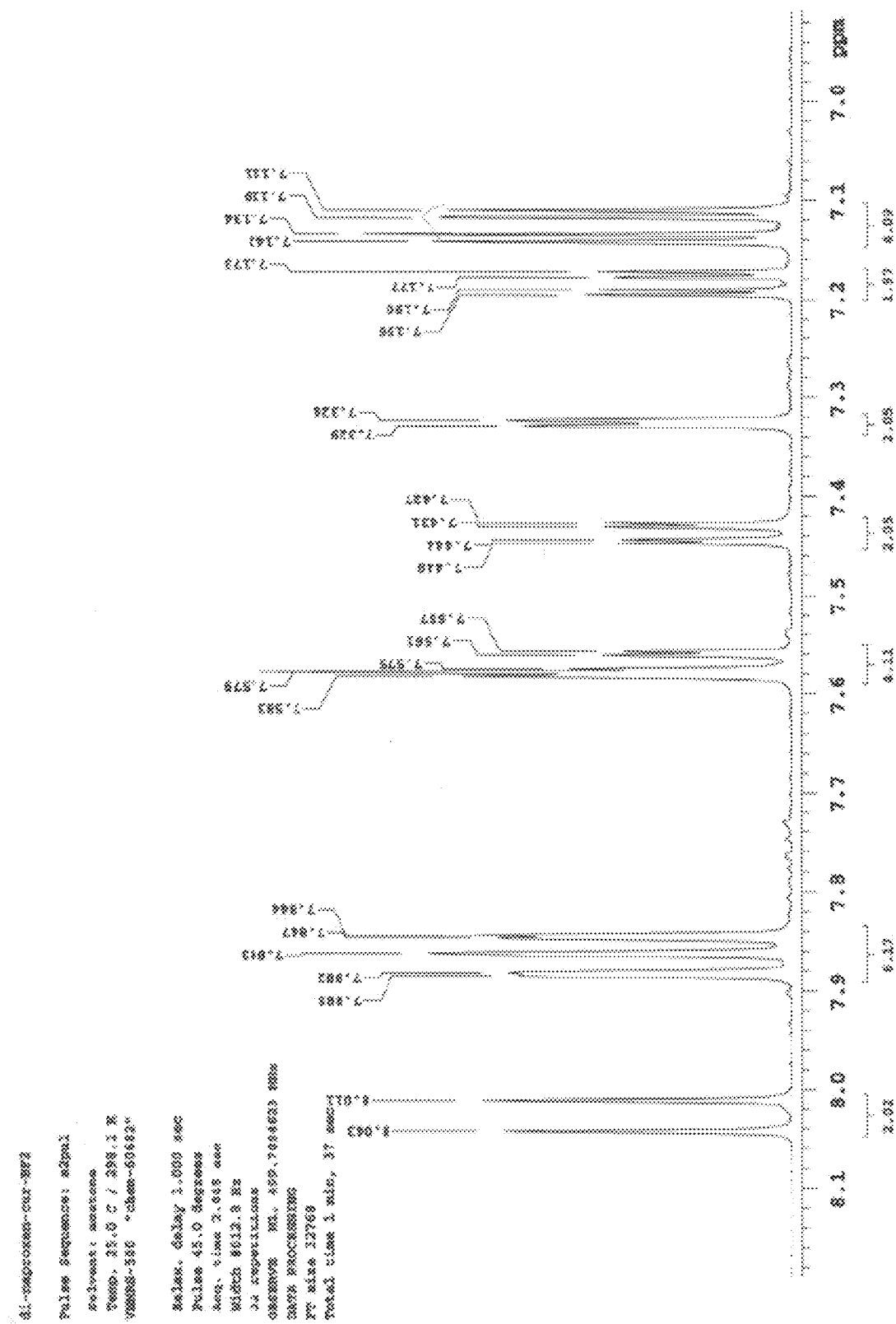

FIG. 174 is a representative NMR spectrum for compound 9 of Example 7.

Figure 175:
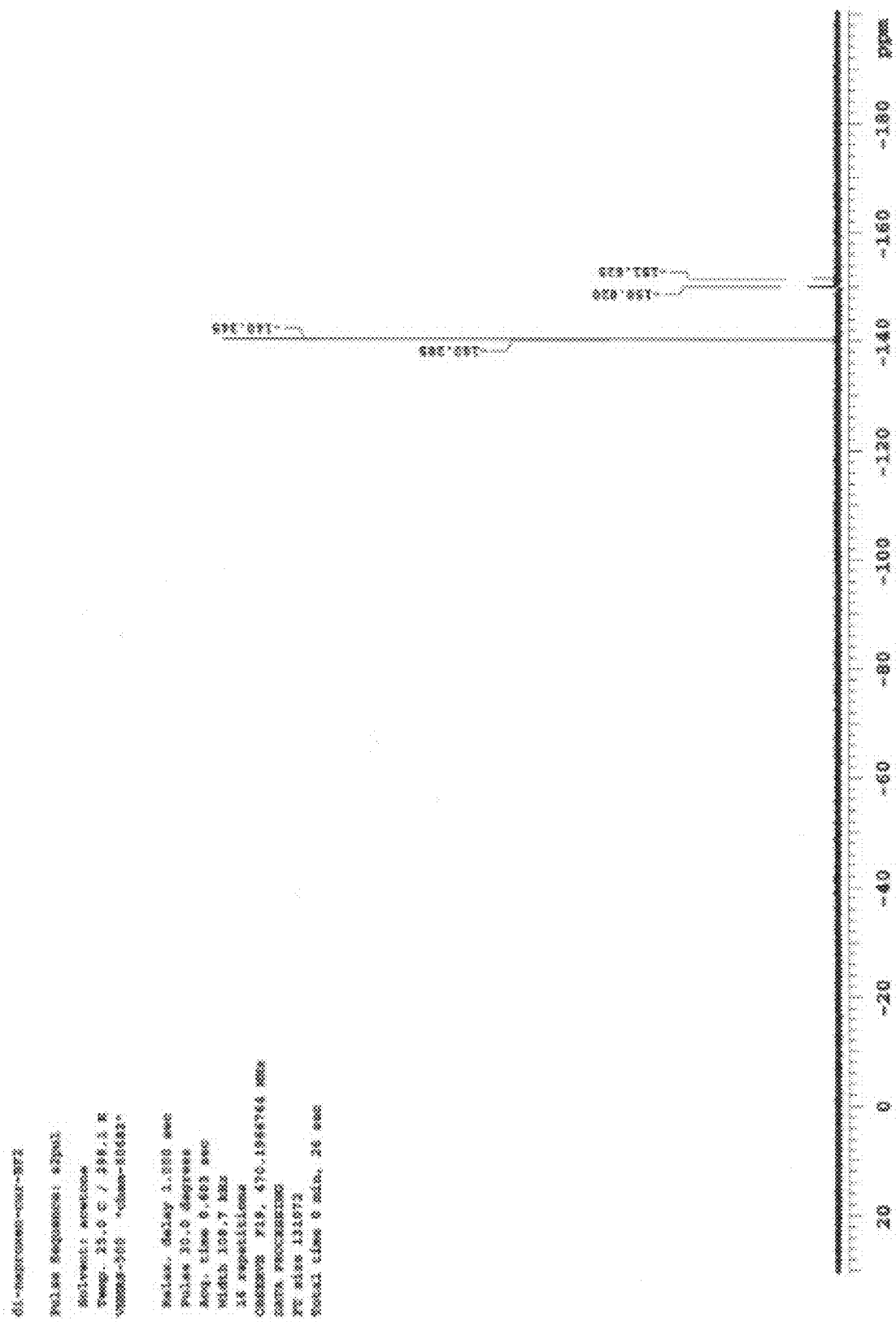

FIG. 175 is a representative NMR spectrum for compound 9 of Example 7.

Figure 176:
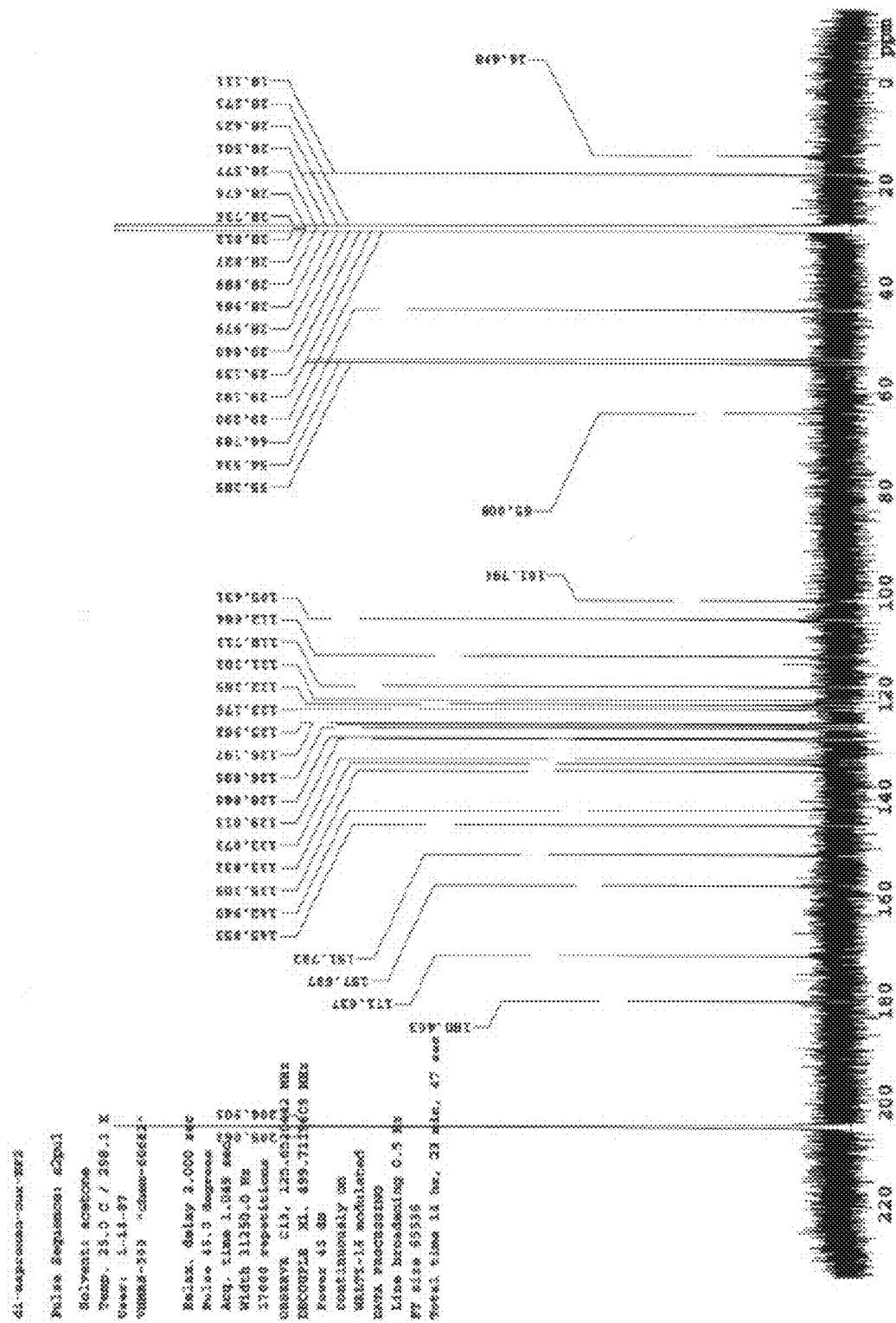

FIG. 176 is a representative NMR spectrum for compound 9 of Example 7.

Figure 177:
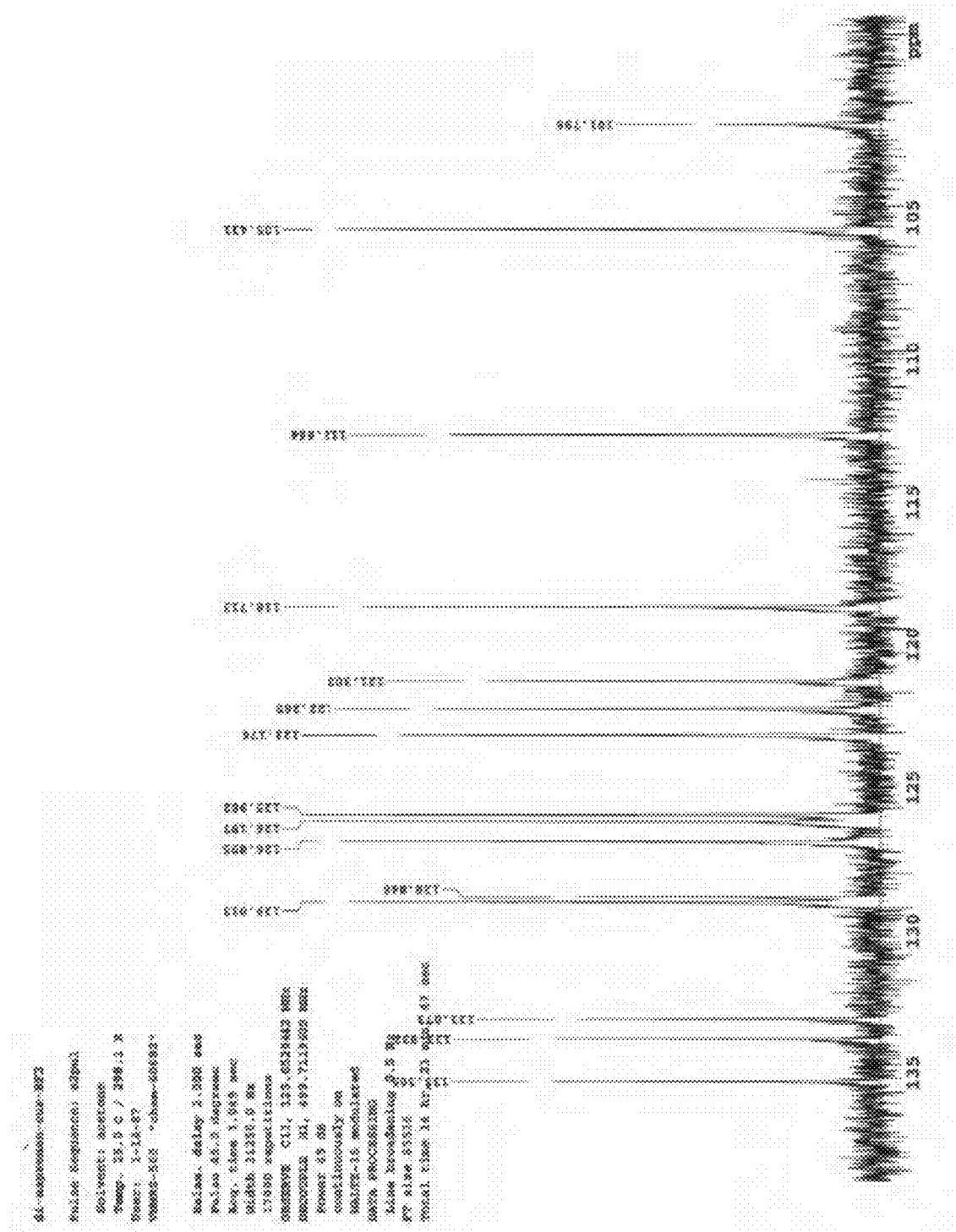

FIG. 177 is a representative NMR spectrum for compound 9 of Example 7.

Figure 178:
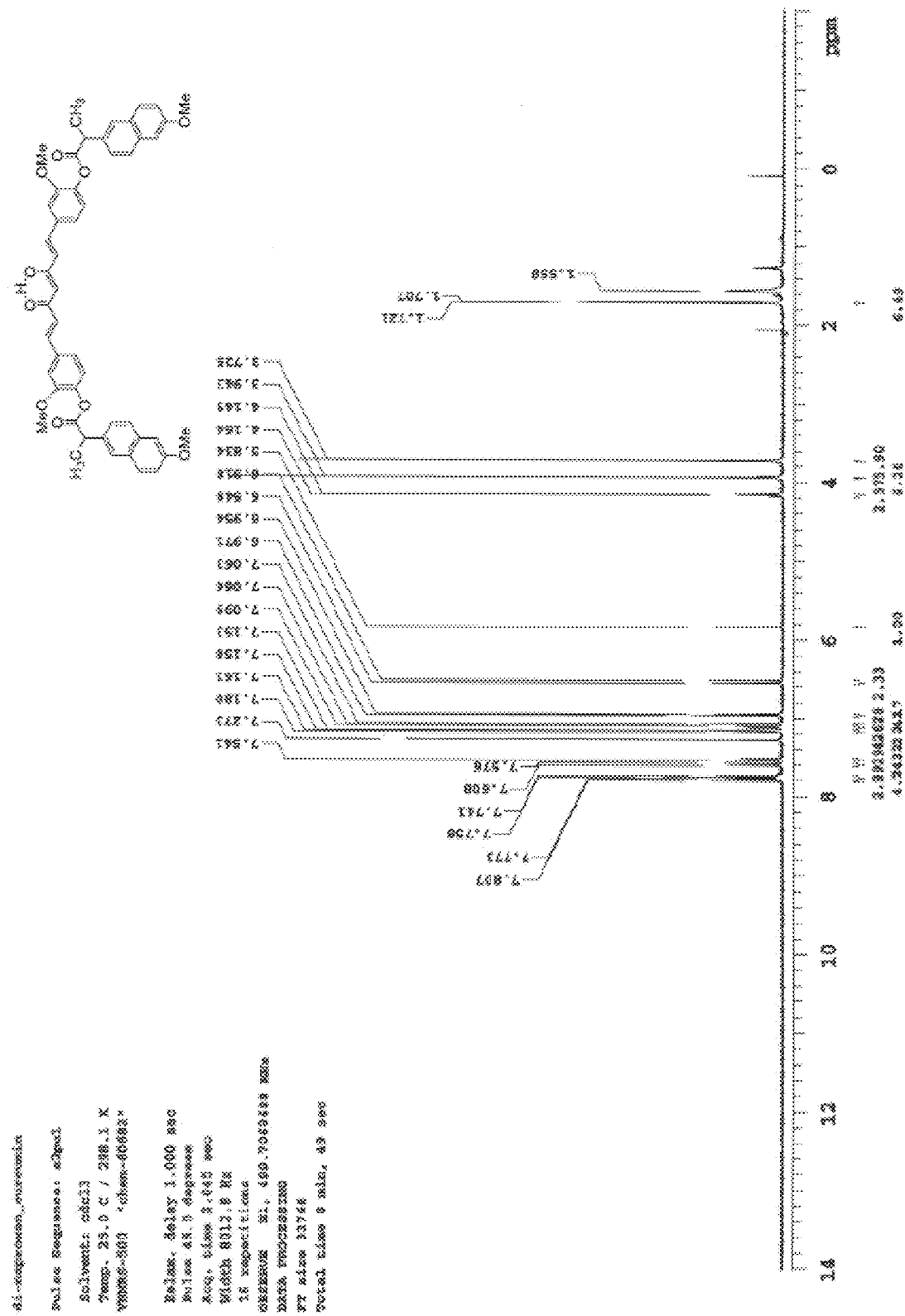

FIG. 178 is a representative NMR spectrum for compound 19 of Example 7.

Figure 179:
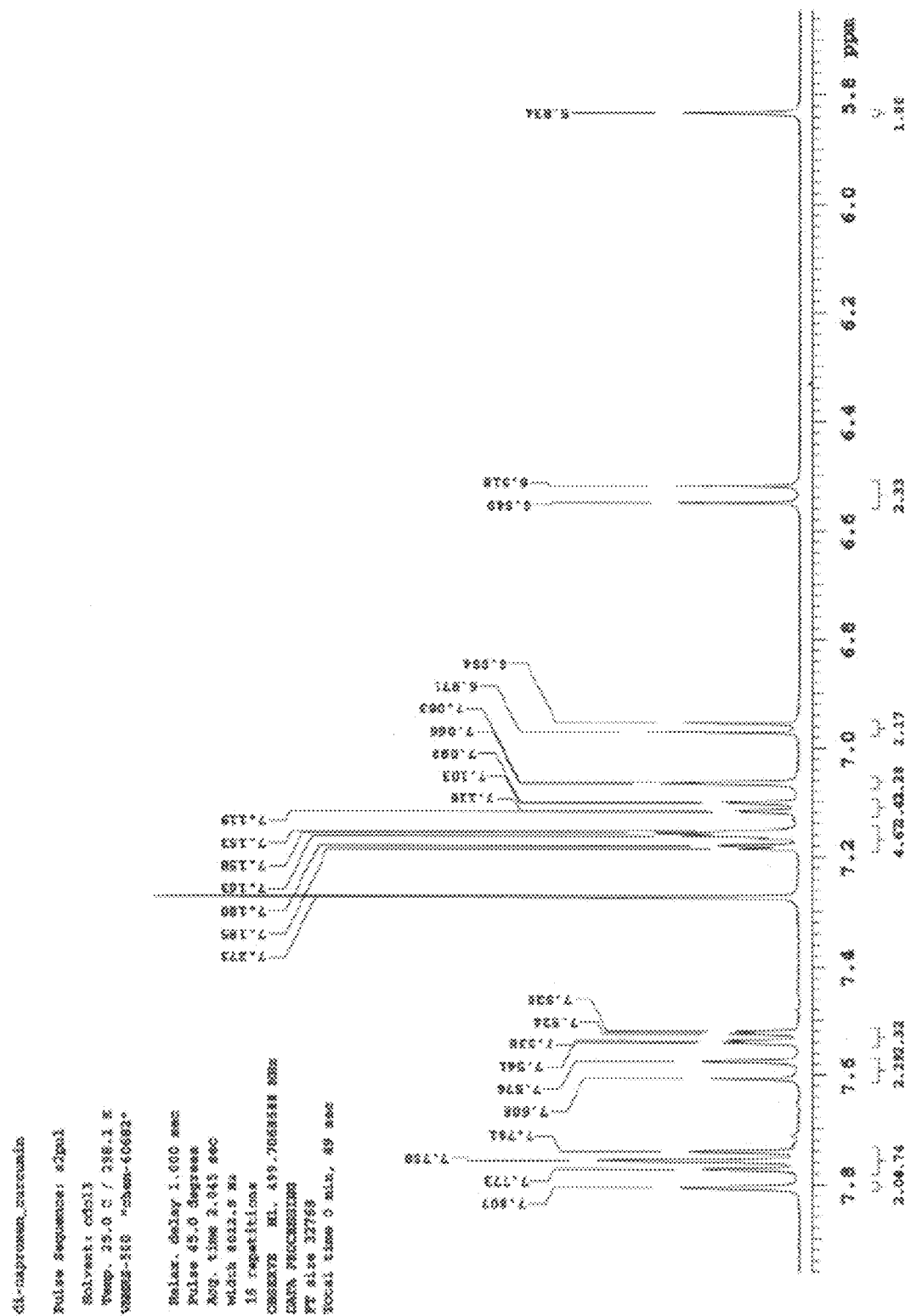

FIG. 179 is a representative NMR spectrum for compound 19. of Example 7

Figure 180:
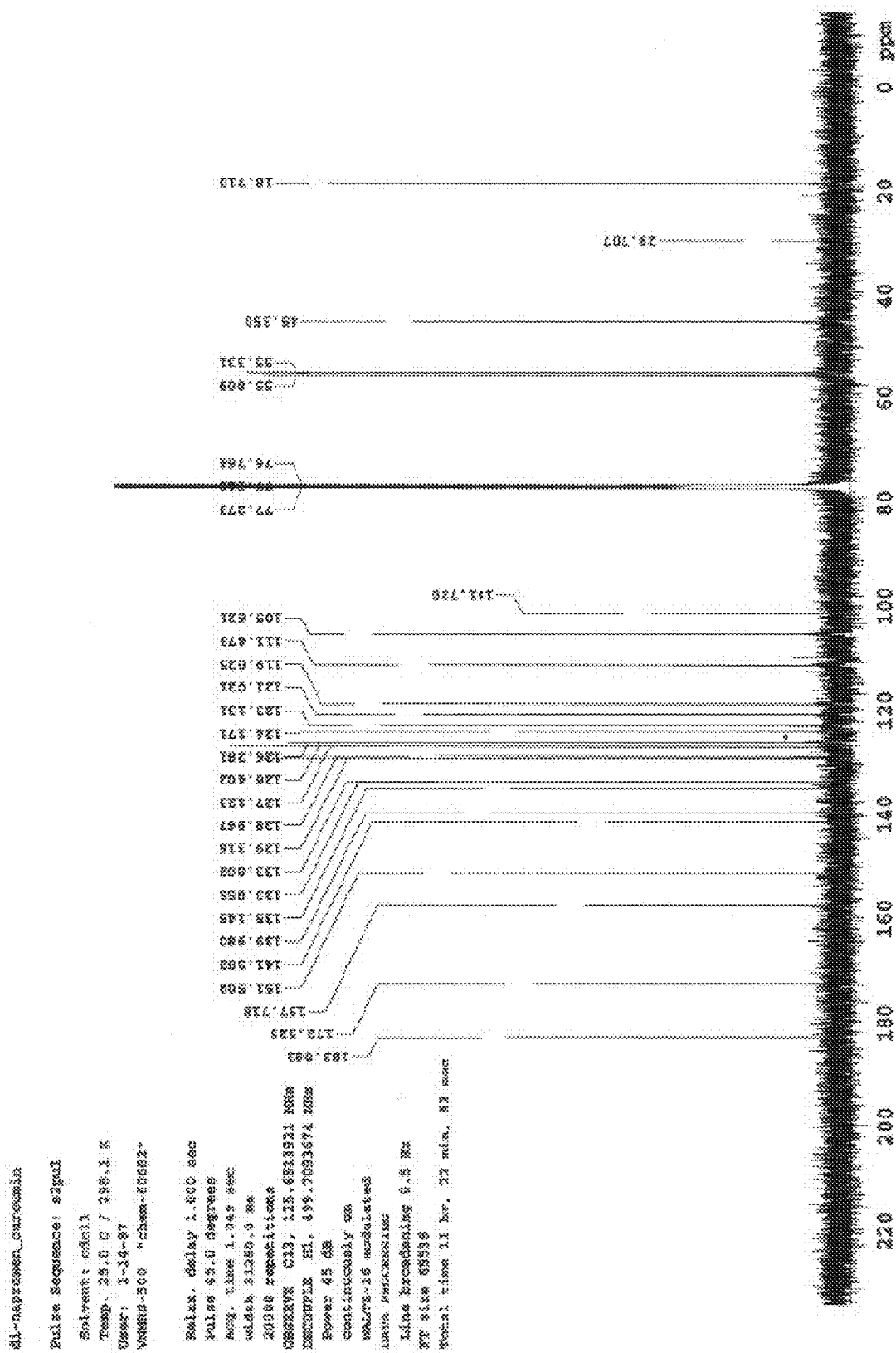

FIG. 180 is a representative NMR spectrum for compound 19 of Example 7.

Figure 181:
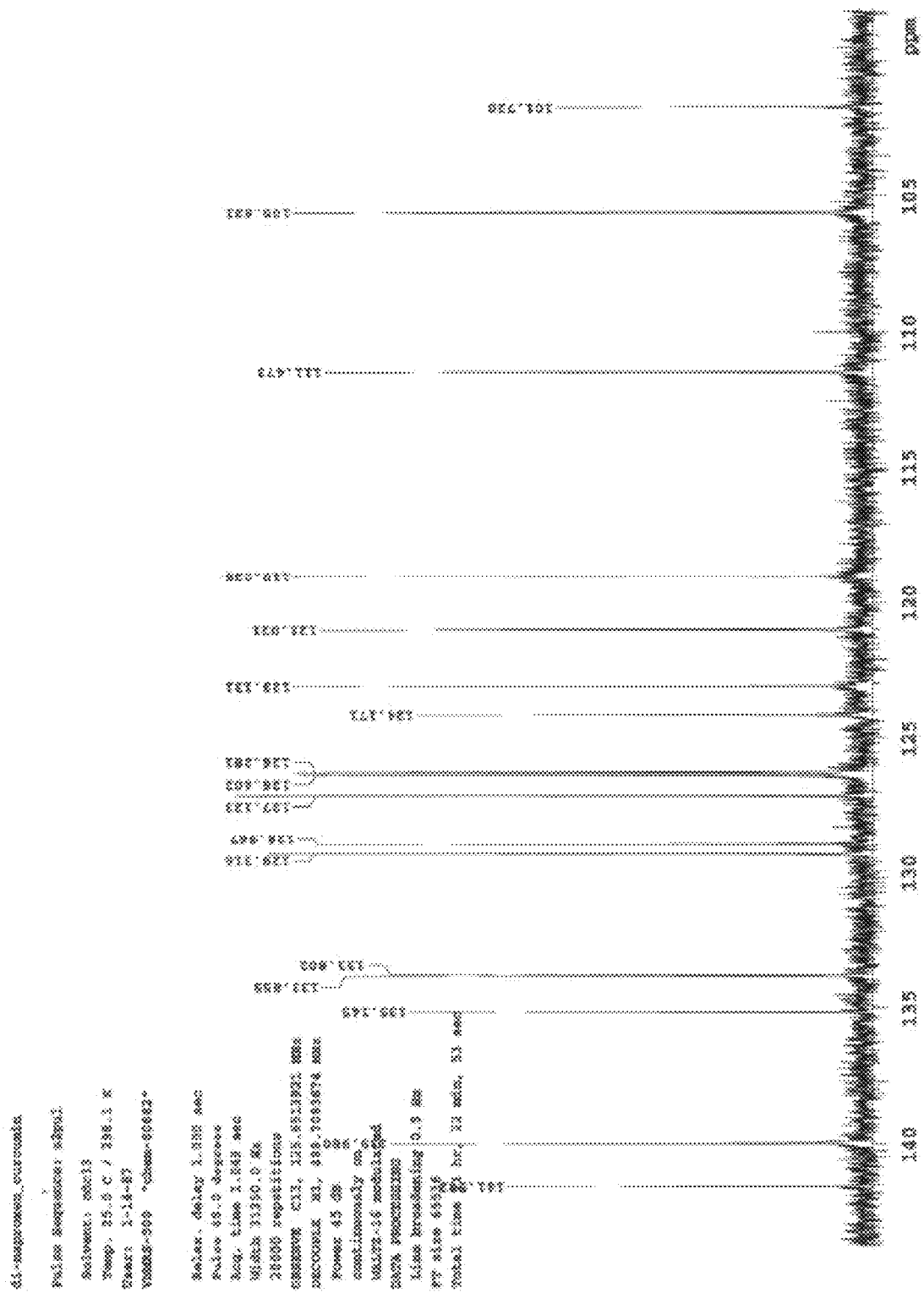

FIG. 181 is a representative NMR spectrum for compound 19 of Example 7.

Figure 182:
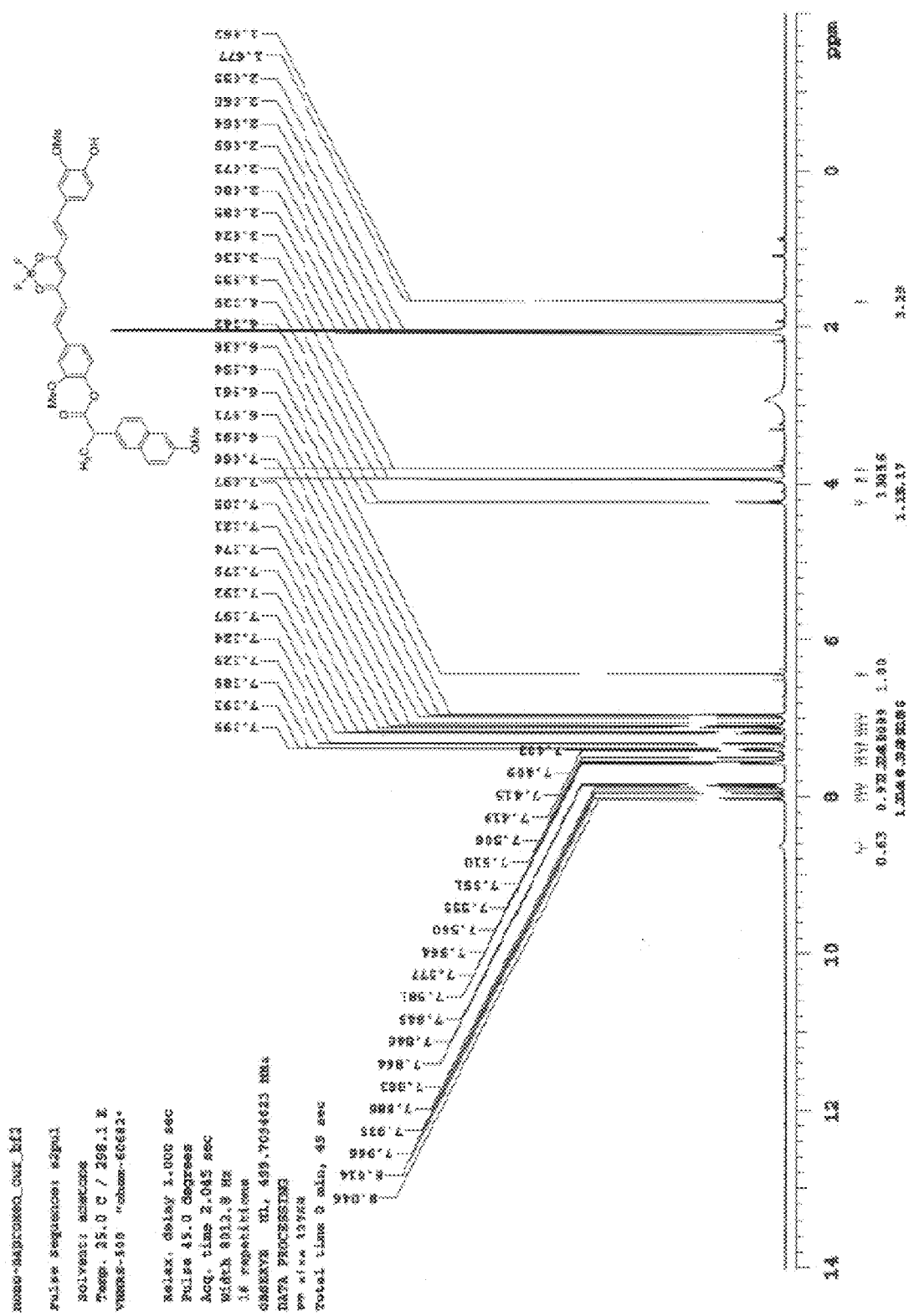

FIG. 182 is a representative NMR spectrum for compound 10 of Example 7.

Figure 183:
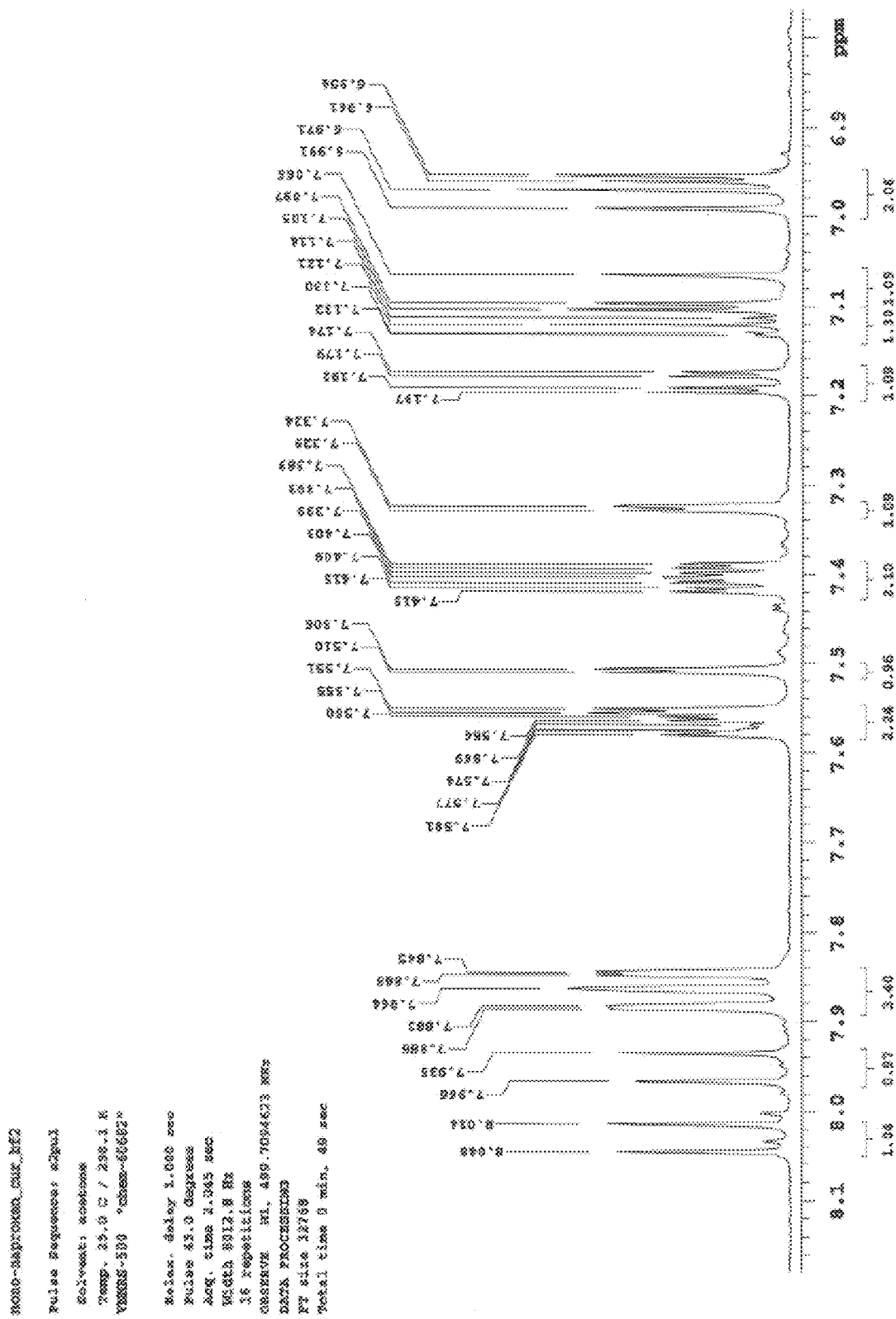

FIG. 183 is a representative NMR spectrum for compound 10 of Example 7.

Figure 184:
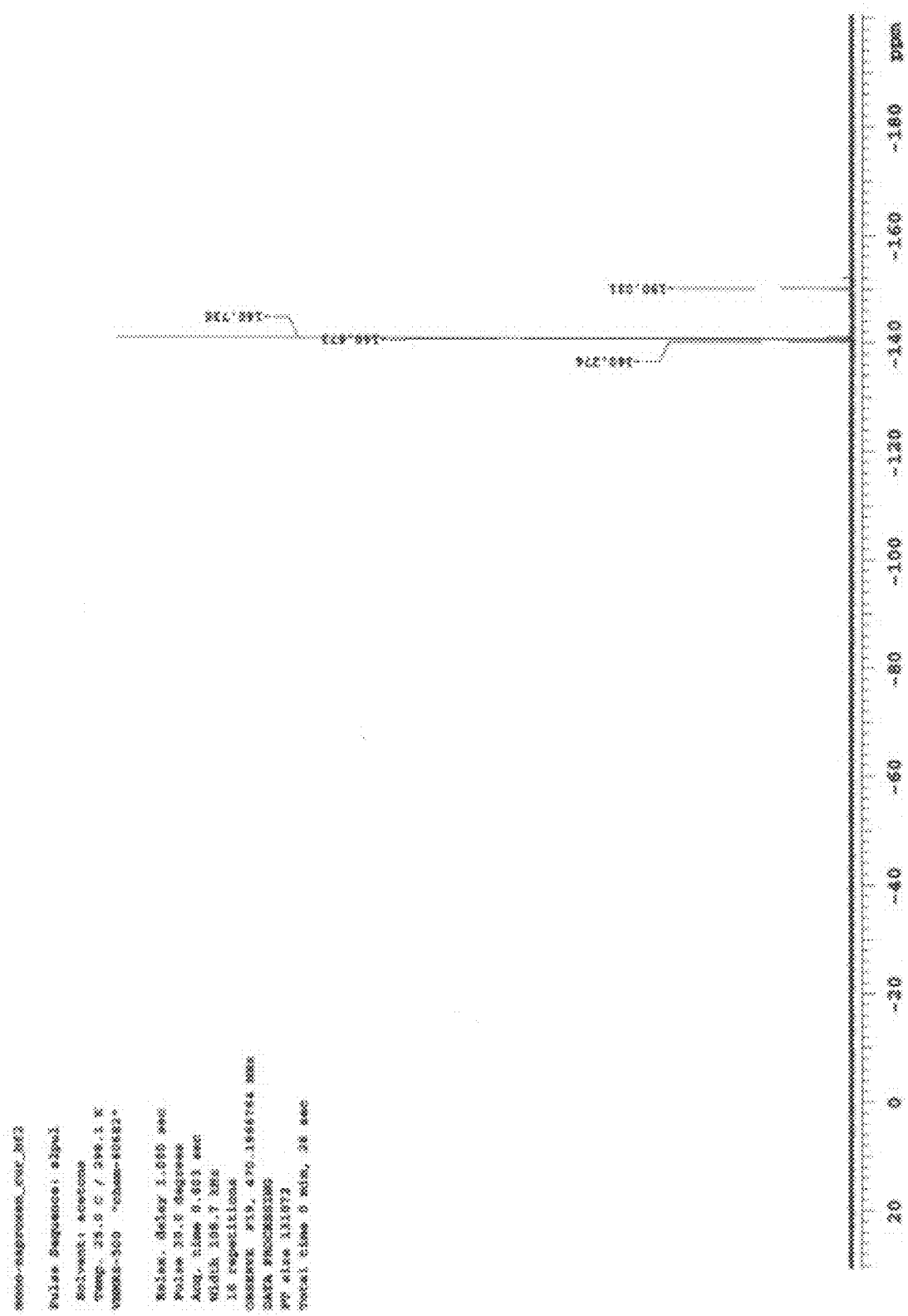

FIG. 184 is a representative NMR spectrum for compound 10 of Example 7.

Figure 185:
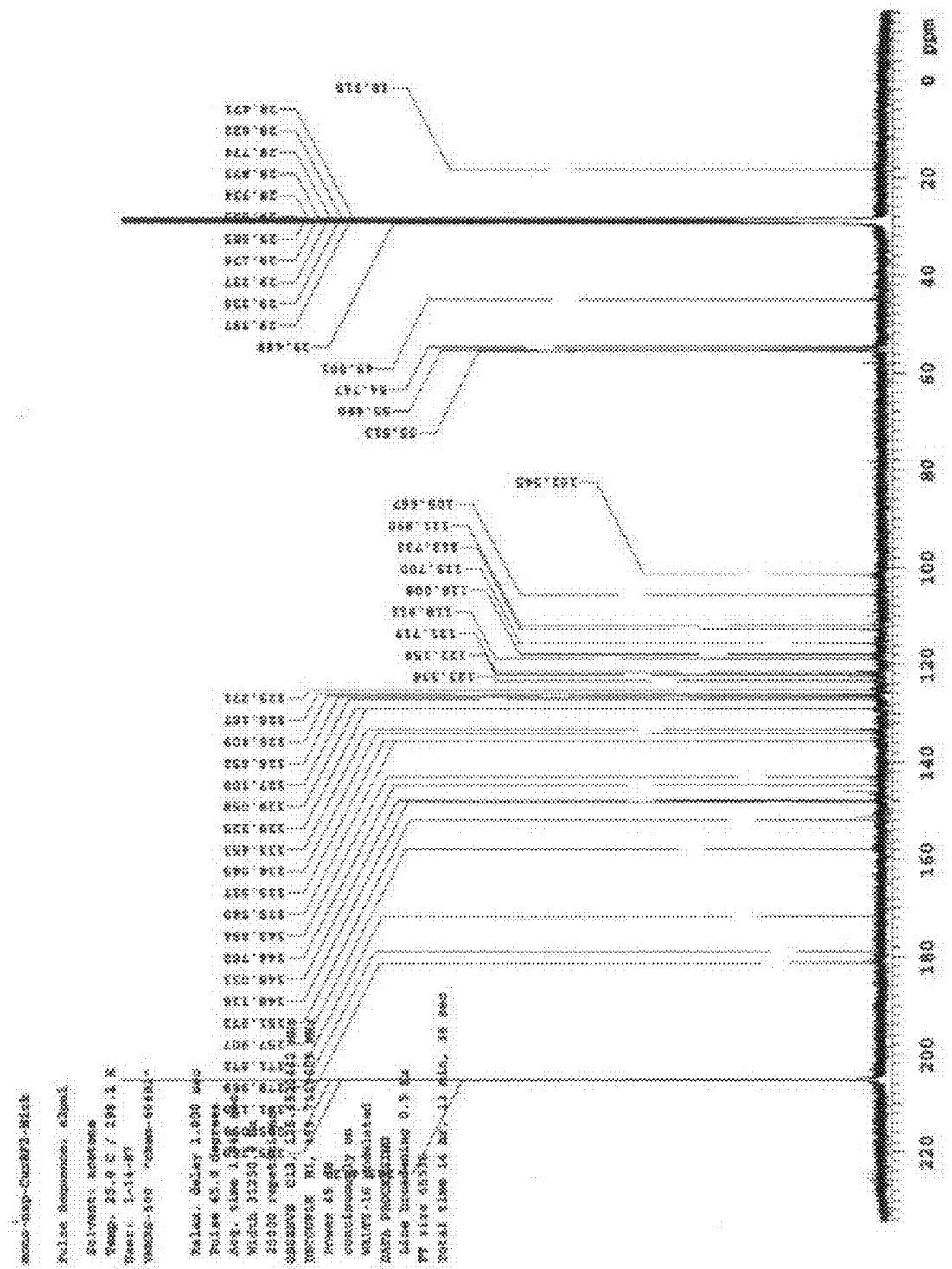

FIG. 185 is a representative NMR spectrum for compound 10 of Example 7.

Figure 186:
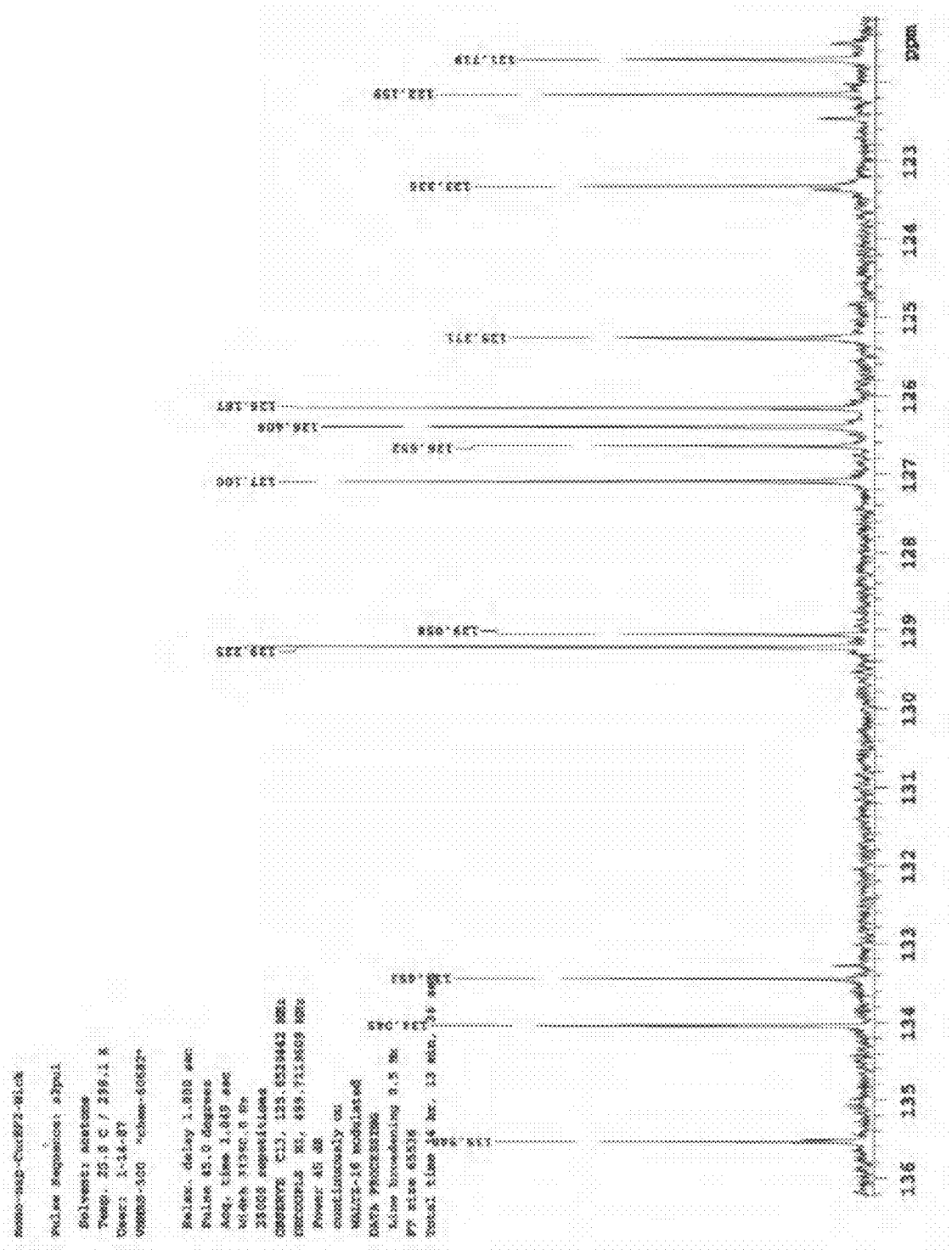

FIG. 186 is a representative NMR spectrum for compound 10 of Example 7.

Figure 187:
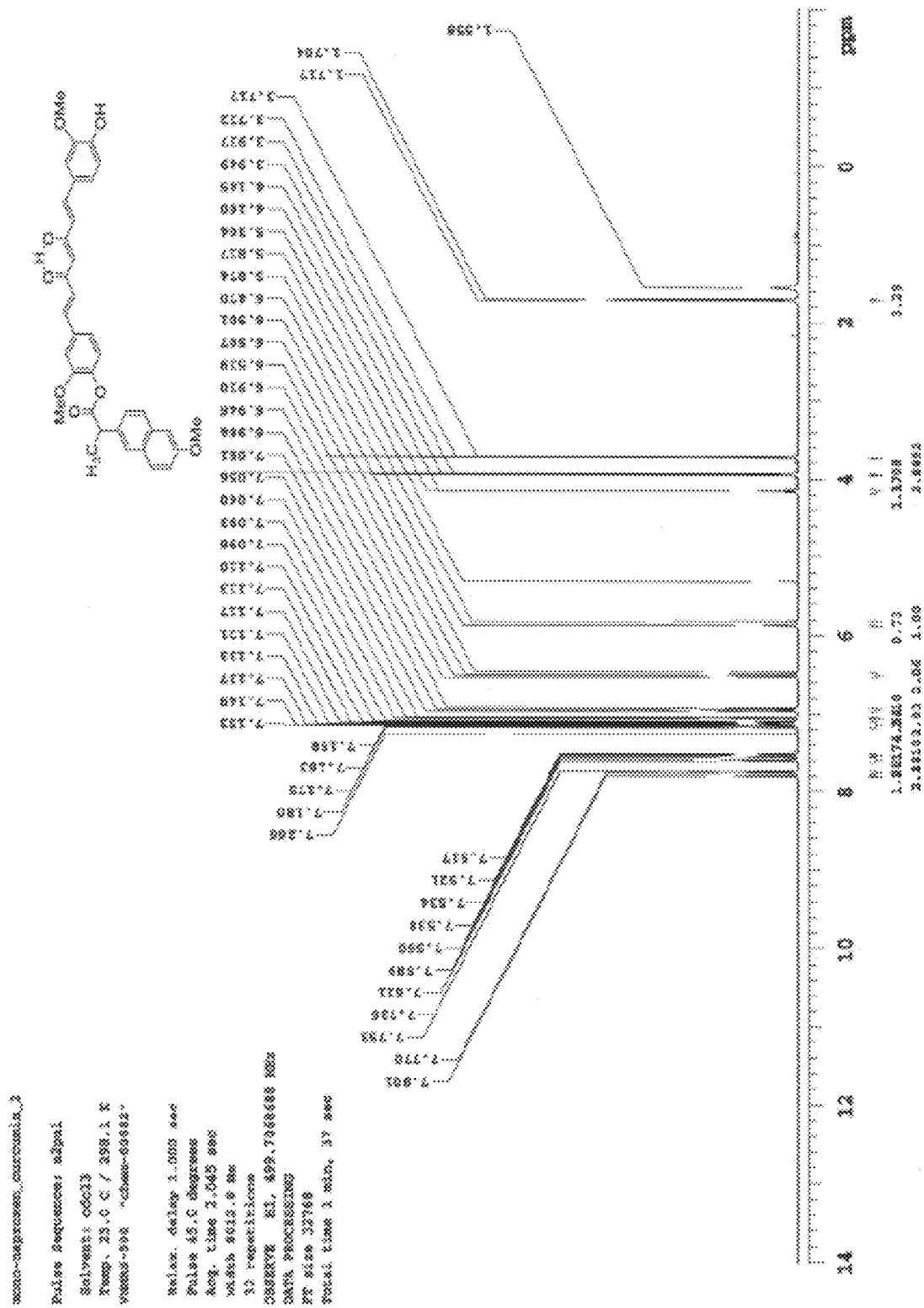

FIG. 187 is a representative NMR spectrum for compound 20 of Example 7.

Figure 188:
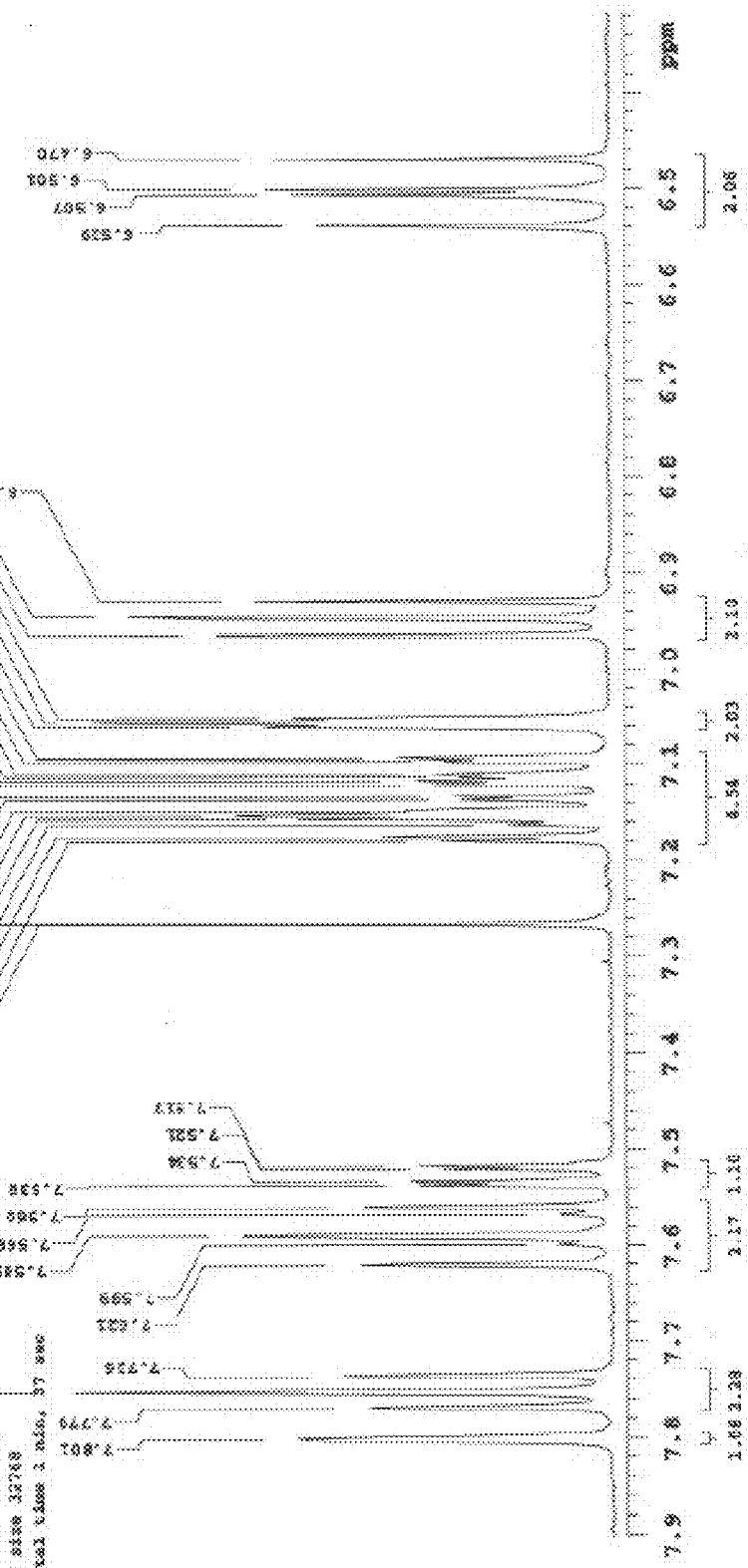

FIG. 188 is a representative NMR spectrum for compound 20 of Example 7.

Figure 189:
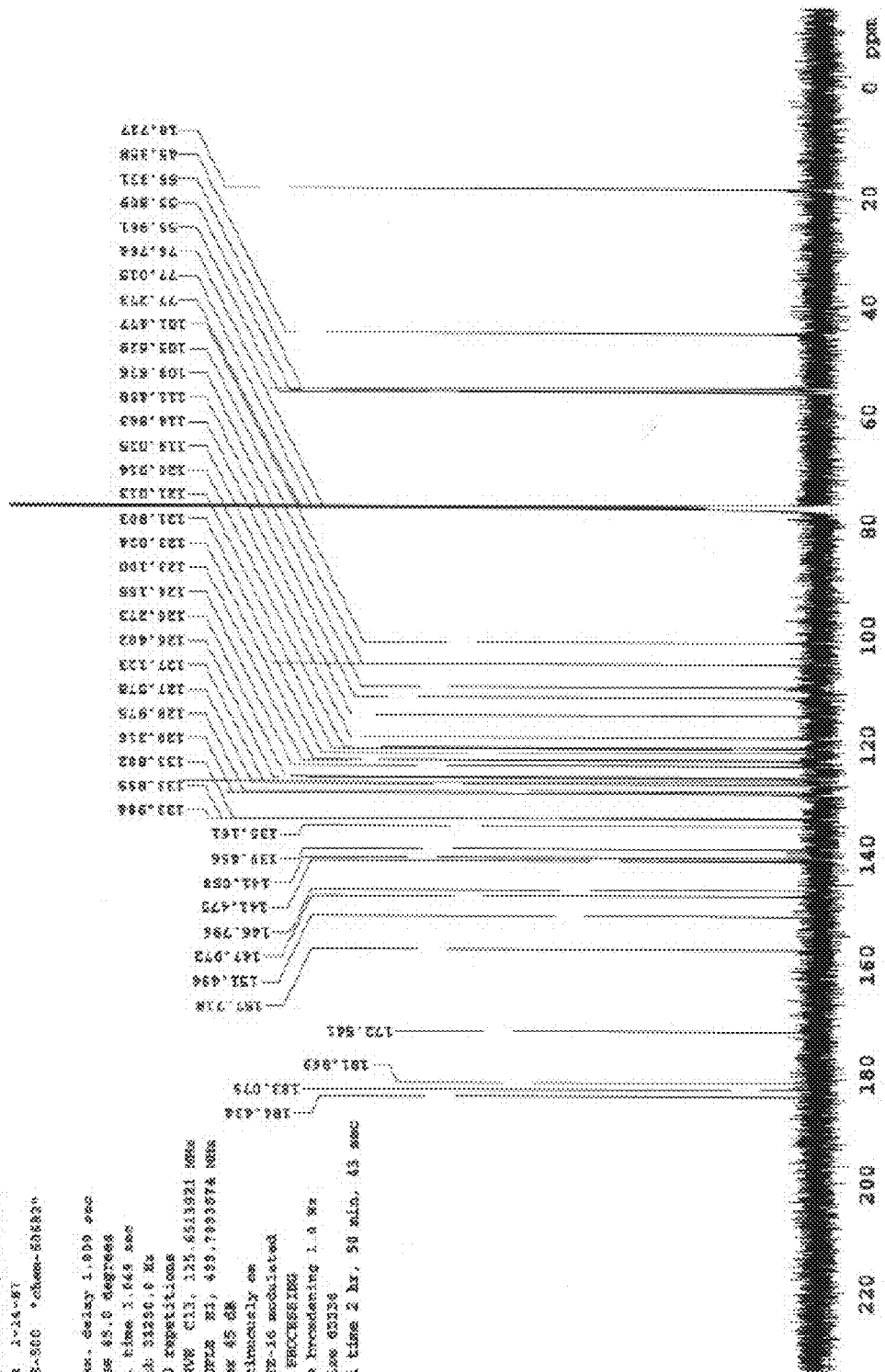

FIG. 189 is a representative NMR spectrum for compound 20 of Example 7.

Figure 190:
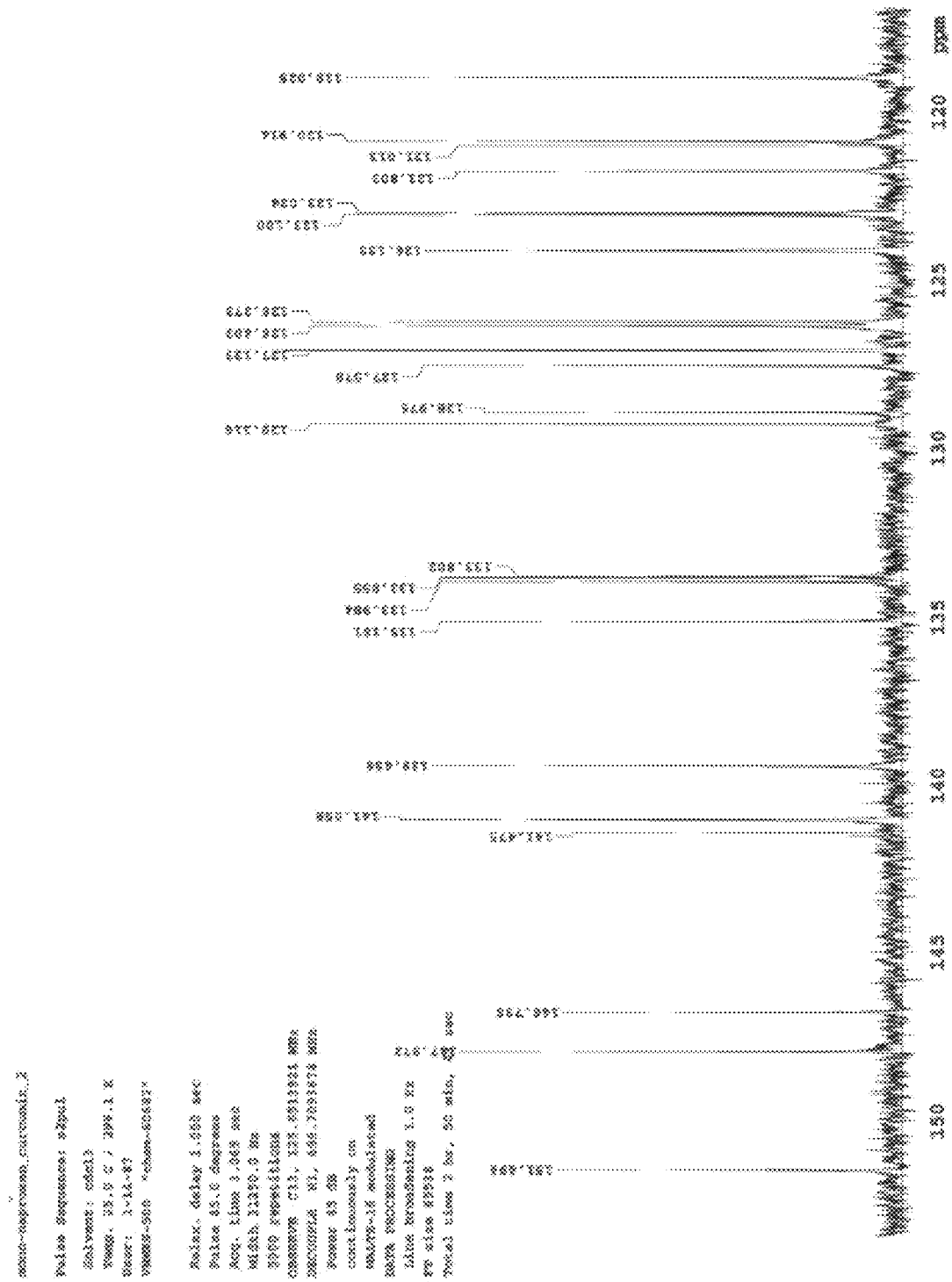

FIG. 190 is a representative NMR spectrum for compound 20 of Example 7.

Figure 191:
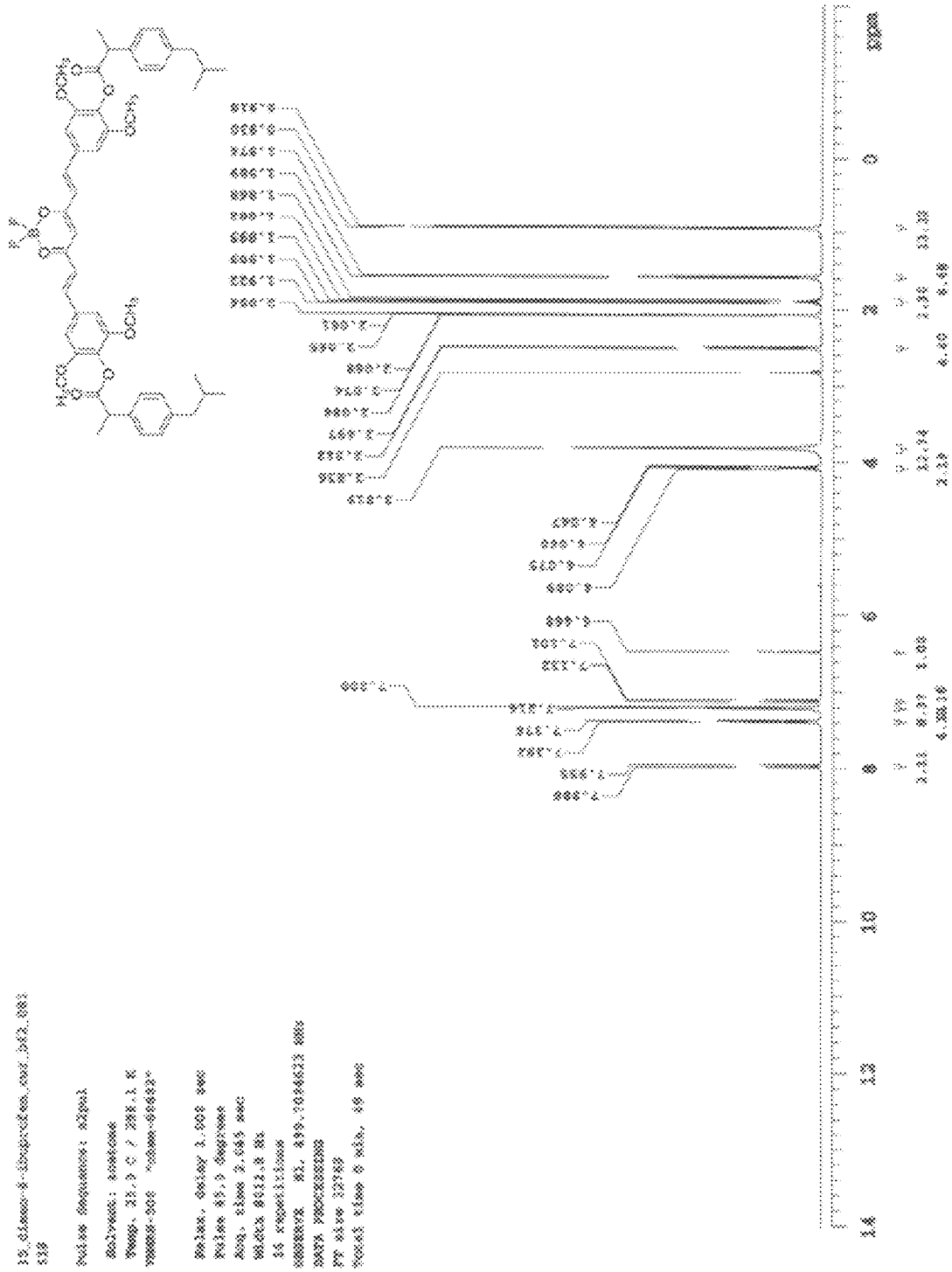

FIG. 191 is a representative NMR spectrum for compound 12 of Example 7.

Figure 192:
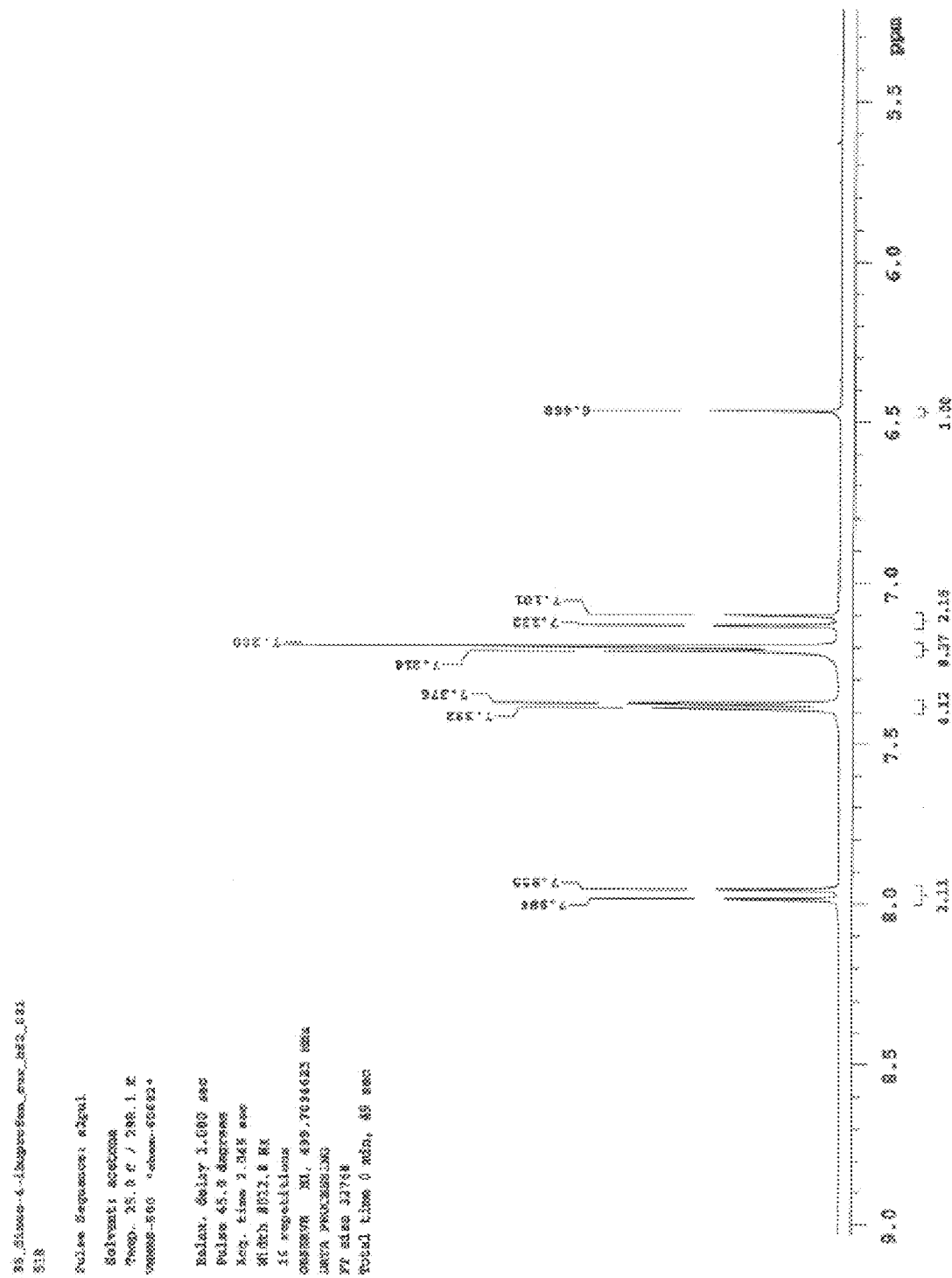

FIG. 192 is a representative NMR spectrum for compound 12 of Example 7.

Figure 193:
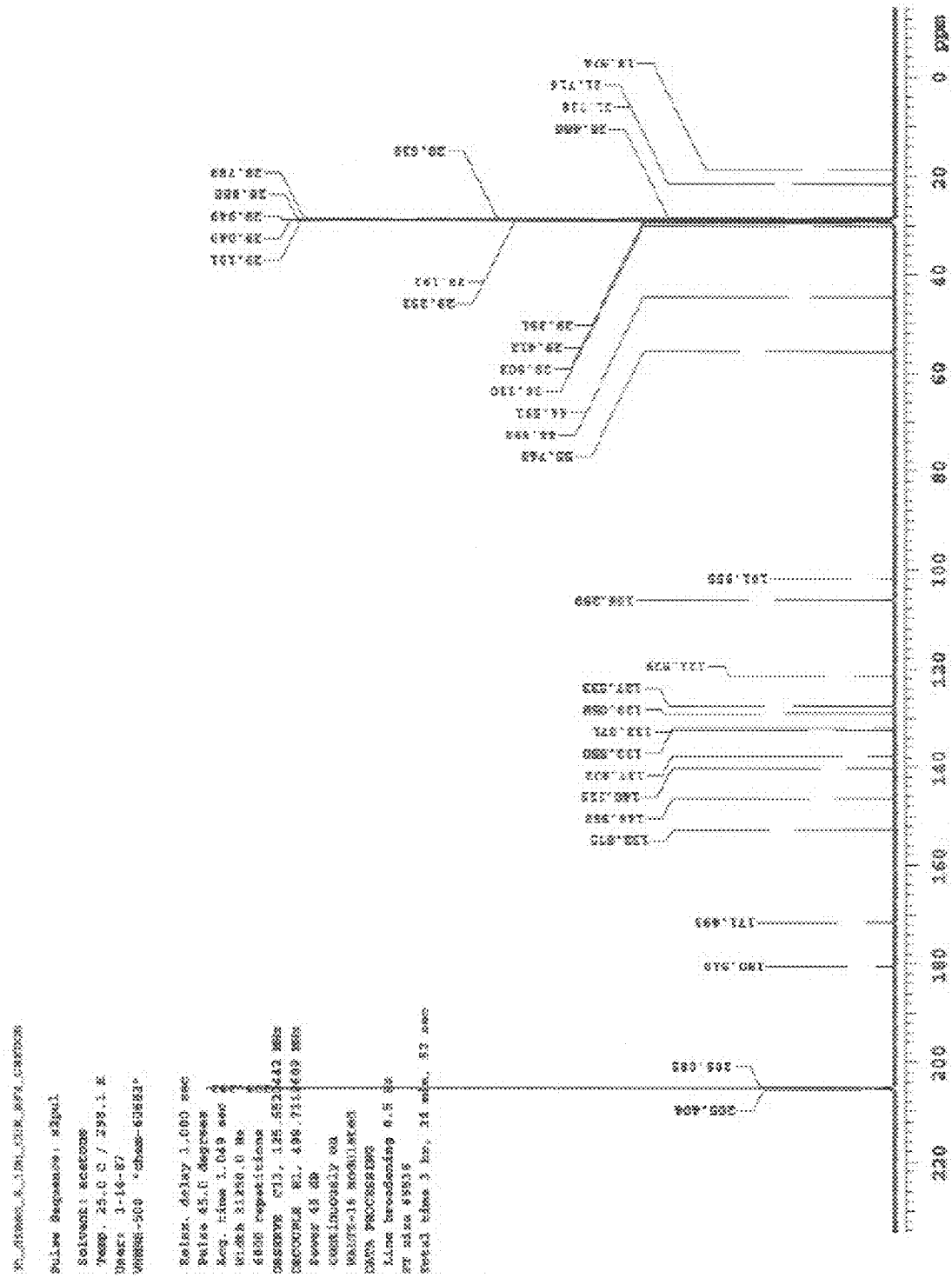

FIG. 193 is a representative NMR spectrum for compound 12 of Example 7.

Figure 194:
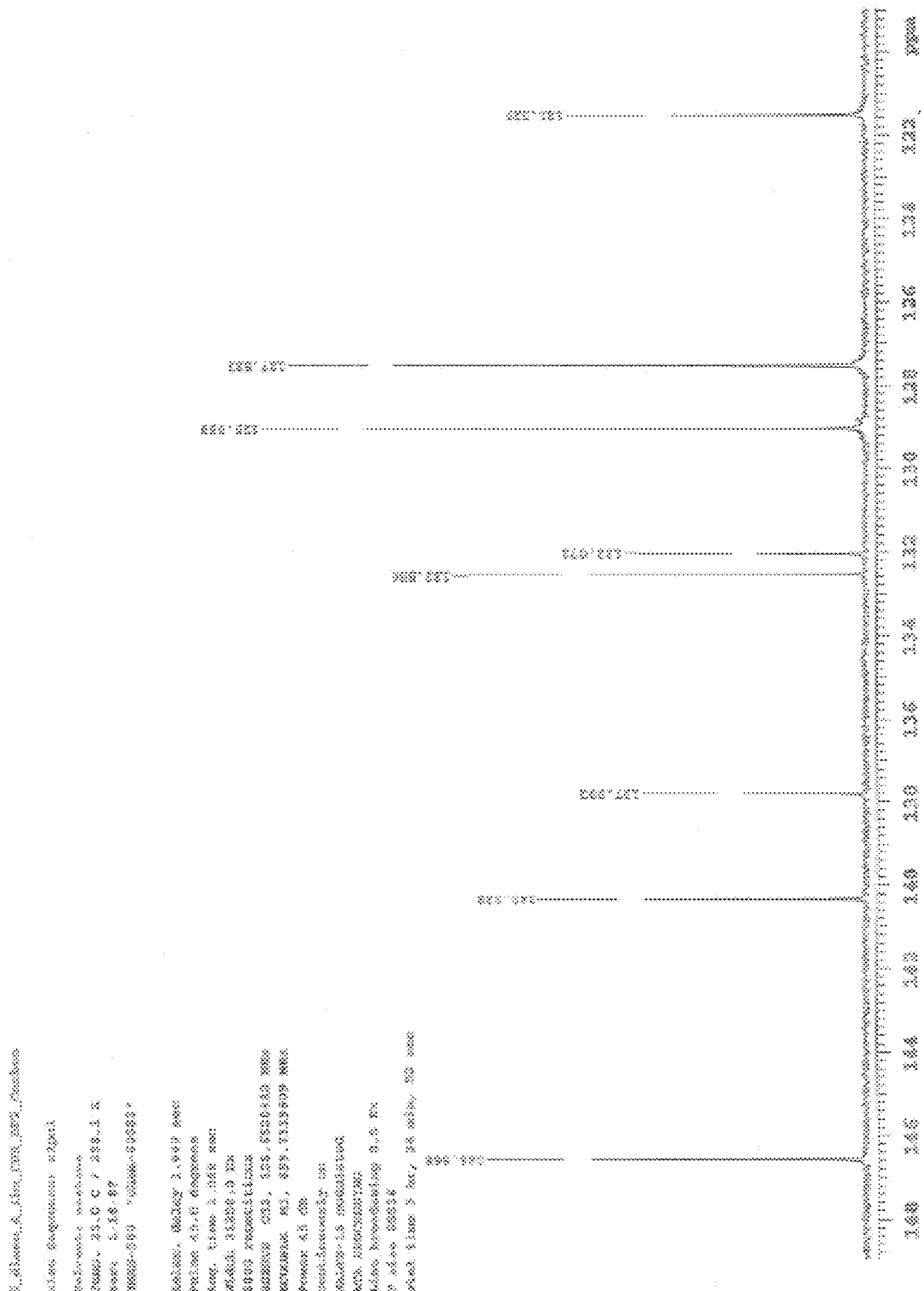

FIG. 194 is a representative NMR spectrum for compound 12 of Example 7.

Figure 195:
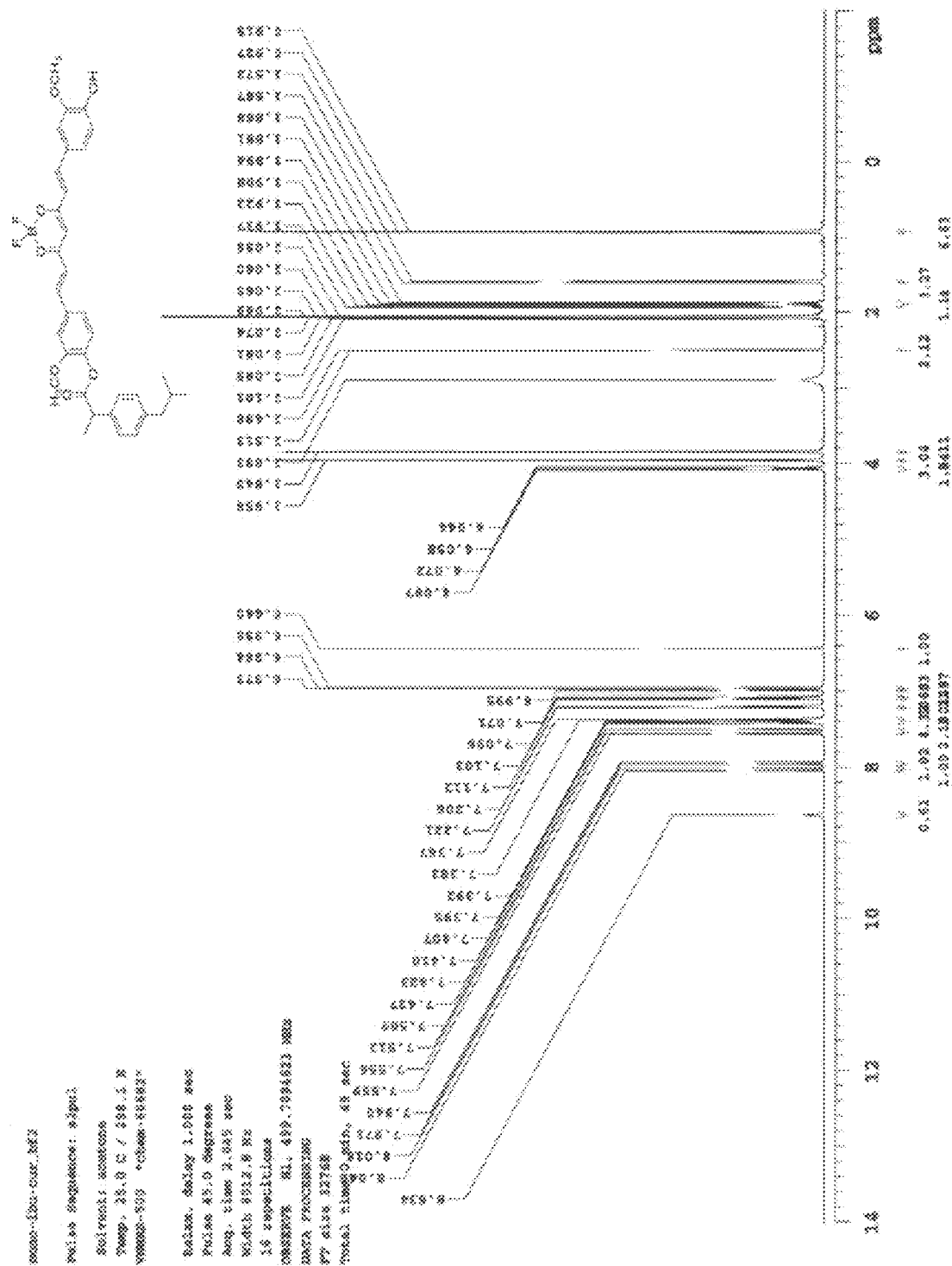

FIG. 195 is a representative NMR spectrum for compound 13 of Example 7.

Figure 196:
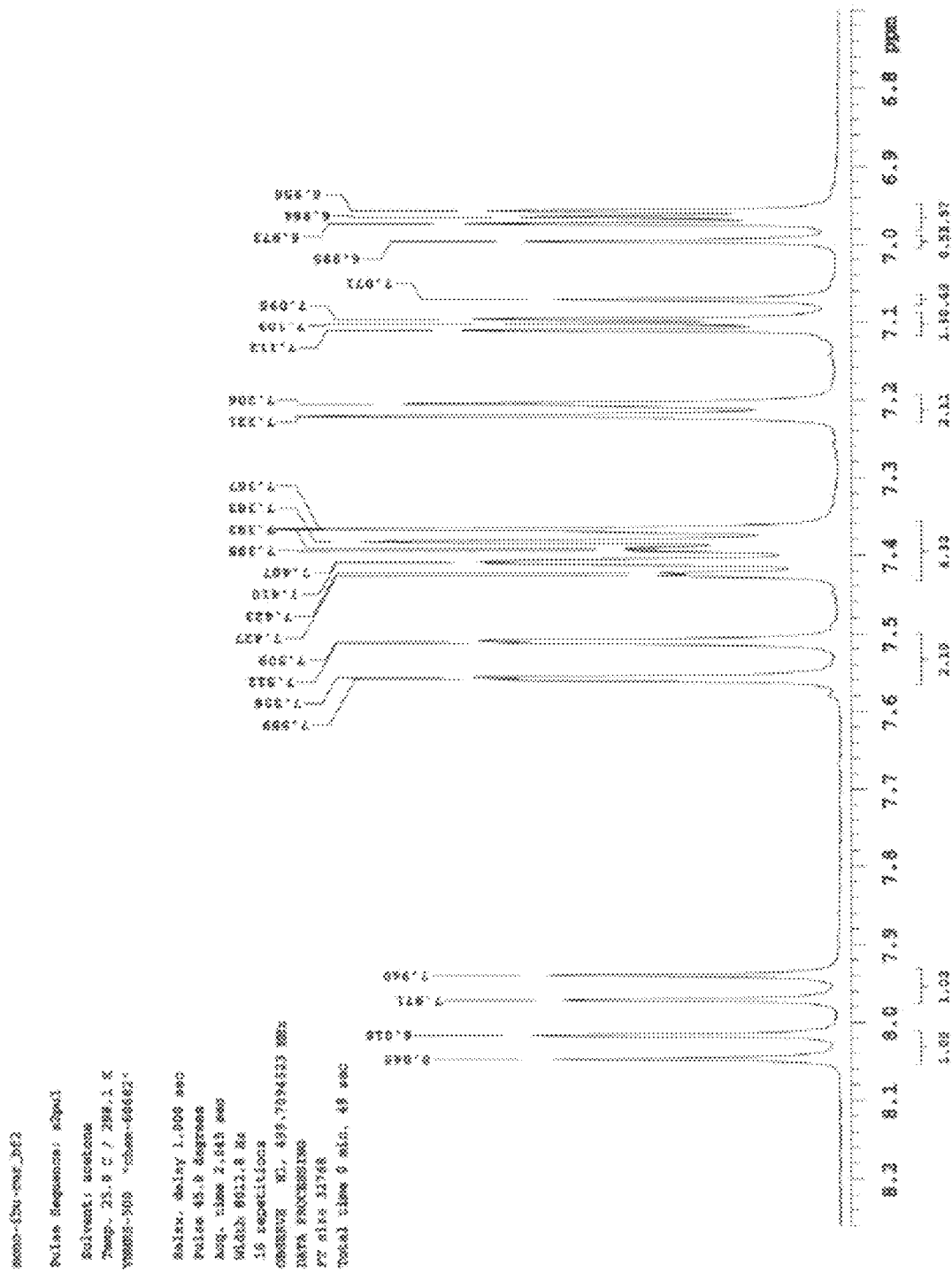

FIG. 196 is a representative NMR spectrum for compound 13 of Example 7.

Figure 197:
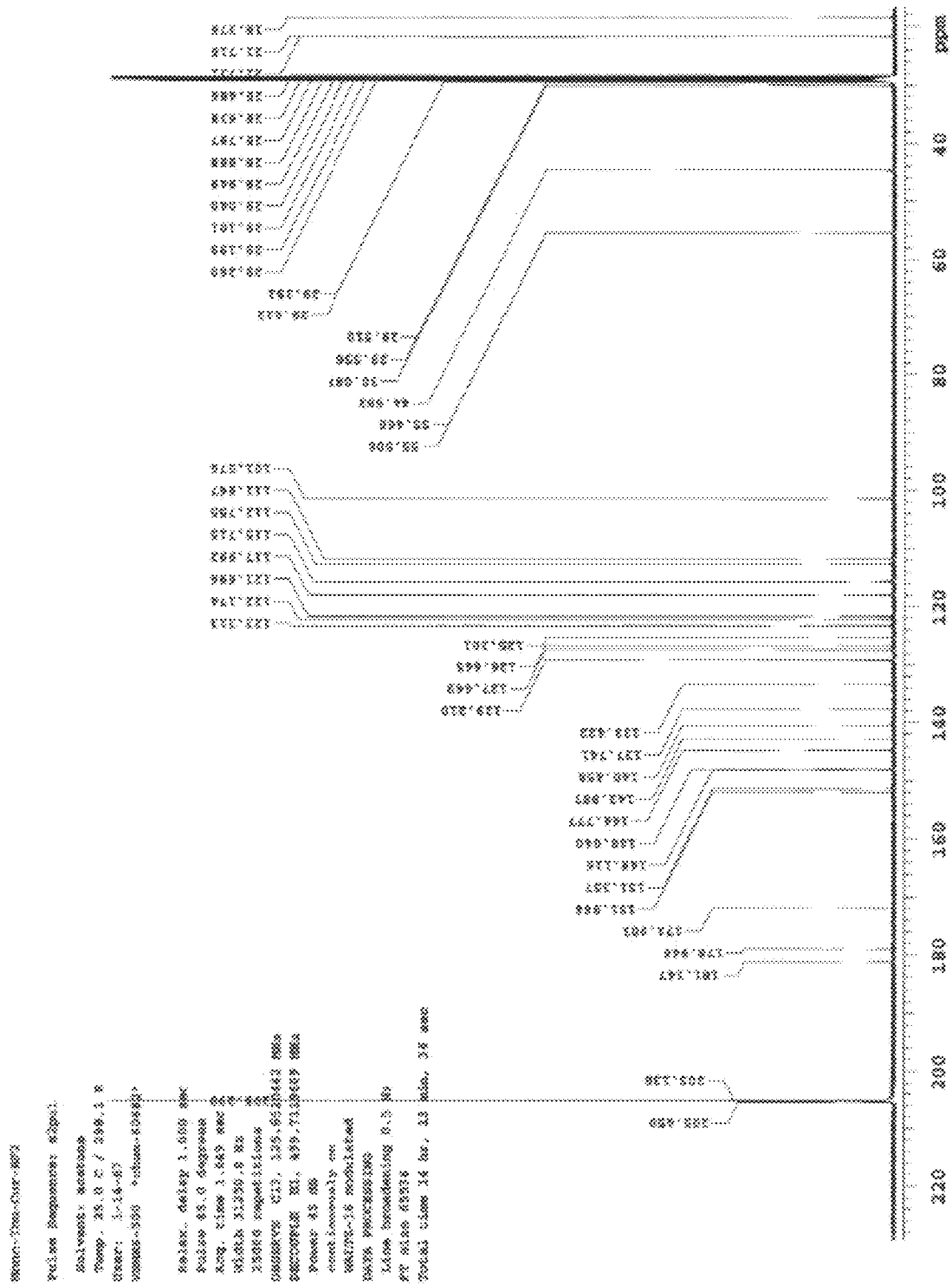

FIG. 197 is a representative NMR spectrum for compound 13 of Example 7.

Figure 198:
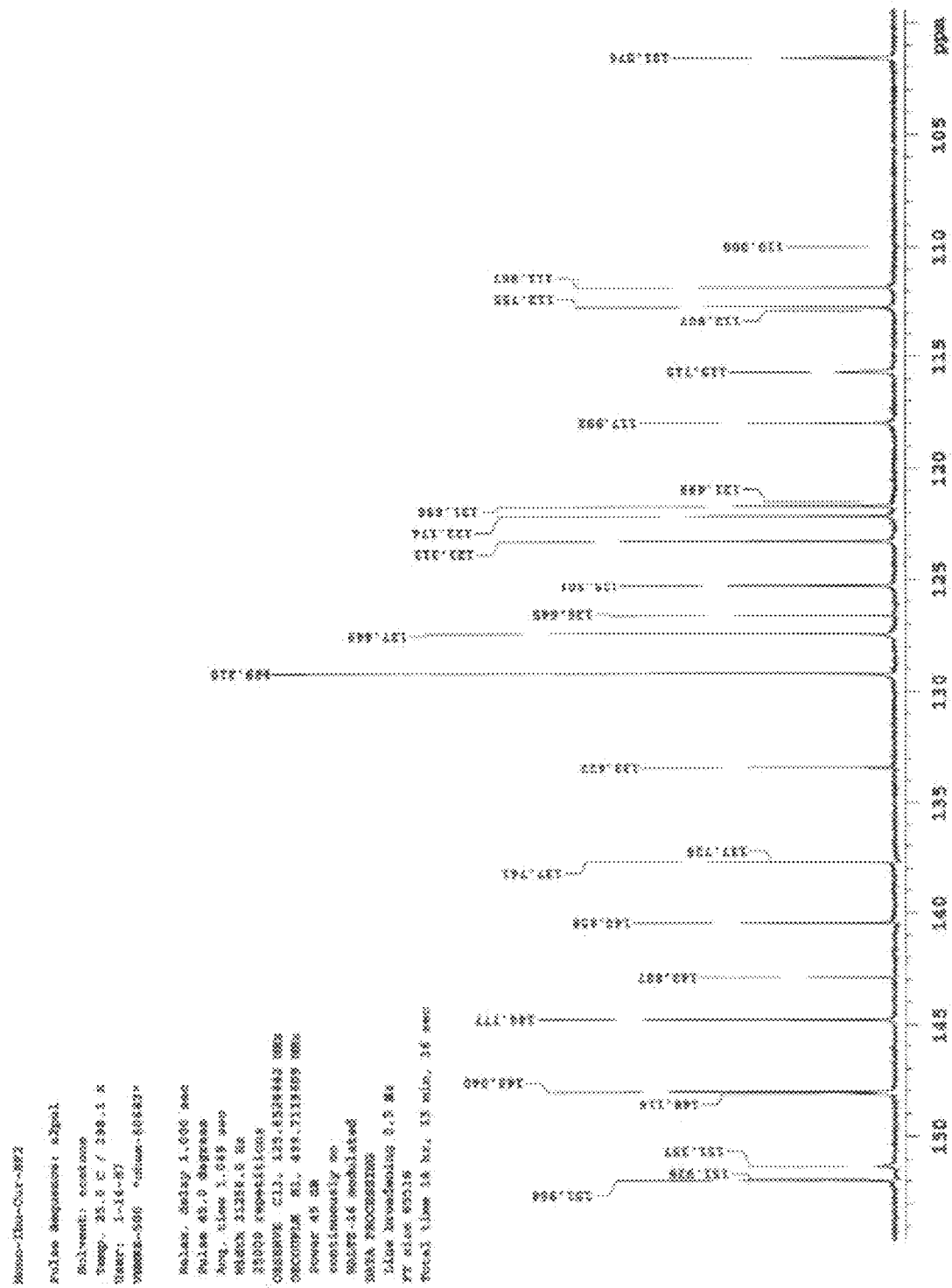

FIG. 198 is a representative NMR spectrum for compound 13 of Example 7.

Figure 199:
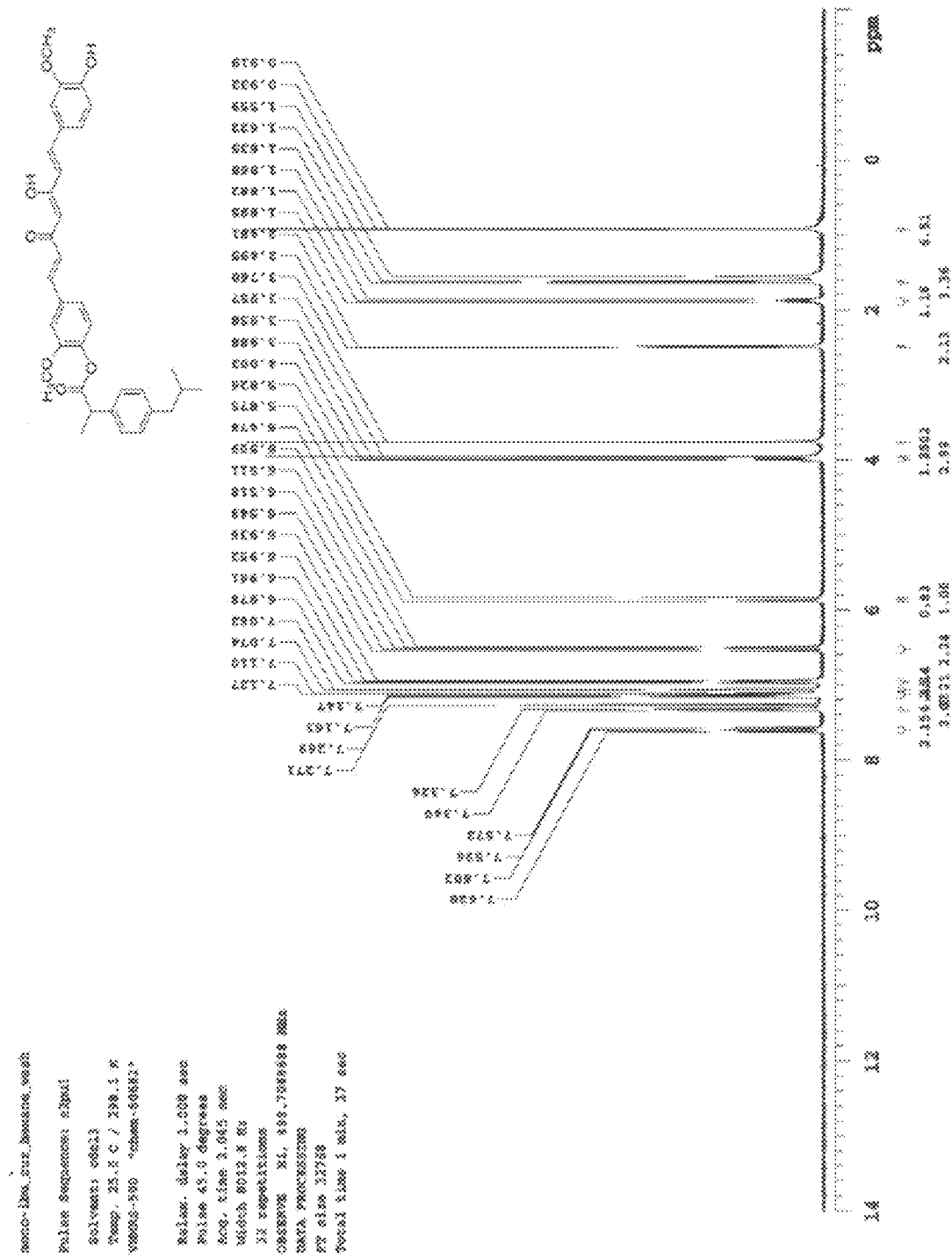

FIG. 199 is a representative NMR spectrum for compound 21 of Example 7.

Figure 200:
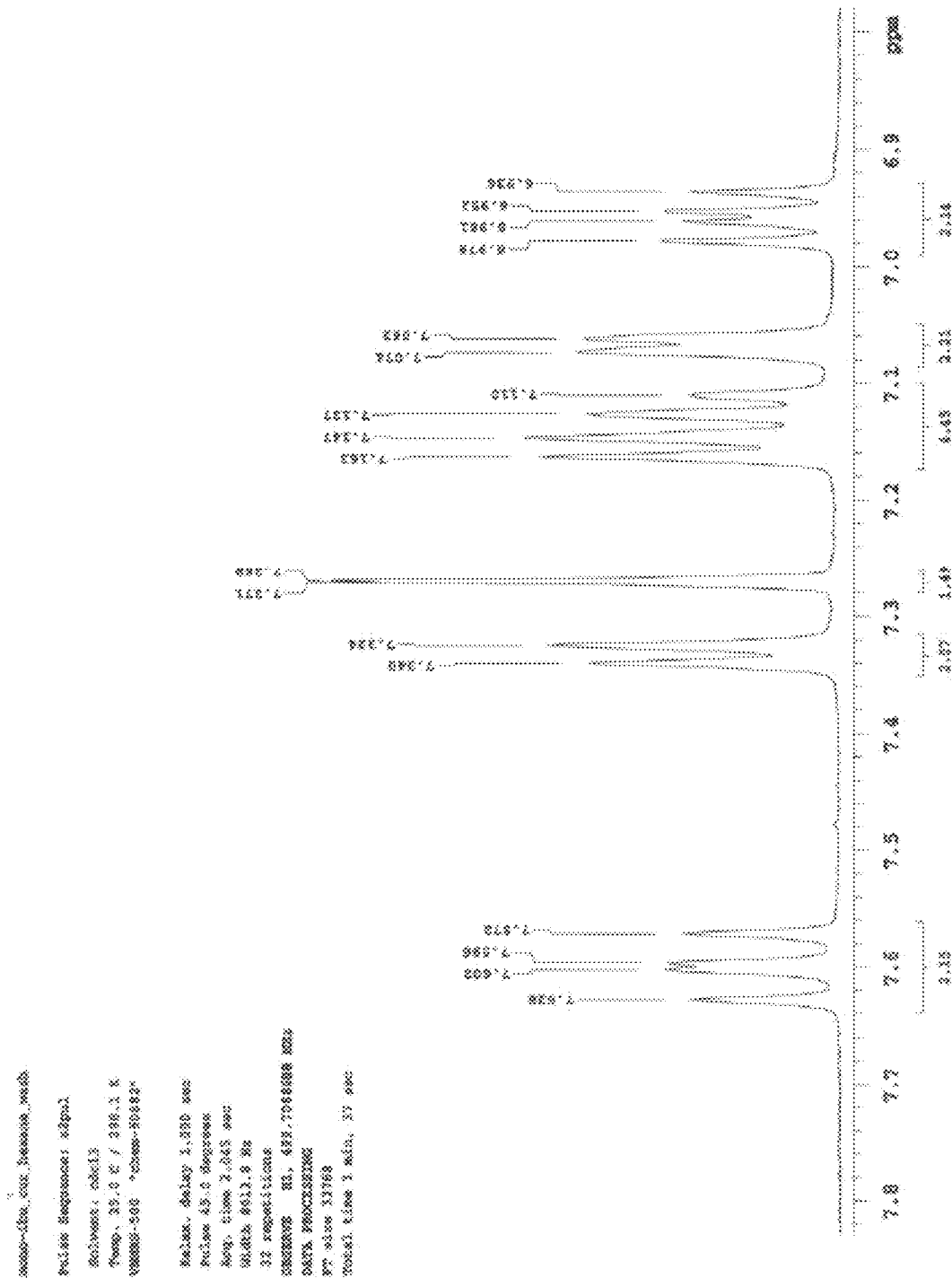

FIG. 200 is a representative NMR spectrum for compound 21 of Example 7.

Figure 201:
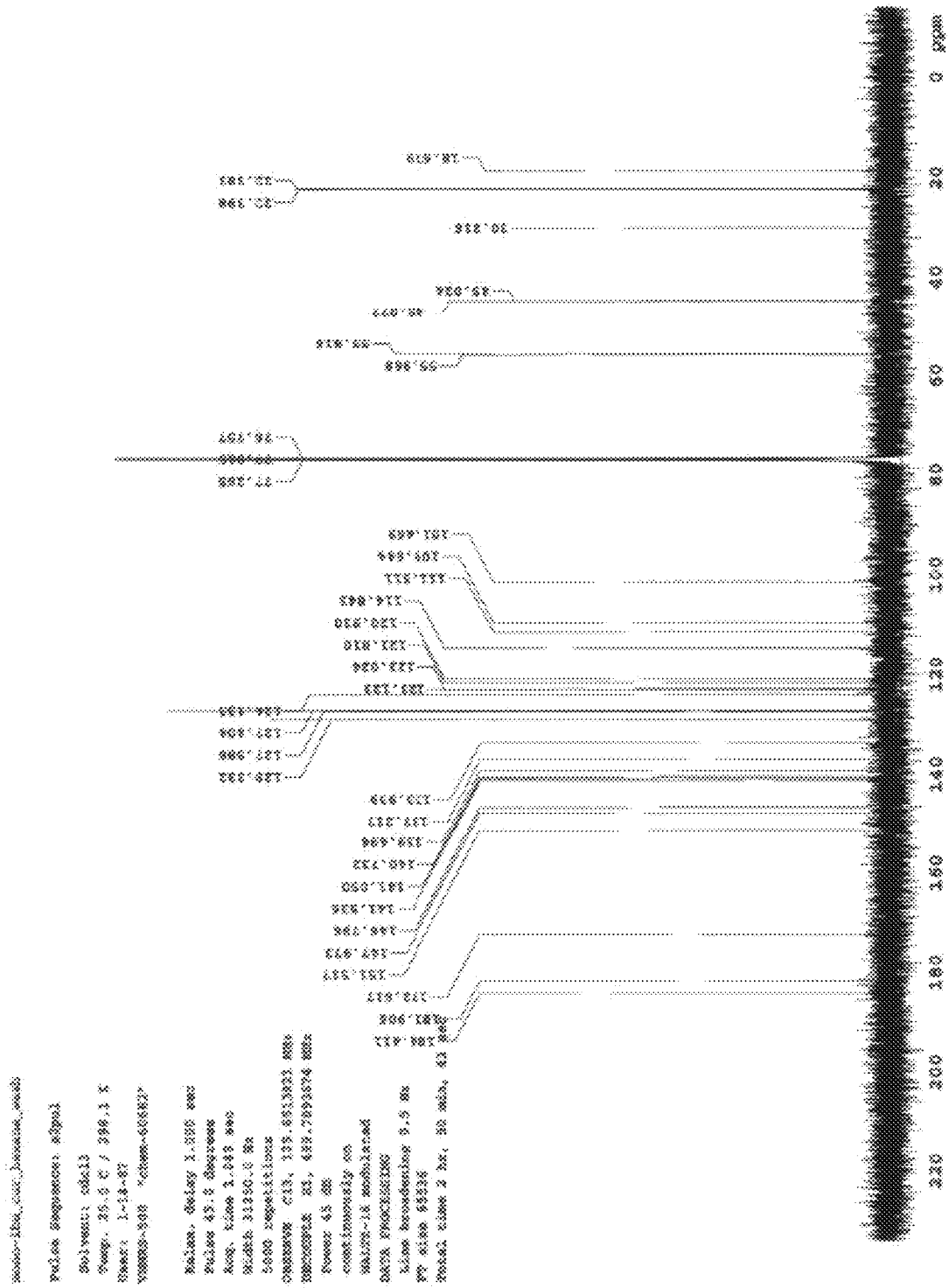

FIG. 201 is a representative NMR spectrum for compound 21 of Example 7.

Figure 202:
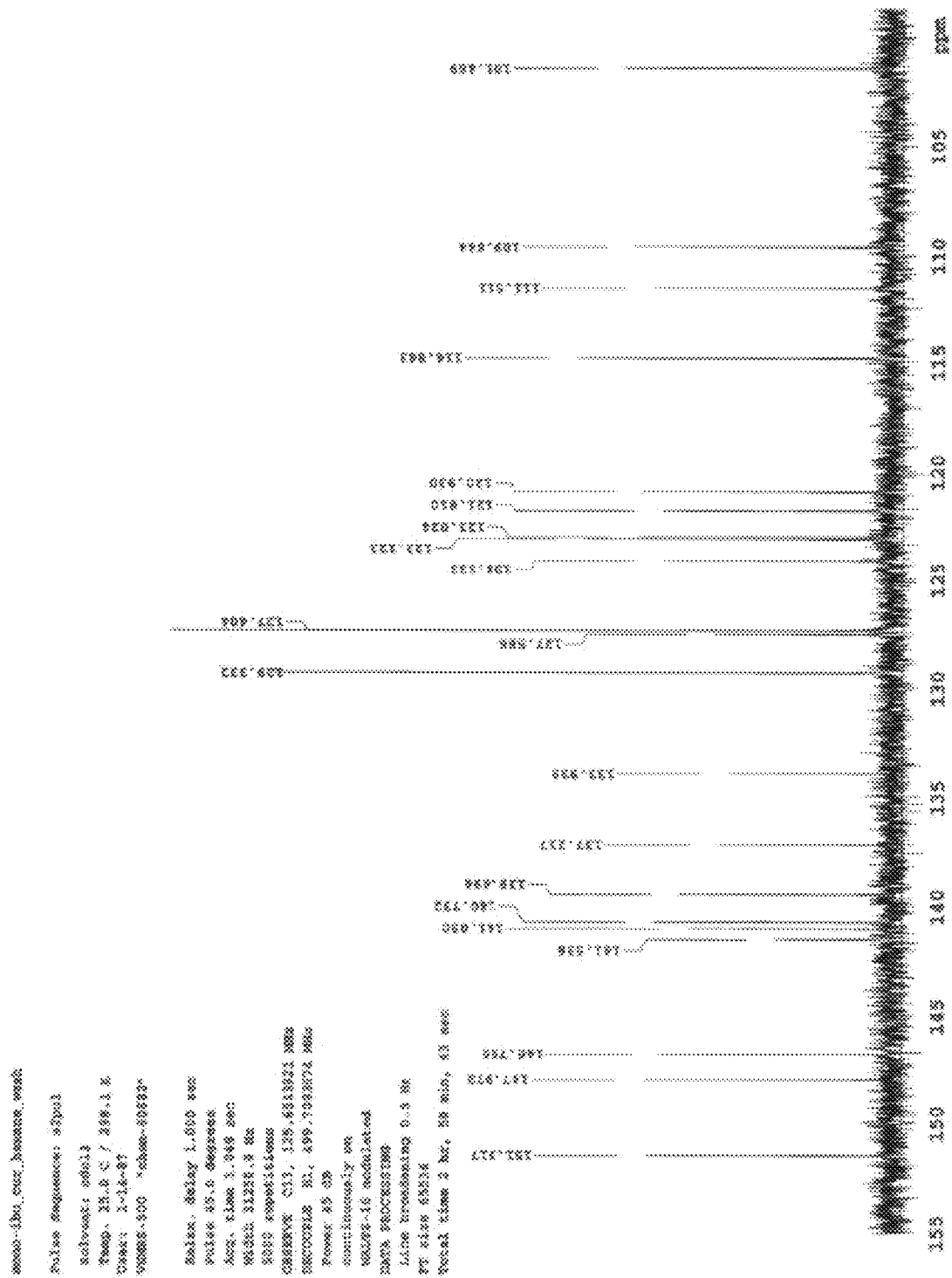

FIG. 202 is a representative NMR spectrum for compound 21 of Example 7.

Figure 203:
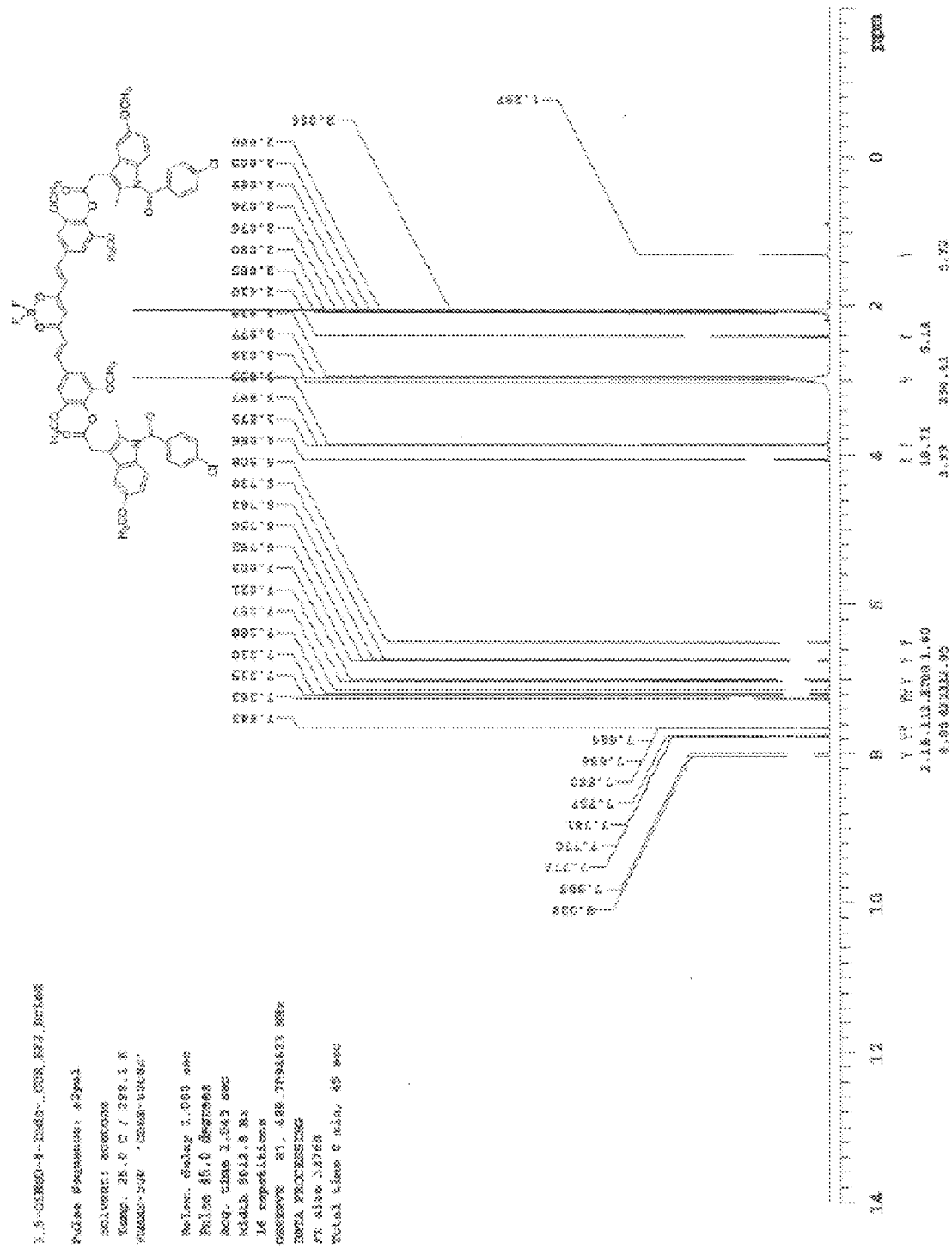

FIG. 203 is a representative NMR spectrum for compound 11 of Example 7.

Figure 204:
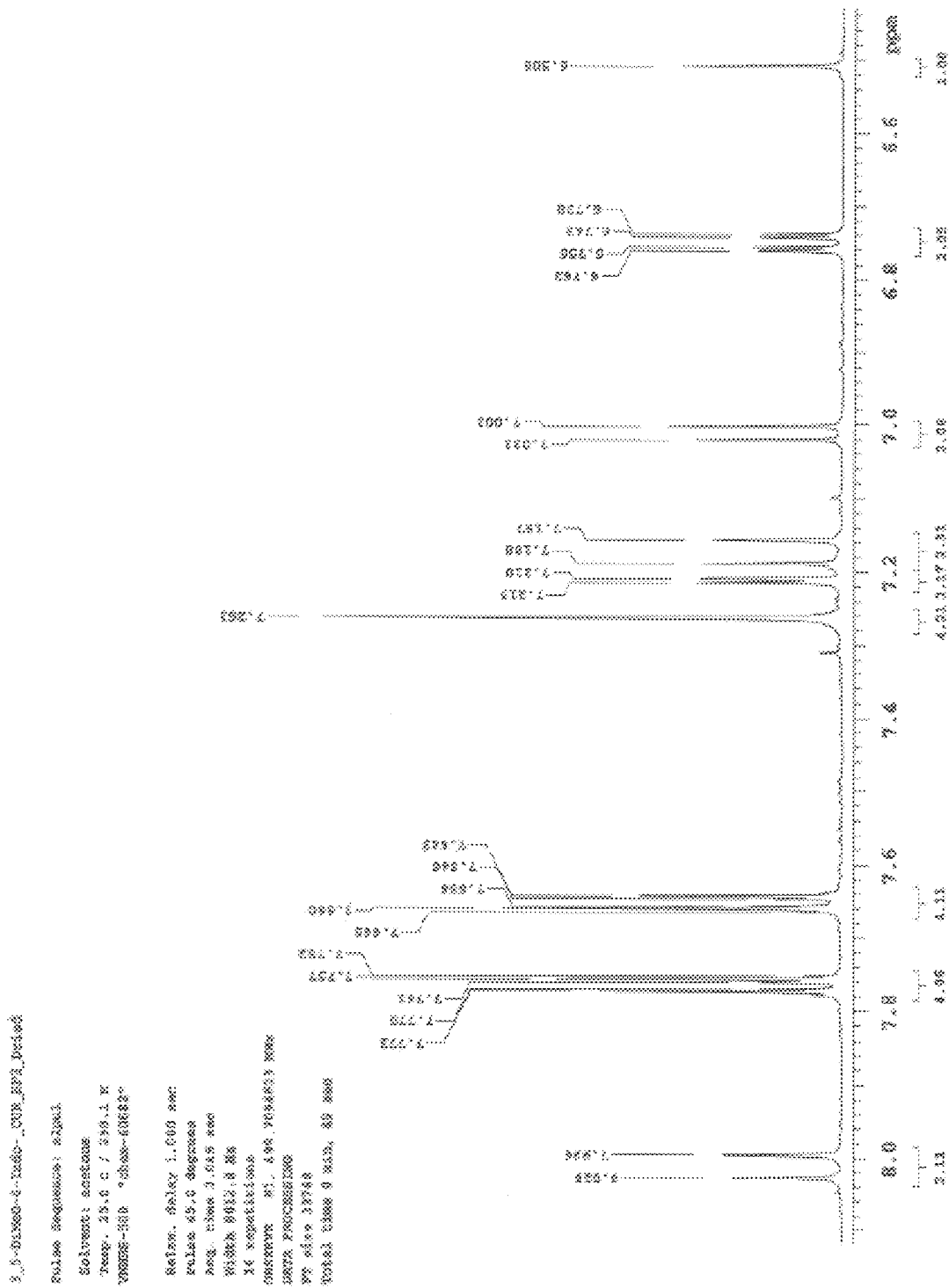

FIG. 204 is a representative NMR spectrum for compound 11 of Example 7.

Figure 205:
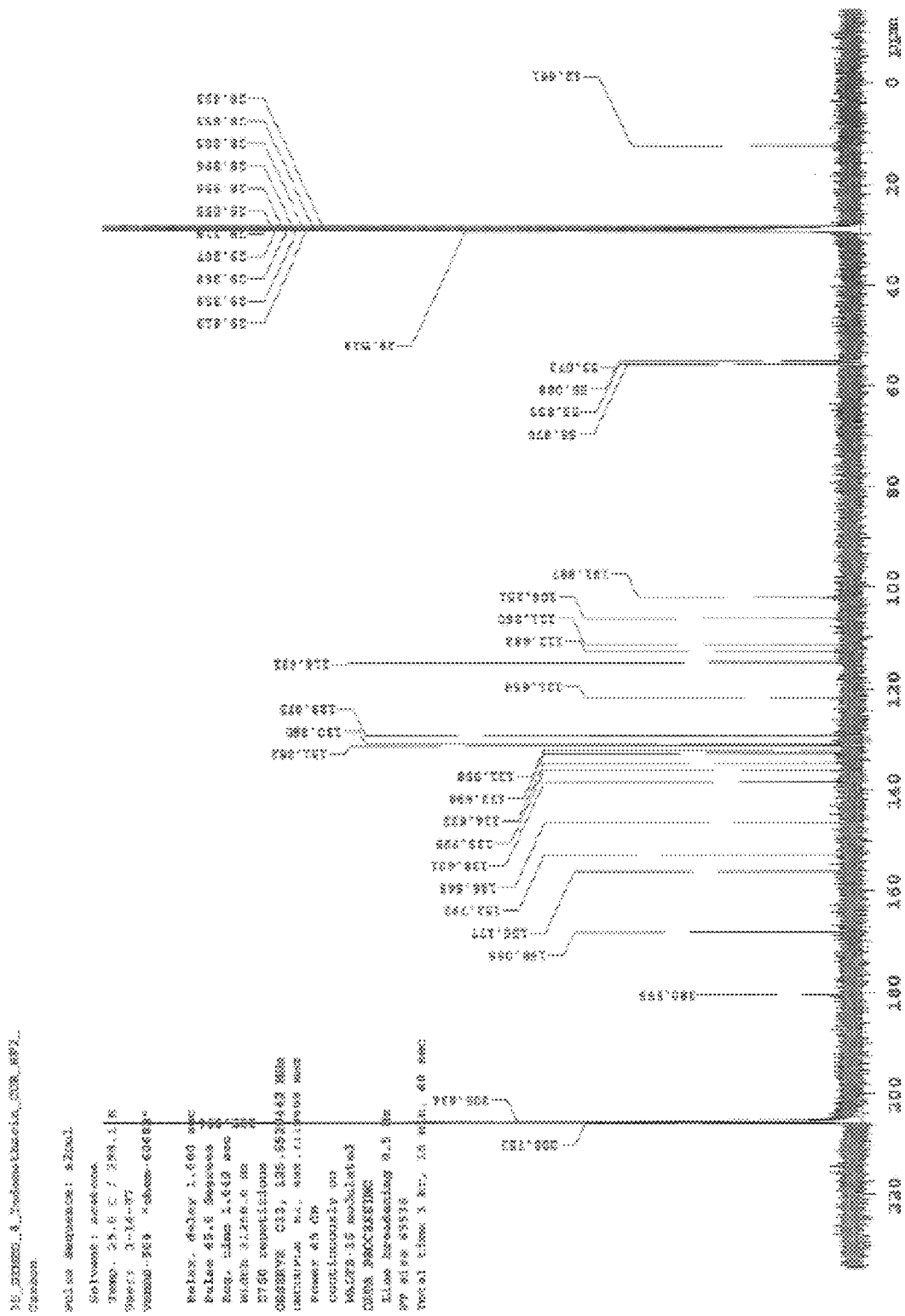

FIG. 205 is a representative NMR spectrum for compound 11 of Example 7.

Figure 206:
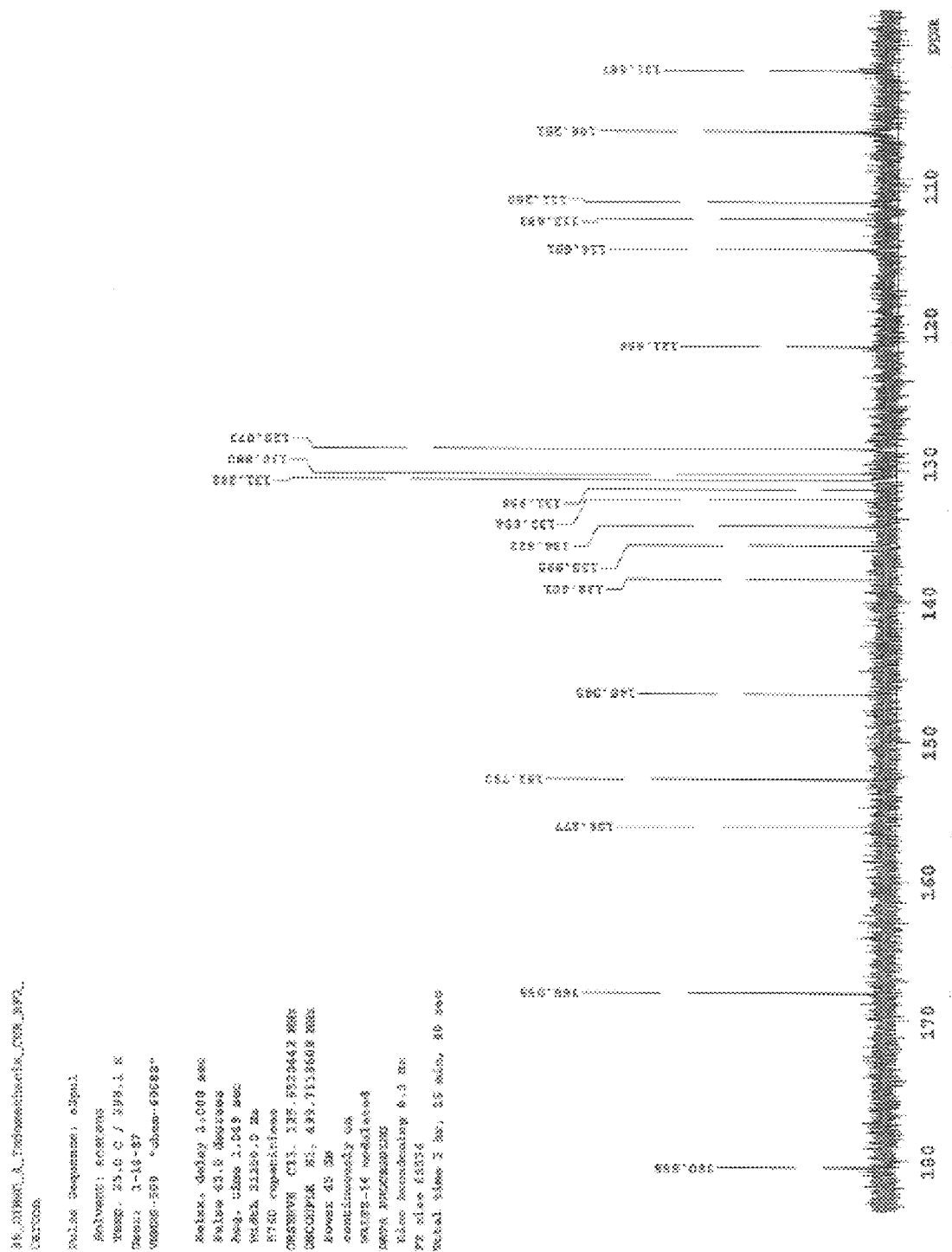

FIG. 206 is a representative NMR spectrum for compound 11 of Example 7.

FIG. 207 is a representative NMR spectrum for compound

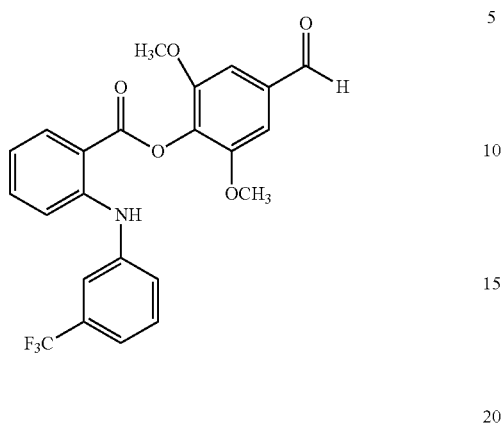

of Example 7.

Figure 208:
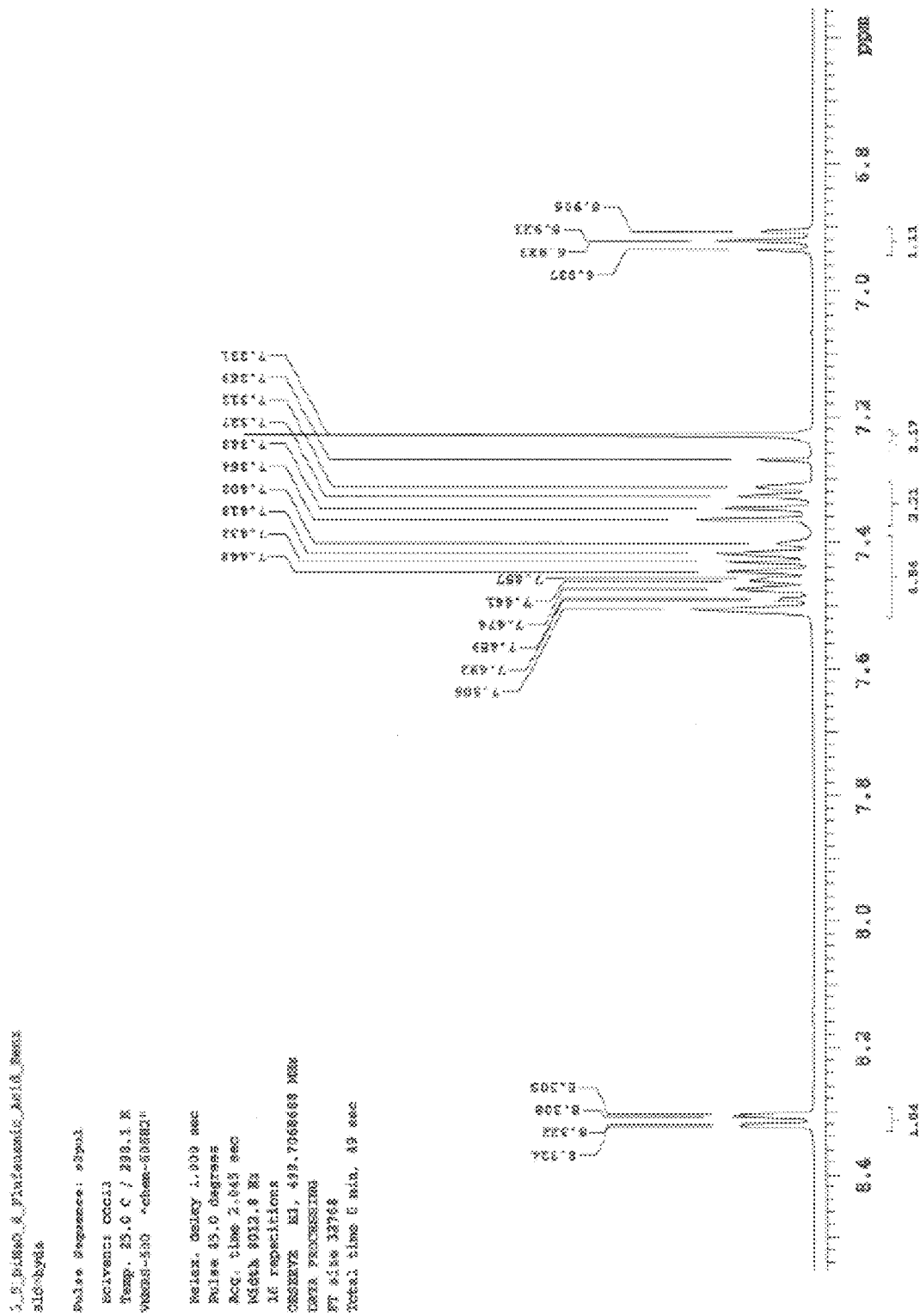

FIG. 208 is a representative NMR spectrum for compound

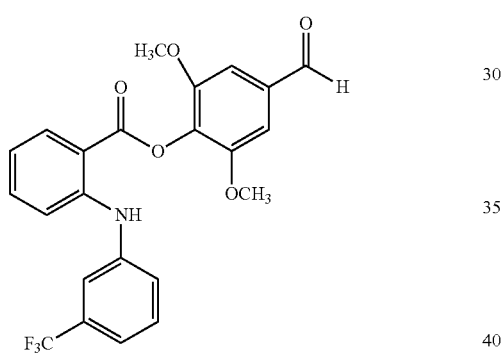

of Example 7.

Figure 209:
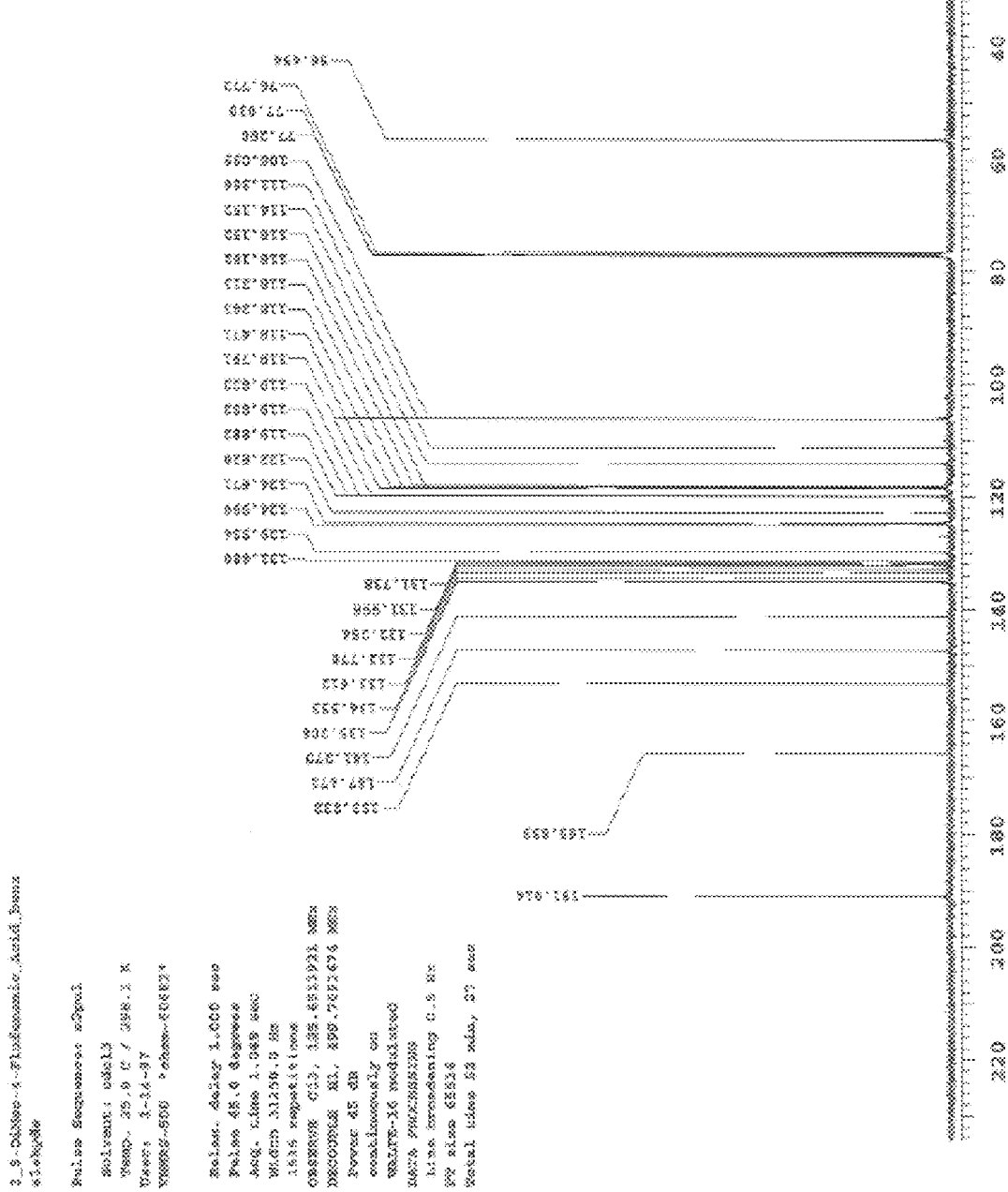

FIG. 209 is a representative NMR spectrum for compound

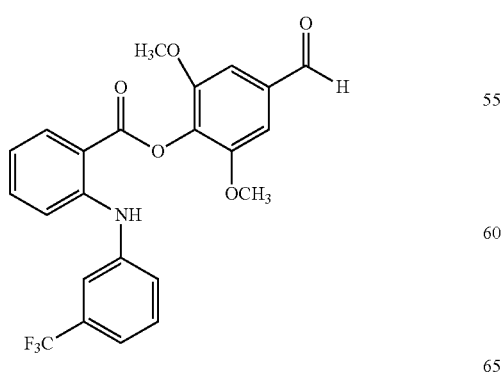

of Example 7.

Figure 210:
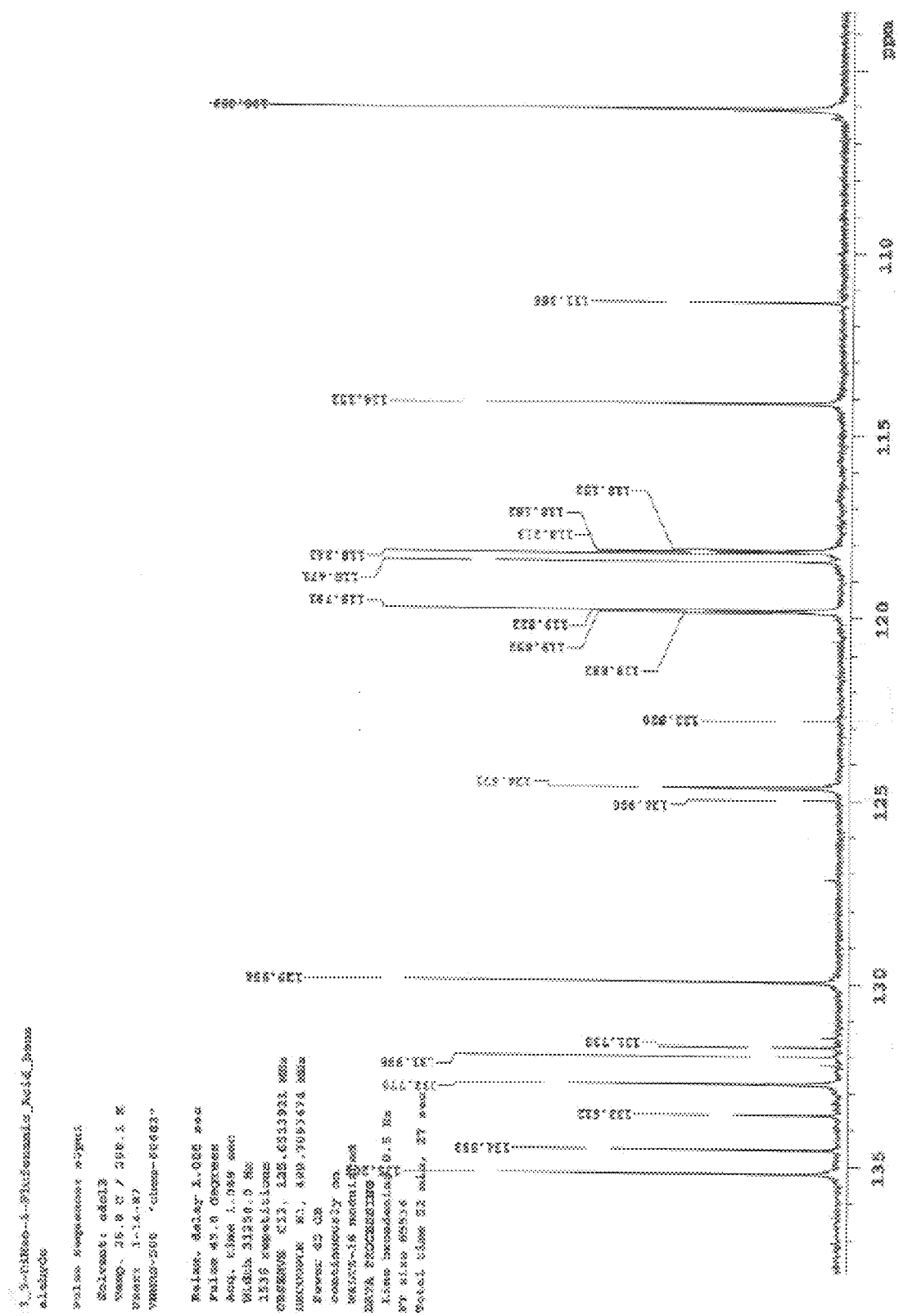

FIG. 210 is a representative NMR spectrum for compound

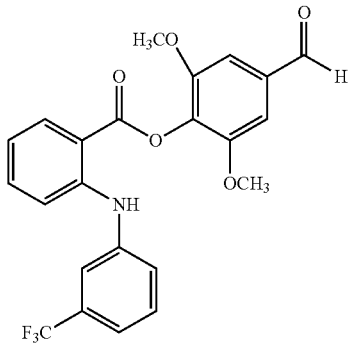 [SMILES: COc1cc(C=O)cc(OC)c1OC(=O)c1ccccc1Nc1cccc(C(F)(F)F)c1]

of Example 7.

Figure 211:
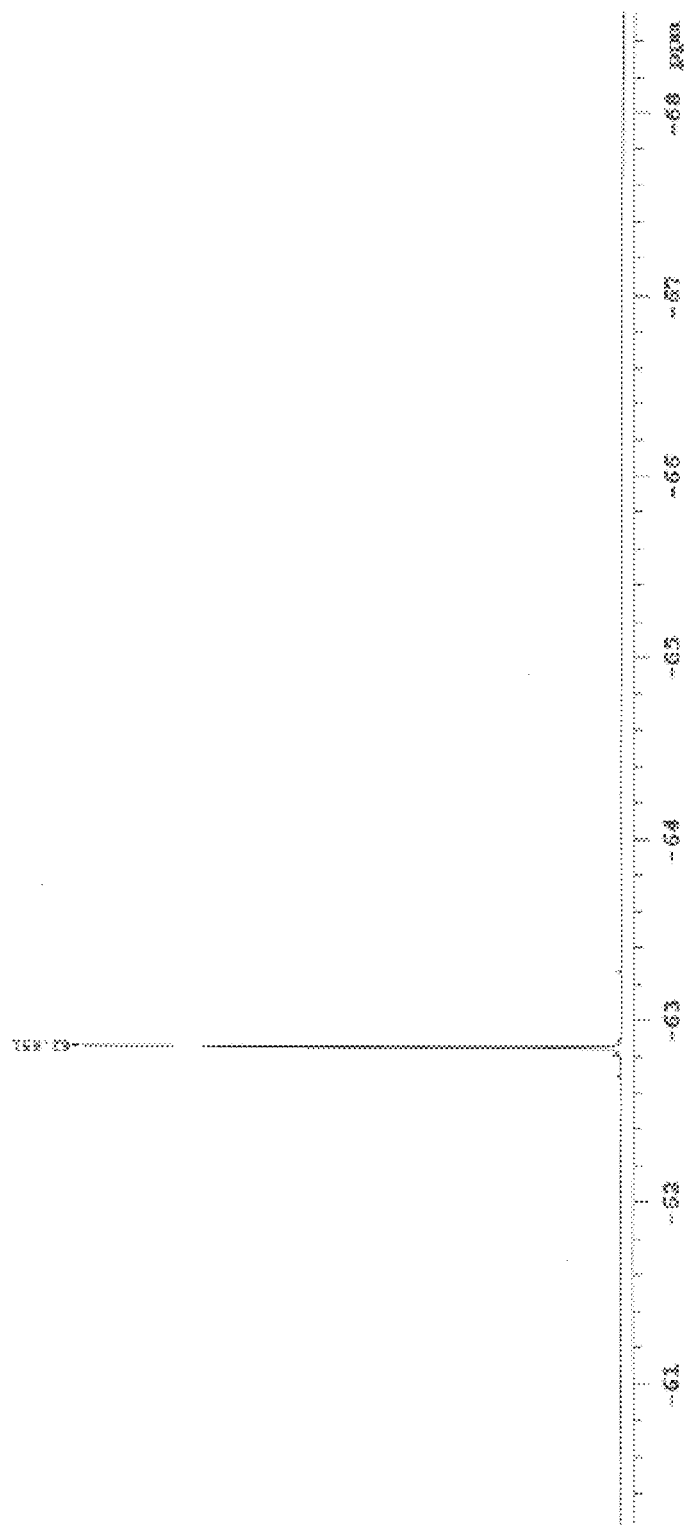

FIG. 211 is a representative NMR spectrum for compound

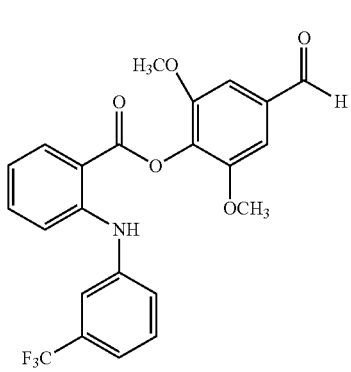 [SMILES: COc1cc(C=O)cc(OC)c1OC(=O)c1ccccc1Nc1cccc(C(F)(F)F)c1]

of Example 7.

Figure 212:
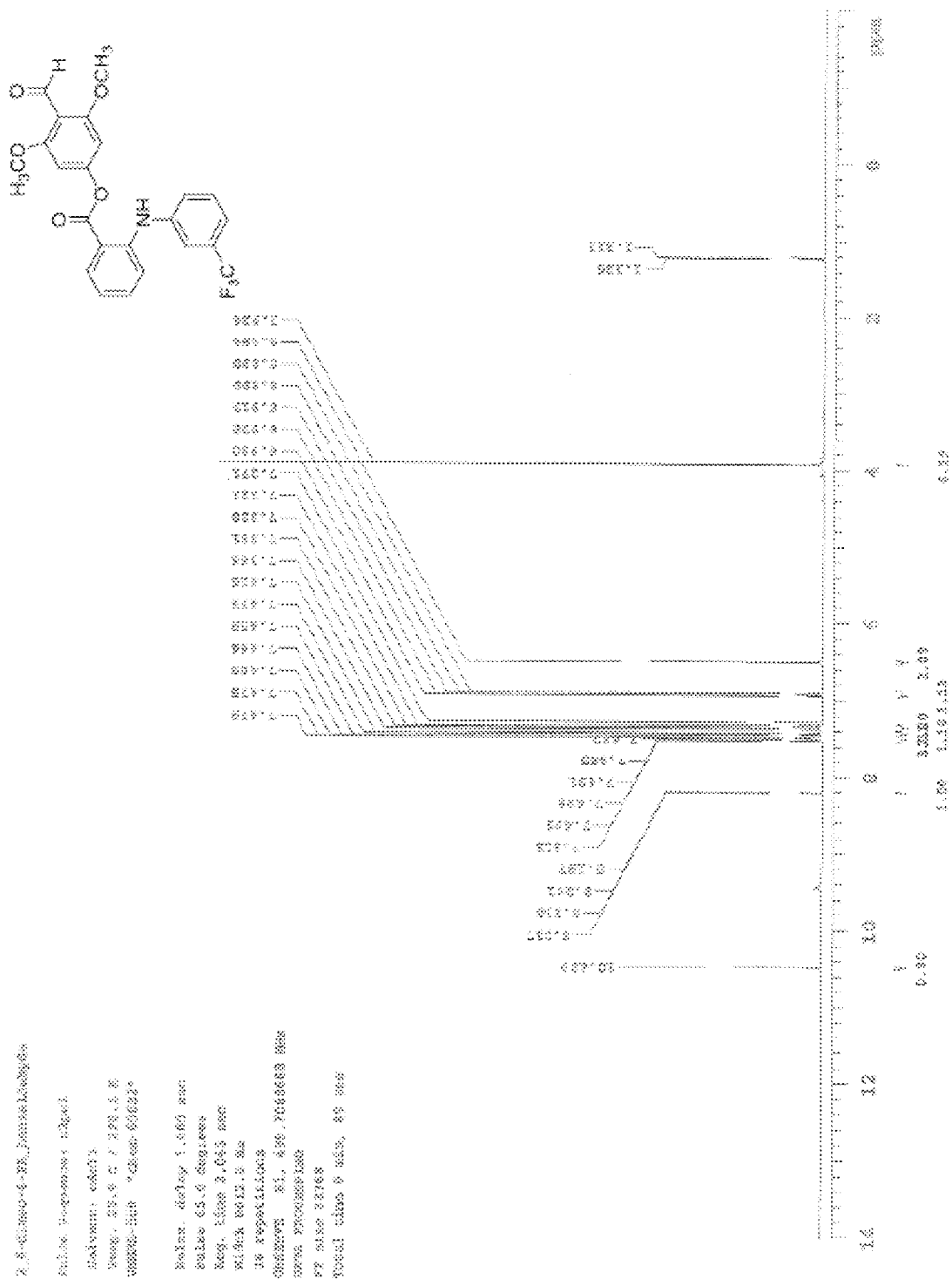

FIG. 212 is a representative NMR spectrum for compound

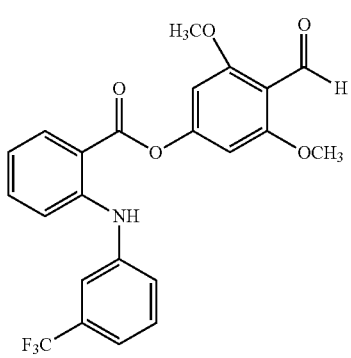 [SMILES: COc1cc(OC(=O)c2ccccc2Nc2cccc(C(F)(F)F)c2)cc(OC)c1C=O]

of Example 7.

Figure 213:
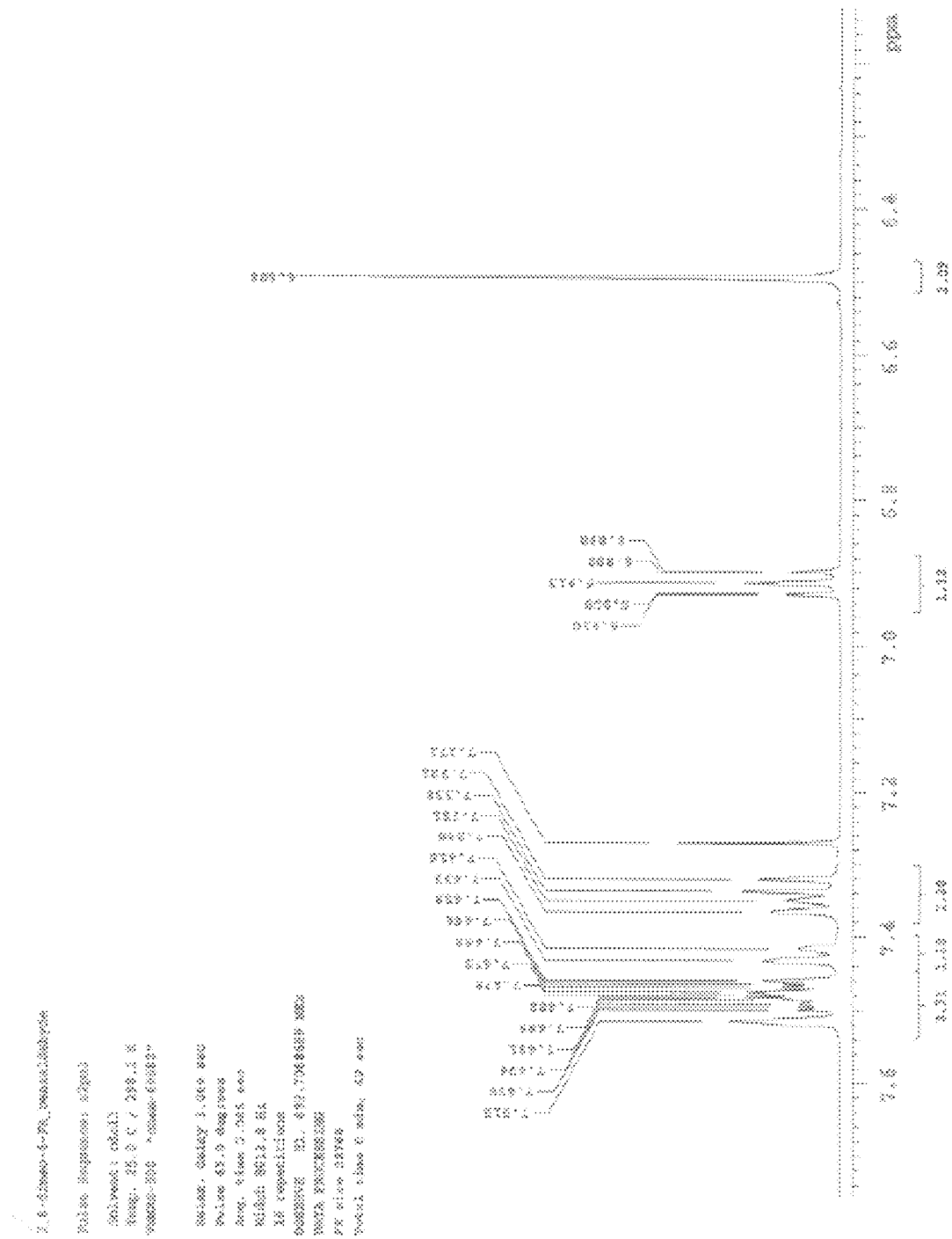

FIG. 213 is a representative NMR spectrum for compound

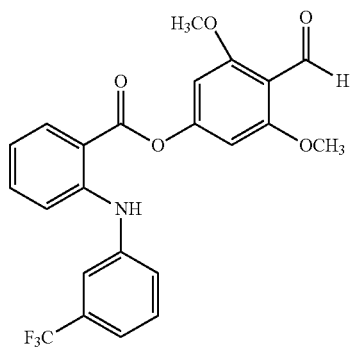 [SMILES: COc1cc(OC(=O)c2ccccc2Nc2cccc(C(F)(F)F)c2)cc(OC)c1C=O]

of Example 7.

Figure 214:
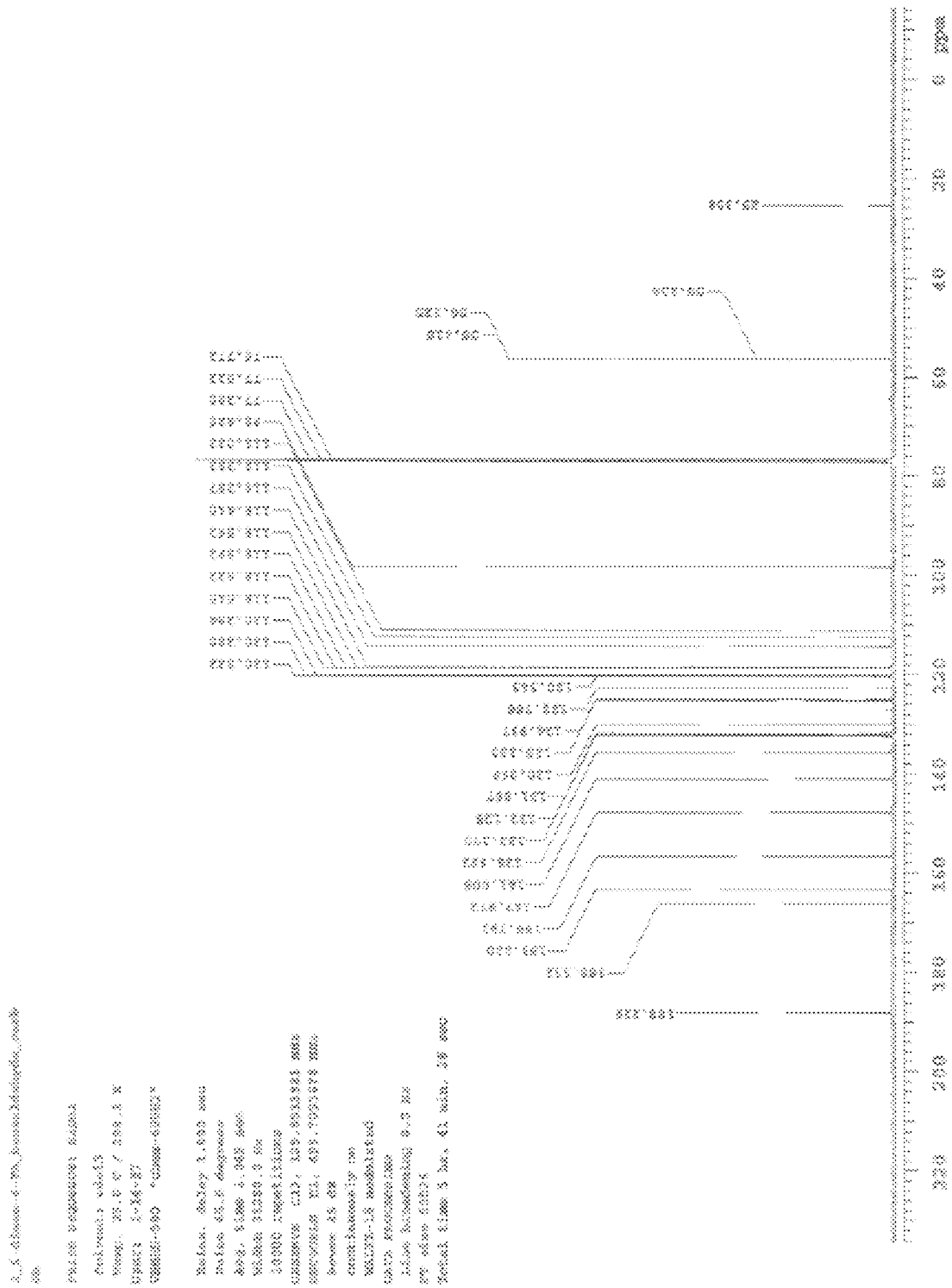

FIG. 214 is a representative NMR spectrum for compound

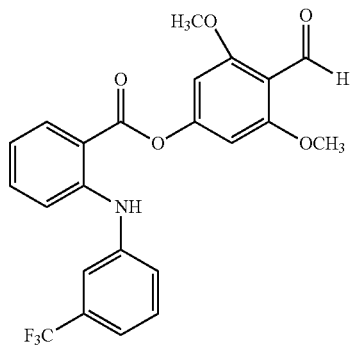 [SMILES: COc1cc(OC(=O)c2ccccc2Nc2cccc(C(F)(F)F)c2)cc(OC)c1C=O]

of Example 7.

Figure 215:
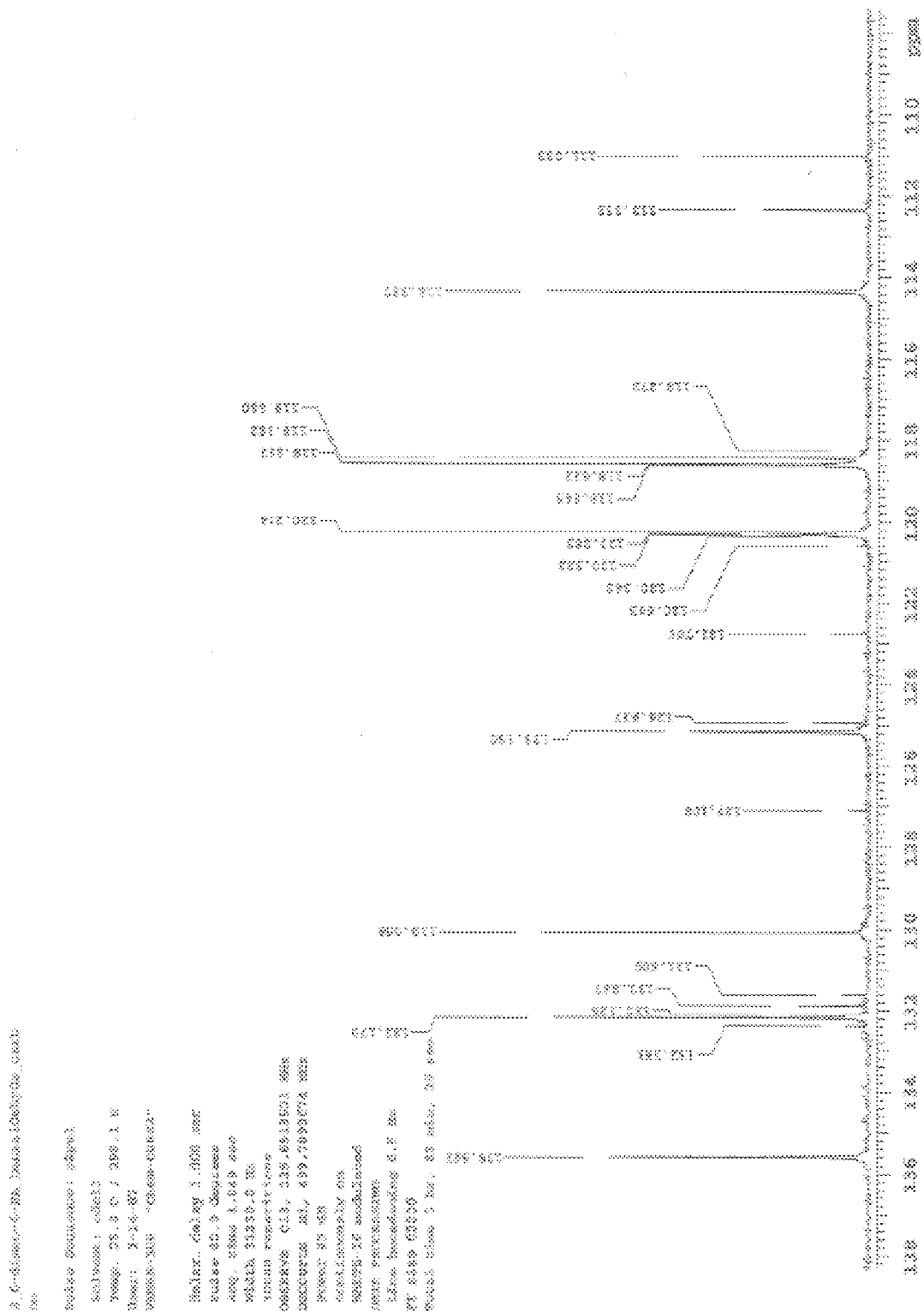

FIG. 215 is a representative NMR spectrum for compound

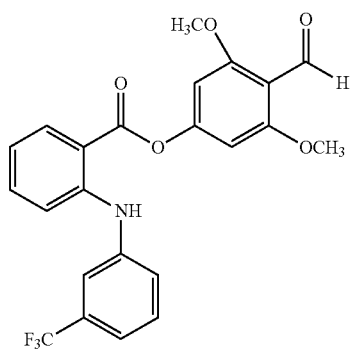 [SMILES: COc1cc(OC(=O)c2ccccc2Nc2cccc(C(F)(F)F)c2)cc(OC)c1C=O]

of Example 7.

Figure 216:
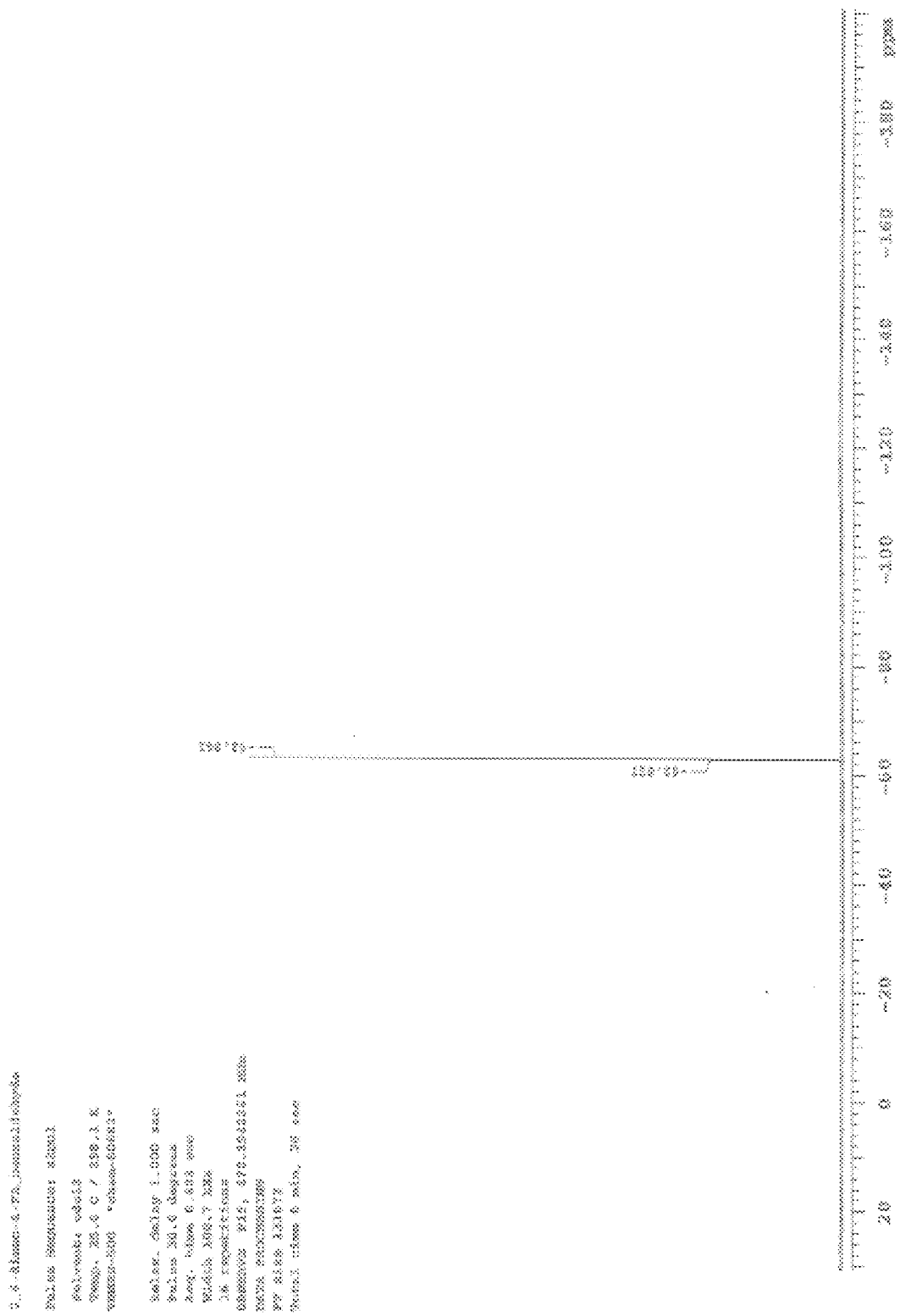

FIG. 216 is a representative NMR spectrum for compound

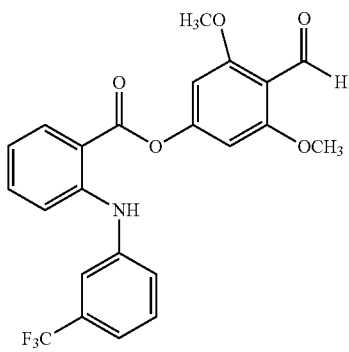 [SMILES: COc1cc(OC(=O)c2ccccc2Nc2cccc(C(F)(F)F)c2)cc(OC)c1C=O]

of Example 7.

Figure 217:
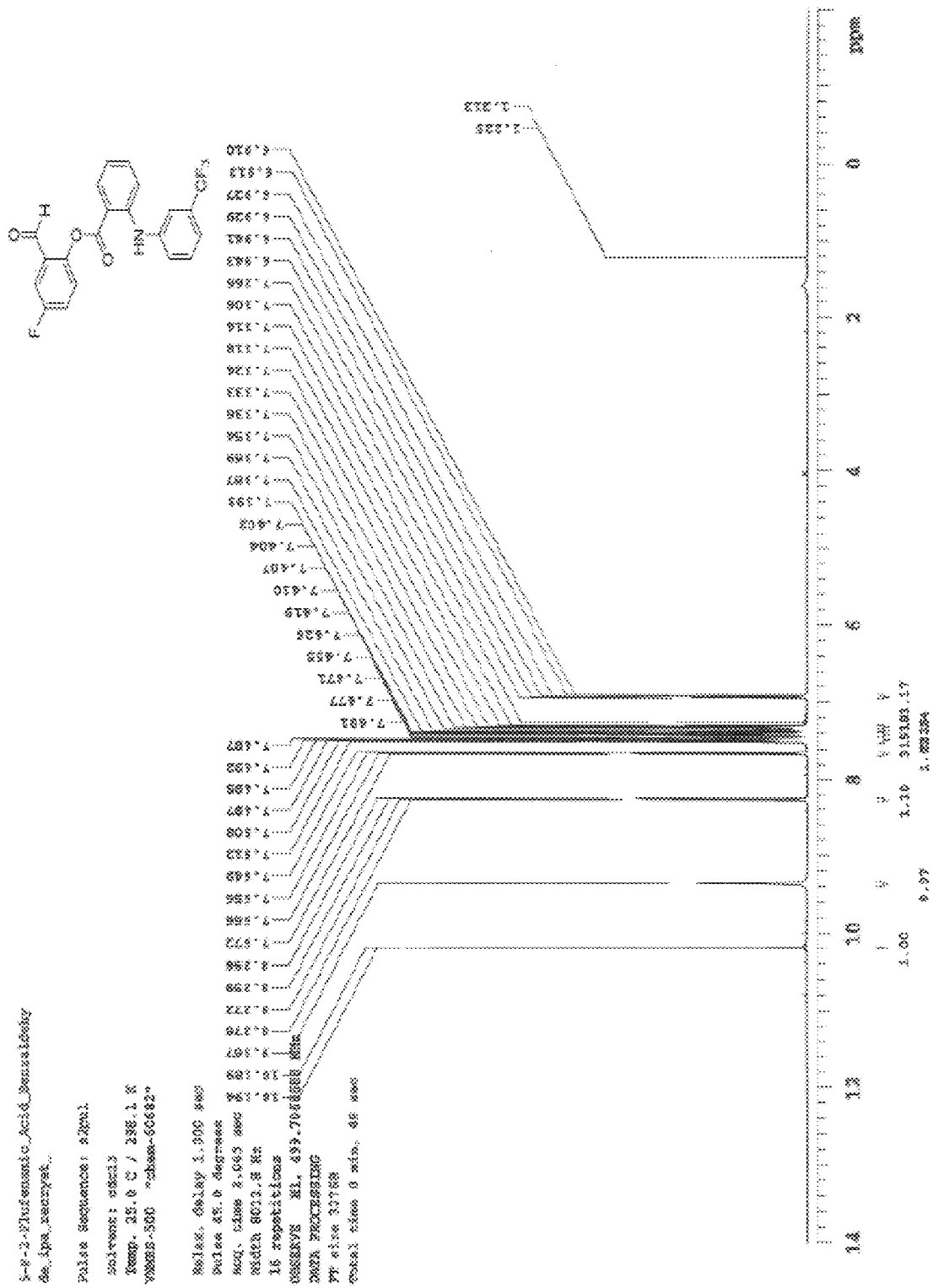

FIG. 217 is a representative NMR spectrum for compound

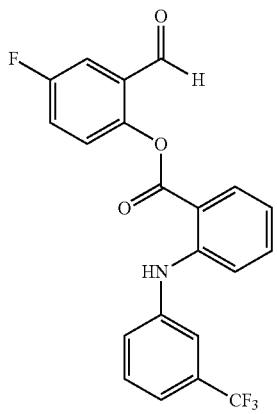 [SMILES: O=Cc1cc(F)ccc1OC(=O)c1ccccc1Nc1cccc(C(F)(F)F)c1]

of Example 7.

Figure 218:
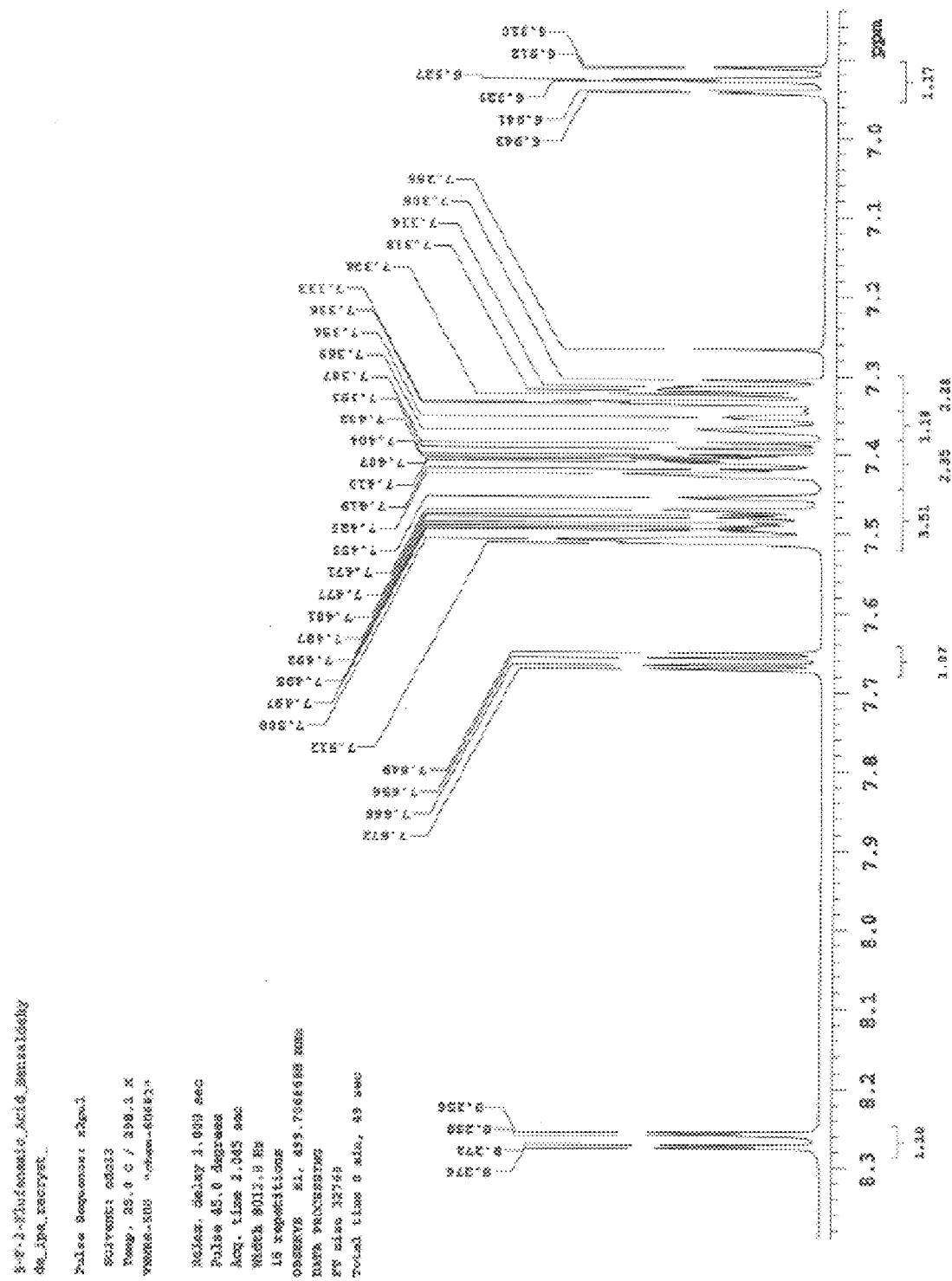

FIG. 218 is a representative NMR spectrum for compound

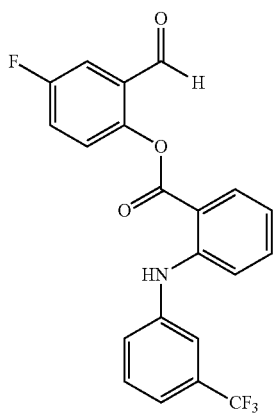 [SMILES: O=Cc1cc(F)ccc1OC(=O)c1ccccc1Nc1cccc(C(F)(F)F)c1]

of Example 7.

Figure 219:
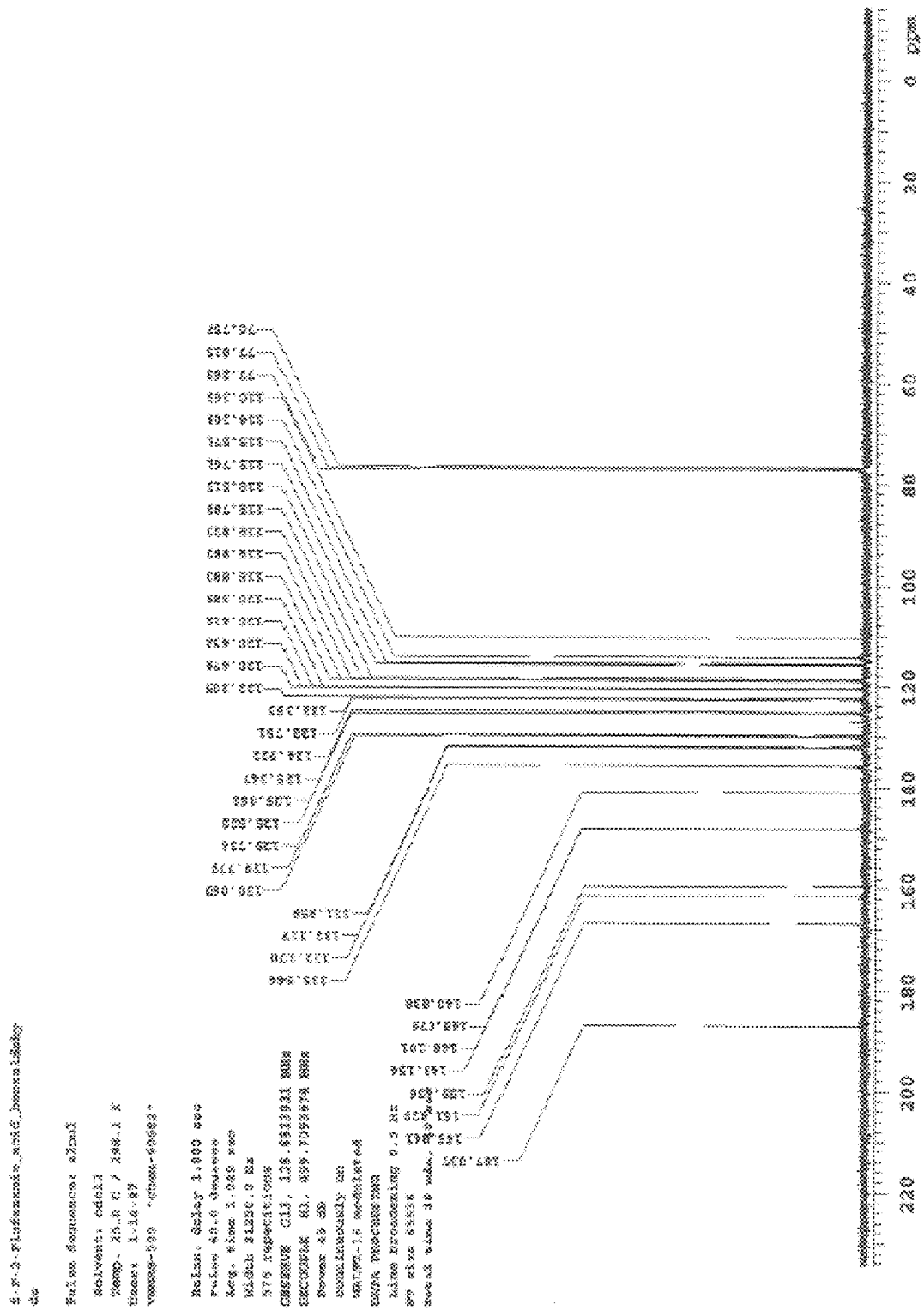

FIG. 219 is a representative NMR spectrum for compound

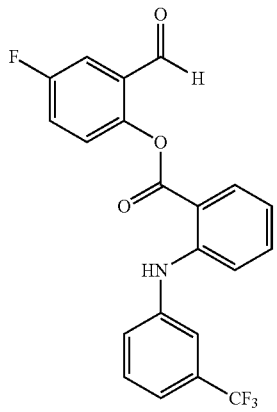 [SMILES: O=Cc1cc(F)ccc1OC(=O)c1ccccc1Nc1cccc(C(F)(F)F)c1]

of Example 7.

Figure 220:
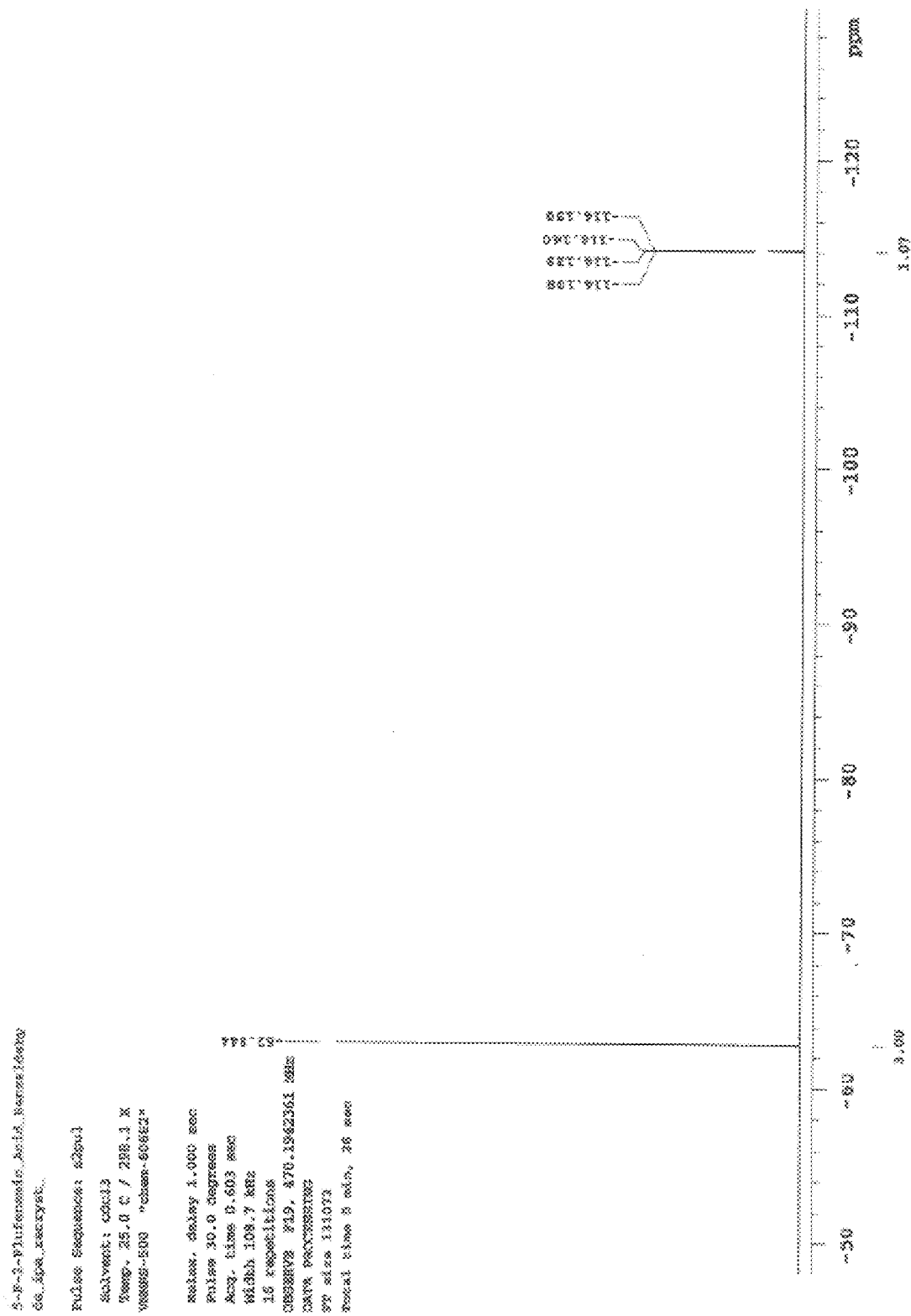
Figure 22I:
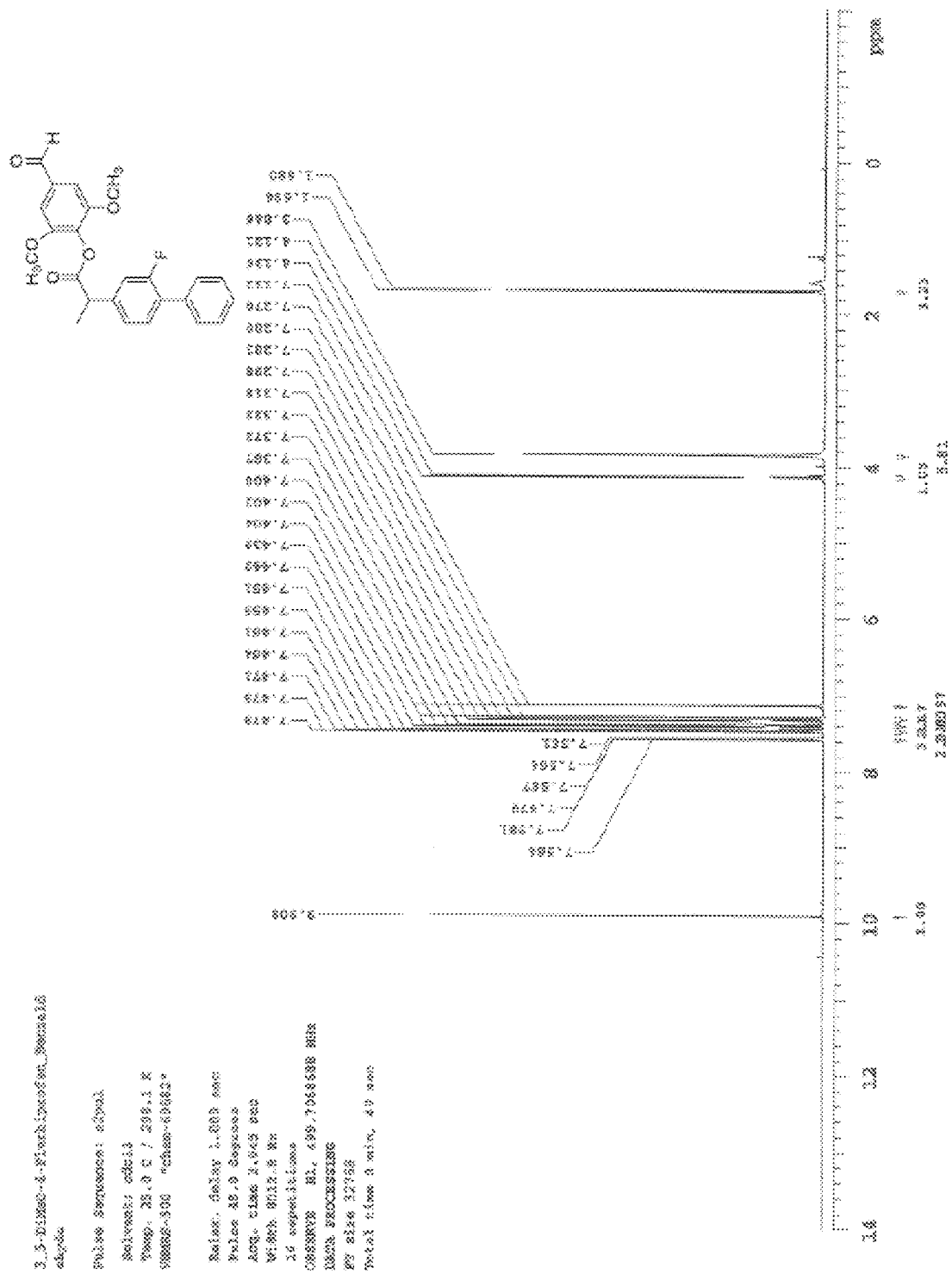

FIG. 220 is a representative NMR spectrum for compound

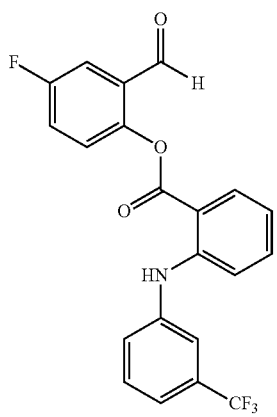 [SMILES: O=Cc1cc(F)ccc1OC(=O)c1ccccc1Nc1cccc(C(F)(F)F)c1]

of Example 7.

FIG. 221 is a representative NMR spectrum for compound

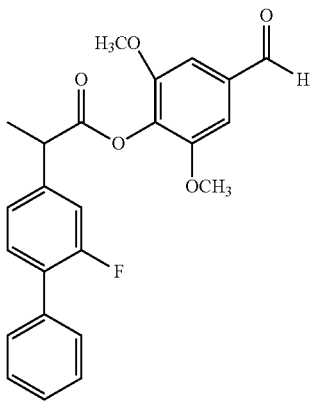 [SMILES: COc1cc(C=O)cc(OC)c1OC(=O)C(C)c1ccc(-c2ccccc2)c(F)c1]

of Example 7.

Figure 222:
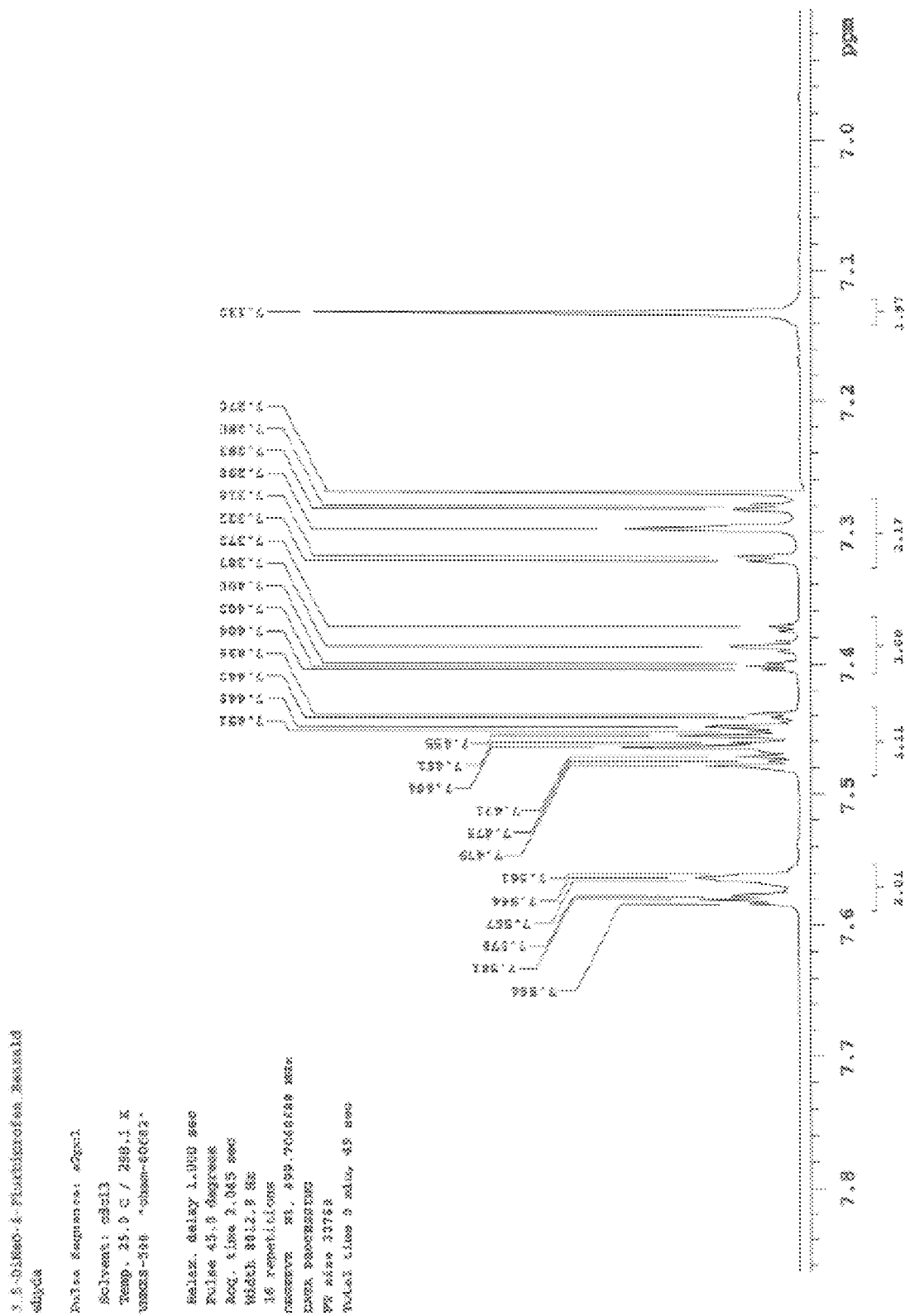

FIG. 222 is a representative NMR spectrum for compound

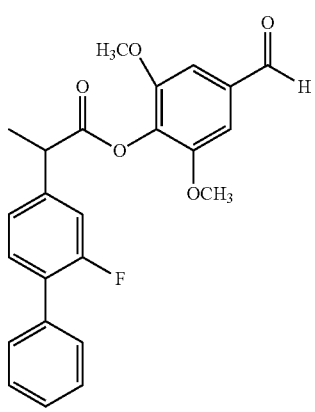 [SMILES: COc1cc(C=O)cc(OC)c1OC(=O)C(C)c1ccc(-c2ccccc2)c(F)c1]

of Example 7.

Figure 223:
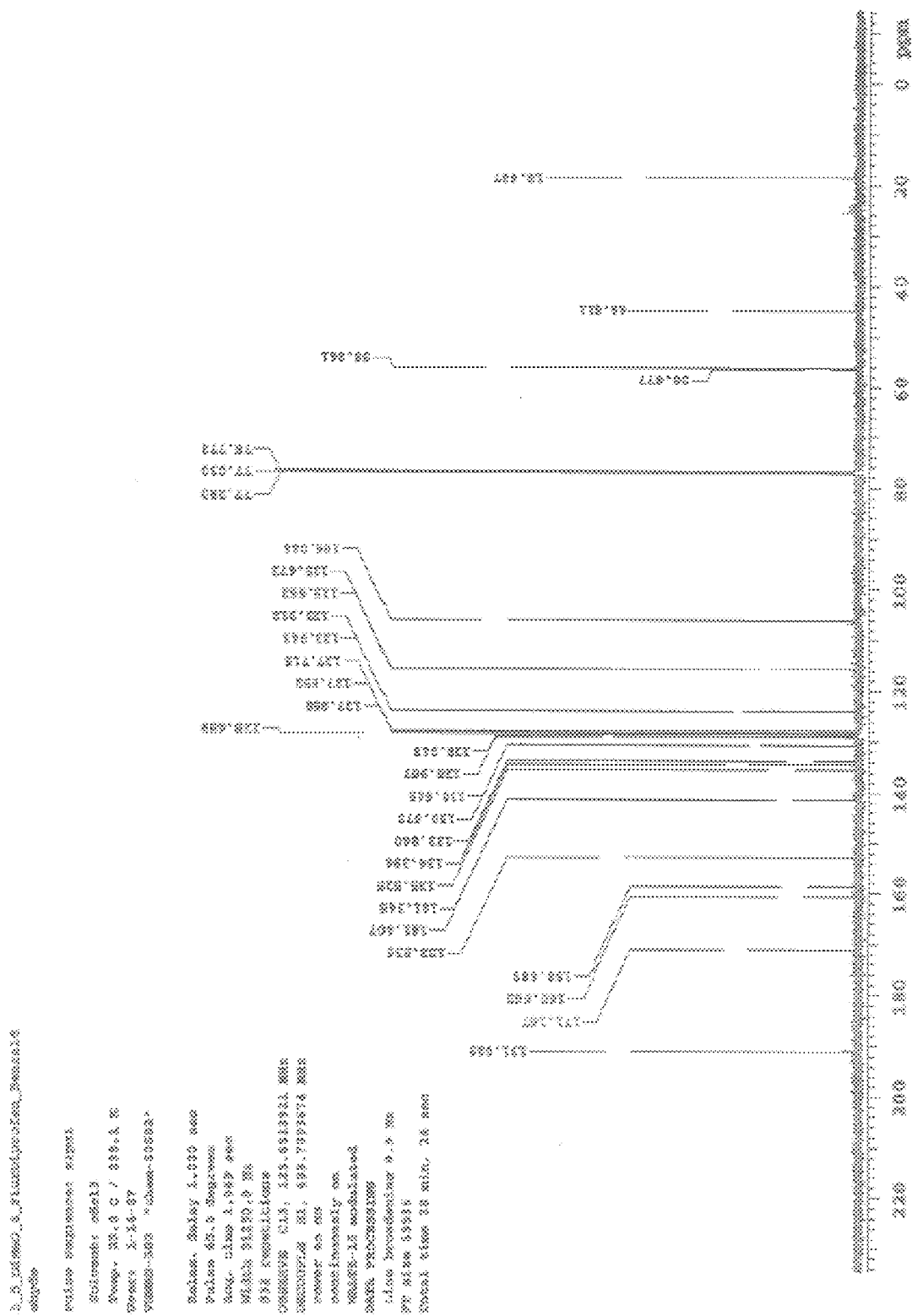

FIG. 223 is a representative NMR spectrum for compound

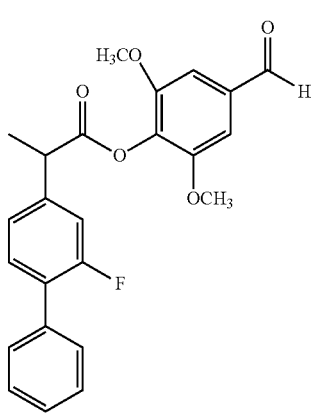 [SMILES: COc1cc(C=O)cc(OC)c1OC(=O)C(C)c1ccc(-c2ccccc2)c(F)c1]

of Example 7.

Figure 224:
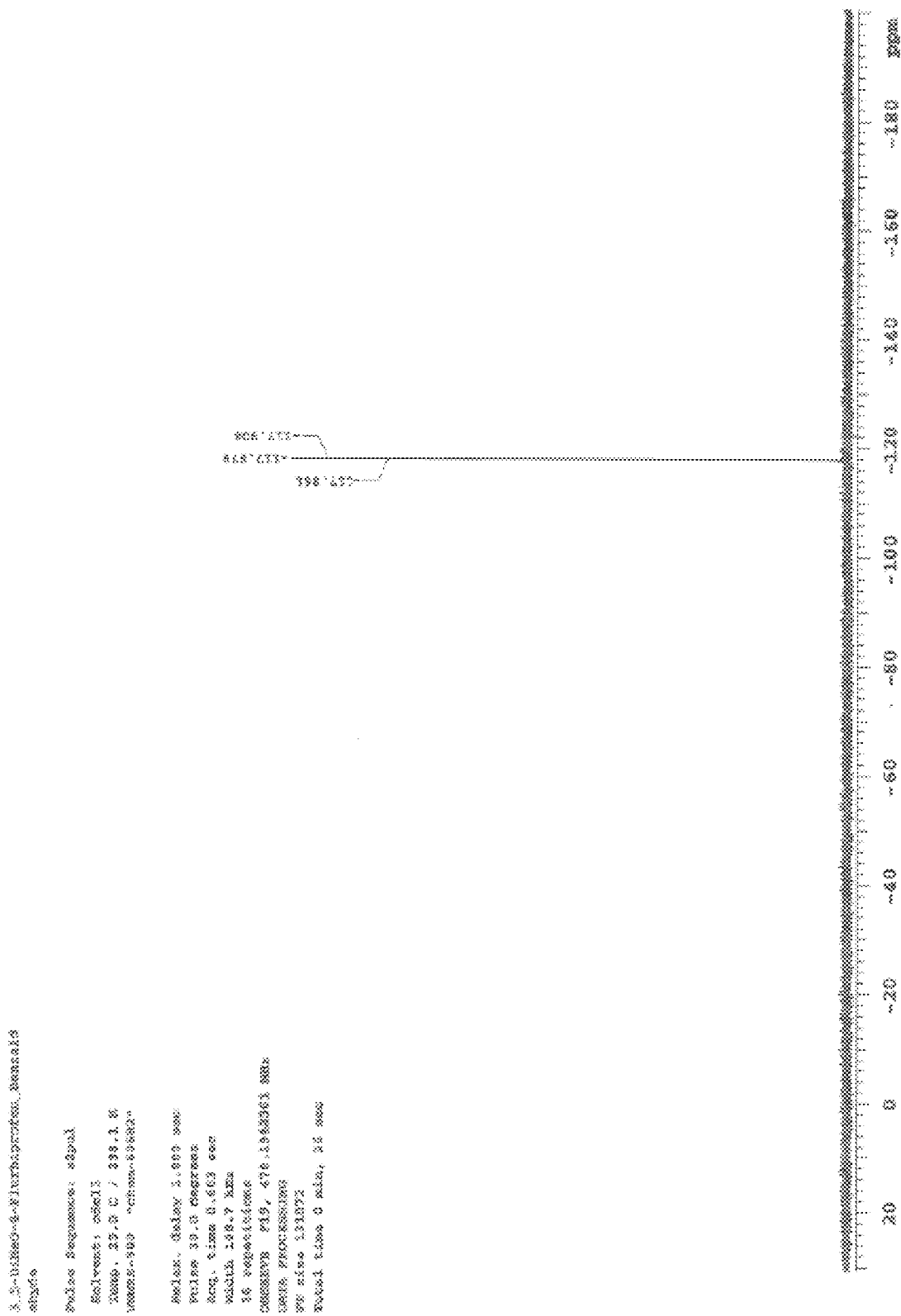

FIG. 224 is a representative NMR spectrum for compound

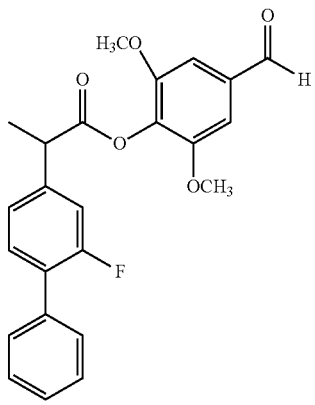 [SMILES: COc1cc(C=O)cc(OC)c1OC(=O)C(C)c1ccc(-c2ccccc2)c(F)c1]

of Example 7.

Figure 225:
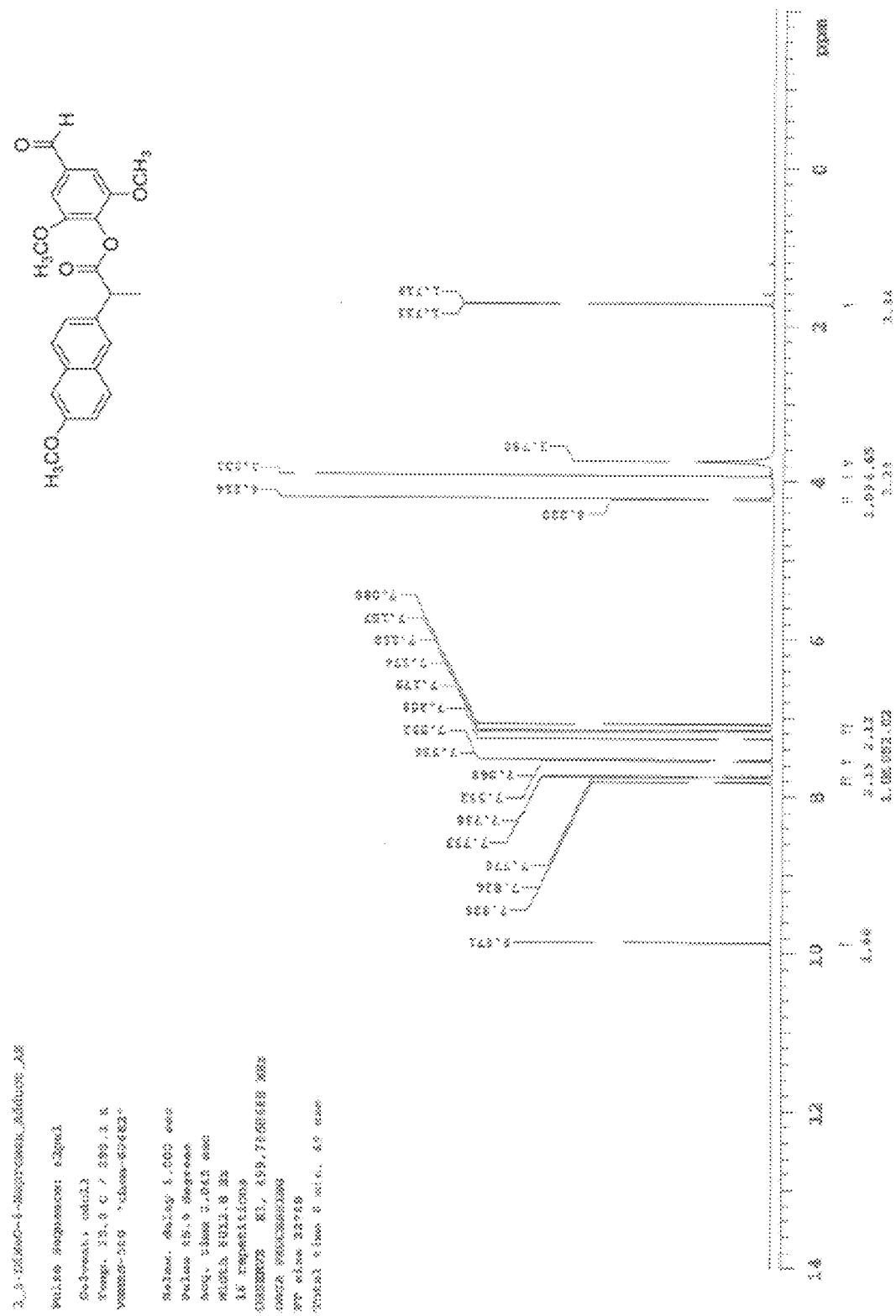

FIG. 225 is a representative NMR spectrum for compound

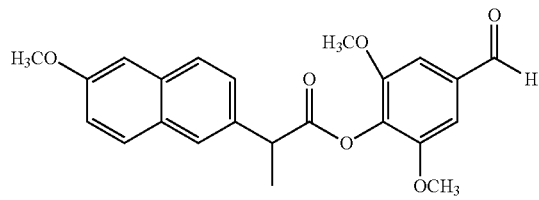 [SMILES: COc1ccc2cc(C(C)C(=O)Oc3c(OC)cc(C=O)cc3OC)ccc2c1]

of Example 7.

Figure 226:
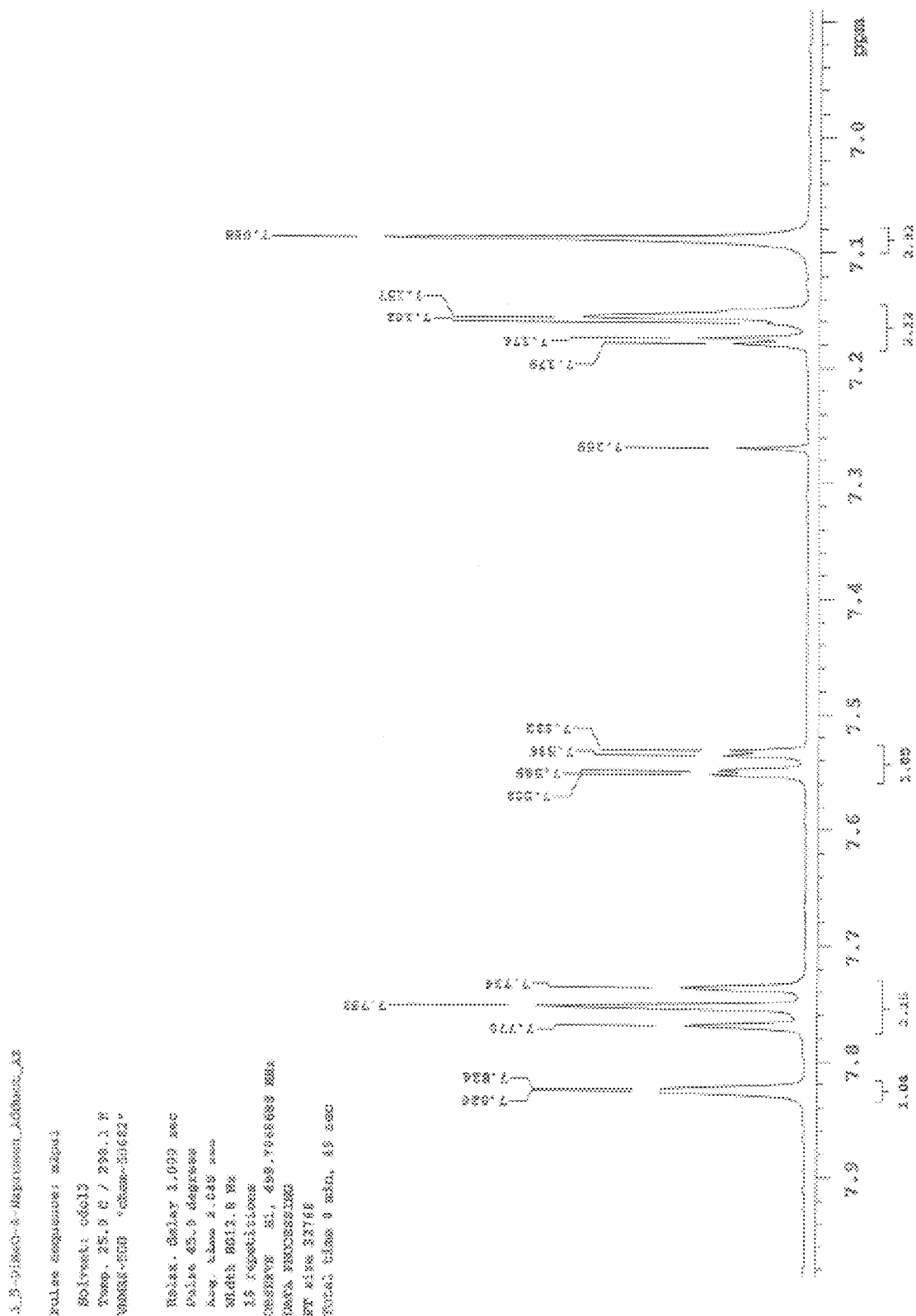

FIG. 226 is a representative NMR spectrum for compound

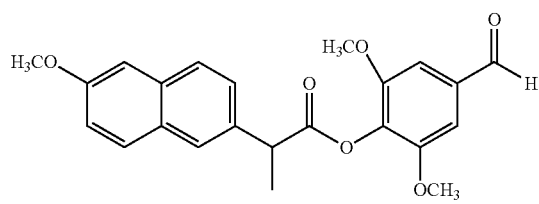 [SMILES: COc1ccc2cc(C(C)C(=O)Oc3c(OC)cc(C=O)cc3OC)ccc2c1]

of Example 7.

Figure 227:
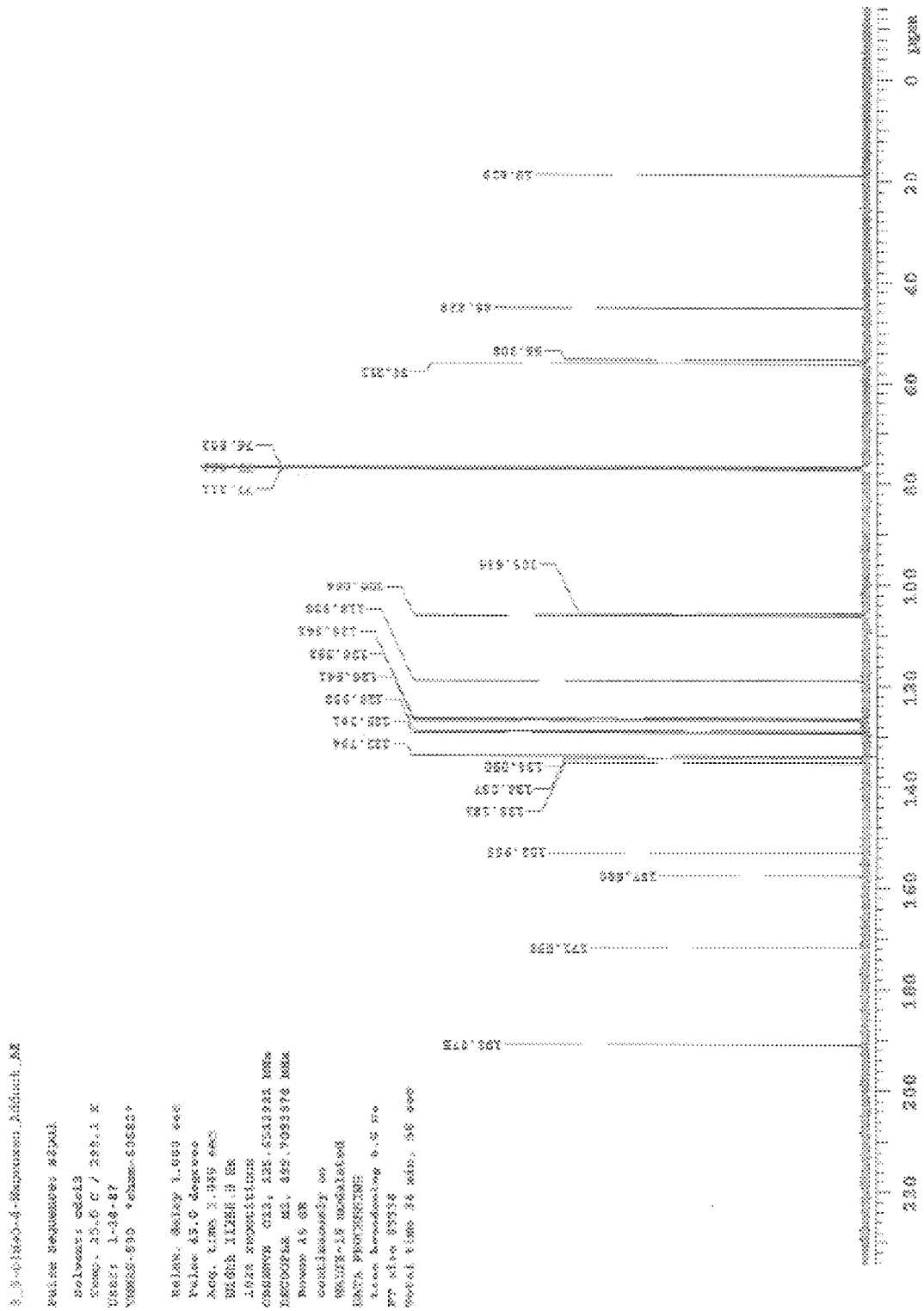

FIG. 227 is a representative NMR spectrum for compound

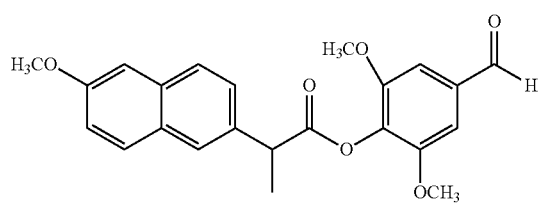 [SMILES: COc1ccc2cc(C(C)C(=O)Oc3c(OC)cc(C=O)cc3OC)ccc2c1]

of Example 7.

FIG. 228 is a representative NMR spectrum for compound

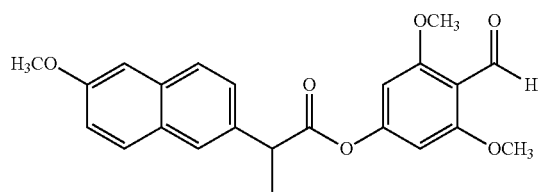 [SMILES: COc1ccc2cc(C(C)C(=O)Oc3cc(OC)c(C=O)c(OC)c3)ccc2c1]

of Example 7.

Figure 229:
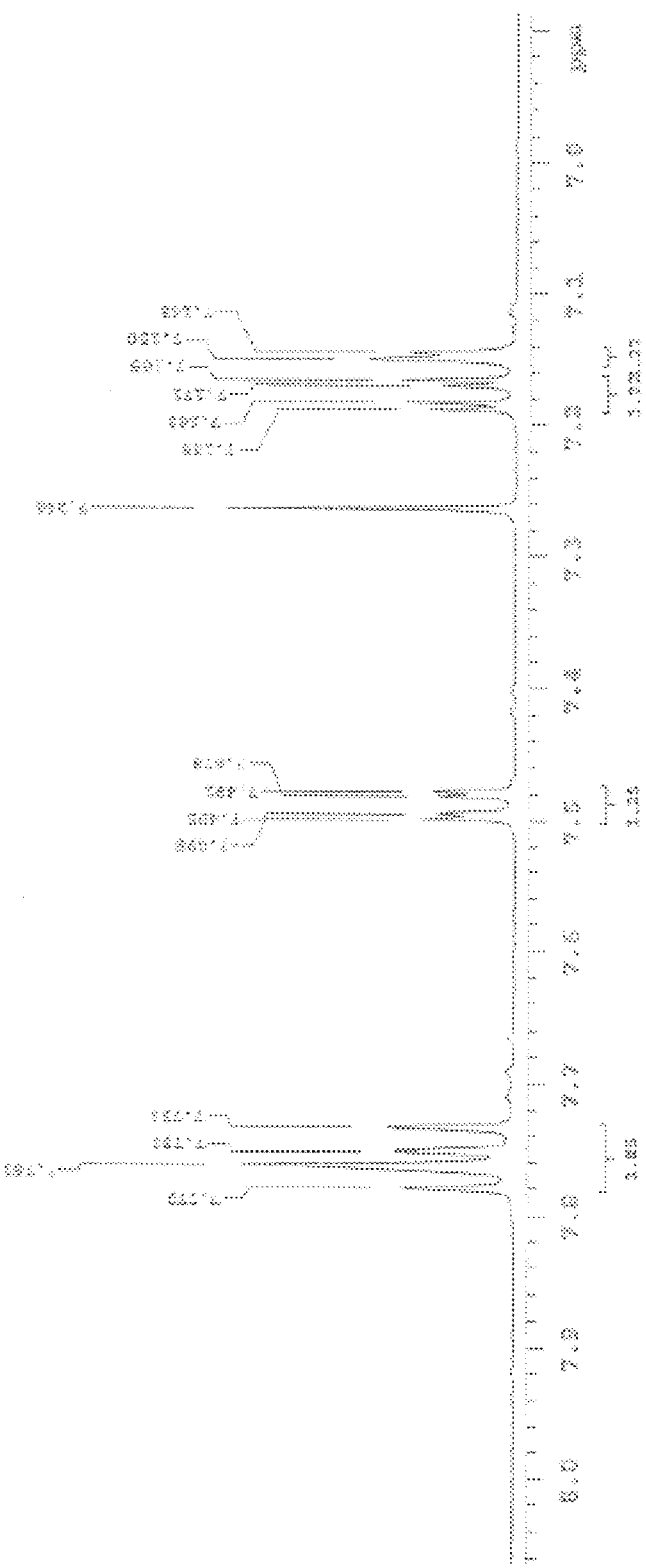

FIG. 229 is a representative NMR spectrum for compound

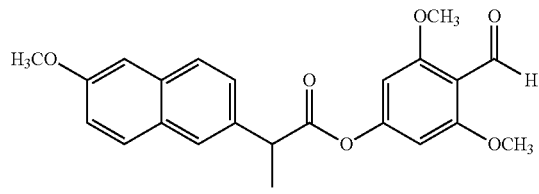 [SMILES: COc1ccc2cc(C(C)C(=O)Oc3cc(OC)c(C=O)c(OC)c3)ccc2c1]

of Example 7.

Figure 230:
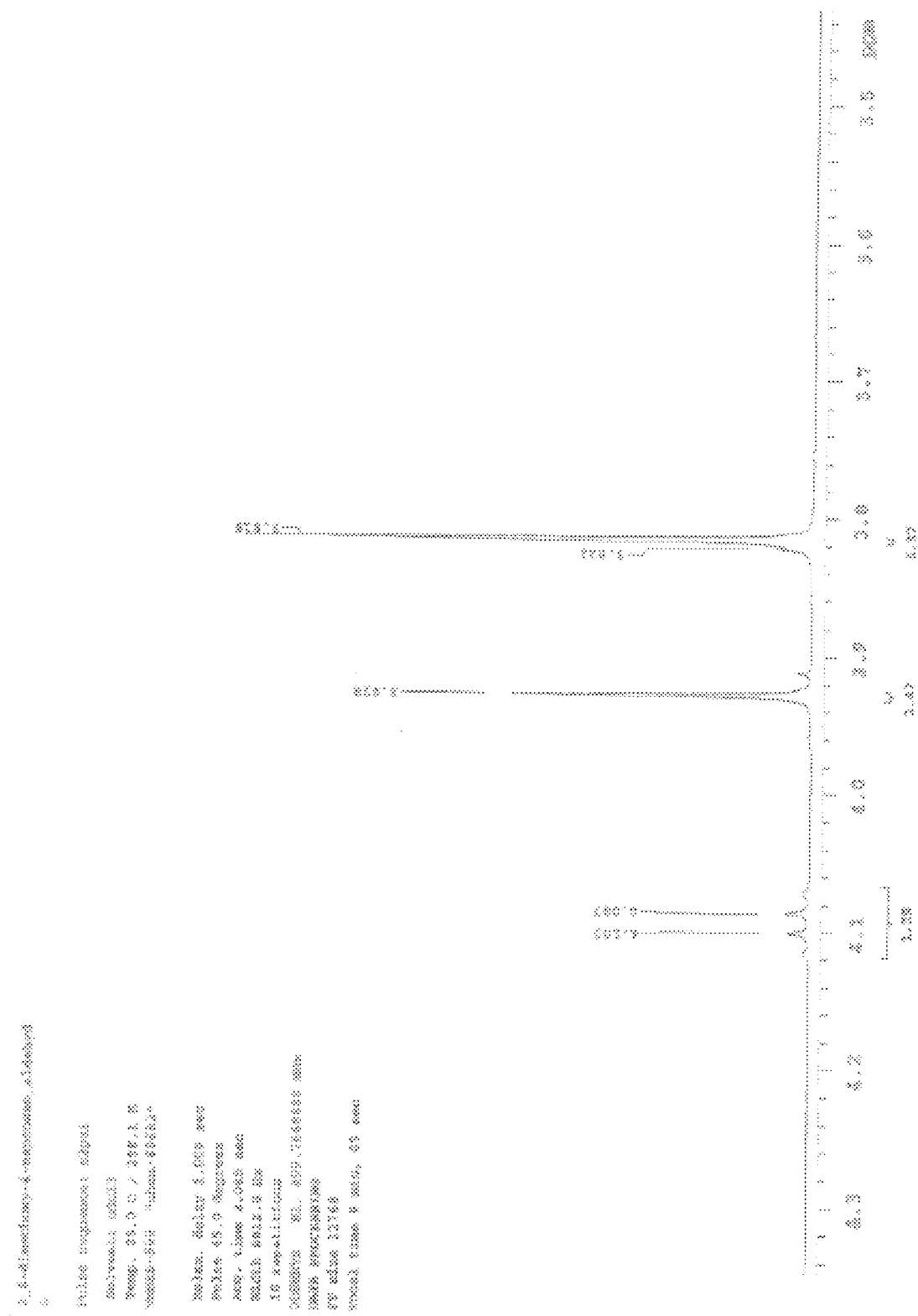

FIG. 230 is a representative NMR spectrum for compound

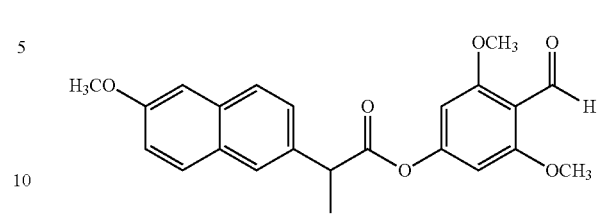

of Example 7.

Figure 231:
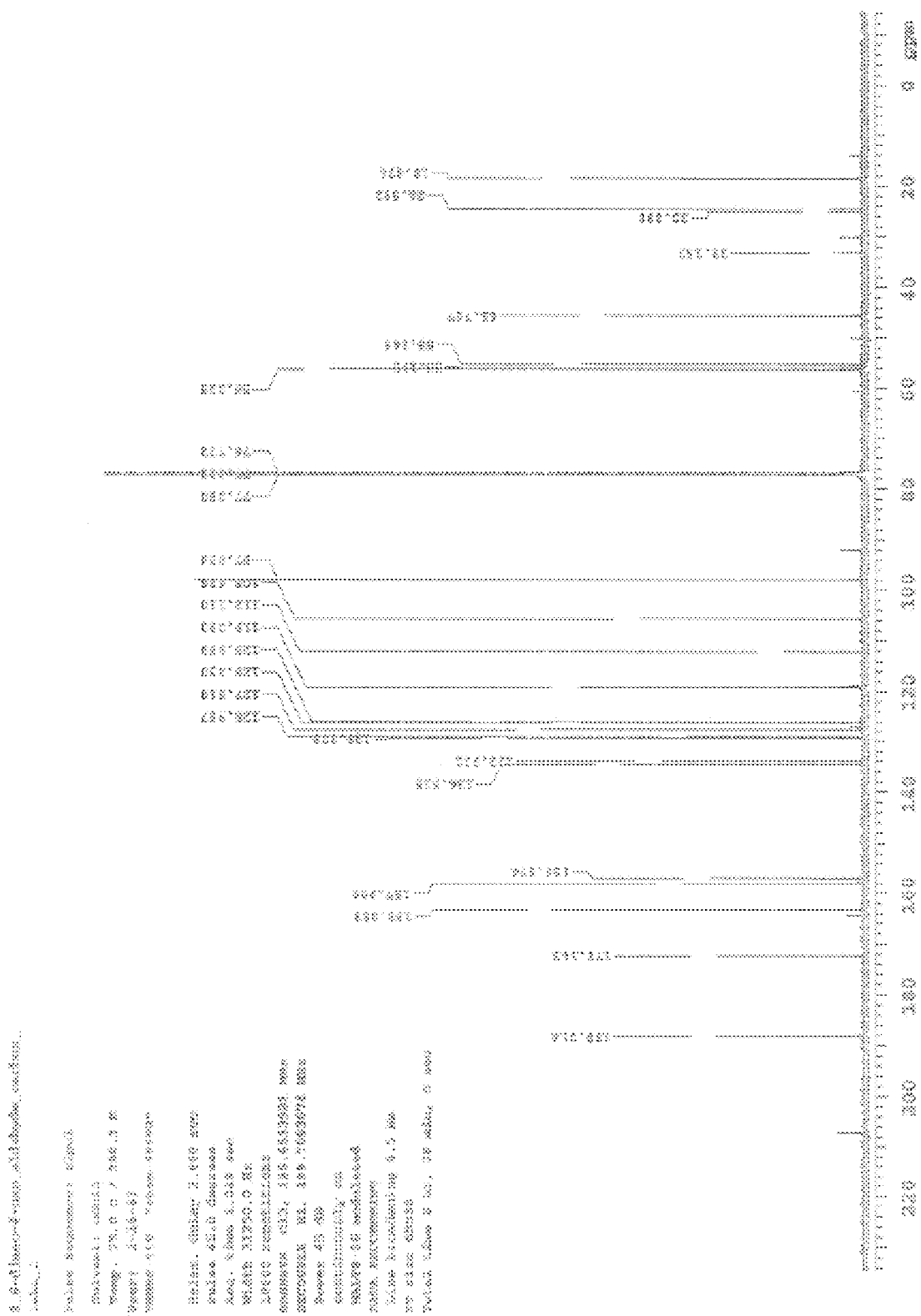

FIG. 231 is a representative NMR spectrum for compound

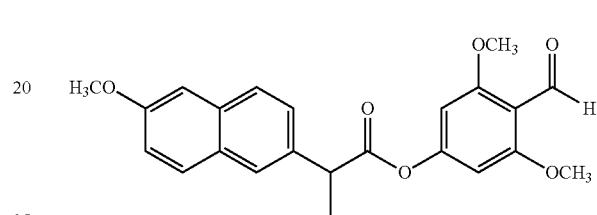

of Example 7.

Figure 232:
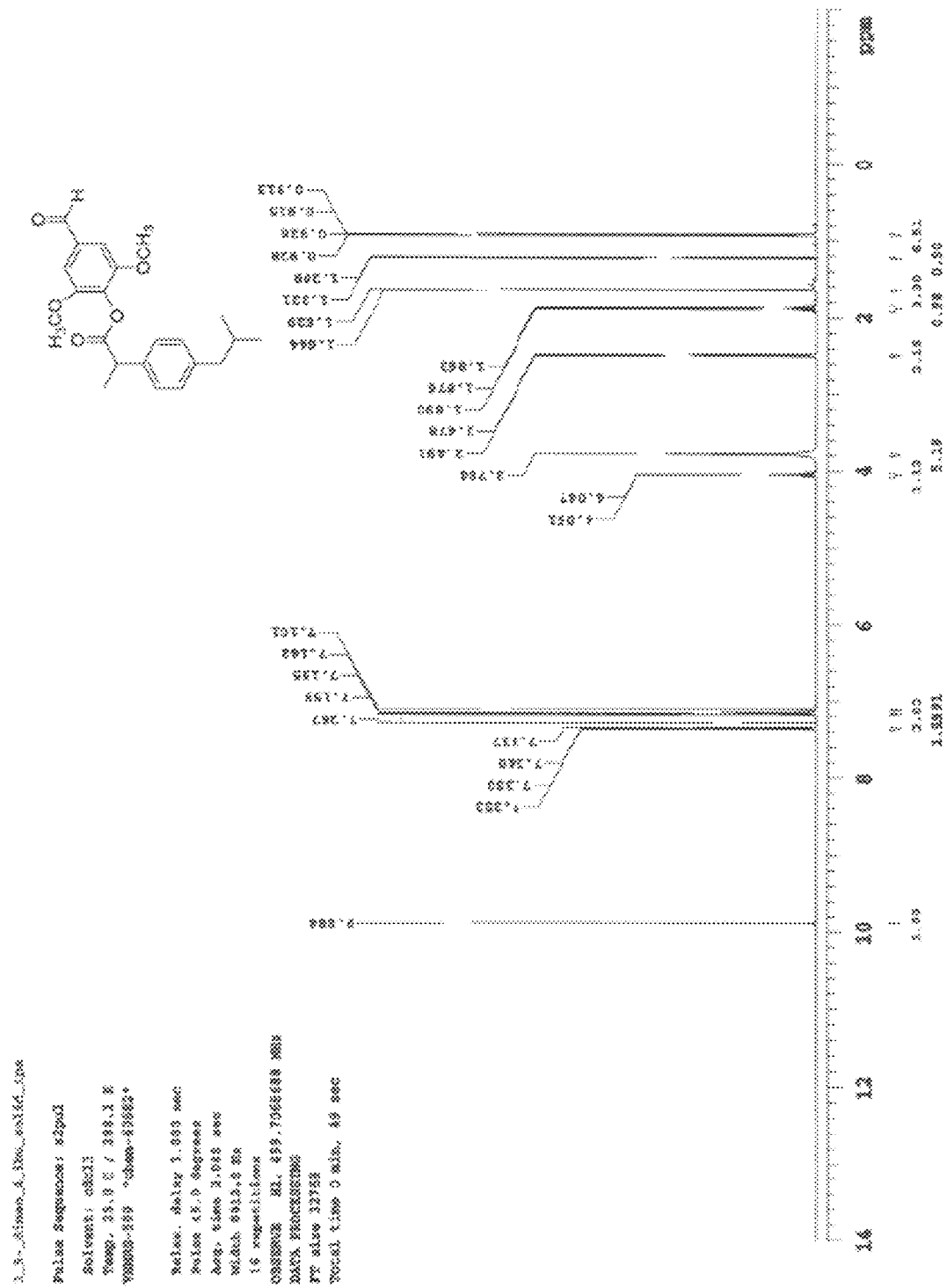

FIG. 232 is a representative NMR spectrum for compound

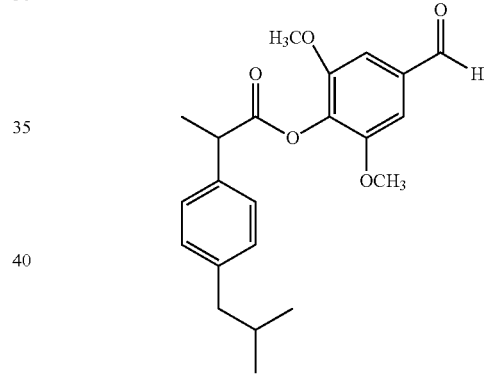

of Example 7.

Figure 233:
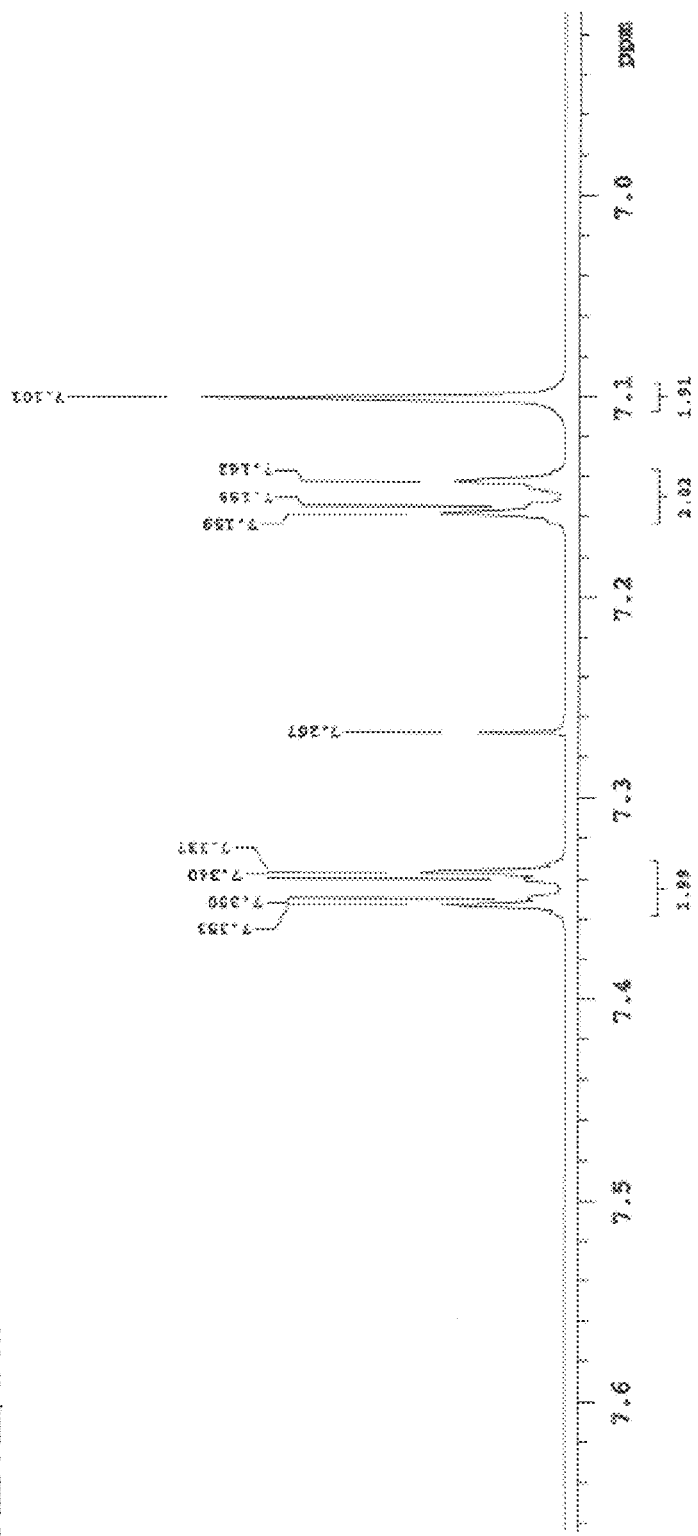

FIG. 233 is a representative NMR spectrum for compound

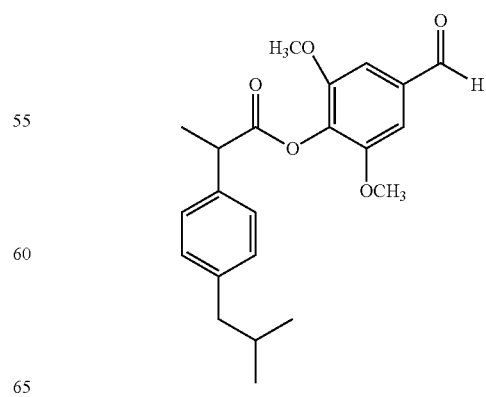

of Example 7.

Figure 234:
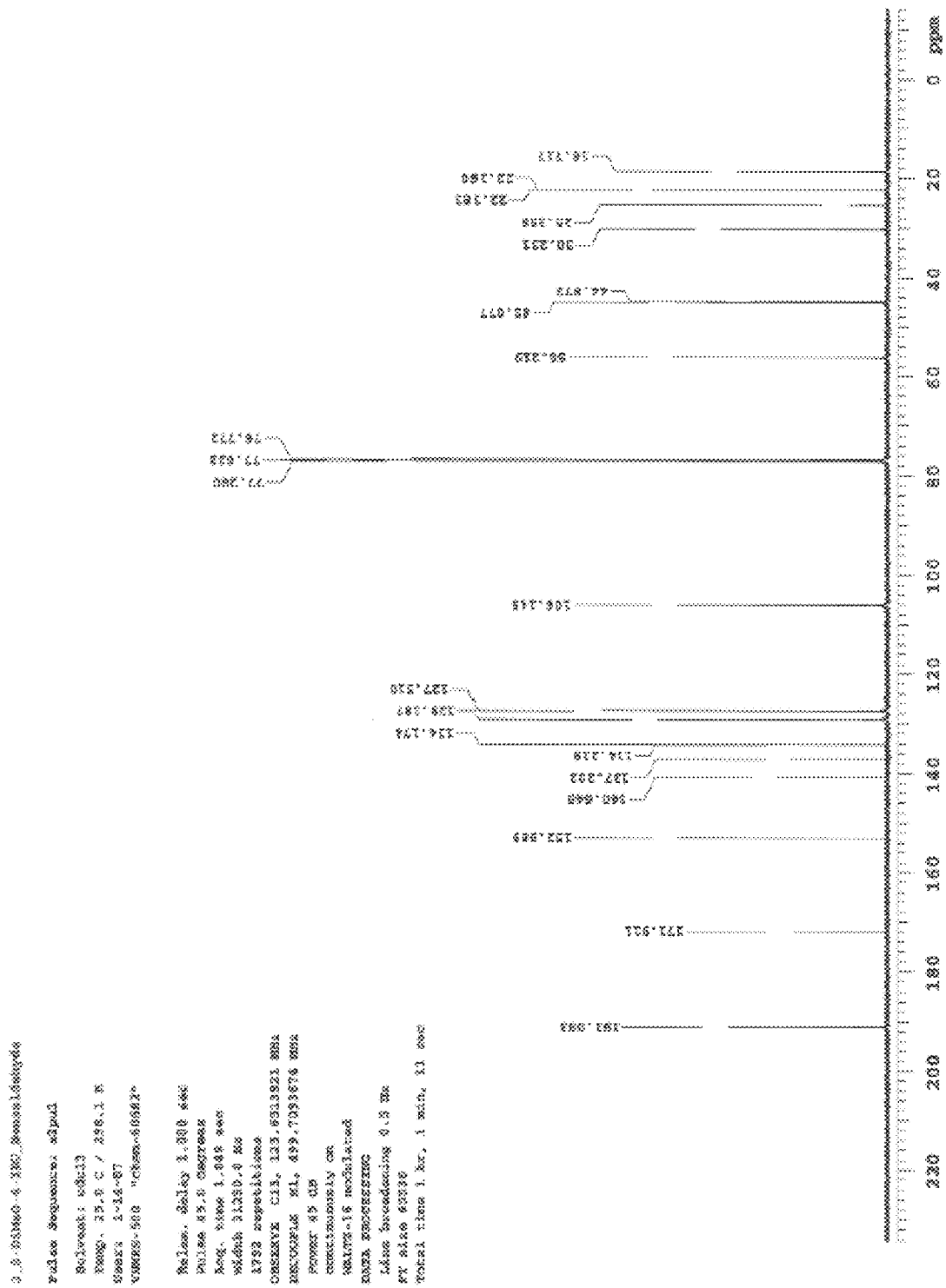

FIG. 234 is a representative NMR spectrum for compound

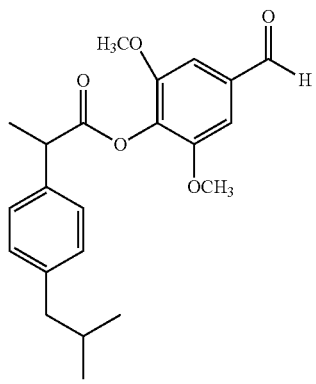 [SMILES: COc1cc(C=O)cc(OC)c1OC(=O)C(C)c1ccc(CC(C)C)cc1]

of Example 7.

Figure 235:
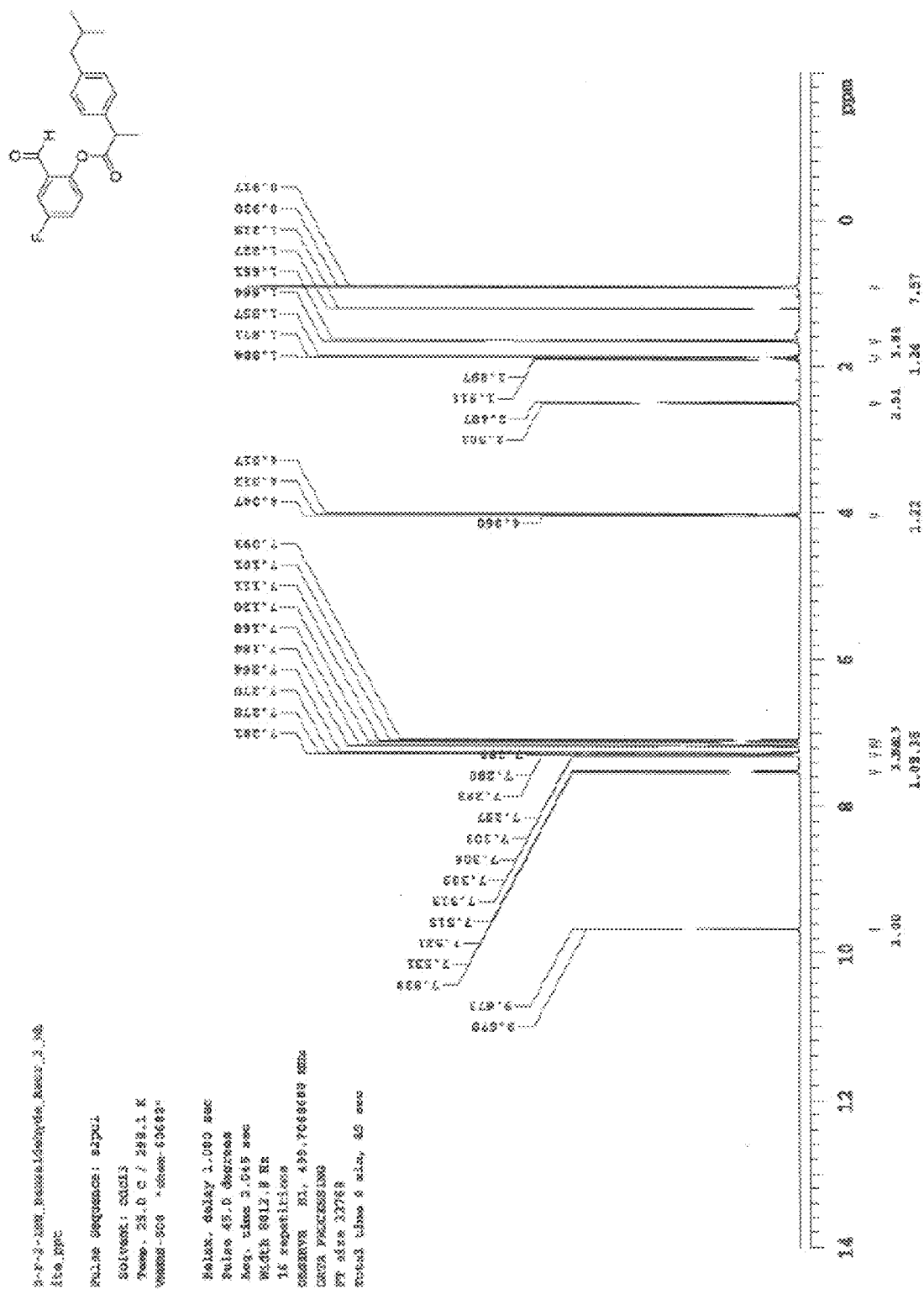

FIG. 235 is a representative NMR spectrum for compound

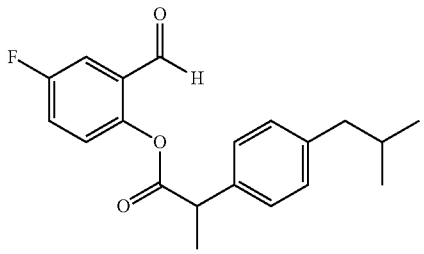 [SMILES: CC(C)Cc1ccc(C(C)C(=O)Oc2ccc(F)cc2C=O)cc1]

of Example 7.

Figure 236:
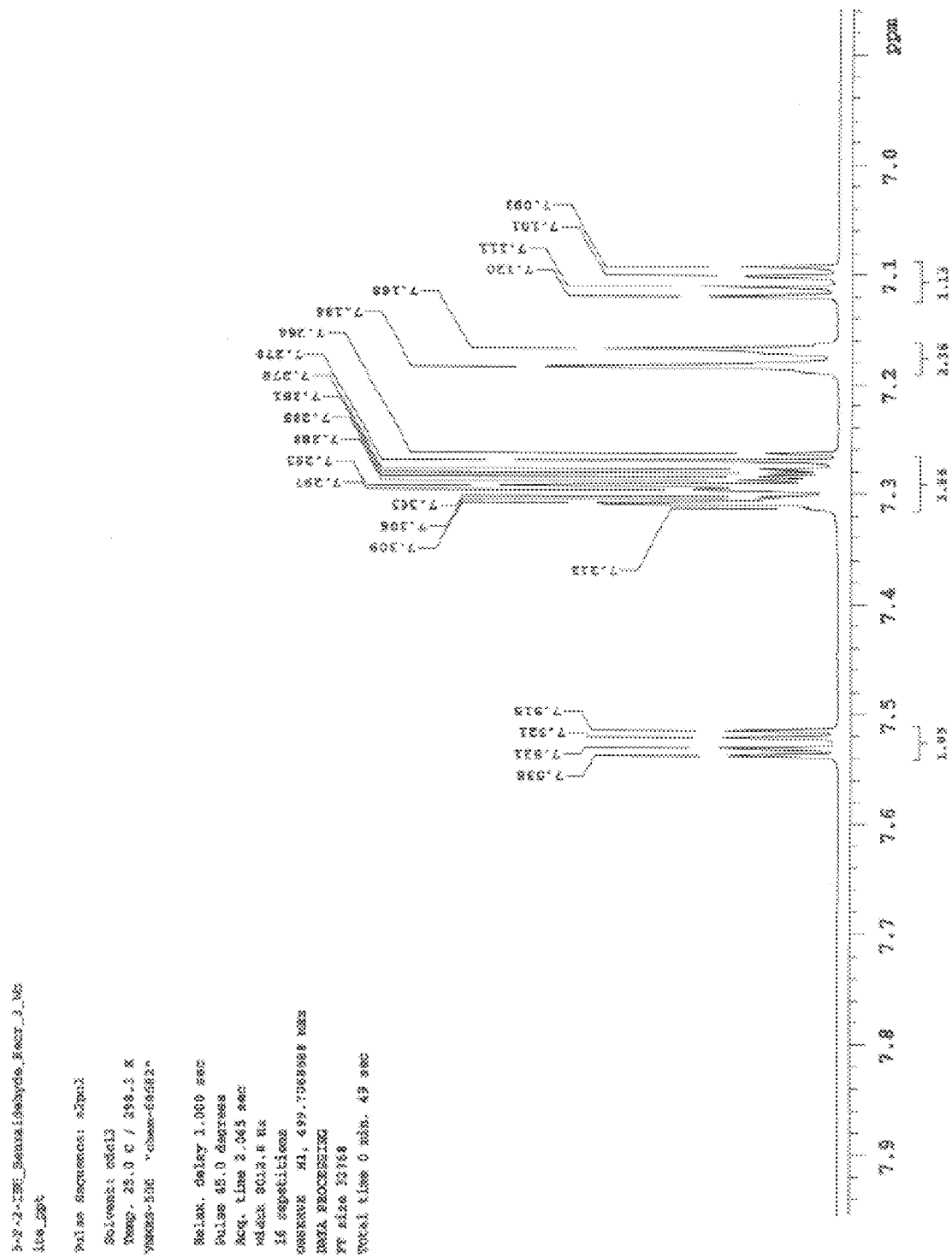

FIG. 236 is a representative NMR spectrum for compound

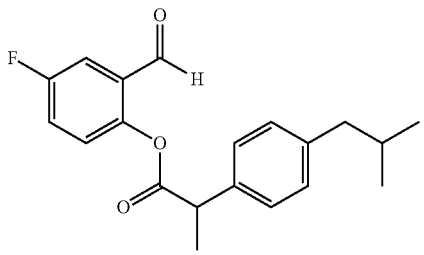 [SMILES: CC(C)Cc1ccc(C(C)C(=O)Oc2ccc(F)cc2C=O)cc1]

of Example 7.

Figure 237:
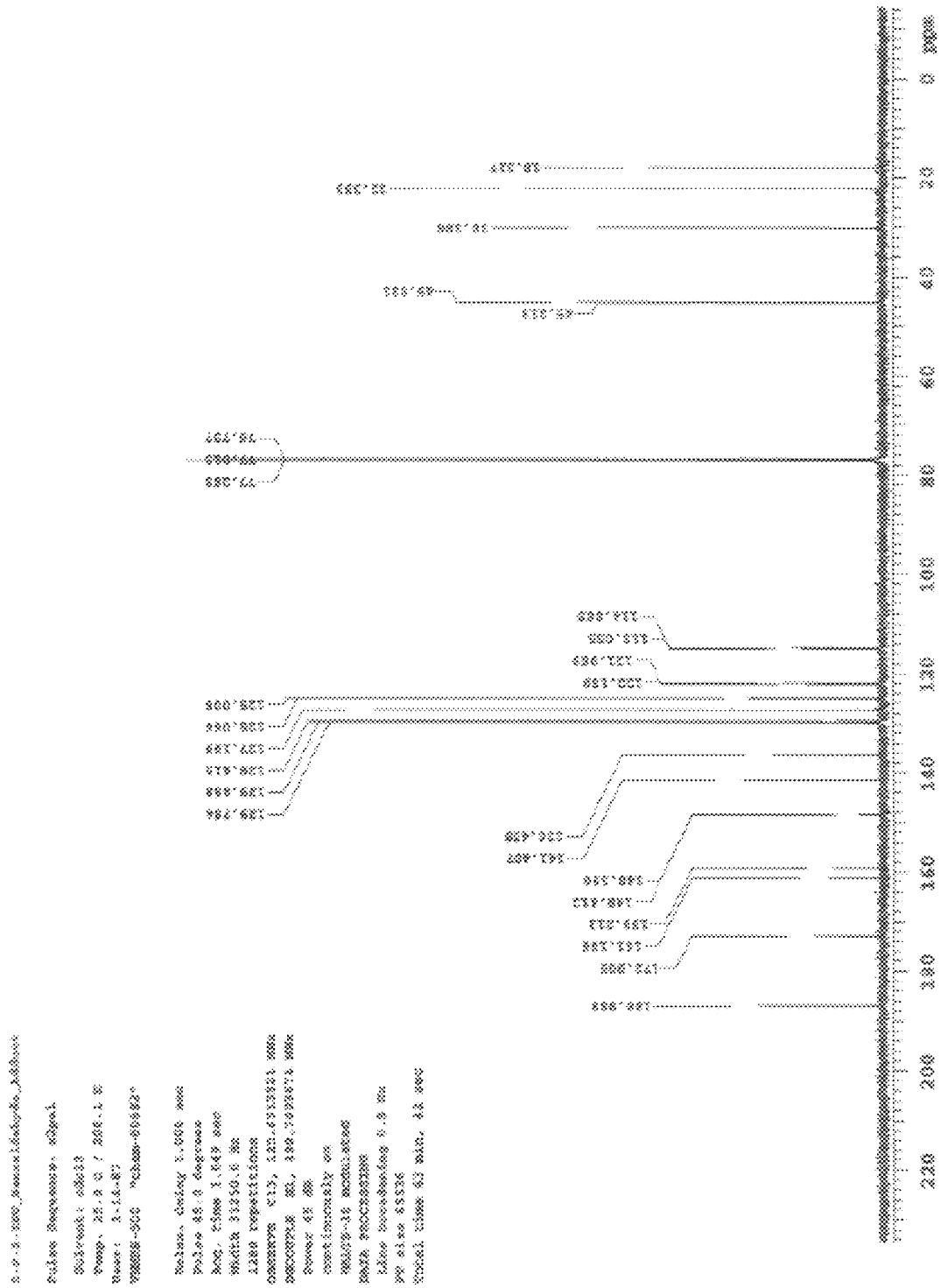

FIG. 237 is a representative NMR spectrum for compound

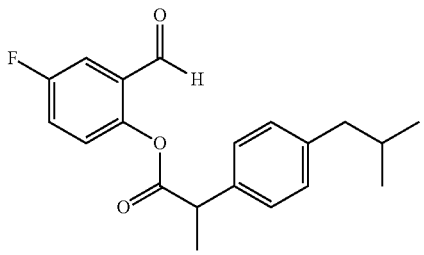 [SMILES: CC(C)Cc1ccc(C(C)C(=O)Oc2ccc(F)cc2C=O)cc1]

of Example 7.

Figure 238:
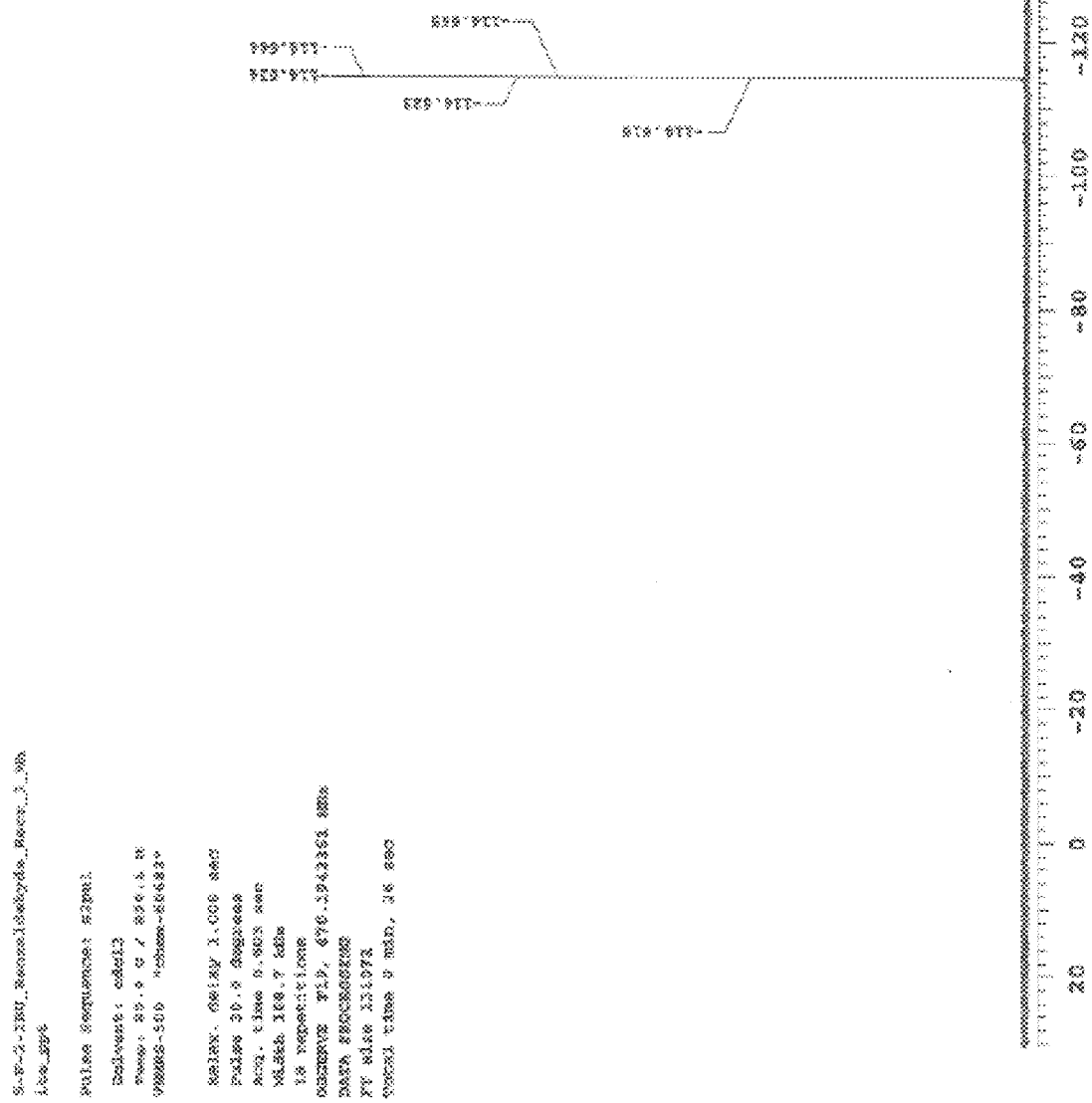

FIG. 238 is a representative NMR spectrum for compound

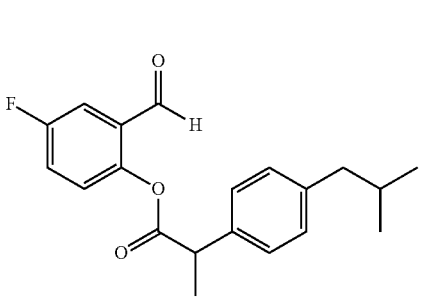 [SMILES: CC(C)Cc1ccc(C(C)C(=O)Oc2ccc(F)cc2C=O)cc1]

of Example 7.

Figure 239:
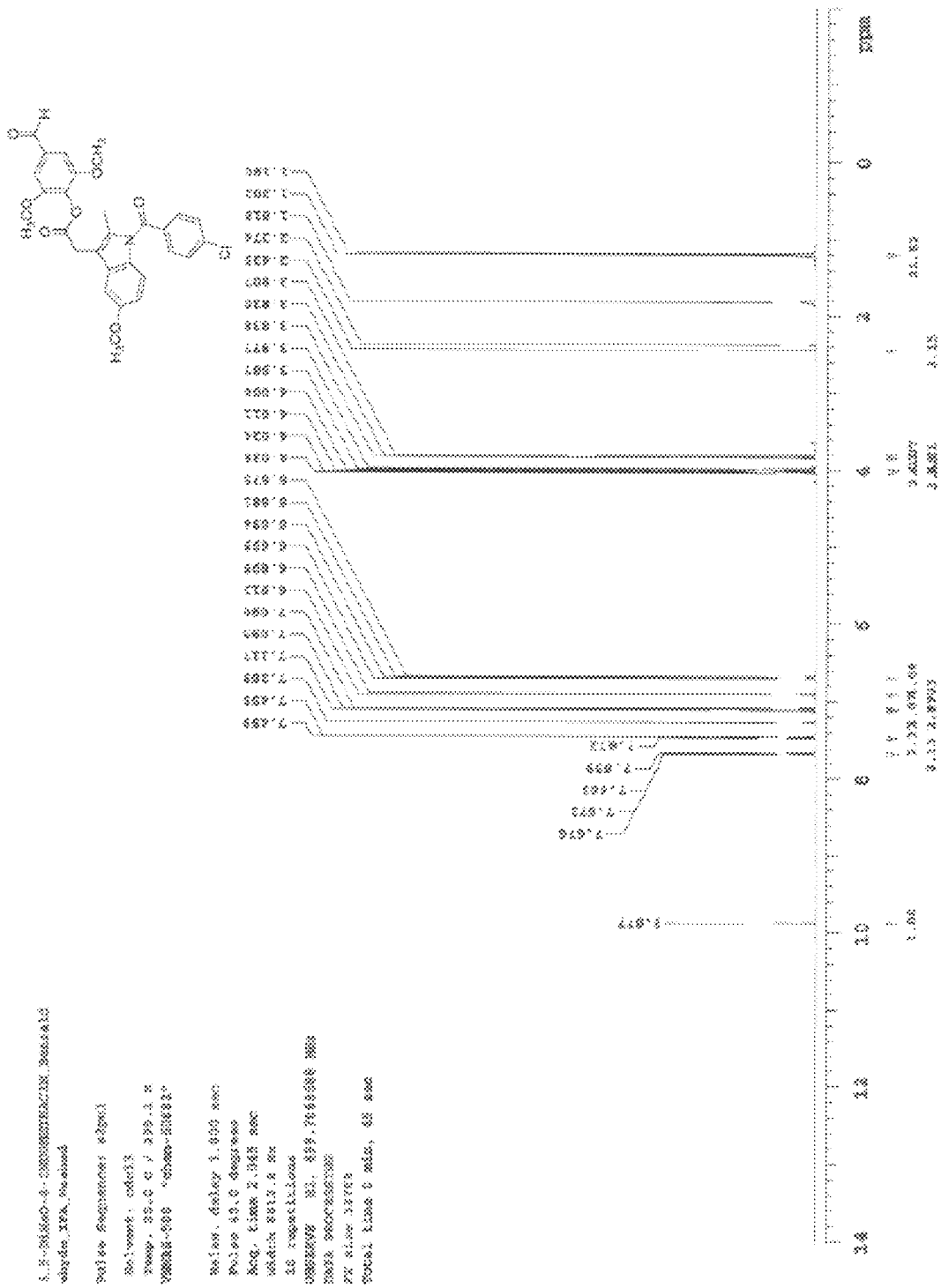

FIG. 239 is a representative NMR spectrum for compound

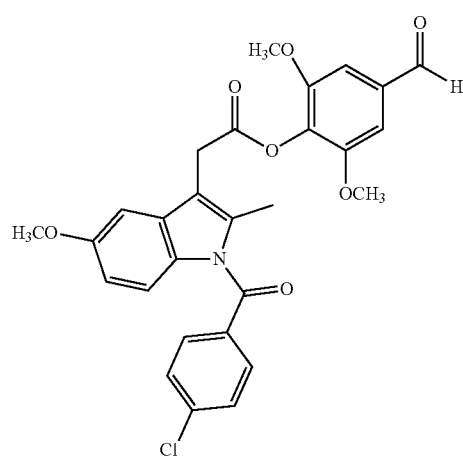 [SMILES: COc1ccc2c(c1)c(CC(=O)Oc1c(OC)cc(C=O)cc1OC)c(C)n2C(=O)c1ccc(Cl)cc1]

of Example 7.

Figure 240:
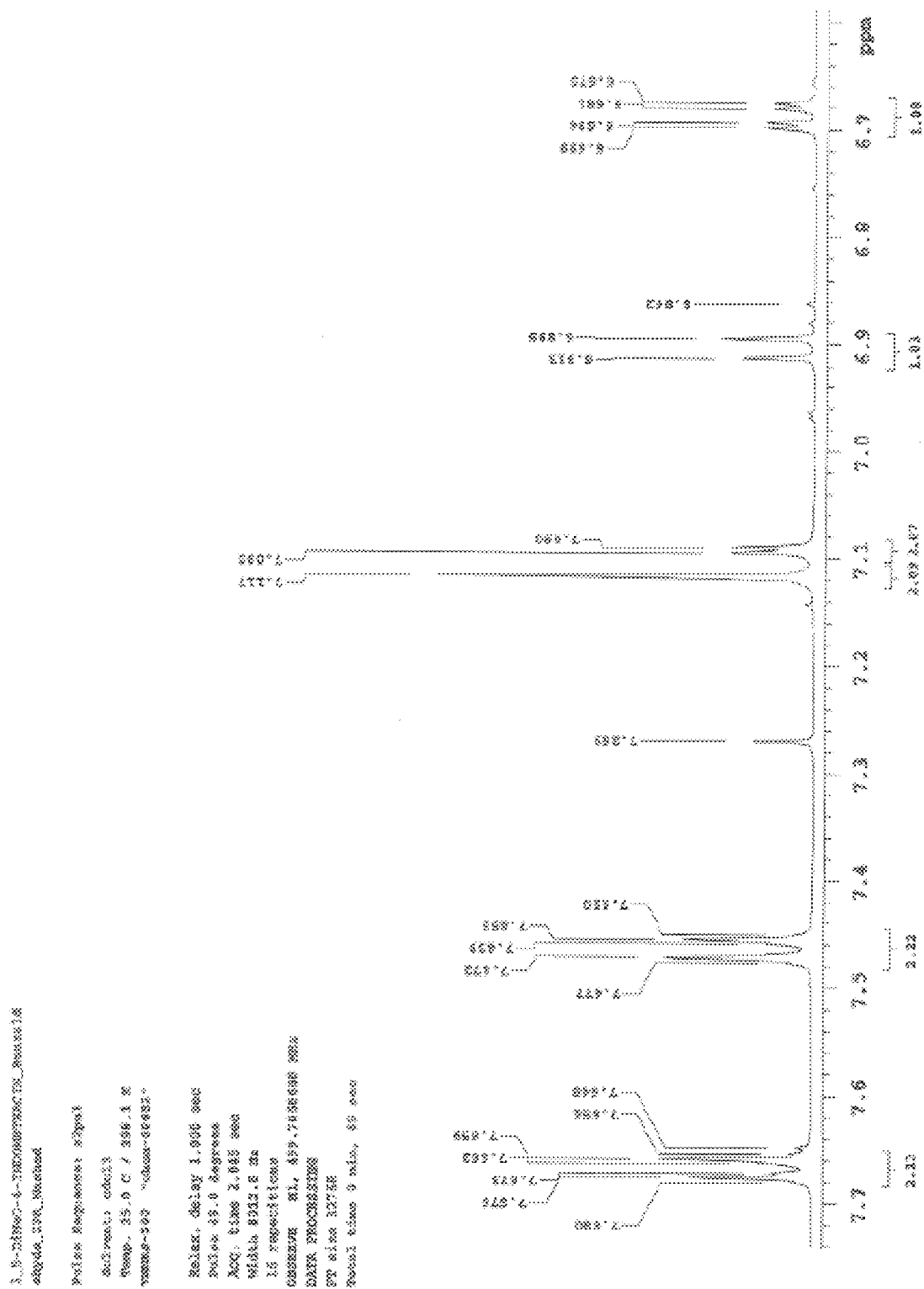

FIG. 240 is a representative NMR spectrum for compound

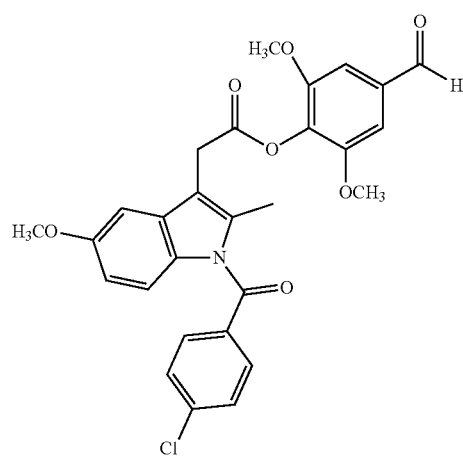 [SMILES: COc1ccc2c(c1)c(CC(=O)Oc1c(OC)cc(C=O)cc1OC)c(C)n2C(=O)c1ccc(Cl)cc1]

of Example 7.

Figure 241:
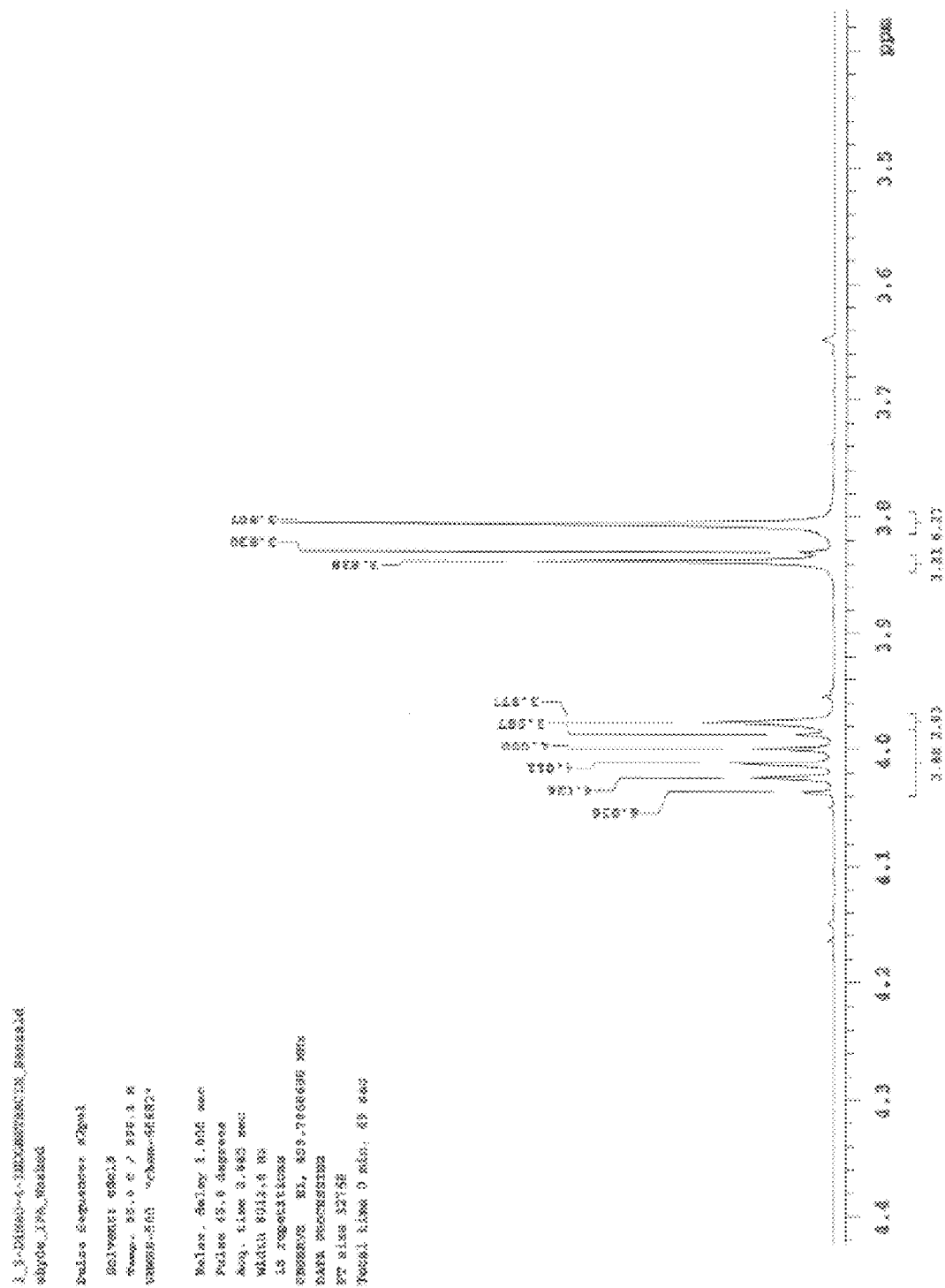

FIG. 241 is a representative NMR spectrum for compound

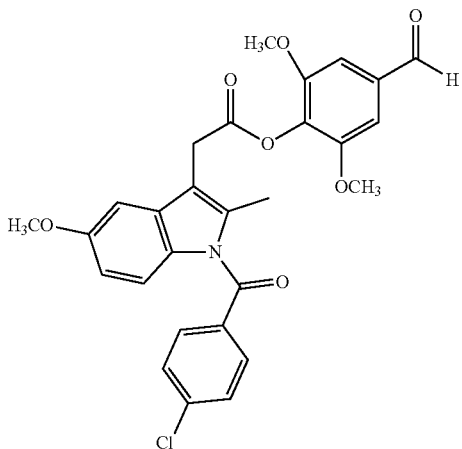 [SMILES: COc1ccc2c(c1)c(CC(=O)Oc1c(OC)cc(C=O)cc1OC)c(C)n2C(=O)c1ccc(Cl)cc1]

of Example 7.

Figure 242:
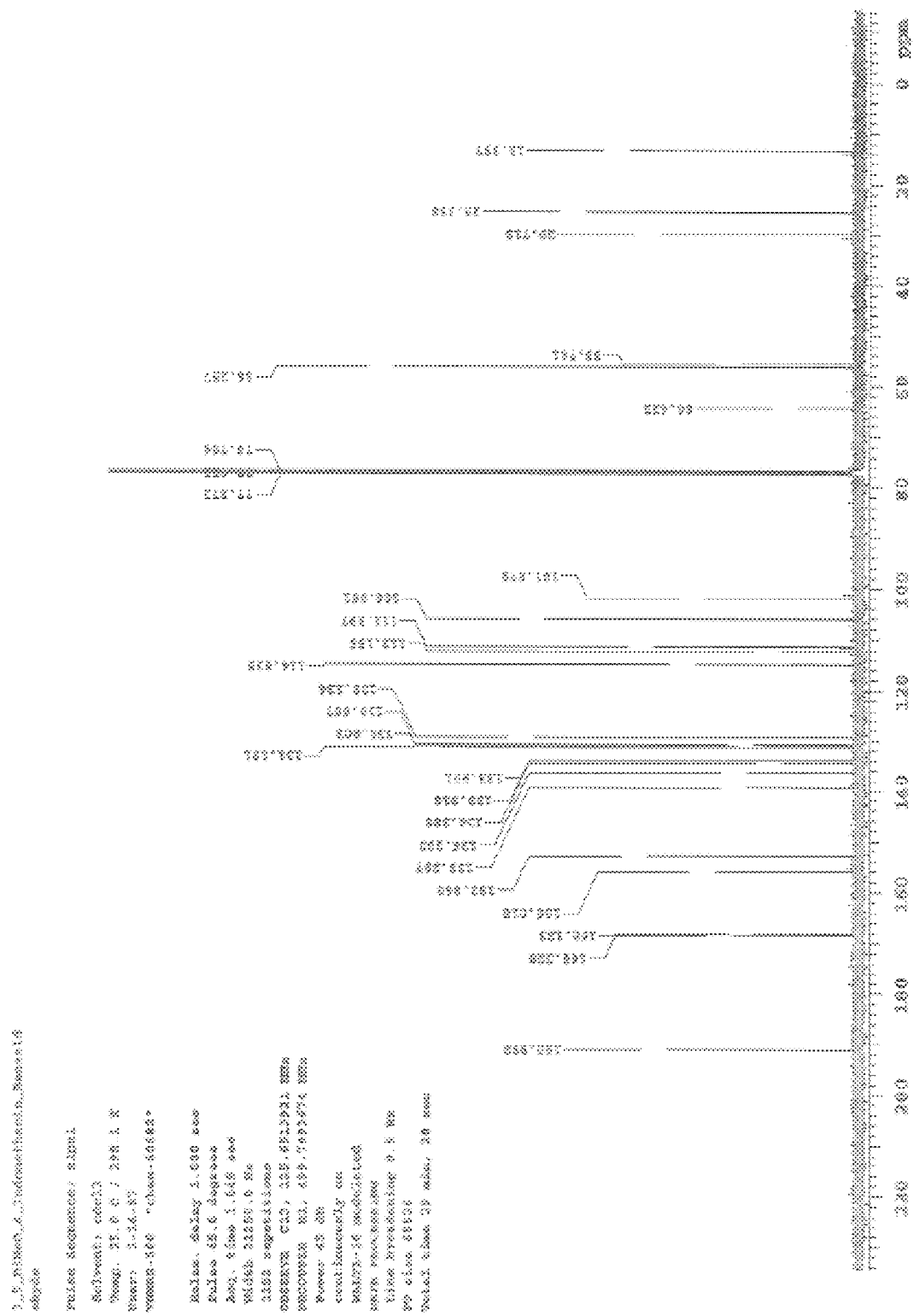

FIG. 242 is a representative NMR spectrum for compound

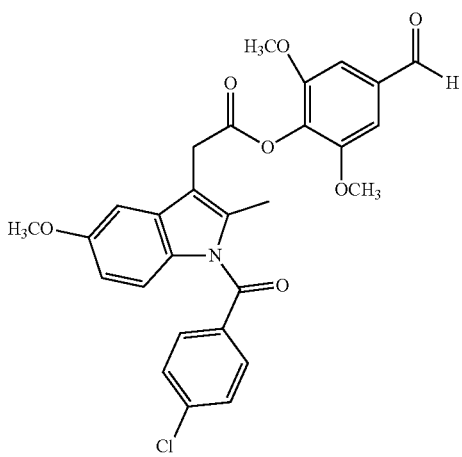 [SMILES: COc1ccc2c(c1)c(CC(=O)Oc1c(OC)cc(C=O)cc1OC)c(C)n2C(=O)c1ccc(Cl)cc1]

of Example 7.

DETAILED DESCRIPTION OF THE PREFERRED EMBODIMENT

In the following detailed description of preferred embodiments, reference is made to the accompanying drawings, which form a part hereof, and within which are shown by way of illustration specific embodiments by which the invention may be practiced. It is to be understood that other embodiments may be utilized and structural changes may be made without departing from the scope of the invention.

Unless otherwise defined, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are described herein. All publications mentioned herein are incorporated herein by reference in their entirety to disclose and describe the methods and/or materials in connection with which the publications are cited. It is understood that the present disclosure supercedes any disclosure of an incorporated publication to the extent there is a contradiction.

All numerical designations, such as pH, temperature, time, concentration, and molecular weight, including ranges, are approximations which are varied up or down by increments of 1.0 or 0.1, as appropriate. It is to be understood, even if it is not always explicitly stated that all numerical designations are preceded by the term "about". It is also to be understood, even if it is not always explicitly stated, that the reagents described herein are merely exemplary and that equivalents of such are known in the art and can be substituted for the reagents explicitly stated herein.

The term "about" or "approximately" as used herein refers to being within 1 or more than 1 standard deviations, per the practice in the art. Alternatively, "about" can mean a range of up to 20% of a given value.

Concentrations, amounts, solubilities, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include the individual values and sub-ranges within the indicated range. Thus, included in this numerical range are individual values such as 2, 3, and 4 and sub-ranges such as from 1-3, from 2-4 and from 3-5, etc. This same principle applies to ranges reciting only one numerical value. Furthermore, such an interpretation should apply regardless of the range or the characteristics being described.

As used herein, the term "comprising" is intended to mean that the products, compositions and methods include the referenced components or steps, but not excluding others. "Consisting essentially of" when used to define products, compositions and methods, shall mean excluding other components or steps of any essential significance. Thus, a composition consisting essentially of the recited components would not exclude trace contaminants and pharmaceutically acceptable carriers. "Consisting of" shall mean excluding more than trace elements of other components or steps.

As used in the specification and claims, the singular form "a", "an" and "the" include plural references unless the context clearly dictates otherwise.

The pharmaceutical compositions of the subject invention can be formulated according to known methods for preparing pharmaceutically useful compositions. Furthermore, as used herein, the phrase "pharmaceutically acceptable carrier" means any of the standard pharmaceutically acceptable carriers. The pharmaceutically acceptable carrier can include diluents, adjuvants, and vehicles, as well as implant carriers, and inert, non-toxic solid or liquid fillers, diluents, or encapsulating material that does not react with the active ingredients of the invention. Examples include, but are not limited to, phosphate buffered saline, physiological saline, water, and emulsions, such as oil/water emulsions. The carrier can be a solvent or dispersing medium containing, for example, ethanol, polyol (for example, glycerol, propylene glycol, liquid polyethylene glycol, and the like), suitable mixtures thereof, and vegetable oils. Formulations are described in a number of sources that are well known and readily available to those skilled in the art. For example, *Remington's Pharmaceutical Sciences* (Martin E W [1995] Easton Pa., Mack Publishing Company, 19th ed.) describes formulations which can be used in connection with the subject invention.

The compounds used in the present invention may be administered individually, or in combination with or concurrently with one or more other compounds used in other embodiments of the present invention. Additionally, compounds used in the present invention may be administered in combination with or concurrently with other therapeutics for cancer.

Examples of cancers benefited by the present invention include, but are not limited to, myelomas; leukemias; lymphomas; sarcomas; carcinomas; myelodysplastic syndrome; brain cancer; cancer of the nervous system including gliomas, meningioma, medulloblastoma, schwannoma, and epidymoma; lung cancer including non-small cell lung cancer and small cell lung cancer; breast cancer; prostate cancer; testicular cancer; bladder cancer; bone marrow cancer; cervical cancer; chronic lymphocytic leukemia; colorectal cancer; esophageal cancer; hepatocellular cancer; lymphoblastic leukemia; follicular lymphoma; lymphoid malignancies of T or B cell origin; melanoma and other skin cancers; myelogenous leukemia; myeloma; oral cancer; ovarian cancer; spleen cancer; pancreatic cancer; stomach cancer; colorectal cancer; renal cell carcinoma; and head and neck carcinoma.

As used herein, "non-fluorinated aryls" or "non-fluorinated aryl compounds" means a molecule lacking one or more fluorine atoms directly connected to an aryl on the molecule.

As used herein, "fluorinated aryls" or "fluorinated aryl compounds" means a molecule possessing one or more fluorine atoms directly connected to an aryl on the molecule.

As used herein, "aryl" means an aromatic hydrocarbon substituent or radical molecule possessing an aromatic hydrocarbon.

As used herein, "boron-difluoride adduct" means a boron-difluoride moiety ($BF_2$) associated with the oxygen atoms of a keto-enol.

As used herein, "patient" means members of the animal kingdom, including mammals, such as but not limited to, primates including humans, gorillas and monkeys; rodents, such as mice, fish, reptiles and birds. The patient may be any animal requiring therapy, treatment, or prophylaxis, or any animal suspected of requiring therapy, treatment, or prophylaxis. The term treatment, as used in this definition only, is intended to mean that regiment described is continued until the underlying disease is resolved, whereas therapy requires that the regiment alleviate one or more symptoms of the underlying disease. Prophylaxis means that regiment is undertaken to prevent a possible occurrence, such as where a high risk of cancer is identified, but tumors or other cancerous growths have not been found. "Patient" and "subject" are used interchangeably herein.

The term "administration" or "administering" is used to describe the process in which the curcuminoid or derivative is provided to the patient. The composition may be administered in various ways including oral, intragastric, and parenteral (referring to intravenous and intra-arterial and other appropriate parenteral routes), among others.

Administration will often depend upon the amount of compound administered, the number of doses, and duration of treatment. In an embodiment, multiple doses of the agent are administered. The frequency of administration of the agent can vary depending on any of a variety of factors, such as timing of treatment from previous treatments, objectives of the treatment, i.e., weight loss or treatment of cancer or neurological disease, and the like. The duration of administration of the agent, e.g., the period of time over which the agent is administered, can vary, depending on any of a variety of factors, including patient response, desired effect of treatment, etc.

The amount of the agent contacted (e.g., administered) can vary according to factors such as the degree of susceptibility of the individual, the age, sex, and weight of the individual, idiosyncratic responses of the individual, the dosimetry, and the like. Detectably effective amounts of the agent of the present disclosure can also vary according to instrument and film-related factors. Optimization of such factors is well within the level of skill in the art.

The "therapeutically effective amount" for purposes herein is thus determined by such considerations as are known in the art. A therapeutically effective amount of individual curcuminoid compound or salt formed from curcuminoid compound, derivatives, or any combination thereof is that amount necessary to provide a therapeutically effective result in vivo. The amount of curcuminoid compound or salt, derivatives, or any combination thereof must be effective to achieve a response, i.e. prophylaxis or treatment. In accordance with the present invention, a suitable single dose size is a dose that is capable of preventing or alleviating (reducing or eliminating) a symptom in a patient when administered one or more times over a suitable time period. As used herein, alleviating includes reducing cancerous growths, limiting spread or metastasis of cancerous cells, or limiting growth of cancerous or precancerous bodies. One of skill in the art can readily determine appropriate single dose sizes for systemic administration based on the size of a mammal and the route of administration.

Example 1—CUR Inspired Compounds Bearing Fluorinated Moieties

Studies were performed to identify suitable solvents for the reaction of 1 with Selectfluor. Experiments were performed by using 0.1 mmol of CUR and 1.1 and 2.1 equivalents of Selectfluor, and the progress of the reactions were monitored by $^{19}F$ NMR (and by TLC). $^{19}F$ NMR provided a convenient and direct method to gauge chemoselectivity in different solvents. Apart from F—CUR and $F_2$—CUR, formation of CUR—$BF_2$ adduct was observed in some solvents, notably in water and in acetone under microwave irradiation (more in section 2.2). Presence of a distinct doublet at δ−195 ppm ($J_{HF}$=50 Hz) signified the 1,3-diketo-tautomer of F—CUR present in different proportions in some solvents. Application of microwave (MW) increased the proportion of CUR—$BF_2$ adduct in acetone as solvent, seen in Table 1.

TABLE 1

$^{19}$F NMR monitoring of solvent effect on fluorination selectivity[a]

| Solvent[b,c] | $^{19}$F NMR signal at −115 ppm (s) F$_2$-CUR | $^{19}$F NMR signal at −140 ppm (s) CUR-BF$_2$ | $^{19}$F NMR signal at −176 ppm (s) F-CUR | $^{19}$F NMR signal at −195 ppm (d) Diketo-tautomer of F-CUR |
|---|---|---|---|---|
| Acetonitrile/ r.t.[d] | — | 11% | 55% | 34% |
| Methanol/ r.t.[e] | 100% | — | — | — |
| Ethanol/reflux[d] | 61% | 33% | 6% | — |
| DMF/reflux[d] | 21% | — | 43% | 36% |
| THF/r.t.[d] | 24% | 27% | 32% | 17% |
| THF /MW[d] | 15% | 36% | 24% | 25% |
| Acetone/ r.t.[e] | 66% | 3% | 23% | 8% |
| Acetone/MW[d] | 24% | 64% | 6% | 6% |
| Water/reflux[e] | — | 100% | — | — |

[a]Reported percentages are based on relative integrals of these species in $^{19}$F NMR (not taking into account signals due to unreacted Selectfluor and its byproducts); [b]R.T. reactions were allowed to run overnight and reflux temp was limited to 70° C.; [c]MW conditions: 200 W until temp reached 140° C.; [d]Selectfluor (1.1 equiv.); [e]Selectfluor (2.1 equiv.).

Based on these studies, MeOH was selected as solvent of choice for direct difluorination of curcuminoids, whereas MeCN was chosen for monofluorination.

To minimize the formation of other species observed in $^{19}$F monitoring study in MeCN solvent, the monofluorinations were performed at 0° C. and continued at r.t. A noteworthy feature in these studies was that competing ring fluorination products were not detected, and further fluorination beyond the formation of F$_2$—CUR was not observed in a control experiment using excess Selectfluor (4 equiv.). Based on these studies compounds 3 and 4 of FIG. 2 were synthesized and isolated according to the scheme shown in FIG. 3.

The base-catalyzed "double aldol" condensation of aldehydes with acetyl acetone serves as a standard method to assemble the curcumin skeleton. Earlier methods employing boric oxide or boric acid as additive had drawbacks with respect to reproducibility, and a more reliable method involving the reaction of acetylacetone-BF$_2$ complex with aldehydes followed by hydrolysis of the complex was developed. (E. V. Rao, et al., *Indian. J. Pharm. Sci.*, 2011, 73, 262-270). Microwave-assisted one-pot methods that employed calcium oxide, and boric acid/sodium sulfate as additives in toluene solvent had also been reported. (S. Elavarasan, et al., *Journal of Chemistry*, 2013, 1-8; M. G. Shioorkar, et al., *Der Chemie Sinica*, 2015, 6, 110-113).

In the present study, the inventors found the reported hydrolytic/decomplexation process involving multiple steps to be inefficient. (E. V. Rao, et al., *Indian. J. Pharm. Sci.*, 2011, 73, 262-270). Instead, the curcuminoid-BF$_2$ adducts and their corresponding curcuminoids were synthesized as outlined in Scheme 1. A microwave-assisted method reported for decomplexation of curcumin-quinolone hybrids was adopted but modified by addition of sodium oxalate. (S. Raghavan, et al., *Bioorg. Med. Chem. Lett.*, 2015, 25, 3601-3605). Sodium oxalate serves as a bidentate ligand and chelating agent to preferentially coordinate with BF$_2$, possibly forming sodium-difluoro(oxalato)borate which is a known compound. (J. Chen, et al., *Chem. Commun.*, 2015, 51, 9809-9812).

In initial studies of solvent effect on fluorination selectivity using Selectfluor, shown in Table 1, formation of curcumin-BF$_2$ adduct was unexpectedly observed under microwave irradiation in acetone or in water. Whereas the method represents an interesting alternative for the synthesis of CUR—BF$_2$ adducts, in practice the isolated yields of this MW-assisted method were lower (see experimental) as compared to the method outlined in FIG. 4, and it was therefore not used in subsequent reactions.

Figure 2:
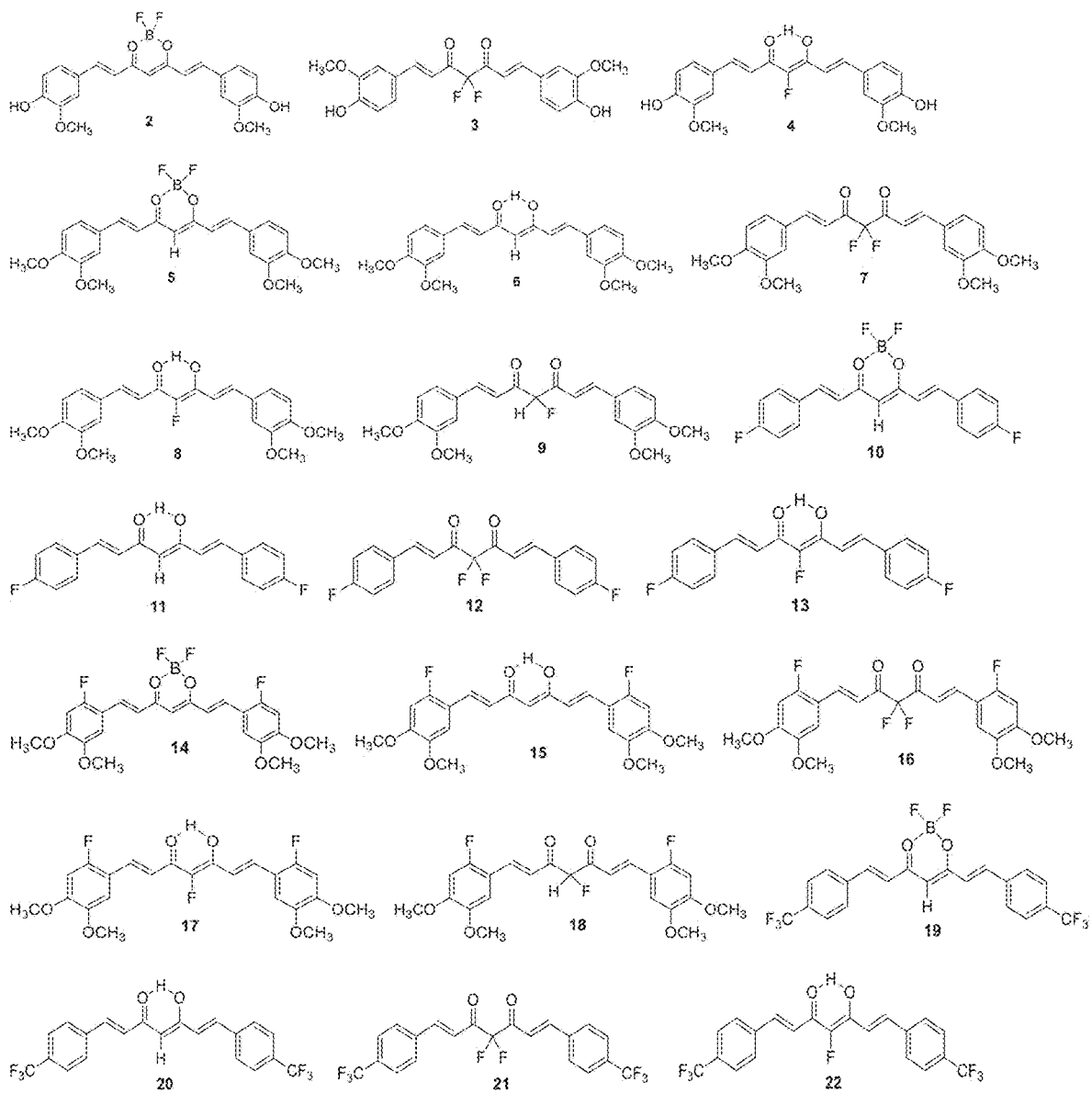
FIG. 2. List of curcuminoid compounds.
Figure 4:
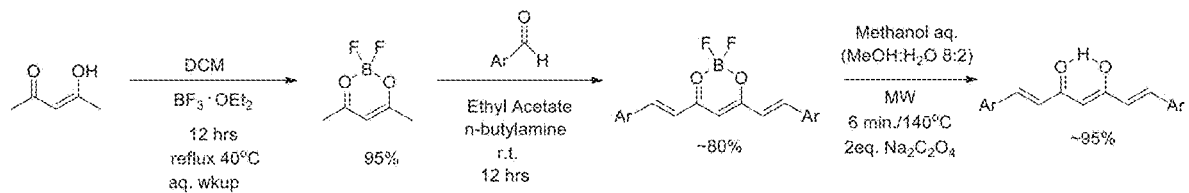
FIG. 4. Synthetic sequence for the preparation of CUR—$BF_2$ compounds and curcuminoids.

By using the method outlined in FIG. 4, symmetrical curcuminoids 6, 11, 15, and 20 were synthesized, as seen in FIG. 2. As with parent 1, these curcuminoids are also exclusively present in the enolic form (NMR). In addition, the corresponding CUR—BF$_2$ adducts 5, 10, 14, and 19, seen in FIG. 2, were isolated in high yields and fully characterized (see exp. section).

Figure 10:
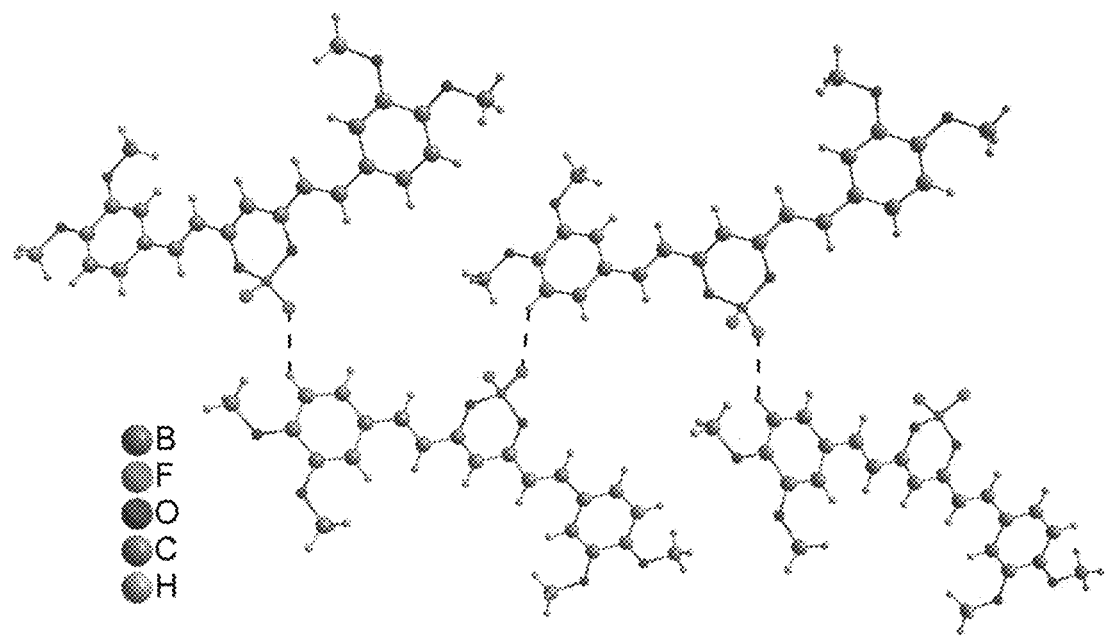
FIG. 10. Crystal packing diagram of 5. Compound 5 crystallizes in the monoclinic space group $P2_1/c$. The asymmetric unit corresponds to one molecule with a total of four molecules in each cell. Each molecule interacts with an adjacent molecule via one H—F contact (2.4455(31) Å).
Figure 11:
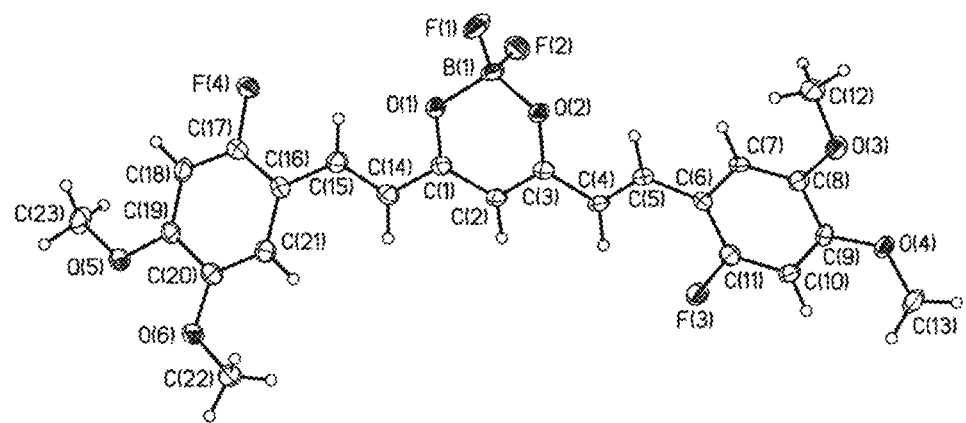
FIG. 11. Thermal ellipsoid plot of 14. Thermal ellipsoids are drawn at 50% probability. Selected inter-atomic distances (Å) and angles (°): B(1)-F(1) 1.368(5), B(1)-F(2) 1.382(5), B(1)-O(2) 1.477(5), B(1)-O(1) 1.480(5), O(1)-C(1) 1.318(4), O(2)-C(3) 1.306(4), F(1)-B(1)-F(2) 111.1(3), F(1)-B(1)-O(2) 108.7(3), F(2)-B(1)-O(2) 109.0(3), F(1)-B(1)-O(1) 108.3(3), F(2)-B(1)-O(1) 108.9(3), O(2)-B(1)-O(1) 110.8(3).

The X-ray structures for CUR—BF$_2$ adducts 5, 10, and 14, seen in FIGS. 7-13, confirm the symmetrical coordination of BF$_2$ to the two oxygens in the enolic configuration. The asymmetric unit in CUR—BF$_2$ 5 corresponds to one molecule with a total of four molecules in each cell. Each molecule interacts with an adjacent molecule via one H—F contact as seen in FIG. 10 and Table 2.

TABLE 2

Summary of crystallographic data for compounds 10, 5, 8 and 14

| Compound | 10 | 5 | 8 | 14 |
|---|---|---|---|---|
| Empirical formula | $C_{19}H_{13}BF_4O_2$ | $C_{23}H_{23}BF_2O$ | $C_{23}H_{23}O_6$ | $C_{23}H_{21}BF_4O_6$ |
| M | 360.10 | 444.22 | 414.41 | 480.21 |
| Crystal System | Monoclinic | Monoclinic | Triclinic | Triclinic |
| Space group | P2$_1$/n | P2$_1$/c | P$\bar{1}$ | P$\bar{1}$ |
| a/Å | 5.1465(11) | 8.0474(9) | 11.7860(15) | 9.605(2) |
| b/Å | 12.696(3) | 17.115(2) | 14.5631(17) | 9.724(2) |
| c/Å | 25.312(5) | 15.2867(17) | 17.659(2) | 12.941(3) |
| α/° | | | 97.683(3) | 72.264(5) |
| β/° | 95.343(5) | 90.983(5) | 93.743(3) | 84.108(6) |
| γ/° | | | 91.750(3) | 67.346(5) |
| V/Å$^3$ | 1646.8(6) | 2105.1(4) | 2995.1(6) | 1062.2(4) |
| ρ$_{calcd}$(g cm$^{-3}$) | 1.452 | 1.402 | 1.379 | 1.501 |

TABLE 2-continued

Summary of crystallographic data for compounds 10, 5, 8 and 14

| Compound | 10 | 5 | 8 | 14 |
|---|---|---|---|---|
| T/K | 105(2) | 105(2) | 105(2) | 105(2) |
| Z | 4 | 4 | 6 | 2 |
| μ/mm$^{-1}$ | 0.122 | 0.111 | 0.105 | 0.129 |
| Crystal size (mm) | 0.20 × 0.15 × 0.05 | 0.30 × 0.05 × 0.05 | 0.15 × 0.04 × 0.04 | 0.30 × 0.05 × 0.05 |
| Reflections collected: | | | | |
| Total | 13015 | 11202 | 36284 | 10942 |
| Unique | 2747 | 3607 | 10590 | 3705 |
| $R_{int}$ | 0.0810 | 0.0534 | 0.0949 | 0.0535 |
| Final $R_1$, $wR_2$ | 0.1079, 0.2257 | 0.0636, 0.1433 | 0.0643, 0.1459 | 0.0590, 0.1471 |

Figure 5:
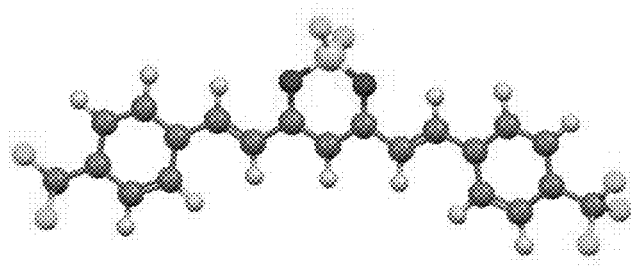
FIG. 5. Optimized structure of $(CF_3)_2$—CUR—$BF_2$ 19 by B3LYP/6-311+G(d,p).

$R_1 = \Sigma[|F_0| - |F_c|]/\Sigma|F_0|$, $wR_2 = [\Sigma[w(|F_0|^2 - |F_c|^2)^2]/\Sigma[w(|F_0|^2)^2]]^{1/2}$
$R = \Sigma||F_0| - |F_c||/\Sigma|F_0|$, $R_w = [\Sigma w (|F_0| - |F_c|)^2 / \Sigma w\, F_0^2]^{1/2}$ Whereas attempts to obtain X-ray quality crystals for the bis-trifluoromethyl-CUR—BF$_2$ adduct 19 were unsuccessful, its DFT-optimized structure, as seen in FIG. 5, fully agrees with a symmetrically BF$_2$-coordinated adduct.

Synthesis of α-Carbonyl Fluorinated Curcuminoids and Structural Features

Figure 1:
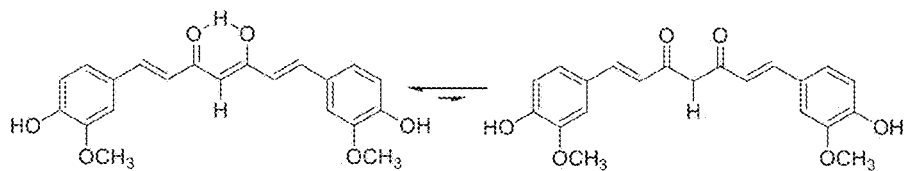
FIG. 1. Tautomerism in curcumin—exclusive presence of the enol tautomer
Figure 6:
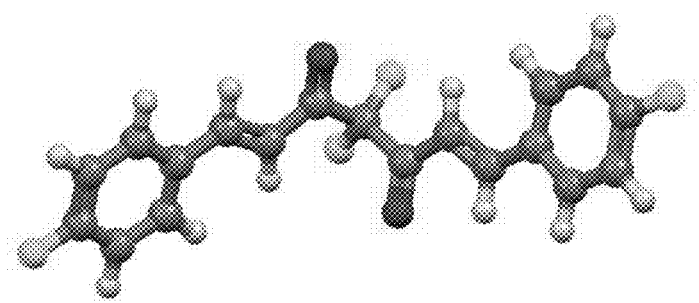
FIG. 6. Optimized structure of 12 by B3LYP/6-311+G(d,p).
Figure 7:
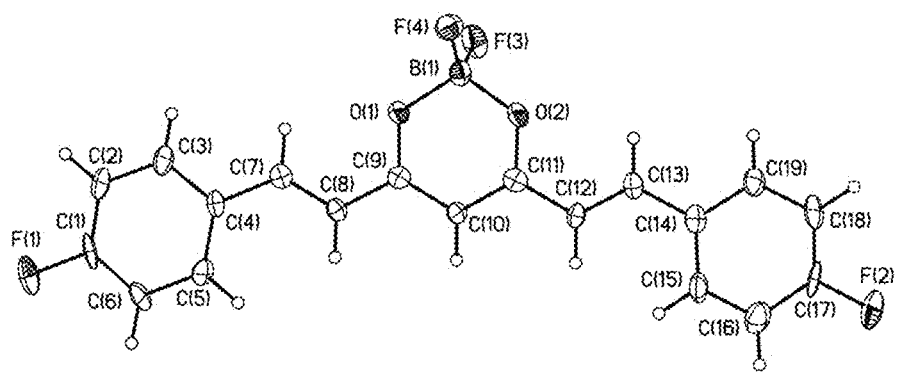
FIG. 7. Thermal ellipsoid plot of 10. Thermal ellipsoids are drawn at 50% probability. Selected inter-atomic distances (Å) and angles (°): B(1)-F(4) 1.372(6), B(1)-F(3) 1.383(6), B(1)-O(2) 1.470(6), B(1)-O(1) 1.477(6), O(1)-C(9) 1.303(5), O(2)-C(11) 1.307(5); F(4)-B(1)-F(3) 110.7(4), F(4)-B(1)-O(2) 109.2(4), F(4)-B(1)-O(2) 108.1(4), F(4)-B(1)-O(1) 108.1(4), F(3)-B(1)-O(1) 108.2(4), O(2)-B(1)-O(1) 112.5(4).
Figure 8:
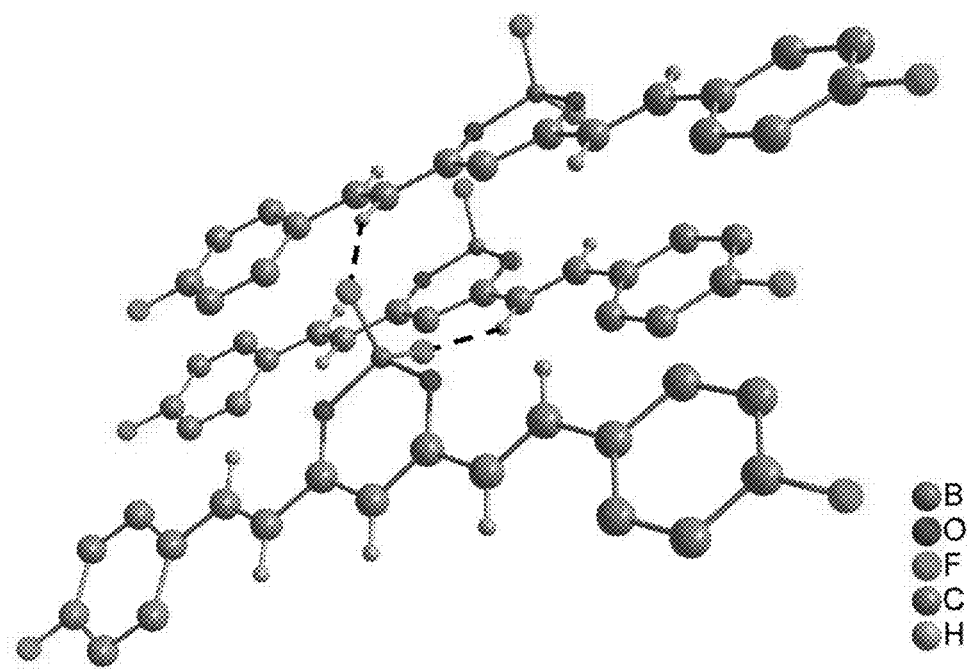
FIG. 8. Crystal packing diagram of 10. Selected hydrogen atoms have been removed for clarity. Compound 10 crystallizes in the monoclinic space group $P2_1/n$. The asymmetric unit corresponds to one molecule with a total of four molecules in each cell. Each molecule interacts with an adjacent molecule via two H—F contacts (2.2813(26) and 2.3582(25) Å).
Figure 9:
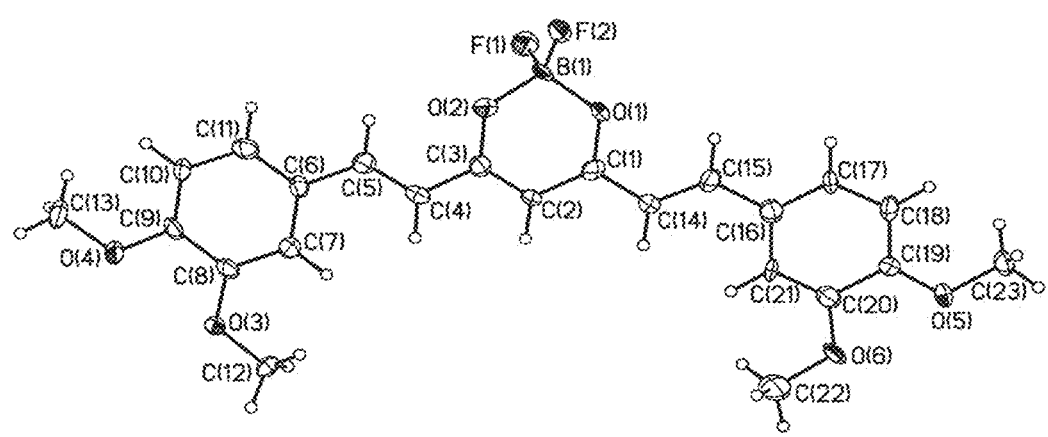
FIG. 9. Thermal ellipsoid plot of 5. Thermal ellipsoids are drawn at 50% probability. Selected inter-atomic distances (Å) and angles (°): B(1)-F(1) 1.382(9), B(1)-F(2) 1.365(8), B(1)-O(1) 1.477(8), B(1)-O(2) 1.488(8), O(1)-C(1) 1.313(7), O(2)-C(3) 1.322(7); F(2)-B(1)-F(1) 111.3(5), F(2)-B(1)-O(1) 107.9(6), F(1)-B(1)-O(1) 109.5(6), F(2)-B(1)-O(2) 108.4(6), F(1)-B(1)-O(2) 107.9(6), O(1)-B(1)-O(2) 111.7(5).

The corresponding α-carbonyl difluorinated analogs (7, 12, 16, and 21 of FIG. 2) were synthesized in good to moderate isolated yields by using 2.1 equivalents of Selectfluor, following the same procedure applied to fluorination of parent 1, seen in FIG. 1. These compounds exhibit distinctive two-bond C/F coupling with the carbonyls, giving rise to a ~28 Hz triplet in $^{13}$C NMR (see experimental). The DFT optimized structure of tetrafluorinated curcuminoid 12, as seen in FIG. 6, shows notable conformational changes resulting from tautomerization.

Figure 3:
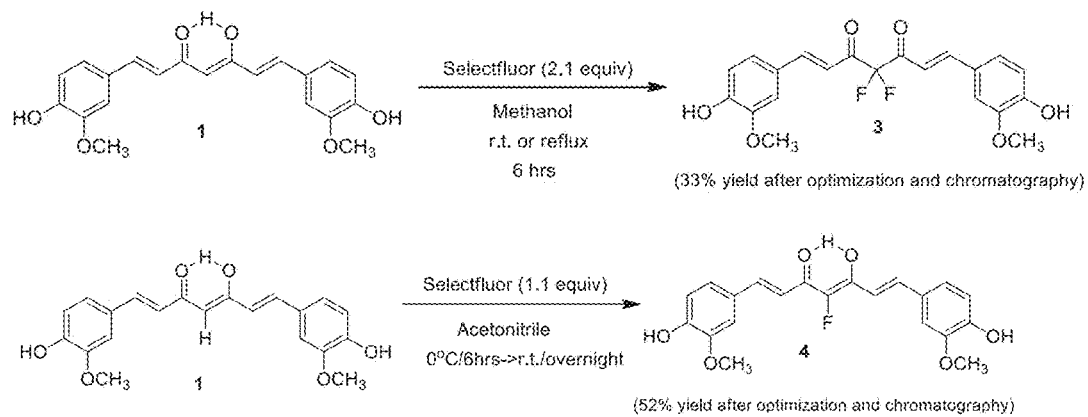
FIG. 3 Synthesis and isolation of $F_2$—CUR (3) and F—CUR (4).

The α-carbonyl monofluorinated analogs (8, 13, 17, and 22 of FIG. 2) were synthesized by reaction with 1.1 equivalent of Selectfluor in MeOH (analogous to synthesis of 4; FIG. 3). Concomitant formation of the difluorinated analogs was observed in the crude reaction mixtures in the monofluorination reactions, which could be minimized by running the reactions initially 0° C., then warming to r.t. and continuing to stir at room temperature.

The α-carbonyl monofluorinated compounds exhibit a distinctive two-bond C/F coupling with the carbonyls, giving rise to a 20-23 Hz doublet in $^{13}$C NMR. The 1,3-diketone tautomer can be readily recognized by the presence of a ~50 Hz doublet in $^{19}$F and $^1$H NMR due to geminal H/F coupling.

Whereas the monofluorinated curcuminoids 4, 13, 17, and 22 (FIG. 2) are exclusively present in the enolic form, compound 8 (FIG. 2) was present as a 75:25 (enol to ketone) tautomeric mixture (by $^{19}$F NMR).

Figure 13:
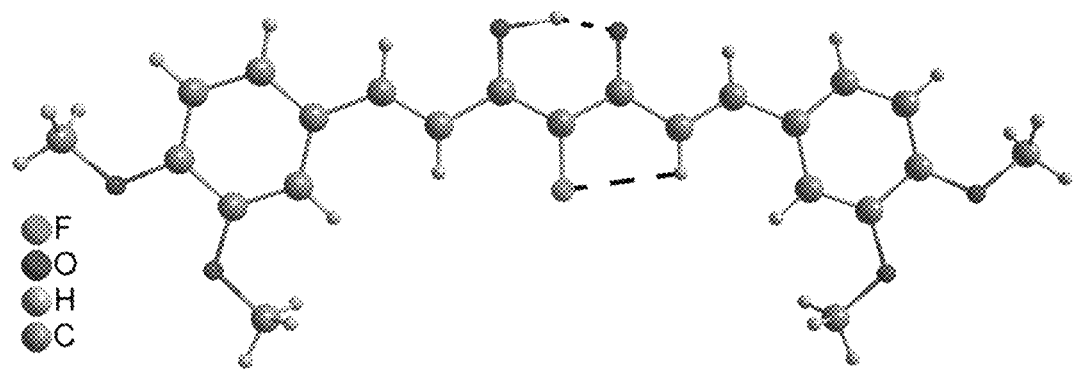
FIG. 13 Ball and stick plot of 8. Compound 8 crystallizes in the triclinic space group $P\bar{1}$. The asymmetric unit corresponds to three crystallographically nonequivalent molecules with a total of six molecules in each unit cell. 8a, 8b, and 8c are illustrated in FIGS. 14a-c respectively. The same gross structural features are found in all three molecules. No significant intermolecular contacts are observed. The molecule contains intramolecular hydrogen bonding and one H—F contact with a distance of 2.4455(31) Å.
Figure 14A:
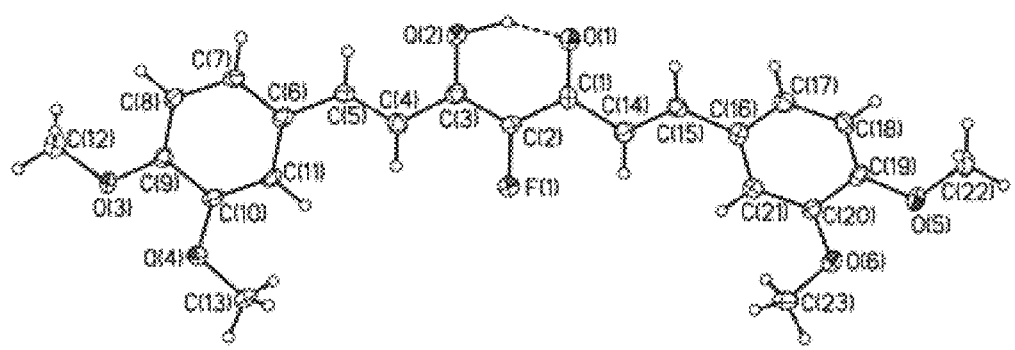
FIG. 14A-B (A) Thermal ellipsoid plot of 8a. Thermal ellipsoids are drawn at 50% probability; (B) Thermal ellipsoid plot of 8b. Thermal ellipsoids are drawn at 50% probability.
Figure 14B:
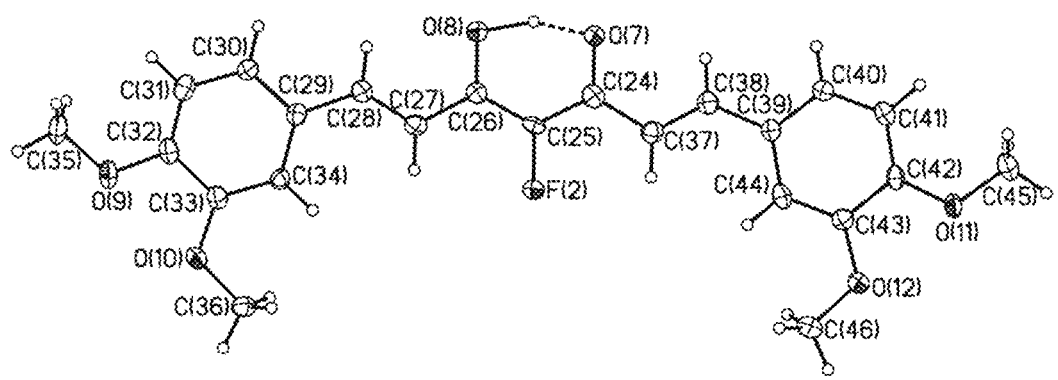
Figure 14C:
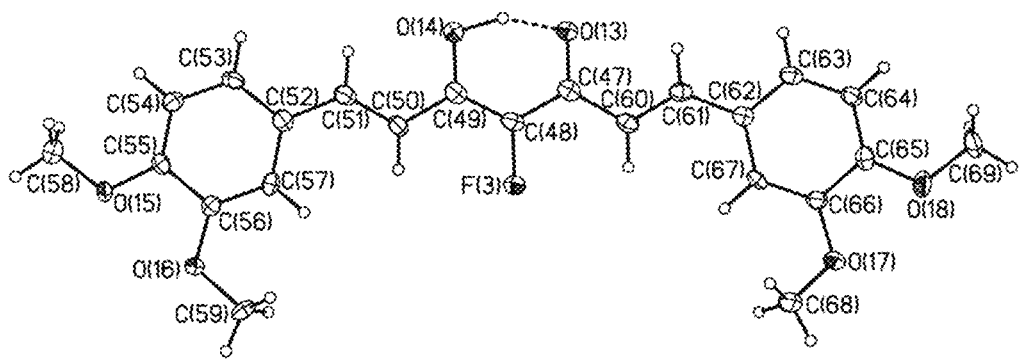
FIG. 14C Thermal ellipsoid plot of 8c. Thermal ellipsoids are drawn at 50% probability.

Interestingly, the X-ray structure of 8 shows only the enolic tautomer and exhibits intramolecular hydrogen bonding and one H—F contact with a distance of 2.44 Å, as seen in FIG. 13. The asymmetric unit for 8 corresponds to three crystallographically nonequivalent molecules with a total of six molecules in each unit cell.

A notable feature in the X-ray crystallographic data is absence of any significant π-π stacking. Intermolecular interactions appear to be predominantly through short H—F contacts.

Cell Growth Inhibitory Effects Against Human Cancer Cells—Bioassay

To evaluate the cell growth inhibitory and apoptosis inducing effects of the fluorinated curcuminoids and their BF$_2$ adducts, in-vitro bioassay tests were performed on four different cancer cell lines namely: MOLT-4 (human leukemia suspension cancer cell line), PC3 and LNCap (human androgen sensitive and insensitive prostate cancer cell lines respectively), A549 (lung cancer), and MDA231 (breast cancer), and the results are sketched in Table 3.

Figure 15:
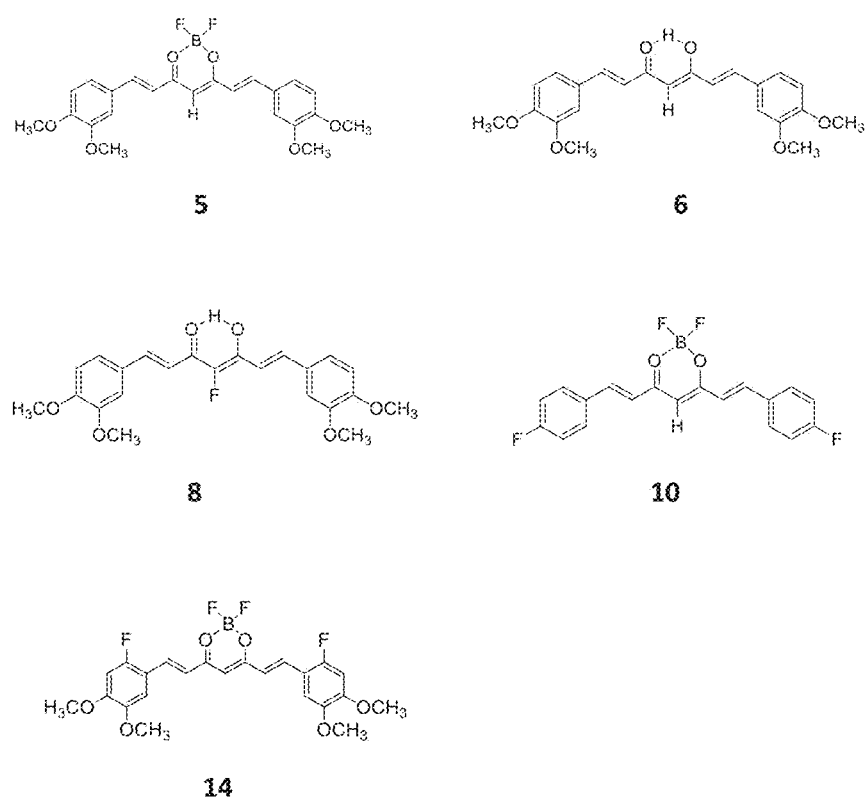
FIG. 15. List of lead curcuminoids identified based on bioassay.
Figure 16:
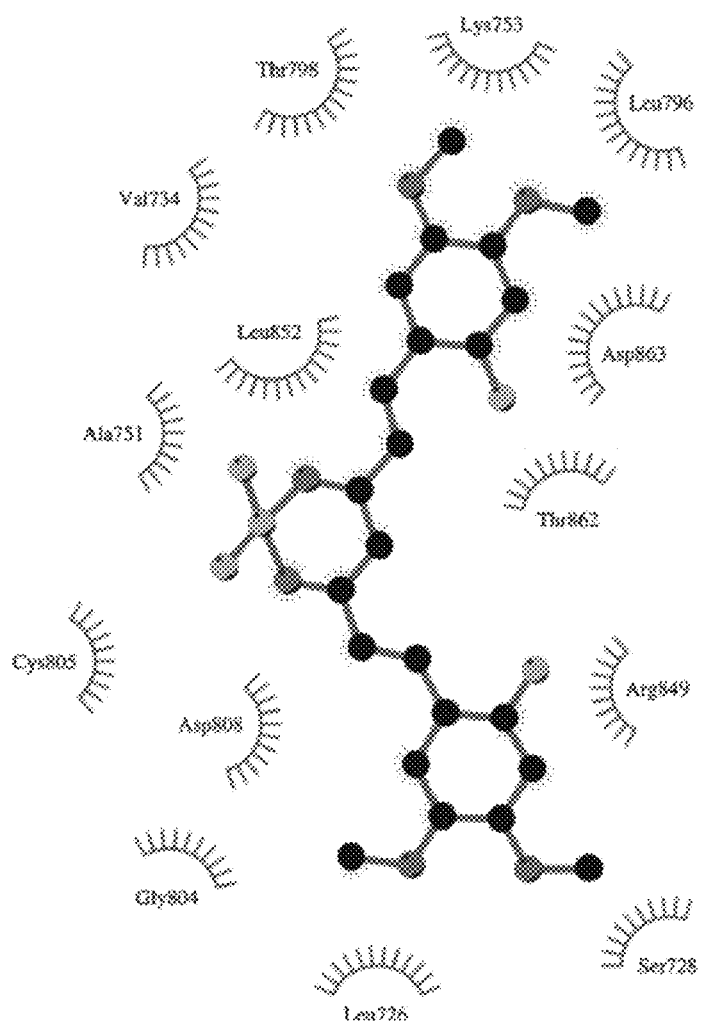
FIG. 16. Binding mode in the active site of HER2 of compound 14 as a model curcuminoid analog (2D-plot).
Figure 17:
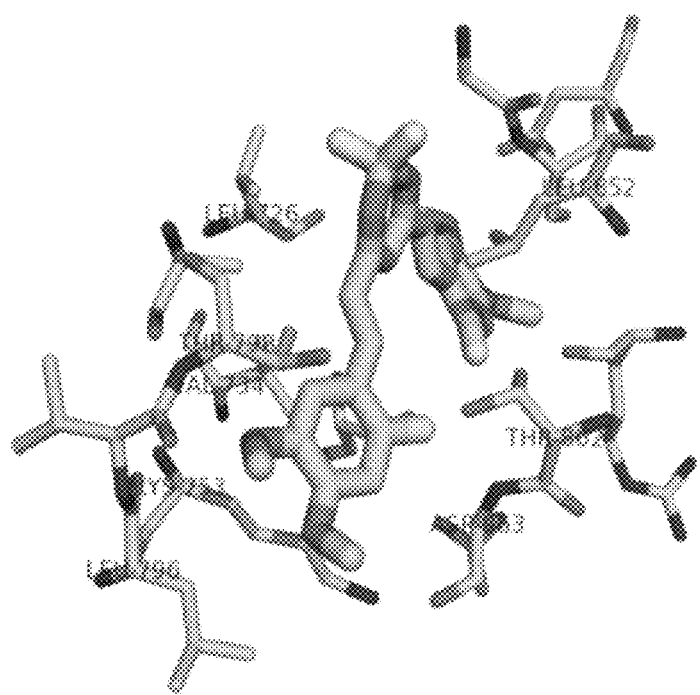
FIG. 17. Binding mode in the active site of HER2 of compound 14 as a model curcuminoid analog (3D-plot).
Figure 18:
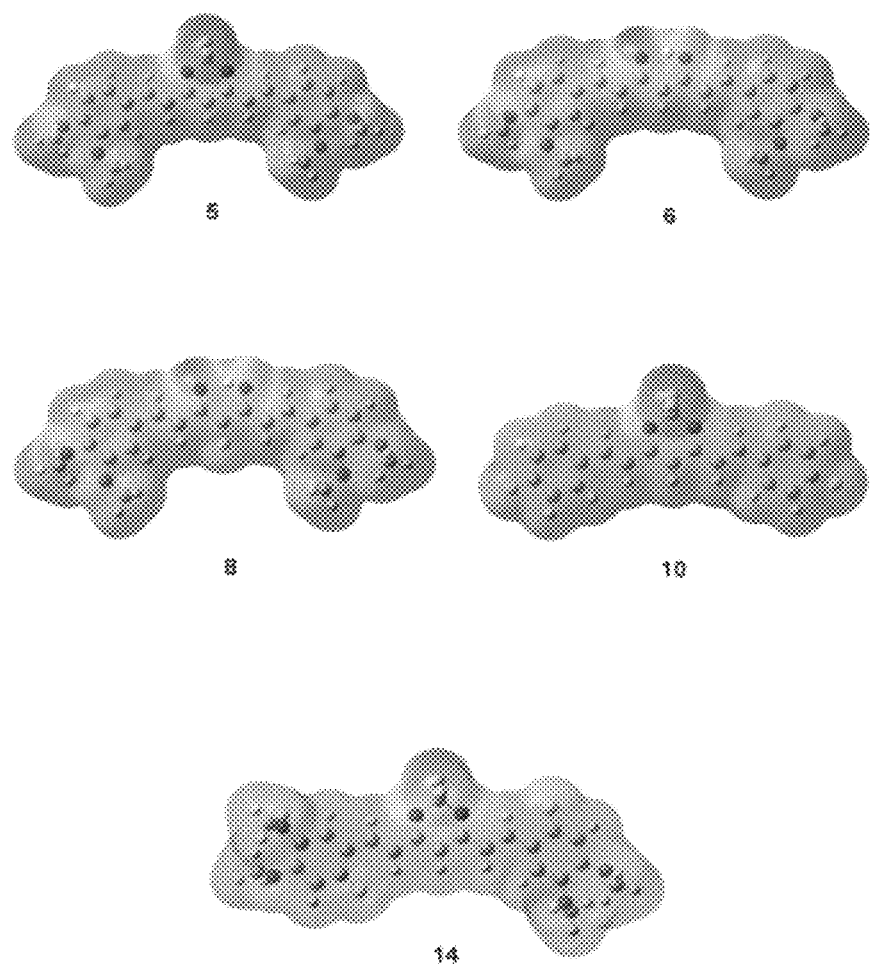
FIG. 18. Electrostatic potential maps for the most active curcuminoid derivatives.

Based on the magnitude of IC$_{50}$ values, seen in Table 3, compounds 5, 6, 8, 10 and 14, depicted in FIG. 15, exhibited high potencies toward multiple cancer cell lines, with measured activities at low micro-molar concentrations, and in the case of compound 5 in nano-molar concentration for leukemia. These anti-proliferative activity trends far exceed those of parent curcumin. It is noteworthy that three of these compounds are CUR—BF$_2$ adducts. Comparing the IC$_{50}$ data for compound 6 with the α-carbonyl-monofluorinated analog 8 indicates increased activity as a result fluorine introduction, notably against breast cancer. Compound 6 (DMC) was previously tested as an anti-prostate cancer agent. (L. Lin, et al., J. Med. Chem., 2006, 49, 3964-3972). The reported IC$_{50}$ values against PC3 and LNCap are near identical to those in the present study.

Some of the other fluorinated curcuminoids were also more active than their precursors, in particular against leukemia. The α-carbonyl-difluorinated analogs 3 and 12 of FIG. exhibited increased potency (against MOLT-4) ascomparedtotheir curcuminoid precursors 1 and 11. Overall, except for compound 11 of FIG. 2 which exhibited lower activity relative to curcumin, all others were more active than parent curcumin, but those shown in FIG. 15 were found to be the most promising lead compounds.

TABLE 3

| | Leukemia IC$_{50}$ (μM)$^{a,b}$ | Prostate Cancer IC$_{50}$ (μM)$^{a,c}$ | | Lung Cancer IC$_{50}$ (μM)$^{a,c}$ | Breast Cancer IC$_{50}$ (μM)$^{a,c}$ |
|---|---|---|---|---|---|
| Cell Line | MOLT-4 | PC3 | LNCap | A549 | MDA231 |
| Curcuminoid | | | | | |
| Parent 1 | 19 | 9.0 | 9.7 | 18.0 | 11.5 |
| 4 | 3.6* | 7.4 | 13.0 | 20.0 | 6.2 |

In vitro cell viability bioassay$^a$ of selected compounds of FIG. 2

TABLE 3-continued

In vitro cell viability bioassay[r] of selected compounds of FIG. 2

| | Leukemia IC$_{50}$ (μM)[a,b] | Prostate Cancer IC$_{50}$ (μM)[a,c] | | Lung Cancer IC$_{50}$ (μM)[a,c] | Breast Cancer IC$_{50}$ (μM)[a,c] |
|---|---|---|---|---|---|
| Cell Line | MOLT-4 | PC3 | LNCap | A549 | MDA231 |
| 3 | 0.66** | 15.0 | 28.0 | 26.0 | 2.2* |
| 10 | 1.5* | 1.9* | 4.3 | 7.3 | 1.0* |
| 11 | 28.0 | 14.0 | 30.0 | 29.0 | 20.0 |
| 13 | 2.8* | 38.0 | 7.0 | 60.0 | 12.0 |
| 6 | 0.043*** | 1.0* | 1.2* | 7.1 | 0.28** |
| 5 | 0.56 (nM)**** | 3.2* | 0.37** | 1.5* | 2.0* |
| 12 | 1.32* | nd | 29.2 | nd | 6.7 |
| 8[+] | 0.076*** | nd | 0.19** | nd | 0.023*** |
| 7 | 1.07* | nd | 21.3 | nd | 2.1* |
| 14 | 0.10** | nd | 2.98* | nd | 1.7* |
| 15 | 1.58* | nd | 13.2 | nd | 20 |

[r]Curcuminoids with: IC$_{50}$ < 4 micro-molar are considered active*; IC$_{50}$ < 1 micro-molar considered highly active; IC50 < 0.1 micro-molar considered potent*; IC$_{50}$ values in the nano-molar range are considered highly potent****; compounds were chemically stable at r.t. in DMSO (solvent used for bioassay)
[a]IC$_{50}$ is drug concentration that can inhibit 50% of cell growth
[b]Cell viability was analyzed by the CellTiter-Glo ® Luminescent Cell Viability Assay
[c]Cell viability was analyzed by the MTT assay
[+]contained circa 25% of the diketo-tautomer 9
nd = not determined The CUR—BF$_2$ adducts 5, 10, and 19, the (CF$_3$)$_2$—CUR 20 and the (CF$_3$)$_2$—CUR—BF$_2$ adduct 21 of FIG. 2 were screened at the National Cancer Institute using NCI-60 cell one-dose protocol ($10^{-5}$ M). Compounds 10, 19, and 21 of FIG. 2 exhibited relatively modest growth inhibition activities (10-20%) that were below the threshold criteria for further testing. The CUR—BF$_2$ adduct 5 of FIG. 2, on the other hand, proved highly active with growth inhibition (70%-80%) and cell death (up to 33%) and has been selected by NCI for further testing.

Computational Docking Study

In an effort to shed some light on the factors determining the bioactivity of these curcumin analogues, molecular docking calculations were performed in the active site of HER2. Human epidermal growth factor receptor 2 (HER2) is one of the tyrosine kinase receptors in EGFR family, which is known to play a central role in the pathogenesis of several human cancers. (N. Iqbal, et al., *Mol. Biol. Int.,* 2014, 2014, 852748). Amplification or overexpression of HER2 occurs in breast, prostate, gastric/gastroesophageal, ovarian, endometrial, bladder, lung, colon, and head and neck cancers. Therefore, it is a drug target for cancer therapy focusing on inhibiting HER2 to reduce tumor growth. (N. Iqbal, et al., *Mol. Biol. Int.,* 2014, 2014, 852748). Taking this into account, binding energies in HER2 were compared with the bioactivity data (IC$_{50}$ MDA231; breast cancer) in the search for correlations between the HER2 inhibitory activity and inhibition of cancer cells growth.

The curcuminoid derivatives fitted nicely in the tunnel-like binding pocket of HER2, where they mainly established hydrophobic contacts. The more bioactive analogs (as in compound 14 of FIG. 2) interacted with the residues Leu726, Thr798, Lys753, Leu796, Thr862, Asp863, Val734, and Leu852, seen in FIGS. 10 and 11, similar to the potent HER2 tyrosine kinase domain (HER2-TK) inhibitor SYR127063 (2-{2-[4-({5-chloro-6-[3-(trifluoromethyl)) phenoxy]pyridin-3-yl}amino)-5H-pyrrolo[3,2-d]pyrimidin-5-yl]ethoxy}ethanol). In addition to its numerous hydrophobic interactions, SYR also formed hydrogen bonds with Met8, Asp863 and Asn850. A hydrogen bond with Met801 was also observed for the difluorinated curcuminoid 3 of FIG. 2. Table 4 provides a comparison between docking energies in HER2 and the measured IC$_{50}$ values for MDA231, showing that curcuminoids-BF$_2$ adducts 10, 14, and 5 of FIG. 2 exhibit both favorable docking energy and cytotoxicity against breast cancer. Inhibition of tumor cellular proteasome has been suggested as the mechanism by which curcumin arrests the proliferation of acute promyelocytic leukemia (APL) cells. (K.-L. Tan, et al., *ChemMedChem.,* 2012, 7, 1567-1579).

TABLE 4

Binding Energies in HER2 for Selected Compounds of FIG. 2

| Compound | AutoDock 4.2 | AutoDock Vina | IC$_{50}$ MDA231 (Breast cancer) |
|---|---|---|---|
| SYR (native ligand) | −5.06 kcal/mol | −11.4 kcal/mol | |
| (structure shown below) | −5.05 kcal/mol | −8.2 kcal/mol[a]<br>−7.9 kcal/mol[b] | 0.023 |

TABLE 4-continued
Binding Energies in HER2 for Selected Compounds of FIG. 2
| Compound | AutoDock 4.2 | AutoDock Vina | IC$_{50}$ MDA231 (Breast cancer) |
|---|---|---|---|
| 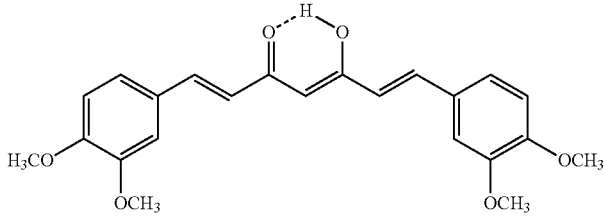 6 | −5.34 kcal/mol | −8.0 kcal/mol[a]<br>−7.8 kcal/mol[b] | 0.28 |
| 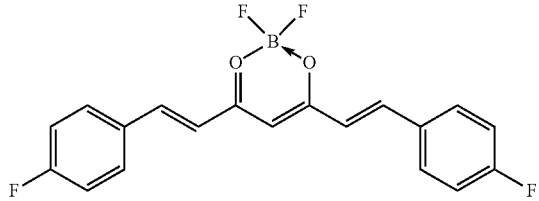 10 | −4.08 kcal/mol | −10.6 kcal/mol | 1.0 |
| 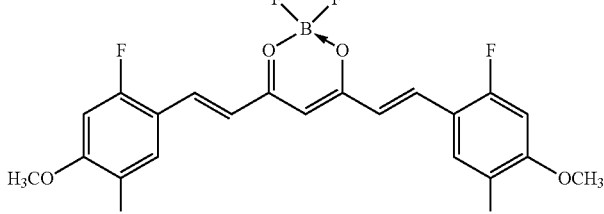 14 | −4.75 kcal/mol[a]<br>−4.36 kcal/mol[b] | −9.1 kcal/mol | 1.7 |
| 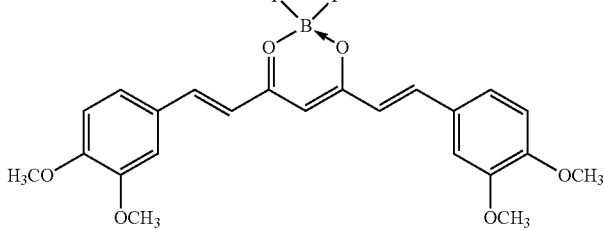 5 | −4.79 kcal/mol<br>−4.42 kcal/mol | −9.6 kcal/mol | 2.0 |
| 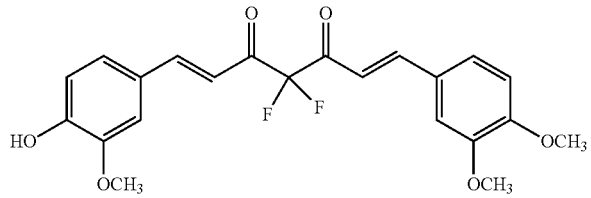 3 | −5.65 kcal/mol | −9.3 kcal/mol[a]<br>−9.0 kcal/mol[b] | 2.2 |

TABLE 4-continued

Binding Energies in HER2 for Selected Compounds of FIG. 2

| Compound | AutoDock 4.2 | AutoDock Vina | IC$_{50}$ MDA231 (Breast cancer) |
|---|---|---|---|
| 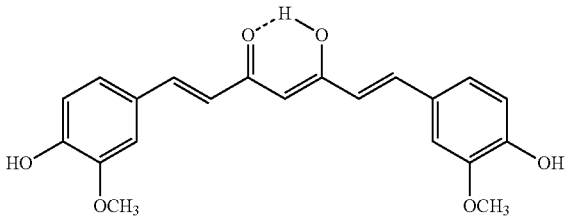 1 | −6.18 kcal/mol[a]<br>−5.61 kcal/mol[b] | −8.4 kcal/mol[a]<br>−7.5 kcal/mol[b] | 11.5 |
| 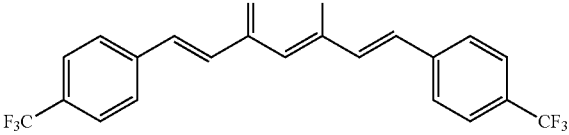 19 | −4.25 kcal/mol[a]<br>−3.30 kcal/mol[b] | −10.5 kcal/mol[a]<br>−10.4 kcal/mol[b] | NCI-60 cell screening modest activity |
| 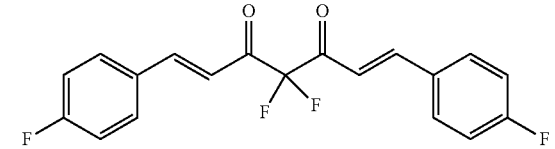 12 | −4.46 kcal/mol | −10.5 kcal/mol[a,b]<br>−10.4 kcal/mol[b] | 6.7 |
| 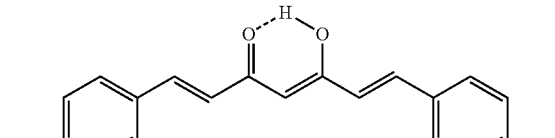 11 | −4.50 kcal/mol | −10.3 kcal/mol | 20 |
| 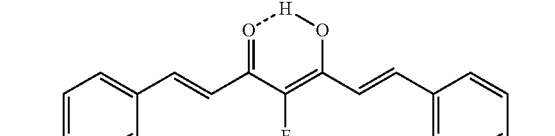 13 | −4.34 kcal/mol | −9.9 kcal/mol | 12.0 |
| 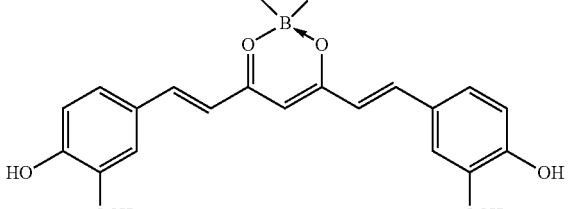 2 | −5.56 kcal/mol | −9.5 kcal/mol | — |

TABLE 4-continued

Binding Energies in HER2 for Selected Compounds of FIG. 2

| Compound | AutoDock 4.2 | AutoDock Vina | $IC_{50}$ MDA231 (Breast cancer) |
|---|---|---|---|
| 4 (fluoro-curcumin analog: two 4-hydroxy-3-methoxyphenyl groups connected via vinyl linkers to a central β-fluoro-β-diketone with intramolecular H-bond) | −5.78 kcal/mol | −8.5 kcal/mol[a]<br>−8.1 kcal/mol[b] | 6.2 |

[a] Most stable binding mode.
[b] Binding pose most similar to SYR.

Considering the high degree of potency against leukemia observed in the present study, in particular by 5, 6, 8, and 14 of FIG. 2, docking calculations were also performed in proteasome, as seen in Table 5. The structure of the 20S proteasome (β5 and β6 subunits) was obtained from the Protein Data Bank. Treatment with proteasome inhibitors results in decrease proliferation, induction of apoptosis, and sensitization of a variety of tumor cells to chemotherapeutic agents and irradiation. Docking calculations for curcuminoids resulted in binding energies that were similar to parent curcumin itself, but judging from their $IC_{50}$ values these compounds are more active.

TABLE 5

Binding Energies in Proteasome for Selected Compounds of FIG. 2

| Compound | AutoDock Vina (kcal/mol) | Leukemia MOLT-4 $IC_{50}$ (μM) |
|---|---|---|
| 1 (curcumin: two 4-hydroxy-3-methoxyphenyl groups linked via vinyls to central β-diketone enol) | −8.0 | 19.0 |
| 6 (tetramethoxy analog: two 3,4-dimethoxyphenyl groups linked via vinyls to central β-diketone enol) | −7.5 | 0.043 |
| 5 (BF$_2$ complex of 6: two 3,4-dimethoxyphenyl groups linked via vinyls to central β-diketonato-BF$_2$ ring) | −7.4 | 0.00056 |

TABLE 5-continued

Binding Energies in Proteasome for Selected Compounds of FIG. 2

| Compound | AutoDock Vina (kcal/mol) | Leukemia MOLT-4 IC$_{50}$ (μM) |
|---|---|---|
| 8 (structure) | −7.2 | 0.076 |
| 14 (structure) | −7.9 | 0.01 |

Figure 12:
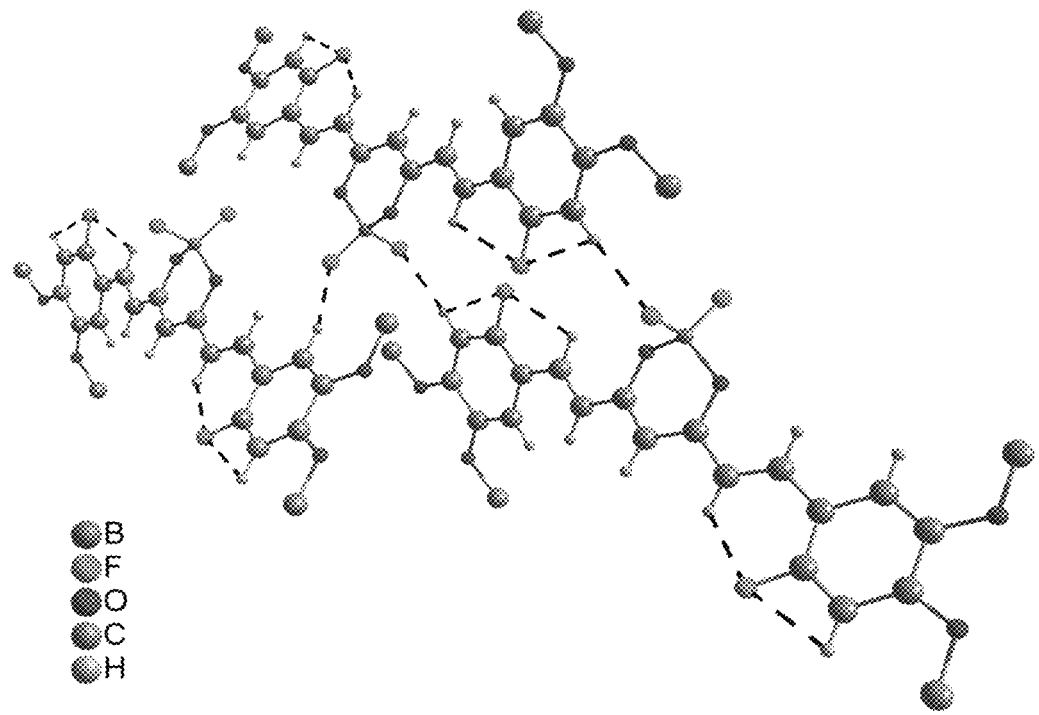
FIG. 12. Crystal packing diagram of 14. Selected hydrogen atoms have been removed for clarity. Compound 14 crystallizes in the triclinic space group $P\bar{1}$. The asymmetric unit corresponds to one molecule with a total of two molecules in each cell. Each molecule interacts with two adjacent molecules via two H—F contacts of 2.2674(19) and 2.3567(29) Å. The molecule also contains two intramolecular H—F contacts with distances of 2.4602(21) and 2.5059(21) Å.

Considering the high bioactivity and favorable docking energies of compounds 5, 6, 8, 10, and 14 of FIG. 2, their electrostatic potential maps were computed and are shown in FIG. 12 for a better visualization of the electronic properties of these molecules. Molecular electrostatic potential is a useful tool for interpreting and getting insight into the role played by electrostatic forces in the interactions between biomolecules and their ligands.

For this family of compounds, the most notable observation is the negative electrostatic potential developed by the BF$_2$ and the keto-enol moiety.

CUR-Inspired Compounds Effectiveness Against Cancer

Figure 19:
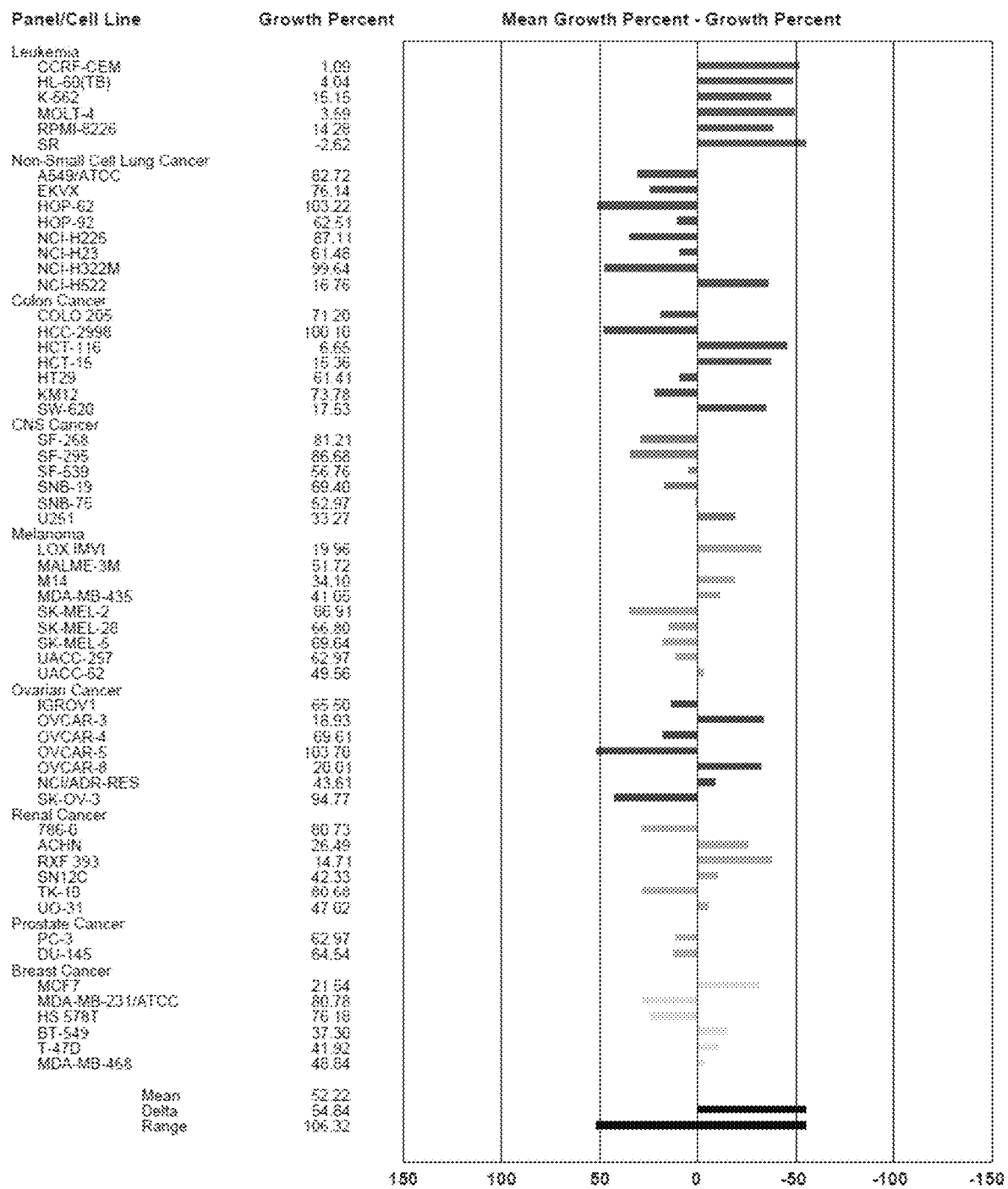
FIG. 19. Dose mean graph of 1,7-bis(2,3,6-trimethoxyphenyl)hepta-1,4,6-triene-3,5-dione for various cancer cell lines at $1 \times 10^{-5}$ M.
Figure 20:
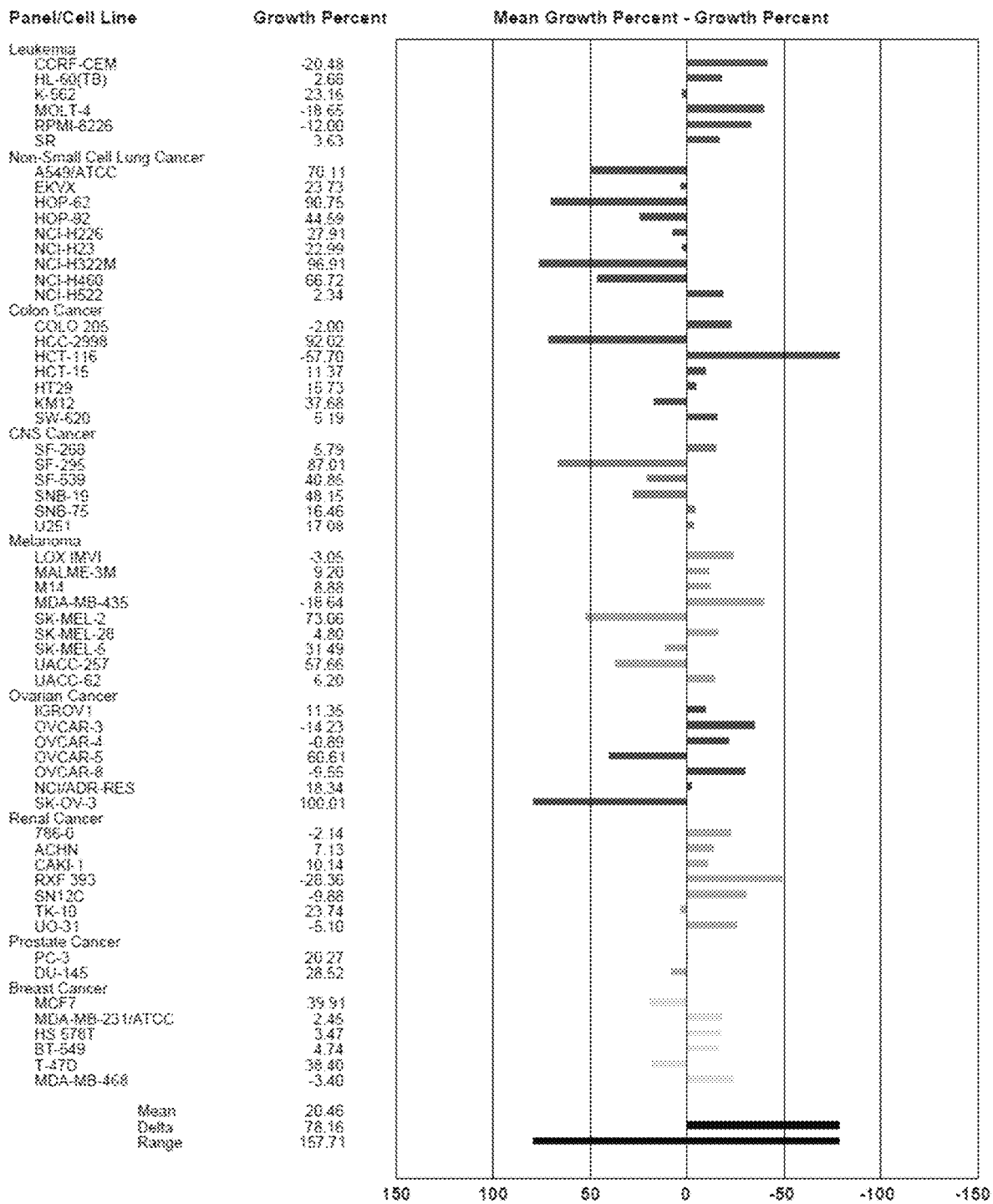
FIG. 20. Dose mean graph of 1,7-bis(3-benzothiophene)hepta-1,4,6-triene-3,5-dione for various cancer cell lines at $1 \times 10^{-5}$ M.
Figure 21:
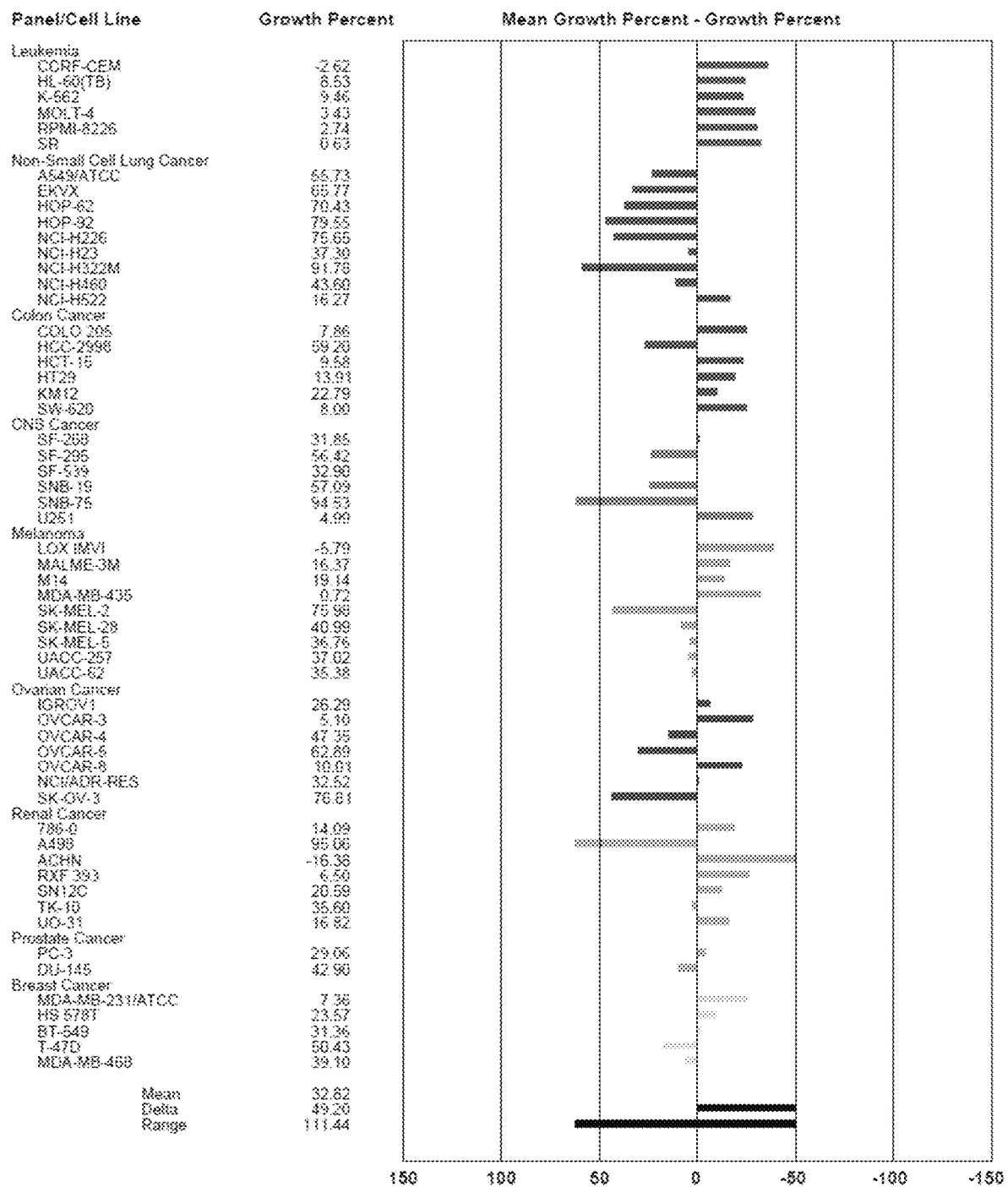
FIG. 21. Dose mean graph of bis(2,3,4-trimethoxy)hepta-1,4,6-triene-3,5-dione boron-difluoride adduct for various cancer cell lines at $1 \times 10^{-5}$ M.
Figure 22:
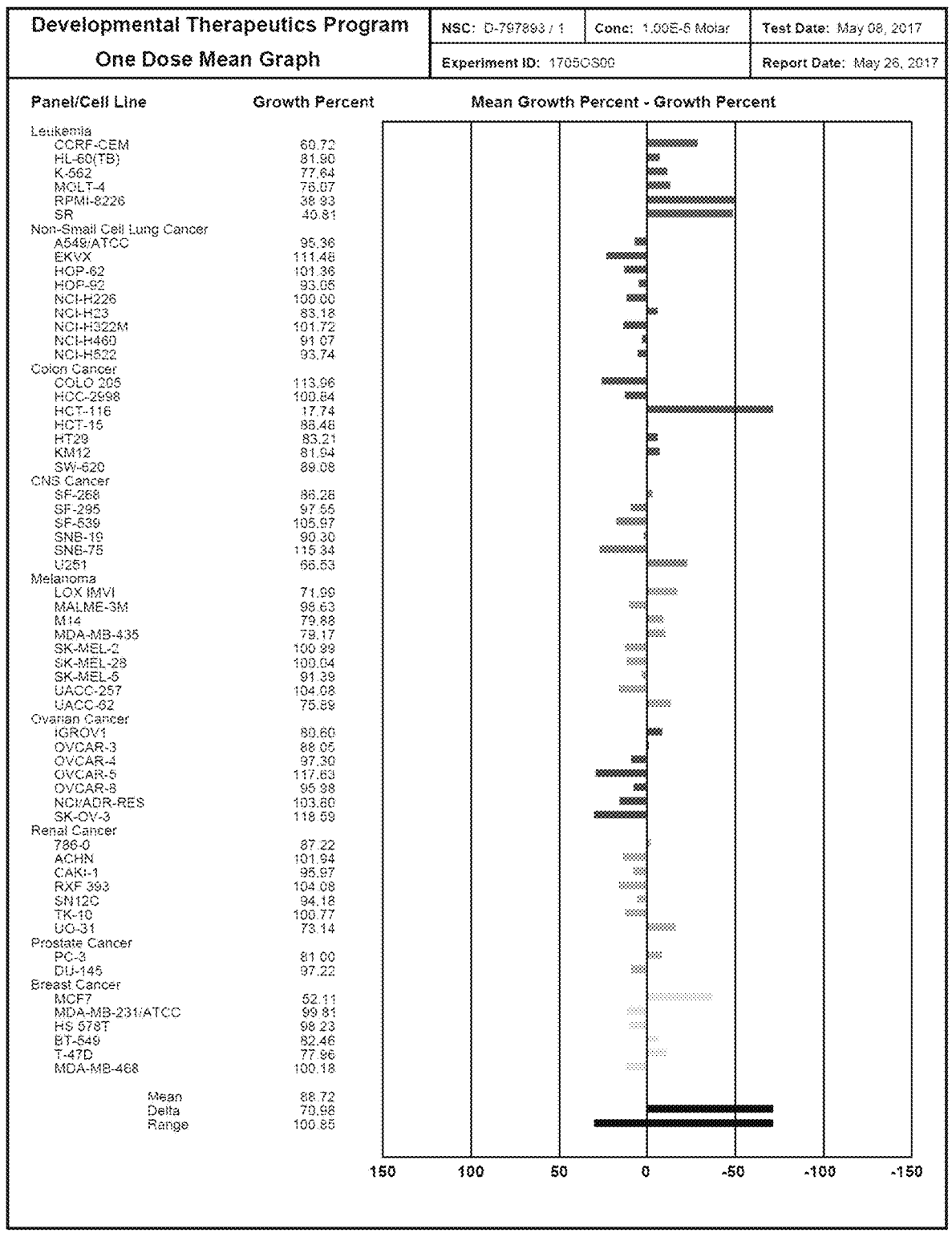
FIG. 22. Dose mean graph of bis(4-Trifluoromethylthio) CUR. It shows high anti-proliferative potency against HCT-116
Figure 23:
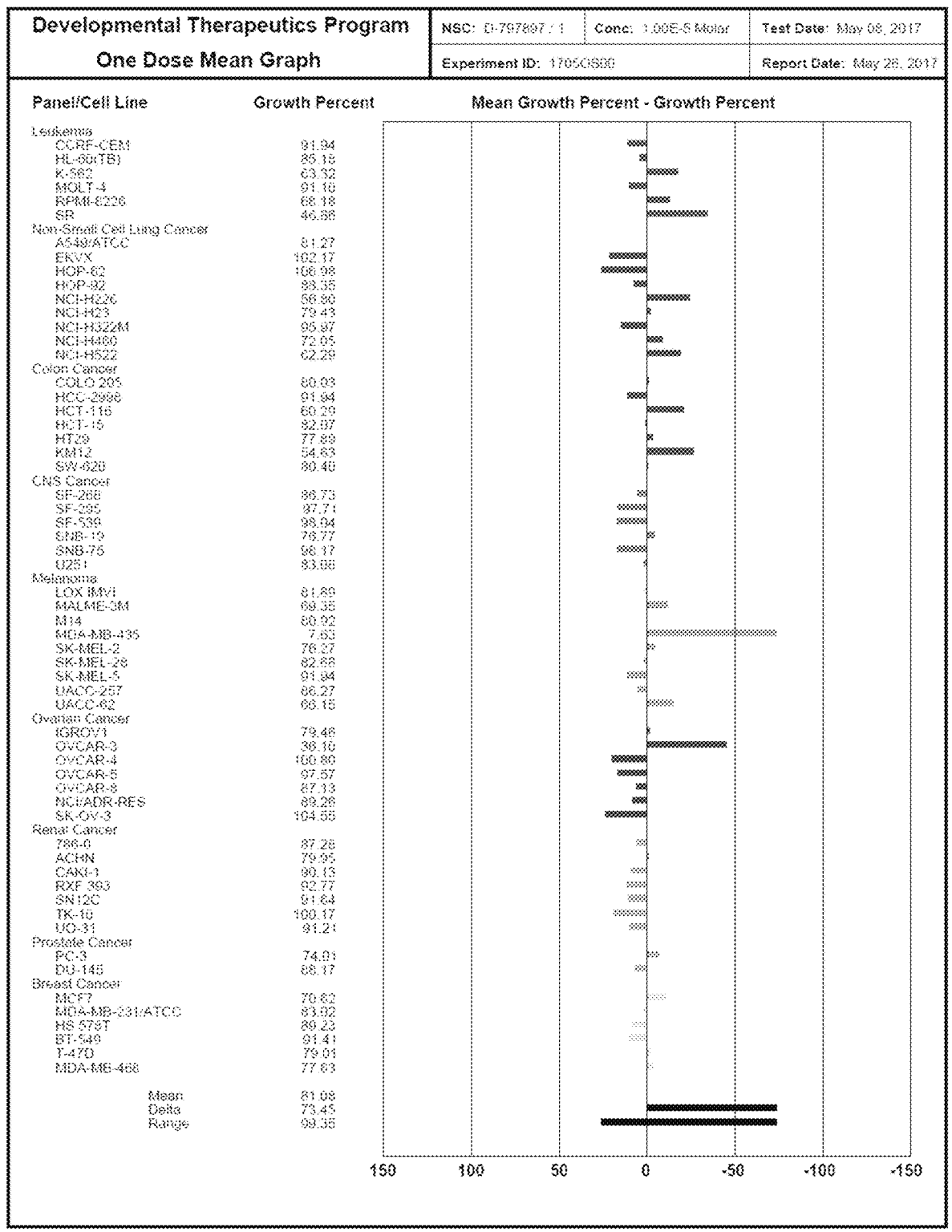
FIG. 23. Dose mean graph of bis(6-Fluoro-3,4-dimethoxy)CUR-isoxazole adduct. It shows notable anti-proliferative potency against Melanoma MDA-MB-433 cell line.
Figure 24:
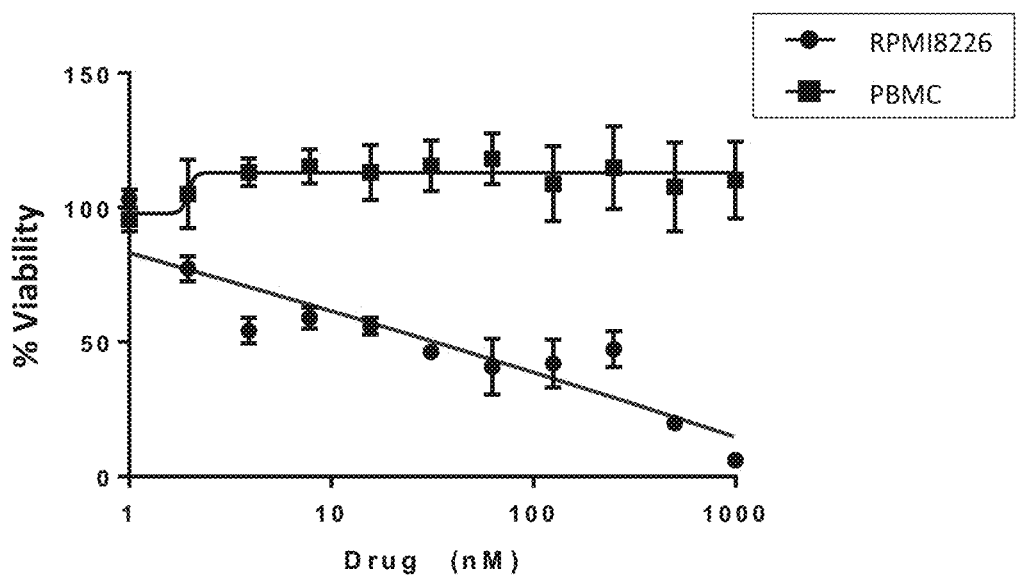
FIG. 24. $IC_{50}$ graph for 1,7-bis(3-benzothiophene)hepta-1,4,6-triene-3,5-dione in cancer cells (RPMI8226) and healthy cells (PBMC).
Figure 25:
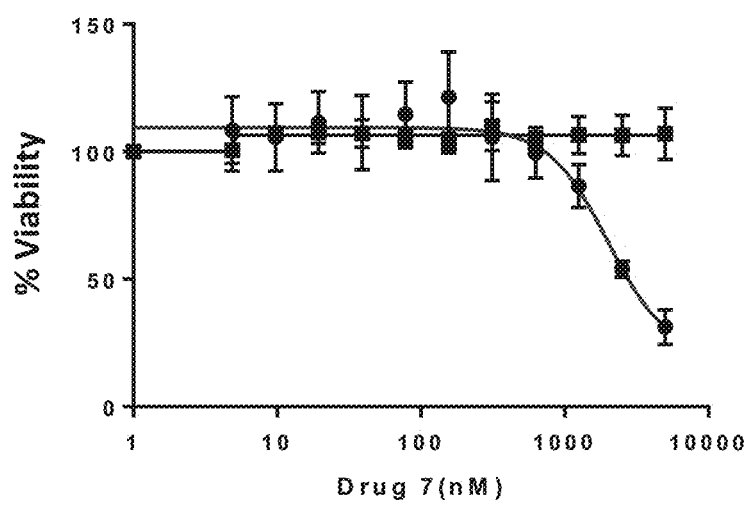
FIG. 25. $IC_{50}$ graph for 1,7-bis(3,4-dimethoxyphenyl)hepta-1,6-diene-3,5-dione in cancer cells (RPMI8226) and healthy cells (PBMC).
Figure 26:
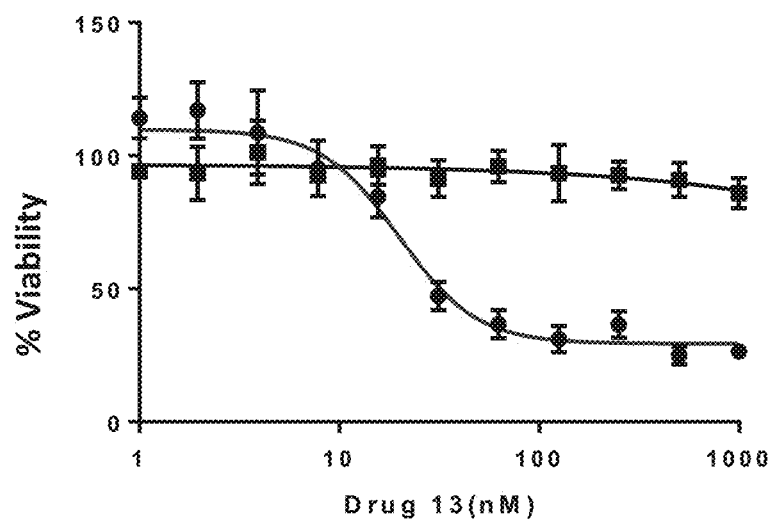
FIG. 26. $IC_{50}$ graph for 1,7-bis(2,3,4-trimethoxyphenyl)hepta-1,4,6-triene-3,5-dione in cancer cells (RPMI8226) and healthy cells (PBMC).
Figure 27:
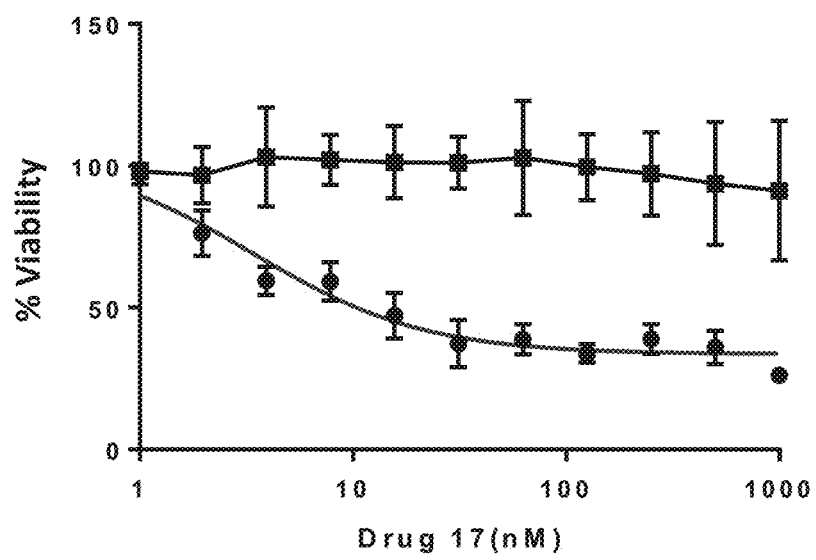
FIG. 27. $IC_{50}$ graph for 1,7-bis(2-benzothiophene)hepta-1,4,6-triene-3,5-dione in cancer cells (RPMI8226) and healthy cells (PBMC).
Figure 28:
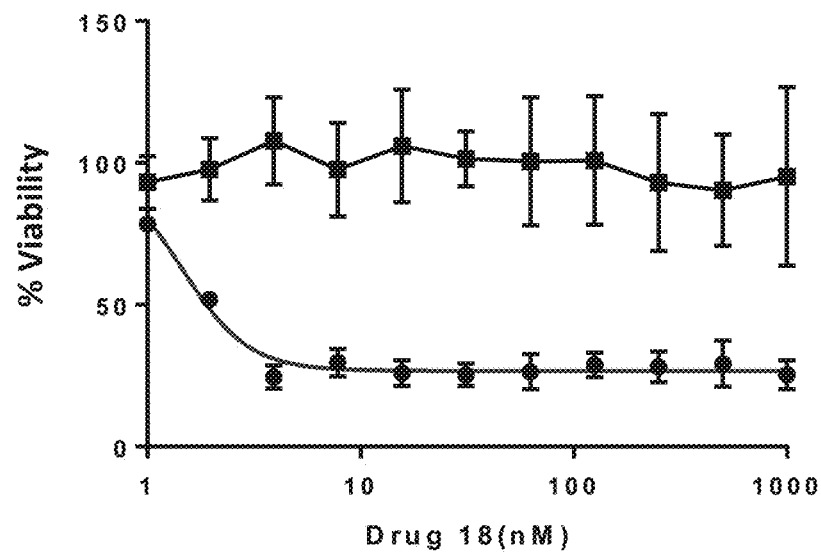
FIG. 28. $IC_{50}$ graph for 1,7-bis(2-benzothiophene)hepta-1,4,6-triene-3,5-dione-boron-difluoride adduct in cancer cells (RPMI8226) and healthy cells (PBMC).
Figure 29:
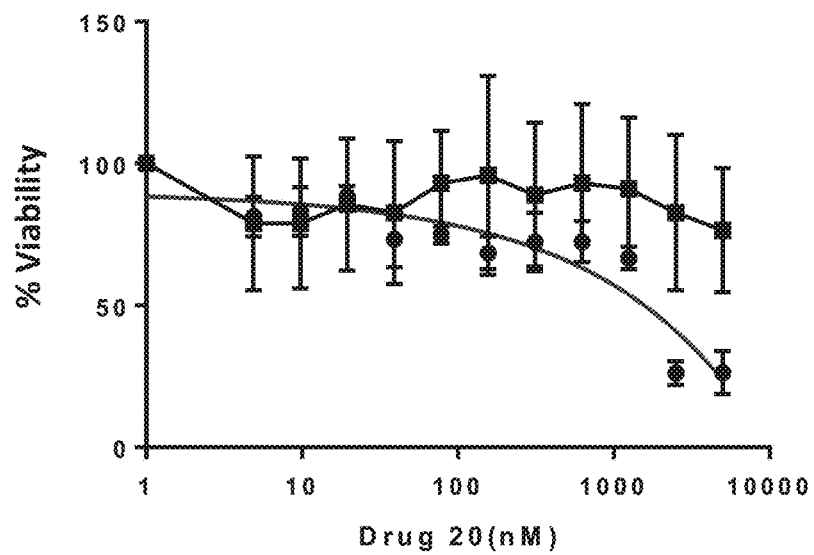
FIG. 29. $IC_{50}$ graph for 1,7-bis(3-trifluoromethoxyphenyl)hepta-1,4,6-triene-3,5-dione-boron-difluoride adduct in cancer cells (RPMI8226) and healthy cells (PBMC).
Figure 30:
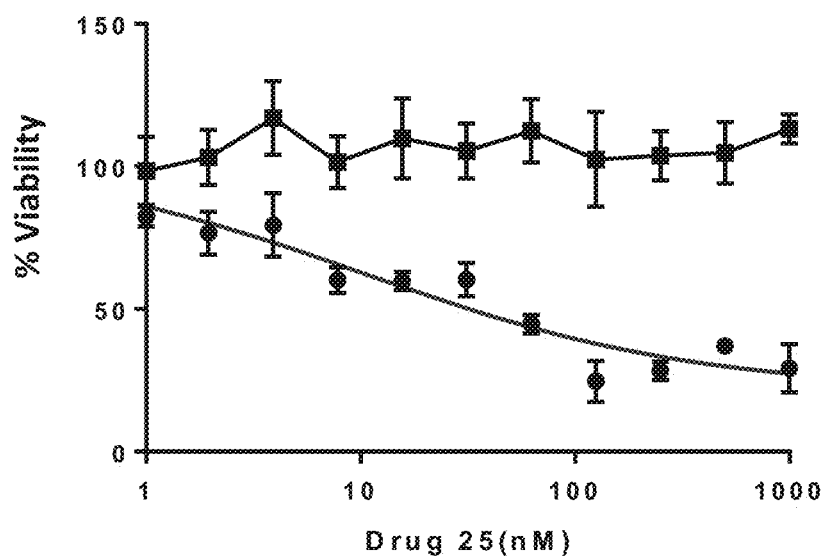
FIG. 30. $IC_{50}$ graph for 1,7-bis(3,4-dibenzyloxyphenyl)hepta-1,4,6-triene-3,5-dione in cancer cells (RPMI8226) and healthy cells (PBMC).
Figure 31:
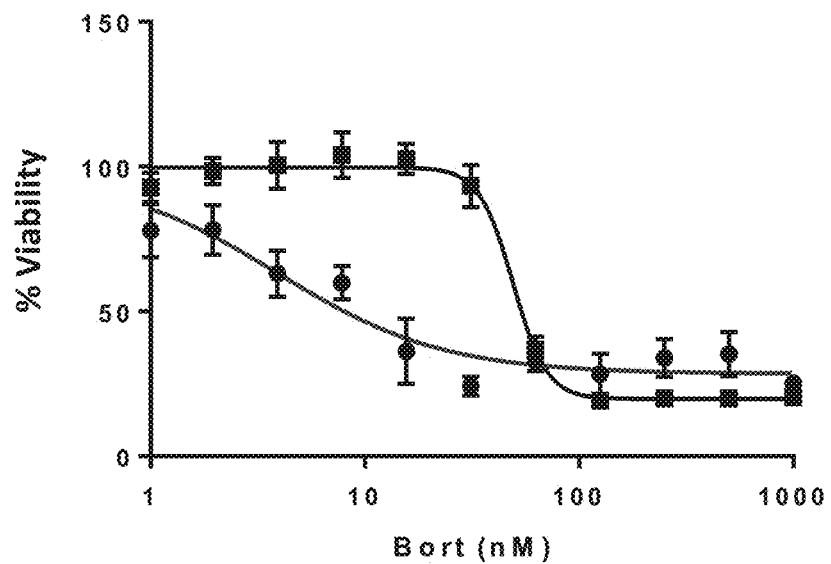
FIG. 31. $IC_{50}$ graph for bortezomib in cancer cells (RPMI8226) and healthy cells (PBMC).
Figure 32:
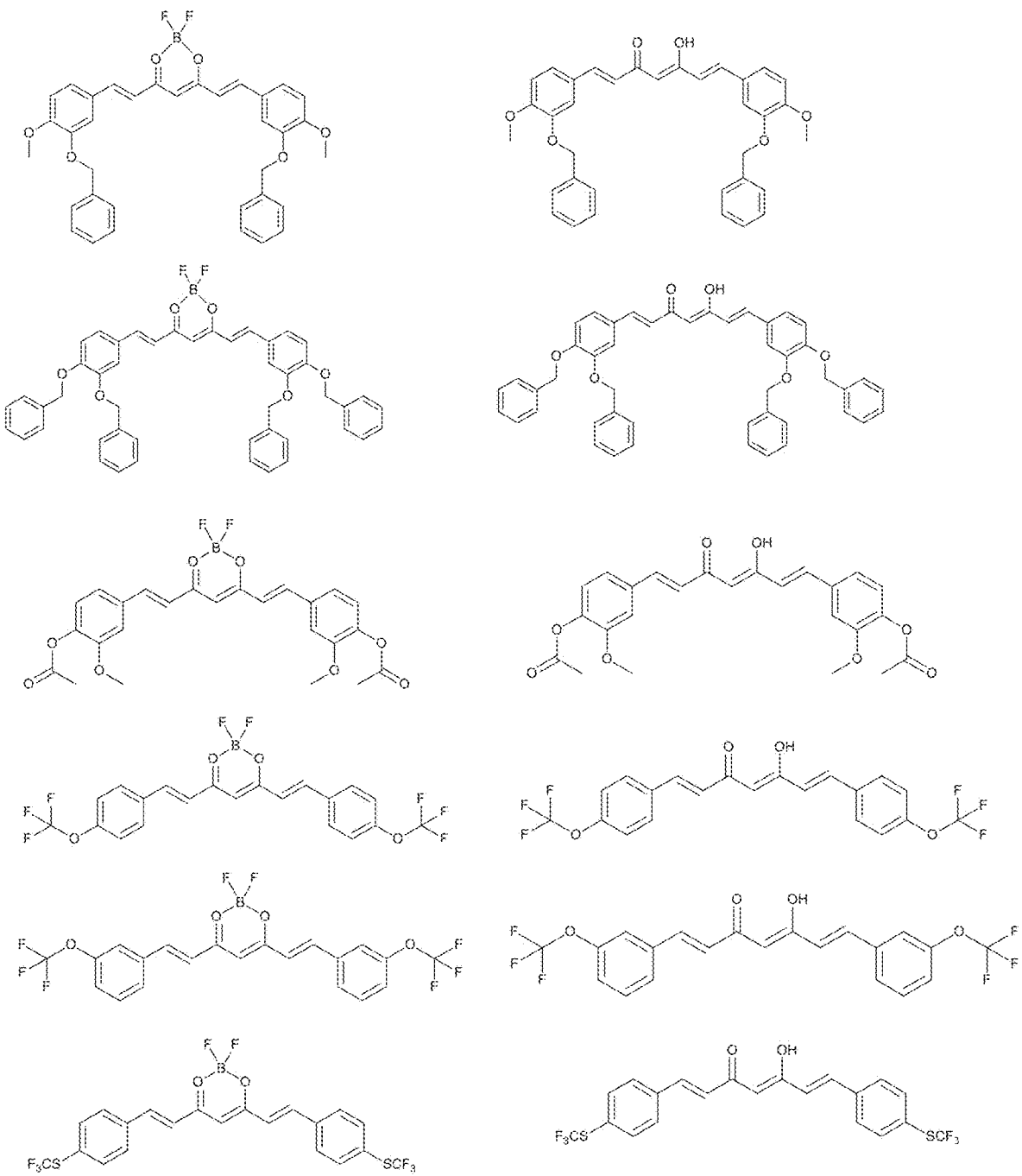
FIG. 32. List of mono- and di-substituted curcuminoid compounds and difluoroboron-curcuminoid adducts.
Figure 33:
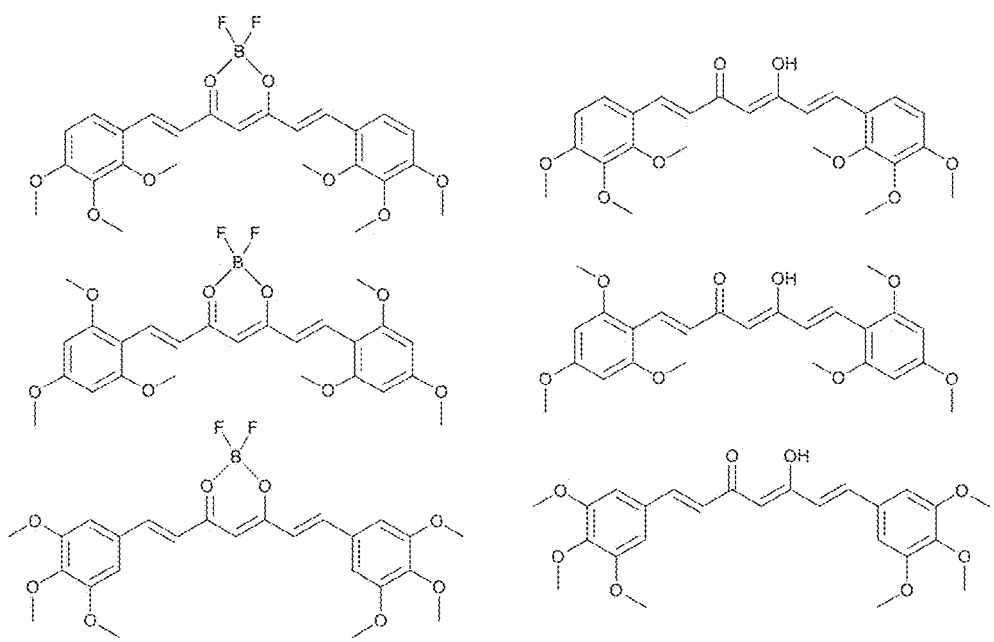
FIG. 33. List of tri-substituted curcuminoid compounds and difluoroboron-curcuminoid adducts.
Figure 34:
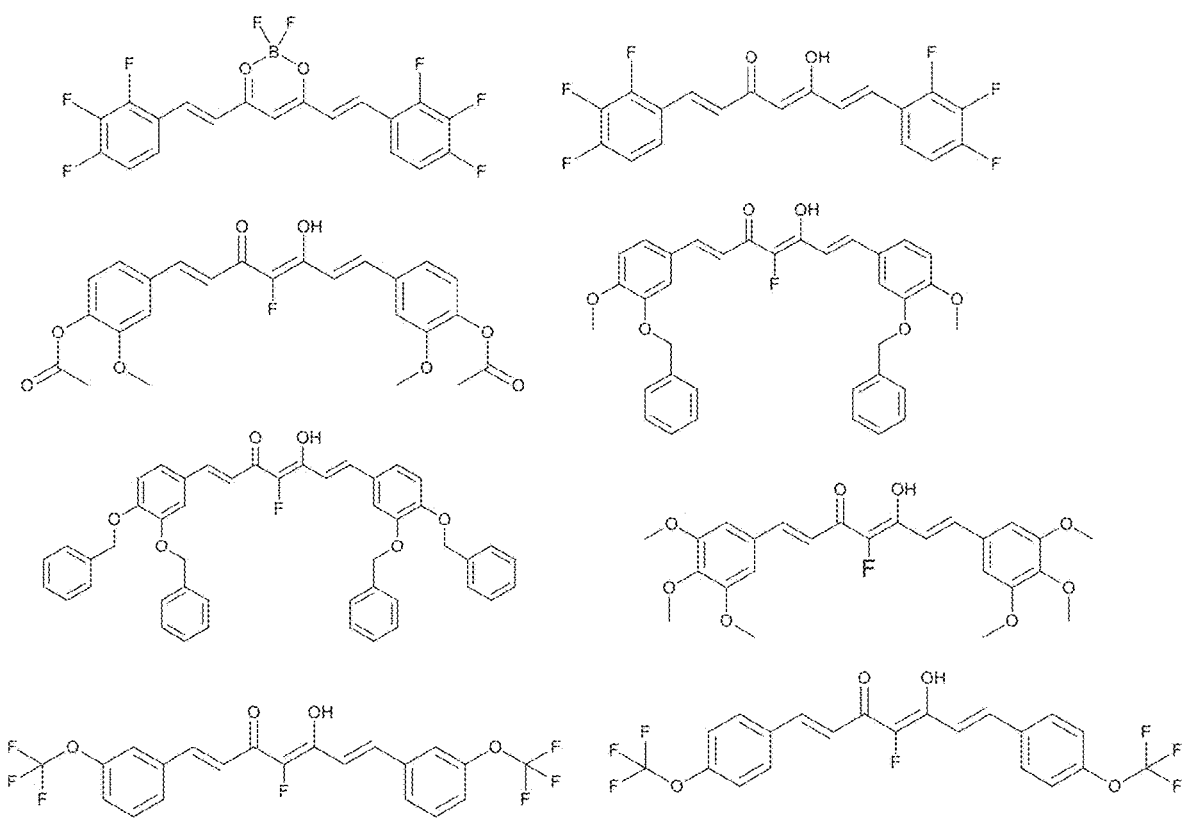
FIG. 34. List of selectively fluorinated curcuminoid compounds and difluoroboron-curcuminoid adducts.

Various cancer cell lines were seeded into 384-well culture plates at 2×10$^3$ cell/well and incubated at 5% CO$_2$, 37° C. The culture media was replaced with 1×10$^{-5}$ M of curcuminoid; 1,7-bis(2,3,6-trimethoxyphenyl)hepta-1,4,6-triene-3,5-dione, 7-bis(3-benzothiophene)hepta-1,4,6-triene-3,5-dione, or D-793176. The cell line growth was measured. As seen in FIG. 19, 1,7-bis(2,3,6-trimethoxyphenyl)hepta-1,4,6-triene-3,5-dione slowed growth for all cancer cell lines, reducing growth to at least 50% that seen in non-treated cells. Further, the compound showed substantial cell reductions for leukemia cells, as well as colon cancer, melanoma, renal, and breast cancer, as well as reduced growth or reduced growth and cell loss in prostate, non-small cell lung cancer, CNS cancer, ovarian cancer. Cell treatment with 1,7-bis(3-benzothiophene)hepta-1,4,6-triene-3,5-dione and D-793176 resulted in similar trends.

To confirm that the compounds targeted cancerous cells, and did not simply possess cytotoxic effects, the compounds were tested against cancer cells and non-cancerous cells. Peripheral blood mononuclear cells (PBMCs) were collected from healthy, i.e. non-cancerous, donors (CONTROL).

RPMI-8266 (Multiple myeloma cell line, MM) and PBCMs cells were seeded into 384-well culture plates at 2×10$^3$ cell/well in quadruplicate, and incubated at 5% CO$_2$, 37° C. The culture media was replaced with compounds (ranges from 0-10,000 nM) and incubated for 72 h. Bortezomib was spiked in control. EC$_{50}$ of bortezomib in RPMI8266 is typically ~10-16 nM. CellTiter-Glo® 2.0 reagent was added at equal volume to the cell culture medium present in each well and the plate was left to incubate at room temperature for 10 minutes to stabilize the luminescent signal. The plates were loaded onto a plate reader and luminescent signal/intensity from the 384-well plate read to provide IC$_{50}$ value graphs, as seen in FIGS. 19-25. EC$_{50}$ values were calculated as seen in Table 6 for run number 1 and Table 7 for run number 2.

TABLE 6

EC50 value calculations beginning with titration of 10,000 nM.

| Drug | RPMI8226 (nM) | PBMC (nM) |
|---|---|---|
| Drug 1 | 19 | >30000 |
| Drug 7 | 3890 | >30000 |
| Drug 13 | 26.33 | >17647 |
| Drug 17 | 26.39 | >30000 |
| Drug 18 | 1.3 | >12335 |
| Drug 20 | 1923 | 1267 |
| Drug 25 | 27.69 | >30000 |

TABLE 7

EC50 value calculations beginning with titration of 30,0000 nM.

| Drug | RPMI8226 (nM) | PBMC (nM) |
|---|---|---|
| Drug 1 | 23.5 | >1000 |
| Drug 7 | 2920 | >5000 |
| Drug 13 | 29.5 | >1000 |

TABLE 7-continued

EC50 value calculations beginning
with titration of 30,0000 nM.

| Drug | RPMI8226 (nM) | PBMC (nM) |
|---|---|---|
| Drug 17 | 13.3 | >1000 |
| Drug 18 | 2.4 | >1000 |
| Drug 20 | 1760 | >5000 |
| Drug 25 | 47.2 | >1000 |
| Bortezomib | 10.6 | 60.5 |

PBMC values between the two runs differ due to differences in the dose titration, which started at 10,000 nM in the first run, and which started at 30,0000 nM in the second run. Additionally, variation in PBMC's $EC_{50}$ are at least partially due to donor differences.

Comparative Discussion and Summary

A series of fluorinated curcumins and curcumin-$BF_2$ adducts have been synthesized and characterized. The α-carbonyl mono- and di-fluorinations were achieved by direct fluorination with Selectfluor, and ring fluorinated/trifluoromethylated CUR—$BF_2$ adducts were assembled in one-pot from the corresponding aldehydes. Structural features of the new curcuminoids were examined by multinuclear NMR, and by X-ray analysis (for three CUR—$BF_2$ adducts and a mono-fluorinated analog). A notable feature observed in the X-ray crystal structures is detection of intermolecular interactions via short H—F contacts. The $IC_{50}$ data from in-vitro cell growth inhibitory bioassay indicated that the majority of curcuminoids were more active relative to parent curcumin, but those shown in FIG. 15 were clearly superior. The bioassay data along with the NCI-60 screening suggest that CUR—$BF_2$ complexes bearing activating substituents in the phenyl rings (as in compound 5 of FIG. 2) may be promising drug candidates, and that introduction of F or $CF_3$ groups into the phenyl rings is not particularly beneficial. The finding that compound 8 of FIG. 2 is more potent than compound 6 of FIG. 2 implies that monofluorinaton at the α-carbonyl position can be beneficial. The fact that activity of $F_2$—CUR analogs (3, 12, 7, and 16 of FIG. 2) were not particularly impressive reinforces the earlier conclusions that the enolic tautomer is an important feature in binding of curcumin to proteins. (S. C. Gupta, et al., *Nat. Prod. Rep.* 2011, 28, 1937-1955; K.-L. Tan, et al., *Chem Med Chem.*, 2012, 7, 1567-1579). Model molecular docking calculations in the active site of HER2 indicated that the curcuminoid derivatives can fit nicely in the tunnel-like binding pocket of HER2 by establishing hydrophobic contacts, leading to favorable docking energies.

In summary, the present study has provided notable structural clues that when brought to bear could lead to the synthesis of effective drug targets based on curcumin. Synthesis and characterization of other fluorocurcuminoids are ongoing in this laboratory and collaborative studies aimed at understanding how fluorination contributes to inhibition of cell viability are planned.

Experimental Section

General. Synthetic curcumin, fluorinated aldehydes (p-fluorobenzaldehyde, 6-fluorovetraldehyde, vetraldehyde, and p-trifluoromethylbenzaldehyde), Selectfluor, and acetylacetone were all high purity commercially available samples and were used without further purification. Regular solvents used for synthesis (MeCN, acetone, DCM, hexane, and EtOAc) were all of sufficient purity and were used as received. Column chromatography was performed on silica gel (63-200 mesh). NMR spectra were recorded on a 500 MHz instrument using $CDCl_3$, DMSO-$d_6$, or MeCN-$d_3$ as solvent. $^{19}F$ NMR and $^{11}B$ NMR spectra were referenced relative to external $CFCl_3$ and $BF_3.Et_2O$ respectively. HRMS analyses were performed on an LC-MS instrument in electrospray mode using DMSO as solvent. FT-IR spectra were recorded in ATR mode in solvent. Microwave reactions were performed in a miniature 400 W lab microwave in 5 mL vials with magnetic stirring. Melting points were measured in open capillaries and are not corrected.

Typical procedure for difluorination of curcuminoids: Selectfluor (2.2 equiv.) was added in one portion to a solution of the curcuminoid (0.75 mmol) in methanol (25 mL) at r.t. (at 55° C. in case of compounds 6 and 11 of FIG. 2) with efficient stirring under a nitrogen atmosphere for the requisite time (either 4 hrs at 55° C. or overnight for r.t.) until completion (TLC monitoring). The MeOH solvent was then removed in vacuo and the reaction mass was dissolved in DCM (3×10 mL), washed with deionized water (3×10), dried (sodium sulfate) and filtered through a coarse sintered glass funnel. The DCM was removed in vacuo and the crude mixture was purified by flash chromatography eluting with hexane and ethyl acetate (refer to analytical data), ramping of the elution solvent was employed in all cases.

Specific procedure—difluorination of 11 of FIG. 2: Selectfluor (2.5 eq, 1.04 mmol, 371 mg) was added in one portion to a solution of 11 (0.42 mmol, 131 mg) in methanol (20 mL) under a nitrogen atmosphere, and the mixture was stirred under mild reflux at 55° C. overnight. Completion of the reaction was confirmed by TLC and the solvent was removed in vacuo. The reaction mass was dissolved in DCM (3×10 mL) and washed with deionized water (3×10). The organic layer was dried (sodium sulfate), filtered through a coarse sintered glass funnel, and the solvent was removed in vacuo. The difluoro-derivative (compound 12) precipitated out of the crude reaction mixture as a white crystalline solid by addition of hexane/EtOAc (20%); 62 mg, 0.18 mmol, 42% yield.

Typical procedure for mono-fluorination of curcuminoids of FIG. 2: Selectfluor (0.8 mmol, 1.05 equiv.) was added in one portion to a solution of the curcuminoid (0.75 mmol) in acetonitrile (25 mL) at 0° C. under a nitrogen atmosphere, and the mixture was stirred for 6 hours at this temperature, followed by overnight stirring at r.t. Upon completion (verified by TLC) the solvent was removed in vacuo and the reaction mass was dissolved in DCM (3×10 mL). The reaction mixture was washed with deionized water (3×10 mL), dried over sodium sulfate and filtered through a coarse sintered glass funnel. The solvent was removed in vacuo and the crude reaction mixture was purified by flash chromatography eluting with hexane/ethyl acetate (refer to analytical data), ramping of the elution solvent was employed in all cases).

Specific procedure—monofluorination of 11 of FIG. 2: Selectfluor (0.81 mmol, 1.05 eq, 286 mg) was added in one portion to a solution of 11 (0.38 mmol, 119 mg) in acetonitrile (20 mL) at 0° C. under a nitrogen atmosphere, and the mixture was stirred for 6 hrs at this temperature, followed by overnight stirring at r.t. Upon completion (monitored by TLC), the acetonitrile was removed in vacuo and the reaction mass was dissolved in DCM (3×10 mL). Following the steps outlined in the typical procedure and flash chromatography (hexane/EtOAc (5%), the monofluorinated product 13 was obtained as a yellow solid (54 mg, 0.1635 mmol, 43% yield).

Synthesis of acetylacetone-difluoroboron adduct: Following a similar procedure described by Fraser et al, to a mixture of acetylacetone (10 mmol, 1 g) in dry DCM (50 mL, distilled from P$_2$O$_5$) under a nitrogen atmosphere BF$_3$.Et$_2$O (~48%; 2.126 g, 1.89 mL, 15 mmol, 1.5 equiv) was slowly added over a period of 5 minutes, and the reaction mixture was refluxed (41° C.) for 12 hrs. (S. Xu, et al., *Inorg. Chem.*, 2013, 52, 3597-3610). Upon completion of the reaction, the reaction mixture was allowed to come to room temperature and quenched with DI water (15 mL). It was transferred to a large separatory funnel, the DCM layer was separated, and the aqueous layer was discarded (the aqueous layer was quite acidic with a pH of about 1 or less). The reaction mixture was subsequently washed several times with DI water (3×15 mL) until the aqueous layer had a pH of about 7. The organic layer was dried (sodium sulfate), filtered through a coarse sintered glass funnel, and the solvent was removed in vacuo to afford a brown crystalline solid (1.422 g, 9.6128 mmol, 96.0% yield), which was shown to be pure by NMR.

Typical procedure for the synthesis of curcuminoid-difluoroboron adducts: These compounds were synthesized by a slight modification of the procedure described by Rao and Sudheer. (E. V. Rao, et al., *Indian. J. Pharm. Sci.*, 2011, 73, 262-270). To a mixture of acetylacetone-BF$_2$ complex (6 mmol, 887 mg) in ethyl acetate (60 mL) under stirring and nitrogen atmosphere, the respective aldehyde (2.2 equivalence, 13.2 mmol) was added in one portion, followed by N-butylamine (0.22 eq., 1.32 mmol, 96.5 mg, 130 µL) over a period of 20 minutes, with continuous stirring at room temperature overnight. The completion of the reaction was confirmed by TLC. The desired product precipitates from ethyl acetate. The reaction mixture was cooled to 0° C. in an ice bath and the product was filtered, washed with cold (0° C.) ethyl acetate and dried for 30 minutes. The purity of this cut was exceptional (NMR) and no further purification was required (~60% isolated yield). The filtrate was transferred to a round bottom flask and concentrated under vacuum and re-filtered to obtain a second cut which was slightly less pure by NMR (combined yield: typically >80%, except for compound 2 which was 64%).

Specific procedure—synthesis of curcuminoid-BF$_2$ adduct 10 of FIG. 2: To a mixture of acetylacetone-BF$_2$ (6 mmol, 887 mg) in ethyl acetate (60 mL) under stirring and nitrogen atmosphere, was added p-fluorobenzaldehyde (2.2 equivalence, 13.2 mmol, 1.638 g) in one portion, followed by slow addition (over 20 min) of N-butylamine (0.22 eq., 1.32 mmol, 96.5 mg, 130 µL). The reaction mixture was stirred continuously at room temperature overnight whereupon compound 10 precipitated from ethyl acetate. The reaction mixture was cooled to 0° C. in an ice bath, filtered, and the product was washed with cold (0° C.) ethyl acetate and dried for 30 minutes to afford compound 11 as a yellow solid (1.723 g, 4.78 mmol, 80% yield) which was confirmed by NMR to be highly pure.

General procedure for decomplexation of curcuminoid-BF$_2$: Using a modified microwave assisted method, the curcuminoid-BF$_2$ complex (0.3 mmol) and sodium oxalate (2 equiv) were added to a clean/dry microwave vial equipped with magnetic stirrer. (S. Raghavan, et al., *Bioorg. Med. Chem. Lett.*, 2015, 25, 3601-3605). Aqueous methanol (5 mL, 8:2 MeOH/H$_2$O) was added and the vial was sealed with a crimp-able cap with septa using a crimping tool and the sealed vial was irradiated for 6 min at 140° C. The vial was cooled to room temperature and the cap removed. The reaction mixture was transferred to a round bottom flask and the methanol removed under vacuum. Upon addition of deionized-water (20 mL) a precipitate was formed which was collected by filtration, washed with 40 mL of deionized-water and dried for 30 min. The resulting curcuminoid product was >98% pure (by NMR).

Typical procedure—decomplexation of curcuminoid-BF$_2$ adduct 10 of FIG. 2: The curcuminoid-BF$_2$ adduct 10 (0.28 mmol, 101 mg) and sodium oxalate (2 equiv, 0.56 mmol, 75 mg) were added to a clean/dry microwave vial equipped with magnetic stirrer. Upon addition of aqueous methanol (5 mL, 8:2 MeOH/H$_2$O) a suspension was formed. The vial was sealed and irradiated for 6 min at 140° C. The vial was cooled to r.t. and the sealed cap was removed. Removal of solvent and addition of deionized-water gave a precipitate which was washed and dried under vacuum to give compound 11 as a yellow solid (79 mg, 0.25 mmol, 90% yield) which was pure by NMR.

Microwave assisted formation of curcumin-BF$_2$ adduct using Selectfluor: To a clean dry microwave vial (5 mL) curcumin 1 (0.75 mmol, 276.3 mg) was added followed by acetone (5 mL) to dissolve the curcumin. Selectfluor (0.825 mmol, 292.3 mg, 1.1 equiv) was then added directly to the solution, and the vial was sealed with a crimp-able cap with septa using a crimping tool. The absorbance was set to very high and the mixture was irradiated at 200 W for 97 seconds until it reached a temperature of 138° C. and a pressure of 10 bar. The reaction was monitored by TLC at intervals by removing ~0.1 mL through the septa with a syringe and diluting in DCM. Upon completion, the acetone was removed in vacuo and reaction mass was dissolved in DCM, washed with deionized water (3×10 mL), dried (sodium sulfate) and filtered through a coarse sinter glass funnel. The solvent was removed in vacuo, and the crude mixture was purified by flash chromatography eluting with ethyl acetate/hexane (40:60). The resulting curcumin-BF$_2$ complex 2 (128 mg, 0.3075 mmol, 41% yield) was pure as confirmed by NMR. For comparison, a 64% isolated yield was obtained for this decomplexation by using BF$_3$.Et$_2$O instead of Selectfluor.

Characterization Data for Compounds of FIG. 2

Curcumin-BF$_2$ adduct (2): Yield: 64% (using BF$_3$.Et$_2$O and 41% by using Selectfluor), red solid, mp>260° C. Rf 0.16 (40% EtOAc in hexane). $^1$H NMR (CD$_3$CN, 500 MHz): δ 7.96 (d, J=16.0 Hz, 2H), 7.42 (br, s, 20H), 7.37 (d, J=2.1 Hz, 2H), 7.30 (dd, J=8.2 and 2.1 Hz, 2H), 6.94 (d, J=8.6 Hz, 2H), 6.89 (d, J=16.0 Hz, 2H), 6.28 (s, 1H), 3.95 (s, 6H, 2OMe). $^{13}$C NMR (CD$_3$CN, 125 MHz): δ 180.5, 151.4, 148.7, 147.6, 127.8, 128.0, 119.2, 116.2, 112.3, 102.4, 56.7. $^{19}$F NMR (CD$_3$CN, 470 MHz): δ −140.97 (s, $^{11}$B—F), −140.91 (s, $^{10}$B—F). $^{11}$B NMR (CD$_3$CN, 160.3 MHz): δ 0.95 (s).

(1E,6E)-4,4-Difluoro-1,7-bis(4-hydroxy-3-methoxyphenyl)hepta-1,6-diene-3,5-dione (3): Yield: 33%, red solid, mp 117-118° C. Rf 0.53 (40% EtOAc in hexane). $^1$H NMR (CD$_3$CN, 500 MHz): δ 7.85 (d, J=16.0 Hz, 2H), 7.35 (d, J=1.5 Hz, 2H), 7.29 (br s, 2OH), 7.25 (dd, J=8.0 and 1.5 Hz, 2H), 7.12 (d, J=16 Hz, 2H), 6.88 (d, J=8.0 Hz, 2H), 3.90 (s, 6H, 2OMe). $^{13}$C NMR (CD$_3$CN, 125 MHz): δ 186.5 (t, $^2$J$_{CF}$=26.7 Hz), 150.5, 148.8, 147.8, 126.2, 125.5, 115.2, 116.5, 111.1, 111.7 (t, $^1$J$_{CF}$=263.2 Hz), 58.9. $^{19}$F NMR (CD$_3$CN, 470 MHz): δ −115.3. HRMS (ESI): m/z [M+H]$^+$ calcd for C$_{21}$H$_{19}$O$_6$F$_2$: 405.1149; found: 405.065. IR (cm$^{-1}$, CH$_2$Cl$_2$/MeCN): 3415 (br, OH), 3182-2847 (C—H package), 1693 (CO), 1681, 1568, 1506, 1431, 1271, 1207, 1122, 1064.

(1E,4E,6E)-4-Fluoro-5-hydroxy-1,7-bis(4-hydroxy-3-methoxyphenyl)hepta-1,4,6-trien-3-one (4): Yield: 52%, purple solid, mp 154-155° C. Rf 0.60 (40% EtOAc in hexane). $^1$H NMR (CD$_3$CN, 500 MHz): δ 14.1 (br, enolic OH), 7.63 (d, J=16 Hz, 2H), 7.31 (d, J=16 Hz, 2H), 7.20 (dd, J=8.5 and 1.5 Hz, 2H), 7.10 (dd, J=16 and 3.5 Hz, 2H), 7.05 (s, 2H, 2OH), 6.87 (d, J=8.0 Hz, 2H), 3.91 (s, 6H, 2OMe). $^{13}$C NMR (CD$_3$CN, 125 MHz): 172.1 (d, $^2J_{CF}$=23 Hz), 149.5, 147.7, 143.0 (d, $^1J_{CF}$=238.0 Hz), 141.9 (d, $^3J_{CF}$=2.9 Hz), 127.4, 123.8, 115.1, 114.3, 110.7, 55.8. $^{19}$F NMR (CD$_3$CN, 470 MHz): δ –176.5 (t, $J_{HF}$=2.8 Hz). HRMS (ESI): m/z [M+H]$^+$ calcd for C$_{21}$H$_{20}$O$_6$F: 387.1243; found: 387.080. IR (cm$^{-1}$, CH$_2$Cl$_2$/MeCN): 3417 (br, OH), 3062-2937 (C—H package), 1620 (CO), 1568, 1504, 1429. 1267, 1122, 1029.

Tetramethoxy-curcuminoid-BF$_2$ complex (5): Yield 83%, purple solid, mp 224-226° C., Rf 0.16 (40% EtOAc in hexane). $^1$H NMR (DMSO-d$_6$, 500 MHz): δ 0.7.97 (d, J=16.0 Hz, 2H), 7.49 (d, J=2.0 Hz, 2H), 7.46 (dd, J=8.0 and 2.0 Hz, 2H), 7.11 (d, J=16 Hz, 2H), 7.07 (d, J=8.0 Hz, 2H), 6.50 (s, 2H), 3.84 (s, 6H). $^{13}$C NMR (DMSO-d$_6$, 125 MHz): δ 179.5, 153.0, 149.6, 147.3, 127.6, 125.6, 119.3, 112.3, 111.7, 101.8, 56.3, 56.1. $^{19}$F NMR (DMSO-d$_6$, 470 MHz): δ –137.9 (s, $^{11}$B—F), –137.8 (s, 1B—F). $^{11}$B NMR (DMSO-d$_6$, 160.3 MHz): δ 0.90 (s). IR (cm$^{-1}$, CH$_2$Cl$_2$): 3003-2841 (CH package), 1610 (CO), 1529, 1508, 1263, 1136.

(1E,4E,6E)-5-Hydroxy-1,7-bis(3,4-dimethoxyphenyl)hepta-1,4,6-trien-3-one (6): Yield 94%, red solid, mp 122-125° C. Rf 0.375 (40% EtOAc in hexane). $^1$H NMR (CDCl$_3$, 500 MHz): δ ~14.8 (br, enolic OH), 7.62 (d, J=16.0 Hz, 2H), 7.17 (dd, J=8.0 and 1.6 Hz, 2H), 7.09 (d, J=1.5 Hz, 2H), 6.89 (d, J=8 Hz, 2H), 6.51 (d, J=16 Hz, 2H), 5.85 (s, 1H), 3.94 (s, 6H), 3.93 (s, 6H). $^{13}$C NMR (DMSO-d$_6$, 125 MHz): δ 183.6, 151.4, 149.5, 140.9, 128.0, 123.5, 122.5, 112.1, 110.8, 101.5, 56.0, 56.1. HRMS (ESI): m/z [M+H]$^+$ calcd for C$_{23}$H$_{25}$O$_6$: 397.1651; found: 397.140. IR (cm$^{-1}$, DCM/CH$_2$Cl$_2$): 3005-2837 (CH package), 1624 (CO), 1581, 1510, 1462, 1259, 1136, 1022.

(1E,6E)-4,4-Difluoro-1,7-bis(3,4-dimethoxyphenyl)hepta-1,6-diene-3,5-dione (7): Yield: 40%, orange solid, mp 148-149° C. Rf 0.425 (40% EtOAc in hexane). $^1$H NMR (CDCl$_3$, 500 MHz): δ 7.87 (d, J=15.5 Hz, 2H), 7.24 (dd, J=8.0 and 2.0 Hz, 2H), 7.13 (d, J=2.0 Hz, 2H), 6.98 (d, J=15.5 Hz, 2H), 6.90 (d, J=8.0 Hz, 2H), 3.95 (s, 6H, 2OMe), 3.96 (s, 6H, 2OMe). $^{13}$C NMR (CDCl$_3$, 125 MHz): δ 186.6 (t, $^2J_{CF}$ 26.8 Hz), 152.7, 149.4, 148.8, 126.7, 125.1, 115.6, 112.0 (t, $^1J_{CF}$=264.1 Hz), 111.0, 110.0, 59.0. $^{19}$F NMR (CDCl$_3$, 470 MHz): δ –115.3 (s, $^{11}$B isotope) and –115.4 (s, 10B isotope). HRMS (ESI): m/z [M+H]$^+$ calcd for C$_{23}$H$_{23}$O$_6$F$_2$: 433.1462; found: 433.0886. IR (cm$^{-1}$, CH$_2$Cl$_2$/DCM): 3003-2937 (CH package), 1681 (CO), 1587, 1573, 1510, 1463, 1421, 1265, 1139.

(1E,4E,6E)-4-Fluoro-5-hydroxy-1,7-bis(3,4-dimethoxyphenyl)hepta-1,4,6-trien-3-one (8) and (E,6E)-4-Fluoro-1,7-bis(3,4-dimethoxyphenyl)hepta-1,6-diene-3,5-dione (9): Tautomeric mixture (75:25 ratio by $^{19}$F NMR). Yield 33%, red solid, mp 145-146° C. Rf 0.525 (40% EtOAc in hexane). Analytical data for 8. $^1$H NMR (CDCl$_3$, 500 MHz): δ ~14.0 (br, enolic OH), 7.67 (d, J=16 Hz, 2H), 7.21 (dd, J=8.0 and 2.0 Hz, 2H), 7.14 (d, J=2 Hz, 2H), 6.99 (dd, J=16.0 and 3.5 Hz, 2H), 6.90 (d, J=8.5 Hz, 2H), 3.96 (s, OMe), 3.94 (s, OMe). $^{19}$F NMR (CDCl$_3$, 470 MHz): δ –175.7 (s). Analytical data for 9: $^1$H NMR (CDCl$_3$, 500 MHz): δ 7.78 (d, J 16 Hz, 2H), 7.22 (dd, not fully resolved), 7.12 (d, J=2 Hz), 6.88 (d, J=8.5 Hz), 5.70 (d, $J_{HF}$=50 Hz), 3.93 (s, OMe), 3.94 (OMe, not fully resolved). $^{19}$F NMR (CDCl$_3$, 470 MHz): δ –194.9 (d, $J_{HF}$=50 Hz). Data for 8 (a) and 9 (b): $^{13}$C NMR (CDCl$_3$, 125 MHz): 189.9 (d, 2J$_{CF}$=20 Hz)$^b$, 172.0 (d, $^2J_{CF}$=22 Hz)$^a$, 152.3, 151.4a, 149.3, 149.2$^a$, 146.9 (d, 3J$_{CF}$=2.7 Hz)$^b$, 143.0 (d, $^1J_{CF}$=236 Hz)$^a$, 141.7 (d, $^3J_{CF}$=3 Hz)$^a$, 128.0$^a$, 126.9$^b$, 123.2$^a$, 117.1$^b$, 115.0$^a$, 111.1$^a$, 111.0, 109.9$^a$, 97.5 (d, $^1J_{CF}$=199 Hz)$^b$, 56.0, 55.0. HRMS (ESI): m/z [M+H]$^+$ calcd for C$_{23}$H$_{24}$O$_6$F: 415.1556; found: 415.120. IR (tautomeric mixture; cm$^{-1}$, CH$_2$Cl$_2$/CDCl$_3$): 3400 (br, OH), 2933, 2839, 1685 (CO), 1589, 1510, 1463, 1265, 1139, 1022.

Difluorocurcuminoid-BF$_2$ adduct (10): Yield 80%, orange solid, mp 258-260° C. Rf 0.05 (5% EtOAc in hexane). $^1$H NMR (acetone-d$_6$, 500 MHz): δ 8.07 (d, J=15.7 Hz, 2H), 7.96 (dd, J=8.5 and 7.0 Hz, 4H), 7.30 (t appearance, J=9.5 Hz, 4H), 7.13 (d, J=15.7 Hz, 2H), 6.65 (s, 1H). $^{13}$C NMR (acetone-d$_6$, 125 MHz): δ 181.7, 165.7 (d, $^1J_{CF}$=251.7 Hz), 146.3, 132.7 (d, $J_{CF}$=8.6 Hz), 131.9 (d, JCF=3.9 Hz), 122.2, 117.2 (d, $J_{CF}$=22 Hz), 103.1. $^{19}$F NMR (acetone-d$_6$, 470 MHz): δ –108.7 (m, 2F), –140.2 (s, $^{11}$B—F), –140.1 (s, $^{10}$B—F). $^{11}$B NMR (acetone-d$_6$, 160.3 MHz): δ 1.01 (s). IR (cm$^{-1}$, CH$_2$Cl$_2$): 3107, 3041, 2922, 2850, 1620 (CO), 1589, 1548, 1508, 1404, 1232, 1155.

(1E,4E,6E)-1,7-Bis(fluorophenyl)-5-hydroxy-hepta-1,4,6-trien-3-one (11): Yield 90%, yellow solid, mp 158-160° C., Rf 0.325 (5% EtOAc in hexane). $^1$H NMR (CDCl$_3$, 500 MHz): δ ~15.9 (br, enolic OH), 7.64 (d, J=16.0 Hz, 2H), 7.56 (dd, J=8.5 and 15.0 Hz, 4H), 7.10 (t appearance, J=8.5 Hz, 4H), 6.51 (d, J=15.9 Hz, 2H), 5.82 (s, 1H). $^{13}$C NMR (CDCl$_3$, 125 MHz): δ 183.1, 163.8 (d, $^1J_{CF}$=250.8 Hz), 139.4, 131.2 (d, $J_{CF}$=2.9 Hz), 129.9 (d, $J_{CF}$=8.6 Hz), 123.7, 116.1 (d, $J_{CF}$=22 Hz), 101.8. $^{19}$F NMR (CDCl$_3$, 470 MHz): δ –109.7 (m). HRMS (ESI): m/z [M+H]$^+$ calcd for C$_{19}$H$_{15}$O$_2$F$_2$: 313.1040; found: 3313.100. IR (cm$^{-1}$, DCM): 3066-2850 (CH package), 1631 (CO), 1593, 1508, 1414, 1234, 1150.

(1E,6E)-4,4-Difluoro-1,7-bis(4-fluorophenyl)hepta-1,6-diene-3,5-dione (12): Yield 42%, white solid, mp 72-73° C., Rf 0.35 (5% EtOAc in hexane). $^1$H NMR (CDCl$_3$, 500 MHz): δ 7.88 (d, J=16.5 Hz, 2H), 7.67-7.63 (m, 4H), 7.15-7.12 (m, 4H), 7.06 (d, J=16.5 Hz, 2H). $^{13}$C NMR (CDCl$_3$, 125 MHz): δ 186.7 (t, $^2J_{CF}$ 27.9 Hz), 164.9 (d, $^1J_{CF}$=254.7 Hz), 147.3, 131.4 (d, $J_{CF}$=8.5 Hz), 129.9 (d, $J_{CF}$=3.9 Hz), 117.6 (d, $J_{CF}$=2.9 Hz), 116.4 (d, $J_{CF}$=22 Hz), 111.4 (t, $^1J_{CF}$=265.1 Hz). $^{19}$F NMR (CDCl$_3$, 470 MHz): δ –106.2 (m, 2F), –115.3 (s, 2F). HRMS (ESI): m/z [M+H]$^+$ calcd for C$_{19}$H$_{13}$O$_2$F$_4$: 349.0851; found: 349.040. IR (cm$^{-1}$, DCM/CDCl$_3$): 3078, 2929, 1697, 1608, 1585, 1508, 1417, 1234, 1159, 1112, 1099, 1058.

(1E,4E,6E)-4-Fluoro-1,7-bis(4-fluorophenyl)-5-hydroxy-hepta-1,4,6-trien-3-one (13): Yield: 43%, yellow solid, mp 152-153° C. Rf 0.45 (5% EtOAc in hexane). $^1$H NMR (CDCl$_3$, 500 MHz): δ ~13.8 (br, enolic OH), 7.68 (d, J=15.9 Hz, 2H), 7.62 (dd, J=8.5 and 5.5. Hz, 4H), 7.12 (t appearance, J=8.5, 4H), 7.06 (dd, J=15.7 and 3.7 Hz, 2H). $^{13}$C NMR (CDCl$_3$, 125 MHz): 172.0 (d, $^2J_{CF}$=21.8 Hz), 164.0 (d, $^1J_{CF}$=251.6 Hz), 145.5, 143.1 (d, $^1J_{CF}$=238.4 Hz), 140.6 (d, $J_{CF}$=1.9 Hz), 131.2 (d, $J_{CF}$=2.9 Hz), 130.3 (d, $J_{CF}$=8.7 Hz), 116.8, 116.2 (d, $J_{CF}$=22.0 Hz). $^{19}$F NMR (CDCl$_3$, 470 MHz): δ –108.9 (m, 2F), –175.2 (t, J=3.3 Hz, 1F). HRMS (ESI): m/z [M+H]$^+$ calcd for C$_{19}$H$_{14}$O$_2$F$_3$: 331.0945; found: 331.110. IR (cm$^{-1}$, DCM/CDCl$_3$): 3072, 2920, 1633, 1597, 1508, 1417, 1319, 1232, 1157.

Tetramethoxydifluoro-curcuminoid-BF$_2$ adduct (14): Yield 90%, red solid, mp 253-255. Rf 0.211 (40% EtOAc in hexane). $^1$H NMR (DMSO-d$_6$, 500 MHz): δ 8.05 (d, J=16.0 Hz, 2H), 7.46 (d, J=7.0 Hz, 2H), 7.16 (d, J=15.5 Hz, 2H), 7.08 (d, J=12 Hz, 2H), 6.65 (s, 1H). $^{13}$C NMR (DMSO-d$_6$, 125 MHz): δ 179.3, 157.2 (d, $^1J_{CF}$=250 Hz), 153.9 (d, $J_{CF}$=11.4 Hz), 145.9, 138.3 (d, $J_{CF}$=2.9 Hz), 120.7 (d, $J_{CF}$=5.7 Hz), 113.1 (d, $J_{CF}$=11.4 Hz), 110.4 (d, $J_{CF}$=3.8 Hz), 101.7, 100.7 (d, $J_{CF}$=28.6 Hz), 56.5, 56.2. $^{19}$F NMR (DMSO-d$_6$, 470 MHz): δ –119.0 (unresolved dd, 2F), –137.7 (s, $^{11}$B—F), –137.6 (s, $^{10}$B—F). $^{11}$B NMR (DMSO-d$_6$, 160.3 MHz): δ0.89 (br, s). IR (cm$^{-1}$, CH$_2$Cl$_2$): 2954, 2922, 2852, 1714, 1597, 1514, 1462, 1278, 1193, 1001.

(1E,4E,6E)-5-Hydroxy-1,7-bis(3,4-dimethoxy-6-fluorophenyl)hepta-1,4,6-trien-3-one (15): Yield 94%, orange solid, mp 154-156° C. Rf 0.447 (40% EtOAc in hexane). $^1$H NMR (CDCl$_3$, 500 MHz): δ 7.74 (d, J=16.0 Hz, 2H), 6.99 (d, J$_{HF}$=7.5 Hz, 2H), 6.67 (d, J$_{HF}$=12.5 Hz, 2H), 6.60 (d, J=16.5 Hz, 2H), 5.88 (s, 1H), 3.92 (s, 12H). $^{13}$C NMR (CDCl$_3$, 125 MHz): δ 183.2, 156.6 (d, $^1J_{CF}$=249.0 Hz), 151.8 (d, J$_{CF}$=10.4 Hz), 145.6 (d, J$_{CF}$=2.0 Hz), 133.0, 124.0 (d, J$_{CF}$=6.6 Hz), 114.1 (d, J$_{CF}$=13.3 Hz), 109.6 (d, JCF=4.8 Hz), 101.4, 100.2 (d, J$_{CF}$=28.5 Hz), 56.4, 56.3. $^{19}$F NMR (CDCl$_3$, 470 MHz): δ −120.1 (dd, J$_{HF}$=11.7 and 5.6 Hz). HRMS (ESI): m/z [M+H]$^+$ calcd for C$_{23}$H$_{23}$O$_6$F$_2$: 433.1462; found: 433.142. IR (cm$^{-1}$, DCM/CH$_2$Cl$_2$): 3005-2835 (CH package), 1614 (CO), 1510, 1440, 1363, 1292, 1273, 1211, 1192, 1139, 1109.

(1E,6E)-4,4-Difluoro-1,7-bis(3,4-dimethoxy-6-fluorophenyl)hepta-1,6-diene-3,5-dione (16): Yield: 26%, brown solid, mp 162-163° C. Rf 0.526 (40% EtOAc in hexane). $^1$H NMR (CDCl$_3$, 500 MHz): δ 8.05 (d, J=16.0 Hz, 2H), 7.05 (d, J=16.0 Hz, 2H), 7.02 (d, J$_{HF}$=6.7 Hz, 2H), 6.67 (d, J$_{HF}$=11.6 Hz, 2H), 3.93 (s, 6H, OMe), 3.92 (s, 6H, OMe). $^{13}$C NMR (CDCl$_3$, 125 MHz): δ 186.7 (t, $^2J_{CF}$=27.6 Hz), 158.0 (d, $^1J_{CF}$=252.6 Hz), 153.8 (d, J$_{CF}$=10.5 Hz), 145.8 (d, J$_{CF}$=2.0 Hz), 140.9, 117.0 (d, J$_{CF}$=6.6 Hz), 113.1 (d, J$_{CF}$=12.4 Hz), 111.7 (t, $^1J_{CF}$=264.2 Hz, CF$_2$), 109.3 (d, J$_{CF}$=3.8 Hz), 100.1 (d, JCF=28.6 Hz), 56.5, 56.4. $^{19}$F NMR (CDCl$_3$, 470 MHz): δ −115.4 (s, 2F), −117.6 (dd, J$_{HF}$=11.7 and 5.8 Hz, 2F). HRMS (ESI): m/z [M+H]$^+$ calcd for C$_{23}$H$_{21}$O$_6$F$_4$: 469.1274; found: 469.0499. IR (cm$^{-1}$, CDCl$_3$/DCM): 308, 2941, 1707, 1693, 1512, 1442, 1365, 1280, 1193.

(1E,4E,6E)-4-Fluoro-5-hydroxy-1,7-bis(3,4-dimethoxy-6-fluorophenyl)hepta-1,4,6-trien-3-one (17): Yield 10%, red solid, mp 148-150° C. Rf 0.579 (40% EtOAc in hexane). $^1$H NMR (CDCl$_3$, 500 MHz): δ 7.82 (d, J=16 Hz, 2H), 7.08-7.03 (m, 4H), 6.67 (d, J$_{HF}$=11.5 Hz), 3.93 (s, OMe), 3.942 (s, OMe). $^{13}$C NMR (CDCl$_3$, 125 MHz): 172.0 (d, $^2J_{CF}$=21 Hz), 156.9 (d, $^1J_{CF}$=250 Hz), 152.2 (d, J$_{CF}$=10.4 Hz), 145.7, 143.1 (d, JCF=238.5 Hz), 134.2, 116.8 (d, J$_{CF}$=5.8 Hz), 114.2 (d, J$_{CF}$=12.4 Hz), 109.6 (d, J$_{CF}$=3.7 Hz), 100.3, 56.4. 56.3. $^{19}$F NMR (CDCl$_3$, 470 MHz): δ −119.5 (dd, J$_{HF}$=11.7 and 6.6. Hz, 2F), −175.3 (distorted t, J=3.3 Hz, 1F). HRMS (ESI): m/z [M+H]$^+$ calcd for C$_{23}$H$_{22}$O$_6$F$_3$ 450.1368; found: 451.0632. IR (cm$^{-1}$, CH$_2$Cl$_2$/CDCl$_3$): 2922, 1608, 1548, 1504, 1367, 1276, 1213, 1157, 1066.

(1E,6E)-4-Fluoro-1,7-bis(3,4-dimethoxy-6-fluorophenyl)hepta-1,6-diene-3,5-dione (18): Yield 12% (by NMR). $^{119}$F NMR (CDCl$_3$, 470 MHz): δ −195.2 (d, J$_{HF}$=50 Hz, 1F), −118.59 (m, 2F)

Bis-trifluoromethylcurcuminoid-BF$_2$ adduct (19): Yield 88%, yellow solid, mp>260° C. Rf 0.14 (10% EtOAc in hexane). $^1$H NMR (DMSO-d$_6$, 500 MHz): δ 8.14 (d, J=15.8 Hz, 2H), 8.10 (d, J=8.5 Hz, 4H), 7.87 (d, J=8.0 Hz, 4H), 7.44 (d, J=15.8 Hz, 2H), 6.77 (s, 1H). $^{13}$C NMR (DMSO-d$_6$, 125 MHz): δ 180.6, 145.2, 145.1, 137.7, 131.0 (q, J$_{CF}$=31.4 Hz), 130.1, 125.9 (q, J$_{CF}$=3.8 Hz), 124.1, 123.9 (q, $^1J_{CF}$=272.7 Hz, CF$_3$), 103.3. $^{19}$F NMR (DMSO-d$_6$, 470 MHz): δ −61.4 (s, CF$_3$), −136.5 ($^{11}$B—F), −136.4 ($^{10}$B—F). $^{11}$B NMR (DMSO-d$_6$, 160.3 MHz): δ0.96 (br, s). IR (cm$^{-1}$, DCM): 1620, 1529, 1514, 1404, 1321, 1166, 1111, 1064.

(1E,4E,6E)-1,7-Bis(4-trifluoromethyl-phenyl)-5-hydroxy-hepta-1,4,6-trien-3-one (20): Yield 88%, yellow solid, mp 153-154° C., Rf 0.56 (10% EtOAc in hexane). $^1$H NMR (CDCl$_3$, 500 MHz): δ ~15.9 (br, enolic OH), 7.95 (d, J=8.0 Hz, 2H), 7.79 (d, J=8.0 Hz, 2H), 7.72 (d, J=15.9 Hz, 2H), 7.13 (d, J=15.8 Hz, 2H), 6.28 (s, 1H). $^{13}$C NMR (CDCl$_3$, 125 MHz): δ 182.9, 138.3, 131.5 (q, J$_{CF}$=31.5 Hz), 128.9, 126.9, 125.7 (q, J$_{CF}$=4 Hz), 124.0 (q, $^1J_{CF}$=271.8 Hz, CF$_3$), 102.6. $^{19}$F NMR (CDCl$_3$, 470 MHz): δ −61.2 (s, CF$_3$). HRMS (ESI): m/z [M+H]$^+$ calcd for C$_{21}$H$_{15}$O$_2$F$_6$: 413.0976; found: 413.087. IR (cm$^{-1}$, DCM): 2928, 1635 (CO), 1579, 1413, 1330, 1265, 11681128, 1066.

(1E,6E)-4,4-Difluoro-1,7-bis(4-trifluoromethyl-phenyl)hepta-1,6-diene-3,5-dione (21): Yield 36%, white solid, mp 75-76° C., Rf 0.72 (10% EtOAc in hexane). $^1$H NMR (CDCl$_3$, 500 MHz): δ 7.93 (d, J=15.9 Hz, 2H), 7.76 (d, J=8.5 Hz, 4H), 7.71 (d, d, J=8.5 Hz, 4H), 7.19 (d, J=16 Hz, 2H). $^{13}$C NMR (CDCl$_3$, 125 MHz): δ 186.6 (t, $^2J_{CF}$=27.7 Hz), 146.6, 136.8, 133.2 (q, J$_{CF}$=3.8 Hz), 129.3, 126.1 (q, J$_{CF}$=3.8 Hz), 123.6 (q, $^1J_{CF}$=272.7 Hz, CF$_3$), 120.0, 112.1 (t, $^1$J=265.1 Hz, CF$_2$). $^{19}$F NMR (CDCl$_3$, 470 MHz): δ −63.1 (s, 6F, CF$_3$), −115.1 (s, 2F, CF$_2$). HRMS (ESI): m/z [M+H]$^+$ calcd for C$_{21}$H$_{13}$O$_2$F$_8$: 449.0787; found: 449.0145. IR (cm$^-$$_1$, CDCl$_3$): 3080, 2933, 1699 (CO), 1608, 1577, 1417, 1319, 1168, 1124, 1066.

(1E,4E,6E)-4-Fluoro-1,7-bis(4-trifluoromethyl-phenyl)-5-hydroxy-hepta-1,4,6-trien-3-one (22): Yield 60% [crude yield, contained 20 (22%) and 19 (18%); 16% yield after recrystallization (purity by NMR was 70%, contained 19 (30%)], orange solid, mp 144-146° C. Rf 0.64 (10% EtOAc in hexane). $^1$H NMR (CDCl$_3$, 500 MHz): δ −13.5 (br, enolic OH), 7.22 (dd, J=15.5 and 3.7 Hz, 2H), 7.76-7-67 (unresolved-m, 10H). $^{19}$F NMR (CDCl$_3$, 470 MHz): δ −62.8 (6F, CF$_3$), −173.9 (t, J$_{HF}$=3.2 Hz, 1F). HRMS (ESI): m/z [M+H]$^+$ calcd for C$_{21}$H$_{14}$O$_2$F$_7$: 431.0882; found: 431.0804.

Bioassay Methods

The cell viability/anti-proliferative activity of the curcuminoids against PC3 (human androgen-insensitive prostate cancer cell line), LNCap (human-androgen sensitive prostate cancer cell line), A549 (lung cancer), and MDA231 (breast cancer) were determined by means of 3-(4,5-dimethyl-2-thiazolyl)-2,5-diphenyl-2H-tetrazolium bromide (MTT) assay (the tetrazolium salt was a commercial sample). (R. N. Khaybullin, et al., *Molecules*, 2014, 19, 18676-18689). The ability of the curcuminoids to affect proliferations of suspension cell lines (MOLT-4) was tested by the CellTiter-Glo® Luminescent Cell Viability Assay (purchased from Promega Madison, Wis., USA) to determine the number of viable cells in culture based on quantitation of the ATP present. The IC$_{50}$ values were obtained from fitting data with GraphPad software to determine the growth inhibition in the presence of test compounds. (R. N. Khaybullin, et al., *Molecules*, 2014, 19, 18676-18689).

X-ray Crystallography

Suitable single crystals for X-ray diffraction studies were obtained for compounds 10, 5 and 8 of FIG. 2 from ethyl acetate and for 14 from dichloromethane. Crystal data of the compounds were collected by exactly the same method by mounting a crystal onto a thin glass fiber from a pool of Fluorolube™ and immediately placing it under a liquid N$_2$ cooled stream, on a Bruker AXS diffractometer upgraded with an APEX II CCD detector. The radiation used is graphite monochromatized Mo Kα radiation (λ=0.7107 Å). The lattice parameters are optimized from a least-squares calculation on carefully centered reflections. Lattice determination, data collection, structure refinement, scaling, and data reduction were carried out using APEX2 Version 2014.11 software package. The data were corrected for absorption using the SCALE program within the APEX2 software package. The structure was solved using SHELXT. This procedure yielded a number of C, B, F and O atoms. Subsequent Fourier synthesis yielded the remaining atom positions. The hydrogen atoms are fixed in positions of ideal geometry (riding model) and refined within the XSHELL software package. These idealized hydrogen atoms had their isotropic temperature factors fixed at 1.2 or 1.5 times the equivalent isotropic U of the C atoms to which they were bonded. A few hydrogen atoms could not be adequately predicted via the riding model within the XSHELL software, these hydrogen atoms were located via difference-Fourier mapping and subsequently refined. The final refinement of each compound included anisotropic thermal parameters on all non-hydrogen atoms. The crystal data for the compounds are given in Table 1. Packing diagrams and thermal ellipsoid plots along with selected interatomic distances and bond angles are included in supplementary data.

Computational Methods

Geometry optimizations of the curcumin derivatives were performed at the B3LYP[36]/6-311+G(d,p) level with the Gaussian 09 package. Distribution of the electrostatic potential derived from the electron density was estimated by energy calculations at the optimized structures. The programs AutoDock 4.2 and AutoDock Vina were employed to carry out automated molecular docking for estimating the interaction energy and modeling the binding modes between the curcuminoid ligands and the enzymes HER2 and proteasome. The three-dimensional coordinates of the proteins were obtained from the Protein Data Bank (PDB codes 3PP0 (HER2) and 3SDK (20S proteasome)). (K. Aertgeerts, et al., *J. Biol. Chem.* 2011, 286, 18756-18765; C. Blackburn, et al., *Bioorg. Med. Chem. Lett.*, 2010, 20, 6581-6586). Chain A of HER2, and chains K (β5 subunit) and L (β6 subunit) of 20S proteasome were selected as target templates for the docking calculations. Co-crystalized ligands and crystallographic water molecules were removed. Addition of hydrogens, merger of non-polar hydrogens to the atom to which they were linked, and assignment of partial charges were achieved with AutoDockTools. Merz-Kollman partial atomic charges were employed for proteins, and Gasteiger charges were assigned to ligands. The docking area was defined using the AutoDock module AutoGrid. The docking area, defined using the AutoDock module AutoGrid, was constrained to a 30×26.2×30 Å box centered at the active site, providing proper space for rotational and translational movement of the ligands. With AutoDock 4.2, the Lamarckian genetic algorithm (LGA) was used, default parameters were applied, and the maximum number of energy evaluations was set to $1.0 \times 10^7$. For each of the 100 independent runs performed for each ligand a maximum number of $2.7 \times 10^4$ genetic algorithm operations were generated on a single population of 150 individuals. Operator weights for crossover, mutation, and elitism were default parameters, 0.80, 0.02, and 1, respectively. The default parameters were used for Vina.

Example 2—Mono- and Di-Fluorinated CUR Inspired Compounds Possessing Non-Fluorinated Aryls To a mixture of acetylacetone (10 mmol, 1 g) in dichloromethane (DCM) (50 mL, distilled from $P_2O_5$) under a nitrogen atmosphere, boron trifluoride complexed to diethyl ether ($BF_3.Et_2O$) (~48%; 2.126 g, 1.89 mL, 15 mmol, 1.5 equiv) was slowly added over a period of 5 minutes, and the reaction mixture was refluxed (41° C.) for 12 hrs, as seen in FIG. 4. The product, i.e. boron-difluoride adduct of acetylacetone, was cooled to room temperature and quenched with 15 mL deionized water. The DCM layer was separated, and the aqueous layer was discarded. The reaction mixture was subsequently washed several times with DI water (3×15 mL) until the aqueous layer had a pH of about 7. The organic layer was dried (sodium sulfate), filtered through a coarse sintered glass funnel, and the solvent was removed in vacuo to afford a brown crystalline solid (1.42 g, 9.61 mmol, 96.0% yield), which was shown to be pure by NMR.

The aryl aldehyde can be phenyl, mono-substituted aryl, di-substituted aryl, or tri-substituted aryl. To a mixture of acetylacetone-BF2 complex (887 mg, 6 mmol) in ethyl acetate (60 mL) under stirring and nitrogen atmosphere, the respective aldehyde (2.2 equivalence, 13.2 mmol) was added in one portion, followed by N-butylamine (0.22 eq., 1.32 mmol, 96.5 mg, 130 mL) over a period of 20 min, with continuous stirring at room temperature overnight. The completion of the reaction was confirmed by TLC. The desired product precipitates from ethyl acetate. The reaction mixture was cooled to 0° C. in an ice bath and the product was filtered, washed with cold (0° C.) ethyl acetate and dried for 30 min. The filtrate was transferred to a round bottom flask and concentrated under vacuum. The resulting bis(aryl) hepta-1,6-diene-3,5-dione boron-difluoride adduct was used as is or reduced to remove the difluoroboride adduct.

The adduct was removed from non-fluorinated aryls by dissolving 0.3 mmol of the compound in 5 mL aqueous methanol (8:2 methanol to water) and adding 2 molar equivalents of sodium oxalate in a clean/dry microwave vial equipped with magnetic stirrer. The vial was sealed and subjected to microwave for 6 minutes using a miniature 400 W lab microwave at 140° C., to form a bis(aryl) hepta-1,6-diene-3,5-dione, i.e. curcuminoid. The reaction mixture was transferred to a round bottom flask and the methanol removed under vacuum. Upon addition of deionized-water (20 mL) a precipitate was formed which was collected by filtration, washed with 40 mL of deionized-water and dried for 30 min.

To difluorinate the curcuminoid backbone, 2.2 equivalents of Selectfluor (1-Chloromethyl-4-fluoro-1,4-diazoniabicyclo[2.2.2]octane bis(tetrafluoroborate); Sigma-Aldrich, Merck KgaA, Damrstadt, Germany) was added in one portion to a solution of the curcuminoid (0.75 mmol) in methanol (25 mL) at r.t. with efficient stirring under a nitrogen atmosphere for the requisite time (either 4 hrs at 55° C. or overnight for r.t.) until completion (TLC monitoring). The MeOH solvent was then removed in vacuo and the reaction mass was dissolved in DCM (3×10 mL), washed with deionized water (3×10 mL), dried (sodium sulfate) and filtered through a coarse sintered glass funnel. The DCM was removed in vacuo and the crude mixture was purified by flash chromatography eluting with hexane and ethyl acetate (refer to analytical data), ramping of the elution solvent was employed in all cases.

To mono-fluorinate the curcuminoid backbone, except compounds possessing fluorinated aryls, 1.05 equivalents of Selectfluor (0.8 mmol) was added in one portion to a solution of the curcuminoid (0.75 mmol) in acetonitrile (25 mL) at 0° C. under a nitrogen atmosphere, and the mixture was stirred for 6 hours at this temperature, followed by overnight stirring at r.t. Upon completion (verified by TLC) the solvent was removed in vacuo and the reaction mass was dissolved in DCM (3×10 mL). The reaction mixture was washed with deionized water (3×10 mL), dried over sodium sulfate and filtered through a coarse sintered glass funnel. The solvent was removed in vacuo and the crude reaction mixture was purified by flash chromatography eluting with hexane/ethyl acetate with ramping of the elution solvent was employed in all cases.

Example 3—Mono- and Di-Fluorinated CUR Inspired Compounds Possessing Fluorinated Aryls To a mixture of acetylacetone (10 mmol, 1 g) in dichloromethane (DCM) (50 mL, distilled from $P_2O_5$) under a nitrogen atmosphere, boron trifluoride complexed to diethyl ether ($BF_3.Et_2O$) (~48%; 2.126 g, 1.89 mL, 15 mmol, 1.5 equiv) was slowly added over a period of 5 minutes, and the reaction mixture was refluxed (41° C.) for 12 hrs, as seen in FIG. 4. To form fluorinated aryl compounds, a mixture of 6 mmol the boron-difluoride adduct of acetylacetone (887 mg) was suspended in ethyl acetate (60 mL) under stirring and nitrogen atmosphere, A fluorinated aryl-aldehyde (2.2 equivalence, 13.2 mmol, 1.638 g) was added in one portion, followed by slow addition of 0.22 equivalents N-butylamine (1.32 mmol, 96.5 mg, 130 μL) over 20 min. The reaction mixture was stirred continuously at room temperature overnight. The reaction mixture was cooled to 0° C. in an ice bath, filtered, and the product was washed with cold (0° C.) ethyl acetate and dried for 30 minutes to afford the desired compound. The aryl aldehyde can be phenyl, mono-substituted aryl, di-substituted aryl, or tri-substituted aryl.

To remove the adduct from fluorinated aryls, 0.28 mmol of the compound (101 mg) was dissolved in 5 mL aqueous methanol (8:2 methanol to water) and adding 2 molar equivalents of sodium oxalate (0.56 mmol, 75 mg) in a clean/dry microwave vial equipped with magnetic stirrer. The vial was sealed and irradiated for 6 min at 140° C. in the microwave. The vial was cooled to r.t. and solvent removed. Deionized-water was added to form a precipitate which was washed and dried under vacuum.

To difluorinate the heptene curcuminoid backbone of fluorinated aryl compounds, 2.5 equivalents of Selectfluor (1.04 mmol, 371 mg) was added in one portion to a solution of 0.42 mmol of a fluorinated aryl compound (131 mg) in methanol (20 mL) under a nitrogen atmosphere, the mixture was stirred under mild reflux at 55° C. overnight, and the solvent was removed in vacuo. The reaction mass was dissolved in DCM (3×10 mL) and washed with deionized water (3×10 mL). The organic layer was dried (sodium sulfate), filtered through a coarse sintered glass funnel, and the solvent was removed in vacuo. The difluoro-derivative was precipitated out of the crude reaction mixture by addition of hexane/EtOAc (20%).

To mono-fluorinate the compounds possessing fluorinated aryls, 1.05 equivalents of Selectfluor (0.81 mmol, 286 mg) was added in one portion to a solution of the compounds possessing fluorinated aryls (0.38 mmol, 119 mg) in acetonitrile (20 mL) at 0° C. under a nitrogen atmosphere, and the mixture was stirred for 6 hrs at this temperature, followed by overnight stirring at r.t. Upon completion (monitored by TLC), the acetonitrile was removed in vacuo and the reaction mass was dissolved in DCM (3×10 mL). Following the steps outlined in the typical procedure and flash chromatography (hexane/EtOAc (5%), the monofluorinated product was obtained.

Example 4—Multiple-Substituted and CUR-Pyrazole and CUR-Isoxazole Compounds

Multiple-substituted curcuminoids shown in FIGS. 32-35 were synthesized from the corresponding aldehydes according to the general synthetic scheme outlined in FIG. 4. FIG. 36 represents binding affinities for CURs listed in FIG. 35. FIG. 37 depicts a table of tumor-cell specific cytotoxicity by cell viability assay to determine EC50 (concentration at which 50% of the cells remain viable). These assays indicated that curcuminoids 9 and 5 of FIG. 35 were highly effective against RPMI-8226 (multiple myeloma cell line) while exhibiting significantly less cytotoxicity in peripheral blood mononuclear cells (PBMCs) from healthy donors (non-tumor control cells). EC50 curve plots for compounds 5 (A) and 9 (B) of FIG. 35 respectively, are shown in FIG. 38A-B. A list of CURs from FIG. 35 with anti-tumor activity based on NCI-60 immunoassay is shown in FIG. 39.

Pyrazole and Isoxazoles

The pyrazole and oxazole analogs, as seen in the exemplary compounds depicted in FIGS. 41-43, were synthesized by reaction of the curcuminoids with the corresponding phenyl-hydrazine or hydroxylamine hydrochloride according to the general methods outlined in FIG. 40.

A general observation is that the studied compounds fitted quite well in the binding pockets of the examined enzymes. Several curcuminoid, CUR-pyrazoles, and CUR-isoxazoles exhibited very favorable binding affinities, particularly the analogs bearing $CF_3$ groups; some of them exhibited even better binding energies than those corresponding to the known inhibitors employed in cancer therapy. Very good docking affinities were also observed for CURs with benzyloxy substituents. Binding affinities for CUR-pyrazoles, and CUR-isoxazoles are shown in FIG. 44.

General Procedure for the Synthesis of CUR-Pyrazoles from FIG. 43

With a microliter syringe phenyl-hydrazine (2 equiv.) was added to a suspension of CUR (1 equiv.) in glacial acetic acid (5 mL) and the mixture was heated to 70° C. on a hotplate with stirring. After 2 h, the suspension had fully dissolved and the reaction had gone to completion (confirmed by TLC showing a new fluorescent spot above the precursor). The reaction mixture was transferred to a large beaker with dichloromethane (20 mL) and the acid was neutralized by gradual addition of saturated sodium bicarbonate solution until no more gas was evolved. The pH of the aqueous phase was confirmed to be seven and the mixture was transferred to a separatory funnel. The DCM layer was separated and the aqueous phase was washed with DCM (3×50 mL). The DCM layer was dried over magnesium sulfate, filtered and the solvent was removed in vacuo to give the crude reaction mixture. The crude product was dissolved in hot iPrOH and allowed to cool to give the desired product in good purity (see below for exceptions).

Exceptions

CUR-pyrazole 23-a two solvent system of iPrOH/hexane was used for recrystallization. CUR-pyrazoles 26, 29, 32, and 34-water was added to the hot reaction mixture until the mixture became cloudy. It was left to cool slowly and the desired product precipitated out of solution, the product was filtered and no further purification was needed. CUR-pyrazole 31—DCM extract was an oil which was crystallized from hexane. CUR-pyrazole 38—The oil from DCM extraction was purified by column chromatography with 10% EtOAc/hexane. CUR-pyrazole 39—the oil from DCM extraction was washed with hexane to produce a dark-red oil confirmed by NMR to be pure.

General Procedure for the Synthesis of CUR-Isoxazoles of FIG. 43

Hydroxylamine hydrochloride (2 equiv.) was added to a suspension of CUR (1 equiv.) in ethanol (100 mL). Concentrated sulfuric acid (1 mL) was added slowly with efficient stirring and the reaction was setup to reflux and left for 48 h after which the progress of the reaction was checked by TLC (the product shows as a fluorescent spot). Once the reaction had mostly gone to completion, the solvent was removed in vacuo and the reaction was worked up by neutralization and separation as described in the pyrazole procedure. The crude reaction mixture was recrystallized to give the CUR-isoxazoles. They were crystallized from iPrOH except 27 from FIG. 43 which was crystallized from chloroform.

Characterization Data for Compounds in FIGS. 32-35 and 43

CUR—BF2 adduct (2): Yield 68%, brown solid, Rf 0.43 (40% EtOAc in hexane). 1H NMR (DMSO-d6, 500 MHz): δ 7.97 (d, J=16.0 Hz, 2H), 7.63 (d, J=1.50 Hz, 2H), 7.49 (pseudo-d, 6H), 7.42 (t, J=8.0 Hz, 4H), 7.36 (t, J=7.5 Hz, 2H), 7.12 (s, 2H), 7.18 (d, J=15.9 Hz, 2H) 7.12 (d, J=7.5 Hz, 2H), 6.51 (s, 1H), 5.17 (s, 4H), 3.86 (s, 6H). 13C NMR (DMSO-d6, 125 MHz): δ 179.5, 153.3, 148.6, 147.2, 137.2, 128.9, 128.5, 127.5, 125.9, 119.4, 113.3, 112.6, 101.9, 70.4, 56.3. 19F NMR (DMSO-d6, 470 MHz): δ −137.9 (s, 11B F), −138.0 (s, 10B F). IR (cm-1): 3001-2839, 1614, 1537, 1499, 1392, 1338, 1300, 1280, 1259, 1134, 1060, 1008.

(1E,4E,6E)-5-Hydroxy-1,7-bis(3-benzyloxy-4-methoxyphenyl)hepta-1,4,6-trien-3-one (3): Yield 87%, orange solid, mp 153-155° C., Rf 0.71 (40% EtOAc in hexane). 1H NMR (DMSO-d6, 500 MHz): δ 16.15 (br, enolic OH), 7.57 (d, J=15.5 Hz, 2H), 7.49-7.47 (overlapping signals/unresolved, 6H), 7.42 (t, J=7.5 Hz, 4H), 7.35 (t, J=7.5 Hz, 2H), 7.29 (d, J=8.5 Hz, 2H), 7.05 (d, J=7.5 Hz, 2H), 6.83 (d, J=16.0 Hz, 2H), 6.10 (s, 1H), 5.16 (s, 4H), 3.82 (s, 6H). 13C NMR (DMSO-d6, 125 MHz): δ 183.7, 151.8, 148.5, 140.8, 137.4, 128.9, 128.4, 128.0, 123.8, 122.6, 112.6, 112.5, 101.5, 70.4, 56.5, 56.2. HRMS (ESI): m/z [M+H]+ calcd for C35H33O6: 549.22771; found: 549.23807. IR (cm-1): 3030-2841, 1627, 1593, 1512, 1456, 1512, 1456, 1413, 1338, 1274, 1259, 1226, 1165, 1134.

Curcuminoid-BF2 adduct 4: Yield 79%, brown solid, Rf 0.75 (40% EtOAc in hexane). 1H NMR (DMSO-d6, 500 MHz): δ 7.94 (d, J=15.5 Hz, 2H), 7.65 (d, J=1.5 Hz, 2H), 7.49 (d, J=7.0 Hz, 4H), 7.48-7.41 (m, 6H), 7.38-7.40 (m, 8H), 7.35-7.31 (m, 4H), 7.18 (d, J=8 Hz, 2H), 7.09 (d, J=15.5 Hz, 2H), 6.49 (s, 1H), 5.24 (s, 4H), 5.22 (s, 4H). 13C NMR (DMSO-d6, 125 MHz): δ 179.6, 152.4, 148.9, 147.1, 137.4, 137.1, 128.9, 128.9, 128.4, 128.2, 128.0, 128.0, 127.8, 125.7, 119.6, 114.4, 102.0, 70.5, 70.4. 19F NMR (DMSO-d6, 470 MHz): δ −137.8 (s, 11B F), −137.9 (s, 10B F). IR (cm-1): 3026-3007 (CH package), 2358, 1622, 1556, 1504, 1456, 1433, 1306, 1277, 1260, 1136, 1063.

(1E,4E,6E)-5-Hydroxy-1,7-bis(3,4-dibenzyloxyphenyl)hepta-1,4,6-trien-3-one (5): Yield 88%, orange solid, mp 150-153° C., Rf 0.92 (40% EtOAc in hexane). 1H NMR (DMSO-d6, 500 MHz): δ 16.25 (br, enolic OH), 7.56 (d, J=15.5 Hz, 2H), 7.49 (d, J=9 Hz, 6H), 7.46 (d, J=7.5 Hz, 4H), 7.41-7.45 (overlapping/unresolved signals, 9H), 7.33 (m, 5H), 7.12 (d, =8J=8.5 Hz, 2H), 6.82 (d, J=15.5 Hz, 2H), 5.76 (s, 1H), 5.21 (s, 8H). 13C NMR (DMSO-d6, 125 MHz): δ 183.6, 150.8, 148.8, 140.7, 137.6, 137.4, 128.9, 128.4, 128.3, 128.1, 128.0, 123.6, 122.8, 114.5, 113.6, 101.6, 70.5, 70.3. HRMS (ESI): m/z [M+H]+ calcd for C47H41O6: 701.29031; found: 701.29706. IR (cm-1): 3034-2989, 2358, 1624, 1591, 1576, 1510, 1454, 1416, 1333, 1277, 1254, 1128, 1001.

Curcuminoid-BF2 adduct 6: Yield: 94%, violet-red solid, mp>240° C. Rf 0.28 (40% EtOAc in hexane). 1H NMR (DMSO-d6, 500 MHz): δ 8.04 (d, J=16.0 Hz, 2H), 7.64 (d, J=9.0 Hz, 2H), 7.09 (d, J=15.5 Hz, 2H), 6.96 (d, J=9.5 Hz, 2H), 6.55 (s, 1H), 3.91 (s, 6H), 3.89 (s, 6H), 3.77 (s, 6H). 13C NMR (DMSO-d6, 125 MHz): δ 179.7, 157.7, 154.1, 142.1, 141.3, 125.4, 120.9, 120.1, 109.2, 102.5, 62.0, 60.9, 56.7. 19F NMR (DMSO-d6, 470 MHz): δ −137.70 (s, 11B F), −137.64 (s, 10B F). IR (cm-1): 3009-2945, 2843, 1607, 1589, 1527, 1489, 1460, 1279, 1156.

(1E,4E,6E)-5-Hydroxy-1,7-bis(2,3,4-trimethoxyphenyl)hepta-1,4,6-trien-3-one (7): Yield: 79%, bright-orange solid, mp 104-106° C. Rf 0.59 (40% EtOAc in hexane). 1H NMR (CDCl3, 500 MHz): δ 7.84 (d, J=16.5 Hz, 2H), 7.30 (d, J=9.5 Hz, 2H), 6.71 (d, J=8.5 Hz, 2H), 6.63 (d, J=16 Hz, 2H), 5.83 (s, 1H), 3.94 (s, 6H), 3.90 (s, 6H), 3.89 (s, 6H). 13C NMR (CDCl3, 125 MHz): δ 183.6, 155.4, 153.4, 142.4, 135.3, 123.4, 123.2, 122.2, 107.7, 101.3, 61.4, 60.9, 56.1. HRMS (ESI): m/z [M+H]+ calcd for C25H29O8: 457.18624; found: 457.19797. IR (cm-1): 2997-2839, 1620, 1589, 1487, 1454, 1413, 1298, 1134, 1091.

Curcuminoid-BF2 adduct 8: Yield: 91%, black solid, mp>240° C. Rf 0.21 (40% EtOAc in hexane). 1H NMR (DMSO-d6, 500 MHz): δ 8.22 (d, J=15.5 Hz, 2H), 7.15 (d, J=16.0 Hz, 2H), 6.33 (s, 4H), 6.40 (s, 1H), 3.93 (s, 12H), 3.89 (s, 6H). 13C NMR (DMSO-d6, 125 MHz): δ 179.3, 165.5, 162.6, 136.9, 119.7, 105.8, 102.7, 91.7, 56.7, 56.3. 19F NMR (DMSO-d6, 470 MHz): δ −138.29 (s, 11B F), −138.23 (s, 10B F). IR (cm-1): 2920-2848, 1608, 1591, 1541, 1448, 1380, 1300, 1203, 1116.

(1E,4E,6E)-5-Hydroxy-1,7-bis(2,4,6-trimethoxyphenyl)hepta-1,4,6-trien-3-one (9): Yield: 85%, dark-purple solid, mp: 187-190° C. Rf 0.39 (40% EtOAc in hexane). 1H NMR (DMSO-d6, 500 MHz): δ 8.05 (d, J=16.0 Hz, 2H), 7.00 (d, J=16.5 Hz, 2H), 6.12 (s, 4H), 5.78 (s, 1H), 3.88 (s, 12H), 3.85 (s, 6H). 13C NMR (DMSO-d6, 125 MHz): δ 184.7, 162.6, 161.2, 131.0, 124.3, 106.6, 101.6, 90.5, 55.7, 55.4. HRMS (ESI): m/z [M+H]+ calcd for C25H29O8: 457.18624; found: 457.19797. IR (cm-1): 2959, 2918, 2849, 1593, 1454, 1317, 1202, 1404, 1155, 1115.

Curcuminoid-BF2 adduct 10: Yield: 74.0%, red-violet solid, mp>240° C. Rf 0.20 (40% EtOAc in hexane). 1H NMR (DMSO-d6, 500 MHz): δ 8.05 (d, J=16.5 Hz, 2H), 7.26 (s, 4H), 7.20 (d, J=14.5 Hz, 2H), 6.58 (s, 1H), 3.86 (s, 12H), 3.75 (s, 6H). 13C NMR (DMSO-d6, 125 MHz): δ 180.0, 153.6, 147.5, 141.5, 130.1, 121.1, 107.8, 102.2, 60.7, 56.6, 19F NMR (DMSO-d6, 470 MHz): δ −137.71 (s, 11B F), −137.65 (s, 10B F). IR (cm-1): 3059-2837, 1622, 1564, 1504, 1469, 1504, 1469, 1340.

(1E,4E,6E)-5-Hydroxy-1,7-bis(3,4,5-trimethoxyphenyl)hepta-1,4,6-trien-3-one (11): Yield: 96.0%, bright-orange solid, mp 181-182° C. Rf 0.47 (40% EtOAc in hexane). 1H NMR (CDCl3, 500 MHz): δ 7.49 (d, J=15.5 Hz, 2H), 6.70 (s, 4H), 6.46 (d, J=15.5 Hz, 2H), 5.81 (s, 1H), 3.83 (s, 18H). 13C NMR (CDCl3, 125 MHz): δ 183.1, 153.4, 140.5, 140.0, 130.5, 123.3, 105.2, 101.6, 60.9, 56.1. HRMS (ESI): m/z [M+H]+ calcd for C25H29O8: 457.18624; found: 457.19880. IR (cm-1): 2941, 2836, 1631, 1579, 1501, 1451, 1413, 1234, 1120.

Curcuminoid-BF2 adduct 12: Yield 71%, brown solid, Rf 0.22 (40% EtOAc in hexane). 1H NMR (DMSO-d6, 500 MHz): δ 8.05 (d, J=15.5 Hz, 2H), 7.66 (d, J=2.0 Hz, 2H), 7.49 (dd, J=8.0 and 1.5 Hz, 2H), 7.28 (d, J=15.5 Hz, 2H), 7.23 (d, J=8.5 Hz, 2H), 6.64 (s, 1H), 3.86 (s, 6H), 2.28 (s, 6H). 19F NMR (DMSO-d6, 470 MHz): δ −137.2 (s, 11B F), −137.2 (s, 10B F). 13C NMR (DMSO-d6, 125 MHz): δ 180.5, 168.8, 151.8, 146.8, 142.7, 133.5, 124.1, 123.3, 122.1, 113.7, 102.7, 56.5, 20.9. IR (cm-1): 3011-2848, 1768, 1755, 1614, 1544, 1499, 1417, 1361, 1300, 1254, 1207, 1150, 1119, 1055.

(1E,4E,6E)-5-Hydroxy-1,7-bis(4-acetoxy-3-methoxyphenyl)hepta-1,4,6-trien-3-one (13): Yield 80%, orange solid, mp 157-160° C., Rf 0.53 (40% EtOAc in hexane). 1H NMR (CDCl3, 500 MHz): δ 7.60 (d, J=16.0 Hz, 2H), 7.14 (dd, J=8.5 and 2.0 Hz, 2H), 7.10 (d, J=1.8 Hz, 2H), 7.05 (d, J=16.0 Hz, 2H), 5.84 (s, 1H), 3.86 (s, 6H), 2.32 (s, 6H). 13C NMR (CDCl3, 125 MHz): δ 183.1, 168.8, 151.4, 141.3, 139.9, 134.0, 124.3, 123.3, 121.1, 111.5, 101.8, 55.9, 20.7. HRMS (ESI): m/z [M+H]+ calcd for C25H25O8: 453.15494; found: 453.15202. IR (cm-1): 3055-2841, 1755, 1628, 1599, 1504, 1411, 1368, 1301, 1250, 1211, 1029.

Curcuminoid-BF$_2$ adduct 14: Yield 33%, yellow solid, Rf=0.64 (40% EtOAc in hexane). 1H NMR (acetone-d6, 500 MHz): δ 8.10 (d, J=15.5 Hz, 2H), 7.88 (d, J=7.5 Hz, 2H), 7.84 (s, 2H), 7.65 (t, J=8.0 Hz, 2H), 7.48 (dd, J=8.0 and 1.8 Hz, 2H), 7.28 (d, J=16 Hz, 2H), 6.38 (s, 1H). 19F NMR (acetone-d6, 470 MHz): δ −58.6 (s, 6F), −139.6 (s, 11B F), −139.6 (s, 10B F). 13C NMR (acetone-d6, 125 MHz): δ 181.0, 149.6, 145.0, 136.7, 131.0, 128.2, 123.8, 123.3, 121.3, 120.5 (q, 1JCF=256 Hz, OCF3), 102.8. IR (cm-1): 2922, 2360, 1627, 1547, 1275, 1261, 1155, 1057.

(1E,4E,6E)-5-Hydroxy-1,7-bis(3-trifluoromethoxyphenyl)hepta-1,4,6-trien-3-one (15): Yield 73%, yellow solid, mp 68-70° C., Rf 0.79. 1H NMR (CDCl3, 500 MHz): δ 7.63 (d, J=16 Hz, 2H), 7.47 (d, J=9.0 Hz, 2H), 7.43 (t, J=7.0 Hz, 2H), 7.40 (s, 2H), 7.23 (d, J=7.5 Hz, 2H), 6.64 (d, J=16 Hz, 2H), 5.88 (s, 1H). 19F NMR (CDCl3, 470 MHz): δ −57.8 (s). 13C NMR (CDCl3, 125 MHz): δ 182.9, 149.7, 139.1, 137.0, 130.3, 126.6, 125.5, 122.3, 120.4 (q, 1JCF=257 Hz, OCF3), 120.0, 102.3. HRMS (ESI): m/z [M+H]+ calcd for C21H14F6O4: 445.08745; found: 445.09910. IR (cm-1): 3067, 1636, 1582, 1435, 1323, 1265, 1123.

Curcuminoid-BF2 adduct 16: Yield 17%, yellow solid, Rf 0.87 (40% EtOAc in hexane). 1H NMR (acetone-d6, 500 MHz): δ 8.07 (d, J=16.0 Hz, 2H), 7.99 (m, 4H), 7.45 (d, J=7.5 Hz, 4H), 7.18 (d, J=16.0 Hz, 2H), 6.59 (s, 1H). 19F NMR (acetone-d6, 470 MHz): δ −58.4 (s, 6F), −139.7 (s, 11B F), −139.7 (s, 10B F). 13C NMR (CDCl$_3$, 125 MHz): δ 180.9, 151.1, 145.0, 133.4, 131.3, 122.4, 121.4, 120.4 (q, 1JCF=257.0 Hz, OCF3), 102.5. IR (cm-1): 3117-2922, 1628, 1558, 1506, 1400, 1215, 1163, 1055, 1001.

(1E,4E,6E)-5-Hydroxy-1,7-bis(4-trifluoromethoxyphenyl)hepta-1,4,6-trien-3-one (17): Yield 94%, fluffy yellow solid, mp 108-111° C., Rf 0.94 (40% EtOAc in hexane). 1H NMR (acetone-d6, 500 MHz): δ 7.88 (m, 4H), 7.73 (d, J=16.0 Hz, 2H), 7.42 (d, J=8.0 Hz, 4H), 6.95 (d, J=15.5 Hz, 2H), 6.17 (s, 1H). 19F NMR (acetone-d6, 470 MHz) δ −58.5 (s). 13C NMR (CDCl3 and acetone-d6, 125 MHz): δ 183.0, 150.3, 139.0, 133.6, 133.5, 129.5, 124.8, 121.2, 120.4 (q, 1JCF=257 Hz, OCF3), 102.1. HRMS (ESI): m/z [M+H]+ calcd for C21H15F6O4: 445.08747; found: 445.09909. IR (cm-1): 3048-2853, 1628, 1585, 1506, 1420, 1278, 1244, 1213, 1141 1109.

Curcuminoid-BF2 adduct 18: Yield 48%, yellow solid, Rf 0.91 (40% EtOAc in hexane), 1H NMR (DMSO-d6, 500 MHz): δ 8.11 (d, J=16.0 Hz, 2H), 8.02 (d, J=8.5 Hz, 4H), 7.83 (d, J=8.5 Hz, 4H), 7.40 (d, J=16.0 Hz, 4H), 6.74 (s, 1H). 19F NMR (DMSO-d6, 470 MHz): δ −41.4 (s, 6F), −136.6 (s, 11B F), −136.6 (s, 10B F). 13C NMR (DMSO-d6, 125 MHz): δ 180.8, 145.7, 137.1, 136.8, 131.0, 129.9 (q, 1JCF=308 Hz, SCF3), 126.9, 124.3, 103.6. IR (cm-1): 3005-2870, 2361, 2342, 1625, 1562, 1523, 1408, 1277, 1260, 1152, 1105, 1080, 1056.

(1E,4E,6E)-5-Hydroxy-1,7-bis(4-trifluoromethylthiophenyl)hepta-1,4,6-trien-3-one (19): Yield 93%, yellow solid, m.p 128-130° C. Rf 0.93 (40% EtOAc in hexane). 1H NMR (CDCl3, 500 MHz): δ 7.67 (d, J=8 Hz, 4H), 7.65 (d, J=15.5 Hz, 2H), 7.58 (d, J=15.5 Hz, 4H), 6.68 (d, J=15.5 Hz, 2H), 5.88 (s, 1H), 19F NMR (CDCl3, 470 MHz): δ −42.3 (s, 6F). 13C NMR (CDCl3, 125 MHz): δ 182.9, 139.1, 137.3, 136.5, 129.4 (q, 1JCF=308 Hz, SCF3), 128.8, 126.1, 126.0, 102.5. HRMS (ESI): m/z [M+H]+ calcd for C21H15F6O2S2: 477.04177; found: 477.05480. IR (cm-1): 3005-2990, 1630, 1566, 1521, 1404, 1275, 1260, 1167, 1103, 1082, 1049.

Curcumin-BF2 adduct 20: Yield: 57.0%, yellow solid, mp>240° C. Rf 0.56 (40% EtOAc in hexane). 1H NMR (DMSO-d6, 500 MHz): δ 7.99 (d, J=16.0 Hz, 2H), 7.88 (m, 2H), 7.51 (m, 2H), 7.31 (d, J=16.0 Hz, 2H), 6.89 (s, 1H). 19F NMR (DMSO-d6, 470 MHz): δ −128-8 (m, 2F), −134-7 (m, 2F), −136.5 (s, 11B F), −136.6 (s, 10B F), −160.3 (m, 2F). IR (cm-1): 2953-2848, 1625, 1597, 1552, 1512, 1479, 1467, 1303, 1159, 1138, 1061.

(1E,4E,6E)-5-Hydroxy-1,7-bis(2,3,4-trifluorophenyl)hepta-1,4,6-trien-3-one (21): Yield: 93.0%, yellow solid, mp: 156-158° C. Rf 0.89 (40% EtOAc in hexane). 1H NMR (DMSO-d6, 500 MHz): δ 7.68 (d, J=15.5 Hz, 2H), 7.88 (m, 2H), 7.51 (m, 2H), 7.31 (d, J=16.0 Hz, 2H), 6.89 (s, 1H). 19F NMR (DMSO-d6, 470 MHz): δ −128-8 (m, 2F), −134-7 (m, 2F), −136.5 (s, 11B F), −136.6 (s, 10B F), −160.3 (m, 2F). 13C NMR (CDCl3, 125 MHz): δ 182.7, 152.0 (ddd, 1JCF=256 Hz, 2JCF=10 Hz, 3JCF=2.9 Hz), 150.4 (ddd, 1JCF=256 Hz, 2JCF=10 Hz, 3JCF=3.0 Hz), 140.4 (td, 1JCF=253 Hz, 2JCF=15.2 Hz), 131.8, 127.2 (m), 123.1 (m), 120.8 (m), 112.7 (m), 102.5. HRMS (ESI): m/z [M+H]+ calcd for C19H11F6O2: 385.06632; found: 385.07822. IR (cm-1): 2955-2851, 1625, 1597, 1508, 1464, 1303, 1298, 1132, 1036.

3,5-bis-(6-Fluoro-3,4-dimethoxystyryl)-1-phenylpyrazole (22): Yield 85%, pale yellow solid, mp 142-144° C., Rf 0.55 (40% EtOAc in hexane). 1H NMR (CDCl3, 500 MHz): δ 7.53 (m, 4H), 7.42 (m, 1H), 7.32 (d, J=16.0 Hz, 1H), 7.22 (d, J=16.5 Hz, 1H), 7.13 (d, J=16.5 Hz, 1H), 7.09 (d, J=7.0 Hz, 1H), 6.92 (s, 1H), 6.85 (d, J=7.0 Hz, 1H), 6.82 (d, J=16.0 Hz, 1H), 6.65 (d, J=4.0 Hz, 1H), 6.63 (d, J=4.0 Hz, 1H), 3.90 (s, 3H), 3.88 (s, 3H), 3.88 (s, 3H), 3.84 (s, 3H). 19F NMR (CDCl3, 470 MHz) δ −123.3 (dd, J=11.3 and 6.5 Hz, 1F), −124.9 (dd, J=11.8 and 6.6 Hz, 1F). 13C NMR (CDCl3, 125 MHz) δ 155.3 (d, 1JCF=245.0 Hz), 154.9 (d, 1JCF=244.0 Hz), 151.4, 150.2 (d, JCF=9.5 Hz), 149.6 (d, JCF=10.4 Hz), 145.5, 142.6, 139.4, 129.2, 128.0, 125.2, 124.9 (d, JCF=2.9 Hz), 122.7 (d, JCF=2.8 Hz), 120.1 (d, JCF=3.9 Hz), 116.0 (d, JCF=13.3 Hz), 115.5 (d, JCF=5.7 Hz), 115.4, 115.3, 109.0 (d, JCF=5.8 Hz), 108.0 (d, JCF=4.8 Hz), 100.7, 100.3 (d, JCF=20.1 Hz), 100.0 (d, JCF=20.0 Hz), 56.5, 56.3, 56.2, 56.2. HRMS (ESI): m/z [M+H]+ calcd for C29H27F2N2O4: 505.19389; found: 505.19228. IR (cm-1) 3057-2833, 1616, 1597, 1506, 1464, 1440, 1408, 1379, 1356, 1318, 1274, 1234, 1209, 1192, 1171, 1105.

3,5-bis-(6-Fluoro-3,4-dimethoxystyryl)-1-(4-trifluoromethoxyphenyl)pyrazole (23): Yield: 42.0%, Yellow-brown solid, mp 80-83° C., Rf=0.74 (40% EtOAc/Hexane). 1H NMR (CDCl3, 500 MHz): δ 7.60 (d, with additional unresolved splitting, J=8.5 Hz, 2H), 7.37 (d, J=8.5 Hz, 2H), 7.32 (d, J=16.5 Hz, 1H), 7.21 (d, J=16.5 Hz, 1H), 7.11 (d, J=16.5 Hz 1H), 7.08 (d, J=3.0 Hz, 1H), 6.91 (s, 1H), 6.85 (d. J=6.5 Hz, 1H), 6.79 (d, J=16.0 Hz, 1H), 6.65 (d, J=12.0 Hz, 2H), 3.90 (s, 3H), 3.89 (s, 6H), 386 (s, 3H). 19F NMR (CDCl3, 470 MHz): δ −57.9 (s, 3F), −123.0 (dd, J=6.6 Hz and 10.8 Hz, 1F), −124.7 (dd, J=6.6 Hz and 11.8 Hz, 1F). 13C NMR (CDCl3, 125 MHz) δ 155.4 (d, J=245 Hz), 154.9 (d, 1JCF=244 Hz), 151.7, 150.4 (d, JCF=9.5 Hz), 149.7 (d, JCF=9.5 Hz), 148.4, 145.5 (q, JCF=1.9 Hz), 142.7, 138.0, 126.4, 125.6 (d, JCF=1.9 Hz), 123.1 (d, JCF=2.9 Hz), 121.7, 120.4 (q, JCF=259 Hz, OCF3), 119.8 (d, JCF=4.7 Hz), 115.8 (d, JCF=13.3 Hz), 115.2, 115.1 (d, JCF=5.8 Hz), 109.8 (d, JCF=4.7), 108.1 (d, JCF=4.7 Hz), 101.2, 100.4, 100.2 (d, JCF=3.9 Hz) 100.0, 56.5, 56.3, 56.2, 56.2. HRMS (ESI): m/z [M+H]+ calculated for C30H26F5O5N2: 589.17619; found:

589.15726. IR (cm-1): 3078-2835, 1616, 1506, 1464, 1454, 1358, 1254-1107 (unresolved bands).

3,5-bis-(6-Fluoro-3,4-dimethoxystyryl)-1-(3-trifluoromethylphenyl)pyrazole (24): Yield 60%, pale yellow solid, mp 130-134° C., Rf 0.65 (40% EtOAc in hexane). 1H NMR (CDCl3, 500 MHz): δ 7.87 (s, 1H), 7.78 (m, 1H), 7.67 (m, 2H), 7.33 (d, J=17.0 Hz, 1H), 7.24 (d, J=16.5 Hz, 1H), 7.11 (d, J=17.0 Hz, 1H), 7.09 (s, 1H), 6.94 (s, 1H), 6.85 (d, J=6.5 Hz, 1H), 6.82 (d, J=16.5 Hz, 1H), 6.67 (d, J=1.0 Hz, 1H), 6.64 (d, J=1.5 Hz, 1H), 3.91 (s, 3H), 3.89 (s, 3H), 3.89 (s, 3H), 3.86 (s, 3H). 19F NMR (CDCl3, 470 MHz): δ −62.7 (s, 3F), −123.3 (dd, J=11.2 and 6.6 Hz, 1F), −124.7 (dd, J=11.8 and 7.1 Hz, 1F). 13C NMR (CDCl3, 125 MHz): δ 155.4 (d, 1JCF=245 Hz), 155.0 (d, 1JCF=244 Hz), 152.1, 150.5 (d, 2JCF=9.5 Hz), 149.8 (d, 2JCF=9.5 Hz), 145.6 (d, JCF=2.9 Hz), 145.5 (d, JCF=1.9 Hz), 142.8, 139.9, 131.8 (q, 2JCF3=33.4 Hz), 129.9, 128.1, 125.7 (d, JCF=1.9 Hz), 123.4 (d, JCF=3.9 Hz), 123.6 (q, 1JCF3=272.7 Hz), 121.1 (q, JCF=3.9 Hz), 119.6 (d, JCF=4.8 Hz), 115.7 (d, 2JCF=13.3 Hz), 115.1 (d, 2JCF=12.4 Hz), 114.8 (d, JCF=6.7 Hz), 108.6 (d, JCF=4.8 Hz), 108.0 (d, JCF=4.8 Hz), 101.4, 100.3 (d, JCF=22.0 Hz), 100.1 (d, JCF=21.0 Hz), 56.3, 56.3, 56.2, 56.2. HRMS (ESI): m/z [M+H]+ calcd for C30H26F5N2O4: 573.18127; found: 573.19228. IR (cm-1): 3071-2839, 1613, 1504, 1450, 1373, 1273, 1172, 1126, 1103, 1072, 1033.

3,5-bis-(6-Fluoro-3,4-dimethoxystyryl)-1-(3,5-difluorophenyl) pyrazole (25): Yield: 53%, Mustard yellow solid, mp 115-117° C., Rf 0.66 (40% EtOAc/Hexane). 1H NMR (CDCl3, 500 MHz): δ 7.31 (d, J=16.5 Hz, 1H), 7.22 (d, J=16.5 Hz, 1H), 7.16 (dd, J=7.7 Hz and 2.5 Hz, 2H), 7.07 (d, J=16.5 Hz, 1H), 7.07 (d, J=7.5 Hz, 1H), 6.89-6.83 (unresolved m, 4H), 6.67 (d, J=6.5 Hz, 1H), 6.64 (d, J=7.0 Hz, 1H), 3.91 (s, 3H), 3.90 (s, 3H), 3.89 (s, 3H), 3.88 (s, 3H). 19F NMR (CDCl3, 470 MHz): δ −107.7 (t appearance, J=8.5 Hz, 2F), −122.9 (dd, J=6.7 Hz and 5.2 Hz, 1F), −124.6 (dd, J=7.1 Hz and 4.7 Hz, 1F). 13C NMR (CDCl3, 125 MHz): δ 163.0 (d, 1JCF=249 Hz), 162.9 (d, 1JCF=250 Hz), 156.4, 155.9, 154.5, 154.0, 152.1, 150.5 (d, JCF=10.6 Hz), 149.8 (d, JCF=10.4 Hz), 145.6 (d, J=2.9 Hz), 145.5 (d, J=2 Hz) 142.8, 141.5 (t, 3JCF=12.3 Hz), 126.1 (d, JCF=1.9 Hz), 123.5 (d, JCF=2.9 Hz), 119.5 (d, JCF=4.8 Hz), 115.7 (d, JCF=13.0 Hz), 115.0, 114.9, 109.2 (d, JCF=4.7 Hz), 108.2, 108.1, 108.0 (d, JCF=7.7 Hz), 103.0 (t, 2JCF=24.6 Hz), 101.9, 100.2 (t, 2JCF=28.6 Hz), 56.5, 56.3, 56.2, 56.1. HRMS (ESI): m/z [M+H]+ calculated for C29H25N2O4F4: 541.17505; found: 541.15787. IR (cm-1): 3053-2986, 1620, 1512, 1466, 1360, 1325, 1263, 1194, 1123.

3,5-bis-(6-Fluoro-3,4-dimethoxystyryl)-1-(4-cyanophenyl)pyrazole (26): Yield: 81%, yellow solid. mp 91-93° C., Rf 0.61 (40% EtOAc/Hexane). 1H NMR (CDCl3, 500 MHz): δ 7.8 (d, J=8.5 Hz, 2H), 7.72 (d, J=8.5 Hz, 2H), 7.32 (d, J=16.5 Hz, 1H), 7.22 (d, J=16.5 Hz, 1H), 7.08 (d, J=17.0 Hz, 1H), 7.08 (s, 1H), 6.92 (s, 1H), 6.86 (s, 1H), 6.83 (d, J=16.5 Hz, 1H), 6.66 (dd, J=6.0 Hz and 11.7 Hz, 2H), 3.91 (s, 3H), 3.90 (s, 3H), 3.89 (s, 3H), 3.87 (s, 3H). 19F NMR (CDCl3, 470 MHz): δ −122.6 (dd, J=6.6 Hz and 12.5 Hz, 1F), −124.6 (dd, J=8.5 Hz and 11.5 Hz, 1F). 13C NMR (CDCl3, 125 MHz): δ 155.5 (d, 1JCF=245 Hz), 155.0 (d, 1JCF=244 Hz), 152.6, 150.6 (d, J=9.5 Hz), 149.9 (d, J=10.4 Hz), 145.6, JCF=1.8 Hz and 4.7 Hz), 145.60 (d, J=4.7 Hz), 142.9, 133.3, 126.4, 124.8, 123.8 (d, J=2.9 Hz), 119.4 (d, J=4.6 Hz), 118.2, 115.6 (d, J=13.0 Hz), 115.0 (d, J=7.5 Hz), 114.9 (d, J=13.3 Hz), 110.9, 109.4 (d, J=4.7 Hz), 108.1 (d, J=4.7 Hz), 102.5, 100.4, 100.2 (d, J=3.7 Hz), 100.0, 56.6, 56.3, 56.7, 56.2. HRMS (ESI): m/z [M+H]+ calcd. for C30H26O4F2N3: 530.18914; found: 530.19228. IR (cm-1): 3055-2835, 2227, 1605, 1335, 1506, 1450, 1410, 1337, 1360, 1313, 1275, 1103, 1033.

3,5-bis-(6-Fluoro-3,4-dimethoxystyryl)-isoxazole (27): Yield 60%, pale yellow solid, mp 158-160° C., Rf 0.55 (40% EtOAc in hexane). 1H NMR (acetone-d6, 500 MHz): δ 7.45 (d, J=16.5 Hz, 1H), 7.40 (d, J=17.0 Hz, 1H), 7.35 (d, J=7.0 Hz, 1H), 7.33 (d, J=6.5 Hz, 1H), 7.18 (d, J=16.5 Hz, 1H), 7.16 (d, J=17.0 Hz, 1H), 6.91 (s, 1H), 6.87 (d, J=9.5 Hz, 1H), 6.86 (d, J=9.5 Hz, 1H), 3.91 (s, 3H), 3.90 (s, 3H), 3.89 (s, 6H). 19F NMR (CDCl3, 470 MHz) δ −122.2 (dd, J=11.8 and 5.7 Hz, 1F), −124.0 (dd, J=11.8 and 8.5 Hz, 1F). 13C NMR (acetone-d6, 125 MHz): δ 168.6, 162.3, 155.6 (d, 1JCF=244.0 Hz), 155.3 (d, 1JCF=244.0 Hz), 151.7 (d, JCF=10.6 Hz), 151.4 (d, JCF=10.6 Hz), 146.3 (d, JCF=1.9 Hz), 127.6 (d, JCF=2.9 Hz), 126.4 (d, JCF=3.8 Hz), 115.8 (d, JCF=4.8 Hz), 114.6 (d, JCF=12.4 Hz), 114.3, 114.2, 113.1 (d, JCF=5.7 Hz), 109.4 (d, JCF=4.8 Hz), 109.2 (d, JCF=4.8 Hz), 100.4 (d, JCF=9.5 Hz), 100.1 (d, JCF=10.4 Hz), 98.2, 55.8 (2 OMe), 55.6, 55.6. HRMS (ESI): m/z [M+H]+ calcd for C23H22F2NO5: 430.14660; found: 430.15628. IR (cm-1): 3061-2837, 1643, 1618, 1510, 1464, 1440, 1414, 1369, 1310, 1279, 1211, 1192, 1105.

3,5-bis-(4-Trifluoromethylthiostyryl)-1-phenylpyrazole (28): Yield 30%, pale yellow solid, mp 119-121° C., Rf 0.94 (40% EtOAc in hexane). 1H NMR (acetone-d6, 500 MHz): δ 7.79-7.68 (unresolved overlapping signals, 7H), 7.62 (d, J=4.0 Hz, 4H). 7.53 (m, 1H), 7.40 (d, J=16.5 Hz, 1H), 7.39 (d, J=16.5 Hz, 1H), 7.36 (d, J=17.0 Hz, 1H), 7.23 (s, 1H), 7.19 (d, J=16.5 Hz, 1H). 19F NMR (acetone-d6, 470 MHz): δ −43.8 (s, 3F), −43.9 (s, 3F). 13C NMR (CDCl3, 125 MHz): δ 150.6, 142.0, 140.4, 139.7, 139.6, 136.7, 136.7, 130.6, 129.9 (q, 1JCF3=308.1 Hz), 129.8 (q, 1JCF3=307.1 Hz), 129.4, 128.7, 128.1, 127.9, 127.6, 125.2, 123.3, 122.9, 122.2, 118.0, 102.3. HRMS (ESI): m/z [M+H]+ calcd for C27H19F6S2N2: 549.08938; found 549.08770. IR (cm-1): 3047, 1597, 1535, 1497, 1404, 1373, 1319, 1265, 1157, 1080.

3,5-bis-(4-trifluoromethylthiostyryl)-1-(3-trifluoromethylphenyl)pyrazole (29): Yield: 30%, pale yellow solid, mp 121-122° C., Rf 0.95 (40% EtOAc in hexane). 1H NMR (CDCl3, 500 MHz): δ 7.88 (s, 1H), 7.74-7.64 (unresolved, 7H), 7.57 (d, J=8.5 Hz, 2H), 7.46 (d, J=9.0 Hz, 2H), 7.24 (pseudo-s, 2H), 7.17 (d, J=16.0 Hz, 1H), 6.96 (s, 1H), 6.92 (d, J=16.5 Hz, 1H). 19F NMR (CDCl3, 470 MHz): δ −42.6 (s, 3F), −42.7 (s, 3F), −62.7 (3F). 13C NMR (CDCl3, 125 MHz): δ 151.3, 142.0, 139.7, 139.4, 138.6, 136.7, 136.7, 132.2 (q, JCF=33.4 Hz), 131.7, 130.8, 130.7, 130.0, 129.8, 128.2, 127.5, 127.4, 124.9 (q, JCF=3.8 Hz), 124.3 (unresolved q), 124.8 (unresolved q), 124.3 (unresolved q), 122.3 (q, JCF=3.9 Hz), 122.2, 116.9, 102.6. HRMS (ESI): m/z [M+H]+ calcd for C28H18F9S2N2: 617.07677; found 617.08770. IR (cm-1) 3065-3036, 1910, 1593, 1537, 1495, 1468, 1375, 1333, 1111, 1013.

3,5-bis-(4-Trifluoromethylthiostyryl)-isoxazole (30): Yield 41%, yellow needle like crystals, mp 165-167° C., Rf 0.95 (40% EtOAc in hexane). 1H NMR (CDCl₃, 500 MHz): δ 7.69 (d, J=7.0 Hz, 4H), 7.58 (d, J=8.5 Hz, 4H), 7.38 (d, J=16.5 Hz, 1H), 7.23 (d, J=15.0 Hz, 1H), 7.19 (d, J=15.5 Hz, 1H), 7.04 (d, J=16.5 Hz, 1H), 6.56 (s, 1H). 19F NMR (CDCl3, 470 MHz) δ −42.5 (s, 3F), −42.5 (s, 3F). 13C NMR (CDCl3, 125 MHz) δ167.9, 161.6, 138.3, 137.9, 136.7, 134.3, 133.5, 129.5 (q, 1JCF3=310.0 Hz), 127.9, 127.8, 125.0, 124.7, 118.3, 114.9, 99.5. HRMS (ESI): m/z [M+H]+ calcd for C21H14F6S2NO: 474.04210; found: 474.05261. IR (cm-1): 2922, 1637, 1591, 1588, 1510, 1492, 1421, 1155, 1105, 1084.

3,5-bis-(4-Fluorostyryl)-1-phenylpyrazole (31): Yield: 55%, light yellow solid, mp 109-111° C. Rf 0.91 (40% EtOAc in hexane). 1H NMR (CDCl3, 500 MHz): δ 7.54-7.37 (unresolved 9H), 7.20 (d, J=17.0 Hz, 1H), 7.13-7.03 (complex m, 6H), 7.11 (d, J=16.5 Hz, 1H), 7.10 (d, J=16.0 Hz, 1H), 7.07 (d, J=10.0 Hz, 1H), 7.05 (d, J=10.0 Hz, 2H), 6.86 (s, 1H), 6.80 (d, J=16.0 Hz, 1H). 19F NMR (CDCl3, 470 MHz): δ −112.6 (m, 1F), −113.8 (m, 1F). 13C NMR (CDCl$_3$, 125 MHz): δ 162.8 (d, 1JCF=248 Hz), 162.5 (d, 1JCF=248 Hz), 151.0, 142.2, 139.3, 133.2 (d, J=3.8 Hz), 132.5 (d, J=3.7 Hz), 131.2, 129.6, 129.3, 128.3, 128.3, 128.1, 128.1, 128.0, 125.4, 120 (d, J=2.0 Hz), 115.9, 115.9, 115.8, 115.7, 115.6, 115.2 (d, J=2.9 Hz), 101.0. HRMS (ESI): m/z [M+H]+ calcd for C25H19N2F2: 385.15163; found: 385.15430. IR (cm-1): 3066, 3042, 1713, 1597, 1533, 1504, 1458, 1375, 1225, 1157.

3,5-bis-(4-Fluorostyryl)-1-(4-trifluoromethoxyphenyl) pyrazole (32): Yield: 37%, light-brown solid, mp 155-156° C. Rf 0.95 (40% EtOAc in hexane). 1H NMR (CDCl3, 500 MHz): δ 7.57-7.55 (m, 2H), 7.50-7.46 (m, 2H), 7.41-7.38 (m, 4H), 7.18 (d, J=16.5 Hz, 1H), 7.11 (d, J=16.5 Hz, 1H), 7.04-7.08 (m, 5H), 6.84 (s, 1H), 6.75 (d, J=16.5 Hz, 1H). 19F NMR (CDCl3, 470 MHz): δ −57.9 (q, 3F), −112.3 (m, 1F), −113.7 (m, 1F). 13C NMR (CDCl3, 125 MHz): δ 162.8 (d, 1JCF=248 Hz), 162.5 (1JCF, J=248 Hz), 151.4, 148.5 (d, J=2.0 Hz), 142.3, 137.9, 133.1 (d, J=3.7 Hz), 132.4 (d, J=2.7 Hz), 131.8, 129.9, 128.3 (d, J=37.0 Hz), 128.2 (d, J=37.0), 126.6, 121.8, 120.4 (q, 1JCF=257.5 Hz), 119.8 (d, J=2 Hz), 116.0, 115.8 (d, J=3.7 Hz), 115.6, 114.7 (d, J=2.9 Hz), 101.4. HRMS (ESI): m/z [M+H]+ calcd for C26H18N2F5: 469.13393; found: 469.12278. IR (cm-1): 3040, 2924, 1597, 1534, 1504, 1373, 1258, 1211, 1157, 1103, 1011.

3,5-bis-(4-Fluorostyryl)-1-(3-trifluoromethylphenyl) pyrazole (33): Yield: 33%, light orange-brown solid, mp 98-100° C. Rf 0.92 (40% EtOAc in hexane). 1H NMR (CDCl3, 500 MHz): δ 7.88 (s, 1H), 7.74-7.64 (m, 3H), 7.51 (dd, J=9.0 and 5.5 Hz, 2H), 7.40 (dd, J=9.0 and 5.5 Hz, 2H), 7.21 (d, J=16.5 Hz, 1H), 7.13 (d, J=16.5 Hz, 1H), 7.12-7.05 (m, 5H), 6.88 (s, 1H), 6.77 (d, J=16.0 Hz, 1H). 19F NMR (CDCl3, 470 MHz): δ −62.7 (q, 3F), −112.2 (m, 1F), −113.6 (m, 1F). 13C NMR (CDCl3, 125 MHz): δ 162.8 (d, J=248.0 Hz), 162.5 (d, J=248.0 Hz), 151.7, 142.3, 139.8, 133.0 (d, JCF=3.7 Hz), 132.3 (d, J=2.5 Hz), 132.2, 130.1, 129.9, 128.4, 128.3, 128.2, 128.1, 128.0, 124.5 (q, JCF=3.9 Hz), 123.5 (q, 1JCF3=273 Hz), 122.2 (q, JCF=3.7 Hz), 119.7, 116.0, 115.9, 115.8, 115.6, 114.5 (d, J=2.0 Hz), 101.5. HRMS (ESI): m/z [M+H]+ calcd for C26H18N2F5: 453.13901; found: 453.12278. IR (cm-1): 3068, 3041, 1599, 1537, 1506, 1467, 1454, 1337, 1332, 1226, 1157, 1122, 1069.

3,5-bis-(4-Fluorostyryl)-1-(3,4-difluorophenyl)pyrazole (34): Yield: 51%, light-yellow solid, mp 169-170° C. Rf 0.95 (40% EtOAc in hexane). 1H NMR (CDCl3, 500 MHz): δ 7.50-7.47 (m, 2H), 7.44-7.41 (m, 2H), 7.18 (d, J=16.5 Hz, 1H), 7.14-7.00 (m, 8H), 6.88 (td, J=9 Hz and 2 Hz, 1H), 6.84 (s, H), 6.81 (d, J=16.0 Hz, 1H). 19F NMR (CDCl3, 470 MHz): δ −107.4 (m, 2F), −112.0 (m, 1F), −113.5 (m, 1F). 13C NMR (CDCl3, 125 MHz): δ 163.1, (d, 1JCF=250 Hz), 163.0 (d, 1JCF=250 Hz), 162.9 (d, 1JCF=250 Hz), 162.6 (d, 1JCF=250 Hz), 151.7, 142.4, 141.2 (t, 3JCF=13.8 Hz), 132 (d, JCF=3.7 Hz), 132.3, 132.2 (d, JCF=2.9 Hz), 130.4, 128.4 (d, JCF=7.7 Hz), 128.1 (d, JCF=8.5 Hz), 119.5 (d, JCF=2 Hz), 116.0, 115.9, 115.8, 115.7, 114.4 (d, JCF=1.8 Hz), 108.5, 108.4, 108.3, 108.2, 103.3 (t, 2JCF=25.7 Hz), 102.2. HRMS (ESI): m/z [M+H]+ calcd for C25H17N2F4: 421.13279; found: 421.08770. IR (cm-1): 3048, 2338, 1883, 1604, 1504, 1481, 1334, 1227, 1157, 1119.

3,5-bis-(4-Fluorostyryl)-1-(4-cyanophenyl)pyrazole (35): Yield: 52%, light-brown solid, mp 209-211° C. Rf 0.89 (40% EtOAc in hexane). 1H NMR (DMSO, 500 MHz): δ 8.03 (dt, J=9.0 and 2.5 Hz, 2H), 7.76 (dt, J=9.0 and 2.5 Hz, 2H), 7.69-7.62 (m, 4H), 7.33 (d, J=16.5 Hz, 1H), 7.31 (d, J=16.5 Hz, 1H), 7.23-7.19 (m, 5H), 7.16 (d, J=16.5 Hz, 1H), 7.01 (d, J=16.5 Hz, 1H). 19F NMR (DMSO, 470 MHz): δ −112.7 (m, 1F), −113.6 (m, 1F). 13C NMR (DMSO, 125 MHz): δ 162.6 (d, 1JCF=246 Hz), 162.3 (d, 1JCF=245 Hz), 152.1, 142.9, 134.2, 134.1, 133.5, 133.0, 132.7, 130.6, 129.5 (d, J=8.5 Hz), 129.0 (d, J=8.5 Hz), 125.4, 124.3, 120.2, 118.8, 116.2 (d, J=6.8 Hz), 116.1 (d, J=6.6 Hz), 115.3, 110.3, 103.4. HRMS (ESI): m/z [M+H]+ calcd for C26H18N3F2: 410.14688; found: 410.15787. IR (cm-1): 3030-3008, 2227, 1600, 1537, 1504, 1373, 1225, 1157.

3,5-bis-(4-Fluorophenylstyryl)-isoxazole (36): Yield: 42%, white solid, mp 158-160° C., Rf 0.93 (40% EtOAc in hexane). 1H NMR (CDCl3, 500 MHz): δ 7.53-7.50 (m, 4H), 7.33 (d, J=16.5 Hz, 1H), 7.15 (d, J=16.5 Hz, 1H), 7.12-7.07 (m, 4H), 7.05 (d, J=17.0 Hz, 1H), 6.89 (d, J=16.0 Hz, 1H), 6.48 (s, 1H). 19F NMR (CDCl3, 470 MHz): δ −111.4 (m, 1F), −111.9 (m, 1F). 13C NMR (CDCl3, 125 MHz): δ 168.1, 163.2 (d, 1JCF=250 Hz), 163.0 (d, 1JCF=250 Hz), 161.9, 134.5, 133.7, 132.0 (d, JCF=4.0 Hz), 131.7 (d, JCF=3.9 Hz), 128.9, 128.8, 128.7, 128.6, 116.1, 116.0, 115.9, 115.8, 115.7, 112.7 (d, J=1.9 Hz), 98.4. HRMS (ESI): m/z [M+H]+ calcd for C19H14ONF2: 310.10435; found: 310.12278. IR (cm-1): 1651, 1593, 1564, 1508, 1433, 1232, 1159.

3,5-bis-(4-Trifluoromethylstyryl)-1-phenylpyrazole (37): Yield: 39%, mp 137-139° C. Rf 0.93 (40% EtOAc in hexane). 1H NMR (CDCl3, 500 MHz): δ 7.62-7.47 (unresolved m, 13H), 7.30 (d, J=17 Hz, 1H), 7.24 (d, J=17.0 Hz, 1H), 7.16 (d, J=17.0 Hz, 1H), 6.97 (d, J=16.8 Hz, 1H), 6.95 (s, 1H). 19F NMR (CDCl3, 470 MHz): δ −62.4 (s, CF$_3$), −62.6 (s, CF$_3$). 13C NMR (CDCl3, 125 MHz): δ 150.6, 141.8, 140.5, 139.7, 139.2, 130.8, 130.1 (q, J=32.5 Hz), 129.3 (q, J=33.0 Hz), 129.4, 129.2, 128.4, 126.8, 126.6, 125.4, 123.1, 123.0, 122.7, 117.7, 101.9. HRMS (ESI): m/z [M+H]+ calcd for C27H19N2F6: 485.14524 found: 485.15710. IR (cm-1): 3067, 3043, 1614, 1597, 1501, 1458, 1408, 1319, 1161, 1107, 1064, 1014.

3,5-bis-(2,3,4-Trimethoxy-styryl)-1-phenylpyrazole (38): Yield: 52%, light orange oil, Rf 0.60 (40% EtOAc in hexane). 1H NMR (CDCl3, 500 MHz): δ 7.55-7.48 (m, 4H), 7.42-7.40 (m, 2H), 7.33 (d, J=8.5 Hz, 1H), 7.32 (d, J=16.4 Hz, 1H), 7.14 (d, J=16.5 Hz, 1H), 7.13 (d, J=9 Hz, 1H), 6.94 (s, 1H), 6.88 (d, J=16.5 Hz, 1H), 6.73 (d, J=8.5 Hz, 1H), 6.67 (d, J=8.5 Hz, 1H), 3.95 (s, 3H), 3.91 (s, 3H), 3.91 (s, 3H), 3.89 (s, 6H), 3.87 (s, 3H). 13C NMR (CDCl3, 125 MHz): δ 153.9, 153.4, 152.0, 151.9, 151.8, 143.0, 142.5, 142.4, 139.6, 129.2, 127.8, 127.0, 125.4, 125.0, 124.3, 123.5, 121.4, 120.9, 119.8, 114.9, 107.9, 107.7, 100.4, 61.4, 61.3, 60.9, 56.1. HRMS (ESI): m/z [M+H]+ calcd for C31H$_{33}$N2O6: 529.23386; found: 529.22805. IR (cm-1): 3044-2837, 1713, 1593, 1533, 1495, 1456, 1406, 1371, 1096, 1042, 1007.

3,5-bis-(2,3,4-Timethoxy-styryl)-1-(4-trifluoromethoxyphenyl) pyrazole (39): Yield: 44%, dark-red oil, Rf 0.78 (40% EtOAc in hexane). 1H NMR (CDCl3, 500 MHz): δ 7.61-7.59 (m, 2H), 7.42 (d, J=16.5 Hz, 1H), 7.37-7.26 (m, 4H), 7.16 (d, J=8.9 Hz, 1H), 7.13 (d, J=16.5 Hz, 1H), 6.92 (s, 1H), 6.84 (d, J=16.5 Hz, 1H), 6.73 (d, J=9.0 Hz, 1H), 6.68 (d, J=8.0 Hz, 1H), 3.96 (s, 3H), 3.92 (s, 3H), 3.92 (s, 3H), 3.90 (s, 6H), 3.89 (s, 3H). 19F NMR (CDCl3, 470 MHz): δ −57.9 (s, OCF3). 13C NMR (CDCl3, 125 MHz): δ 154.1, 153.5, 152.2, 152.1, 151.8, 148.2, 143.1, 142.5, 142.4, 138.1, 127.7, 126.6, 125.5, 124.1, 123.2, 123.1 (q, J=266

Hz), 121.7, 121.5, 121.0, 119.4, 114.3, 107.9, 107.7, 100.9, 61.4, 61.3, 60.9, 56.0. HRMS (ESI): m/z [M+H]+ calcd for C32H32N2O7F3: 613.21616; found: 613.23494. IR (cm-1): 3041-2839, 1595, 1510, 1495, 1464, 1408, 1375, 1294, 1257, 1222, 1165, 1091.

3,5-bis-(2,3,4-Trimethoxystyryl)-isoxazole (40): Yield: 39%, light-brown solid, mp: 136-137° C. Rf 0.62 (40% EtOAc in hexane). 1H NMR (CDCl3, 500 MHz): δ 7.53 (d, J=16.5 Hz, 1H), 7.38 (d, J=16.5 Hz, 1H), 7.33 (d, J=9.0 Hz, 1H), 7.28 (d, J=9.0 Hz, 1H), 7.08 (d, J=16.5 Hz, 1H), 6.96 (d, J=16.5 Hz, 1H), 6.73, (d, J=9.0 Hz, 1H), 6.72 (d, J=8.0 Hz, 1H), 6.51 (s, 1H), 3.95 (s, 3H), 3.94 (s, 3H), 3.90 (s, 12H). 13C NMR (CDCl3, 125 MHz): δ 168.9, 162.6, 154.5, 154.3, 152.5, 152.1, 142.5, 142.3, 130.1, 129.7, 123.0, 122.7, 121.9, 121.4, 115.3, 112.4, 107.8, 107.7, 97.7, 61.5, 61.4, 60.9, 60.9, 56.2, 56.1. HRMS (ESI): m/z [M+H]+ calcd for C25H28NO7: 454.18658; found: 454.19296. IR (cm-1): 3055-2995, 1643, 1593, 1574, 1557, 1493, 1462, 1433, 1412, 1281, 1092, 1038.

3,5-bis-(3,4,5-Trimethoxy-styryl)-1-phenylpyrazole (41): Yield: 77%, pale-orange solid, mp: 144-146° C. Rf 0.35 (40% EtOAc in hexane). 1H NMR (CDCl3, 500 MHz): δ 7.55-7.50 (m, 4H), 7.43 (t, J=7.5 Hz, 1H), 7.15 (d, J=16.5 Hz, 1H), 7.11 (d, J=16.5 Hz, 1H), 7.07 (d, J=16.0 Hz, 1H), 6.86 (s, 1H), 6.78 (d, J=16.5 Hz, 1H), 6.77 (s, 2H), 6.64 (s, 2H), 3.91 (s, 6H), 3.88 (s, 3H), 3.87 (s, 6H), 3.87 (s, 3H). 13C NMR (CDCl3, 125 MHz): δ 153.5, 153.4, 151.1, 142.3, 139.4, 138.7, 138.0, 132.8, 132.5, 132.1, 129.3, 128.0, 125.2, 119.9, 115.0, 104.0, 103.5, 101.0, 61.0, 56.2, 56.1. HRMS (ESI): m/z [M+H]+ calcd for C31H33N2O6: 529.23386; found: 529.22805. IR (cm-1): 2940, 2832, 2361, 1582, 1497, 1458, 1412, 1373, 1327, 1234, 1118.

3,5-bis-(3,4,5-Trimethoxy-styryl)-1-(4-trifluoromethoxyphenyl) pyrazole (42): Yield: 31%, dark-orange solid, mp: 140-142° C. Rf 0.61 (40% EtOAc in hexane). 1H NMR (CDCl3, 500 MHz): δ 7.61-7.58 (m, 2H), 7.38 (d, J=8.0 Hz, 2H), 7.15 (d, J=16.5 Hz, 1H), 7.09 (d, J=16.0 Hz, 1H), 7.07 (d, J=16.5 Hz, 1H), 6.85 (s, 1H), 6.67 (s, 2H), 6.72 (d, J=16.5 Hz, 1H), 6.64 (s, 2H), 3.91 (s, 6H), 3.89 (s, 6H), 3.88 (s, 3H), 3.87 (s, 3H). 19F NMR (CDCl3, 470 MHz): δ −57.9 (s, OCF3). 13C NMR (CDCl3, 125 MHz): δ 153.5, 153.4, 151.4, 148.4, 142.4, 138.9, 138.2, 137.9, 133.2, 132.6, 131.8, 131.1, 126.5, 121.8, 120.5 (q, J=258 Hz), 119.5, 114.4, 104.0, 103.6, 101.5, 61.0, 61.0, 56.2, 56.1. HRMS (ESI): m/z [M+H]+ calcd for C32H32N2O7F3: 613.21616; found: 613.22805. IR (cm-1): 3001-2837, 1581, 1504, 1465, 1415, 1377, 1301, 1240-1101, 1005.

3,5-bis-(3,45-Trimethoxystyryl)-1-(3,4-difluorophenyl) pyrazole (43): Yield: 32%, light-brown solid, mp: 54-56° C., Rf 0.62 (40% EtOAc in hexane). 1H NMR (DMSO-d6, 500 MHz): δ 7.15-7.06 (unresolved, 5H), 6.88 (tt, JHF=8.5 Hz, JHH=2.5 Hz, 1H), 6.85 (s, 1H), 6.80 (d, J=16.5 Hz, 1H), 6.77 (s, 2H), 6.67 (s, 2H), 3.92 (s, 6H), 3.90 (s, 6H), 3.89 (s, 3H), 3.88 (s, 3H). 19F NMR (CDCl3, 470 MHz): δ −107-5 (t, J=8.0 Hz). 13C NMR (CDCl3, 125 MHz): δ 163.0, (d, 1JCF=250 Hz), 162.8 (d, 1JCF=250 Hz), 153.5, 152.0, 143.1, 141.7 (t, 3JCF=12.0 Hz), 138.6, 138.0, 134.2, 132.7, 132.2, 132.0, 119.7, 115.0, 108.6, 108.4, 105.0, 104.4, 103.5 (t, 2JCF=26.0 Hz), 103.1, 60.6, 60.5, 56.4, 56.3. HRMS (ESI): m/z [M+H]+ calcd for C31H31N2O6F2: 565.21502; found: 565.22207. IR (cm-1): 3080-2837, 1621, 1581, 1505, 1464, 1414, 1346, 1331, 1242, 1122.

Computational Methods

Geometry optimizations of the curcumin, pyrazole, and isoxazole derivatives were performed at the B3LYP/6-31G* level with the Gaussian 09 package. Automated molecular docking calculations with the program AutoDock Vina were carried out for estimating the interaction energies and modeling the binding modes of the studied compounds as ligands for a series of enzymes involved in diverse carcinogenic processes (HER2, proteasome, VEGFR2, BRAF, and BCL-2). The three-dimensional coordinates of the proteins were obtained from the Protein Data Bank (PDB codes 3PP0 (HER2), 3SDK (20S proteasome), 4AG8 (VEGFR2), 4XV2 (BRAF), and 4LVT (BCL-2)). Chain A of HER2, VEGFR2, BRAF and BCL-2, and chains K (β5 subunit) and L (β6 subunit) of 20S proteasome were selected as target templates for the docking calculations. Co-crystalized ligands and crystallographic water molecules were removed. Addition of hydrogens, merger of non-polar hydrogens to the atom to which they were linked, and assignment of partial charges were achieved with Auto-DockTools. Docking areas were constrained to a 30×30×30 Å box centered at the active site, providing proper space for rotational and translational movement of the ligands.

X-Ray Crystallography

Suitable single crystals for X-ray diffraction studies were obtained for 2, and 4 from chloroform and 15, 17, 19 and 21 from methanol. Crystal data of compounds 2, 4, 15, 17, 19 and 21 of FIG. 43 were collected by exactly the same method by mounting a crystal onto a thin glass fiber from a pool of Fluorolube™ and immediately placing it under a liquid N2 cooled stream, on a Bruker AXS diffractometer upgraded with an APEX II CCD detector. The radiation used is graphite monochromatized Mo Kα radiation (λ=0.7107 Å). The lattice parameters are optimized from a least-squares calculation on carefully centered reflections.

Lattice determination, data collection, structure refinement, scaling, and data reduction were carried out using APEX2 Version 2014.11 software package. The data were corrected for absorption using the SCALE program within the APEX2 software package. The structures were solved using SHELXT. This procedure yielded a number of the C, B, F, S and O atoms. Subsequent Fourier synthesis yielded the remaining atom positions. The hydrogen atoms are fixed in positions of ideal geometry (riding model) and refined within the XSHELL software package. These idealized hydrogen atoms had their isotropic temperature factors fixed at 1.2 or 1.5 times the equivalent isotropic U of the C atoms to which they were bonded. A few hydrogen atoms could not be adequately predicted via the riding model within the XSHELL software. These hydrogen atoms were located via difference-Fourier mapping and subsequently refined. The final refinement of each compound included anisotropic thermal parameters on all non-hydrogen atoms.

Bioassay Methods

NCI-60 Assay

Samples were submitted to the National Cancer Institute (NCI of NIH) Developmental Therapeutics anticancer screening program (DTP) for human tumor cell line assay by NCI-60 screening against leukemia, lung, colon, and CNS cancers, as well as melanoma, ovarian, renal, prostate, and breast cancers. Compounds are initially tested at a single dose of 10-5 molar. Data are reported as mean graph of percent growth (GP). Growth inhibition is shown by values between 0 and 100 and lethality by values less than zero. Compounds that meet selection criteria based on one-dose assay are then tested against 60 cell panel at five concentrations.

Cell Viability Assay to Determine EC50

Cells (2×103 cell/well) were incubated with compounds (concentration range 0-30000 nM) in a 384-well plate for 72 h in a $CO_2$ incubator (5% CO2, 37° C.). Cell lines and PBCMs (peripheral blood mononuclear cells from healthy donors as non-cancer CONTROL) were seeded in quadruplicate (technical replicates). CellTiter-Glo® 2.0 reagent equal to the volume of cell culture medium present in each well was added and the plate was left to incubate at room temperature for 10 min to stabilize the luminescent signal. Luminescent signal/intensity from the 384-well plate was read on a plate reader. Cells/cell lines used: BCWM.1 (Waldenstrom macroglobulinemia cell line, WM); RPMI-8266 (Multiple myeloma cell line, MM); RS4; 11 (Acute lymphoblastic leukemia, ALL)* reported to be dependent on Bcl-2 protein.

Example 5—Heterocyclic Compounds Including Indole-Based, Benzothiophene-Based and Benzofuran-Based CUR—$BF_2$ Adducts and CUR Compounds and their Pyrazoles A novel series of heterocyclic CUR—$BF_2$ adducts and CUR compounds based on indole, benzothiophene, and benzofuran along with their aryl-pyrazoles were synthesized. Exemplary indole-based curcuminoid compounds, thiocyano-curcuminoid compounds and difluoroboron-curcuminoid adducts are shown in FIG. 45 and exemplary benzothiophene-curcuminoid compounds, benzofuran-curcuminoid compounds, and difluoroboron-curcuminoid adducts are shown in FIG. 46. S-methylated curcuminoid di-cation salts were formed using a variation of the synthetic methods, as seen in FIG. 47.

Computational/docking studies were performed on 20 heterocyclic CUR—$BF_2$ and CUR compounds to compare binding efficiency to target proteins involved in specific cancers, namely HER2, proteasome, VEGFR, BRAF, and BCL-2 versus known inhibitor drugs. The majority presented very favorable binding affinities that were comparable and, in some cases, more favorable than the known-inhibitors. The indole-based CUR—$BF_2$ and CUR compounds and their bis-thiocyanato derivatives exhibited high anti-proliferative and apoptotic activity by in-vitro bioassay against a panel of 60 cancer cell lines, and more specifically against multiple myeloma (MM) cell lines (KMS11, MM1.S, and RPMI-8226) with significantly lower IC50s versus healthy PBMC cells. The indole-based CUR—$BF_2$ adducts and their bis-thiocyanato derivatives exhibited significantly higher anti-proliferative activity in human colorectal cancer cells (HCT116, HT29, DLD-1, RKO, SW837, and Caco2) compared to parent curcumin, while showing significantly lower cytotoxicity in normal cells (CCD112CoN and CCD841CoN).

The inventors used the earlier described one-pot method in Example 1 for the synthesis of CUR—$BF_2$ adducts for the synthesis of heterocyclic analogues starting with the corresponding aldehydes. In the majority of cases, the CUR—$BF_2$ adducts precipitated from ethyl acetate after overnight stirring at r.t. as detailed below.

1) Synthesis of Indole-Based CUR—$BF_2$ Adducts and CUR Compounds a) From indole 5-aldehyde: The initial crop that precipitated out of EtOAc was a tautomeric mixture of 2a-$BF_2$ and 2-$BF_2$ in 60:40 ratio by NMR (FIG. 48). By adding, some more base to the filtrate and continuing stirring overnight a second crop was produced that proved to be the enolic tautomer 2-$BF_2$. In independent runs 2-$BF_2$ was isolated as the sole product by using 0.66 equivalent of base after overnight stirring.

When a portion of crop 1 (CUR—$BF_2$ tautomeric mixture) was subjected to microwave (MW)-assisted decomplexation, a tautomeric mixture of the corresponding CURs 2a and 2 were obtained with the enolic tautomer 2 predominating. Decomplexation of another portion of the tautomeric mixture similarly resulted in a tautomeric mixture in which 2 was major. Finally, MW-assisted decomplexation of the 2-$BF_2$ furnished compound 2 purely as the enol tautomer in 94% isolated yield (FIG. 49).

b) From indole 4-aldehyde: In initial studies (on a 500 mg scale), no precipitate was formed after 3 days mixing at r.t. Removal of EtOAc gave a dark residue which after washing with diethyl ether was shown by NMR to be a tautomeric mixture of enolic and the diketo forms in 4:1 ratio. By addition of more base and by using less EtOAc in a subsequent reaction, 3-$BF_2$ precipitated solely as the enol tautomer. The MW-assisted decomplexation cleanly gave the corresponding curcuminoid 3 as an enolic compound in 77% isolated yield (FIG. 50).

c) Synthesis of bis-Thiocyanato-Derivatives of Indole-Based CUR—$BF_2$ and CUR compounds: There is considerable current interest in the introduction of thiocyano group into bioactive compounds, and this has in turn stimulated a search for new thiocyanation methods. (T. Castanheiro, et al., *Chem. Soc. Rev.* 2016, 45, 494; G. Malik, et al., *Chem. Sci.*, 2017, 8, 8050-8060; D. Wu, et al., *J. Org. Chem.* 2018, 83, 1576-1583). Development of a new method in this laboratory for facile introduction of SCN and SeCN groups into medicinally important heterocycles, enabled the synthesis of bis-thiocyanato CUR—$BF_2$ and CUR compounds starting from the SCN-substituted benzaldehydes (FIG. 51).

Since attempts to obtain X-ray quality crystals from the CUR—$BF_2$ or CUR compounds in this class did not meet with success, their structure were optimized by DFT. Two representative examples (4-$BF_2$ and 5-$BF_2$) are shown (FIG. 52) while two others are shown in FIG. 53.

d) From N-Methylindole-3-aldehyde: Following our standard protocol, in a small scale experiment N-methylindole-5-carboxaldehyde reacted to give the 1,3-diketo tautomer 6a-$BF_2$ as a deep-purple solid which was harvested in two crops in 22% combined yield (FIG. 54). The MW-assisted decomplexation of 6a-$BF_2$ cleanly furnished the corresponding curcuminoid 6a solely as the 1,3-diketo-tautomer in 64% isolated yield.

A second synthesis (FIG. 55) employing less ethyl acetate produced two crops, the first crop precipitated overnight (a red solid) as a 4: 1 tautomeric mixture, and a second crop was harvested (after addition of more base to the filtrate and stirring at r.t. for 2 days) which was solely the enolic 6-$BF_2$ (a green solid). Decomplexation of 6-$BF_2$ required multiple runs in the MW, followed by re-crystallization from methanol, to cleanly furnish compound 6 as a bright-red solid (FIG. 55).

2) Synthesis of Heterocyclic Benzothiophene- and Benzofuran-Based CUR—$BF_2$ and CUR Compounds and their Aryl-Pyrazoles Following the general one-pot method described in Example 4, the corresponding CUR—$BF_2$ adducts and CUR compounds in FIG. 56 were synthesized starting from the corresponding aldehydes. NMR spectra confirmed the sole presence of the enolic tautomers in every case.

With the goal to determine the significance of the keto-enolic moiety in bioactivity for this class of compounds, a small library of aryl-pyrazoles 10-15 were also synthesized (FIG. 57) following the earlier reported method.

Computational Docking Study

Molecular docking calculations were carried out with the aim to shed light on factors governing the biological activity of the heterocyclic curcuminoids. Binding affinities in the active site of various proteins involved in carcinogenic mechanisms were determined, and computed binding energies were compared with those of the corresponding known inhibitors (Table 8). The proteins selected for docking studies comprise a variety of oncogenic processes, described as follows.

Human epidermal growth factor receptor 2 (HER2), which is one of the tyrosine kinase receptors in EGFR family, has a crucial role in the evolution of several human cancers. (N. Iqbal, et al., *Mol. Biol. Int.*, 2014, 2014, 852748). It is a target for therapies pointing to inhibition of HER2 to reduce tumor growth, since amplification or overexpression of this protein appears in breast, prostate, gastric/gastroesophageal, ovarian, endometrium, bladder, lung, colon, and head and neck cancers. (N. Iqbal, et al., *Mol. Biol. Int.*, 2014, 2014, 852748). It has been suggested that inhibition of tumor cellular proteasome is the mechanism by which curcumin prevents the proliferation of acute promyelocytic leukemia (APL) cells. (K.-L. Tan, et al., *ChemMedChem* 2012 7, 1567-1579). Treatment with proteasome inhibitors causes a decrease in proliferation, induction of apoptosis and sensitization of diverse tumor cells by chemotherapeutic drugs and irradiation. (S. B. Wan, et al., *Int. J. Mol. Med.*, 2010, 26, 447-455). The vascular endothelial growth factor receptor (VEGFR) tyrosine kinases are clinically confirmed target of inhibitors applied in the renal cell carcinoma therapy. (M. McTigue, et al., *Proc. Nat. Acad. Sci. USA*, 2012, 109, 18281-18289). The treatment of metastatic melanoma significantly evolved by selective inhibition of BRAF, as oncogenic activation of this protein stimulates cancer cell growth. (C. Zhang, et al., *Nature*, 2015, 526, 583-586). The connection of proteins in the BCL-2 family (crucial regulators of normal apoptosis) with tumor initiation, disease progression and drug resistance makes them crucial targets for antitumor therapy. (A. J. Souers, et al., *Nat. Med.*, 2013, 19, 202-208). BCL-2 is over-expressed in acute and chronic leukemias and presents a central role in the survival of multiple lymphoid malignancies. (A. J. Souers, et al., *Nat. Med.*, 2013, 19, 202-208). The studied CUR—$BF_2$ and CUR compounds were able to fit nicely into the binding pocket of the considered proteins, and several compounds revealed markedly favored binding affinities (Table 8). In proteasome, VEGFR, and in BCL-2, several CUR derivatives presented enhanced binding energies in comparison with known inhibitors that are used in chemotherapy. It is noteworthy that docking energy for the 1,3-diketo tautomer (as in $2aBF_2$) is also predicted to be highly favorable, suggesting that in case of tautomeric mixtures both tautomers are capable of favorable docking interactions. Binding interactions for the compounds exhibiting highly favorable docking energies in the active site of each protein are displayed in FIG. 58. The principle interactions observed are hydrophobic contacts between the atoms of the ligands and the protein residues (red radial lines). In addition, hydrogen bond interactions were found between F and N ligand atoms and hydrogen bond donor groups in neighboring protein residues. FIG. 59 depicts a 3D representation of 3-$BF_2$ in BCl-2.

TABLE 8

| | Binding Energies | | | | |
| --- | --- | --- | --- | --- | --- |
| | AutoDock Vina (kcal/mol)[a] | | | | |
| Heterocyclic Compounds | HER2 | Proteasome | VEGFR | BRAF | BCL-2 |
| Known inhibitor | −11.4 (SYR) | −7.8 (Bortezomib) −7.8 (Ixazomib) −8.5 (Carfilzomib) | −9.2 (Axitinib) −10.8 (Sorafenib) −8.9 (Lenvatinib) | −9.3 (Vemurafenib) −12.9 (Dabrafenib) | −8.3 (Navitoclax) −8.2 (Venetoclax) |
| 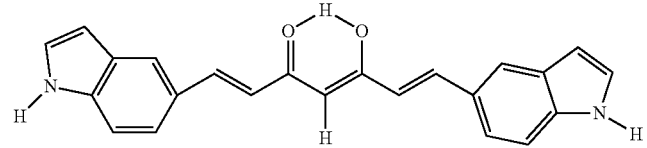 | −11.0 | −9.6 | −11.7 | −10.2 | −8.6 |
| 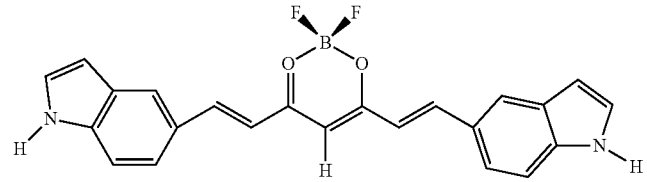 | −10.8 | −10.4 | −12.6 | −10.6 | −8.7 |
| 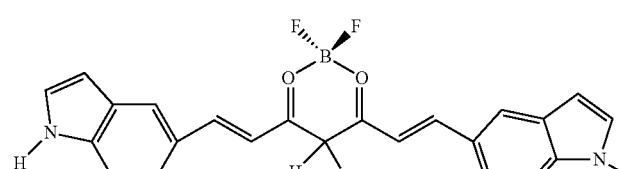 | −10.5 | −10.3 | −12.5 | −10.7 | −9.4 |

TABLE 8-continued

| | Binding Energies | | | | |
|---|---|---|---|---|---|
| | AutoDock Vina (kcal/mol)[a] | | | | |
| Heterocyclic Compounds | HER2 | Proteasome | VEGFR | BRAF | BCL-2 |
| (structure) | −10.4 | −9.9 | −12.4 | −10.9 | −8.3 |
| (structure) | −8.9 | −10.1 | −11.5 | −9.8 | −9.4 |
| (structure) | −10.1 | −9.6 | −10.5 | −10.2 | −7.7 |
| (structure) | −10.2 | −10.5 | −11.7 | −10.3 | −9.4 |
| (structure) | −9.3 | −10.8 | −10.0 | −10.1 | −7.7 |
| (structure) | −8.7 | −9.4 | −9.4 | −9.2 | −6.6 |
| (structure) | −9.0 | −9.6 | −9.9 | −9.5 | −9.3 |

TABLE 8-continued

| | Binding Energies | | | | |
|---|---|---|---|---|---|
| | AutoDock Vina (kcal/mol)[a] | | | | |
| Heterocyclic Compounds | HER2 | Proteasome | VEGFR | BRAF | BCL-2 |
| | −9.4 | −10.1 | −11.2 | −10.2 | −9.2 |
| | −9.6 | −10.5 | −11.8 | −10.7 | −8.5 |
| | −10.2 | −9.4 | −10.8 | −10.9 | −9.0 |
| | −11.7 | −10.5 | −11.4 | −11.1 | −8.7 |
| | −9.8 | −9.3 | −10.4 | −9.6 | −8.8 |
| | −10.5 | −9.9 | −11.1 | −10.4 | −8.5 |

TABLE 8-continued

Binding Energies

| Heterocyclic Compounds | AutoDock Vina (kcal/mol)[a] | | | | |
|---|---|---|---|---|---|
| | HER2 | Proteasome | VEGFR | BRAF | BCL-2 |
| 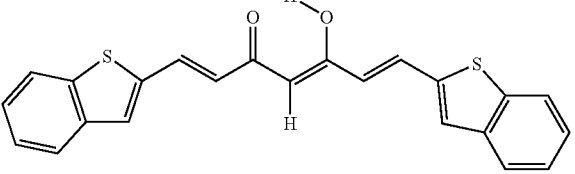 | −9.8 | −8.9 | −11.2 | −9.5 | −8.0 |
| 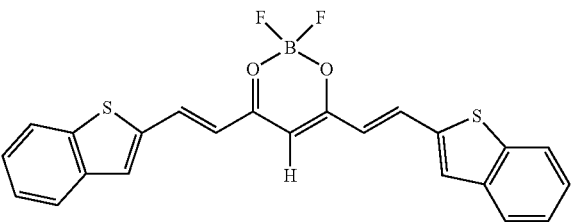 | −10.7 | −9.1 | −12.7 | −10.8 | −7.7 |
| 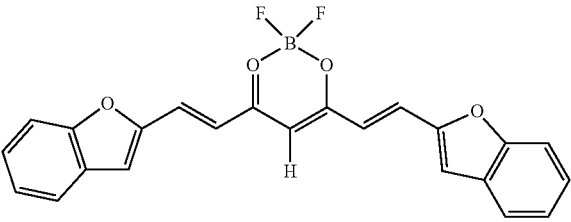 | −11.6 | −10.0 | −13.3 | −11.0 | −8.0 |
| 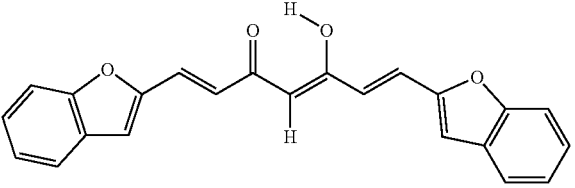 [SMILES: O=C(/C=C(O)/C=C/c1cc2ccccc2o1)/C=C/c1cc2ccccc2o1] | −9.9 | −9.9 | −11.7 | −10.1 | −8.2 |

[a]Most stable binding mode.
[b]Binding energies in bold = more favorable than known inhibitors In-Vitro Bioassay Study The heterocyclic CUR—$BF_2$ and CUR compounds synthesized in the present study along with representative aryl-pyrazoles were initially tested for their anti-proliferative activity by the NCI-60 in-vitro assay. Among these, the indole-based CUR—$BF_2$ and CUR compounds, and in particular their bis-thiocyanato-derivatives (FIG. 60), exhibited notable anti-proliferative and apoptotic activity in a number of cell lines in several types of cancers, as reflected in either low or negative growth percent values respectively under standard $10^{-5}$ molar concentration. Subsequent five-dose assay on these compounds (performed at the NCI) showed significant anti-proliferative activity remaining at $10^{-6}$ molar concentrations, followed by a rapid drop at lower concentrations. Among the N-methyl-indole derivatives and the benzothiophene- and benzofuran-derived CUR—$BF_2$ and CUR compounds only 7-$BF_2$ of FIG. 60 showed notable anti-proliferative activity, while the corresponding aryl-pyrazoles proved to be ineffective.

Compounds shown in FIG. 60 were subsequently tested to determine their ability to induce cytotoxicity in a small panel of hematologic cancer cell lines in comparison to healthy (non-cancer) peripheral blood mononuclear cells (PBMCs). The indole-CUR and CUR—$BF_2$ compounds exhibited significant cytotoxicity in multiple myeloma (MM) cancer cells, with little to no cell death noted in healthy donor PBMCs.

Further bioassay studies focused on an expanded panel of MM cell lines that capture some of the genetic variability as seen in MM patients. Notably, these MM cell lines included MM1.S cells (TP53 wild type), KMS11 cells (TP53 biallelic deletion) and RPMI-8226 cells (c-MYC dependent). Among these select group of heterocyclic curcuminoids, 3-$BF_2$ and 2 of FIG. 60 exhibited remarkable tumor-selective activity with median $IC_{50}$ concentration in the aforementioned MM cell lines of 2.1 uM and 1.4 uM, respectively. They also showed notable MM-cell specific cytotoxicity with mean activity of 33.7-fold (range, 4—2,445-fold) greater in the MM cell lines relative to healthy PBMCs (FIG. 61). It is noteworthy that the MM standard-of-care agent, bortezomib (a proteasome inhibitor) has an in vitro tumor-specificity profile of roughly 2-3-fold ($IC_{50}$ in MM cells ~2 nM and $IC_{50}$ of PBMCs is ~4-6 nM).

Figure 72:
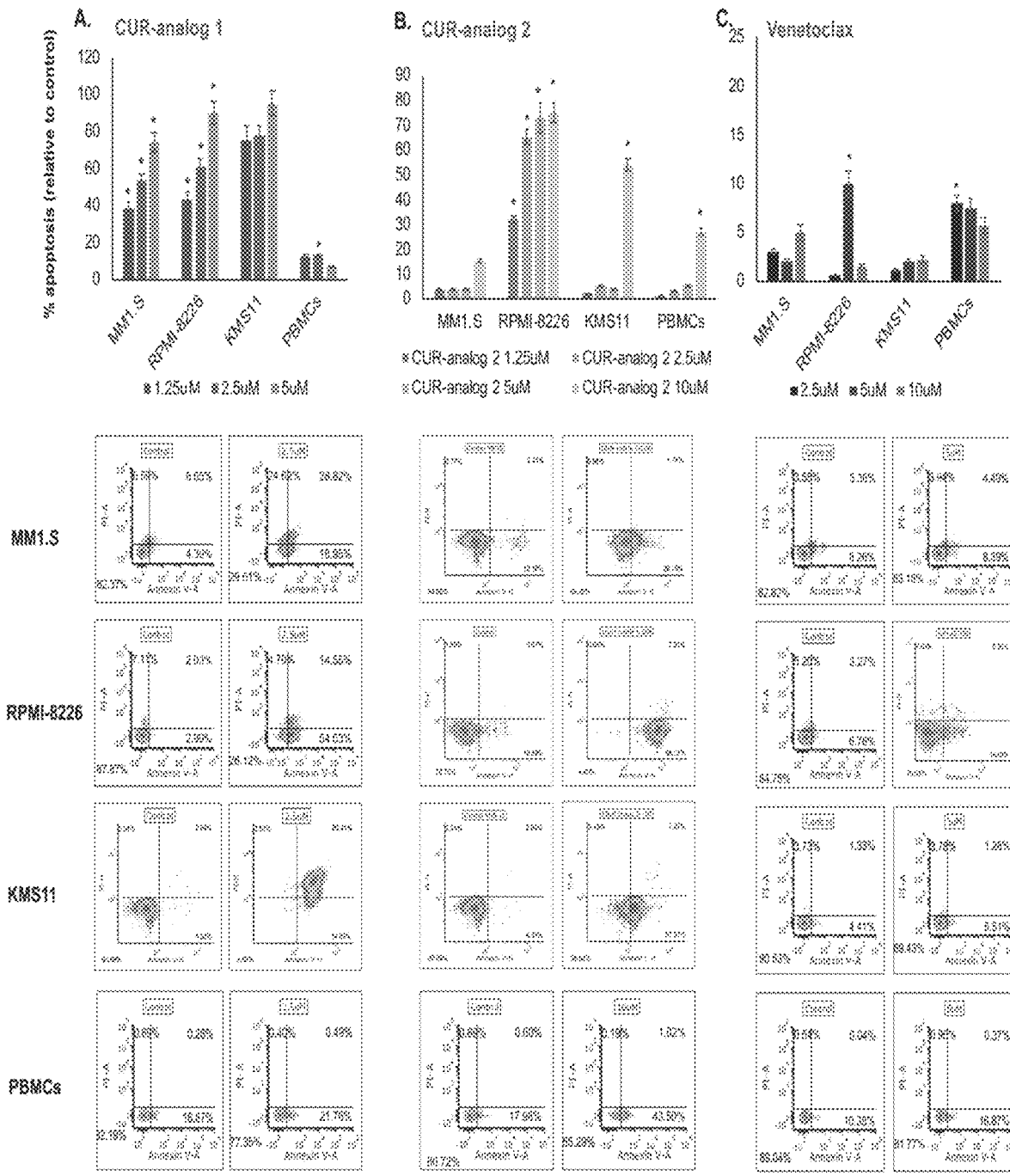

Next, the ability of these hit compounds to induce cell death was assessed through apoptosis at 1.25 uM and 2.5 uM concentrations for 24 h (FIG. 73). With 3-$BF_2$ of FIG. 60, significant apoptosis in MM1.S (34% and 47%), KMS-11 (75% and 79%), and RPMI-8226 (39% and 60%) cells occurred relative to healthy donor PBMCs, treated with the same concentrations (23-28% apoptosis observed). Next, the MM cells and PBMCs were tested with CUR-analog 2, showing that in line with cell proliferation assay data (FIG. 61), RPMI-8226 cells were most sensitive to this compound with 32% and 65% of cells undergoing apoptosis at 1.25 uM and 2.5 uM concentrations. In contrast, in KMS11 and MM1.S cells, notable apoptosis (54% and 15%, respectively) was seen only at a 10 uM concentration. For comparison, the same MM cell lines were exposed to venetoclax (FDA-approved anti-Bcl-2 inhibitor, activator of apoptosis) at 1.25, 2.5, 5 uM and at 10 uM concentration, showing a median apoptosis of 15%; with ~10% cell death seen in healthy donor PBMCs (FIG. 72).

Compounds shown in FIG. 60 along with two other CUR—$BF_2$ compounds from FIG. 73 were subsequently tested for their anti-proliferative activity and cytotoxicity in colorectal cancer (CRC) cells and in normal colon cells in comparison to parent curcumin. The CUR—$BF_2$ adducts and in particular, the bis-SCN derivatives exhibited significantly higher anti-cancer activity (growth inhibition) compared to curcumin, while the corresponding CUR compounds were less effective. Moreover, in comparison to parent curcumin, the CUR—$BF_2$ adducts were noticeably more toxic to cancer cells than to normal colon cells (see FIG. 61 and FIG. 74).

In summary, the inventors have synthesized a series of new heterocyclic CUR—$BF_2$ and CUR compounds based on indole, benzothiophene and benzofuran were synthesized and characterized. Whereas computational docking studies showed that a fairly large subset of these compounds are capable of favorable docking interactions with several key proteins involved in carcinogenic mechanisms, bioassay studies pointed to a smaller subset and in particular two curcuminoids (3-$BF_2$ and 2) with favorable cytotoxicity characteristics as potential hit compounds. Guided by the initial NCI-60 data, the anti-proliferative and apoptotic efficacy of the CUR—$BF_2$ and CUR compounds (FIG. 74) were studied in colorectal cancer (CRC) cells. The CUR—$BF_2$ adducts, and in particular the bis-SCN derivatives, exhibited significantly higher anti-cancer activity compared to curcumin. Moreover, these compounds proved to possess more cancer cell-specific cell growth inhibition and lower toxicity to normal cells.

Experimental Section

General: The substituted benzaldehydes used in this study were all high purity commercially available samples and were used without further purification. Regular solvents used for synthesis and isolation (MeCN, acetone, DCM, hexane, and EtOAc) were all of sufficient purity and were used as received. NMR spectra were recorded on a 500 MHz instrument using $CDCl_3$, DMSO-$d_6$ or acetone-$d_6$ as solvent. $^{19}F$ NMR were referenced relative to external $CFCl_3$. HRMS analyses were performed on a Finnigan Quantum ultra-AM in electrospray mode using methanol as solvent. Microwave reactions were performed in Biotage miniature 400 W lab microwave in 5 mL vials with magnetic stirring. FT-IR spectra were recorded in ATR mode (as thin films formed via DCM evaporation). Melting points were measured in open capillaries and are not corrected.

General procedure for the synthesis of curcuminoid-$BF_2$ adducts: To a mixture of acetyl acetone-$BF_2$ complex (1 equiv.) in ethyl acetate (minimal) under stirring and nitrogen atmosphere, the respective aldehyde (2.2 equiv.) was added in one portion, followed by dropwise addition of N-butyl amine (0.22 equiv.) over a period of 20 minutes. The CUR—$BF_2$ adduct precipitated out of EtOAc upon overnight stirring at r.t. The reaction mixture was subsequently cooled to 0° C. and the product was filtered, washed with cold (0° C.) EtOAc and dried under high vacuum, typically for 1 h.

Variations thereof—in cases where the product had precipitated but the yield was poor <40%, the reaction mixture was returned to the flask with additional N-butyl amine (0.22 equiv.), and the reaction mixture was left to stir for an additional 48 hours whereupon additional product precipitated out of EtOAc. This was required for all of the indole-based curcuminoids, and for 8-$BF_2$. (FIG. 56) For 7-$BF_2$ the crude mixture was left in the freezer for 2 days to harvest an additional crop. (FIG. 56)

General procedure for the decomplexation of CUR—$BF_2$: The curcuminoid-$BF_2$ complex (1 equiv.) and sodium oxalate (2 equiv.) were added to a 5 mL microwave vial equipped with a magnetic stirrer bar. Aqueous MeOH (5 mL, 8:2 MeOH:$H_2O$) was added and the vial was sealed with a crimp cap with septa. The sealed vial was irradiated at 100 W for 6 min at 140° C. with stirring set at 900 rpm. Decomplexation resulted in significant color change. The vial was cooled, the cap removed, and the reaction mixture was filtered, washed with de-ionized water, and the product was dried for 15 min on the sinter and then under high vacuum.

Variations thereof: 7-$BF_2$ of FIG. 56 required 4 equivalents of sodium oxalate to fully decomplex in the microwave at 145° C. for 10 minutes.

Synthesis of the Aryl-pyrazole derivatives 10-15 of FIG. 57: these were synthesized by reacting the corresponding CUR compound with aryl-pyrazoles in acetic acid using the previously described procedure in Example 4.

Representative Procedure: Curcuminoid 7 of FIG. 56 (60 mg, 0.155 mmol, 1 equiv.) was added to a small Erlenmeyer flask along with 5 mL of glacial acetic acid, and phenyl hydrazine (67 mg, 0.62 mmol, 4 equiv.) was then added. The reaction mixture was placed on a hotplate with stirring at 80° C. for 2 hours. Following overnight mixing at r.t, the reaction mixture was reheated to 80° C. and $H_2O$ was slowly added until the solution was almost turbid. The flask was then removed from the heat and left to cool in an ice-bath. The product precipitated by cooling in an ice-bath. It was washed with 3×5 mL portions of $H_2O$, and dried on high vacuum for an hour to give 36 mg of a light-brown solid.

Variations: in the reaction with substituted phenyl hydrazines only 2 equivalents of the phenyl hydrazine was used. For compound 15 of FIG. 57, the product had to be further purified by re-crystallization from $Et_2O$/hexane.

Characterization Data for Compounds in FIGS. 48-51, 54-57, 60 and 64

Indole-5-Curcuminoid-$BF_2$ adduct (2-$BF_2$): Yield 65%, brown powder. $R_f$ 0.11 (40% EtOAc in hexane). $^1H$ NMR (acetone-$d_6$, 500 MHz): δ 10.65 (br s, 2H), 8.18 (d, J=16.0 Hz, 2H), 8.11 (s, 2H), 7.67 (dd, J=8.5 Hz and 1.5 Hz, 2H), 7.56 (d, J=8.5 Hz, 2H), 7.45 (unresolved dd, J=3 Hz, 2H), 7.04 (d, J=15.5 Hz, 2H), 6.62 (d, J=3.0 Hz, 2H), 6.45 (s, 1H). $^{13}C$ NMR (DMSO-$d_6$, 125 MHz): δ 178.7, 148.7, 138.2, 128.2, 127.3, 125.6, 124.6, 122.0, 117.5, 112.5, 102.7, 101.2. $^{19}F$ NMR (acetone-$d_6$, 470 MHz): δ −141.1 (s, $^{11}B$—F), −141.2 (s, $^{10}B$—F). IR (cm$^{-1}$): 3418, 3005-2989, 1602, 1564, 1497, 1456, 1355, 1300, 1275, 1260, 1171, 1149, 1124, 1043.

Indole-5-Curcuminoid-$BF_2$ adduct (2a-$BF_2$) (1,3-diketo tautomer in a mixture with 2-$BF_2$): $R_f$ 0.26 (40% EtOAc in hexane): $^1H$ NMR (acetone-$d_6$, 500 MHz): δ 8.16 (d, J=16.0

Hz, 2H), 8.09 (unresolved, 2H), 7.61 (overlapping dd, 2H), 7.44 (unresolved, 2H), 7.0 (d, J=16.0 Hz, 2H), 6.61 (unresolved, 2H), 6.43 (s, 2H).

(1E,4E,6E)-5-Hydroxy-1,7-bis(indole-5)hepta-1,4,6-trien-3-one (2): Yield 94%, red-brown powder, mp decomposes at 250° C., $R_f$ 0.38 (40% EtOAc in hexane). $^1$H NMR (DMSO-d$_6$, 500 MHz): δ 11.35 (s, 2H), 7.90 (s, 2H), 7.74 (d, J=16.0 Hz, 2H), 7.52 (d, J=8.5 Hz, 2H), 7.44 d, 8.0 Hz, s, 2H), 7.40 (br, s, 2H), 6.82 (d, J=16.0 Hz, 2H), 6.50 (br s, 2H), 6.11 (s, 1H). $^{13}$C NMR (DMSO-d$_6$, 125 MHz): δ183.7, 142.8, 137.7, 128.5, 127.2, 126.4, 122.8, 121.4, 121.1, 112.6, 102.9, 101.4. IR (cm$^{-1}$): 3385, 2988, 2365, 1622, 1521, 1472, 1418, 1339, 1274, 1260, 1124. HRMS (ESI): m/z [M+H]$^+$ calcd for C$_{23}$H19O$_2$N$_2$: 355.1446; found: 355.1396.

Indole-4-Curcuminoid-BF$_2$ adduct (3-BF$_2$): Yield 29%, black solid, $R_f$ 0.16 (40% EtOAc in hexane). $^1$H NMR (acetone-d$_6$, 500 MHz): δ 10.75 (s, 2H, br), 8.45 (d, J=16.0 Hz, 2H), 7.68 (d, 8.0 Hz, 2H), 7.64-7.62 (overlapping dd, and d, 4H), 7.27 (t, J=8.0 Hz, 2H), 7.25 (d, J=7.5 Hz, 2H), 6.95 (d, J=3.5 Hz, 1H), 6.94 (s, 1H, br), 6.57 (s, 1H). $^{13}$C NMR (DMSO-d$_6$, 125 MHz): δ 179.7, 146.4, 137.1, 128.8, 127.4, 125.9, 124.0, 121.7, 121.1, 116.7, 102.4, 101.0. $^{19}$F NMR (acetone-d$_6$, 470 MHz): δ −140.6 (s, $^{11}$B—F), −140.7 (s, $^{10}$B—F). IR (cm$^{-1}$): 3431, 3412, 2951-2930, 1613, 1597, 1541, 1483, 1433, 1389, 1354, 1296, 1153, 1119, 1044.

(1E,4E,6E)-5-Hydroxy-1,7-bis(indole-4)hepta-1,4,6-trien-3-one (3): Yield 77%, dark-brown solid, mp 201-204° C., $R_f$ 0.42 (40% EtOAc in hexane). $^1$H NMR (methanol-d$_4$, 500 MHz): δ 8.08 (d, J 15.5 Hz, 2H), 7.47 (d, J=8.5 Hz, 2H), 7.40-7.39 (unresolved doublets, 4H), 7.17 (t, J=7.5 Hz, 2H), 6.94 (d, J=15.5 Hz, 2H), 6.85 (dd, J=2.5 and 1 Hz, 2H), 6.13 (s, 1H). $^{13}$C NMR (methanol-d$_4$, 125 MHz): δ 183.7, 140.0, 136.9, 127.1, 126.5, 125.9, 123.3, 121.0, 119.9, 113.3, 101.1, 99.7. HRMS (ESI): m/z [M+H]$^+$ calcd for C$_{23}$H$_{19}$O$_2$N$_2$: 355.1446; found: 355.1294. IR (cm$^{-1}$): 3418, 3269-2872, 1620, 1557, 1416, 1344, 1277, 1201, 1141, 1111.

3-Thiocyanato-Indole-5-Curcuminoid-BF$_2$ adduct (4-BF$_2$): Yield 49%, reddish-orange solid, $R_f$ 0.05 (40% EtOAc in hexane). $^1$H NMR (DMSO-d$_6$, 500 MHz): δ 12.3 (s, 2H), 8.24 (d, J=15.5 Hz, 2H), 8.25 (s, 2H), 8.11 (d, J=2.5 Hz, 2H), 7.83 (dd, J=8.5 Hz and 1.5 Hz, 2H), 7.63 (d, J=8.5 Hs, 2H), 7.25 (d, J=15.5 Hz, 2H), 6.74 (s, 1H). $^{13}$C NMR (DMSO-d$_6$, 125 MHz): δ 179.8, 148.3, 138.6, 128.5, 128.1, 124.3, 121.7, 119.9, 114.2, 112.6, 102.0, 91.9. $^{19}$F NMR (DMSO-d$_6$, 470 MHz): δ −137.5 (s, $^{11}$B—F), −137.6 (s, $^{10}$B—F). IR (cm$^-$): 3417, 2916, 2848, 2152, 1739, 1612, 1552, 1541, 1500, 1382, 1300, 1058.

(1E,4E,6E)-5-Hydroxy-1,7-bis(3-thiocyanoindole-5)hepta-1,4,6-trien-3-one (4): Yield 73%, red solid, mp decomposes at 250° C., $R_f$ 0.08 (40% EtOAc in hexane). $^1$H NMR (DMSO-d$_6$, 500 MHz): δ 16.3 (s, 1H, br), 12.21 (d, J=2 Hz, 2H), 8.06 (d, J=2.5 Hz, 2H), 8.03 (s, 2H), 7.86 (d, J=16.0 Hz, 2H), 7.70 (d, J=9.0 Hz, 2H), 7.58 (d, J=8.5 Hz, 2H), 6.96 (d, J=16.0 Hz, 2H), 6.30 (s, 1H). $^{13}$C NMR (DMSO-d$_6$, 125 MHz): δ 183.7, 141.8, 138.0, 135.0, 128.6, 128.4, 123.3, 123.1, 119.6, 114.0, 112.7, 101.6, 91.2. HRMS (ESI): m/z [M+H]$^+$ calcd for C$_{25}$H$_{16}$O$_2$N$_4$S$_2$: 469.56574; found: 469.47375. IR (cm$^{-1}$): 3300, 2924, 2152, 1705, 1622, 1604, 1273, 1138, 1124, 958.

3-Thiocyanato-Indole-4-Curcuminoid-BF$_2$ adduct (5-BF$_2$): Yield 62%, dark-brown powder, $R_f$ 0.09 (40% EtOAc in hexane). $^1$H NMR (acetone-d$_6$, 500 MHz): δ 9.34 (d, J=15.0 Hz, 2H), 8.14 (d, 2.0 Hz, 2H), 7.90 (d, J=7.0 Hz, 2H), 7.77 (d, J=7.0 Hz, 2H), 7.42* (t, J=8.0 Hz, 2H), 7.27* (d, J=16.5 Hz, 2H), 6.71 (s, 1H) [NH signal is observed in DMSO-d$_6$ at δ 12.39 (s, 2H) in which signals marked with * are overlapping]. $^{13}$C NMR (DMSO-d$_6$, 125 MHz): δ 180.0, 142.8, 138.0, 137.5, 126.9, 125.9, 123.7, 122.5, 121.7, 117.3, 113.1, 103.1, 90.4. $^{19}$F NMR (DMSO-d$_6$, 470 MHz): δ −137.5 (s, $^{11}$B—F), −137.6 (s, $^{10}$B—F). IR (cm$^{-1}$): 3395, 3335, 2154, 2156, 1616, 1601, 1555, 1541, 1508, 1493, 1410, 1275, 1161, 1128, 1062.

(1E,4E,6E)-5-Hydroxy-1,7-bis(3-thiocyano-indole-4)hepta-1,4,6-trien-3-one (5): Yield 82%, red powder, decomposes at 250° C., $R_f$ 0.10 (40% EtOAc in hexane). $^1$H NMR (DMSO-d$_6$, 500 MHz): δ 12.27 (s, 2H), 9.00 (d, J=15.5 Hz, 2H), 8.12 (d, J=2 Hz, 2H), 7.74 (d, J=8.0 Hz, 2H), 7.61 (d, J=8.0 Hz, 2H), 7.33 (t, J=7.5 Hz, 2H), 7.04 (d, J=16.0 Hz, 2H), 6.24 (s, 1H). $^{13}$C NMR (DMSO-d$_6$, 125 MHz): δ 183.6, 137.9, 136.9, 136.7, 127.8, 125.6, 125.3, 123.7, 120.3, 115.4, 113.3, 102.6, 90.0. IR (cm$^{-1}$): 3313, 2155, 1624, 1602, 1396, 1275, 1119. HRMS (ESI): m/z [M+H]$^+$ calcd for C$_2$H$_{17}$O$_2$N$_4$S$_2$: 469.07929; found: 469.3449.

N-methyl-Indole-3-Curcuminoid-BF$_2$ adduct (6-BF$_2$): Yield 60%, dark-green solid, $R_f$ 0.32 (40% EtOAc in hexane). $^1$H NMR (acetone-d$_6$, 500 MHz): δ 8.20 (d, J=15.5 Hz, 2H), 8.10 (d, J=7.5 Hz, 2H), 8.03 (s, 2H), 7.58 (d, J=8.5 Hz, 2H), 7.38 (dt, J=7 Hz and 1 Hz, 2H), 7.33 (dt, J=7 Hz and 1 Hz, 2H), 6.90 (d, J=15.5 Hz, 2H), 6.39 (s, 1H), 4.0 (s, 6H). $^{13}$C NMR (acetone-d$_6$, 125 MHz): δ 178.1, 139.3, 138.9, 138.0, 126.0, 123.4, 122.0, 120.7, 115.0, 113.2, 110.9, 100.1, 32.8. $^{19}$F NMR (acetone-d$_6$, 470 MHz): δ −142.0 (s, $^{11}$B—F), −141.9 (s, 1B—F). IR (cm$^{-1}$): 1599, 1557, 1501, 1456, 1445, 1422, 1389, 1371, 1340, 1371, 1287, 1251, 1153, 1124, 1072.

(1E,4E,6E)-5-Hydroxy-1,7-bis(N-methyl-indole-3)hepta-1,4,6-trien-3-one (6); Yield 98%, bright-red powder, mp 195-198° C., $R_f$ 0.54. $^1$H NMR (acetone-d$_6$, 500 MHz): δ 8.04 (d, J=8 Hz, 2H), 7.91 (d, J=16.0 Hz, 2H), 7.78 (s, 2H), 7.52 (d, J=8.5 Hz, 2H), 7.33 (t, J=7 Hz, 2H), 7.26 (t, J=8.5 Hz, 2H), 6.77 (d, J=15.5 Hz, 2H), 6.04 (s, 1H), 3.92 (s, 6H). $^{13}$C NMR (acetone-d$_6$, 500 MHz): δ 183.8, 138.5, 134.4, 133.5, 126.1, 122.7, 121.1, 120.3, 118.9, 112.5, 110.4, 100.1, 32.5. HRMS (ESI): m/z [M+H]$^+$ calcd for C$_{25}$H$_{23}$O$_2$N$_2$: 383.17595; found: 383.16476. IR (cm$^{-1}$): 3100 to 2824, 1746, 1715, 1607, 1556, 1519, 1494, 1454, 1421, 1373, 1330, 1255, 1157, 1126, 1070.

N-methyl-Indole-3-Curcuminoid-BF$_2$ adduct (1,3-diketo tautomer; 6a-BF$_2$): Yield 22%, deep-purple solid, $R_f$ 0.44 (40% EtOAc in hexane). $^1$H NMR (DMSO-d$_6$, 500 MHz): δ 8.31 (d, J=15.5 Hz, 2H), 8.26 (s, 2H), 8.12 (d, J=7 Hz, 2H), 7.62 (d, J=8 Hz, 2H), 7.39 (t, J=7 Hz, 2H), 7.33 (t, J=7 Hz, 2H), 6.85 (d, J=15.5 Hz, 2H), 6.40 (s, 2H), 3.89 (s, 6H). $^{13}$C NMR (DMSO-d$_6$, 125 MHz): δ 186.3, 181.0, 143.8, 141.4, 139.1, 125.7, 124.2, 123.1, 121.3, 113.0, 112.8, 112.0, 100.4, 34.0, 23.9. $^{19}$F NMR (DMSO-d$_6$, 470 MHz): δ −137.6 (s, $^{11}$B—F), −137.5 (s, $^{10}$B—F). IR (cm$^{-1}$): 3055, 2988, 1620, 1558, 1516, 1375, 1294, 1263, 1169, 1063.

(1E,6E)-1,7-bis(N-methyl-indole-3)hepta-1,6-dien-3,5-dione (6a): Yield 64%, light-red powder, mp 126-128° C., $R_f$ 0.72 (40% EtOAc in hexane). $^1$H NMR (CDCl$_3$, 500 MHz): δ 7.93 (d, J=8 Hz, 2H), 7.85 (d, J=15.5 Hz, 2H), 6.49 (d, J=15.5 Hz, 2H), 5.41 (s, 2H), 3.82 (s, 6H). $^{13}$C NMR (CDCl$_3$, 125 MHz): δ 194.7, 180.5, 138.2, 134.0, 133.2, 126.0, 123.0, 121.3, 120.5, 117.7, 112.8, 110.1, 99.9, 33.2, 26.3. HRMS (ESI): m/z [M+H]$^+$ calcd for C$_{25}$H$_{12}$O$_2$N$_2$: 383.17595; found: 383.16467. IR (cm$^{-1}$): 3098 to 2914, 1716, 1626, 1534, 1422, 1375, 1263, 1159, 1132, 1072.

Benzothiophene-3-Curcuminoid-BF$_2$ adduct (7-BF$_2$): Yield: 70%, bright-orange solid, mp>240° C. $R_f$ 0.81 (40% EtOAc in hexane). $^1$H NMR (DMSO-d$_6$, 500 MHz): δ 8.75 (s, 2H), 8.33 (d, J=20 Hz, 2H), 8.34 (s, 2H), 8.14 (d, J=8.0

Hz, 2H), 7.58 (t, J=7.5 Hz, 2H), 7.52 (t, J=7.5 Hz, 2H), 7.30 (d, J=16.0 Hz, 2H), 6.97 (s, 1H). $^{13}$C NMR (DMSO-d$_6$, 125 MHz): δ 180.2, 140.5, 138.5, 136.9, 135.8, 132.1, 126.1, 124.0, 123.0, 121.7, 110.0, 102.3. $^{19}$F NMR (DMSO-d$_6$, 470 MHz): δ −137.4 (s, $^{11}$B—F), −137.3 (s, $^{10}$B—F).

(1E,4E,6E)-5-Hydroxy-1,7-bis(benzo[b]thiophen-3-yl) hepta-1,4,6-trien-3-one (7): Yield: 85%, orange solid, mp: 159-160° C. R$_f$ 0.74 (40% EtOAc in hexane). $^1$H NMR (DMSO-d$_6$, 500 MHz): δ 8.43 (s, 2H), 8.22 (d, J=7.5 Hz, 2H), 8.09 (d, J=7.5 Hz, 2H), 8.79 (d, J=16.5 Hz, 2H), 7.53 (t, J=7.5 Hz, 2H), 7.48 (t, J=7.5 Hz, 2H), 7.05 (d, J=16.5 Hz, 2H), 6.44 (s, 1H). $^{13}$C NMR (DMSO-d$_6$, 125 MHz): δ183.7, 140.4, 137.3, 132.4, 132.1, 130.6, 125.7, 125.2, 123.8, 122.7, 102.0. HRMS (ESI): m/z [M+H]$^+$ calcd for C$_{23}$H$_{17}$O$_2$S$_2$: 389.06700; found: 389.06055. IR (cm$^{-1}$): 3093 to 2852, 1614, 1489, 1421, 1269, 1134, 958.

Benzothiophene-2-Curcuminoid-BF$_2$ adduct (8-BF$_2$): Yield 28%, black solid, R$_f$ 0.85 (40% EtOAc in hexane). $^1$H NMR (DMSO-d$_6$, 500 MHz): δ 8.38 (d, J=15.5 Hz, 2H), 8.11 (s, 2H), 8.06 (d, J=8.0 Hz, 2H), 7.97 (d, J=7.5 Hz, 2H), 7.51 (dt, J=7.5 and 1.5 Hz, 2H), 7.46 (dt, J=8.0 and 1.5 Hz, 2H), 6.89 (d, J=15 Hz, 2H), 6.83 (s, 1H). $^{13}$C NMR (DMSO-d$_6$, 125 MHz): δ 179.5, 141.4, 140.5, 140.0, 139.8, 133.8, 128.1, 125.9, 123.4, 122.5, 110.0, 103.5. $^{19}$F NMR (DMSO-d$_6$, 470 MHz): δ −137.2 (s, $^{11}$B—F), −137.3 (s, $^{10}$B—F). IR (cm$^{-1}$): 3057 to 2851, 1599, 1533, 1485, 1385, 1283, 1136, 1051.

(1E,4E,6E)-5-Hydroxy-1,7-bis(benzo[b]thiophen-2-yl) hepta-1,4,6-trien-3-one (8): Yield 93%, orange solid, R$_f$ 0.92 (40% EtOAc in hexane). $^1$H NMR (DMSO-d$_6$, 500 MHz): δ 16.0 (br s, 1H), 8.00 (d, J=7.5 Hz, 2H), 7.97 (d, J=16 Hz, 2H), 7.90 (d, J=7.0 Hz, 2H), 7.87 (s, 2H), 7.45 (dt, J=7.5 and 2 Hz, 2H), 7.41 (dt, J=7.5 and 2.0 Hz, 2H), 6.65 (d, J=16 Hz, 2H), 6.36 (s, 1H). HRMS (ESI): m/z [M+H]$^+$ calcd for C$_{23}$H$_{17}$O$_2$S$_2$: 389.06700; found: 389.05377.

Benzofuran-2-Curcuminoid-BF$_2$ adduct (9-BF$_2$): Yield: 70%, dark-red solid, mp>240° C. R$_f$ 0.84 (40% EtOAc in hexane). $^1$H NMR (CDCl$_3$, 500 MHz): δ 7.91 (d, J=15.0 Hz, 2H), 7.65 (d, J=7.5 Hz, 2H), 7.53 (dd, J=8.5 Hz, 2H), 7.45 (dt, J=7.0 Hz and 1.0 Hz, 2H), 7.23 (dt, J=7.0 Hz and 1.0 Hz, 2H), 7.14 (s, 2H), 6.88 (d, J=15.5 Hz, 2H), 6.16 (s, 1H). $^{13}$C NMR (CDCl$_3$, 125 MHz): δ 179.3, 156.4, 152.3, 132.8, 128.5, 127.9, 123.9, 122.5, 120.9, 115.5, 111.6, 103.5. $^{19}$F NMR (CDCl$_3$, 470 MHz): δ −140.15 (s, $^{11}$B—F), −140.1 (s, $^{10}$B—F). IR (cm$^{-1}$): 2918, 1614, 1557, 1508, 1396, 1348, 1288, 1155, 1124, 1057, 947.

(1E,4E,6E)-5-Hydroxy-1,7-bis(benzo[b]furan-2-yl) hepta-1,4,6-trien-3-one (9): Yield: 88% yellow-orange solid, mp: 178-180° C. R$_f$ 0.92 (40% EtOAc in hexane). $^1$H NMR (acetone-d$_6$, 500 MHz): δ 7.73 (dd, J=7.5 and 1.5 Hz, 2H), 7.67 (d, J=15.0 Hz, 2H), 7.59 (d, J=7.5 Hz, 2H), 7.44 (dd, J=7.5 and 1.5 Hz, 2H), 7.31 (dt, J=7.5 and 1.7 Hz, 2H), 7.31 (s, 2H), 6.91 (d, J=15.0 Hz, 2H), 6.31 (s, 1H). $^{13}$C NMR (CDCl$_3$, 125 MHz): δ 182.5, 155.7, 153.1, 128.6, 127.2, 126.5, 124.6, 123.4, 121.7, 111.4, 111.3, 103.3. HRMS (ESI): m/z [M+H]$^+$ calcd for C$_{23}$H$_{17}$O$_4$: 357.11268; found: 357.10632. IR (cm$^{-1}$): 3080, 2953, 1608, 1557, 1516, 1348, 1286, 1256, 1200.

3,5-bis((E))-(benzo[b]thiophen-3-yl)vinyl)-1-phenyl-1H-pyrazole (10): Yield: 50%, light-brown/orange solid, mp: 141-143° C., R$_f$ 0.87 (40% EtOAc in hexane). $^1$H NMR (CDCl$_3$, 500 MHz): δ 8.10 (d, J=8.0 Hz, 1H), 7.94 (d, J=8.0 Hz, 1H), 7.90 (d, J=8.0 Hz, 1H), 7.89 (d, J=8.0 Hz, 1H), 7.39-7.47 (m, unresolved, 6H), 7.62-7.52 (m, unresolved, 7H), 7.31 (d, J=16.0 Hz, 1H), 7.01 (s, 1H), 6.98 (d, J=16.5 Hz, 1H). $^{13}$C NMR (CDCl$_3$, 125 MHz): δ 151.2, 142.5, 140.5, 139.3, 127.7, 137.4, 133.8, 133.2, 129.4, 128.2, 125.5, 124.8, 124.6, 124.6, 124.5, 124.4, 123.4, 123.1, 123.0, 122.6, 122.1, 121.8, 121.5, 116.7, 101.0. HRMS (ESI): m/z [M+H]$^+$ calcd for C$_{29}$H$_{20}$N$_2$S$_2$: 461.11462; found: 461.10458. IR (cm$^{-1}$): 3028, 3010, 1694, 1645, 1633, 1603, 1494, 1440, 1404, 1373, 1249, 1153, 1028.

3,5-bis((E)-(benzo[b]thiophen-3-yl)vinyl)-1-(3-(trifluoromethyl)phenyl)-1H-pyrazole (11): Yield 63.0%, light-brown solid, mp: 95-96° C., R$_f$ 0.91 (40% EtOAc in hexane). $^1$H NMR (CDCl$_3$, 500 MHz): δ 8.11 (d, J=8.5 Hz, 1H), 7.96 (d, J=8.5 Hz, 1H), 7.95 (s, 1H), 7.91 (d, J=8.0 Hz, 2H), 7.79 (d, J=7.5 Hz, 1H), 7.78 (d, J=7.5 Hz, 1H), 7.72 (d, J=7.5 Hz, 1H), 7.67 (d, J=7.5 Hz, 1H), 7.64 (s, 1H), 7.56 (d, J=15.5 Hz, 1H), 7.54 (s, 1H), 7.50-7.40 (m, unresolved, 5H), 7.30 (d, J=16.5 Hz, 1H), 7.03 (s, 1H), 6.97 (d, J=16.5 Hz, 1H). $^{13}$C NMR (CDCl$_3$, 125 MHz): δ 151.9, 142.7, 140.6, 140.6, 139.9, 137.6, 137.3, 133.7, 133.0, 132.0 (q, $^1J_{CF}$=250 Hz), 130.0, 128.3, 125.5, 124.9, 124.7, 124.7 124.6, 124.4, 124.0, 123.5, 123.1, 123.0, 122.9, 122.2 (q, $J_{CF}$=3.5 Hz), 122.1, 121.8, 121.2, 116.0, 101.7. $^{19}$F NMR (CDCl$_3$, 470 MHz): δ −62.60 (s, CF$_3$). HRMS (ESI): m/z [M+H]$^+$ calcd for C$_{30}$H$_{19}$N$_2$F$_3$: 529.102001; found: 529.10034. IR (cm$^{-1}$): 3067, 1699, 1614, 1597, 1497, 1456, 1423, 1377, 1360, 1325, 1277, 1263, 1168, 1126, 1093, 1067, 1022.

3,5-bis((E))-(benzo[b]thiophen-3-yl)vinyl)-1-(3,5-difluorophenyl)-1H-pyrazole (12): Yield: 50%, yellow solid, mp: 178-179° C. R$_f$ 0.85 (40% EtOAc in hexane). $^1$H NMR (CDCl$_3$, 500 MHz): δ 8.09 (d, J=8.0 Hz, 1H), 7.97 (d, J=8.0 Hz, 1H), 7.91 (d, J=8.0 Hz, 1H), 7.90 (d, J=7.5 Hz, 1H), 7.62 (s, 1H), 7.58 (s, 1H), 7.53 (d, J=16.0 Hz, 1H), 7.39-7.40 (unresolved region, 5H), 7.27-7.19 (unresolved region, 2H), 7.00 (d, J=17.0 Hz, 2H), 6.98 (s, 1H), 6.89 (tt, J=5.5 Hz and 2.5 Hz, 1H). $^{13}$C NMR (CDCl$_3$, 125 MHz): δ 163.1 (d, $^1J_{CF}$=249.0 Hz), 163.0 (d, $^1J_{CF}$=249.0 Hz), 152.0, 142.7, 141.4 (t, $^3J_{CF}$=12.3 Hz), 140.6, 140.5, 137.6, 137.3, 133.6, 133.0, 125.5, 124.9, 124.7, 124.7, 124.5, 123.9, 123.7, 123.1, 123.0, 122.9, 122.1, 121.7, 121.1, 116.0, 108.4, 103.3 (t, $^2J_{CF}$=25.7 Hz), 102.3. $^{19}$F NMR (CDCl$_3$, 470 MHz): δ −107.37 (m, 2F). HRMS (ESI): m/z [M+H]$^+$ calcd for C$_{29}$H$_{19}$N$_2$S$_2$F$_2$: 497.09577; found: 497.08199. IR (cm$^{-1}$): 3080, 1620, 1597, 1539, 1481, 1462, 1425, 1304, 1263, 1223, 1119.

3,5-bis((E))-(benzofuran-2-yl)vinyl)-1-phenyl-1H-pyrazole (13): Yield: 67%, yellow solid, mp: 149-151° C. R$_f$ 0.95 (40% EtOAc in hexane). $^1$H NMR (CDCl$_3$, 500 MHz): δ 7.57-7.47 (unresolved region, 8H), 7.54 (d, J=8.0 Hz, 1H), 7.35 (d, J=17.5 Hz, 1H), 7.30-7.26 (complex region, 2H), 7.21 (t, J=8.0 Hz, 2H), 7.18 (d, J=16.5 Hz, 1H), 7.09 (d, J=15.5 Hz, 1H), 7.00 (d, J=16.0 Hz, 1H), 6.87 (s, 1H), 6.73 (s, 1H), 6.71 (s, 1H). $^{13}$C NMR (CDCl$_3$, 125 MHz): δ 155.0, 155.0, 154.8, 153.9, 150.4, 141.9, 139.2, 129.4, 129.1, 128.8, 128.3, 125.6, 125.2, 124.7, 123.1, 122.9, 121.5, 121.1, 120.9, 119.9, 118.6, 116.3, 111.0, 106.9, 105.5, 102.2. HRMS (ESI): m/z [M+H]$^+$ calcd for C$_{29}$H$_{21}$N$_2$O$_2$: 429.16030; found: 429.15786. IR (cm$^{-1}$, CH$_2$Cl$_2$): 3055, 2924, 1713, 1597, 1497, 1451, 1366, 1288, 1250, 1188, 1126, 1011.

3,5-bis((E))-(benzofuran-2-yl)vinyl)-1-(3,5-difluorophenyl)-1H-pyrazole (14): Yield: 54%, yellow solid, mp: 158-160° C. R$_f$ 0.91 (40% EtOAc in hexane). $^1$H NMR (CDCl$_3$, 500 MHz): δ 7.57-7.54 (overlapping pair of doubles, triplet appearance, 2H), 7.50-7.46 (overlapping pair of doubles, triplet appearance, 2H), 7.34-7.15 (unresolved region, 8H), 7.14 (d, J=16.0 Hz, 1H), 7.06 (d, J=16 Hz, 1H), 6.93 (tt, J=9.0 Hz and 2.0 Hz, 1H), 6.86 (s, 1H), 6.78 (s, 1H), 6.74 (s, 1H). $^{13}$C NMR (CDCl$_3$, 125 MHz): δ 163.1 (d, $^1J_{CF}$=249.0 Hz), 163.0 (d, $^1J_{CF}$=249.0 Hz) 155.2, 155.0, 154.5, 153.5, 151.1, 142.1, 141.2 (t, $^3J_{CF}$=12.4 Hz), 129.0, 128.8, 125.5, 124.9, 123.2, 123.0, 121.2, 121.1, 121.0, 120.8, 119.2, 115.4, 111.1, 111.0, 108.6, 107.5, 105.9, 103.5 (t, 2J$_{CF}$=25.7 Hz), 103.2. $^{19}$F NMR (CDCl$_3$, 470 MHz): δ −107.4 (m, 2F). HRMS (ESI): m/z [M+H]$^+$ calcd for C$_{29}$H$_{19}$N$_2$O$_2$F$_2$: 465.14146; found: 465.13156. IR (cm$^{-1}$): 3086 to 2926, 1620, 1600, 1562, 1526, 1481, 1450, 1381, 1348, 1329, 1285, 1254, 1225, 1196, 1118.

3,5-bis((E))-(benzofuran-2-yl)vinyl)-1-(3-(trifluoromethoxy)phenyl)-1H-pyrazole (15): Yield: 22%, light brown solid, mp: 128-129° C. R$_f$ 0.96 (40% EtOAc in hexane). $^1$H NMR (CDCl$_3$, 500 MHz): δ 7.63 (overlapping pair of doubles, 2H), 7.57 (d, J=7.5 Hz, 1H), 7.56 (d, J=8.0 Hz, 1H), 7.50 (d, 8 Hz, 1H), 7.46-7.42 (unresolved, 3H), 7.35-7.22 (complex region, 5H), 7.18 (d, J=16.0 Hz, 1H), 7.07 (d, J=16.0 Hz, 1H), 7.03 (d, J=16.0 Hz, 1H), 6.89 (s, 1H), 6.77 (s, 1H), 6.73 (s, 1H). $^{13}$C NMR (CDCl$_3$, 125 MHz): δ 150.3, 150.2, 149.9, 148.9, 146.1, 143.9, 137.3, 133.0, 124.3, 124.0, 122.0, 120.6, 120.0, 118.4, 118.2, 117.1, 116.6, 116.4, 116.1, 115.5, 114.0, 111.0, 106.3, 106.3, 102.5, 101.0, 97.8. $^{19}$F NMR (CDCl$_3$, 470 MHz): δ 57.83 (s, OCF$_3$). HRMS (ESI): m/z [M+H]$^+$ calcd for C$_{30}$H$_{20}$N$_2$O$_3$F$_3$: 513.14260; found: 513.13940. IR (cm$^{-1}$): 3116 to 2926, 1717, 1668, 1609, 1564, 1510, 1452, 1371, 1384, 1254, 1205, 1161, 1033, 1015.

Computational Methods

B3LYP/6-31G* geometry optimizations were performed with the Gaussian 09 suite of programs. Molecular docking calculations were carried out with the program AutoDock Vina for modeling the binding modes and gauging the interaction energies of the studied compounds as ligands for HER2, proteasome, VEGFR2, BRAF, and BCL-2 proteins. The three-dimensional coordinates of the proteins were obtained from the Protein Data Bank (PDB codes 3PP0 (HER2), 3SDK (20S proteasome), 4AG8 (VEGFR2), 4XV2 (BRAF), and 4LVT (BCL-2)). (T. Castanheiro, et al., Chem. Soc. Rev. 2016, 45, 494; G. Malik, et al., Chem. Sci., 2017, 8, 8050-8060; D. Wu, et al., J. Org. Chem. 2018, 83, 1576-1583; A. Vyas, et al., Curr. Pharm. Des. 2013, 19, 2047-2069; G. R. Pillail, et al., Cancer Letters 2004, 208, 163-170; A. L. Loprestil, et al., J. Psychopharmacology 2012, 26, 1512-1524; D. Perrone, et al., Experimental and Therapeutic Medicine 2015, 10, 1615-1623; M. Mimeault, et al., Chin. Med. 2011, 6, 31; C. Cheng, et al., RSC Adv. 2017, 7, 25978-25986; L. Zhang, et al., Environ. Tox. Pharm. 2016, 48, 31-38; M. M. Yallapu, et al., Colloids and Surfaces B: Biointerfaces 2010, 79, 113-125; J. Liu, et al., Curr. Pharm. Des. 2013, 19, 1974-1993).

Chain A of HER2, VEGFR2, BRAF and BCL-2, and chains K (β5 subunit) and L (β6 subunit) of 20S proteasome were selected as target templates for the docking calculations. Co-crystallized ligands and crystallographic water molecules were removed. Addition of hydrogens, merger of non-polar hydrogens to the atom to which they were attached, and assignment of partial charges were computed with AutoDockTools. Docking areas were constrained to a 30×30×30 Å box centered at the active site, which provided suitable space for rotational and translational movement of the ligands.

Bioassay Methods

NCI-60 assay: Samples were submitted to the National Cancer Institute (NCI of NIH) Developmental Therapeutics anticancer screening program (DTP) for human tumor cell line assay by NCI-60 screening against leukemia, lung, colon, and CNS cancers, as well as melanoma, ovarian, renal, prostate, and breast cancers. Compounds are initially tested at a single dose of 10$^{-5}$ molar. Data are reported as mean graph of percent growth (GP). Growth inhibition is shown by values between 0 and 100 and lethality by values less than zero. Compounds that meet selection criteria based on one-dose assay are then tested against 60 cell panel at five concentrations.

Cell Viability assay to determine EC50: Cells (2×10$^3$ cell/well) were incubated with the compounds (concentration range 0-30000 nM) in a 384-well plate for 72 hours in a CO$_2$ incubator (5% CO$_2$, 37° C.). Cell lines and PBCMs (peripheral blood mononuclear cells from healthy donors as non-cancer CONTROL) were seeded in quadruplicate (technical replicates). CellTiter-Glo® 2.0 reagent equal to the volume of cell culture medium present in each well was added and the plate was left to incubate at room temperature for 10 minutes to stabilize the luminescent signal. Luminescent signal/intensity from the 384-well plate was read on a plate reader. Cells/cell lines used: BCWM.1 (Waldenstrom macroglobulinemia cell line, WM); RPMI-8266 (Multiple myeloma cell line, MM); RS4; 11 (Acute lymphoblastic leukemia, ALL). For Apoptosis study cells were treated with the indicated agents and concentrations (FIG. 74) for 24 h and stained with annexin-V and propidium iodide (PI), followed by flow cytometry analysis.

Cell culture. Colorectal cancer and normal colon cell lines were obtained from ATCC (Manassas, Va.). Cells were maintained in DMEM medium (Life Technologies, Carlsbad, Calif.) supplemented with 10% fetal bovine serum (Life Technologies), 1% non-essential amino acids (Life Technologies), 1% penicillin-streptomycin (Life Technologies), and 1% glutamine (Life Technologies) at 37° C. and 5% CO$_2$.

Cell viability. Cells were seeded in 96-well plates with approximately 5.0×10$^3$ cells/well and incubated in RPMI1640 medium (supplemented with 10% fetal bovine serum and 1% glutamine) for 24 hours. Cells were then treated with RPMI1640 medium containing CURs (10 M) or vehicle (DMSO) for 48 hours and the number of viable cells determined using CellTiter-Fluor™ cell viability assay kit (Promega, Madison Wis.). The fluorescence (excitation 400 nm, emission 505 nm) was detected using infinite M200 Pro microplate reader (TECAN).

Luciferase reporter gene assay. Cells stably transfected with luciferase reporter gene containing AHR binding elements were cultured with DMEM media containing 10 M CURs or 0.1% DMSO for 6 hours. The luciferase activity was measured using the dual luciferase reporter assay system (Promega) according to manufacturer's instructions, and infinite M200 Pro microplate reader (TECAN).

Example 6—Deuterated CUR Compounds

Synthesis of a library of deuterated CUR—BF$_2$ and CUR compounds has been accomplished and bioassay data are being collected. These studies aim to determine if deuterated analogs are metabolically more stable.

Deuterated compounds were formed from aryl-aldehydes or fluorinated aryl-aldehydes, as seen in FIG. 78. The aryl aldehyde was mixed with deuterated water and deuterated sulfates and placed into a microwave vial equipped with magnetic stirrer. The vial was sealed and irradiated for 6 min at 140° C. in the microwave. The vial was cooled to r.t. and solvent removed. The deuterated curcuminoids, such as those shown in FIGS. 76 and 77, were synthesized according to the general protocols outlined in Examples 2 and 3 above, starting with the deuterated aldehydes. A new library of deuterated CUR—BF$_2$ and CUR compounds were synthesized along with their corresponding non-deuterated analogs for side by side study of their bio-activity, by replacing the —OCH$_3$ groups with —OCD$_3$ as shown in FIG. 76. In other examples H/D exchange has been achieved in the aromatic rings. The NCI-60 data on a hexa-deuterated analog is shown in FIG. 79.

Example 7—Curcumin Conjugates of
Non-Steroidal Anti-Inflammatory Drugs

Whereas potential health benefits of parent curcumin and its anticancer, anti-inflammatory, antioxidant, and anti-mutagenic effects have been extensively studied, its complex signaling pathways and biological profile, coupled to poor pharmacokinetic properties have been major obstacles in developing a CUR-based anti-cancer drug, despite much effort to devise delivery methods by nanotechnology formulation or encapsulation into liposomes, or by inclusion into water soluble host molecules such as O-cyclodextrin. (G. Radhakrishna Pillai, A. S. Srivastava, T. I. Hassanein, D. P. Chauhan, E. Carrier, Cancer Lett. 2004, 208, 163-170; A. L. Lopresti, S. D. Hood, P. D. Drummond, J. Psychopharmacol. 2012, 26, 1512-1524; D. Perrone, F. Ardito, G. Giannatempo, M. Dioguardi, G. Troiano, L. Lo Russo, A. De Lillo, L. Laino, L. Lo Muzio, Exp. Ther. Med. 2015, 10, 1615-1623; S. C. Gupta, S. Prasad, J. H. Kim, S. Patchva, L. J. Webb, I. K. Priyadarsini, B. B. Aggarwal, Nat. Prod. Rep. 2011, 28, 1937-1955; D. Perrone, F. Ardito, G. Giannatempo, M. Dioguardi, G. Troiano, L. Lo Russo, A. De Lillo, L. Laino, L. Lo Muzio, Exp. Ther. Med. 2015, 10, 1615-1623; A. Minassi, G. Sánchez-Duffhues, J. A. Collado, E. Muñoz, G. Appendino, J. Nat. Prod. 2013, 76, 1105-1112; A. Rajasekhar Reddy, P. Dinesh, A. S. Prabhakar, K. Umasankar, B. Shireesha, M. Bhagavan Raju, Mini-Rev. Med. Chem. 2013, 13, 1769-1777; J. Liu, S. Chen, L. Lv, L. Song, S. Guo, S. Hunag, Curr. Pharm. Des. 2013, 19, 1974-1993; M. Mimeault, S. K. Batra, Chin. Med. 2011, 6, 1-19; C. Cheng, S. Peng, Z. Li, L. Zou, W. Liu, C. Liu RSC Adv. 2017, 7, 25978-25986; L. Zhang, S. Man, H. Qiu, Z. Liu, M. Zhang, L. Ma, Environ. Toxicol. Pharmacol. 2016, 48, 31-38; b) M. M. Yallapu, M. Jaggi, S. C. Chauhan, Colloids Surf. B 2010, 79, 113-125; c) B. Tang, L. Ma, H.-Y. Wang, G.-Y. Zhang, J. Agric. Food Chem. 2002, 50, 1355-1361.

Much work has been devoted to improving solubility, metabolic stability, lipophilicity, and other properties through synthesis of analogs, and these developments have been summarized in recent reviews. (K. Bairwa, J. Grover, M. Kania, S. M. Jachak, RSC Adv. 2014, 4, 13946-13978; A. Vyas, P. Dandawate, P. S. Padhye, A. Ahmad, A. F. Sarkar, Curr. Pharm. Des. 2013, 19, 2047-2069). The inventors have focused on structural modifications by tuning steric and electronic effects through introduction of activating and deactivating substituents, introducing fluorinated moieties in an effort to improve lipophilicity and metabolic stability, synthesis of pyrazole and isoxazole derivatives, and synthesis of libraries of CUR-inspired heterocyclic analogs. (K. K. Laali, B. M. Rathman, S. D. Bunge, X. Qi, G. L. Borosky, J. Fluorine Chem. 2016, 191, 29-41; K. K. Laali, W. J. Greves, S. J. Correa Smits, A. T. Zwarycz, S. D. Bunge, G. L. Borosky, A. Manna, A. Paulus, A. Chanan-Khand, J. Fluorine Chem. 2018, 206, 82-98; K. K. Laali, W. J. Greves, A. T. Zwarycz, S. J. Correa Smits, F. J. Troendle, G. L. Borosky, S. Akhtar, A. Manna, A. Paulus, A. Chanan-Khan, M. Nukaya, G. D. Kennedy ChemMedChem 2018, 13, 1895-1908; K. K. Laali, A. T. Zwarycz, S. D. Bunge, G. L. Borosky, M. Nukaya, G. D. Kennedy, ChemMedChem 2019, 14, 1173-1184). Libraries of deuterated-CUR—BF2 and CUR analogs were also synthesized and studied. (K. K. Laali, A. T. Zwarycz, S. D. Bunge, G. L. Borosky, M. Nukaya, G. D. Kennedy, ChemMedChem 2019, 14, 1173-1184). These strategies produced diverse libraries of "CUR-inspired" compounds, and in-vitro bioassay studies identified several potential "hit compounds" with high anti-proliferative and apoptotic efficacy, most notably in multiple myeloma and colorectal cancer (CRC). The CUR—BF2 adducts of some of these compounds proved especially effective. Other laboratories have found new applications for some CUR—BF2 analogs as fluorescence imaging probes for detecting amyloids, and half-CUR—BF2 compounds as PET imaging probes. (X. Zhang, Y. Tian, Z. Li, X. Tian, H. Sun, H. Liu, A. Moore, C. Ran J Am, Chem. Soc. 2013, 135, 16397-16409; X. Zhang, Y. Tian, P. Yuan, Y. Li, M. A. Yaseen, J. Grutzendler, A. Moore, C. Ran, Chem. Commun. 2014, 50, 11550-11553; J. Yang, R. Cheng, H. Fu, J. Yang, M. Kumar, J. Lu, Y. Xu, S. H. Liang, M. Cui, C. Ran, Chem. Commun. 2019, 55, 3630-3633).

Taking into account the connection between inflammatory response and development of cancer, synthesis of hybrid compounds that could combine the anti-cancer properties of a pro-drug with the anti-inflammatory response of an NSAID is a desirable goal. (A. Mullard, Nat. Rev. Drug Discovery 2016, 15, 219-221; E. Elinav, R. Nowarski, C. A. Thaiss, B. Hu, C. Jin, R. A. Flavell, Nat. Rev. Cancer 2013, 13, 759-771; S. Rakoff-Nahoum, Yale J. Biol. Med. 2006, 79, 123-130). There are two published studies on CUR/NSAIDs, with one study reporting inhibitory effect on proliferation of RAW 264.5 cell line. (W. Liu, Y. Li, Y. Yue, K. Zhang, Q. Chen, H. Wang, Y. Lu, M.-T. Hunag, X. Zheng, Z. Du, Bioorg. Med. Chem. Lett. 2015, 25, 3044-3051; S. Srivastava, P. Gupta, A. Sethi, R. P. Singh J. Mol. Struct. 2016, 1117, 173-180). The reported IC50 values showed low cytotoxicity for most, except for a mono-NSAID/CUR adduct employing flufenamic acid and a bis-NSAID/CUR adduct with salicylic acid. A salicylic acid monoadduct, and a salalate bis-adduct showed notable anti-inflammatory effect against RAW 264.4 cell line. The other study reported spectroscopic and computational study on the monoibuprofen/CUR compound. (Srivastava et al. 2016)

CUR has recently been classified as both a PAINS (pan-assay interference compounds) and an IMPS (invalid/improbable metabolic panaceas) candidate. (K. M. Nelson, J. L. Dahlin, J. Bisson, J. Graham, G. F. Pauli, M. A. Walters, J. Med. Chem. 2017, 60, 1620-1637; K. M. Nelson, J. L. Dahlin, J. Bisson, G. F. Pauli, M. A. Walters ACS Med. Chem. Lett. 2017, 8, 467-470 and references cited therein). In view of the ongoing active debate in the medicinal chemistry community concerning the therapeutic efficacy of parent curcumin, a continuing search for CUR-inspired compounds that could overcome these drug-discovery challenges appears worthy. (K. M. Nelson, J. L. Dahlin, J. Bisson, J. Graham, G. F. Pauli, M. A. Walters, J. Med. Chem. 2017, 60, 1620-1637; K. M. Nelson, J. L. Dahlin, J. Bisson, G. F. Pauli, M. A. Walters ACS Med. Chem. Lett. 2017, 8, 467-470 and references cited therein; F. Bahadori, M. Demiray ACS Med. Chem. Lett. 2017, 8, 893-896 and references cited therein).

The inventors have synthesized a diverse set of bis-NSAID/CUR—BF$_2$, bis-NSAID/CUR, and mono-NSAID/CUR compounds, and performed computational docking studies to determine binding energies to HER2, VEGFR2, BRAF, Bcl-2, COX-1, and COX-2. Anti-proliferative activity was assessed as compared to CUR—BF2 and CUR compounds in in-vitro bioassay against a panel of 60 cancer cell lines, and more specifically in human CRC cells (HCT116, HT29, DLD-1, RKO, SW837, and Caco2), and comparative anti-inflammatory assays were conducted for a subset of flufenamic acid, indomethacin, and ibuprofen conjugates with THP-1 human macrophages in comparison to the parent NSAIDs and parent curcumin.

Several factors were considered in the selection of the NSAIDS used. Flufenamic acid and flurbiprofen were chosen because of the presence of fluorines, well known to increase lipophilicity and metabolic stability, with the added benefit of 19F NMR as a diagnostic tool to monitor reaction progress and to confirm structural integrity of the synthesized hybrid compounds. Selection of naproxen and ibuprofen stemmed from their wide use as over the counter drugs, and indomethacin because of its efficacy in pancreatic cancer by downregulating of COX-2. (L. Sun, K. Chen, Z. Jiang, X. Chen, J. Ma, Q. Ma, W. Duan, Oncol. Rep. 2018, 39, 2243-2251).

Variously substituted hydroxybenzaldehydes were coupled to flufenamic acid, flurbiprofen, indomethacin, naproxen, and ibuprofen using classical Steglich esterification protocol, employing DCC/DMAP, and the coupling adducts were obtained in good to excellent isolated yields. These were then reacted with acetylacetone-$BF_2$ complex (Scheme 1) in 2:1 ratio, following previously established procedures, to obtain the corresponding bis-NSAID/CUR—BF2 adducts. (K. K. Laali, B. M. Rathman, S. D. Bunge, X. Qi, G. L. Borosky, J. Fluorine Chem. 2016, 191, 29-41; K. K. Laali, W. J. Greves, S. J. Correa Smits, A. T. Zwarycz, S. D. Bunge, G. L. Borosky, A. Manna, A. Paulus, A. Chanan-Khand, J. Fluorine Chem. 2018, 206, 82-98; K. K. Laali, W. J. Greves, A. T. Zwarycz, S. J. Correa Smits, F. J. Troendle, G. L. Borosky, S. Akhtar, A. Manna, A. Paulus, A. Chanan-Khan, M. Nukaya, G. D. Kennedy ChemMedChem 2018, 13, 1895-1908; K. K. Laali, A. T. Zwarycz, S. D. Bunge, G. L. Borosky, M. Nukaya, G. D. Kennedy, ChemMedChem 2019, 14, 1173-1184; K. K. Laali, A. T. Zwarycz, S. D. Bunge, G. L. Borosky, M. Nukaya, G. D. Kennedy, ChemMedChem 2019, 14, 1173-1184). Thermal decomplexation of the BF2 adducts in the Monowave reactor were successful in some cases depending on the NSAID, and from this simple route the corresponding bis-NSAID/CUR compounds were directly obtained (Scheme 1). (D. Obermayer, D. Znidar, G. Glotz, A. Stadler, D. Dallinger, C. O. Kappe, J. Org. Chem. 2016, 81, 11788-1180). Scheme 1 is depicted in FIG. 80. While these exemplary NSAIDs were tested, other NSAIDs are contemplated for use in the present invention.

By using a different strategy (Scheme 2) a library of bis-NSAID/CUR and mono-NSAID/CUR conjugates were synthesized, from which the corresponding CUR—BF2 adducts were obtained by reaction with BF3. (R. Abonia, K. K. Laali, D. Raja-Somu, S. D. Bunge, E. C. Wang, ChemMedChem 2020, 15, 354-362). Scheme 2 is depicted in FIG. 81.

Collectively these efforts led to the synthesis and isolation of libraries of hybrid compounds shown in FIGS. 82 and 83. Octanol/water partition coefficients (Log P) are displayed below each structure. Log P is a measure of lipophilicity, useful in estimating the distribution of drugs within the body. Hydrophobic compounds with high log P values are mainly distributed into hydrophobic regions such as lipid bilayers, while hydrophilic molecules (low log P values) are primarily found in blood serum.

Structural Studies

Since efforts to grow crystals suitable for X-ray analysis were unsuccessful, the geometries of the compounds were optimized by density functional theory (DFT) computations at the B3LYP/6-31G* level. Some representative analogs are shown in FIG. 84A-D. The planar bis-$\alpha,\beta$-unsaturated-o-diketone backbone converged to the enolic tautomer, and the CUR—$BF_2$ adducts presented a symmetrically $BF_2$-coordinated structure.

In-Vitro Bioassay

The bis-NSAID/CUR—$BF_2$ and their corresponding CUR adducts proved to have little or no cytotoxicity by the NCI-60 assay (SI file and experimental section). Similar results were also observed in independent cell viability assay on colorectal cancer (CRC) cells (HCT116, HT29, DLD-1, RKO, SW837, CaCo2) and in normal CR cells (CCD841CoN) (FIG. 85). By contrast the mono-NSAID/CUR—BF2 compounds proved to be highly active, with mono-flurbiprofen/CUR—BF2 8 and mono-naproxin/CUR—BF2 10 exhibiting remarkable inhibitory effect on proliferation and apoptosis (mean values 20.3 and 36.6 respectively), in particular for colon, ovarian, and renal cancer cells (FIGS. 102, 103 and 98, 99), while the mono-flufenamic acid/CUR—BF2 adduct 5 was less potent (mean value 81). Removal of the BF2 results in significant loss of activity with the mean values for the mono-naproxin/CUR 20 and mono-ibuprofen/CUR 21 dropping to 89.8 and 87.9 respectively, and with mono-flufenamtic acid/CUR adduct 16 displaying essentially no cytotoxicity. Compounds 8 and 10 were then subjected to the five-dose screening assay by the NCI at concentrations $10^{-5}$ to $10^{-8}$ molar. Whereas compound 10 retained anti-proliferative activity at $10^{-6}$ molar, notably toward leukemia (RPMI 8226), colon (HCT-116), CNS (U-251), and ovarian (OVAR-8) cancer cells (FIG. 103), compound 8 lost significant anti-proliferative activity at $10^{-6}$ molar concentration.

Stability in Plasma and in Solvent

Since one of the important functions of the proteins in human plasma is to transport drugs, in a test experiment the bis-NSAID/CUR—$BF_2$ compound 1 was allowed to incubate with citrated human plasma in water/DMSO (see experimental section) at 37° C. with 5% CO2 for 8 hours. The $^{19}F$ and $^{1}H$ NMR spectra (and relative integrals) of the recovered material showed that circa 90% of the compound had remained structurally intact, implying that the release of NSAID is not a major contributor to the observed bioactivity. Furthermore, the NMR samples of NSAID/CUR—$BF_2$ and NSAID/CUR compounds remained unchanged when stored at r.t. for days.

Computational/Docking Studies

Molecular docking calculations for model compounds were performed with the aim to elucidate the factors determining the bioactivity of the hybrid compounds. Binding energies in the active site of various proteins involved in carcinogenic processes were determined and compared with the binding affinities of their corresponding known inhibitors applied in anticancer therapies. The proteins selected for these docking studies are involved in diverse oncogenic pathways, which were described in previous works, incorporated herein by reference. (K. K. Laali, B. M. Rathman, S. D. Bunge, X. Qi, G. L. Borosky, J. Fluorine Chem. 2016, 191, 29-41; K. K. Laali, W. J. Greves, S. J. Correa Smits, A. T. Zwarycz, S. D. Bunge, G. L. Borosky, A. Manna, A. Paulus, A. Chanan-Khand, J. Fluorine Chem. 2018, 206, 82-98; K. K. Laali, W. J. Greves, A. T. Zwarycz, S. J. Correa Smits, F. J. Troendle, G. L. Borosky, S. Akhtar, A. Manna, A. Paulus, A. Chanan-Khan, M. Nukaya, G. D. Kennedy ChemMedChem 2018, 13, 1895-1908; K. K. Laali, A. T. Zwarycz, S. D. Bunge, G. L. Borosky, M. Nukaya, G. D. Kennedy, ChemMedChem 2019, 14, 1173-1184).

In addition, the potential anti-inflammatory activity of the CUR-NSAID conjugates was evaluated by docking calculations in the active site of cyclooxygenase enzymes COX-1 and COX-2. These enzymes are responsible for inflammatory processes, and their pharmacological inhibition can relieve the symptoms of inflammation and pain. (G. Banuppriya, R. Sribalan, V. Padmini, V. Shanmugaiah, Bioorg. Med. Chem. Lett. 2016, 26, 1655-1659; C. Selvam, S. M. Jachak, R. Thilagavathib, A. K. Chakraborti, Bioorg. Med. Chem. Lett. 2005, 15, 1793-1797). Moreover, the expression of COX-2 was found to be increased in a variety of malignancies including pancreatic cancer, and COX-2-mediated synthesis of prostaglandins favors the growth of tumor cells by stimulating proliferation and angiogenesis. (S. Padhye, S. Banerjee, D. Chavan, S. Pandye, K. V. Swamy, S. Ali, J. Li, Q. P. Dou, F. H. Sarkar, Pharm. Res. 2009, 26, 2438-2445).

In general, the studied curcuminoids yielded very good binding energies that were similar to, and in several cases more favorable than, the usually employed chemotherapeutic inhibitors (Tables 9 and 10). The main interactions between the ligands and the proteins were hydrophobic, although some hydrogen bonds were also observed (FIGS. 86 and 87). It should be noted that in COX-1 the binding mode of the conjugates were different from that of the NSAIDs. In COX-2, the studied compounds docked into the same site as meloxicam and indomethacin.

TABLE 9

Binding Affinities for selected CUR-NSAIDs and known chemotherapeutic drugs (highly favorable binding energies in bold)

| Compounds | AutoDock Vina (kcal/mol) | | | | |
| --- | --- | --- | --- | --- | --- |
| | HER2 | Proteasome | VEGFR | BRAF | BCL-2 |
| Known inhibitors | −11.4 (SYR127063) | −7.8 (Bortezomib) | −9.2 (Axitinib) | −9.3 (Vemurafenib) | −8.3 (Navitoclax) |
| | −10.7 (Lapatinib) | −7.8 (Ixazomib) | −10.8 (Sorafenib) | −12.9 (Dabrafenib) | −8.2 (Venetoclax) |
| | −9.4 (Afatinib) | −8.5 (Carfilzomib) | −8.9 (Lenvatinib) | | |
| | | | −10.8 (Regorafenib) | | |
| bis-NSAID/CUR-BF$_2$ Adduct 1 | −10.6 | −8.6 | −11.0 | −11.0 | 3.4 |
| bis-NSAID/CUR-BF$_2$ Adduct 2 | −10.2 | −10.1 | −10.3 | −10.4 | −7.9 |
| bis-NSAID/CUR-BF$_2$ Adduct 3 | −10.2 | −10.1 | −12.0 | −11.2 | −7.1 |
| bis-NSAID/CUR-BF$_2$ Adduct 6 | −9.4 | −9.7 | −10.6 | −9.7 | −5.7 |
| bis-NSAID/CUR-BF$_2$ Adduct 8 | −10.9 | −10.7 | −11.0 | −10.2 | −7.9 |
| bis-NSAID/CUR-BF$_2$ Adduct 10 | −10.1 | −9.5 | −12.4 | −9.5 | −7.6 |
| bis-NSAID/CUR-BF$_2$ Adduct 11 | −7.9 | −8.6 | −10.3 | −9.6 | −4.2 |
| bis-NSAID/CUR-BF$_2$ Adduct 12 | −9.3 | −8.8 | −9.4 | −9.9 | −5.4 |
| bis-NSAID/CUR-BF$_2$ Adduct 14 | −9.8 | −8.7 | −9.0 | −10.7 | −8.0 |
| bis-NSAID/CUR-BF$_2$ Adduct 15 | −10.7 | −9.2 | −11.7 | −10.8 | −9.9 |
| bis-NSAID/CUR-BF$_2$ Adduct 16 | −10.7 | −9.8 | −11.8 | −10.8 | −10.0 |
| bis-NSAID/CUR-BF$_2$ Adduct 17 | −11.0 | −10.0 | −11.6 | −9.4 | −7.7 |
| bis-NSAID/CUR-BF$_2$ Adduct 18 | −9.6 | −9.2 | −11.9 | −10.3 | −5.8 |
| bis-NSAID/CUR-BF$_2$ Adduct 19 | −10.0 | −9.2 | −11.7 | −9.5 | −8.4 |
| bis-NSAID/CUR-BF$_2$ Adduct 21 | −10.5 | −8.7 | −11.0 | −9.4 | −8.2 |
| bis-NSAID/CUR-BF$_2$ Adduct 22 (not in the synthesized library) | −10.0 | −9.2 | −10.3 | −10.0 | −8.2 |

TABLE 10

Binding affinities for selected CUR-NSAIDs and NSAIDs in cyclooxygenase enzymes (highly favorable binding energies shown in bold)

| Compounds | AutoDock Vina (kcal/mol) | |
|---|---|---|
|  | COX-1 | COX-2 |
| Known Inhibitors: | | |
| Meloxicam | −8.6 | −7.8 |
| Ibuprofen | −6.9 | −7.6 |
| Flurbiprofen | −8.7 | −8.9 |
| Indomethacin | −8.6 | −7.3 |
| Flufenamic acid | −8.7 | −8.6 |
| bis-NSAID/CUR-BF$_2$ Adduct 1 | −3.4 | −3.3 |
| bis-NSAID/CUR-BF$_2$ Adduct 2 | −7.4 | −8.1 |
| bis-NSAID/CUR-BF$_2$ Adduct 3 | −8.6 | −10.3 |
| bis-NSAID/CUR-BF$_2$ Adduct 6 | −3.5 | −5.1 |
| mono-NSAID/CUR Adduct 8 | −8.7 | −9.3 |
| mono-NSAID/CUR Adduct 10 | −8.6 | −9.3 |
| bis-NSAID/CUR-BF$_2$ Adduct 11 | 1.0 | 0.9 |
| bis-NSAID/CUR-BF$_2$ Adduct 12 | −3.5 | −3.3 |
| bis-NSAID/CUR Adduct 14 | −7.2 | −3.3 |
| bis-NSAID/CUR Adduct 15 | −7.5 | −6.0 |
| mono-NSAID/CUR Adduct 16 | −8.9 | −10.5 |
| bis-NSAID/CUR Adduct 17 | −7.5 | −4.9 |
| mono-NSAID/CUR Adduct 18 | −8.0 | −9.1 |
| bis-NSAID/CUR Adduct 19 | −8.7 | −7.5 |
| mono-NSAID/CUR Adduct 21 | −7.7 | −8.5 |
| bis-ibuprofen/CUR Adduct 22 | −7.2 | −7.6 |

Among the NSAID/CUR—BF2 and NSAID-CUR conjugates that showed significant binding affinities with cyclooxygenases, most presented greater inhibitory action against the inducible isoform COX-2 (FIG. 105) which is implicated in the inflammatory response, than against the constitutive form of this enzyme (COX-1), inhibition of which is associated with gastric, renal and other adverse effects, such as inhibition of platelet aggregation. (J. R. Vane, R. M. Botting, Inflammation Res. 1995, 44, 1-10). These observations appear promising for the development of new anti-inflammatory agents with an improved tolerability profile. Nevertheless, although favorable docking is a necessary requirement for bioactivity, processes that occur prior to ligand-protein interaction, such as solubility, absorption, transport, metabolism, and membrane permeability, can affect the observed in vitro and in vivo activities.

Anti-Inflammatory Assay

Lack of cytotoxicity in the bis-NSAID-CUR—BF2 adducts prompted a preliminary investigation into their anti-inflammatory effect. A comparative anti-inflammatory assay using IL-1β, a pre-inflammatory cytokine, with THP-1 human macrophage cell line on a sub-set of six NSAIDS-CUR compounds showed better anti-inflammatory response (suppression of LPS-induced IL-1β expression) compared to parent curcumin. (FIG. 88). The flufenamic acid/CUR conjugate induced better suppression of LPS-induced inflammatory response than the parent flufenamate acid (FIG. 89), while the anti-inflammatory response by ibuprofen/CUR and flurbiprofen/CUR conjugates was not significantly improved compared to the respective parent NSAIDS.

It has been reported that fenamate NSAIDs (e. g., flufenamic acid, meclofenamic acid, and metenamic acid) suppressed the release and production of IL-1β in mouse bone marrow-derived macrophages (BMDMs) via inhibition of NLRP3 inflammasome which is one of the most well-characterized inflammasome pathways. (M. J. Daniels J Rivers-Auty, T. Schilling N G Spencer, W. Watremez, V. Fasolino, S. J. Booth, C. S. White, A. G. Baldwin, S. Freeman, R. Wong R, C. Latta, S. Yu, J. Jackson J, N. Fischer, V. Koziel, T. Pillot, J. Bagnall, S. M. Allan, P. Paszek, J. Galea, M. K. Harte, C. Eder, C. B. Lawrence, D. Brough, Nat. Commun. 2016, 7, 12504). By contrast, ibuprofen hardly inhibited the release and production of IL-1β and NLRP3 inflammasome pathway in BMDMs. Interestingly, parent curcumin also suppressed the release and production of IL-1β through the inhibition of NLRP3 inflammasome in BMDMs. (M. T. Palizgir, M. Akhtari, M. Mahmoudi, S. Mostafaei, A. Rezaiemanesh, F. Shahram, Immunopharmacol. Immunotoxicol. 2018, 40, 297-302). Therefore, the inventors surmise that flufenamic acid/CUR conjugates may act as selective and synergistic NLRP3 inflammasome inhibitors.

Summary of Results

A series of the bis- and the mono-NSAID/CUR—BF2 and NSAID-CUR hybrids were synthesized and characterized. Whereas the bis-adducts exhibited little or no cytotoxicity in in-vitro bioassay, the mono-NSAID-CUR—BF2 compounds, in particular the naproxen and flurbiprofen conjugates 8 and 10, proved to be highly potent. Removal of the BF2 group, as in the mono-naproxin/CUR 20 and mono-ibuprofen/CUR 21 resulted in significant loss of activity. Computational molecular docking calculations showed favorable binding energies to HER2, VEGFR2, BRAF, and Bcl-2 as well as to COX-2. Finally, the inventors found that the CUR-conjugated flufenamic acid compounds showed better anti-inflammatory response relative to parent flufenamaic acid, parent curcumin, and other NSAIDs (ibuprofen, flurbiprofen). Present studies suggest that fenamate NSAIDs/CUR conjugates could become effective and selective drug candidates for several inflammatory diseases implicated in IL-1β and NLRP3 inflammasome. (C. A. Dinarello, Blood 2011, 117, 3720-32).

It is worth noting that some of the new molecules show promising activity toward multiple targets. The multitarget approach of drug discovery has several advantages (lower dose requirement, less side effects, reduced pharmaceutical pollution, etc.), especially in treating complex diseases.

Experimental Section

General: The NSAIDs, substituted hydroxyl-benzaldehydes, DCC and DMAP were all high purity commercially available samples and were used without further purification. NMR spectra were recorded on a 500 MHz instrument using CDCl3, DMSO-d6 or acetone-d6 as solvent. 19F NMR were referenced relative to external CFCl3. HRMS analyses were performed on a Finnigan Quantum ultra-AM in electrospray mode using methanol as solvent. Decomplexation of CUR—BF2 adducts to CUR was affected by using a benchtop Monowave reactor (Anton Paar). FT-IR spectra were recorded in ATR mode (as thin films formed via DCM evaporation). Melting points were measured in open capillaries and are not corrected.

Synthesis of NSAID-Aldehyde Adducts: The selected hydroxybenzaldehyde was added to a round bottom flask and dissolved in a minimal amount of chloroform. The NSAID (1.5 mmol), DCC (1.6 mmol), and DMAP (1.6 mmol) were subsequently added and the reaction mixture was flushed with nitrogen and allowed to stir at room temperature overnight. Upon completion (monitored by TLC) it was transferred to a freezer to allow the dicyclohexylurea (DCU) side product to fall out of solution. The reaction mixture was then quickly filtered through a Buchner funnel and the filtrate was transferred to a small beaker, washed with a 5% HCl solution (3×10 mL) and extracted with chloroform. The organic layer was dried (sodium sulfate), filtered, and the solvent was evaporated under vacuum to give the crude product as an oil, which was purified by crystallization from isopropanol followed by vacuum drying.

Synthesis of bis-NSAID-CUR—BF$_2$ Adducts (Method 1)—To the NSAID-aldehyde adduct (0.55 mmol) charged into a multi-neck round bottom flask, was added acetylacetone-BF$_2$ adduct (0.25 mmol) and the mixture was dissolved in a minimal amount of ethyl acetate and flushed with nitrogen. Then n-butylamine (0.055 mmol) was introduced dropwise under stirring and the reaction was allowed to continue overnight, whereupon a solid precipitate was formed. When the spot due to NSAID-aldehyde adduct was no longer detectable by TLC, the reaction mixture was cooled to 0° C. and the solid product was filtered through a Buchner funnel, washed with cold ethyl acetate and dried under vacuum.

Synthesis of bis-NSAID-CUR Adducts (Method 1)—The bis-NSAIDCUR—BF$_2$ adduct synthesized via method 1 (0.1 mmol) was mixed with sodium oxalate (0.2 mmol) and charged into a Monowave reactor vial equipped with a stir bar. Then 6 mL of 8:2 methanol/water was added and the tube was sealed and heated to 140° C. for 6 minutes in the Monowave reactor. After cooling, the product was filtered, washed with water, and dried under vacuum.

Synthesis of bis- and mono-NSAID-CUR Adducts (Method 2)—synthetic curcumin (0.5 mmol), DCC (0.55 mmol), DMAP (0.05 mmol) and the NSAID (1.05 mmol for bis-adduct and 0.45 mmol for the mono-adduct) were added to a round bottom flask and dissolved in DCM (15 mL). The mixture was stirred and the reaction was allowed to continue for 24 hours. TLC analysis of the crude reaction mixture showed the formation of both mono-, and bis-adducts (irrespective of molar equivalence of NSAID) along with unreacted curcumin. The crude mixture was washed with saturated NaHCO3 solution, and the DCM layer was separated. The products were separated by column chromatography using hexane/ethyl acetate (40%). Fractions containing the respective products were combined and the solvent was removed leaving behind an oil, which was crystallized by dissolving in DCM and adding hexane, followed by filtration and vacuum drying.

Synthesis of bis- and mono-NSAID-CUR—BF$_2$ Adducts (Method 2)—To a multi-neck round bottom flask, 0.05 mmol of either the bis- or the mono-NSAID-CUR conjugate synthesized via method 2 was added and was dissolved in dry DCM. The solution was flushed with nitrogen with efficient stirring, then 0.075 mmol of BF$_3$ (as a solution of 48% BF3-etherate) diluted in 0.5 mL of dry DCM was added dropwise into the flask via a syringe through a septum, and the reaction was allowed to stir at r.t. for circa 2 hours (completion was checked by TLC). The solvent was evaporated and the product was washed with diethyl ether, filtered, and dried under vacuum.

Stability Tests in Human Plasma and in Solvent

Compound 1 (20 mg) was dissolved in DMSO and allowed to mix with citrated human plasma (sigma-Aldrich) (1 mL) in a 24-well plate and incubated at 37° C. with 5% CO$_2$ for 8 hours. The resulting mixture was freeze-dried, extracted with acetone-d$_6$ and directly checked by $^{19}$F and $^1$H NMR.

NMR samples of the bis- and the mono-NSAID/CUR—BF$_2$ adducts in acetone-d$_6$ or DMSO-d$_6$ and those of the bis- and mono-NSAID/CUR adducts dissolved in CDCl$_3$ showed minimal decomposition (<5%) by NMR when kept at r.t. overnight or stored in refrigerator for several days.

bis-Flufenamic acid/CUR—BF$_2$ Adduct (1): Yield 55%, off-white solid, mp 240-242° C., Rf 0.70 (40% EtOAc in hexane). $^1$H NMR (acetone-d$_6$, 500 MHz): δ 9.43 (s, 2H), 8.28 (dd, J=1.5 and 8.0 Hz, 2H), 8.08 (d, 16.0 Hz, 2H), 7.65-7.57 (unresolved m, 8H), 7.45-7.41 (unresolved m, 4H), 7.36 (s, 4H), 7.23 (d, J=15.5 Hz, 2H), 7.01 (pseudo-dt, J=1.0 and 8.5 Hz, 2H), 6.54 (s, 1H), 3.94 (s, 12H). $^{19}$F NMR (acetone-d$_6$, 470 MHz): δ −63.30 (6F, CF3), −140.25 (s, $^{11}$B—F), −140.18 (s, $^{10}$B—F). $^{13}$C NMR (acetone-d$_6$, 125 MHz): δ 180.6, 165.4, 153.1, 147.0, 146.9, 146.5, 141.7, 141.6, 135.3, 133.0, 132.4, 131.4, 131.2, 130.4, 124.8, 121.8, 119.6 (q, JCF=3.9), 118.8, 117.7 (q, JCF=3.8), 114.7, 112.0, 106.2, 102.1, 55.9. IR (cm$^{-1}$): 2941, 1705, 1620, 1593, 1557, 1501, 1456, 1423, 1331, 1256, 1207, 1130, 1047.

bis-Flufenamic acid/CUR Adduct (14): Yield 96%, Yellow solid, mp 209° C., Rf 0.62 (40% EtOAc in hexane). 1H NMR (CDCl3, 500 MHz): δ 9.50 (s, 2H), 8.32 (d, J=7.7 and 2.0 Hz, 2H), 7.65 (d, J=16.5 Hz, 2H), 7.50-7.30 (unresolved m, 14H!), 6.93-6.90 (unresolved m, 2H), 6.88 (s, 4H), 6.61 (d, J=15.5 Hz, 2H), 5.93 (s, 1H), 3.89 (s, 12H). $^{19}$F NMR (CDCl3, 470 MHz): δ −62.87. $^{13}$CNMR (CDCl$_3$, 125 MHz): δ 183.1, 166.3, 152.8, 147.3, 141.4, 140.4, 135.0, 133.6, 132.8, 131.8 (q, J=32.4 Hz), 130.1, 129.9, 124.5, 124.4, 123.9 (q, J=271.8 Hz), 119.7 (q, J=3.8), 118.5, 118.0 (q, J=3.9), 114.2, 111.7, 104.8, 101.8, 56.3. HRMS (ESI): m/z [M+H]+ calcd for C$_{51}$H$_{41}$F$_6$N$_2$O$_{10}$: 955.26654; found: 955.2612. IR (cm$^{-1}$): 3331, 2961-2843, 1701, 1595, 1506, 1456, 1418, 1333, 1254, 1206, 1130, 1040.

bis-Flufenamic acid/CUR—BF$_2$ Adduct (2): Yield 67%, red solid, mp 273° C., Rf 0.61 (40% EtOAc in hexane). $^1$H NMR (DMSO-d$_6$, 500 MHz): δ 9.24 (br s, NH), 8.28 (d, J=16.0 Hz, 2H), 8.17 (dd, J=8.2, 2.0 Hz, 2H), 7.61-7.54 (m, 9H), 7.38-7.34 (m, 6H), 7.04 (pseudo-dt, J=7.0, 1.0 Hz, 2H), 6.81 (s, 4H), 6.64 (s, 1H), 3.94 (s, 12H). $^{19}$F NMR (DMSO-d$_6$, 470 MHz): δ −61.31 (s, 6F), −137.74 (s, $^{11}$B—F). $^{13}$C NMR (DMSO-d$_6$, 125 MHz): δ 180.3, 165.7, 161.7, 155.9, 146.3, 142.5, 136.6, 135.9, 132.6, 131.1, 130.7 (q, J=31.4 Hz), 124.0 (q, J=271.8 Hz), 124.1, 122.8, 120.0, 119.2 (q, J=4.0 Hz), 116.9 (q, J=2.9 Hz), 116.7, 113.8, 109.7, 103.7, 99.8, 57.1. IR (cm$^{-1}$): 3331, 2947-2845, 1695, 1599, 1530, 1454, 1335, 1304, 1254, 1223, 1123, 1057.

bis-Flufenamic acid/CUR—BF$_2$ Adduct (3): Yield 32%, orange solid, mp 224-226° C., Rf 0.62 (40% EtOAc in hexane). 1H NMR (acetone-d$_6$, 500 MHz): δ 9.36 (s, NH), 8.35 (dd, J=8.2 and 2.0 Hz), 8.12 (dd, J=1.5 and 16.0 Hz, 2H), 7.84 (dd, J=3.0 and 9.5 Hz, 2H), 7.63-7.53 (m, 8H), 7.55 (d, J=5 Hz, 1H), 7.52 (d, J=5 Hz, 1H), 7.47-7.41 (m, 6H), 7.29 (d, J=16.0 Hz, 2H), 7.04-7.01 (m, 2H), 6.54 (s, 1H). $^{19}$F NMR (acetone-d$_6$, 470 MHz): δ −63.31 (s, 6F), −116.92 (m, 2F), −139.53 (s, $^{11}$B—F), −139.46 (s, $^{10}$B—F). 13C NMR (acetone-d$_6$, 125 MHz): δ 180.8, 166.3, 160.4 (d, JCF=244 Hz), 147.5, 146.5 (d, JCF=2.8 Hz), 141.4, 138.5 (d, JCF=1.9 Hz), 135.7, 132.2, 131.3 (q, JCF=31.5 Hz), 130.4, 129.1 (d, JCF=8.7 Hz), 125.3 (q, JCF=271.8 Hz), 125.9 (d, JCF=8.5 Hz), 125.2, 124.7, 119.8 (q, JCF=3.9 Hz), 119.4 (d, J=23.8 Hz), 118.9, 118.1 (JCF=3.8 Hz), 114.7, 114.1 (d, JCF=24.9 Hz), 111.4, 103.5. IR (cm$^{-1}$): 2359, 1715, 1620, 1585, 1541, 1541, 1520, 1491, 1456, 1418, 1337, 1258, 1221, 1163, 1123, 1042.

bis-Flufenamic acid/CUR—BF$_2$ Adduct (4): Yield 96.8%, orange solid, mp 199° C., Rf 0.86 (40% EtOAc in hexane). 1H NMR (acetone-d$_6$, 500 MHz): δ 9.42 (s, 2H), 8.27 (dd, J=8.3 Hz and 2.0 Hz, 2H), 8.12 (d, J=16.0 Hz, 2H), 7.73 (d, J=2.0 Hz, 2H), 7.64-7.57 (m, 10H), 7.46-7.42 (m, 6H), 7.23 (d, J=15.5 Hz, 2H), 7.02 (t, J=7.5 Hz, 2H), 6.59 (s, 1H), 3.97 (s, 6H). $^{19}$F NMR (acetone-d$_6$, 470 MHz): δ −63.32 (6F), −140.23 (s, $^{10}$B—F), −140.29 (s, $^{11}$B—F). $^{13}$C NMR (acetone-d$_6$, 125 MHz): δ 180.6, 165.7 152.1, 147.1, 146.1, 142.7, 141.7, 135.3, 133.5, 132.2, 131.3 (q, JCF=32.4 Hz), 130.4, 124.5 (q, JCF=271.8 Hz), 124.0, 122.5, 121.7, 119.9 (distorted-q, JCF=3 Hz), 118.8, 114.7, 112.9, 112.1, 102.1, 55.7.

bis-Flufenamic acid/CUR Adduct (15): Yield 57.5%, yellow solid, mp 107° C., Rf (40% EtOAc in hexane). 1H NMR (CDCl3, 500 MHz): 9.50 (s, 2H), 8.28 (dd, J=8.3 Hz and 1.5 Hz, 2H), 7.69 (d, J=15.5 Hz, 2H), 7.51-7.32 (unresolved m, 12H), 7.26-7.21 (m, 6H), 6.92 (dt, J=8.0 Hz and 1.0 Hz, 2H), 6.63 (d, J=16.0 Hz, 2H), 5.91 (s, 1H), 3.91 (s, 6H). $^{19}$F NMR (CDCl$_3$, 470 MHz): δ −62.85 (CF3). $^{13}$C NMR (CDCl$_3$, 125 MHz): δ 183.1, 166.5, 151.7, 147.5, 141.3, 141.2, 140.0, 135.2, 134.2, 132.5, 131.9 (q, JCF=32.4 Hz), 130.0, 124.7, 124.4, 123.6, 123.9 (q, JCF=272.7 Hz), 121.2, 119.9 (q, J=3.8 Hz), 118.4, 118.2 (q, 3.9 Hz), 114.2, 111.6, 101.9, 56.1. HRMS (ESI): m/z [M+H]+ calcd for C$_{49}$H$_{37}$F$_6$N$_2$O$_8$: 895.245411; found: 895.1868. IR (cm$^{-1}$): 3331, 3074-2841, 1699, 1632, 1582, 1506, 1454, 1416, 1333, 1252, 1227, 1200, 1161, 1119, 1045.

mono-Flufenamic acid/CUR—BF2 Adduct (5): Yield 67.8%, red solid, mp 170° C., Rf 0.20 (40% EtOAc in hexane). 1H NMR (acetone-d$_6$, 500 MHz): δ 9.42 (s, NH), 8.64 (s, 1H), 8.27 (dd, J=8.5 Hz and 1.5 Hz, 1H), 8.05 (d, J=15.5 Hz, 1H), 8.03 (d, J=16.0 Hz, 1H), 7.69 (d, J=2.0, 1H), 7.64-7.53 (m, 6H), 7.46-7.40 (m, 4H), 7.16 (d, J=15.5 Hz, 1H), 7.03-6.97 (m, 3H), 6.47 (s, 1H), 3.97 (s, 3H), 3.96 (s, 3H). $^{19}$F NMR (acetone-d$_6$, 470 MHz): δ −63.32 (CF3), −140.70 (s, $^{10}$B—F), −140.76 (s, $^{11}$B—F). $^{13}$C NMR (acetone-d$_6$, 125 MHz): δ 181.2, 178.9, 165.7, 152.1, 151.4, 148.1, 147.0, 144.7, 142.4, 141.7, 135.2, 133.7, 132.3, 131.3 (q, JCF=32 Hz), 130.4, 126.6, 125.3, 124.8, 124.7, 123.9 (q, JCF=271.0 Hz), 122.2, 121.9, 119.5 (q, JCF=3.7 Hz), 118.8, 118.0, 117.7 (q, JCF=4.7 Hz), 115.7, 114.7, 112.7, 112.1, 111.9, 101.6, 55.7, 55.5.

mono-Flufenamic acid/CUR Adduct (16): Yield 29.5%, yellow solid, mp 133° C., Rf 0.53 (40% EtOAc in hexane). 1H NMR (CDCl$_3$, 500 MHz): δ 9.48 (s, 1H), 8.27 (dd, J=8.0 Hz and 1.0 Hz, 1H), 7.64 (d, J=15.5 Hz, 1H), 7.62 (d, J=15.5 Hz, 1H), 7.49-7.30 (m, 6H), 7.24-7.19 (m, 3H), 7.13 (dd, J=8.0 Hz and 1.5 Hz, 1H), 7.06 (s, 1H), 6.94 (d, J=8.0 Hz, 1H), 6.91 (t, J=6.5 Hz, 1H), 6.59 (d, J=16.0 Hz, 1H), 6.50 (d, J=16.0 Hz, 1H), 5.89 (br s, 1H), 5.85 (s, 1H), 5.30 (s, 1H), 3.95 (s, 3H), 3.89 (s, 3H). $^{19}$F NMR (CDCl$_3$, 470 MHz): δ −62.85 (CF$_3$). $^{13}$C NMR (CDCl$_3$, 125 MHz): δ 184.6, 181.8, 166.5, 151.7, 148.0, 147.5, 146.8, 141.3, 141.2, 141.0, 139.4, 135.2, 134.3, 132.5, 131.9 (q, JCF=32.4 Hz), 130.0, 127.6, 124.7, 124.4, 123.9 (q, JCF=272.7 Hz), 123.5, 123.1, 121.8, 121.0, 119.9 (q, JCF=3.8 Hz), 118.4, 118.2 (q, J=3.8 Hz), 114.9, 114.2, 111.6, 111.5, 109.7, 101.6, 56.0, 55.9. HRMS (ESI): m/z [M+H]+ calcd for C35H29O7F3N: 632.1896; found: 632.2006. IR (cm$^{-1}$): 3331, 3069-2841, 1699, 1628, 1582, 1506, 1454, 1429, 1416, 1333, 1254, 1202, 1161, 1121, 1034.

bis-Flurbiprofen/CUR—BF$_2$ Adduct (6): Yield 63%, Dark orange solid, mp: 230-232° C., Rf 0.36 (40% EtOAc in hexane). 1H NMR (acetoned$_6$, 500 MHz): δ 8.02 (d, J=15.5 Hz, 2H), 7.63-7.37 (complex region, 16H), 7.26 (s, 4H), 7.17 (d, J=15.5 Hz, 2H), 6.50 (s, 1H), 4.22 (q, J=7.0 Hz, 2H), 3.88 (s, 12H), 1.65 (d, J=7.5 Hz, 6H). $^{19}$F NMR (acetone-d$_6$, 470 MHz): δ −119.5 (t, J=11.8 Hz, 2F), −140.2 (s, $^{10}$B—F), −140.3 (s, $^{11}$B—F). $^{13}$C NMR (acetone-d$_6$, 125 MHz): δ 180.6, 170.9, 159.5 (d, JCF=246.0 Hz), 152.8, 146.5, 142.3 (JCF=8.5 Hz), 135.5, 132.7, 131.8, 130.7 (d, J=4.0 Hz), 128.8, 128.5, 127.7, 127.6 (JCF=13.0 Hz), 124.3 d, J=3.7 Hz), 121.7, 115.4 (J=24.0 Hz), 106.2, 102.0, 55.8, 44.4, 18.3. IR (cm$^{-1}$): 2359, 1759, 1622, 1593, 1558, 1501, 1456, 1420, 1342, 1254, 1132, 1065, 1011.

bis-Flurbiprofen/CUR—BF2 Adduct (7): Yield 73.6%, orange solid, mp 198° C., Rf 0.39 (40% EtOAc in hexane). 1H NMR (acetone-d$_6$, 500 MHz): δ 8.05 (d, J=15.5 Hz, 2H), 7.62-7.37 (complex region, 20H), 7.20 (d, J=8.5 Hz, 2H), 7.15 (d, J=16.0 Hz, 2H), 6.53 (s, 1H), 4.22 (q, J=7.0 Hz, 2H), 3.89 (s, 6H), 1.66 (d, J=7.0 Hz, 6H). $^{19}$F NMR (acetone-d$_6$, 470 MHz): δ −119.33 (2F), −140.22 (s, $^{10}$B—F), −140.28 (s, $^{11}$B—F). $^{13}$C NMR (acetone-d$_6$, 125 MHz): δ 180.6, 171.3, 160.5, 158.6, 151.9, 146.1, 143.0, 142.2 (d, JCF=8.6 Hz), 135.5, 133.4, 130.8 (d, JCF=3.9 Hz), 128.9 (d, JCF=3.8 Hz), 128.5, 127.7, 127.6, 124.2 (d, JCF=2.9 Hz), 123.4, 123.1 (q, JCF=245.0 Hz), 122.5, 121.6, 115.4 (d, JCF=23.9 Hz), 112.9, 102.0, 55.5, 44.5, 18.2.

bis-Flurbiprofen/CUR Adduct (17): Yield 24%, yellow solid, mp 131° C., Rf 0.84 (40% EtOAc in hexane). 1H NMR (CDCl3, 500 MHz): δ 7.69 (d, J=16.0 Hz, 2H), 7.59-7.57 (m, 4H), 7.48-7.46 (m, 6H), 7.46-7.37 (m, 2H), 7.29 (unresolved d, 4H), 7.15 (dd, J=8.5 Hz and 1.5 Hz, 2H), 7.10 (d, J=2.0 Hz, 2H), 7.03 (d, J=8.0 Hz, 2H), 6.56 (d, J=15.5 Hz, 2H), 5.86 (s, 1H), 4.07 (q, J=7.5 Hz, 2H), 3.81 (s, 6H), 1.68 (d, J=7.5 Hz, 6H). $^{19}$F NMR (CDCl$_3$, 470 MHz): δ □ 117.6 (pseudo-t). $^{13}$C NMR (CDCl$_3$, 125 MHz): δ 183.1, 171.8, 160.7, 158.7, 151.4, 141.4, 141.3 (d, JCF=7.7 Hz), 139.9, 135.5, 134.0, 130.8 (d, JCF=3.9 Hz), 129.0 (d, JCF=2.9 Hz), 128.0 (d, JCF=7.5 Hz), 127.7, 124.3, 123.8 (d, JCF=2.9 Hz), 123.1, 121.1, 115.5 (d, JCF=24.0 Hz), 111.4, 101.8, 55.8, 44.9, 18.6. HRMS (ESI): m/z [M−H]$^-$ calcd for C$_{51}$H$_{41}$F$_2$O$_8$: 819.276951; found: 819.2860. IR (cm$^{-1}$): 3059-2938, 1759, 1628, 1599, 1506, 1483, 1418, 1300, 1254, 1121, 1072, 1034.

mono-Flurbiprofen/CUR—BF$_2$ Adduct (8): Yield 62.9%, dark-red solid, mp 227° C., Rf 0.15 (40% EtOAc in hexane). 1H NMR (acetone-d$_6$, 500 MHz): δ 8.63 (s, 1H), 8.04 (d, J=15.5 Hz, 1H), 7.97 (d, J=15.5 Hz, 1H), 7.63-7.57 (m, 4H)), 7.51-7.49 (m, 3H), 7.54-7.36 (m, 5H), 7.18 (d, J=7.5 Hz, 1H), 7.11 (d, J=16.0 Hz, 1H), 6.98 (d, J=15.5 Hz, 1H), 6.97 (d, J=8.5 Hz, 1H), 6.45 (s, 1H), 4.22 (q, J=7.5 Hz, 1H), 3.96 (s, 3H), 3.89 (s, 3H), 1.66 (d, J=6.5 Hz, 3H). $^{19}$F NMR (acetone-d$_6$, 470 MHz): δ −119.34 (pseudo-t, 1F), −140.68 (s, $^{10}$B—F), −140.74 (s, $^{11}$B—F). 13C NMR (acetone-d$_6$, 125 MHz): δ 181.2, 179.0, 171.3, 160.7, 158.7, 151.9, 151.4, 151.2, 148.0 (d, JCF=6.6 Hz), 144.7, 142.7, 142.2 (d, JCF=8.5 Hz), 135.5, 133.6, 130.8 (d, JCF=4.7 Hz), 128.9 (d, JCF=2.7 Hz), 128.5, 127.7 (d, JCF=3.0 Hz), 126.6, 125.3, 124.2 (d, JCF=2.8 Hz), 123.3, 122.2, 121.8, 117.9, 115.6, 115.4 (d, JCF=24.7 Hz), 112.7, 111.8, 101.6, 55.5, 44.5, 18.2.

mono-Flurbiprofen/CUR Adduct (18): Yield 17.2%, orange solid, mp 92° C., Rf 0.58 (40% EtOAc in hexane). 1H NMR (CDCl$_3$, 500 MHz): 7.62 (d, J=16.0 Hz, 1H), 7.60 (d, J=15.0 Hz, 1H), 7.58 (d, J=8.5 Hz, 2H), 7.48-7.45 (m, 3H), 7.39 (pseudo-tt, 1H), 7.37 (d and s overlapping, 3H), 7.16-7.14 (m, 2H), 7.08 (dd, J=15.7 Hz and 1.5 Hz, 2H), 7.03 (d, J=8.5 Hz, 1H), 6.95 (d, J=8.0 Hz, 1H), 6.55 (d, J=16.0 Hz, 1H), 6.50 (d, J=15.5 Hz, 1H), 5.84 (s, 1H), 4.06 (q, J=7.5 Hz, 1H), 3.96 (s, 3H), 3.81 (s, 3H), 1.68 (d, J=7.5 Hz, 3H). $^{19}$F NMR (CDCl$_3$, 470 MHz): δ −117.7 (pseudo t). 13C NMR (CDCl$_3$, 125 MHz): δ 184.5, 181.8, 171.9, 160.7, 158.7, 151.4, 148.0, 146.8, 141.3 (d, JCF=7.7 Hz), 141.3, 141.1, 139.4, 135.5, 134.2, 130.8 (d, JCF=3.8 Hz), 129.0 (d, JCF=2.9 Hz), 128.5, 128.0 (d, JCF=13.3 Hz), 127.7, 127.6, 124.3, 123.8 (d, JCF=2.9 Hz), 123.0 (d, JCF=2.8 Hz), 121.8, 120.9, 115.5 (d, JCF=23.7 Hz), 111.4, 109.7, 101.5, 56.0, 55.8, 44.9, 18.6. HRMS (ESI): m/z [M−H]$^-$ calcd for C$_{36}$H$_{30}$FO$_7$: 593.19756; found: 593.1715. IR (cm$^{-1}$): 3524, 3416, 3061-2841, 1757, 1626, 1587, 1506, 1450, 1418, 1296, 1267, 1204, 1121, 1072, 1032.

bis-Naproxen/CUR—BF2 Adduct (9): Yield 75.5%, dark red solid, mp 167° C., Rf 0.30 (40% EtOAc in hexane). 1H NMR (acetone-$d_6$, 500 MHz): δ 8.03 (d, J=16.0 Hz, 2H), 7.88 (d, J=1.5 Hz, 2H), 7.86 (s, 2H), 7.84 (d, J=1.5 Hz, 2H), 7.58-7.55 (partially overlapping doublets, J=2.0 Hz, 4H), 7.44 (dd, J=8.5 Hz and 2.0 Hz, 2H), 7.33 (d, J=2.5 Hz, 2H), 7.18 (dd, J=9.0 Hz and 3.0 Hz, 2H), 7.13 (d, J=15.5 Hz, 2H), 7.12 (d, J=7.5 Hz, 2H), 6.52 (s, 1H), 4.24 (q, J=7.0 Hz, 2H), 3.94 (s, 6H), 3.83 (s, 6H), 1.67 (d, J=6.5 Hz, 6H). 19F NMR (acetone-$d_6$, 470 MHz): δ −140.28 (s, $^{10}$B—F), −140.34 (s, $^{11}$B—F). $^{13}$C NMR (acetone-$d_6$, 125 MHz): δ 188.4, 171.6, 157.7, 151.8, 145.8, 142.9, 135.5, 133.8, 133.0, 129.0, 128.8, 126.9, 126.2, 126.0, 123.2, 122.3, 121.3, 118.7, 112.6, 105.4, 101.8, 65.0, 55.3, 54.5, 18.1, 14.5.

bis-Naproxen/CUR Adduct (19): Yield 20%, yellow solid, mp 179° C., Rf 0.49 (40% EtOAc in hexane). 1H NMR (CDCl$_3$, 500 MHz): δ 7.80 (s, 2H), 7.56 (pseudo-t, J=7.5 Hz, 4H), 7.59 (d, J=16.0 Hz, 2H), 7.53 (dd, J=8.7 Hz and 2.0 Hz, 2H), 7.18-7.15 (m, 4H), 7.11 (dd, J=8.25 Hz and 2.0 Hz, 2H), 7.06 (d J=1.5 Hz, 2H), 6.96 (d, J=8.5 Hz, 2H), 6.53 (d, J=7.5 Hz, 2H), 5.83 (s, 1H), 4.16 (q, J=7.5 Hz, 2H), 3.94 (s, 6H), 3.72 (s, 6H), 1.71 (d, J=7.0 Hz, 6H). $^{13}$C NMR (CDCl$_3$, 125 MHz): δ 183.1, 172.5, 157.7, 151.5, 141.6, 140.4, 135.1, 133.9, 129.3, 129.0, 127.1, 126.4, 126.3, 124.2, 123.1, 121.0, 119.0, 111.5, 105.6, 101.7, 55.8, 55.3, 45.3, 18.7. HRMS (ESI): m/z [M+H]+ calcd for $C_{49}H_{45}O_{10}$: 793.301275; found: 793.2805. IR (cm$^{-1}$): 2934, 1755, 1630, 1605, 1506, 1452, 1416, 1300, 1265, 1121, 1070, 1032.

mono-Naproxen/CUR—BF$_2$ Adduct (10): Yield 83.0%, maroon solid, mp 151° C., Rf 0.12 (40% EtOAc in hexane). 1H NMR (acetone-$d_6$, 500 MHz): δ 8.64 (s, 1H), 8.03 (d, J=16.0 Hz, 1H), 7.95 (d, J=15.5 Hz, 1H), 7.88 (d, J=1.5 Hz, 1H), 7.86 (s, 1H), 7.85 (d, J=1.5 Hz, 1H), 7.57 (dd, J=8.5 Hz and 2.0 Hz, 1H), 7.55 (d, J=2.0 Hz, 1H), 7.51 (d, J=2.0 Hz, 1H), 7.42-7.39 (m, 2H), 7.33 (d, J=2.5 Hz, 1H), 7.18 (dd, J=9.0 Hz and 2.5 Hz, 1H), 7.11 (d, J=8.0 Hz, 1H), 7.08 (d, J=15.5 Hz, 1H), 6.98 (d, J=15.0 Hz, 1H), 6.96 (d, J=8.5 Hz, 1H), 6.44 (s, 1H), 4.23 (q, J=6.5 Hz, 1H), 3.95 (s, 3H), 3.94 (s, 3H), 3.82 (s, 3H), 1.67 (d, J=7.5 Hz, 3H). $^{19}$F NMR (acetone-$d_6$, 470 MHz): δ −140.67 (s, $^{10}$B—F), −140.74 (s, $^{11}$B—F). $^{13}$C NMR (acetone-$d_6$, 125 MHz): δ 181.2, 179.0, 171.9, 158.0, 151.9, 148.1, 148.0, 144.7, 142.9, 135.5, 134.0, 133.4, 129.2, 129.0, 127.1, 126.6, 126.4, 126.1, 125.2, 123.3, 123.3, 122.1, 121.7, 118.9, 118.9, 115.7, 112.7, 111.9, 105.6, 101.5, 55.5, 55.4, 45.0, 18.3.

mono-Naproxen/CUR Adduct (20): Yield 30%, yellow solid, mp 148° C., Rf 0.34 (40% EtOAc in hexane). 1H NMR (CDCl3, 500 MHz): δ 7.80 (s, 1H), 7.75 (pseudo-t, 8.5 Hz, 2H), 7.60 (d, J=16.0 Hz, 1H), 7.57 (d, J=14.5 Hz, 1H), 7.53 (dd, J=8.5 Hz and 2.0 Hz, 1H), 7.18-7.19 (overlapping set of doublets, 4H), 7.06-7.01 (overlapping doublets, 2H), 6.96 (d, J=9.0 Hz, 1H), 6.94 (d, J=8.0 Hz, 1H), 6.52 (d, J=16.0 Hz, 1H), 6.49 (d, J=15.5 Hz, 1H), 5.87 (s, 1H), 5.82 (s, 1H), 4.15 (q, J=7.5, 1H), 3.95 (s, 3H), 3.94 (s, 3H), 1.71 (d, J=6.5 Hz, 3H). $^{13}$C NMR (CDCl$_3$, 125 MHz): δ 184.4, 181.9, 172.5, 157.7, 151.5, 148.0, 146.8, 141.5, 141.1, 139.5, 135.2, 134.0, 133.8, 129.3, 129.0, 127.6, 127.1, 126.4, 126.3, 124.2, 123.1, 123.0, 121.8, 120.9, 119.0, 114.8, 111.5, 109.6, 105.6, 101.5, 55.9, 55.8, 55.3, 45.3, 18.7. HRMS (ESI): m/z [M+H]+ calcd for $C_{35}H_{33}O_8$: 581.2175; found: 581.2328. IR (cm$^{-1}$): 3524, 3408, 3003-2839, 1755, 1628, 1601, 1508, 1462, 1267, 1123, 1032.

bis-Indomethacin/CUR—BF2 Adduct (11): Yield 54%, dark-red solid, mp 168-170° C., Rf 0.27 (40% EtOAc in hexane). 1H NMR (acetone-$d_6$, 500 MHz): δ 8.01 (d, J=16.0 Hz, 2H), 7.77 (d, J=8.0 Hz, 4H), 7.65 (d, J=8.5 Hz, 4H), 7.26 (s, 4H), 7.21 (d, J=2.5 Hz, 2H), 7.17 (d, J=15.5 Hz, 2H), 7.01 (d, J=9.0 Hz, 2H), 6.75 (dd, J=3.0 Hz and 9.2 Hz, 2H), 6.51 (s, 1H), 4.07 (s, 4H), 3.87 (s, 12H), 3.86 (s, 6H), 2.41 (s, 6H). $^{19}$F NMR (acetone-$d_6$, 470 MHz): δ −140.26 (s, $^{10}$B—F), −140.32 (s, $^{11}$B—F). 13C NMR (acetone-$d_6$, 125 MHz): δ 180.6, 168.1, 156.2, 152.8, 146.5, 138.4, 136.0, 134.6, 132.7, 132.0, 131.3, 130.9, 129.1, 121.7, 114.7, 112.5, 111.3, 106.3, 101.9, 55.9, 55.1, 12.7. IR (cm$^{-1}$): 2916, 2848, 1763, 1684, 1616, 1593, 1541, 1503, 1458, 1342, 1260, 1130.

bis-Ibuprofen/CUR—BF2 Adduct (12): Yield 68%, orange solid, mp: 239-240° C., Rf 0.64 (40% EtOAc in hexane). 1H NMR (acetone-$d_6$, 500 MHz): δ 7.97 (d, J=15.5 Hz, 2H), 7.38 (d, J=8.0 Hz, 4H), 7.21 (d, J=7.0 Hz, 4H), 7.20 (s, 4H), 7.12 (d, J=15.5 Hz, 2H), 6.47 (s, 1H), 4.07 (q, J=7.5 Hz, 2H), 3.82 (s, 12H), 2.50 (d, J=7.5 Hz, 4H), 1.90 (septet, J=6.5 Hz, 2H), 1.58 (d, J=7.5 Hz, 6H), 0.92 (d, J=6.0 Hz, 12H). $^{19}$F NMR (acetone-$d_6$, 470 MHz): δ −140.08 (s, $^{10}$B—F), −140.74 (s, $^{11}$B—F). $^{13}$C NMR (acetone-$d_6$, 125 MHz): δ 180.5, 171.5, 152.9, 146.6, 140.3, 137.8, 132.6, 132.1, 129.1, 127.5, 121.5, 106.3, 102.0, 55.7, 44.7, 44.6, 30.1, 21.7, 18.6. IR (cm$^{-1}$): 2953, 1749, 1618, 1595, 1531, 1504, 1456, 1425, 1383, 1341, 1308, 1258, 1130, 1063, 1015.

mono-Ibuprofen/CUR—BF2 Adduct (13): Yield 81%, red solid, mp: 120° C., Rf 0.33 (40% EtOAc in hexane). 1H NMR (acetone-$d_6$, 500 MHz): δ 8.96 (s, 1H), 8.04 (d, J=16.0 Hz, 1H), 7.95 (d, J=16.0 Hz, 1H), 7.55 (d, J=2.0 Hz, 1H), 7.51 (d, J=2.0 Hz, 1H), 7.41 (pseudo-dt, J=5.0 Hz and 2.0 Hz, 2H), 7.37 (distorted d, J=8.0 Hz, 2H), 7.21 (d, J=8.0 Hz, 2H), 7.10 (d, J=8.0 Hz, 1H), 7.08 (d, J=15.5 Hz, 1H), 6.97 (d, J=15.0 Hz, 1H), 6.96 (d, J=8.5 Hz, 1H), 6.44 (s, 1H), 4.06 (q, J=6.5 Hz, 1H), 3.96 (s, 3H), 3.84 (s, 3H), 2.50 (d, J=7.5 Hz, 2H), 1.89 (sept, J=6.5 Hz, 1H), 1.58 (d, 7.5 Hz, 3H), 0.92 (d, J=6.5 Hz, 6H). $^{19}$F NMR (acetone-d6, 470 MHz): δ −140.66 (s, $^{10}$B—F), −140.71 (s, $^{11}$B—F). $^{13}$C NMR (acetone-$d_6$, 125 MHz): δ 181.1, 179.0, 172.0, 152.0, 148.1, 148.0, 144.7, 142.8, 140.4, 137.7, 133.4, 129.2, 127.4, 126.6, 125.3, 123.3, 122.2, 121.7, 121.5, 118.0, 115.7, 112.7, 111.8, 101.5, 55.5, 55.4, 44.6, 30.0, 21.73, 21.71, 18.4.

mono-Ibuprofen/CUR Adduct (21): Yield 29%, yellow solid, mp 100° C., Rf 0.62 (40% EtOAc in hexane). 1H NMR (CDCl$_3$, 500 MHz): δ 7.61 (d, J=16.0 Hz, 1H), 7.58 (d, J=16 Hz, 1H), 7.33 (d, J=8.0 Hz, 2H), 7.27 (d, J=2.0 Hz, 1H), 7.16-7.11 (overlapping doublets, 4H), 7.07 (d, J=6.5 Hz, 2H), 6.97 (d, J=8.0 Hz, 1H), 6.94 (d, J=8.0 Hz, 1H), 6.53 (d, J=15.5 Hz, 1H), 6.49 (d, J=16.0 Hz, 1H), 5.87 (s, 1H), 5.82 (s, 1H), 3.99 (q, J=6.5 Hz, 1H), 3.95 (s, 3H), 3.76 (s, 3H), 2.49 (d, J=7.5 Hz, 2H), 1.88 (sept, J=6.5 Hz, 1H), 1.63 (d, J=7.5 Hz, 3H), 0.92 (d, J=6.5 Hz, 6H). 13C NMR (CDCl3, 125 MHz): δ 184.4, 181.9, 172.6, 151.5, 147.9, 146.8, 141.5, 141.0, 140.7, 139.5, 137.2, 134.0, 129.3, 127.6, 127.4, 124.1, 123.1, 123.0, 121.8, 121.0, 114.8, 111.5, 109.6, 101.5, 55.9, 55.8, 45.1, 30.2, 22.39, 22.38, 18.6. HRMS (ESI): m/z [M−H]$^-$ calcd for $C_{34}H_{35}O_7$: 555.2382; found: 555.2431.

3,5-Dimethoxybenzaldehyde/4-Flufenamic Adduct: Yield 72%, white solid, mp 118° C., Rf 0.65 (40% EtOAc in hexane). 1H NMR (CDCl$_3$, 500 MHz): δ 9.97 (s, 1H), 9.44 (s, 1H), 8.31 (dd, J=8.3 Hz and 1.0 Hz, 1H), 7.51-7.40 (m, 4H), 7.36 (d, J=8.0 Hz, 1H), 7.32 (d, J=7.5 Hz, 1H), 7.23 (s, 2H), 6.92 (t, J=8.0 Hz, 1H), 3.93 (s, 6H). 19F NMR (CDCl$_3$, 470 MHz): δ −62.85. $^{13}$C NMR (CDCl$_3$, 125 MHz): δ191.0, 165.8, 153.2, 147.5, 141.2, 135.2, 134.6, 133.6, 131.9 (q, JCF=32.4 Hz), 130.0, 124.7, 123.9 (q, JCF=272.7 Hz), 119.8 (q, JCF=3.8 Hz), 118.5, 118.2 (q, JCF=7.7 Hz), 114.2, 111.4, 106.1, 56.5. HRMS (ESI): m/z [M+H]+ calcd for $C_{23}H_{19}F_3NO_5$: 446.1214; found: 446.1326.

2,6-Dimethoxybenzaldehyde/4-Flufenamic Adduct: Yield 37%, white solid, mp 105° C., Rf 0.57 (40% EtOAc in hexane). 1H NMR (CDCl$_3$, 500 MHz): δ 10.48 (s, 1H), 8.21 (dd, J=8.2 Hz and 1.5 Hz, 1H), 7.51-7.42 (m, 4H), 7.37-7.32 (m, 2H), 3.92 (s, 6H). $^{13}$C NMR (CDCl$_3$, 125 MHz): δ 188.2, 166.3, 163.2, 156.8, 148.0, 141.0, 135.6, 132.2, 132.0 (q, JCF=32.4 Hz), 130.1, 125.1, 123.9 (q, JCF=272.8 Hz), 120.3 (q, JCF=4.6 Hz), 118.6 (q, JCF=3.8 Hz), 118.4, 114.4, 112.4, 111.0, 98.4, 56.3. $^{19}$F NMR (CDCl$_3$, 470 MHz): δ −62.84 (3F). HRMS (ESI): m/z [M+H]+ calcd for C$_{23}$H$_{19}$F$_3$NO$_5$: 446.12153; found: 446.1058.

5-Fluorobenzaldehyde/2-Flufenamic Adduct: Yield 47%, light yellow solid, mp 96° C., Rf 0.82 (40% EtOAc in hexane). 1H NMR (CDCl$_3$, 500 MHz): δ 10.19 (d, J=2.5 Hz, 1H), 9.34 (s, 1H), 8.27 (dd, J=8.2 Hz and 2.0 Hz, 1H), 7.66 (dd, J=8.2 Hz and 3.0 Hz, 1H), 7.51-7.46 (m, 3H), 7.43-7.39 (m, 2H), 7.36 (d, J=7.5 Hz, 1H), 7.35-7.31 (m, 2H), 6.93 (td, J=7.0 Hz and 1.0 Hz, 1H). $^{19}$F NMR (CDCl$_3$, 470 MHz): δ −62.84 (3F), −114.13 (q, J=9.9 Hz, 1F). $^{13}$C NMR (CDCl3, 125 MHz): δ 187.0, 166.8, 160.4 (d, JCF=248.0 Hz), 148.2, 148.1 (JCF=2.8 Hz), 140.8, 135.8, 132.2, 132.0 (q, JCF=32.4 Hz), 130.1, 129.8 (JCF=5.7 Hz), 123.8 (q, JCF=273.0 Hz), 125.5 (JCF=7.7 Hz), 125.3, 122.3 (JCF=23.9 Hz), 120.4 (q, JCF=4.8 Hz), 118.8 (q, JCF=3.8 Hz), 118.5, 115.7 (JCF=24.0 Hz), 114.3, 110.4. HRMS (ESI): m/z [M+H]+ calcd for C$_{21}$H$_{14}$F$_4$NO$_3$: 404.09098; found: 404.0966.

3,5-Dimethoxybenzaldehyde/4-Flurbiprofen Adduct: Yield 37.3% (141 mg), white solid, mp 115-116° C., Rf 0.82 (40% EtOAc in hexane). 1H NMR (CDCl$_3$, 500 MHz): δ 9.91 (s, 1H), 7.58-7.56 (m, 2H), 7.48-7.44 (m, 3H), 7.39 (tt, J=7.5 Hz and 1.0 Hz, 1H), 7.32-7.28 (complex m, 2H), 4.13 (q, J=7.5 Hz, 1H), 3.85 (s, 6H), 1.69 (d, J=7.0 Hz, 3H). $^{13}$C NMR (CDCl$_3$, 125 MHz): δ 191.0, 171.2, 160.7, 158.7, 152.9, 141.4 (JCF=7.7 Hz), 135.5, 134.4, 133.8, 130.7 (JCF=3.8 Hz), 129.0 (JCF=2.8 Hz), 128.5, 128.0, 127.9, 127.7, 56.2, 44.8, 18.7. $^{19}$F NMR (CDCl$_3$, 470 MHz): δ −117.88 (pseudo-t, J=8.5 Hz). HRMS (ESI): m/z [M+H]+ calcd for C24H22FO5: 409.14513; found: 409.1482.

3,5-Dimethoxybenzaldehyde/4-Naproxen Adduct: Yield 46%, white solid, mp 69-71° C., Rf 0.61 (40% EtOAc in hexane). 1H NMR (CDCl$_3$, 500 MHz): δ 9.87 (s, 1H), 7.83 (d, J=1 Hz, 1H), 7.75 (t, J=8.5 Hz, 2H), 7.54 (dd, J=8.2 and 2.0 Hz, 1H), 7.18-7.16 (m, 2H), 7.09 (s, 2H), 4.22 (q, J=7.5 Hz, 1H), 3.93 (s, 3H), 3.75 (br s, 6H), 1.73 (d, J=7.5 Hz, 3H). $^{13}$C NMR (CDCl3, 125 MHz): δ 191.1, 171.9, 157.7, 153.0, 135.2, 134.3, 134.1, 133.8, 129.3, 129.0, 126.9, 126.6, 126.3, 119.0, 106.1, 105.6, 56.2, 55.3, 45.2, 18.8. HRMS (ESI): m/z [M+H]+ calcd for C$_{23}$H$_{23}$O$_6$: 395.149465; found: 395.1459.

2,6-Dimethoxybenzaldehyde/4-Naproxen Adduct: Yield 47%, white solid, mp 140-141° C., Rf 0.41 (40% EtOAc in hexane). 1H NMR (CDCl$_3$, 500 MHz): δ 10.39 (s, 1H), 7.78-7.73 (m, 3H), 7.49 (dd, J=7.0 Hz and 1.5 Hz, 1H), 7.18 (dd, J=6.0 Hz and 2.5 Hz, 1H), 7.15 (d, J=2.5 Hz, 1H), 6.26 (s, 2H), 4.09 (q, J=6.5 Hz, 1H), 3.93 (s, 3H), 3.82 (s, 6H), 1.71 (d, J=7.0 Hz, 3H). $^{13}$C NMR (CDCl$_3$, 125 MHz): δ 188.2, 172.3, 163.1, 157.9, 157.0, 134.5, 133.9, 129.3, 129.0, 127.5, 126.2, 126.0, 119.3, 112.1, 105.6, 97.8, 56.2, 55.3, 45.7, 18.5. HRMS (ESI): m/z [M+H]+ calcd for C$_{23}$H$_{23}$O$_6$: 395.149465; found: 395.1400.

3,5-Dimethoxybenzaldehyde/4-Ibuprofen Adduct: Yield 60%, white solid, mp 83° C., Rf 0.63 (40% EtOAc in hexane). 1H NMR (CDCl$_3$, 500 MHz): δ 9.88 (s, 1H), 7.35 (d, J=8.0 Hz, 2H), 7.15 (d, J=8.5 Hz, 2H), 7.10 (s, 2H), 4.05 (q, J=7.0 Hz, 1H), 3.78 (s, 6H), 2.48 (d, J=6.5 Hz, 2H), 1.88 (septet, J=7.0 Hz, 1H), 1.64 (d, J=7.5 Hz, 3H), 1.22 (d, J=6.0 Hz), 0.92 (dd, J=6.5 Hz and 1.0 Hz, 6H). $^{13}$C NMR (CDCl$_3$, 125 MHz): δ 191.1, 171.9, 153.0, 140.6, 137.2, 134.2, 129.2, 127.5, 106.1, 56.2, 45.1, 44.9, 30.2, 25.4, 22.4, 18.7. HRMS (ESI): m/z [M+H]+ calcd for C$_{22}$H$_{27}$O$_5$: 371.18585; found: 371.1897.

5-Fluorobenzaldehyde/2-Ibuprofen Adduct: Yield 13%, white solid, mp 85° C., Rf 0.86 (40% EtOAc in hexane). 1H NMR (CDCl$_3$, 500 MHz): δ 9.68 (d, J=2.5 Hz, 1H), 7.53 (dd, J=8.2. and 3.5 Hz, 1H), 7.31-7.28 (m, 3H), 7.18 (d, J=8.0 Hz, 2H), 7.11 (dd, J=9.2 and 4.5 Hz, 1H), 4.04 (q, J=6.5 Hz, 1H), 2.49 (d, J=7.0 Hz, 2H), 1.88 (sept, J=6.5 Hz, 1H), 1.66 (d, J=6.5 Hz, 3H), 0.92 (d, J=6.5 Hz, 6H). $^{13}$C NMR (CDCl$_3$, 125 MHz): δ 187.0, 172.9, 160.2 (J=247.9 Hz), 148.4 (J=2.8 Hz), 141.4, 136.5, 129.8, 129.4 (J=6.7 Hz), 127.2, 125.0 (J=7.7 Hz), 122.1 (J=23.9 Hz), 115.0 (J=23.9 Hz), 45.2, 45.0, 30.2, 22.4, 18.0. $^{19}$F NMR (CDCl$_3$, 470 MHz): δ −114.63 (m).

3,5-Dimethoxybenzaldehyde/4-Indomethacin Adduct: Yield 96%, white solid, mp 149° C., Rf 0.56 (40% EtOAc in hexane). 1H NMR (CDCl$_3$, 500 MHz): δ 7.67 (dt, J=6.5 Hz and 2.0 Hz, 2H), 7.46 (dt, J=8.5 Hz and 2.5 Hz, 2H), 7.12 (s, 2H), 7.09 (d, J=2.5 Hz, 1H), 6.90 (d, J=9.0 Hz, 1H), 6.69 (dd, J=9.2 Hz and 2.5 Hz, 1H), 3.98 (s, 2H), 3.84 (s, 3H), 3.81 (s, 6H), 2.44 (s, 3H). $^{13}$C NMR (CDCl$_3$, 125 MHz): δ 191.0, 168.3, 168.1, 156.0, 152.9, 139.3, 136.3, 134.4, 133.9, 131.2, 130.9, 130.7, 129.1, 114.8, 112.2, 111.7, 111.4, 106.1, 101.9, 101.3, 56.3, 55.7, 29.7, 13.4. HRMS (ESI): m/z [M+H]+ calcd for C$_{28}$H$_{25}$ClNO$_7$: 522.13195; found: 522.14.

Computational Methods

B3LYP/6-31G* geometry optimizations were carried out with the Gaussian 09 program. Molecular docking calculations were performed with the software AutoDock Vina (version 1.1.2) for modeling the binding modes and assessing the interaction energies of the studied compounds as ligands for several enzymes. The three-dimensional coordinates of the proteins were obtained from the RCSB Protein Data Bank (PDB IDs: 3PP0 (HER2), 3SDK (20S proteasome), 4AG8 (VEGFR2), 4XV2 (BRAF), 4LVT (Bcl-2), 4O1Z (COX-1), and 4PH9 (COX-2)). (K. Aertgeerts, R. Skene, J. Yano, B.-C. Sang, H. Zou, G. Snell, A. Jennings, K. Iwamoto, N. Habuka, A. Hirokawa, T. Ishikawa, T. Tanaka, H. Miki, Y. Ohta, S. J. Sogabe, J. Biol. Chem. 2011, 286, 18756-18765; C. Blackburn, C. Barrett, J. L. Blank, F. J. Bruzzese, N. Bump, L. R. Dick, P. Fleming, K. Garcia, P. Hales, Z. Hu, M. Jones, J. X. Liu, D. S. Sappal, M. D. Sintchak, C. Tsu, K. M. Gigstad, Bioorg. Med. Chem. Lett. 2010, 20, 6581-6586; M. McTigue, B. W. Murray, J. H. Chen, Y.-L. Deng, J. Solowiej, R. S. Kania, Proc. Natl. Acad. Sci. USA 2012, 109, 18281-18289; C. Zhang, W. Spevak, Y. Zhang, E. A. Burton, Y. Ma, G. Habets, J. Zhang, J. Lin, T. Ewing, B. Matusow, G. Tsang, A. Marimuthu, H. Cho, G. Wu, W. Wang, D. Fong, H. Nguyen, S. Shi, P. Womack, M. Nespi, R. Shellooe, H. Carias, B. Powell, E. Light, L. Sanftner, J. Walters, J. Tsai, B. L. West, G. Visor, H. Rezaei, P. S. Lin, K. Nolop, P. N. Ibrahim, P. Hirth, G. Bollag, Nature 2015, 526, 583-586; A. J. Souers, J. D. Leverson, E. R. Boghaert, S. L. Ackler, N. D. Catron, J. Chen, B. D. Dayton, H. Ding, S. H. Enschede, W. J. Fairbrother, D. C. S. Huang, S. G. Hymowitz, S. Jin, S. L. Khaw, P. J. Kovar, L. T. Lam, J. Lee, H. L. Maecker, K. C. Marsh, K. D. Mason, M. J. Mitten, P. M. Nimmer, A. Oleksijew, C. H. Park, C.-M. Park, D. C. Phillips, A. W. Roberts, D. Sampath, J. F. Seymour, M. L. Smith, G. M. Sullivan, S. K. Tahir, C. Tse, M. D. Wendt, Y. Xiao, J. C. Xue, H. Zhang, R. A. Humerickhouse, S. H. Rosenberg, S. W. Elmore, Nat. Med. 2013, 19, 202-208; S. Xu, D. J. Hermanson, S. Banerjee, K.

Ghebreselasie, G. M. Clayton, R. M. Garavito, L. J. Marnett, J. Biol. Chem. 2014, 289, 6799-6808; B. J. Orlando, M. J. Lucido, M. G. Malkowski, J. Struct. Biol. 2015, 189, 62-66).

Chain A of HER2, VEGFR2, BRAF, Bcl-2, COX-1 and COX-2, and chains K (β5 subunit) and L (β6 subunit) of 20S proteasome were selected as target templates for the docking computations. Co-crystallized ligands and crystallographic water molecules were removed. Addition of hydrogens, merger of nonpolar hydrogens to the atom to which they were linked, and assignment of partial charges were computed with AutoDockTools. Docking areas were constrained to a 30×30×30 Å box centered at the active site of the proteins, providing proper space for rotational and translational movement of the ligands. Octanol/water partition coefficients (Log P) were evaluated by free Molinspiration molecular property calculation service.

Bioassay Methods

NCI-60 assay: samples were submitted to the National Cancer Institute (NCI of NIH) Developmental Therapeutics anticancer screening program (DTP) for human tumor cell line assay by NCI-60 screening against leukemia, lung, colon, and CNS cancers, as well as melanoma, ovarian, renal, prostate, and breast cancers. Compounds are initially tested at a single dose of $10^{-5}$ molar. Data are reported as mean graph of percent growth (GP). Selected data output are shown in SI file. Growth inhibition is represented by values between 0 and 100 and lethality by values less than zero.

Cell Viability, Cytotoxicity and Apoptosis Assay for Colorectal Cells

Colorectal cancer (HCT116, HT29, DLD-1, RKO, SW837 and Caco2) and normal colon cell lines (CCD841CoN) were obtained from the American Type Culture Collection (ATCC, Manassas, Va.). Cells were maintained in DMEM medium (Life Technologies, Carlsbad, Calif.) supplemented with 10% fetal bovine serum (Life Technologies), 1% non-essential amino acids (Life Technologies), 1% penicillin-streptomycin (Life Technologies), and 1% glutamine (Life Technologies) at 37° C. and 5% CO2. For the assessment of cell viability, cells were seeded in 96-well plates with approximately $5.0 \times 10^3$ cells/well and incubated in RPMI1640 medium (supplemented with 10% fetal bovine serum and 1% glutamine) for 24 hours. Cells were then treated with DMEM medium containing CUR compounds (10 μM) or vehicle (DMSO) for 72 hours and the number of viable cells was determined using CellTiter-Glo® cell viability assay system (Promega, Madison Wis.). After addition of the reagent (CytoTox-Glo™ or Caspase-Glo® 3/7 Assay System) to the cell culture medium, luminescence was measured by infinite M200 Pro microplate reader (TECAN).

Inflammation Response

Human macrophage cells (THP-1) was obtained from the ATCC (Manassas, Va.). Cells were maintained in DMEM medium supplemented with 10% fetal bovine serum, 1% non-essential amino acids, 1% penicillin-streptomycin, and 1% glutamine at 37° C. and 5% CO2. For the inflammation assay, cells were seeded in T75 flask with approximately $9.0 \times 10^5$ cells/flask and incubated in DMEM medium for 24 hours. Cells were treated for 2 hours with Lipopolysaccharide (LPS, Millipore-Sigma, St Louis, Mo.) at a concentration of 100 ng/ml or vehicle control (Phosphate-Buffered Saline (PBS, Life Technologies) to induce an inflammatory state. After the incubation, culture media containing LPS or PBS was removed and replaced for 24 hours with DMEM media containing curcumin derivatives, the parent compound at a concentration of 10 μM or vehicle control (DMSO). Twenty-four hours after the treatment, cells were rinsed by PBS, and total RNAs were isolated using Qiagen's RNeasy Micro Kit (Qiagen, Hilden, Germany) per the manufacturer's instructions. Complimentary DNA (cDNA) was generated using High Capacity cDNA Reverse Transcription Kit (Applied Biosystems, Foster City, Calif.). The mRNA levels of Interleukin 1β (IL-1β) and β-actin (the structural housekeeping gene) were measured using TaqMan Gene Expression Assay (Applied Biosystems) and QuantStudio 6 Quantitative Real-Time PCR (qRT-PCR) system (Thermo Fisher Scientific, Waltham, Mass.). Raw cycle threshold (Ct) values were used via the ΔΔCt method to calculate fold change in gene expression.

Statistical Analysis

All statistical analyses were performed using GraphPad Prism 7 software. A statistically significant difference was determined using unpaired t-test with Welch's correction. Data were presented as mean±standard error of mean and was considered statistically significant when p-value was <0.05.

CONCLUSION

The inventors have synthesized numerous CUR-inspired compounds which have shown anti-proliferative activity against multiple cancer cells lines. These compounds can be used in drug development for cancer treatments.

In the preceding specification, all documents, acts, or information disclosed does not constitute an admission that the document, act, or information of any combination thereof was publicly available, known to the public, part of the general knowledge in the art, or was known to be relevant to solve any problem at the time of priority.

The disclosures of all publications cited above are expressly incorporated herein by reference, each in its entirety, to the same extent as if each were incorporated by reference individually.

It will be seen that the advantages set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween. Now that the invention has been described,

What is claimed is:

1. A composition comprising formula (I):

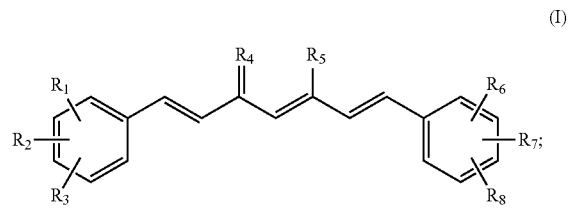

where $R_1$ is o-OCH$_3$, m-OCH$_3$, or H;
where $R_2$ is o-OCH$_3$, m-OCH$_3$, H, or m-F;

where R₃ is
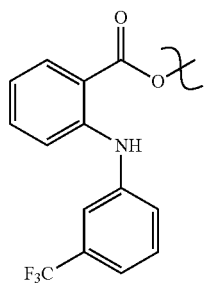 [SMILES: COC(=O)c1ccccc1Nc1cccc(C(F)(F)F)c1]
at a para position,
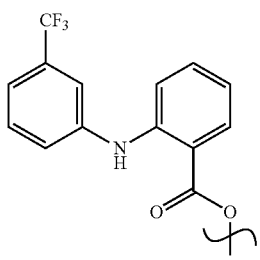 [SMILES: COC(=O)c1ccccc1Nc1cccc(C(F)(F)F)c1]
at an ortho position,
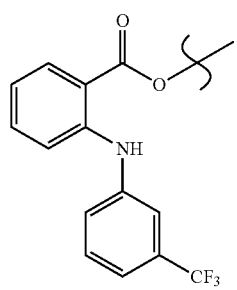 [SMILES: CCOC(=O)c1ccccc1Nc1cccc(C(F)(F)F)c1]
at a para position,
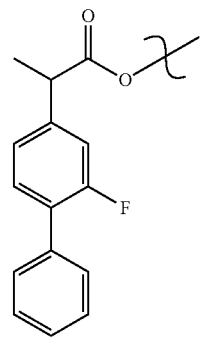 [SMILES: CCOC(=O)C(C)c1ccc(-c2ccccc2)c(F)c1]
at a para position,
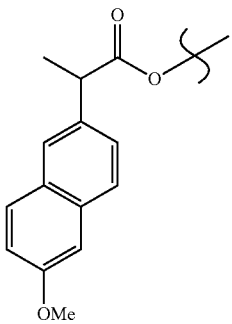 [SMILES: CCOC(=O)C(C)c1ccc2cc(OC)ccc2c1]
at a para position,
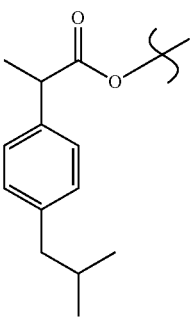 [SMILES: CCOC(=O)C(C)c1ccc(CC(C)C)cc1]
at a para position, or
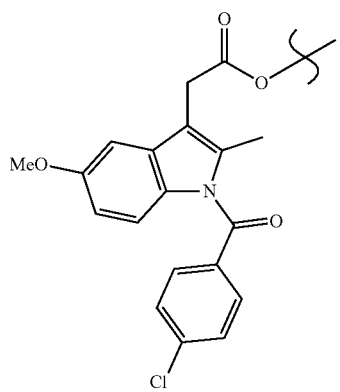 [SMILES: CCOC(=O)Cc1c(C)n(C(=O)c2ccc(Cl)cc2)c2ccc(OC)cc12]
in a para position;
  where R₄ is O or O associated with a difluoroboron adduct formed with R₅;
  where R₅ is OH or O associated with a difluoroboron adduct formed with R₄;

where R₆ is o-OCH₃, m-OCH₃, or H;
where R₇ is o-OCH₃, m-OCH₃, H, or m-F; and
where R₈ is p-OH,

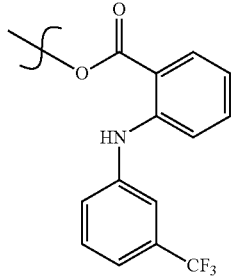 [SMILES: CCOC(=O)c1ccccc1Nc1cccc(C(F)(F)F)c1]

in a para position,

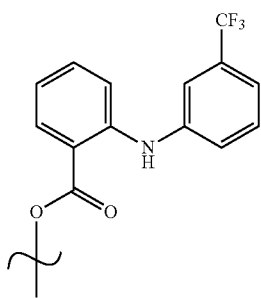 [SMILES: CCOC(=O)c1ccccc1Nc1cccc(C(F)(F)F)c1]

in an ortho position,

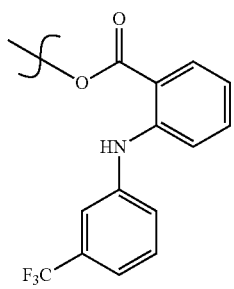 [SMILES: CCOC(=O)c1ccccc1Nc1cccc(C(F)(F)F)c1]

in a para position,

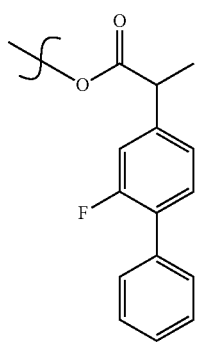 [SMILES: CCOC(=O)C(C)c1ccc(-c2ccccc2)c(F)c1]

in a para position,

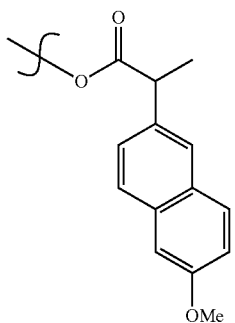 [SMILES: CCOC(=O)C(C)c1ccc2cc(OC)ccc2c1]

in a para position,

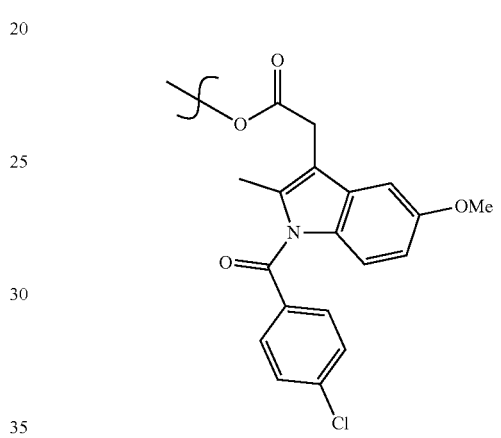

in a para position, or

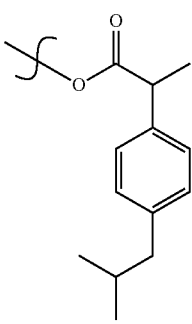 [SMILES: CCOC(=O)C(C)c1ccc(CC(C)C)cc1]

in a para position.

2. The composition of claim 1, wherein R₄ is O associated with a difluoroboron adduct formed with R₅.

3. The composition of claim 2, wherein R₅ is O associated with a difluoroboron adduct formed with R₄.

4. A method of inhibiting proliferation of at least one cancer cell comprising:
   identifying the at least one cancer cell wherein the at least one cancer cell is selected from the group consisting of leukemia cells, prostate cancer cells, lung cancer cells, colon cancer cells, and breast cancer cells;

administering a therapeutically effective amount of a composition comprising formula (I)
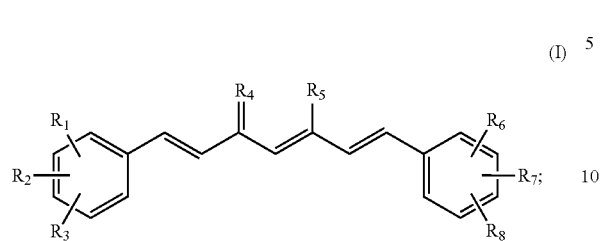
(I)
where $R_1$ is o-OCH$_3$, m-OCH$_3$, or H;
where $R_2$ is o-OCH$_3$, m-OCH$_3$, H, or m-F;
where $R_3$ is
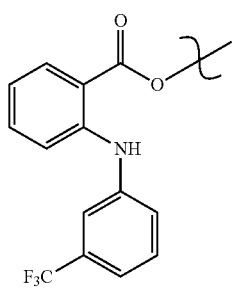 [SMILES: CCOC(=O)c1ccccc1Nc1cccc(C(F)(F)F)c1]
at a para position,
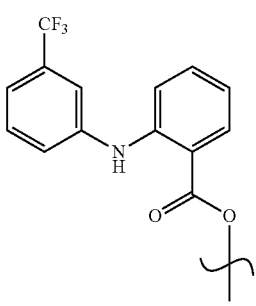 [SMILES: CCOC(=O)c1ccccc1Nc1cccc(C(F)(F)F)c1]
at an ortho position,
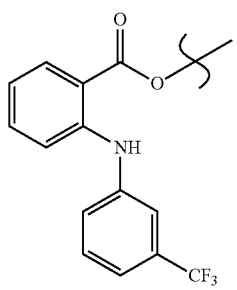 [SMILES: CCOC(=O)c1ccccc1Nc1cccc(C(F)(F)F)c1]
at a para position,
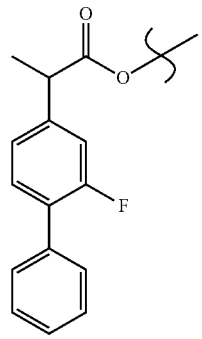 [SMILES: CCOC(=O)C(C)c1ccc(-c2ccccc2)c(F)c1]
at a para position,
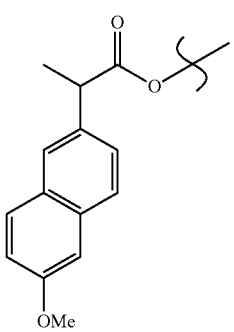 [SMILES: CCOC(=O)C(C)c1ccc2cc(OC)ccc2c1]
at a para position,
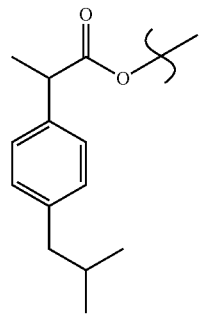 [SMILES: CCOC(=O)C(C)c1ccc(CC(C)C)cc1]
at a para position, or
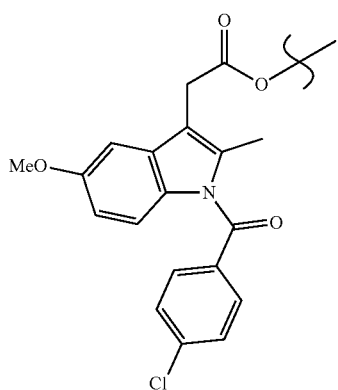 [SMILES: CCOC(=O)Cc1c(C)n(C(=O)c2ccc(Cl)cc2)c2ccc(OC)cc12]

in a para position;

where $R_4$ is O or O associated with a difluoroboron adduct formed with $R_5$;

where $R_5$ is OH or O associated with a difluoroboron adduct formed with $R_4$;

where $R_6$ is o-OCH$_3$, m-OCH$_3$, or H;

where $R_7$ is o-OCH$_3$, m-OCH$_3$, H, or m-F; and where $R_8$ is p-OH,

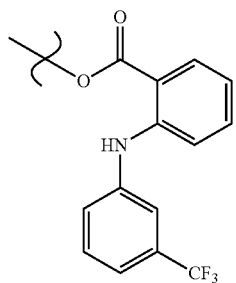 [SMILES: CCOC(=O)c1ccccc1Nc1cccc(C(F)(F)F)c1]

in a para position,

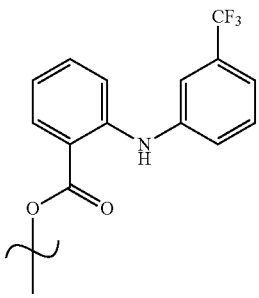 [SMILES: CCOC(=O)c1ccccc1Nc1cccc(C(F)(F)F)c1]

in an ortho position,

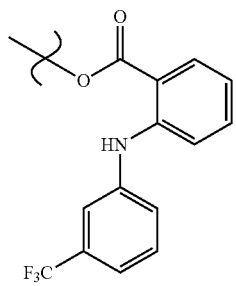 [SMILES: CCOC(=O)c1ccccc1Nc1cccc(C(F)(F)F)c1]

in a para position,

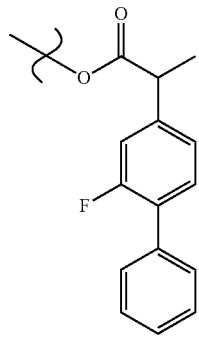 [SMILES: CCOC(=O)C(C)c1ccc(-c2ccccc2)c(F)c1]

in a para position,

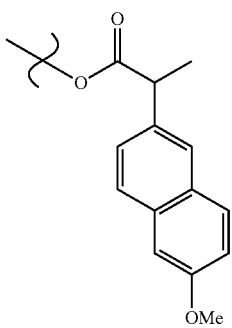 [SMILES: CCOC(=O)C(C)c1ccc2cc(OC)ccc2c1]

in a para position,

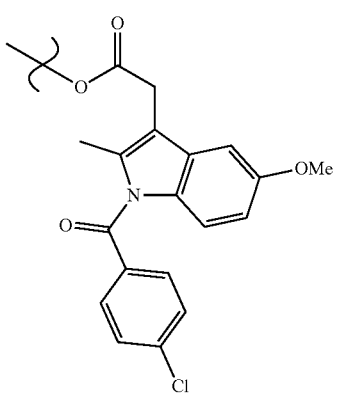 [SMILES: CCOC(=O)Cc1c(C)n(C(=O)c2ccc(Cl)cc2)c2ccc(OC)cc12]

in a para position, or

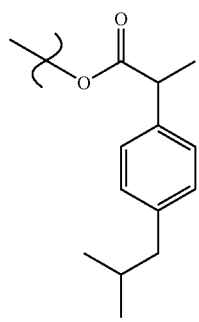 [SMILES: CCOC(=O)C(C)c1ccc(CC(C)C)cc1]

in a para position.

5. The method of claim 4, wherein $R_4$ is O associated with a difluoroboron adduct formed with $R_5$.

6. The method of claim 5, wherein $R_5$ is O associated with a difluoroboron adduct formed with $R_4$.

7. The method of claim 6, wherein $R_8$ is p-OH.

8. The method of claim 7, wherein the at least one cancer cell is a colon cancer cell.

9. A composition comprising formula (I):

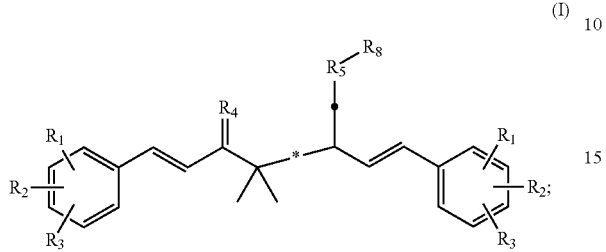

(I)

where * is a double bond or a single bond;
wherein * is a double bond when at least one of $R_6$ and $R_7$ is unsubstituted or a single bond when $R_6$ is fluorine or hydrogen and $R_7$ is fluorine;
where * is a double bond or a single bond;
wherein * is a double bond when * is a single bond;
where $R_1$ is o-OCH$_3$, m-OCH$_3$, o-F, or H;
where $R_2$ is o-OCH$_3$, m-OCH$_3$, H, m-OCF$_3$,

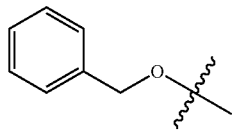 [SMILES: *OCc1ccccc1]

at a meta position, a pyrrole formed with $R_1$ or $R_3$, or a thiocyanate-substituted pyrrole formed with $R_1$ or $R_3$;

where $R_3$ is p-F, p-OCH$_3$, m-CF$_3$, p-CF$_3$, p-SCF$_3$, p-OH, m-OCF$_3$, or p-OCF;

where $R_4$ is a pyrazole formed with $R_5$;

where $R_5$ is a pyrazole formed with $R_4$;

where $R_6$ is H, F, or unsubstituted forming a double bond at *; and where $R_7$ is H or F; and where $R_8$ is H or

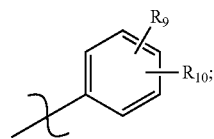

where R9 is H, p-OCF3, m-CF3, F, or CN; and
where R10 is H or F.

10. The composition of claim 9, further comprising at least one deuterated substituent on the aryl.

11. The composition of claim 10, wherein the at least one deuterated substitution is a plurality of deuterated substitutions.

12. The composition of claim 11, wherein the plurality of deuterated substitutions is at the meta positions.

* * * * *